(12) United States Patent
Albrecht et al.

(10) Patent No.: US 10,280,149 B2
(45) Date of Patent: May 7, 2019

(54) THERAPEUTIC COMPOUNDS AND USES THEREOF

(71) Applicants: GENENTECH, INC., South San Francisco, CA (US); CONSTELLATION PHARMACEUTICALS, INC., Cambridge, MA (US)

(72) Inventors: Brian K. Albrecht, Cambridge, MA (US); Alexandre Cote, Cambridge, MA (US); Victor Gehling, Cambridge, MA (US); Vickie Hsiao-Wei Tsui, South San Francisco, CA (US); James Richard Jr. Kiefer, South San Francisco, CA (US); Jun Liang, South San Francisco, CA (US); Steven Magnuson, South San Francisco, CA (US); Christopher G. Nasveschuk, Cambridge, MA (US); Richard Pastor, South San Francisco, CA (US); F. Anthony Romero, South San Francisco, CA (US); Alexander M. Taylor, Cambridge, MA (US); Birong Zhang, South San Francisco, CA (US)

(73) Assignees: GENENTECH, INC., South San Francisco, CA (US); CONSTELLATION PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 15/643,808

(22) Filed: Jul. 7, 2017

(65) Prior Publication Data
US 2018/0022727 A1    Jan. 25, 2018

Related U.S. Application Data

(63) Continuation of application No. PCT/US2016/012638, filed on Jan. 8, 2016.

(60) Provisional application No. 62/101,927, filed on Jan. 9, 2015.

(51) Int. Cl.
| | |
|---|---|
| *C07D 401/06* | (2006.01) |
| *C07D 405/06* | (2006.01) |
| *C07D 409/06* | (2006.01) |
| *C07D 413/06* | (2006.01) |
| *C07D 241/04* | (2006.01) |
| *C07D 211/30* | (2006.01) |

(52) U.S. Cl.
CPC .......... *C07D 401/06* (2013.01); *C07D 211/30* (2013.01); *C07D 241/04* (2013.01); *C07D 405/06* (2013.01); *C07D 409/06* (2013.01); *C07D 413/06* (2013.01)

(58) Field of Classification Search
None
See application file for complete search history.

(56) References Cited

U.S. PATENT DOCUMENTS 8,541,572 B2 * 9/2013 Kozlowski .......... C07D 403/14
544/106

FOREIGN PATENT DOCUMENTS

| DE | 2822360 A1 | 1/1979 | |
|---|---|---|---|
| WO | WO-0122964 A1 * | 4/2001 | .......... C07D 211/52 |
| WO | 2007059323 A2 | 5/2007 | |
| WO | 2012071469 A2 | 5/2012 | |
| WO | 2014151106 A1 | 9/2014 | |

OTHER PUBLICATIONS

Wills, L. et al., J. Pharmacol. Exper.Thera. (2012), 342(1), 106-118.*
Pichika, R. et al., Nuclear Medicine and Biology (2010), 37(8), 989-996.*
Abuhammad, et al., "Exploration of Piperidinols as Potential Antitubercular Agents", Molecules 19, 16274-16290 (2014).
Dimmock, et al., "4-(β-Arylvinyl)-3-(β-arylvinylketo)-1-ethyl-4-piperidinols and Related Compounds: A Novel Class of Cytotoxic and Anticancer Agents", J Med Chem 41, 4012-4020 (1998).
Germain, et al., "Identification of small-molecule inhibitors of Trypansoma cruzi replication", Bioorganic & Medicinal Chemistry Letters 21, 7197-7200 (2011).
Muzalevskiy, et al., "Experimental and Theoretical Study of an Intramolecular CF3-Group Shift in the Reactions of alpha-Bromoenones with 1,2-Diamines", Chemistry—A European Journal 21(47), 16982-16989 (2015).
Patent Cooperation Treaty, International Searching Authority, Search Report and Written Opinion for PCT/US2016/012638, 16 pages, dated Mar. 21, 2016.
Pavel, et al., "Synthesis of hydrogenated heterocyclic compounds from alpha-methylidene-1, 5-diketones. 4. Hydropyridines based on the reaction of 1,3,5-triphenyl-2-aminomethyl-4-methylidene-1,5-pentadione with primary amines", Chemistry of Heterocyclic Compounds 15(10), 1107-1109 (1979).

(Continued)

*Primary Examiner* — Heidi Reese
(74) *Attorney, Agent, or Firm* — Viksnins Harris Padys Malen LLP

(57) ABSTRACT

The present invention relates to compounds useful as inhibitors of one or more histone demethylses, such as KDM2b. The invention also provides pharmaceutically acceptable compositions comprising compounds of the present invention and methods of using said compositions in the treatment of various disorders.

21 Claims, No Drawings

(56) References Cited

OTHER PUBLICATIONS

Pavel, et al., "Synthesis of substituted 3-benzoyl-1,2,3,4-tetrahydropyridines by the addition of primary amines to 1,3,5-triphenyl-2-methylidene-1,5-pentanedione", Chemistry of Heterocyclic Compounds 15(1), 85-86 (1979).
Upton, et al., "Conformationally-restricted ligands for the histamine H1 receptor", Bioorganic & Medicinal Chemistry Letters 10, 1277-1279 (2000).

* cited by examiner

THERAPEUTIC COMPOUNDS AND USES THEREOF

CROSS-REFERENCE TO RELATED APPLICATION(S)

This patent application is a continuation of international application serial no. PCT/US2016/012638, filed Jan. 8, 2016, which claims the benefit of priority of U.S. provisional application Ser. No. 62/101,927, filed Jan. 9, 2015, which applications are herein incorporated by reference.

TECHNICAL FIELD

Compounds useful as inhibitors of histone demethylases, such as KDM2b are provided.

BACKGROUND

Packaging the 3 billion nucleotides of the human genome into the nucleus of a cell requires tremendous compaction. To accomplish this feat, DNA in our chromosomes is wrapped around spools of proteins called histones to form dense repeating protein/DNA polymers known as chromatin. Far from serving as mere packaging modules, chromatin templates form the basis of a newly appreciated and fundamentally important set of gene control mechanisms termed epigenetic regulation. By conferring a wide range of specific chemical modifications to histones and DNA, epigenetic regulators modulate the structure, function, and accessibility of our genome, thereby exerting a tremendous impact on gene expression. Hundreds of epigenetic effectors have recently been identified, many of which are chromatin-binding or chromatin-modifying enzymes. Significantly, an increasing number of these enzymes have been associated with a variety of disorders such as cancer. Thus, therapeutic agents directed against this emerging class of gene regulatory enzymes promise new approaches to the treatment of human diseases.

There is currently a need for compounds that inhibit of KDM2 demethylases for treating hyperproliferative diseases.

SUMMARY OF THE INVENTION

One aspect provides a compound of formula (I):

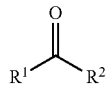

or a salt thereof, wherein:
$R^1$ is:
a) a carbon-linked piperidine ring that is substituted on the piperidine ring nitrogen with a group $R^x$ and that is optionally further substituted with one or more groups independently selected from the group consisting of $C_{1-6}$alkyl, $C_{2-6}$alkenyl, $C_{2-6}$alkynyl, $C_{3-8}$carbocycle, 3-8 membered heterocycle, aryl, heteroaryl, halo, —NO$_2$, —N(R$^b$)$_2$, —CN, —C(O)—N(R$^b$)$_2$, —S(O)—N(R$^b$)$_2$, —S(O)$_2$—N(R$^b$)$_2$, —O—R$^b$, —S—R$^b$, —O—C(O)—R$^b$, —C(O)—R$^b$, —C(O)—OR$^b$, —S(O)—R$^b$, —S(O)$_2$—R$^b$, —N(R$^b$)—C(O)—R$^b$, —N(R$^b$)—S(O)—R$^b$, —N(R$^b$)—C(O)—N(R$^b$)$_2$, and —N(R$^b$)—S(O)$_2$—R$^b$; wherein each $C_{1-6}$alkyl, $C_{2-6}$alkenyl, $C_{2-6}$alkynyl, $C_{3-8}$carbocycle, 3-8 membered heterocycle, aryl, and heteroaryl is optionally substituted with one or more groups independently selected from the group consisting of halo, —NO$_2$—N(R$^b$)$_2$, —CN, —C(O)—N(R$^b$)$_2$, —S(O)—N(R$^b$)$_2$, —S(O)$_2$—N(R$^b$)$_2$, —O—R$^b$, —S—R$^b$, —O—C(O)—R$^b$, —C(O)—R$^b$, —C(O)—OR$^b$, —S(O)—R$^b$, —S(O)$_2$—R$^b$, —N(R$^b$)—C(O)—R$^b$, —N(R$^b$)—S(O)—R$^b$, —N(R$^b$)—C(O)—N(R$^b$)$_2$, —N(R$^b$)—S(O)$_2$—R$^b$, and $C_{1-6}$alkyl that is optionally substituted with one or more groups independently selected from halo; or b) a carbon-linked piperazine ring that is substituted with one or more groups independently selected from the group consisting of $C_{1-6}$alkyl, $C_{2-6}$alkenyl, $C_{2-6}$alkynyl, $C_{3-8}$carbocycle, 3-8 membered heterocycle, aryl, heteroaryl, halo, —NO$_2$—N(R$^b$)$_2$, —CN, —C(O)—N(R$^b$)$_2$, —S(O)—N(R$^b$)$_2$, —S(O)$_2$—N(R$^b$)$_2$, —O—R$^b$, —S—R$^b$, —O—C(O)—R$^b$, —C(O)—R$^b$, —C(O)—OR$^b$, —S(O)—R$^b$, —S(O)$_2$—R$^b$, —N(R$^b$)—C(O)—R$^b$, —N(R$^b$)—S(O)—R$^b$, —N(R$^b$)—C(O)—N(R$^b$)$_2$, and —N(R$^b$)—S(O)$_2$—R$^b$; wherein each $C_{1-6}$alkyl, $C_{2-6}$alkenyl, $C_{2-6}$alkynyl, $C_{3-8}$carbocycle, 3-8 membered heterocycle, aryl, and heteroaryl is optionally substituted with one or more groups independently selected from the group consisting of halo, —NO$_2$—N(R$^b$)$_2$, —CN, —C(O)—N(R$^b$)$_2$, —S(O)—N(R$^b$)$_2$, —S(O)$_2$—N(R$^b$)$_2$, —O—R$^b$, —O—C(O)—R$^b$, —C(O)—R$^b$, —C(O)—OR$^b$, —S(O)—R$^b$, —S(O)$_2$—R$^b$), —N(R$^b$)—C(O)—R$^b$, —N(R$^b$)—S(O)—R$^b$, —N(R$^b$)—C(O)—N(R$^b$)$_2$, —N(R$^b$)—S(O)$_2$—R$^b$, and $C_{1-6}$alkyl that is optionally substituted with one or more groups independently selected from halo;

each $R^b$ is independently selected from the group consisting of hydrogen, $C_{1-6}$alkyl, $C_{2-6}$alkenyl, aryl, and $C_{2-6}$alkynyl, wherein each $C_{1-6}$alkyl, $C_{2-6}$alkenyl, aryl, and $C_{2-6}$alkynyl is optionally substituted with one or more groups independently selected from the group consisting of halo, —N(R$^c$)$_2$, —CN, —C(O)—N(R$^c$)$_2$, —S(O)—N(R$^c$)$_2$, —S(O)$_2$—N(R$^c$)$_2$, —O—R$^c$, —S—R$^c$, —O—C(O)—R$^c$, —C(O)—R$^c$, —C(O)—OR$^c$, —S(O)—R$^c$, —S(O)$_2$—R$^c$, —N(R$^c$)—C(O)—R$^c$, —N(R$^c$)—S(O)—R$^c$, —N(R$^c$)—C(O)—N(R$^c$)$_2$, and —N(R$^c$)—S(O)$_2$—R$^c$; or two $R^b$ are taken together with the nitrogen to which they are attached to form a pyrrolidino, piperidino, or piperazino ring;

each $R^c$ is independently selected from the group consisting of hydrogen, $C_{1-6}$alkyl, $C_{2-6}$alkenyl, and $C_{2-6}$alkynyl, wherein each $C_{1-6}$alkyl, $C_{2-6}$alkenyl, and $C_{2-6}$alkynyl is optionally substituted with one or more groups independently selected from the group consisting of oxo, halo, amino, hydroxy, and $C_{1-6}$alkoxy; or two $R^c$ are taken together with the nitrogen to which they are attached to form a heterocyclyl that is optionally substituted with one or more groups independently selected from the group consisting of oxo, halo and $C_{1-3}$alkyl that is optionally substituted with one or more groups independently selected from the group consisting of oxo and halo;

$R^x$ is $C_{1-6}$alkyl, $C_{2-6}$alkenyl, $C_{2-6}$alkynyl, $C_{3-8}$carbocycle, oxetanyl, tetrahydrofuranyl, or tetrahydropyranyl, wherein each $C_{1-6}$alkyl, $C_{2-6}$alkenyl, $C_{2-6}$alkynyl, $C_{3-8}$carbocycle is optionally substituted with one or more groups independently selected from the group consisting of halo, —CN, $C_{1-3}$alkoxy, oxetanyl, tetrahydrofuranyl, tetrahydropyranyl, and $C_{3-8}$carbocycle that is optionally substituted with one or more groups independently selected from the group consisting of halo and $C_{1-3}$alkyl;

$R^2$ is a 5-10 membered heteroaryl or a 6-12 membered aryl, which 5-10 membered heteroaryl, and 6-12 membered aryl is optionally substituted with one or more groups independently selected from the group consisting of $C_{1-6}$alkyl, $C_{2-6}$alkenyl, $C_{2-6}$alkynyl, carbocycle, heterocycle, aryl, heteroaryl, halo, —$NO_2$, —$N(R^d)_2$, —CN, —C(O)—$N(R^d)_2$, —S(O)—$N(R^d)_2$, —$S(O)_2$—$N(R^d)_2$, —O—$R^d$, —S—$R^d$, —O—C(O)—$R^d$, —C(O)—$R^d$, —C(O)—$OR^d$, —S(O)—$R^d$, —$S(O)_2$—$R^d$, —$N(R^d)$—C(O)—$R^d$, —$N(R^d)$—S(O)—$R^d$, —$N(R^d)$—C(O)—$N(R^d)_2$, and —$N(R^d)$—$S(O)_2$—$R^d$; wherein each $C_{1-6}$alkyl, $C_{2-6}$alkenyl, $C_{2-6}$alkynyl, carbocycle, heterocycle, aryl, and heteroaryl is optionally substituted with one or more groups independently selected from the group consisting of halo, —$NO_2$—$N(R^d)_2$, —CN, —C(O)—$N(R^d)_2$, —S(O)—$N(R^d)_2$, —$S(O)_2$—$N(R^d)_2$, —O—$R^d$, —S—$R^d$, —O—C(O)—$R^d$, —C(O)—$R^d$, —C(O)—$OR^d$, —S(O)—$R^d$, —$S(O)_2$—$R^d$, —$N(R^d)$—C(O)—$R^d$, —$N(R^d)$—S(O)—$R^d$, —$N(R^d)$—C(O)—$N(R^d)_2$, —$N(R^d)$—$S(O)_2$—$R^d$, and $C_{1-6}$alkyl that is optionally substituted with one or more groups independently selected from halo;

each $R^d$ is independently selected from the group consisting of hydrogen, $C_{1-6}$alkyl, $C_{2-6}$alkenyl, aryl, and $C_{2-6}$alkynyl, wherein each $C_{1-6}$alkyl, $C_{2-6}$alkenyl, aryl, and $C_{2-6}$alkynyl is optionally substituted with one or more groups independently selected from the group consisting of halo, —$N(R^e)_2$, —CN, —C(O)—$N(R^e)_2$, —S(O)—$N(R^e)_2$, —$S(O)_2$—$N(R^e)_2$, —O—$R^e$, —S—$R^e$, —O—C(O)—$R^e$, —C(O)—$R^e$, —C(O)—$OR^e$, —S(O)—$R^e$, —$S(O)_2$—$R^e$, —$N(R^e)$—C(O)—$R^e$, —$N(R^e)$—S(O)—$R^e$, —$N(R^e)$—C(O)—$N(R^e)_2$, and —$N(R^e)$—$S(O)_2$—$R^e$; or two $R^d$ are taken together with the nitrogen to which they are attached to form a pyrrolidino, piperidino, or piperazino ring; and each $R^e$ is independently selected from the group consisting of hydrogen, $C_{1-6}$alkyl, $C_{2-6}$alkenyl, and $C_{2-6}$alkynyl, wherein each $C_{1-6}$alkyl, $C_{2-6}$alkenyl, and $C_{2-6}$alkynyl is optionally substituted with one or more groups independently selected from the group consisting of oxo, halo, amino, hydroxy, and $C_{1-6}$alkoxy; or two $R^e$ are taken together with the nitrogen to which they are attached to form a heterocyclyl that is optionally substituted with one or more groups independently selected from the group consisting of oxo, halo and $C_{1-3}$alkyl that is optionally substituted with one or more groups independently selected from the group consisting of oxo and halo;

provided that when $R^2$ is 6-methoxy-2-naphthyl, then $R^1$ is not 1-(cyclopropylmethyl)piperidin-3-yl, 1-(cyclobutyl)piperidin-3-yl, 1-(cyclopentyl)piperidin-3-yl, or 1-(tetrahydropyranyl)piperidin-3-yl; and provided that when $R^2$ is phenyl, naphthyl, 4-quinolyl, 5-quinolyl, 6-quinolyl, 7-quinolyl, 8-quinolyl, 2-methyl-6-quinolyl, 1,5-benzodioxepin-7-yl, benzo[b]thien-7-yl, 2,3-dihydro-1,4-benzodioxin-6-yl, 1H-1-(tert-butoxycarbonyl)-4-bromo-indol-2-yl, 1H-1-(tert-butoxycarbonyl)-4-cyano-indol-2-yl, 3,4-dihydroxyphenyl, 3-methoxy-4-hydroxyphenyl, 3,4-dimethoxyphenyl, 3-methoxycarbonyl-4-hydroxyphenyl, 4-hydroxyphenyl, or 2-hydroxyphenyl, then $R^1$ is not optionally substituted piperizine-2-yl.

Another aspect includes a composition, comprising a compound of formula (I), or a pharmaceutically acceptable salt thereof, and a pharmaceutically acceptable adjuvant, carrier, or vehicle.

Another aspect includes a method of treating a disease associated with KDM2b activity, comprising administering an therapeutically effective amount of a compound of formula (I), or a pharmaceutically acceptable salt thereof, to a patient in need thereof.

Another aspect includes the use of a compound of formula (I), or a pharmaceutically acceptable salt thereof, in therapy.

Another aspect includes the use of a compound of formula (I), or a pharmaceutically acceptable salt thereof, in treating a disease associated with KDM2b activity.

Another aspect includes the use of a compound of formula (I), or a pharmaceutically acceptable salt thereof, in the manufacture of a medicament for the treatment of a disease associated with KDM2b activity.

Another aspect includes a method of increasing the efficacy of a cancer treatment comprising a cancer therapy agent, comprising administering to a patient (a) an effective amount of a compound of formula (I), or a pharmaceutically acceptable salt thereof, and (b) an effective amount of the cancer therapy agent.

Another aspect includes a method of treating an individual with cancer who has an increased likelihood of developing resistance to a cancer therapy agent comprising administering to the individual (a) an effective amount of a compound of formula (I), or a pharmaceutically acceptable salt thereof, and (b) an effective amount of the cancer therapy agent.

Another aspect includes a method of treating cancer in a mammal in need thereof, comprising administering to the mammal, a compound of formula (I), or a pharmaceutically acceptable salt thereof.

Another aspect includes a method of inducing differentiation of a cancer stem/progenitor cell(s) in a mammal in need thereof, comprising administering to the mammal, an effective amount of a compound of formula (I), or a pharmaceutically acceptable salt thereof.

Another aspect includes a method of reducing activity of a cancer stem/progenitor cell(s) in a mammal in need thereof, comprising administering to the mammal, an effective amount of a compound of formula (I), or a pharmaceutically acceptable salt thereof.

Another aspect includes a method of depleting a cancer stem/progenitor cell in a mammal in need thereof, comprising administering to the mammal, an effective amount a compound of formula (I), or a pharmaceutically acceptable salt thereof.

Another aspect includes a method of decreasing cancer initiation in a mammal in need thereof, comprising administering to the mammal, an effective amount of a compound of formula (I), or a pharmaceutically acceptable salt thereof.

Another aspect includes a compound of formula (I), or a pharmaceutically acceptable salt thereof for the therapeutic or prophylactic treatment of cancer.

Another aspect includes a compound of formula (I), or a pharmaceutically acceptable salt thereof for inducing differentiation of a cancer stem/progenitor cell(s).

Another aspect includes a compound of formula (I), or a pharmaceutically acceptable salt thereof for reducing activity of a cancer stem/progenitor cell(s).

Another aspect includes a compound of formula (I), or a pharmaceutically acceptable salt thereof for depleting a cancer stem/progenitor cell.

Another aspect includes a compound of formula (I), or a pharmaceutically acceptable salt thereof for decreasing cancer initiation.

Another aspect includes the use of a compound of formula (I), or a pharmaceutically acceptable salt thereof to prepare a medicament for treating cancer in a mammal.

Another aspect includes the use of a compound of formula (I), or a pharmaceutically acceptable salt thereof to prepare a medicament for inducing differentiation of a cancer stem/progenitor cell(s) in a mammal.

Another aspect includes the use of a compound of formula (I), or a pharmaceutically acceptable salt thereof to prepare a medicament for reducing activity of a cancer stem/progenitor cell(s) in a mammal.

Another aspect includes the use of a compound of formula (I), or a pharmaceutically acceptable salt thereof to prepare a medicament for depleting a cancer stem/progenitor cell in a mammal.

Another aspect includes the use of a compound of formula (I), or a pharmaceutically acceptable salt thereof to prepare a medicament for decreasing cancer initiation in a mammal.

Another aspect includes a method of treating cancer in an individual in need thereof, comprising administering an effective amount of a KDM2 inhibitor to the individual.

Another aspect includes a method of inducing differentiation of a cancer stem/progenitor cell(s) in an individual in need thereof, comprising administering an effective amount of a KDM2 inhibitor to the individual.

Another aspect includes a method of reducing activity of a cancer stem/progenitor cell(s) in an individual in need thereof, comprising administering an effective amount of a KDM2 inhibitor to the individual.

Another aspect includes a method of depleting a cancer stem/progenitor cell population in an individual in need thereof, comprising administering an effective amount of a KDM2 inhibitor to the individual.

Another aspect includes a method of decreasing cancer initiation in an individual in need thereof, comprising administering an effective amount of a KDM2 inhibitor to the individual.

Another aspect includes a processes and synthetic intermediates that are useful for preparing a compound of formula (I), or a salt thereof.

Another aspect includes compounds for the study of histone demethylases, such as KDM2b, the study of intracellular signal transduction pathways mediated by such histone demethylases, and the comparative evaluation of modulators of these demethylases.

DETAILED DESCRIPTION

Definitions

Definitions of specific functional groups and chemical terms are described in more detail below. Chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5$^{th}$ Edition, John Wiley & Sons, Inc., New York, 2001; Larock, Comprehensive Organic Transformations, VCH Publishers, Inc., New York, 1989; Carruthers, Some Modern Methods of Organic Synthesis, 3$^{rd}$ Edition, Cambridge University Press, Cambridge, 1987; the entire contents of each of which are incorporated herein by reference.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are included.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are included. Such compounds are useful, for example, as analytical tools, as probes in biological assays, or as therapeutic agents.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The term "a compound as described herein" includes the compounds described in the Examples herein and salts and free-bases thereof, as well as compounds of formula (I) and salts thereof.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^{+}$ (as in N-substituted pyrrolidinyl)).

As used herein a "direct bond" or "covalent bond" refers to a single, double or triple bond. In certain embodiments, a "direct bond" or "covalent bond" refers to a single bond.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl) alkyl, (cycloalkenyl)alkyl or (cycloalkyl)alkenyl.

The term "unsaturated", as used herein, means that a moiety has one or more units of unsaturation.

The terms "cycloaliphatic", "carbocycle", "carbocyclyl", "carbocyclo", or "carbocyclic", used alone or as part of a larger moiety, refer to a saturated or partially unsaturated cyclic aliphatic monocyclic, bicyclic, or spior ring systems, as described herein, having from 3 to 10 members, wherein the aliphatic ring system is optionally substituted as described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. Also included within the scope of the term "cycloaliphatic", "carbocycle", "carbocyclyl", "carbocyclo", or "carbocyclic", as it is used herein, is a group in which an "cycloaliphatic", "carbocycle", "carbocyclyl", "carbocyclo", or "carbocyclic" is fused to one or more aryl, heterocyclyl, or heteroaryl rings, wherein the point of attachment is a carbon of the "cycloaliphatic", "carbocycle", "carbocyclyl", "carbocyclo", or "carbocyclic" ring.

The term "alkyl," as used herein, refers to a monovalent saturated, straight- or branched-chain hydrocarbon radical derived from an aliphatic moiety containing between one and six carbon atoms by removal of a single hydrogen atom. In some embodiments, alkyl contains 1-5 carbon atoms. In another embodiment, alkyl contains 1-4 carbon atoms. In still other embodiments, alkyl contains 1-3 carbon atoms. In yet another embodiment, alkyl contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. In certain embodiments, alkenyl contains 2-6 carbon atoms. In certain embodiments, alkenyl contains 2-5 carbon atoms. In some embodiments, alkenyl contains 2-4 carbon atoms. In another embodiment, alkenyl contains 2-3 carbon atoms. Alkenyl groups include, for example, ethenyl ("vinyl"), propenyl ("allyl"), butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. In certain embodiments, alkynyl contains 2-6 carbon atoms. In certain embodiments, alkynyl contains 2-5 carbon atoms. In some embodiments, alkynyl contains 2-4 carbon atoms. In another embodiment, alkynyl contains 2-3 carbon atoms. Representative alkynyl groups include, but are not limited to, ethynyl, 2-propynyl ("propargyl"), 1-propynyl, and the like.

The term "aryl" used alone or as part of a larger moiety as in "aralkyl", "aralkoxy", or "aryloxyalkyl", refers to monocyclic and bicyclic ring systems having a total of 6, 7, 8, 9, 10, 11, or 12 ring members, wherein at least one ring in the system is aromatic. The term "aryl" may be used interchangeably with the term "aryl ring". In certain embodiments, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic carbon ring is fused to one or more cycloaliphatic, heterocyclyl, or heteroaryl rings, wherein the point of attachment is a carbon of the aromatic carbon ring.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, wherein the point of attachment is a carbon of the heteroaromatic ring.

Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic.

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, 2-azabicyclo[2.2.1]heptanyl, octahydroindolyl, or tetrahydroquinolinyl, where the radical or point of attachment is any atom in the heterocyclyl ringsystem. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms but is not aromatic. The term "partially unsaturated" is intended to encompass rings having multiple sites of unsaturation, but is not intended to include aryl or heteroaryl moieties, as herein defined.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

As used herein, the term "inhibitor" refers to a compound that binds to and inhibits a KDM2b enzyme with measurable affinity and activity. In certain embodiments, an inhibitor has an $IC_{50}$ and/or binding constant of less about 50 µM, less than about 1 µM, less than about 500 nM, less than about 100 nM, or less than about 10 nM.

The terms "measurable affinity" and "measurably inhibit," as used herein, refer to a measurable reduction in activity of a KDM2b enzyme between: (i) a sample comprising a compound as described herein and such KDM2b enzyme, and (ii) an equivalent sample comprising such KDM2b enzyme, in the absence of said compound.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly organic non-toxic bases are isopropylamine, diethylamine, ethanolamine, tromethamine, dicyclohexylamine, choline, and caffeine.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "solvate" refers to an association or complex of one or more solvent molecules and a compound or pharmaceutically acceptable salt thereof as described herein. Examples of solvents include water, isopropanol, ethanol, methanol, DMSO, ethyl acetate, acetic acid and ethanolamine. The term "hydrate" refers to the complex where the solvent molecule is water.

"Therapeutically effective amount" refers to an amount of a compound or pharmaceutically acceptable salt thereof as described herein that (i) treats the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. For cancer therapy, efficacy can, for example, be measured by assessing the time to disease progression (TTP) and/or determining the response rate (RR). In the case of immunological disorders, the therapeutic effective amount is an amount sufficient to decrease or alleviate an allergic disorder, the symptoms of an autoimmune and/or inflammatory disease, or the symptoms of an acute inflammatory reaction (e.g. asthma). In some embodiments, a therapeutically effective amount is an amount of a chemical entity described herein sufficient to significantly decrease the activity or number of drug tolerant or drug tolerant persisting cancer cells.

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include one or more of preventing occurrence or recurrence of disease, alleviation of symptoms, diminishment of any direct or indirect pathological consequences of the disease, stabilized (i.e., not worsening) state of disease, preventing metastasis, decreasing the rate of disease progression, amelioration or palliation of the disease state, prolonging survival as compared to expected survival if not receiving treatment and remission or improved prognosis. In certain embodiments, a compound as described herein is used to delay development of a disease or disorder or to slow the progression of a disease or disorder. Those individuals in need of treatment include those already with the condition or disorder as well as those prone to have the condition or disorder, (for example, through a genetic mutation or abberent expression of a gene or protein) or those in which the condition or disorder is to be prevented.

Exemplary Values

In one embodiment the compound is a compound of formula (Ia):

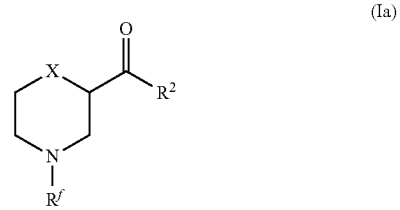

(Ia)

or a salt thereof, wherein:
X is $CR^gR^h$ or $NR^k$;
each $R^f$ is independently selected from the group consisting of H, $C_{1-6}$alkyl, $C_{2-6}$alkenyl, $C_{2-6}$alkynyl, $C_{3-8}$carbocycle, 3-8 membered heterocycle, aryl, heteroaryl, halo, —NO₂, —N(R$^b$)₂, —CN, —C(O)—N(R$^b$)₂, —S(O)—N(R$^b$)₂, —S(O)₂—N(R$^b$)₂, —O—R$^b$, —S—R$^b$, —O—C(O)—R$^b$, —C(O)—R$^b$, —C(O)—OR$^b$, —S(O)—R$^b$, —S(O)₂—R$^b$, —N(R$^b$)—C(O)—R$^b$, —N(R$^b$)—S(O)—R$^b$, —N(R$^b$)—C(O)—N(R$^b$)₂, and —N(R$^b$)—S(O)₂—R$^b$; wherein each C$_{1-6}$alkyl, C$_{2-6}$alkenyl, C$_{2-6}$alkynyl, C$_{3-8}$carbocycle, 3-8 membered heterocycle, aryl, and heteroaryl is optionally substituted with one or more groups independently selected from the group consisting of halo, —NO₂—N(R$^b$)₂, —CN, —C(O)—N(R$^b$)₂, —S(O)—N(R$^b$)₂, —S(O)₂—N(R$^b$)₂, —O—R$^b$, —S—R$^b$, —O—C(O)—R$^b$, —C(O)—R$^b$, —C(O)—OR$^b$, —S(O)—R$^b$, —S(O)₂—R$^b$, —N(R$^b$)—C(O)—R$^b$, —N(R$^b$)—S(O)—R$^b$, —N(R$^b$)—C(O)—N(R$^b$)₂, —N(R$^b$)—S(O)₂—R$^b$, and C$_{1-6}$alkyl that is optionally substituted with one or more groups independently selected from halo;

each R$^g$ is independently selected from the group consisting of H, C$_{1-6}$alkyl, C$_{2-6}$alkenyl, C$_{2-6}$alkynyl, C$_{3-8}$carbocycle, 3-8 membered heterocycle, aryl, heteroaryl, halo, —NO₂, —N(R$^b$)₂, —CN, —C(O)—N(R$^b$)₂, —S(O)—N(R$^b$)₂, —S(O)₂—N(R$^b$)₂, —O—R$^b$, —S—R$^b$, —O—C(O)—R$^b$, —C(O)—R$^b$, —C(O)—OR$^b$, —S(O)—R$^b$, —S(O)₂—R$^b$, —N(R$^b$)—C(O)—R$^b$, —N(R$^b$)—S(O)—R$^b$, —N(R$^b$)—C(O)—N(R$^b$)₂, and —N(R$^b$)—S(O)₂—R$^b$; wherein each C$_{1-6}$alkyl, C$_{2-6}$alkenyl, C$_{2-6}$alkynyl, C$_{3-8}$carbocycle, 3-8 membered heterocycle, aryl, and heteroaryl is optionally substituted with one or more groups independently selected from the group consisting of halo, —NO₂—N(R$^b$)₂, —CN, —C(O)—N(R$^b$)₂, —S(O)—N(R$^b$)₂, —S(O)₂—N(R$^b$)₂, —O—R$^b$, —S—R$^b$, —O—C(O)—R$^b$, —C(O)—R$^b$, —C(O)—OR$^b$, —S(O)—R$^b$, —S(O)₂—R$^b$, —N(R$^b$)—C(O)—R$^b$, —N(R$^b$)—S(O)—R$^b$, —N(R$^b$)—C(O)—N(R$^b$)₂, —N(R$^b$)—S(O)₂—R$^b$, and C$_{1-6}$alkyl that is optionally substituted with one or more groups independently selected from halo;

each R$^h$ is independently selected from the group consisting of H, C$_{1-6}$alkyl, C$_{2-6}$alkenyl, C$_{2-6}$alkynyl, C$_{3-8}$carbocycle, 3-8 membered heterocycle, aryl, heteroaryl, and halo, wherein each C$_{1-6}$alkyl, C$_{2-6}$alkenyl, C$_{2-6}$alkynyl, C$_{3-8}$carbocycle, 3-8 membered heterocycle, aryl, and heteroaryl is optionally substituted with one or more groups independently selected from the group consisting of halo, —NO₂—N(R$^b$)₂, —CN, —C(O)—N(R$^b$)₂, —S(O)—N(R$^b$)₂, —S(O)₂—N(R$^b$)₂, —O—R$^b$, —S—R$^b$, —O—C(O)—R$^b$, —C(O)—R$^b$, —C(O)—OR$^b$, —S(O)—R$^b$, —S(O)₂—R$^b$, —N(R$^b$)—C(O)—R$^b$, —N(R$^b$)—S(O)—R$^b$, —N(R$^b$)—C(O)—N(R$^b$)₂, —N(R$^b$)—S(O)₂—R$^b$, and C$_{1-6}$alkyl that is optionally substituted with one or more groups independently selected from halo; and each R$^k$ is independently selected from the group consisting of H, C$_{1-6}$alkyl, C$_{2-6}$alkenyl, C$_{2-6}$alkynyl, C$_{3-8}$carbocycle, 3-8 membered heterocycle, aryl, and heteroaryl, wherein each C$_{1-6}$alkyl, C$_{2-6}$alkenyl, C$_{2-6}$alkynyl, C$_{3-8}$carbocycle, 3-8 membered heterocycle, aryl, and heteroaryl is optionally substituted with one or more groups independently selected from the group consisting of halo, —NO₂—N(R$^b$)₂, —CN, —C(O)—N(R$^b$)₂, —S(O)—N(R$^b$)₂, —S(O)₂—N(R$^b$)₂, —O—R$^b$, —S—R$^b$, —O—C(O)—R$^b$, —C(O)—R$^b$, —C(O)—OR$^b$, —S(O)—R$^b$, —S(O)₂—R$^b$, —N(R$^b$)—C(O)—R$^b$, —N(R$^b$)—S(O)—R$^b$, —N(R$^b$)—C(O)—N(R$^b$)₂, —N(R$^b$)—S(O)₂—R$^b$, and C$_{1-6}$alkyl that is optionally substituted with one or more groups independently selected from halo.

In one embodiment the compound is a compound of formula (Ib):

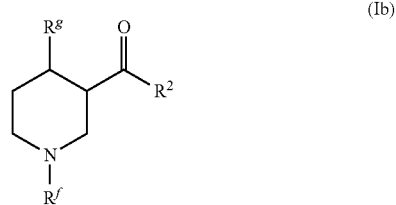

or a salt thereof.

In one embodiment the compound is a compound of formula (Ic):

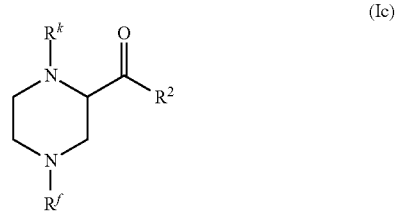

or a salt thereof.

In one embodiment when R² is 2-naphthyl or 6-methoxy-2-naphthyl, then R¹ is not optionally substituted piperidin-3-yl.

In one embodiment R² is a ring selected from the group consisting of naphthyl, tetralinyl, phenyl, benzisoxazolyl, benzo[7]annulenyl, 1,4-benzodioxinyl, benzimidazolyl-2-one, indolyl, indazolyl, thiophenyl, pyridyl, quinolyl, tetrahydroquinolyl, isoquinolyl, tetrahydroisoquinolyl, and pyrazolyl; which ring is optionally substituted with one or more groups independently selected from the group consisting of C$_{1-6}$alkyl, C$_{2-6}$alkenyl, C$_{2-6}$alkynyl, carbocycle, heterocycle, aryl, heteroaryl, halo, —NO₂, —N(R$^d$)₂, —CN, —C(O)—N(R$^d$)₂, —S(O)—N(R$^d$)₂, —S(O)₂—N(R$^d$)₂, —O—R$^d$, —S—R$^d$, —O—C(O)—R$^d$, —C(O)—R$^d$, —C(O)—OR$^d$, —S(O)—R$^d$, —S(O)₂—R$^d$, —N(R$^d$)—C(O)—R$^d$, —N(R$^d$)—S(O)—R$^d$, —N(R$^d$)—C(O)—N(R$^d$)₂, and —N(R$^d$)—S(O)₂—R$^d$; wherein each C$_{1-6}$alkyl, C$_{2-6}$alkenyl, C$_{2-6}$alkynyl, carbocycle, heterocycle, aryl, and heteroaryl is optionally substituted with one or more groups independently selected from the group consisting of halo, —NO₂—N(R$^d$)₂, —CN, —C(O)—N(R$^d$)₂, —S(O)—N(R$^d$)₂, —S(O)₂—N(R$^d$)₂, —O—R$^d$, —S—R$^d$, —O—C(O)—R$^d$, —C(O)—R$^d$, —C(O)—OR$^d$, —S(O)—R$^d$, —S(O)₂—R$^d$, —N(R$^d$)—C(O)—R$^d$, —N(R$^d$)—S(O)—R$^d$, —N(R$^d$)—C(O)—N(R$^d$)₂, —N(R$^d$)—S(O)₂—R$^d$, and C$_{1-6}$alkyl that is optionally substituted with one or more groups independently selected from halo.

In one embodiment R¹ is selected from the group consisting of:

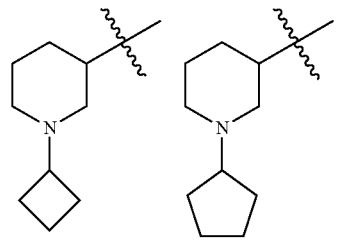

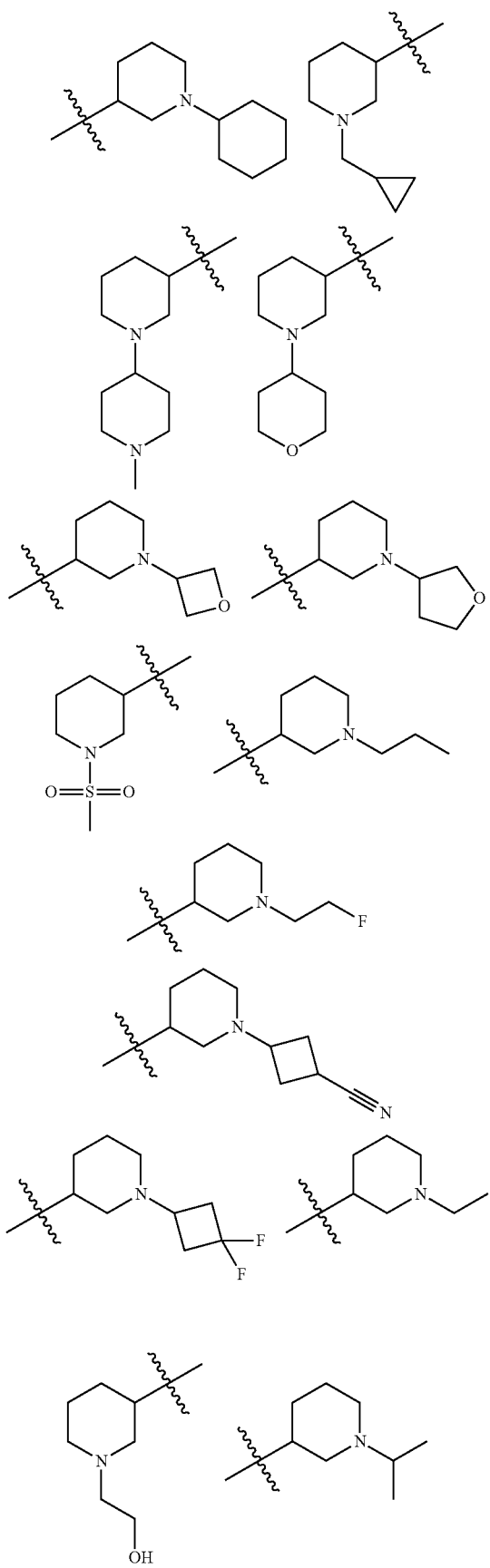
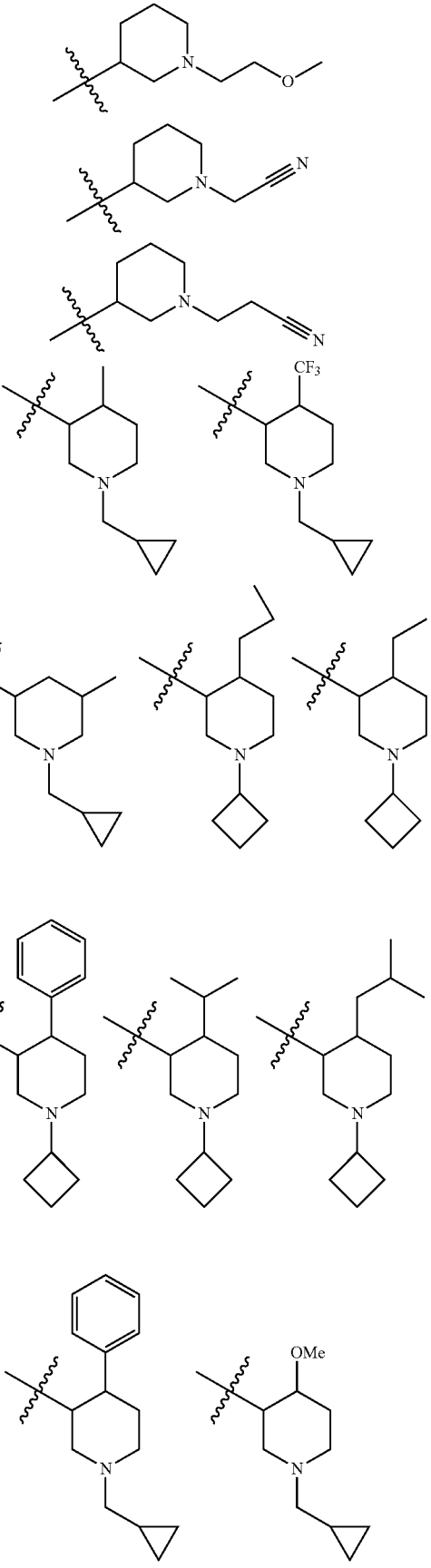

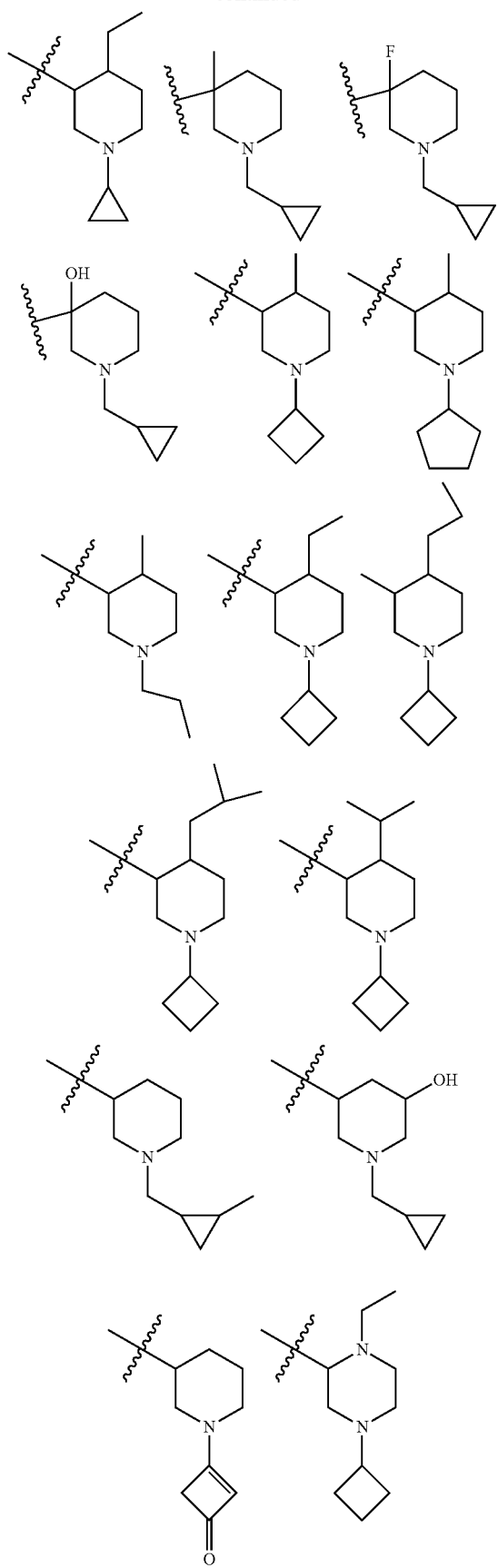
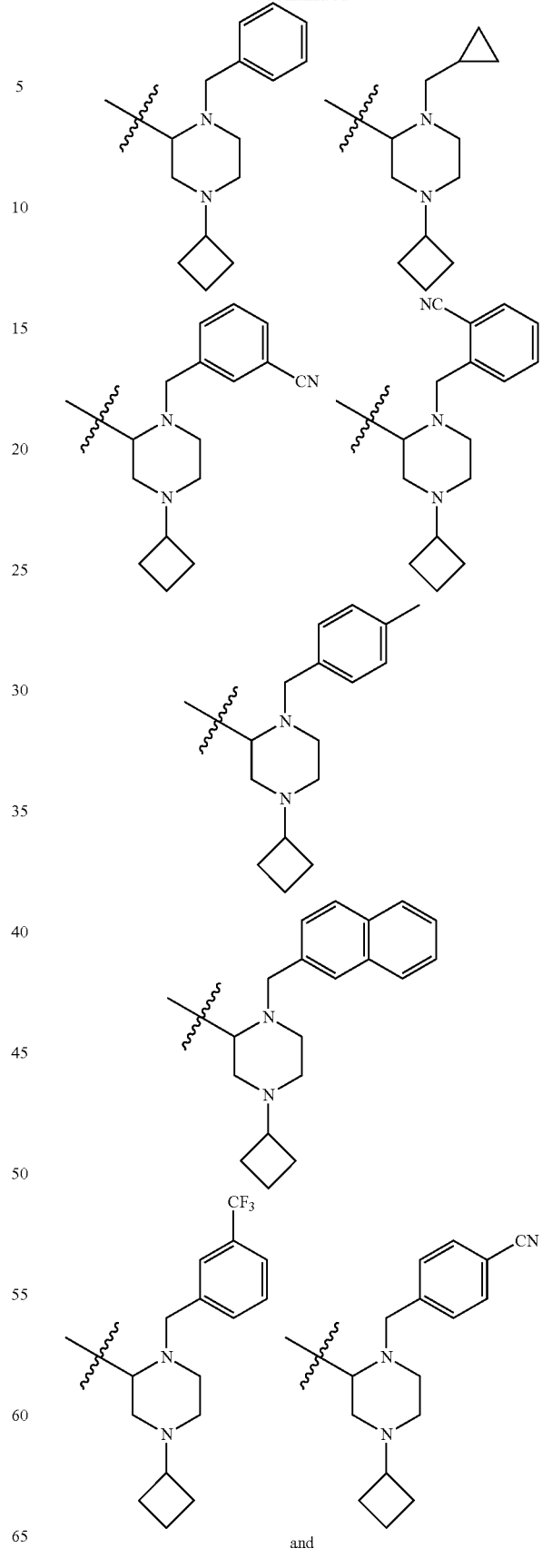

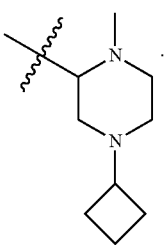

In one embodiment R² is a ring selected from the group consisting of:

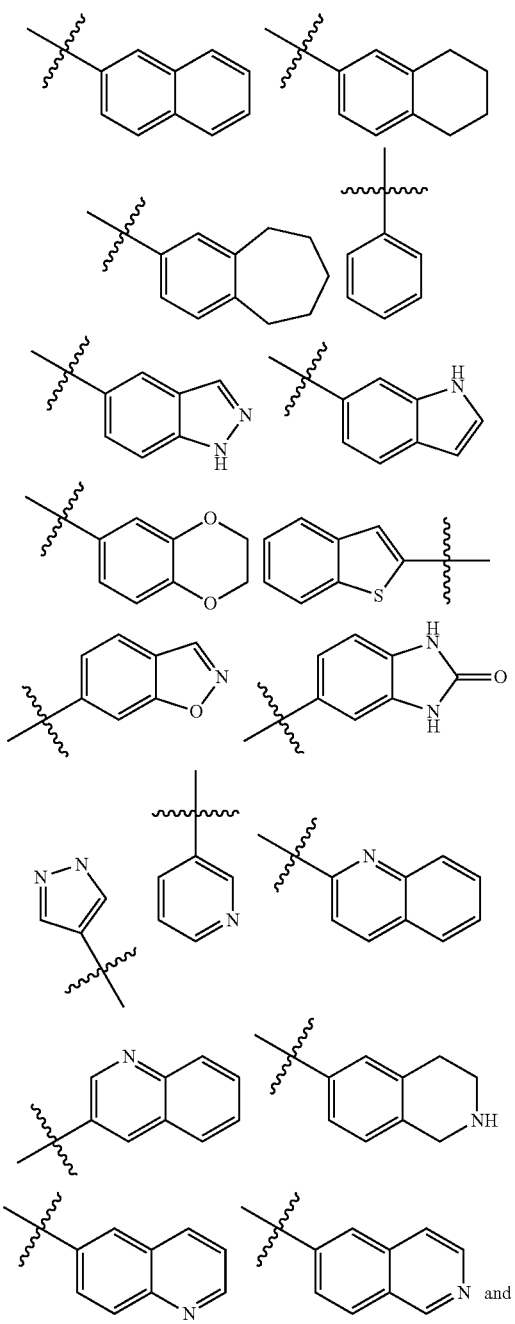

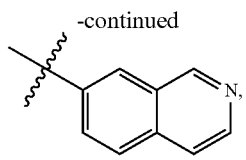

which ring is optionally substituted with one or more groups independently selected from the group consisting of $C_{1-6}$alkyl, $C_{2-6}$alkenyl, $C_{2-6}$alkynyl, carbocycle, heterocycle, aryl, heteroaryl, halo, —NO₂, —N(R$^d$)₂, —CN, —C(O)—N(R$^d$)₂, —S(O)—N(R$^d$)₂, —S(O)₂—N(R$^d$)₂, —O—R$^d$, —S—R$^d$, —O—C(O)—R$^d$, —C(O)—R$^d$, —C(O)—OR$^d$, —S(O)—R$^d$, —S(O)₂—R$^d$, —N(R$^d$)—C(O)—R$^d$, —N(R$^d$)—S(O)—R$^d$, —N(R$^d$)—C(O)—N(R$^d$)₂, and —N(R$^d$)—S(O)₂—R$^d$; wherein each $C_{1-6}$alkyl, $C_{2-6}$alkenyl, $C_{2-6}$alkynyl, carbocycle, heterocycle, aryl, and heteroaryl is optionally substituted with one or more groups independently selected from the group consisting of halo, —NO₂—N(R$^d$)₂, —CN, —C(O)—N(R$^d$)₂, —S(O)—N(R$^d$)₂, —S(O)₂—N(R$^d$)₂, —O—R$^d$, —S—R$^d$, —O—C(O)—R$^d$, —C(O)—R$^d$, —C(O)—OR$^d$, —S(O)—R$^d$, —S(O)₂—R$^d$, —N(R$^d$)—C(O)—R$^d$, —N(R$^d$)—S(O)—R$^d$, —N(R$^d$)—C(O)—N(R$^d$)₂, —N(R$^d$)—S(O)₂—R$^d$, and $C_{1-6}$alkyl that is optionally substituted with one or more groups independently selected from halo.

In one embodiment R² is a naphthyl ring that is optionally substituted with one or more groups independently selected from the group consisting of $C_{1-6}$alkyl, $C_{2-6}$alkenyl, $C_{2-6}$alkynyl, carbocycle, heterocycle, aryl, heteroaryl, halo, —NO₂, —N(R$^d$)₂, —CN, —C(O)—N(R$^d$)₂, —S(O)—N(R$^d$)₂, —S(O)₂—N(R$^d$)₂, —O—R$^d$, —S—R$^d$, —O—C(O)—R$^d$, —C(O)—R$^d$, —C(O)—OR$^d$, —S(O)—R$^d$, —S(O)₂—R$^d$, —N(R$^d$)—C(O)—R$^d$, —N(R$^d$)—S(O)—R$^d$, —N(R$^d$)—C(O)—N(R$^d$)₂, and —N(R$^d$)—S(O)₂—R$^d$; wherein each $C_{1-6}$alkyl, $C_{2-6}$alkenyl, $C_{2-6}$alkynyl, carbocycle, heterocycle, aryl, and heteroaryl is optionally substituted with one or more groups independently selected from the group consisting of halo, —NO₂—N(R$^d$)₂, —CN, —C(O)—N(R$^d$)₂, —S(O)—N(R$^d$)₂, —S(O)₂—N(R$^d$)₂, —O—R$^d$, —S—R$^d$, —O—C(O)—R$^d$, —C(O)—R$^d$, —C(O)—OR$^d$, —S(O)—R$^d$, —S(O)₂—R$^d$, —N(R$^d$)—C(O)—R$^d$, —N(R$^d$)—S(O)—R$^d$, —N(R$^d$)—C(O)—N(R$^d$)₂, —N(R$^d$)—S(O)₂—R$^d$, and $C_{1-6}$alkyl that is optionally substituted with one or more groups independently selected from halo.

In one embodiment R² is a naphthyl ring that is optionally substituted with one or more groups independently selected from the group consisting of $C_{1-6}$alkyl, carbocycle, aryl, halo, —NO₂, —N(R$^d$)₂, —CN, —C(O)—N(R$^d$)₂, —S(O)—N(R$^d$)₂, —S(O)₂—N(R$^d$)₂, —O—R$^d$, —S—R$^d$, —O—C(O)—R$^d$, —C(O)—R$^d$, —C(O)—OR$^d$, —S(O)—R$^d$, —S(O)₂—R$^d$, —N(R$^d$)—C(O)—R$^d$, —N(R$^d$)—S(O)—R$^d$, —N(R$^d$)—C(O)—N(R$^d$)₂, and —N(R$^d$)—S(O)₂—R$^d$; wherein each $C_{1-6}$alkyl, $C_{2-6}$alkenyl, $C_{2-6}$alkynyl, carbocycle, heterocycle, aryl, and heteroaryl is optionally substituted with one or more groups independently selected from the group consisting of halo, —NO₂—N(R$^d$)₂, —CN, —C(O)—N(R$^d$)₂, —S(O)—N(R$^d$)₂, —S(O)₂—N(R$^d$)₂, —O—R$^d$, —S—R$^d$, —O—C(O)—R$^d$, —C(O)—R$^d$, —C(O)—OR$^d$, —S(O)—R$^d$, —S(O)₂—R$^d$, —N(R$^d$)—C(O)—R$^d$, —N(R$^d$)—S(O)—R$^d$, —N(R$^d$)—C(O)—N(R$^d$)₂, —N(R$^d$)—S(O)₂—R$^d$, and $C_{1-6}$alkyl that is optionally substituted with one or more groups independently selected from halo.

In one embodiment R² is a phenyl ring that is optionally substituted with one or more groups independently selected from the group consisting of C₁₋₆alkyl, C₂₋₆alkenyl, C₂₋₆alkynyl, carbocycle, heterocycle, aryl, heteroaryl, halo, —NO₂, —N(Rᵈ)₂, —CN, —C(O)—N(Rᵈ)₂, —S(O)—N(Rᵈ)₂, —S(O)₂—N(Rᵈ)₂, —O—Rᵈ, —S—Rᵈ, —O—C(O)—Rᵈ, —C(O)—Rᵈ, —C(O)—ORᵈ, —S(O)—Rᵈ, —S(O)₂—Rᵈ, —N(Rᵈ)—C(O)—Rᵈ, —N(Rᵈ)—S(O)—Rᵈ, —N(Rᵈ)—C(O)—N(Rᵈ)₂, and —N(Rᵈ)—S(O)₂—Rᵈ; wherein each C₁₋₆alkyl, C₂₋₆alkenyl, C₂₋₆alkynyl, carbocycle, heterocycle, aryl, and heteroaryl is optionally substituted with one or more groups independently selected from the group consisting of halo, —NO₂—N(Rᵈ)₂, —CN, —C(O)—N(Rᵈ)₂, —S(O)—N(Rᵈ)₂, —S(O)₂—N(Rᵈ)₂, —S—Rᵈ, —O—C(O)—Rᵈ, —C(O)—Rᵈ, —C(O)—ORᵈ, —S(O)—Rᵈ, —S(O)₂—Rᵈ, —N(Rᵈ)—C(O)—Rᵈ, —N(Rᵈ)—S(O)—Rᵈ, —N(Rᵈ)—C(O)—N(Rᵈ)₂, —N(Rᵈ)—S(O)₂—Rᵈ, and C₁₋₆alkyl that is optionally substituted with one or more groups independently selected from halo.

In one embodiment R² is a phenyl ring that is optionally substituted with one or more groups independently selected from the group consisting of C₁₋₆alkyl, carbocycle, aryl, halo, —NO₂, —N(Rᵈ)₂, —CN, —C(O)—N(Rᵈ)₂, —S(O)—N(Rᵈ)₂, —S(O)₂—N(Rᵈ)₂, —O—Rᵈ, —S—Rᵈ, —O—C(O)—Rᵈ, —C(O)—Rᵈ, —C(O)—ORᵈ, —S(O)—Rᵈ, —S(O)₂—Rᵈ, —N(Rᵈ)—C(O)—Rᵈ, —N(Rᵈ)—S(O)—Rᵈ, —N(Rᵈ)—C(O)—N(Rᵈ)₂, and —N(Rᵈ)—S(O)₂—Rᵈ; wherein each C₁₋₆alkyl, C₂₋₆alkenyl, C₂₋₆alkynyl, carbocycle, heterocycle, aryl, and heteroaryl is optionally substituted with one or more groups independently selected from the group consisting of halo, —NO₂—N(Rᵈ)₂, —CN, —C(O)—N(Rᵈ)₂, —S(O)—N(Rᵈ)₂, —S(O)₂—N(Rᵈ)₂, —O—Rᵈ, —S—Rᵈ, —O—C(O)—Rᵈ, —C(O)—Rᵈ, —C(O)—ORᵈ, —S(O)—Rᵈ, —S(O)₂—Rᵈ, —N(Rᵈ)—C(O)—Rᵈ, —N(Rᵈ)—S(O)—Rᵈ, —N(Rᵈ)—C(O)—N(Rᵈ)₂, —N(Rᵈ)—S(O)₂—Rᵈ, and C₁₋₆alkyl that is optionally substituted with one or more groups independently selected from halo.

In one embodiment R² is a quinolyl or isoquinolyl ring, which ring is optionally substituted with one or more groups independently selected from the group consisting of C₁₋₆alkyl, C₂₋₆alkenyl, C₂₋₆alkynyl, carbocycle, heterocycle, aryl, heteroaryl, halo, —NO₂, —N(Rᵈ)₂, —CN, —C(O)—N(Rᵈ)₂, —S(O)—N(Rᵈ)₂, —S(O)₂—N(Rᵈ)₂, —O—Rᵈ, —S—Rᵈ, —O—C(O)—Rᵈ, —C(O)—Rᵈ, —C(O)—ORᵈ, —S(O)—Rᵈ, —S(O)₂—Rᵈ, —N(Rᵈ)—C(O)—Rᵈ, —N(Rᵈ)—S(O)—Rᵈ, —N(Rᵈ)—C(O)—N(Rᵈ)₂, and —N(Rᵈ)—S(O)₂—Rᵈ; wherein each C₁₋₆alkyl, C₂₋₆alkenyl, C₂₋₆alkynyl, carbocycle, heterocycle, aryl, and heteroaryl is optionally substituted with one or more groups independently selected from the group consisting of halo, —NO₂—N(Rᵈ)₂, —CN, —C(O)—N(Rᵈ)₂, —S(O)—N(Rᵈ)₂, —S(O)₂—N(Rᵈ)₂, —O—Rᵈ, —S—Rᵈ, —O—C(O)—Rᵈ, —C(O)—Rᵈ, —C(O)—ORᵈ, —S(O)—Rᵈ, —S(O)₂—Rᵈ, —N(Rᵈ)—C(O)—Rᵈ, —N(Rᵈ)—S(O)—Rᵈ, —N(Rᵈ)—C(O)—N(Rᵈ)₂, —N(Rᵈ)—S(O)₂—Rᵈ, and C₁₋₆alkyl that is optionally substituted with one or more groups independently selected from halo.

In one embodiment R² is a quinolyl or isoquinolyl ring, which ring is optionally substituted with one or more groups independently selected from the group consisting of C₁₋₆alkyl, carbocycle, halo, —NO₂, —N(Rᵈ)₂, —CN, —C(O)—N(Rᵈ)₂, —S(O)—N(Rᵈ)₂, —S(O)₂—N(Rᵈ)₂, —O—Rᵈ, —S—Rᵈ, —O—C(O)—Rᵈ, —C(O)—Rᵈ, —C(O)—ORᵈ, —S(O)—Rᵈ, —S(O)₂—Rᵈ, —N(Rᵈ)—C(O)—Rᵈ, —N(Rᵈ)—S(O)—Rᵈ, —N(Rᵈ)—C(O)—N(Rᵈ)₂, and —N(Rᵈ)—S(O)₂—Rᵈ; wherein each C₁₋₆alkyl, C₂₋₆alkenyl, C₂₋₆alkynyl, carbocycle, heterocycle, aryl, and heteroaryl is optionally substituted with one or more groups independently selected from the group consisting of halo, —NO₂—N(Rᵈ)₂, —CN, —C(O)—N(Rᵈ)₂, —S(O)—N(Rᵈ)₂, —S(O)₂—N(Rᵈ)₂, —O—Rᵈ, —S—Rᵈ, —O—C(O)—Rᵈ, —C(O)—Rᵈ, —C(O)—ORᵈ, —S(O)—Rᵈ, —S(O)₂—Rᵈ, —N(Rᵈ)—C(O)—Rᵈ, —N(Rᵈ)—S(O)—Rᵈ, —N(Rᵈ)—C(O)—N(Rᵈ)₂, —N(Rᵈ)—S(O)₂—Rᵈ, and C₁₋₆alkyl that is optionally substituted with one or more groups independently selected from halo.

In one embodiment R² is selected from the group consisting of:

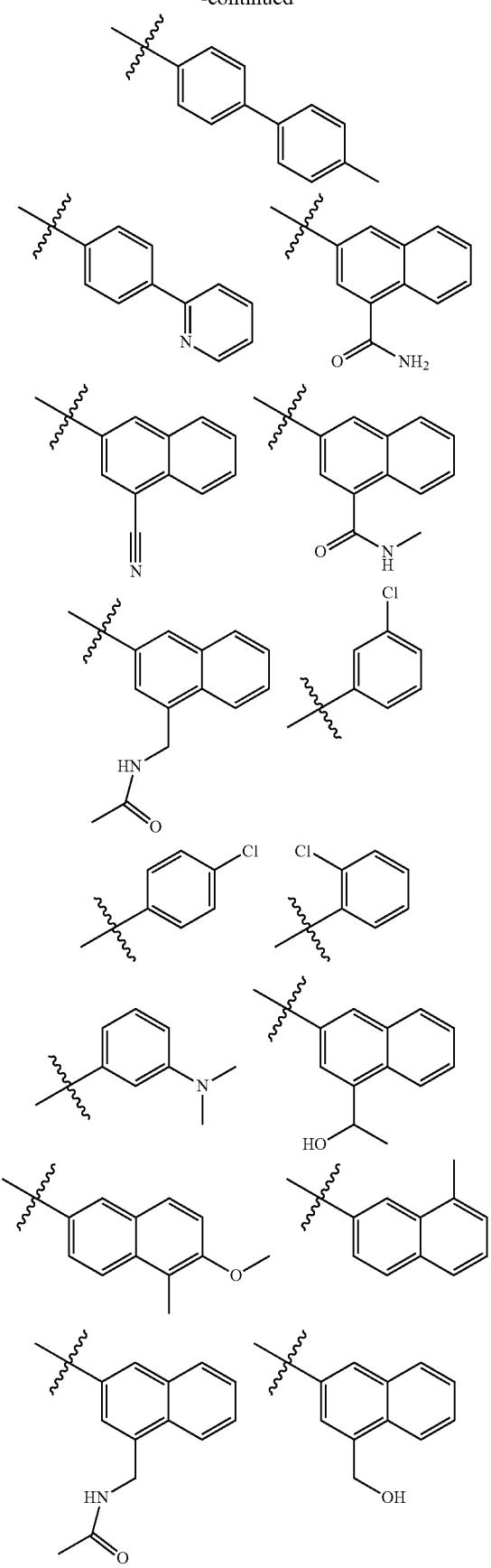
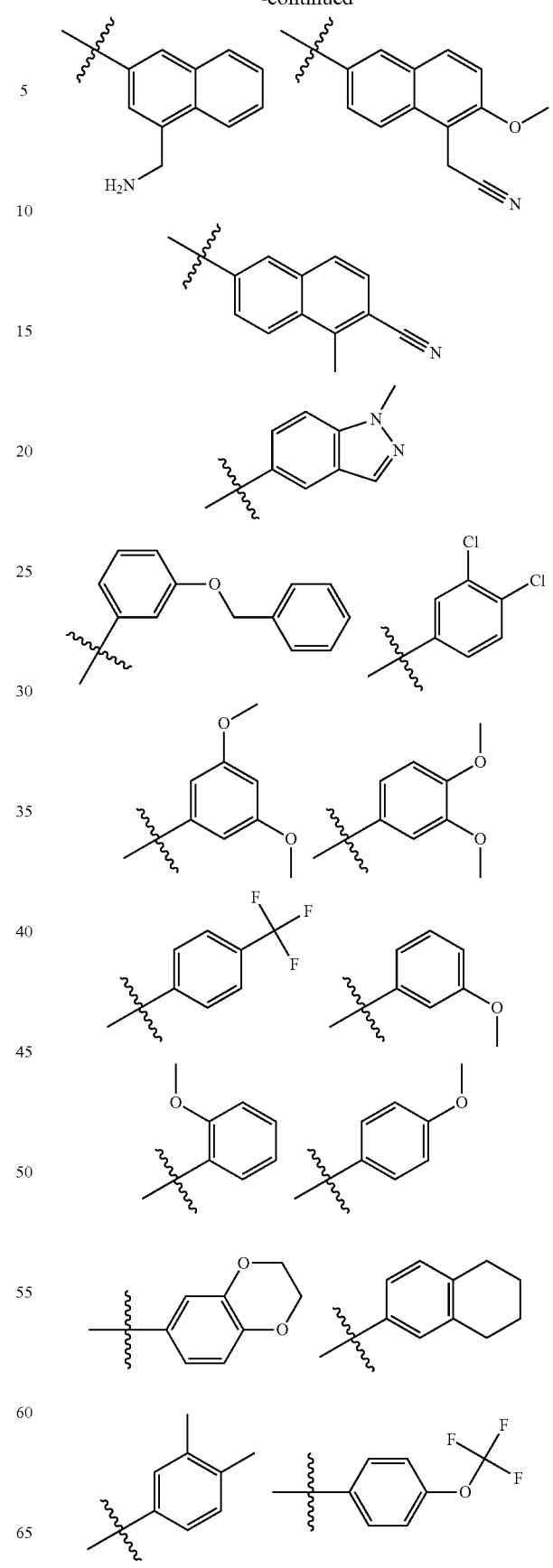

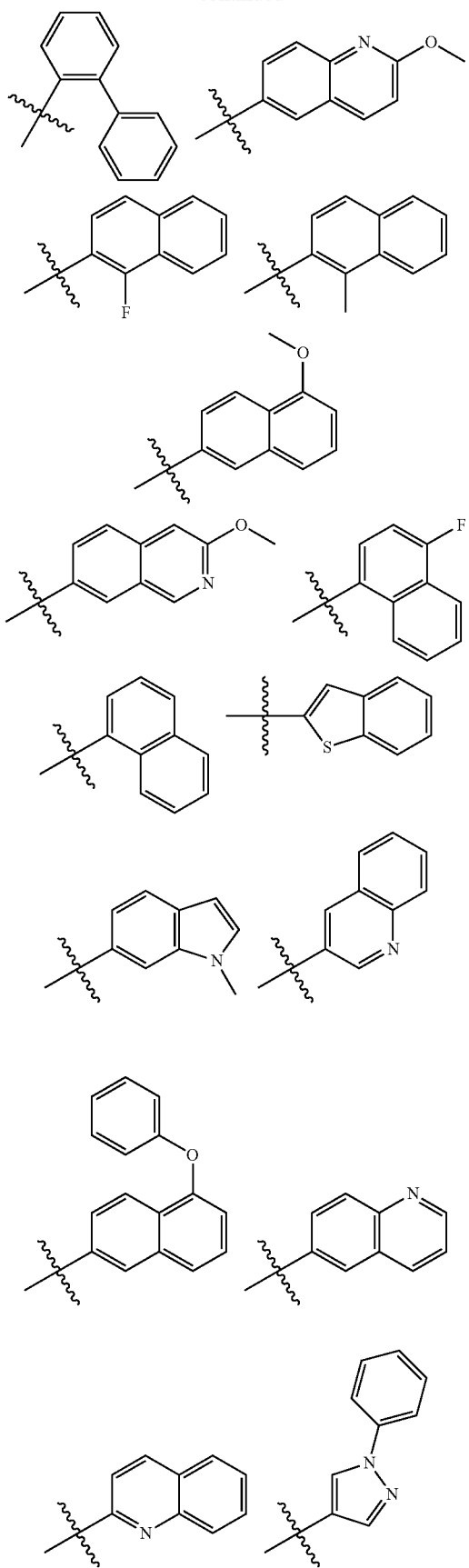
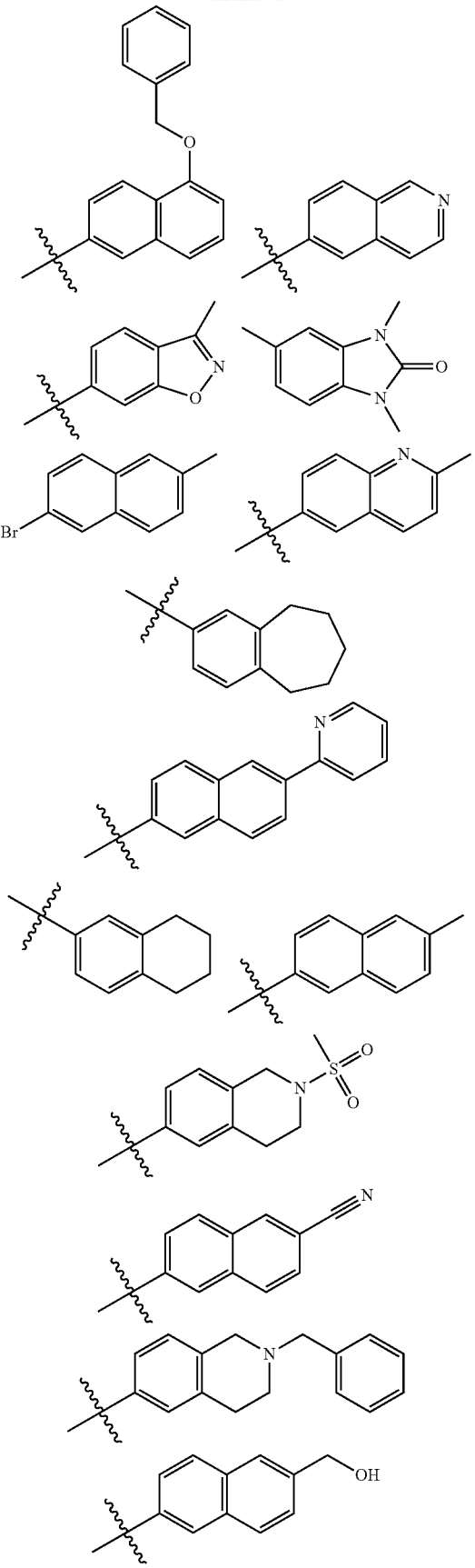

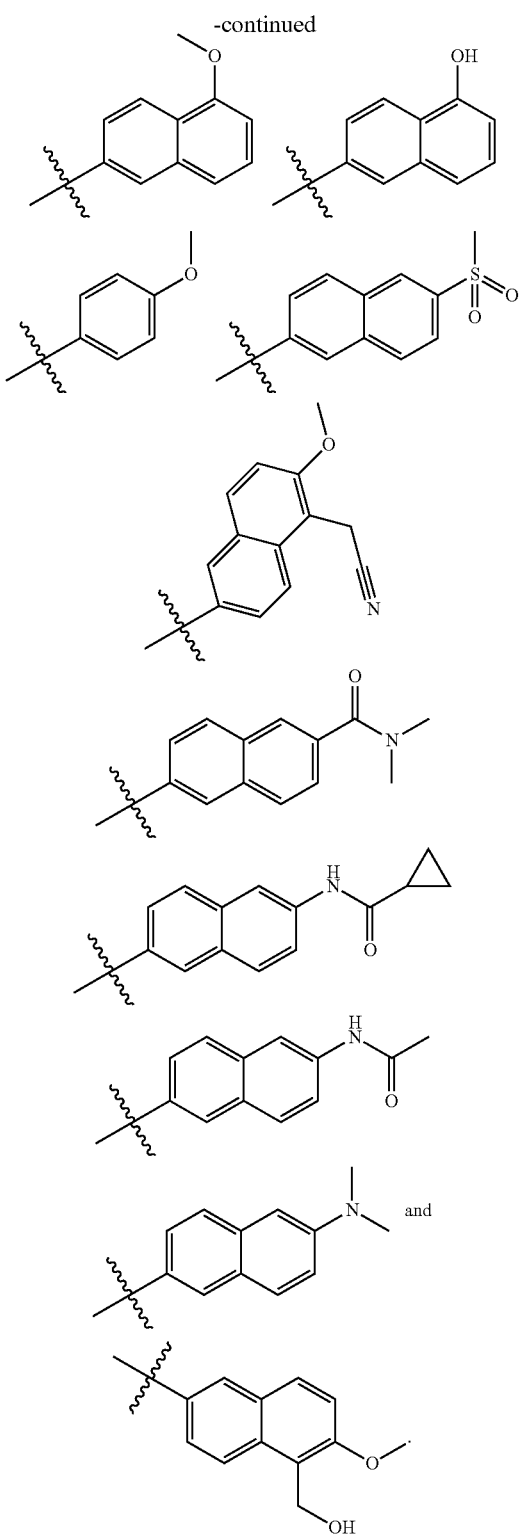

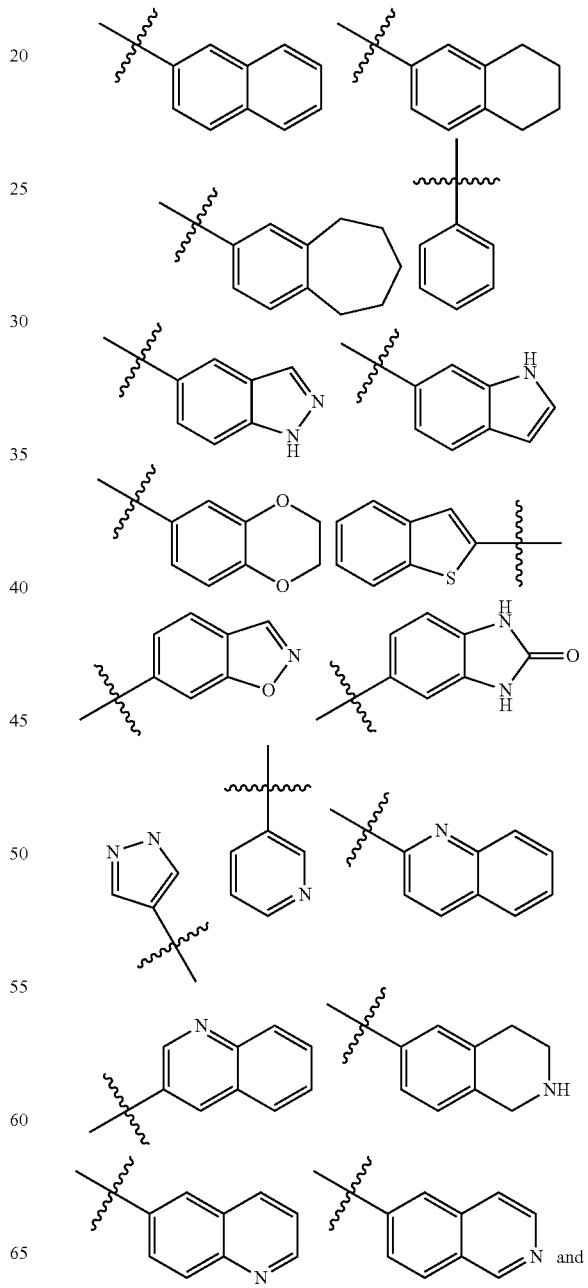

(O)—R$^b$, —C(O)—R$^b$, —C(O)—OR$^b$, —S(O)—R$^b$, —S(O)$_2$—R$^b$, —N(R$^b$)—C(O)—R$^b$, —N(R$^b$)—S(O)—R$^b$, —N(R$^b$)—C(O)—N(R$^b$)$_2$, and —N(R$^b$)—S(O)$_2$—R$^b$; wherein each C$_{1-6}$alkyl, C$_{2-6}$alkenyl, C$_{2-6}$alkynyl, C$_{3-8}$carbocycle, 3-8 membered heterocycle, aryl, and heteroaryl is optionally substituted with one or more groups independently selected from the group consisting of halo, —NO$_2$, —N(R$^d$)$_2$, —CN, —C(O)—N(R$^b$)$_2$, —S(O)—N(R$^b$)$_2$, —S(O)$_2$—N(R$^b$)$_2$, —O—R$^b$, —S—R$^b$, —O—C(O)—R$^b$, —C(O)—R$^b$, —C(O)—OR$^b$, —S(O)—R$^b$, —S(O)$_2$—R$^b$, —N(R$^b$)—C(O)—R$^b$, —N(R$^b$)—S(O)—R$^b$, —N(R$^b$)—C(O)—N(R$^b$)$_2$, —N(R$^b$)—S(O)$_2$—R$^b$, and C$_{1-6}$alkyl that is optionally substituted with one or more groups independently selected from halo; and R$^2$ is a ring selected from the group consisting of:

In one embodiment: R$^1$ is a carbon-linked piperidine ring that is substituted on the piperidine ring nitrogen with a group R$^x$ and that is optionally further substituted with one or more groups independently selected from the group consisting of C$_{1-6}$alkyl, C$_{2-6}$alkenyl, C$_{2-6}$alkynyl, C$_{3-8}$carbocycle, 3-8 membered heterocycle, aryl, heteroaryl, halo, —NO$_2$, —N(R$^b$)$_2$, —CN, —C(O)—N(R$^b$)$_2$, —S(O)—N(R$^b$)$_2$, —S(O)$_2$—N(R$^b$)$_2$, —O—R$^b$, —S—R$^b$, —O—C

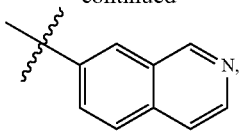

which ring is optionally substituted with one or more groups independently selected from the group consisting of $C_{1-6}$alkyl, $C_{2-6}$alkenyl, $C_{2-6}$alkynyl, carbocycle, heterocycle, aryl, heteroaryl, halo, —$NO_2$, —$N(R^d)_2$, —CN, —C(O)—$N(R^d)_2$, —S(O)—$N(R^d)_2$, —$S(O)_2$—$N(R^d)_2$, —O—$R^d$, —S—$R^d$, —O—C(O)—$R^d$, —C(O)—$R^d$, —C(O)—$OR^d$, —S(O)—$R^d$, —$S(O)_2$—$R^d$, —$N(R^d)$—C(O)—$R^d$, —$N(R^d)$—S(O)—$R^d$, —$N(R^d)$—C(O)—$N(R^d)_2$, and —$N(R^d)$—$S(O)_2$—$R^d$; wherein each $C_{1-6}$alkyl, $C_{2-6}$alkenyl, $C_{2-6}$alkynyl, carbocycle, heterocycle, aryl, and heteroaryl is optionally substituted with one or more groups independently selected from the group consisting of halo, —$NO_2$—$N(R^d)_2$, —CN, —C(O)—$N(R^d)_2$, —S(O)—$N(R^d)_2$, —$S(O)_2$—$N(R^d)_2$, —O—$R^d$, —S—$R^d$, —O—C(O)—$R^d$, —C(O)—$R^d$, —C(O)—$OR^d$, —S(O)—$R^d$, —$S(O)_2$—$R^d$, —$N(R^d)$—C(O)—$R^d$, —$N(R^d)$—S(O)—$R^d$, —$N(R^d)$—C(O)—$N(R^d)_2$, —$N(R^d)$—$S(O)_2$—$R^d$, and $C_{1-6}$alkyl that is optionally substituted with one or more groups independently selected from halo.

In one embodiment: $R^1$ is a carbon-linked piperazine ring that is substituted with one or more groups independently selected from the group consisting of $C_{1-6}$alkyl, $C_{2-6}$alkenyl, $C_{2-6}$alkynyl, $C_{3-8}$carbocycle, 3-8 membered heterocycle, aryl, heteroaryl, halo, —$NO_2$, —$N(R^b)_2$, —CN, —C(O)—$N(R^b)_2$, —S(O)—$N(R^b)_2$, —$S(O)_2$—$N(R^b)_2$, —O—$R^b$, —S—$R^b$, —O—C(O)—$R^b$, —C(O)—$R^b$, —C(O)—$OR^b$, —S(O)—$R^b$, —$S(O)_2$—$R^b$, —$N(R^b)$—C(O)—$R^b$, —$N(R^b)$—S(O)—$R^b$, —$N(R^b)$—C(O)—$N(R^b)_2$, and —$N(R^b)$—$S(O)_2$—$R^b$; wherein each $C_{1-6}$alkyl, $C_{2-6}$alkenyl, $C_{2-6}$alkynyl, $C_{3-8}$carbocycle, 3-8 membered heterocycle, aryl, and heteroaryl is optionally substituted with one or more groups consisting of halo, —$NO_2$—$N(R^b)_2$, —CN, —C(O)—$N(R^b)_2$, —S(O)—$N(R^b)_2$, —$S(O)_2$—$N(R^b)_2$, —O—$R^b$, —S—$R^b$, —O—C(O)—$R^b$, —C(O)—$R^b$, —C(O)—$OR^b$, —S(O)—$R^b$, —$S(O)_2$—$R^b$, —$N(R^b)$—C(O)—$R^b$, —$N(R^b)$—S(O)—$R^b$, —$N(R^b)$—C(O)—$N(R^b)_2$, —$N(R^b)$—$S(O)_2$—$R^b$, and $C_{1-6}$alkyl that is optionally substituted with one or more groups independently selected from halo; and $R^2$ is a ring selected from the group consisting of:

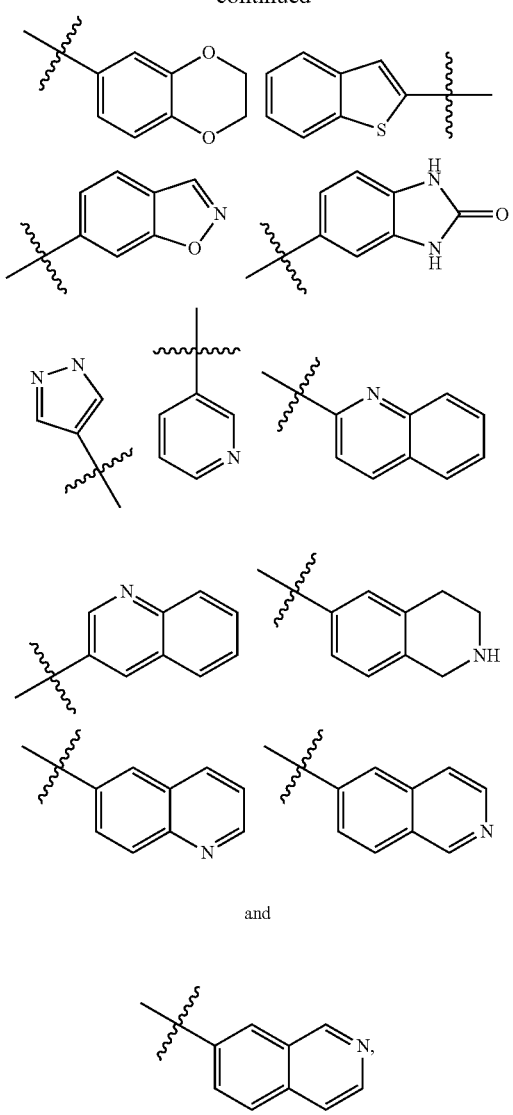

and which ring is optionally substituted with one or more groups independently selected from the group consisting of $C_{1-6}$alkyl, $C_{2-6}$alkenyl, $C_{2-6}$alkynyl, carbocycle, heterocycle, aryl, heteroaryl, halo, —$NO_2$, —$N(R^d)_2$, —CN, —C(O)—$N(R^d)_2$, —S(O)—$N(R^d)_2$, —$S(O)_2$—$N(R^d)_2$, —O—$R^d$, —S—$R^d$, —O—C(O)—$R^d$, —C(O)—$R^d$, —C(O)—$OR^d$, —S(O)—$R^d$, —$S(O)_2$—$R^d$, —$N(R^d)$—C(O)—$R^d$, —$N(R^d)$—S(O)—$R^d$, —$N(R^d)$—C(O)—$N(R^d)_2$, and —$N(R^d)$—$S(O)_2$—$R^d$; wherein each $C_{1-6}$alkyl, $C_{2-6}$alkenyl, $C_{2-6}$alkynyl, carbocycle, heterocycle, aryl, and heteroaryl is optionally substituted with one or more groups independently selected from the group consisting of halo, —$NO_2$—$N(R^d)_2$, —CN, —C(O)—$N(R^d)_2$, —S(O)—$N(R^d)_2$, —$S(O)_2$—$N(R^d)_2$, —O—$R^d$, —S—$R^d$, —O—C(O)—$R^d$, —C(O)—$R^d$, —C(O)—$OR^d$, —S(O)—$R^d$, —$S(O)_2$—$R^d$, —$N(R^d)$—C(O)—$R^d$, —$N(R^d)$—S(O)—$R^d$, —$N(R^d)$—C(O)—$N(R^d)_2$, —$N(R^d)$—$S(O)_2$—$R^d$, and $C_{1-6}$alkyl that is optionally substituted with one or more groups independently selected from halo.

In one embodiment: $R^1$ is selected from the group consisting of:

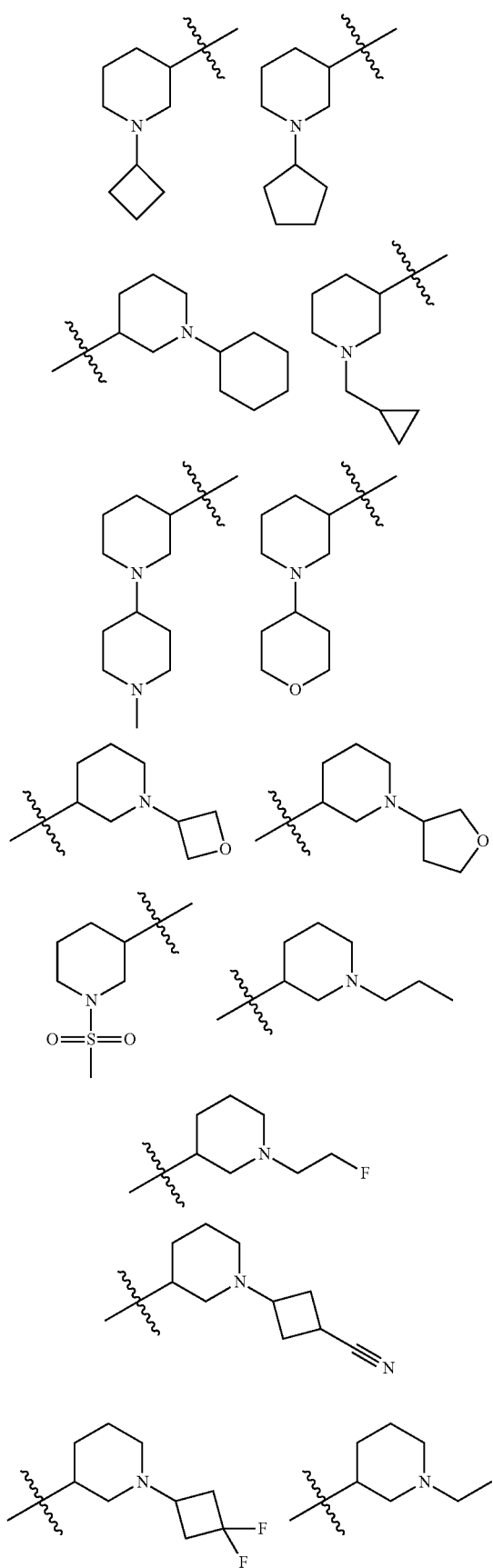
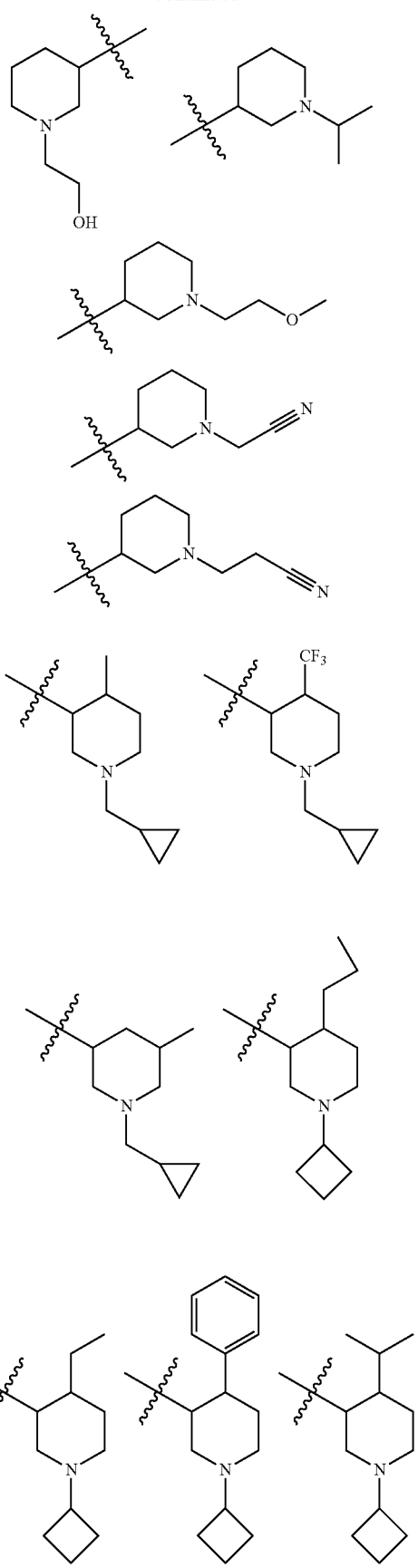
-continued

-continued
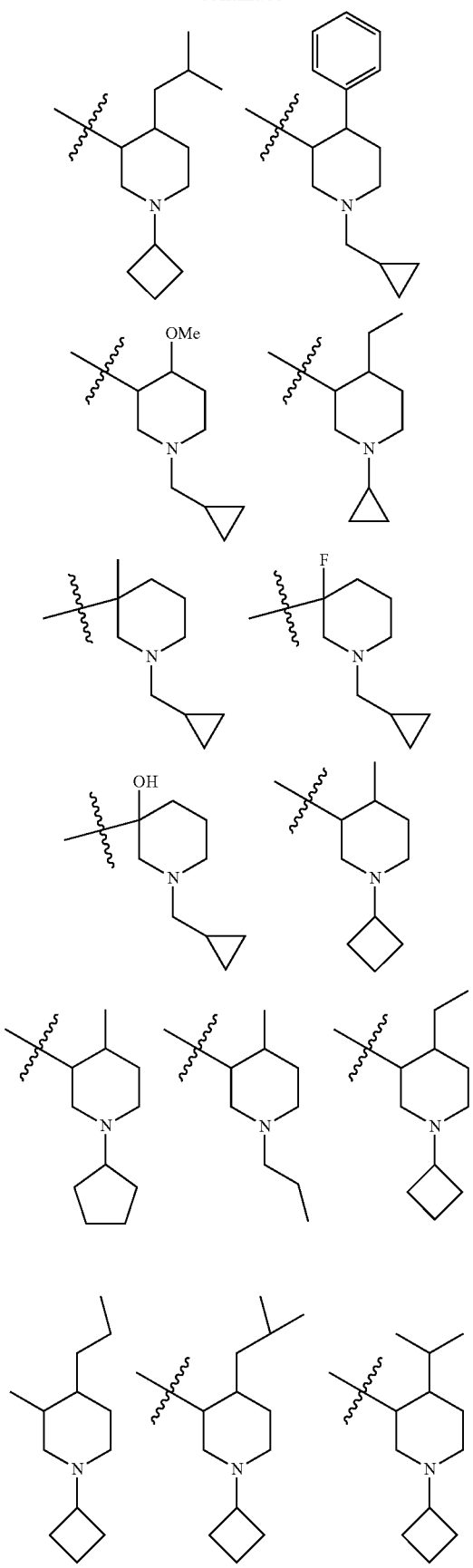
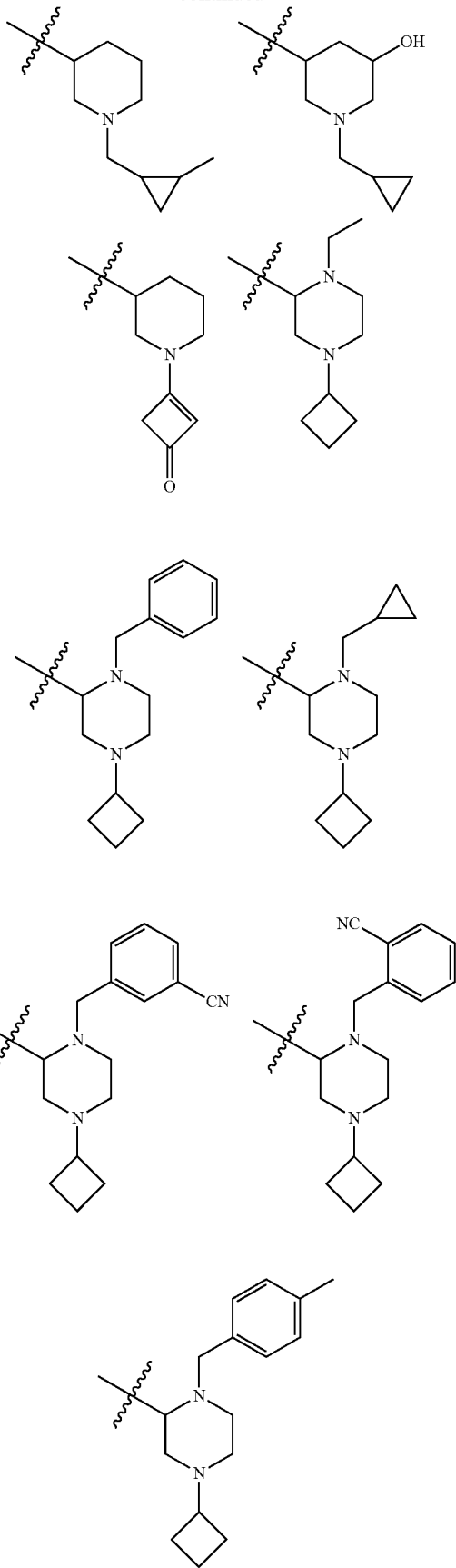

-continued

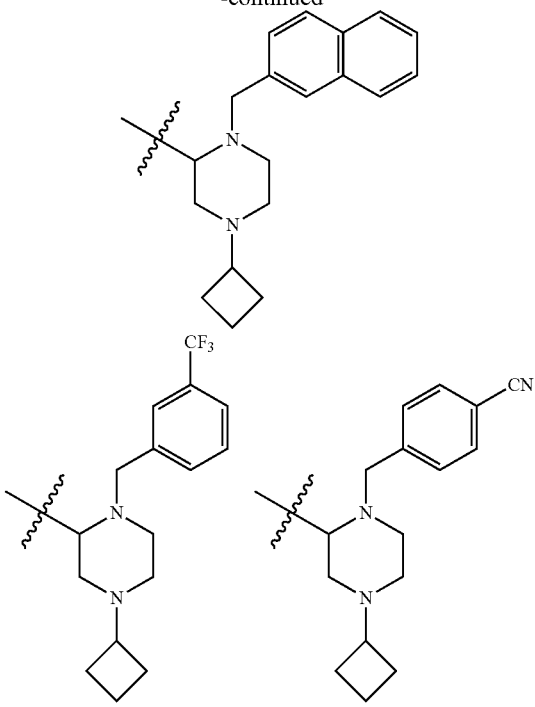

and
R² is a ring selected from the group consisting of:

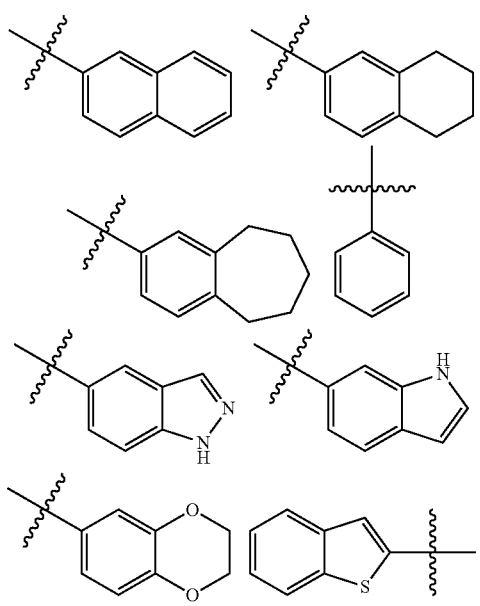

-continued

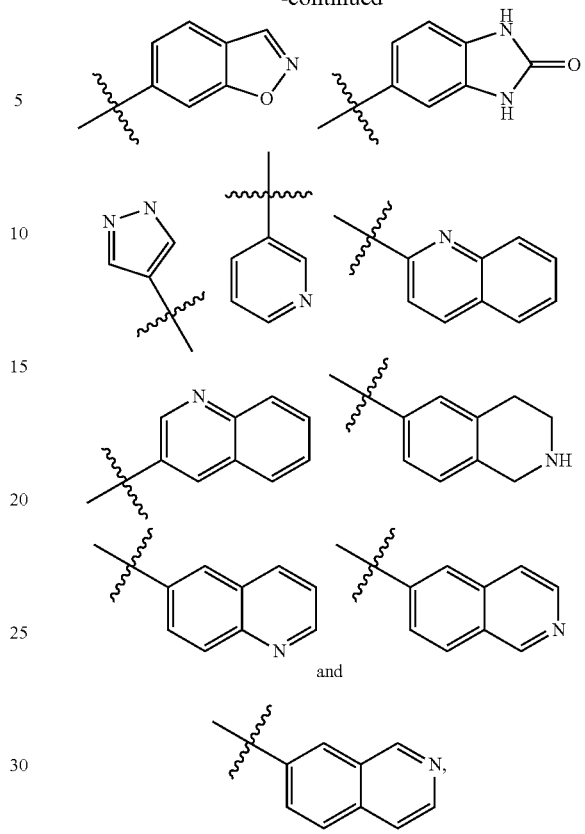

which ring is optionally substituted with one or more groups independently selected from the group consisting of $C_{1-6}$alkyl, $C_{2-6}$alkenyl, $C_{2-6}$alkynyl, carbocycle, heterocycle, aryl, heteroaryl, halo, —$NO_2$, —$N(R^d)_2$, —CN, —C(O)—$N(R^d)_2$, —S(O)—$N(R^d)_2$, —$S(O)_2$—$N(R^d)_2$, —O—$R^d$, —S—$R^d$, —O—C(O)—$R^d$, —C(O)—$R^d$, —C(O)—$OR^d$, —S(O)—$R^d$, —$S(O)_2$—$R^d$, —$N(R^d)$—C(O)—$R^d$, —$N(R^d)$—S(O)—$R^d$, —$N(R^d)$—C(O)—$N(R^d)_2$, and —$N(R^d)$—$S(O)_2$—$R^d$; wherein each $C_{1-6}$alkyl, $C_{2-6}$alkenyl, $C_{2-6}$alkynyl, carbocycle, heterocycle, aryl, and heteroaryl is optionally substituted with one or more groups independently selected from the group consisting of halo, —$NO_2$, —$N(R^d)_2$, —CN, —C(O)—$N(R^d)_2$, —S(O)—$N(R^d)_2$, —$S(O)_2$—$N(R^d)_2$, —O—$R^d$, —S—$R^d$, —O—C(O)—$R^d$, —C(O)—$R^d$, —C(O)—$OR^d$, —S(O)—$R^d$, —$S(O)_2$—$R^d$, —$N(R^d)$—C(O)—$R^d$, —$N(R^d)$—S(O)—$R^d$, —$N(R^d)$—C(O)—$N(R^d)_2$, —$N(R^d)$—$S(O)_2$—$R^d$, and $C_{1-6}$alkyl that is optionally substituted with one or more groups independently selected from halo.

In one embodiment: R¹ is selected from the group consisting of:

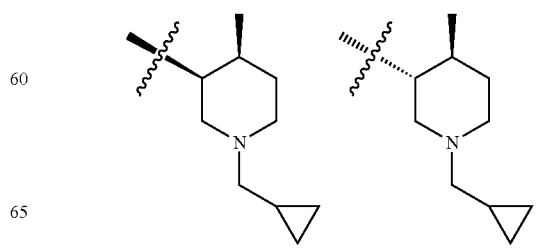

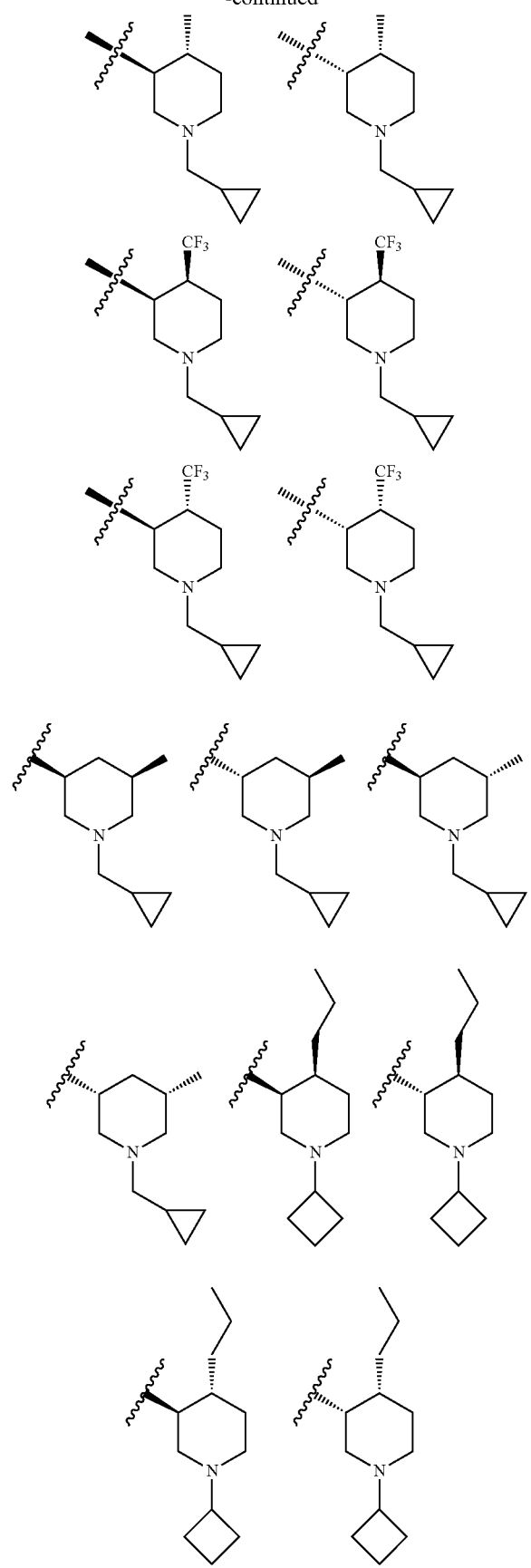
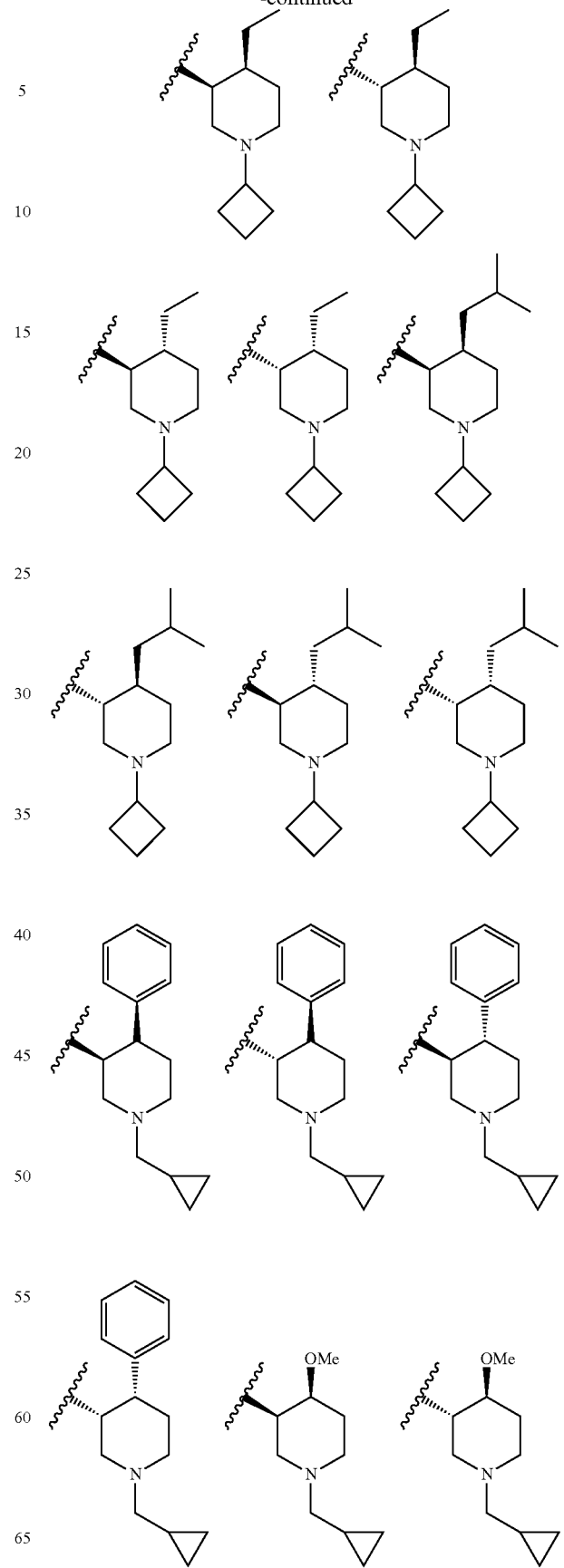

37
-continued
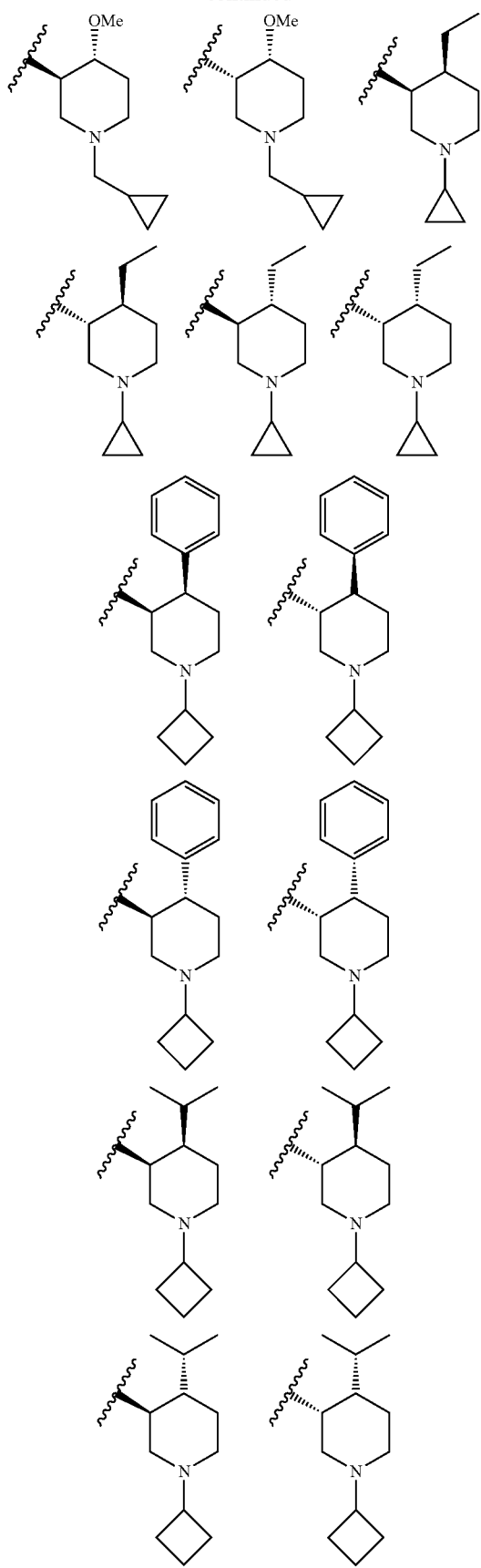
38
-continued
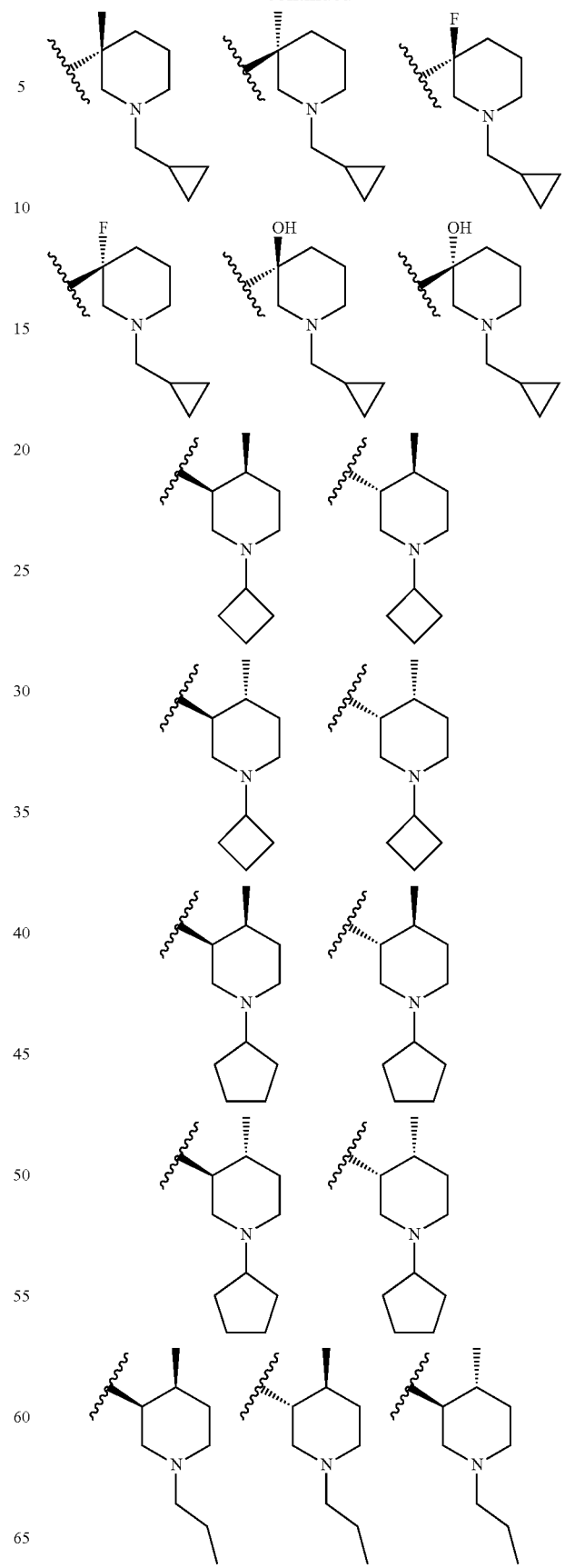

-continued
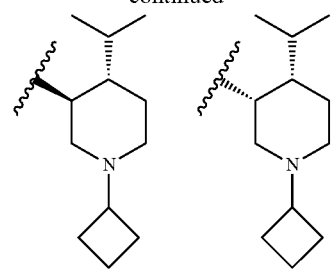
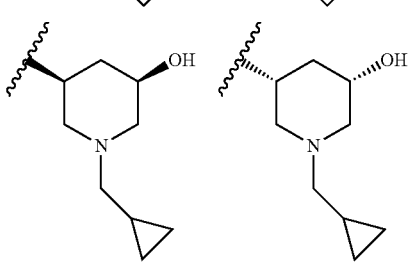
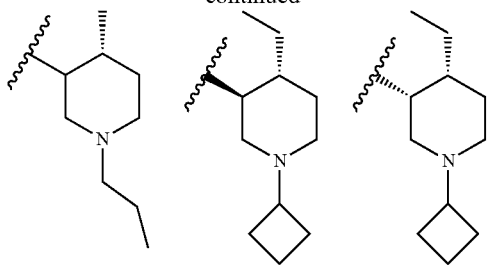
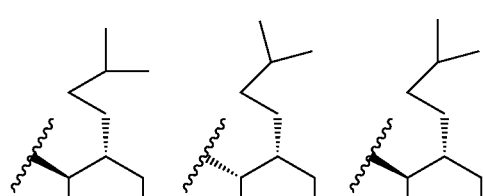
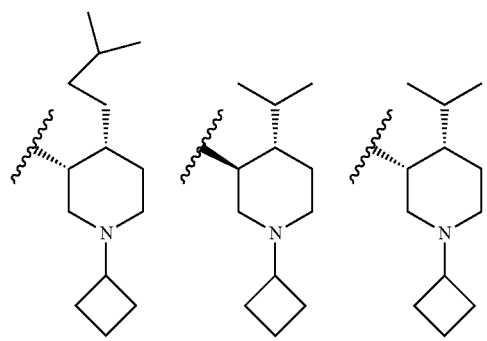
and
R² is a ring selected from the group consisting of:
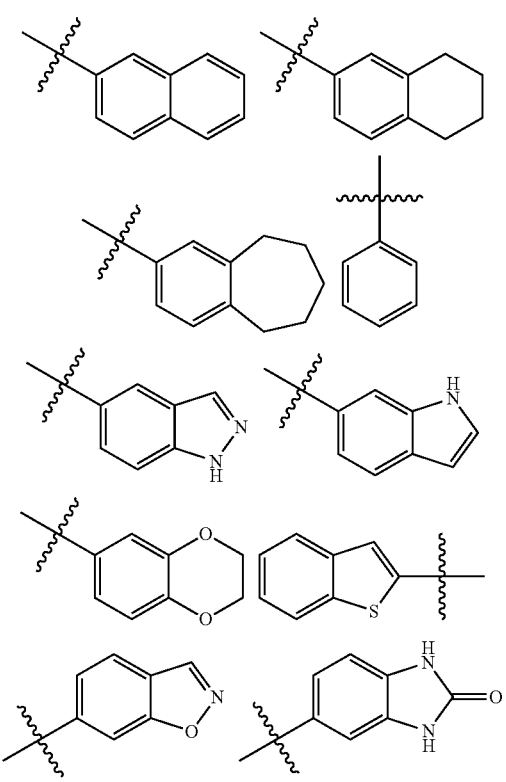

-continued

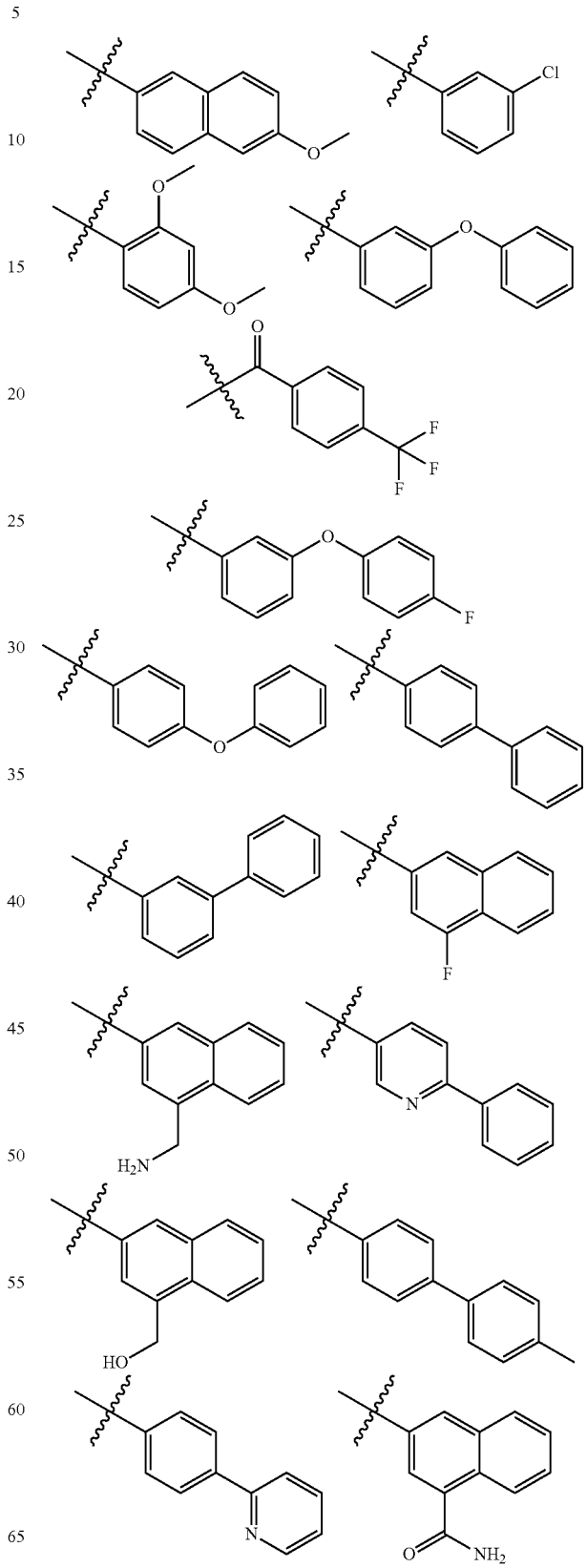

which ring is optionally substituted with one or more groups independently selected from the group consisting of $C_{1-6}$alkyl, $C_{2-6}$alkenyl, $C_{2-6}$alkynyl, carbocycle, heterocycle, aryl, heteroaryl, halo, —$NO_2$, —$N(R^d)_2$, —CN, —C(O)—$N(R^d)_2$, —S(O)—$N(R^d)_2$, —$S(O)_2$—$N(R^d)_2$, —O—$R^d$, —S—$R^d$, —O—C(O)—$R^d$, —C(O)—$R^d$, —C(O)—$OR^d$, —S(O)—$R^d$, —$S(O)_2$—$R^d$, —$N(R^d)$—C(O)—$R^d$, —$N(R^d)$—S(O)—$R^d$, —$N(R^d)$—C(O)—$N(R^d)_2$, and —$N(R^d)$—$S(O)_2$—$R^d$; wherein each $C_{1-6}$alkyl, $C_{2-6}$alkenyl, $C_{2-6}$alkynyl, carbocycle, heterocycle, aryl, and heteroaryl is optionally substituted with one or more groups independently selected from the group consisting of halo, —$NO_2$—$N(R^d)_2$, —CN, —C(O)—$N(R^d)_2$, —S(O)—$N(R^d)_2$, —$S(O)_2$—$N(R^d)_2$, —O—$R^d$, —S—$R^d$, —O—C(O)—$R^d$, —C(O)—$R^d$, —C(O)—$OR^d$, —S(O)—$R^d$, —$S(O)_2$—$R^d$, —$N(R^d)$—C(O)—$R^d$, —$N(R^d)$—S(O)—$R^d$, —$N(R^d)$—C(O)—$N(R^d)_2$, —$N(R^d)$—$S(O)_2$—$R^d$, and $C_{1-6}$alkyl that is optionally substituted with one or more groups independently selected from halo.

In one embodiment: $R^1$ is a carbon-linked piperidine ring that is substituted on the piperidine ring nitrogen with a group $R^x$ and that is optionally further substituted with one or more groups independently selected from the group consisting of $C_{1-6}$alkyl, $C_{2-6}$alkenyl, $C_{2-6}$alkynyl, $C_{3-8}$carbocycle, 3-8 membered heterocycle, aryl, heteroaryl, halo, —$NO_2$, —$N(R^b)_2$, —CN, —C(O)—$N(R^b)_2$, —S(O)—$N(R^b)_2$, —$S(O)_2$—$N(R^b)_2$, —O—$R^b$, —S—$R^b$, —O—C(O)—$R^b$, —C(O)—$R^b$, —C(O)—$OR^b$, —S(O)—$R^b$, —$S(O)_2$—$R^b$, —$N(R^b)$—C(O)—$R^b$, —$N(R^b)$—S(O)—$R^b$, —$N(R^b)$—C(O)—$N(R^b)_2$, and —$N(R^b)$—$S(O)_2$—$R^b$; wherein each $C_{1-6}$alkyl, $C_{2-6}$alkenyl, $C_{2-6}$alkynyl, $C_{3-8}$carbocycle, 3-8 membered heterocycle, aryl, and heteroaryl is optionally substituted with one or more groups independently selected from the group consisting of halo, —$NO_2$— $N(R^d)_2$, —CN, —C(O)—$N(R^b)_2$, —S(O)—$N(R^b)_2$, —$S(O)_2$—$N(R^b)_2$, —O—$R^b$, —S—$R^b$, —O—C(O)—$R^b$, —C(O)—$R^b$, —C(O)—$OR^b$, —S(O)—$R^b$, —$S(O)_2$—$R^b$, —$N(R^b)$—C(O)—$R^b$, —$N(R^b)$—S(O)—$R^b$, —$N(R^b)$—C(O)—$N(R^b)_2$, —$N(R^b)$—$S(O)_2$—$R^b$, and $C_{1-6}$alkyl that is optionally substituted with one or more groups independently selected from halo; and $R^2$ is selected from the group consisting of:

-continued
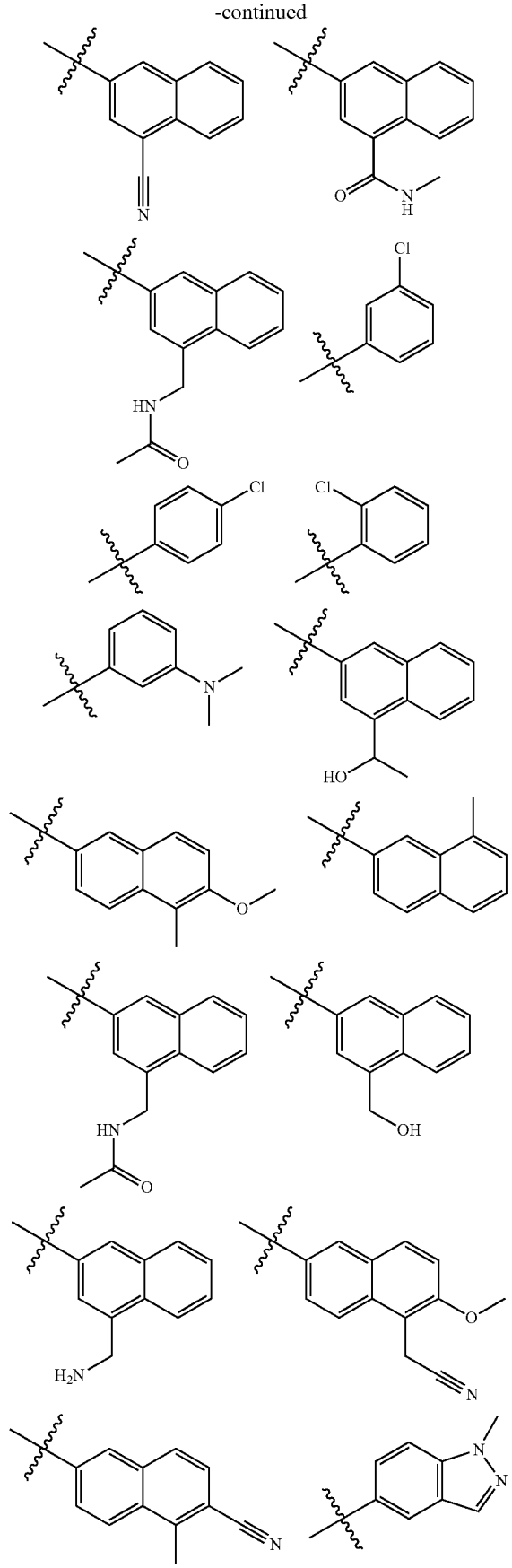
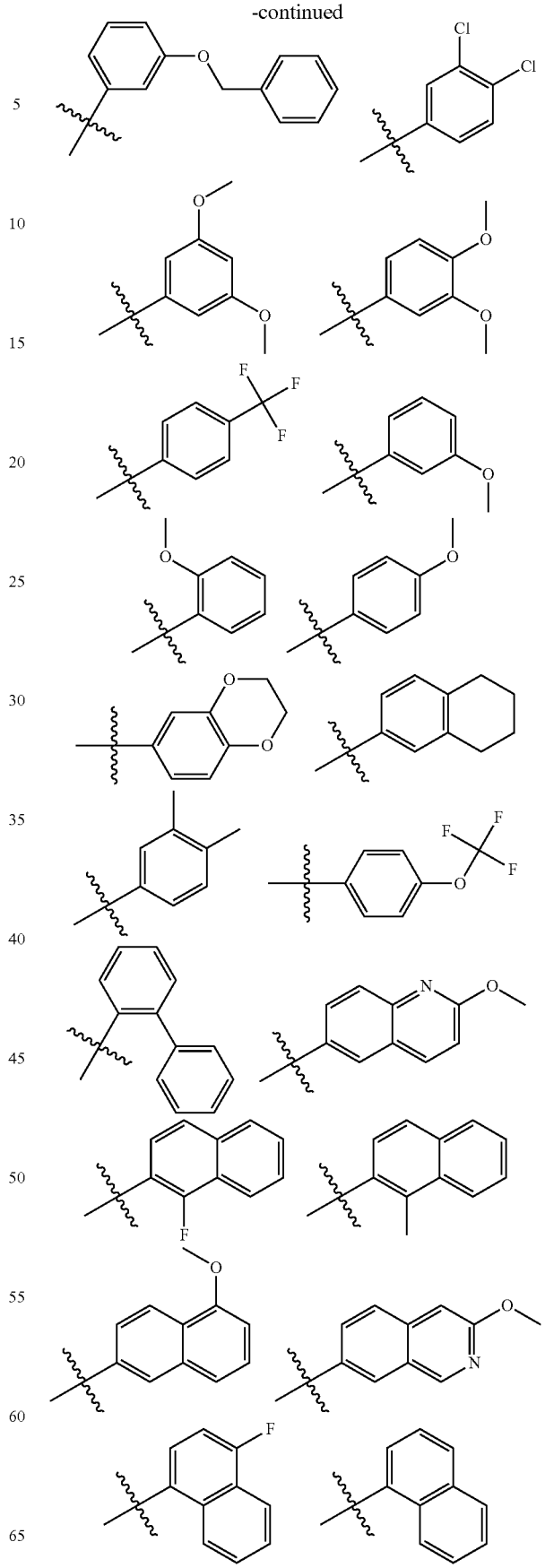

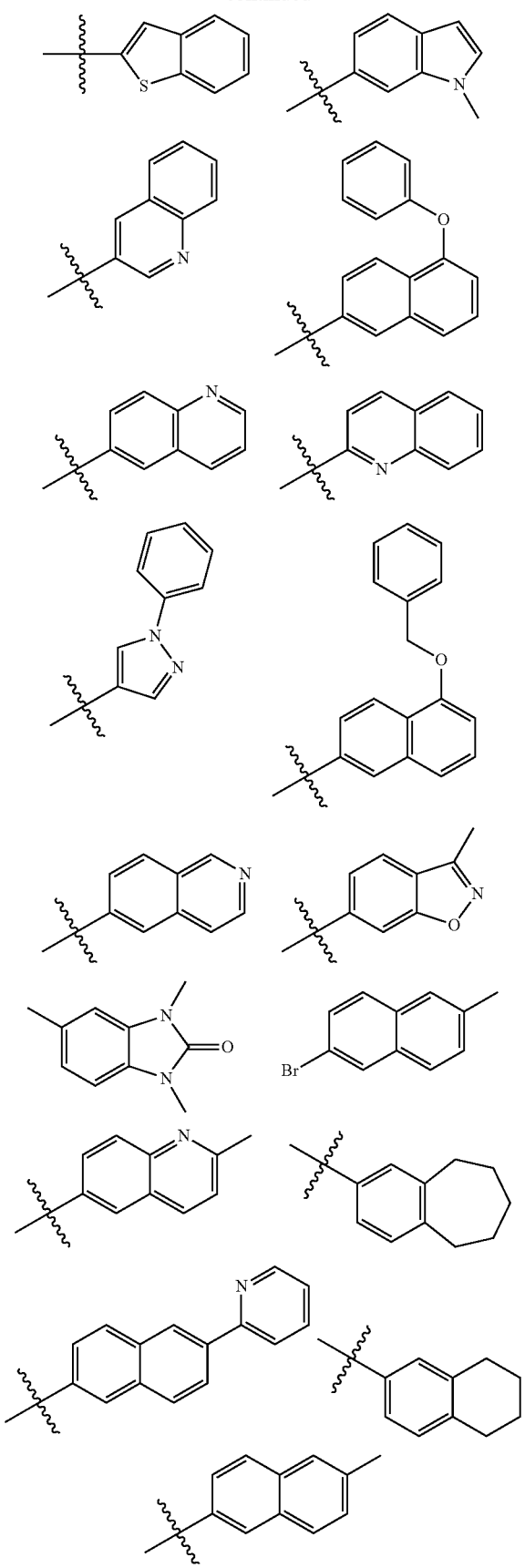
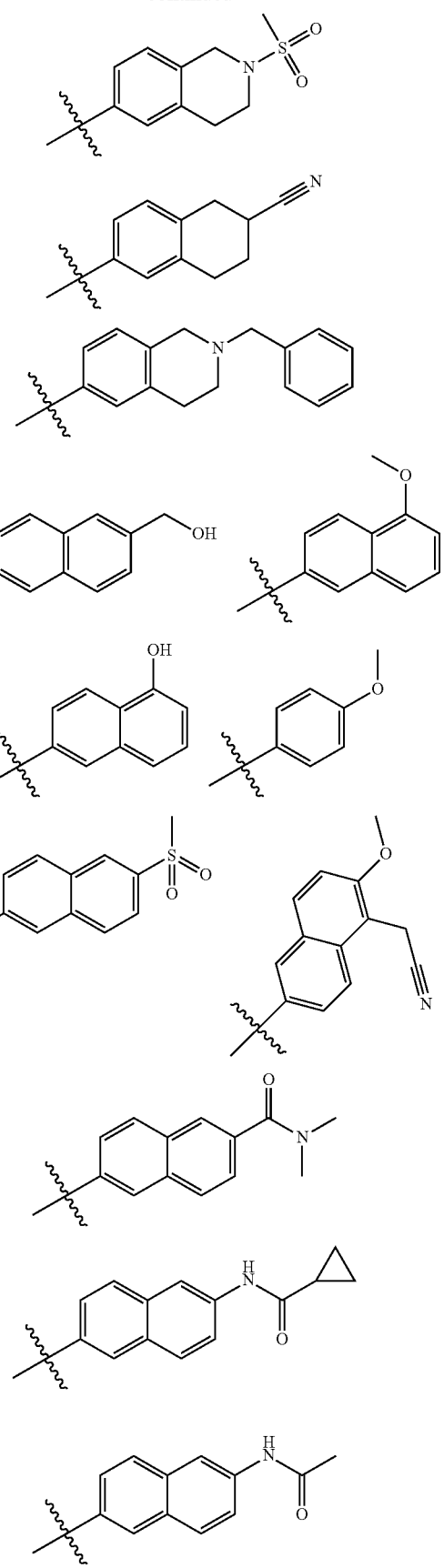

-continued

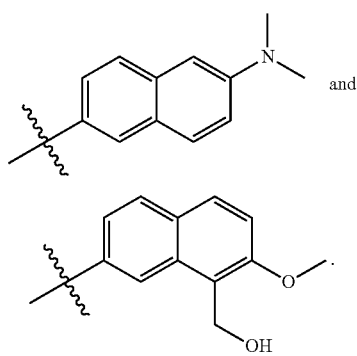
and

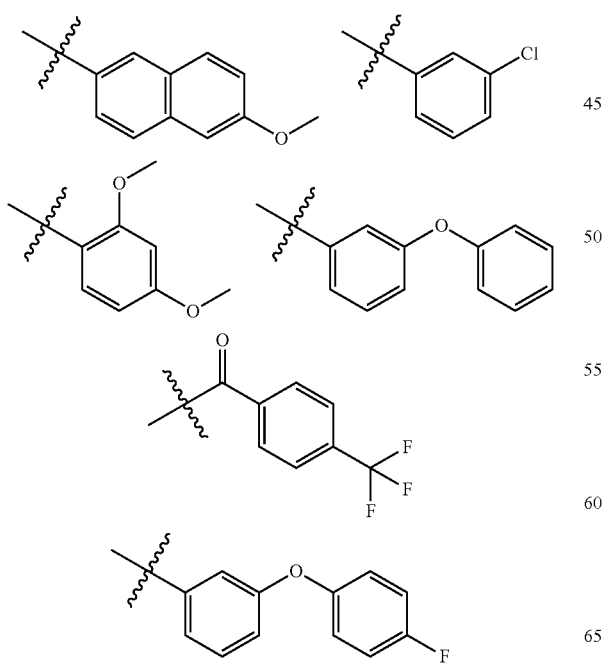

In one embodiment: $R^1$ is a carbon-linked piperazine ring that is substituted with one or more groups independently selected from the group consisting of $C_{1-6}$alkyl, $C_{2-6}$alkenyl, $C_{2-6}$alkynyl, $C_{3-8}$carbocycle, 3-8 membered heterocycle, aryl, heteroaryl, halo, —$NO_2$, —$N(R^b)_2$, —CN, —C(O)—$N(R^b)_2$, —S(O)—$N(R^b)_2$, —$S(O)_2$—$N(R^b)_2$, —O—$R^b$, —S—$R^b$, —O—C(O)—$R^b$, —C(O)—$R^b$, —C(O)—$OR^b$, —S(O)—$R^b$, —$S(O)_2$—$R^b$, —$N(R^b)$—C(O)—$R^b$, —$N(R^b)$—S(O)—$R^b$, —$N(R^b)$—C(O)—$N(R^b)_2$, and —$N(R^b)$—$S(O)_2$—$R^b$; wherein each $C_{1-6}$alkyl, $C_{2-6}$alkynyl, $C_{3-8}$carbocycle, 3-8 membered heterocycle, aryl, and heteroaryl is optionally substituted with one or more groups independently selected from the group consisting of halo, —$NO_2$—$N(R^b)_2$, —CN, —C(O)—$N(R^b)_2$, —S(O)—$N(R^b)_2$, —$S(O)_2$—$N(R^b)_2$, —O—$R^b$, —S—$R^b$, —O—C(O)—$R^b$, —C(O)—$R^b$, —C(O)—$OR^b$, —S(O)—$R^b$, —$S(O)_2$—$R^b$, —$N(R^b)$—C(O)—$R^b$, —$N(R^b)$—S(O)—$R^b$, —$N(R^b)$—C(O)—$N(R^b)_2$, —$N(R^b)$—$S(O)_2$—$R^b$, and $C_{1-6}$alkyl that is optionally substituted with one or more groups independently selected from halo; and $R^2$ is selected from the group consisting of:

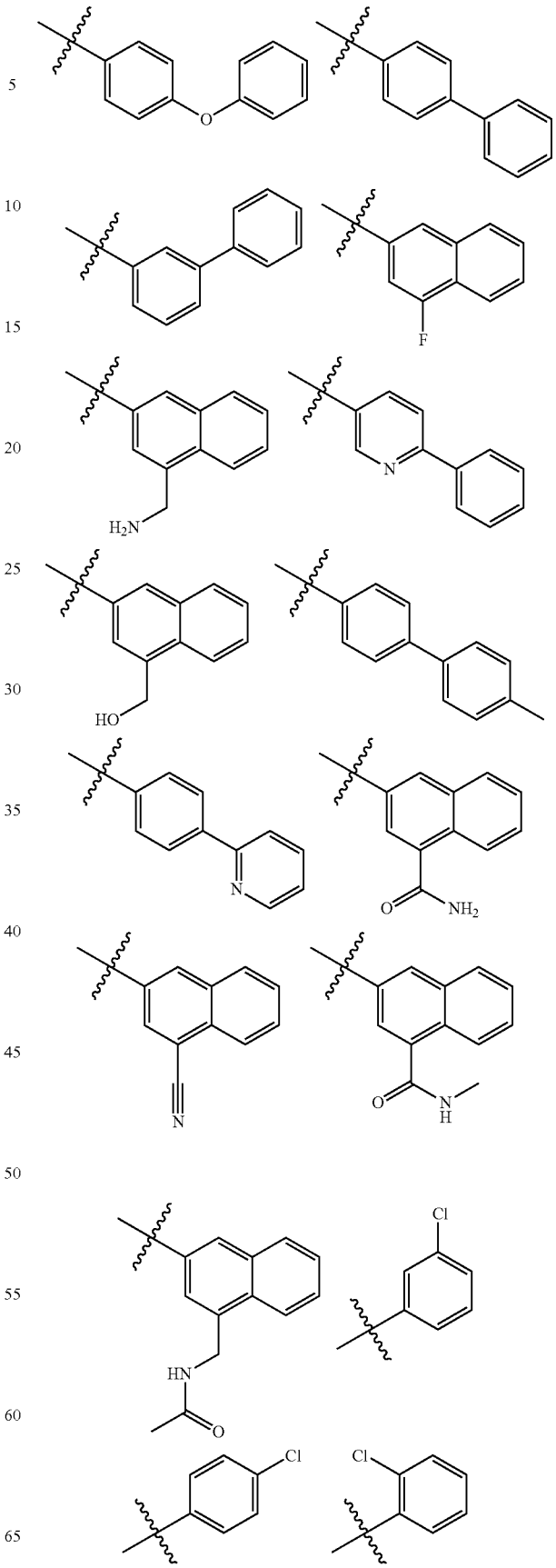

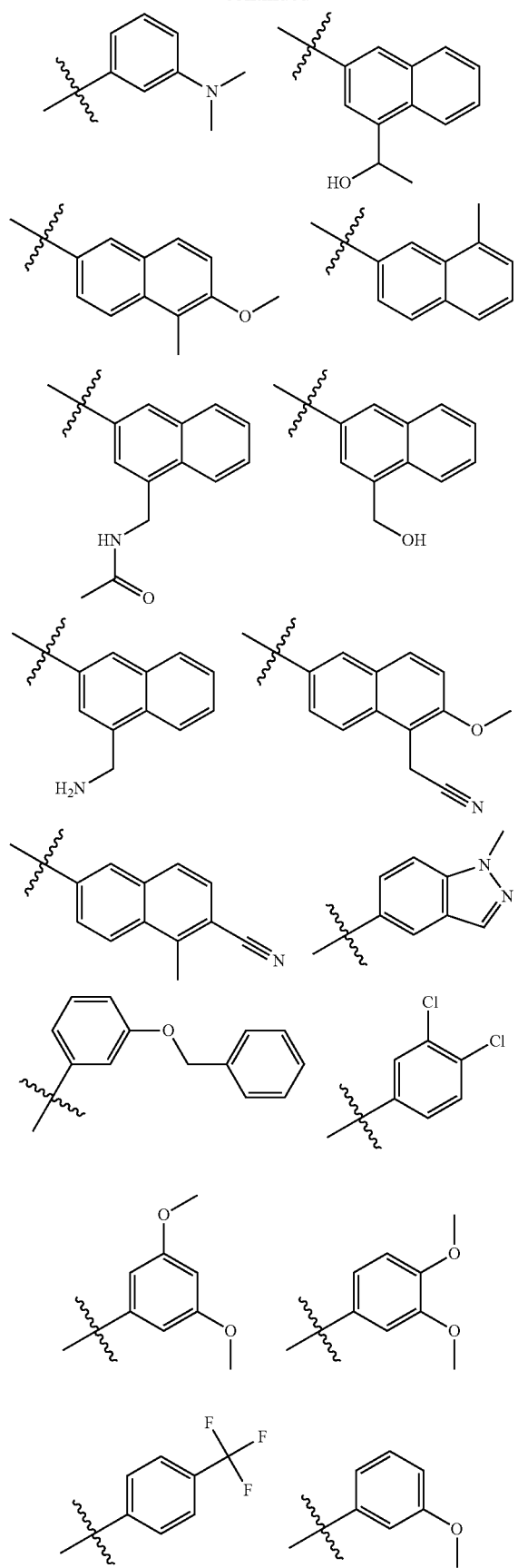
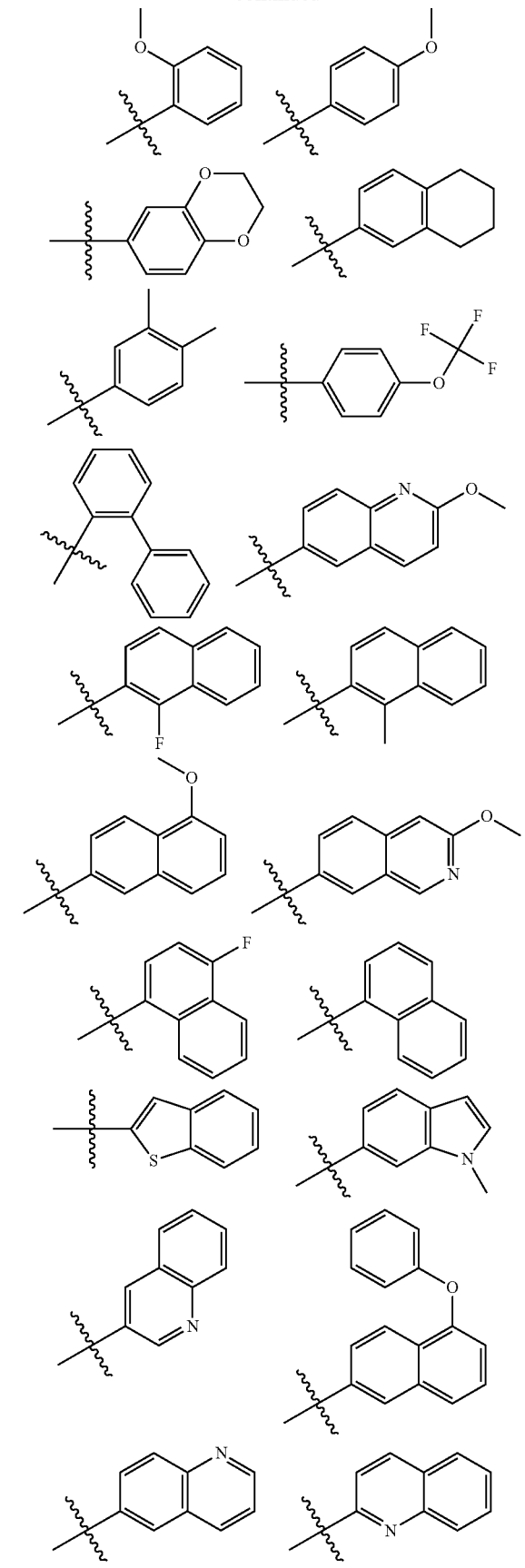

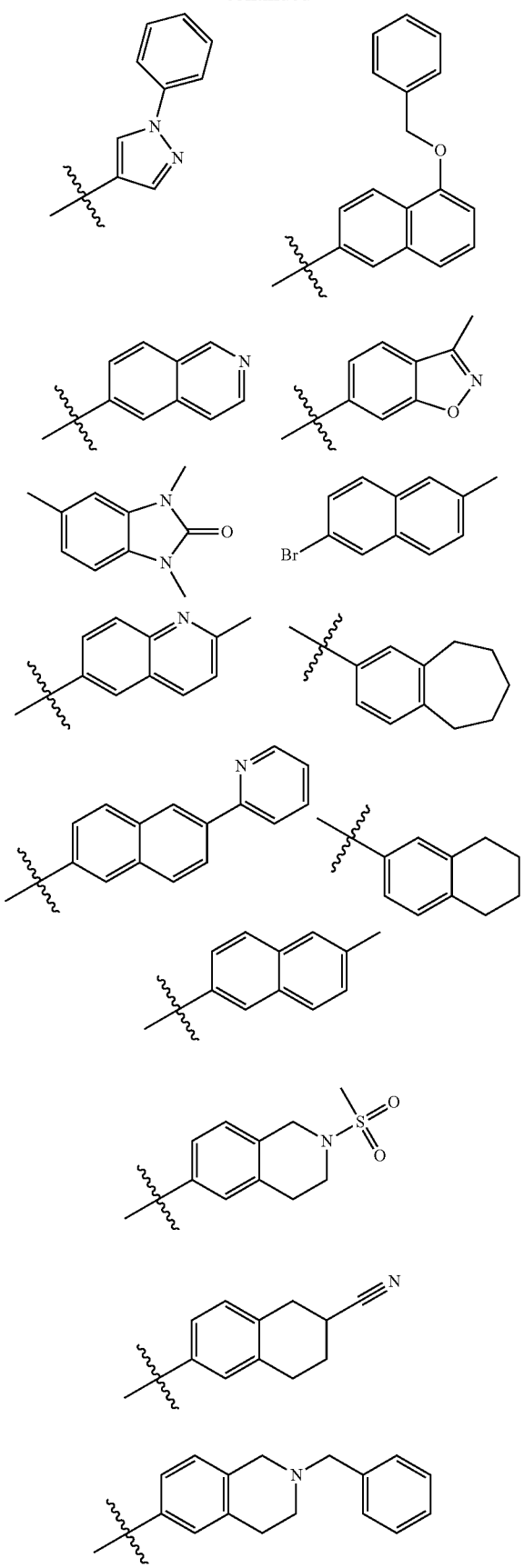
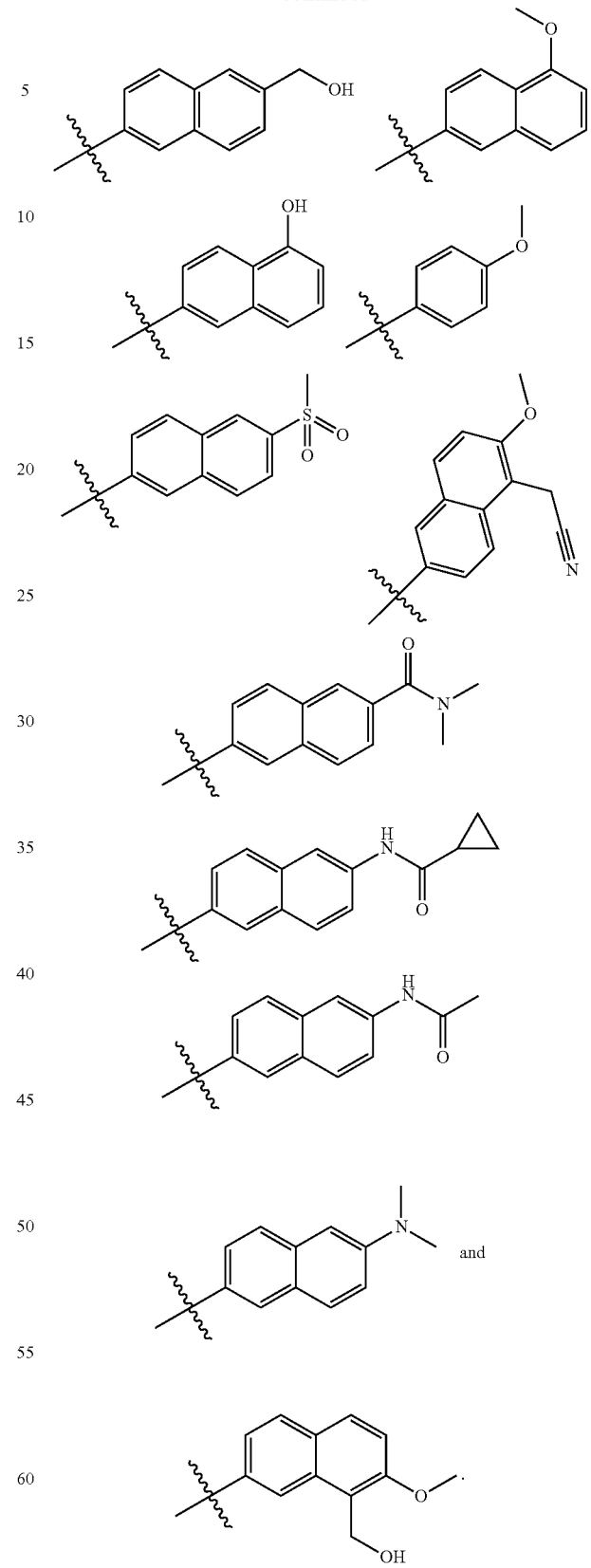
In one embodiment: R[1] is selected from the group consisting of:

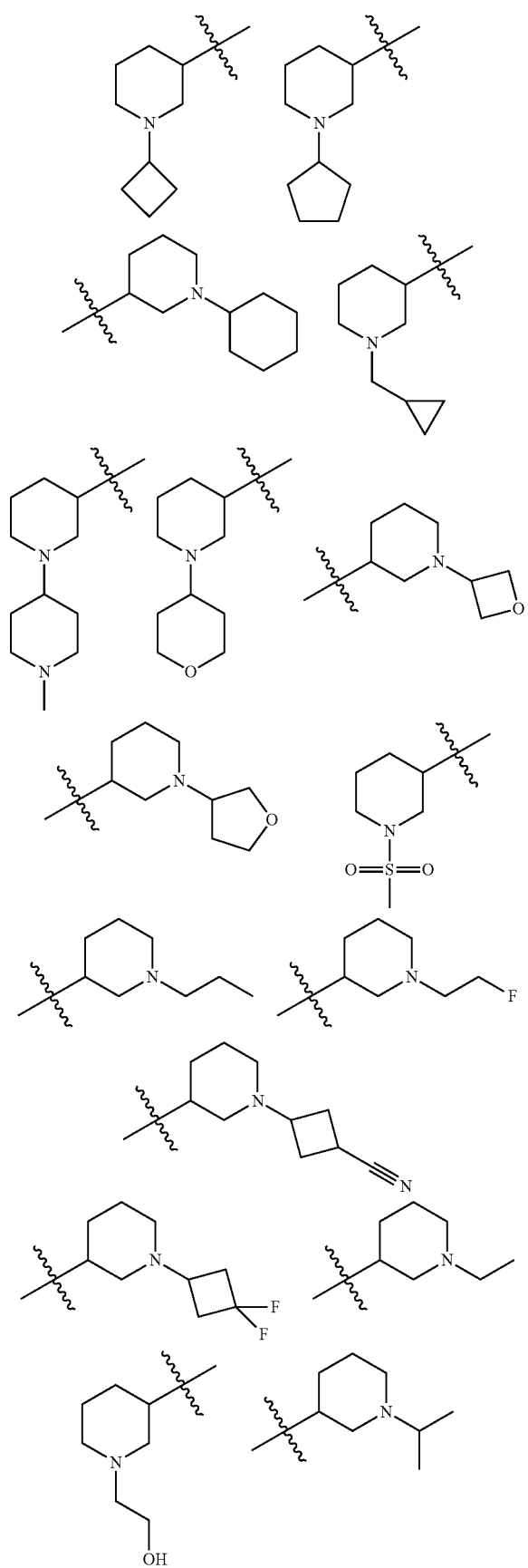
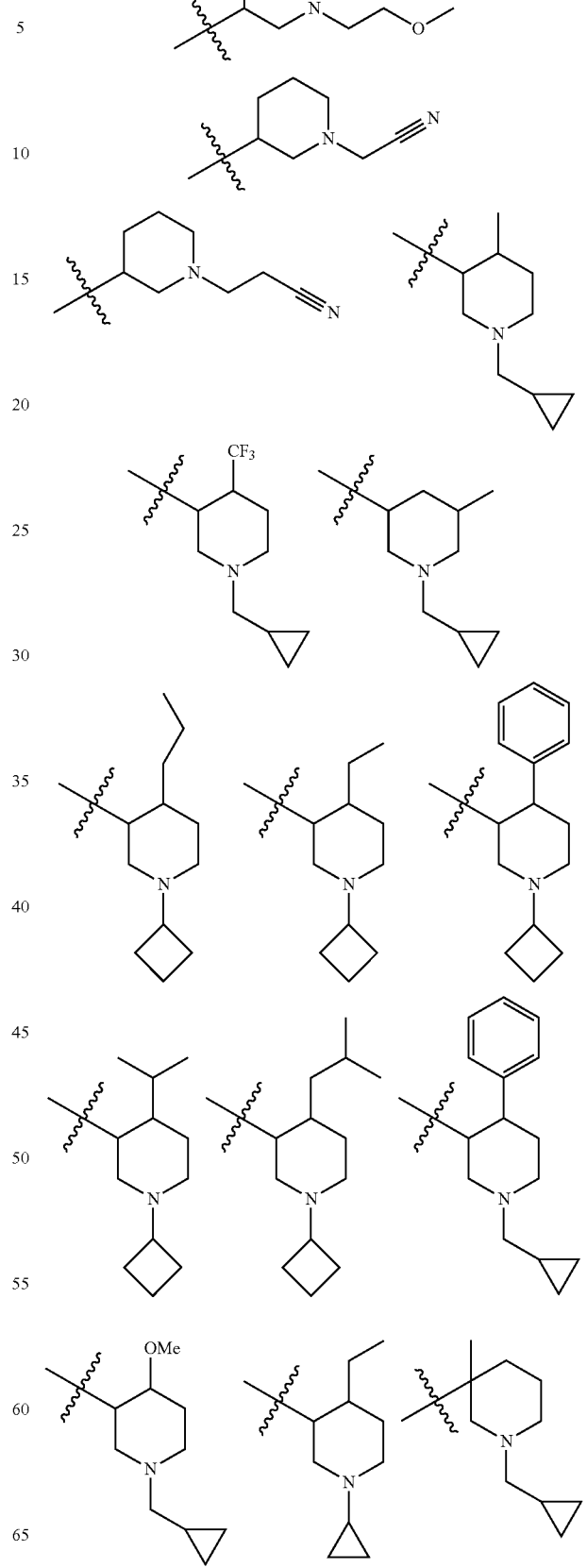

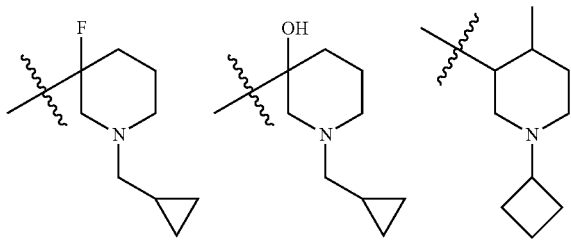
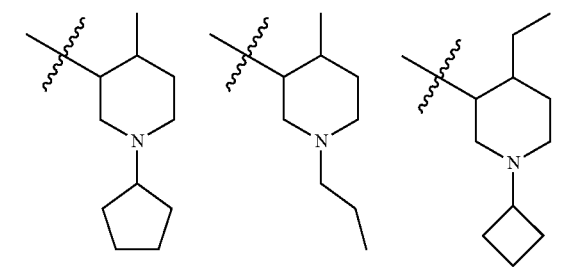
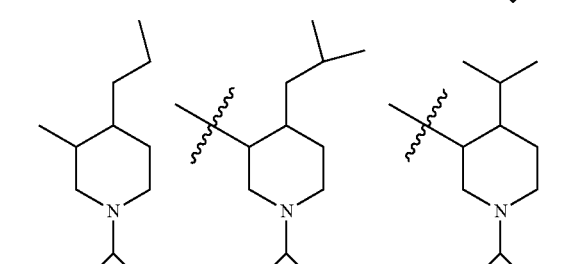
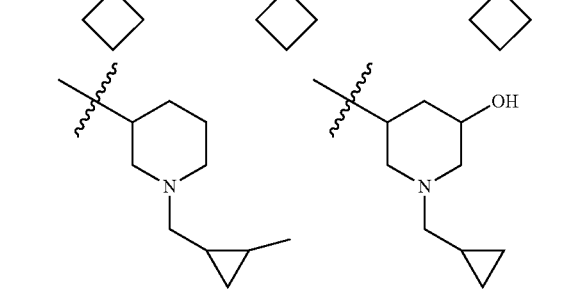
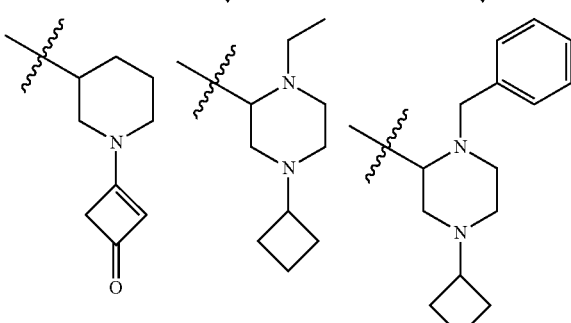
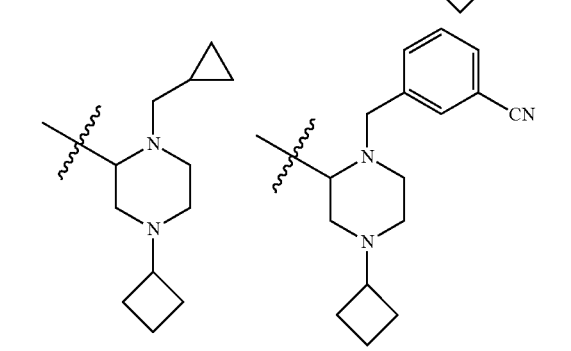
and
R² is selected from the group consisting of:
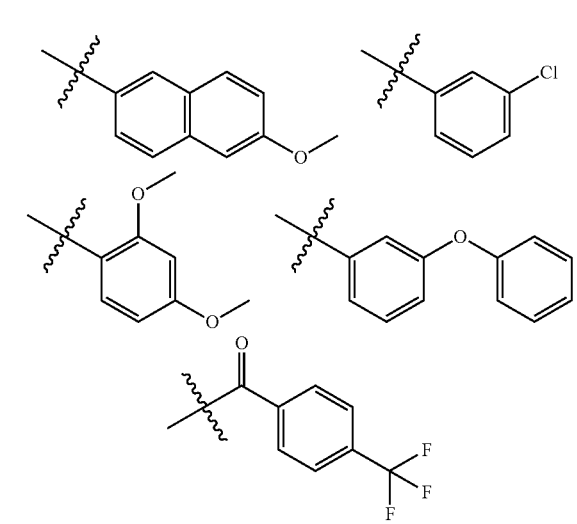

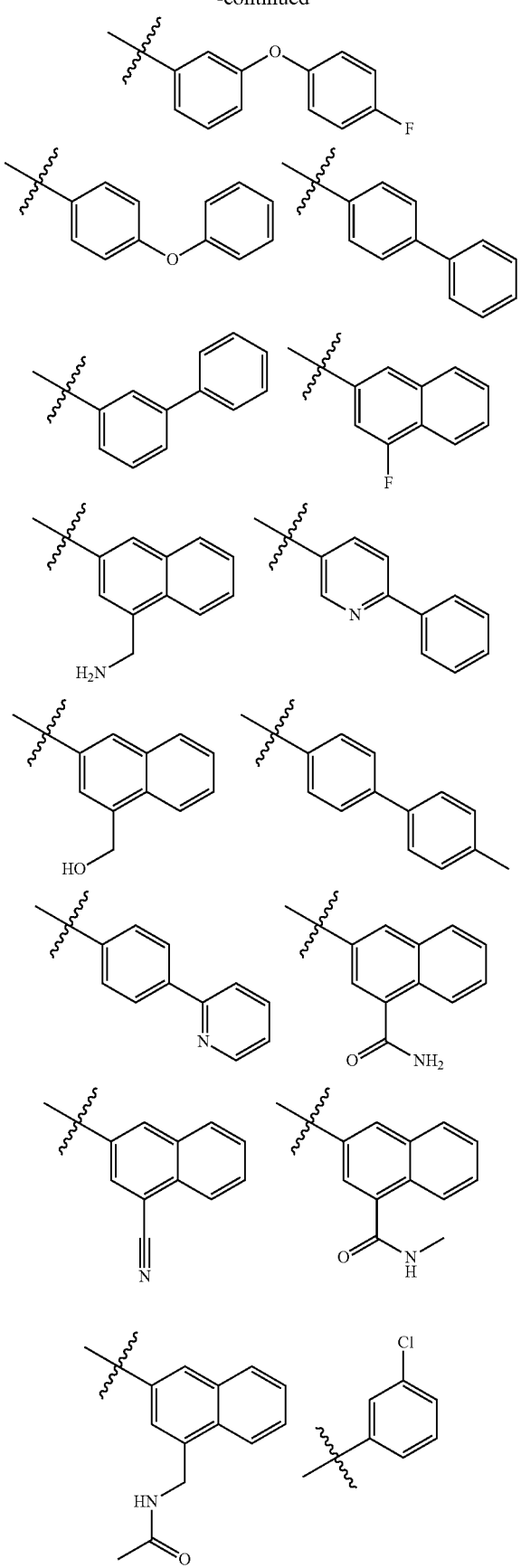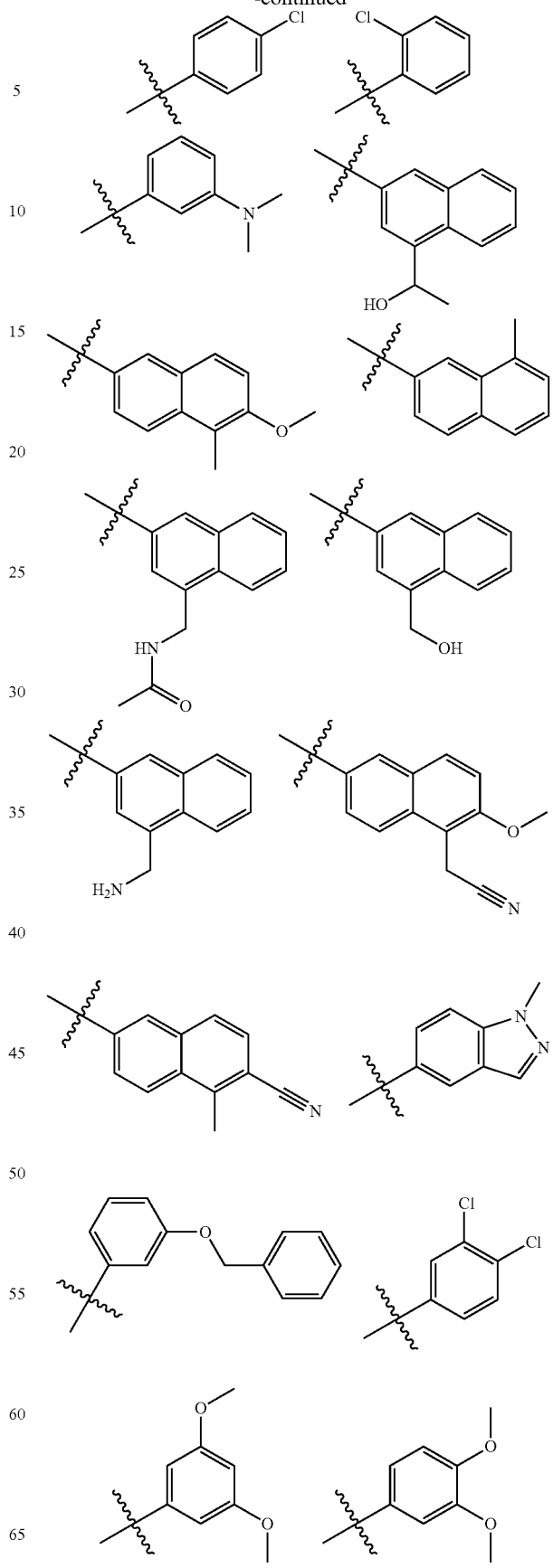

-continued
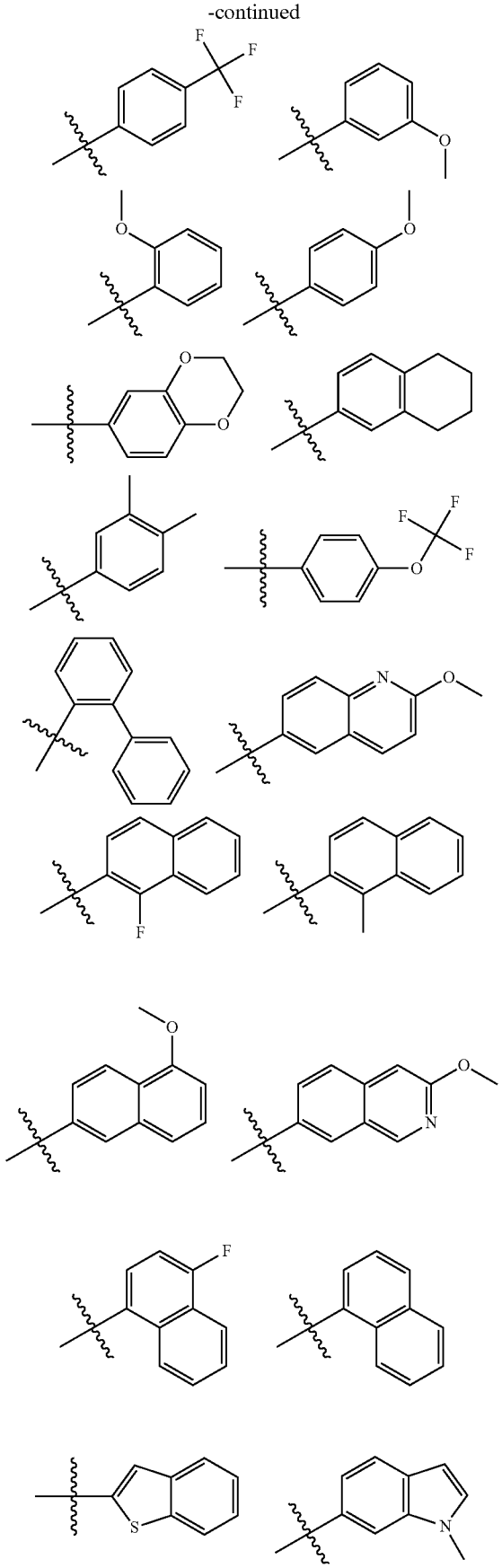
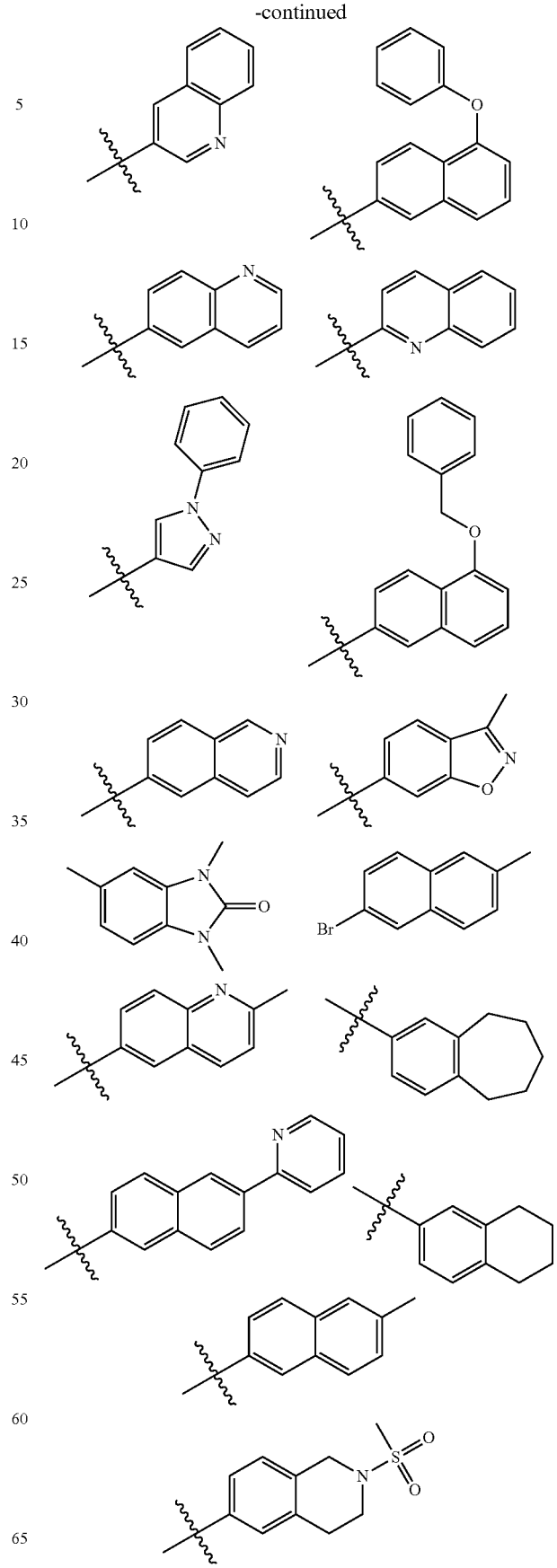

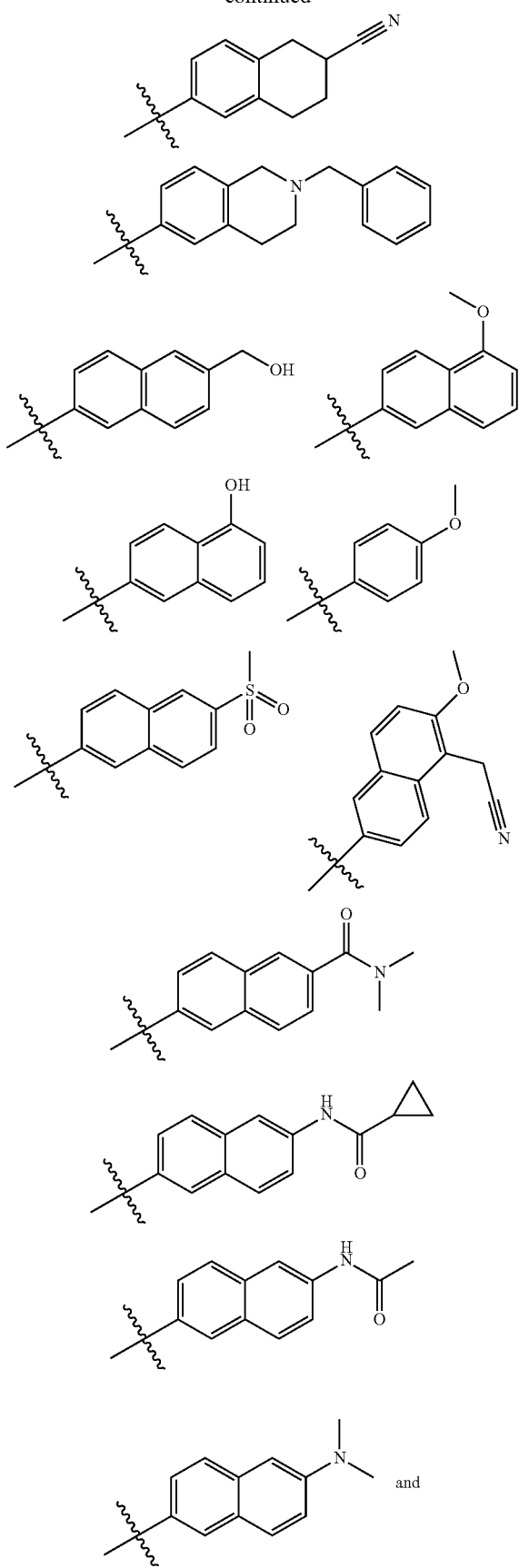
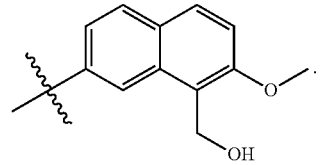
In one embodiment: $R^1$ is selected from the group consisting of:
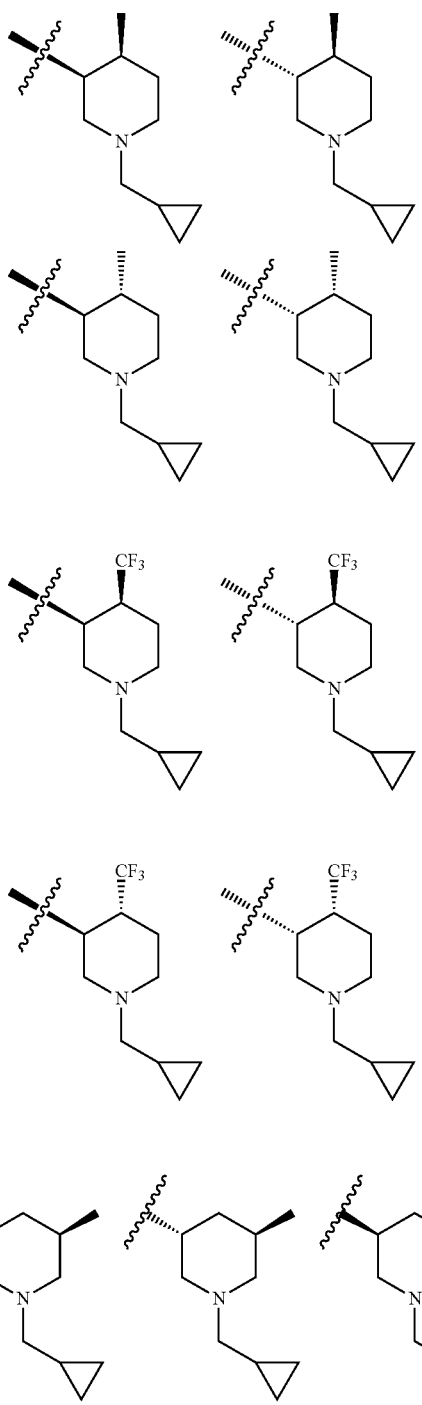

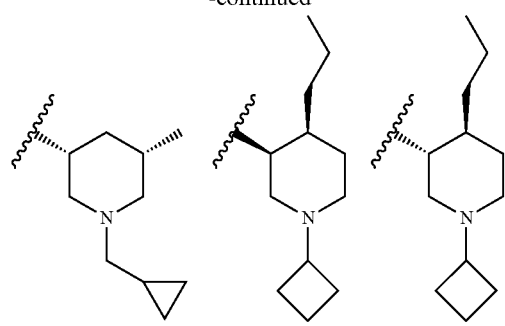
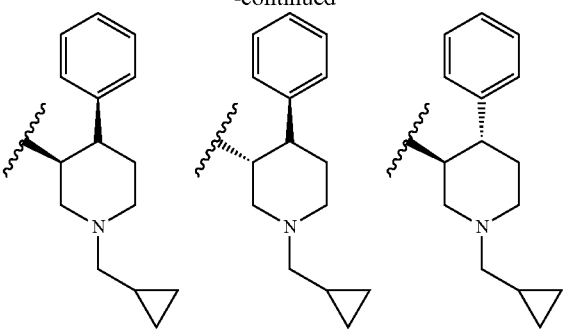
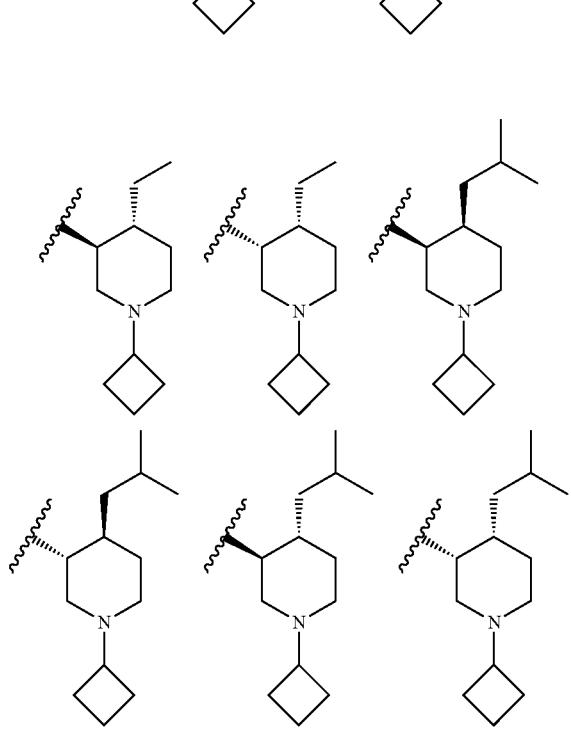
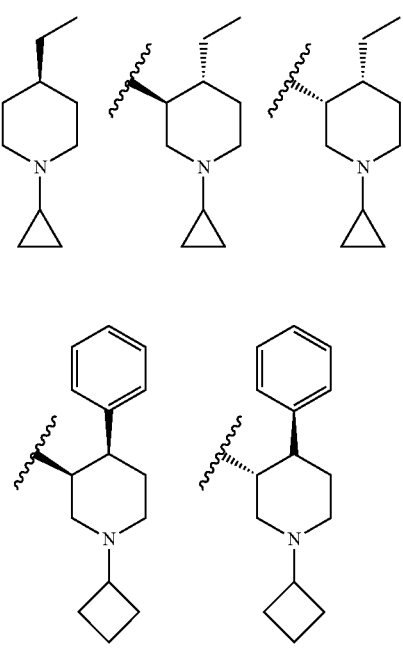

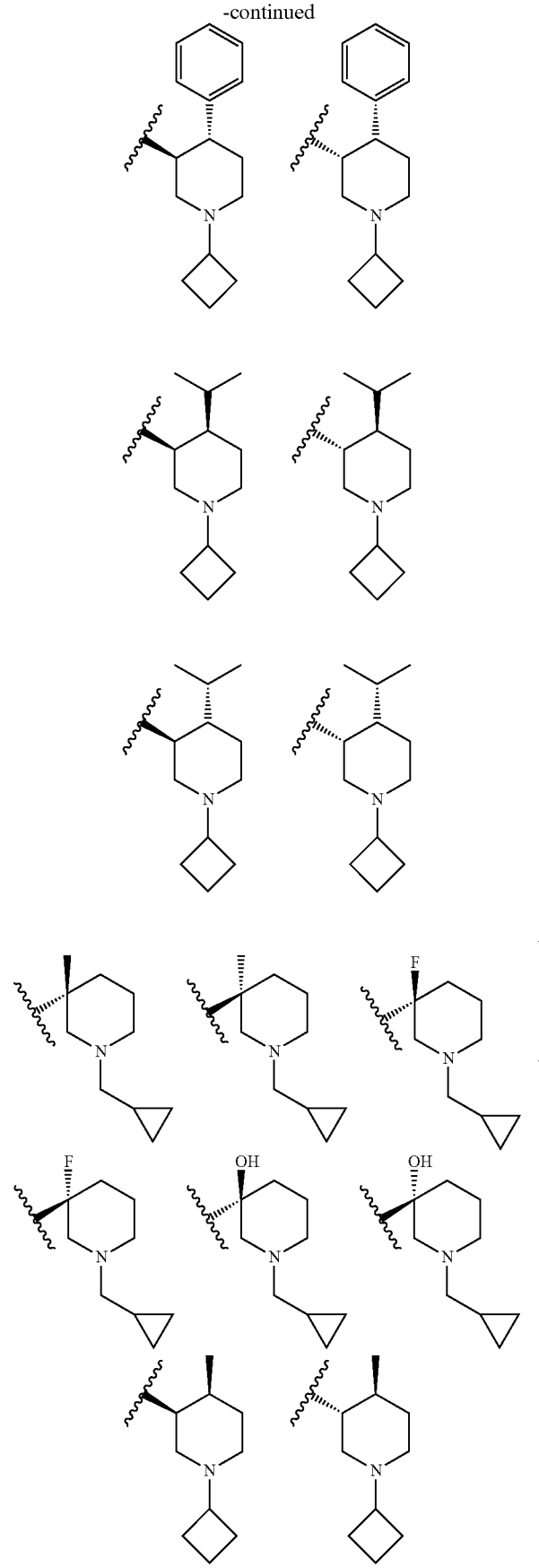
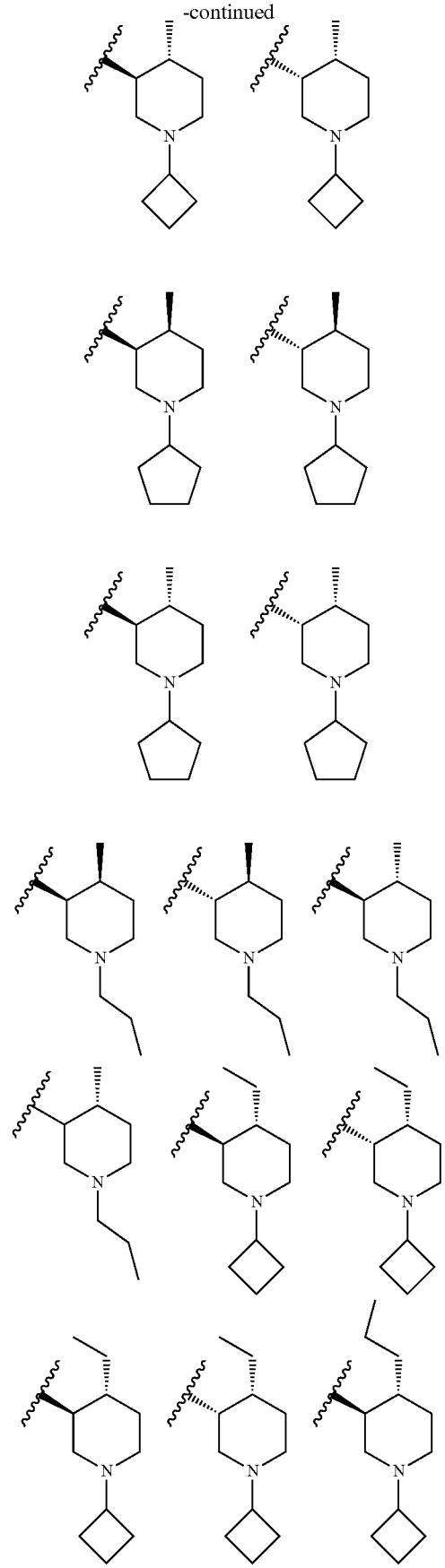

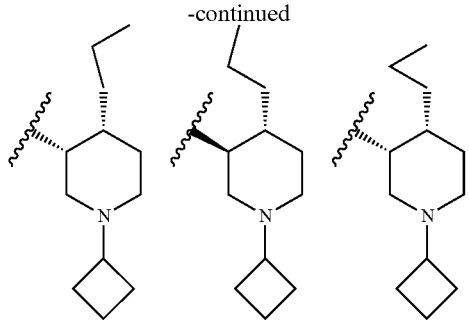
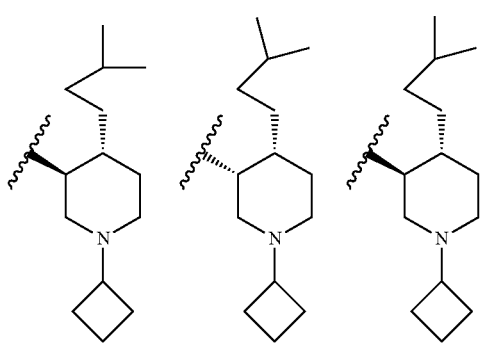
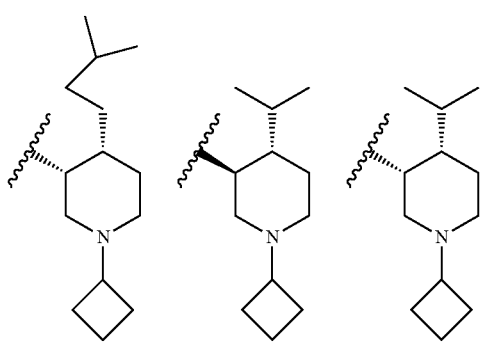
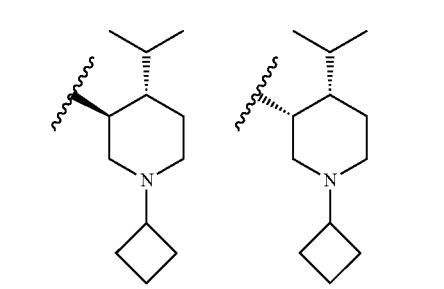
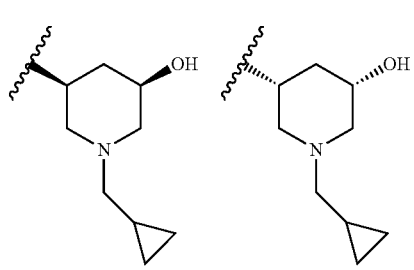
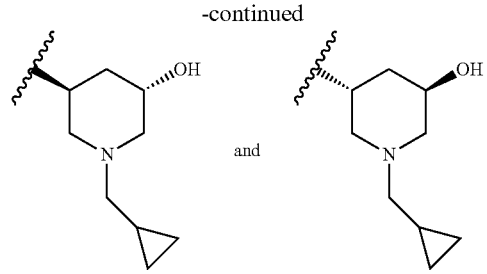
and
R² is selected from the group consisting of:
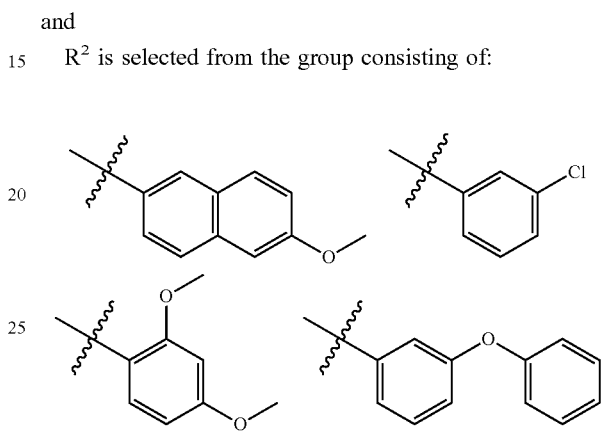
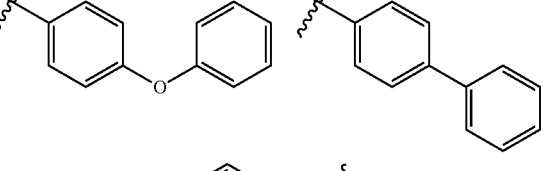
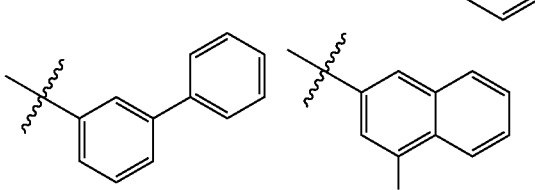
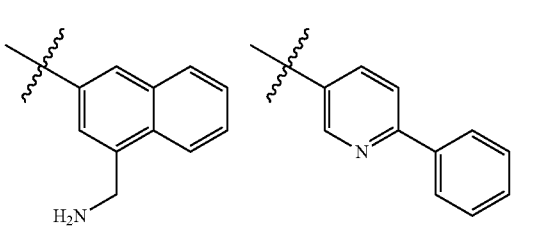

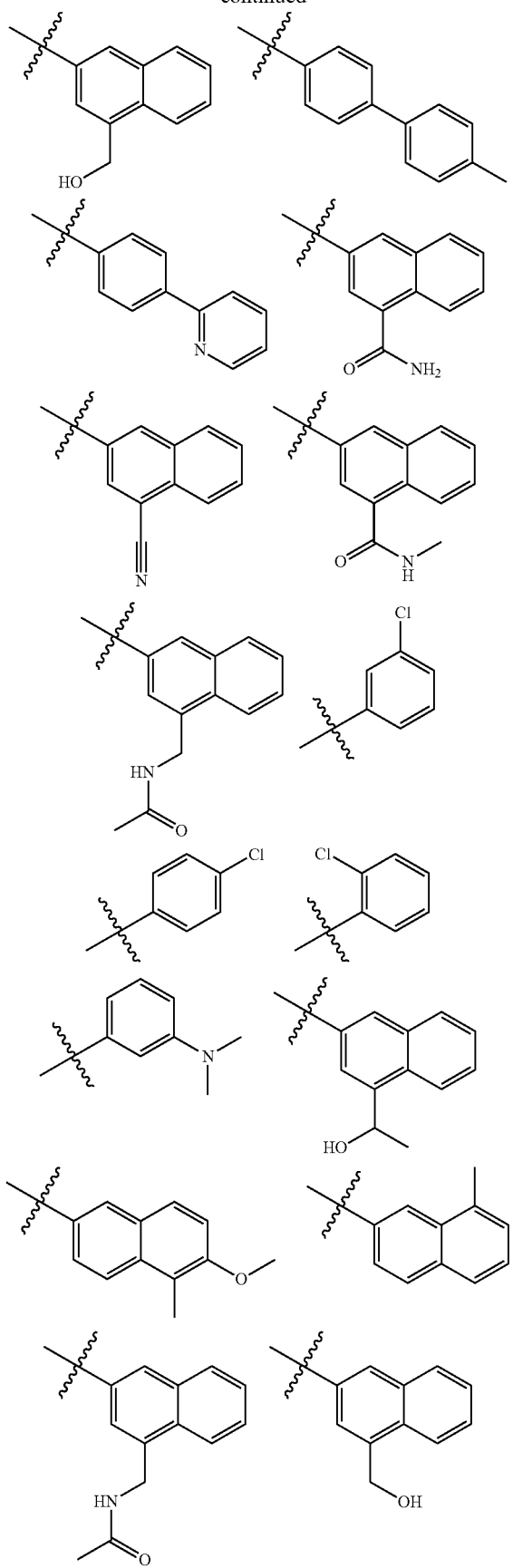
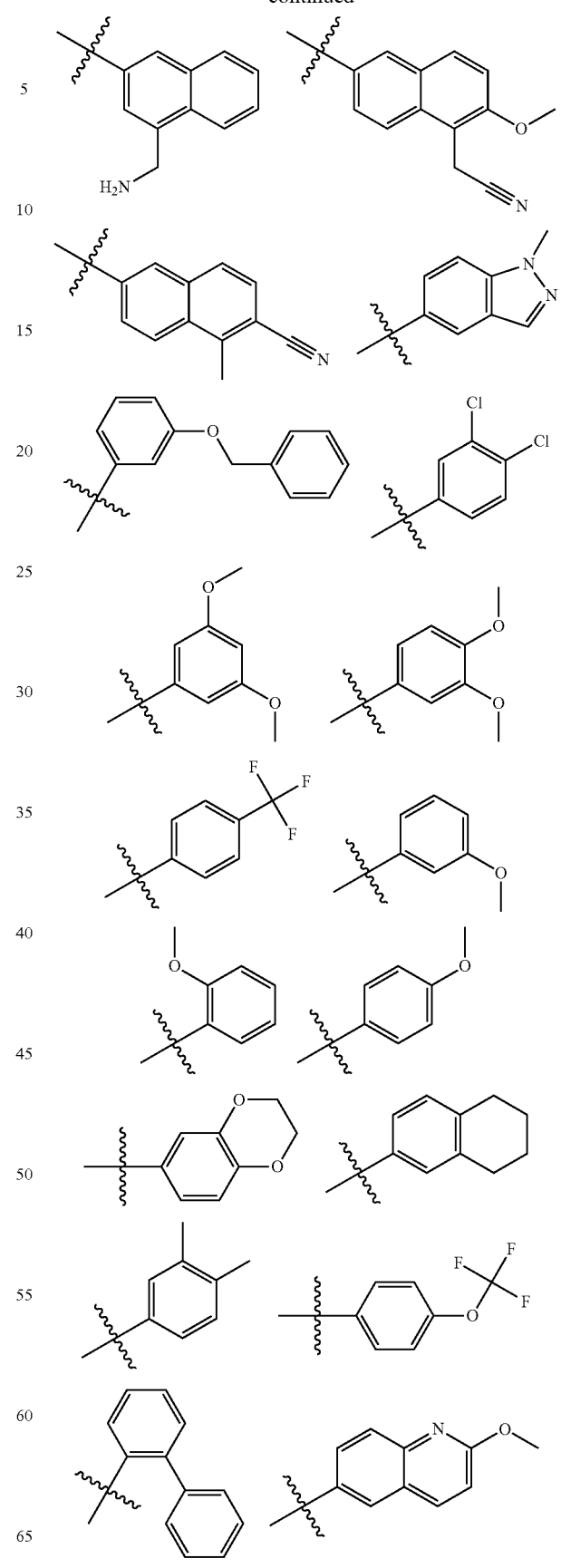

-continued
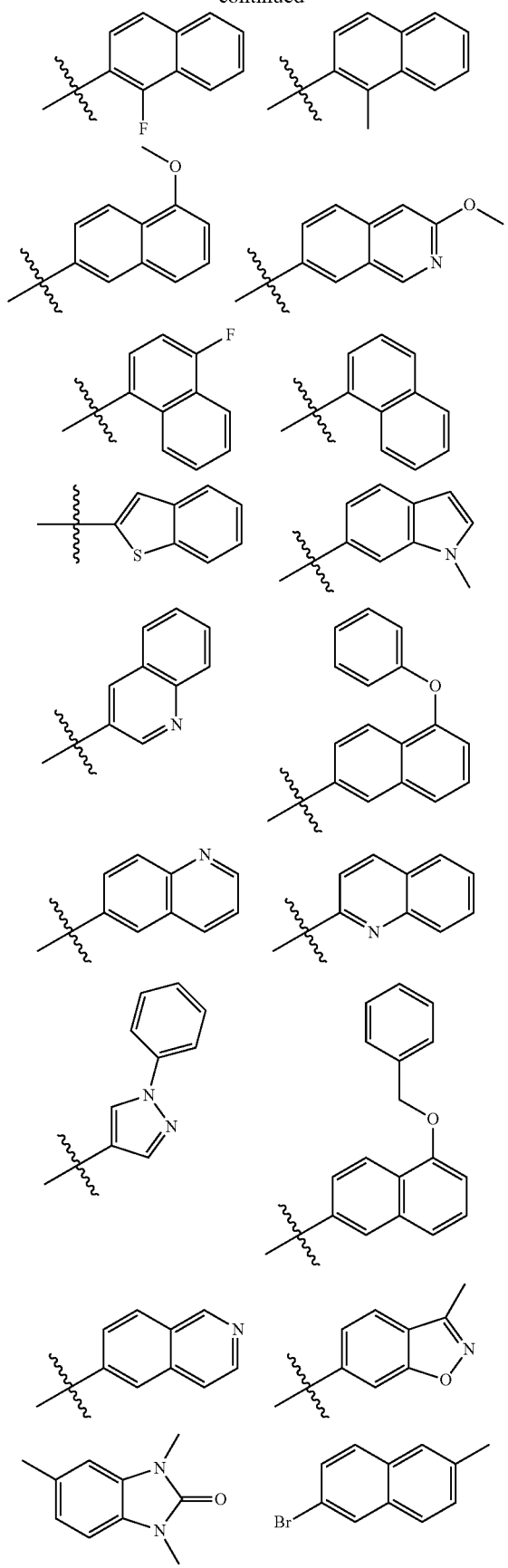
-continued
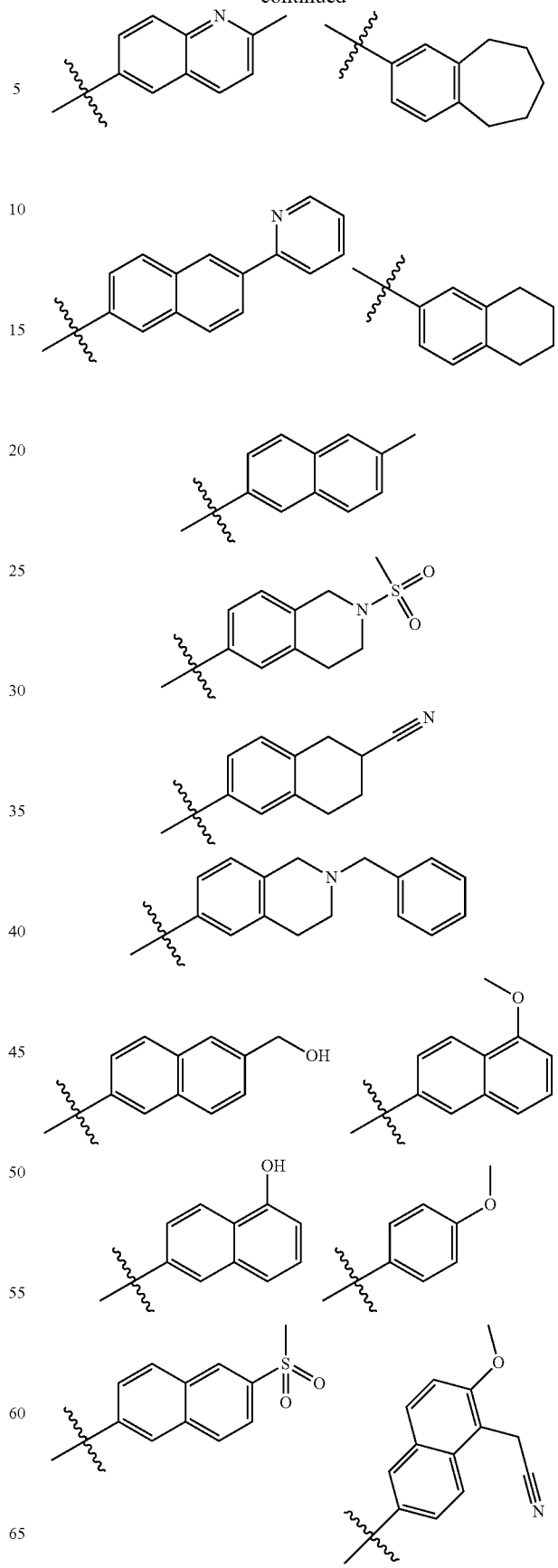

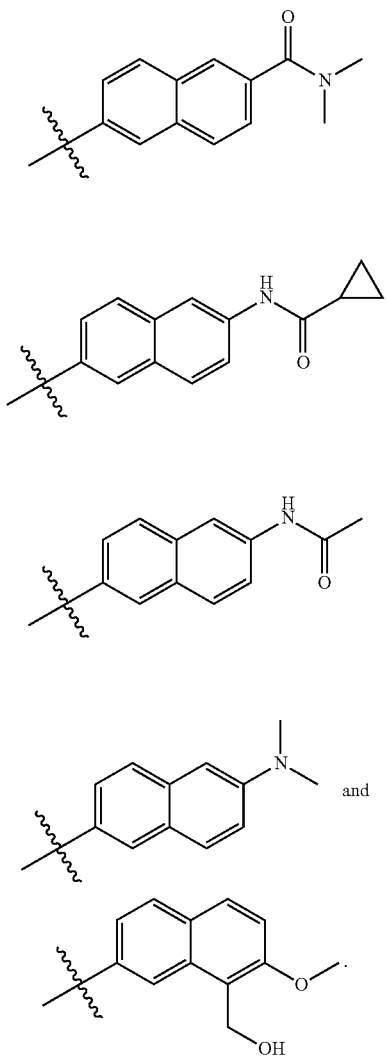
In one embodiment the compound is selected from the group consisting of:
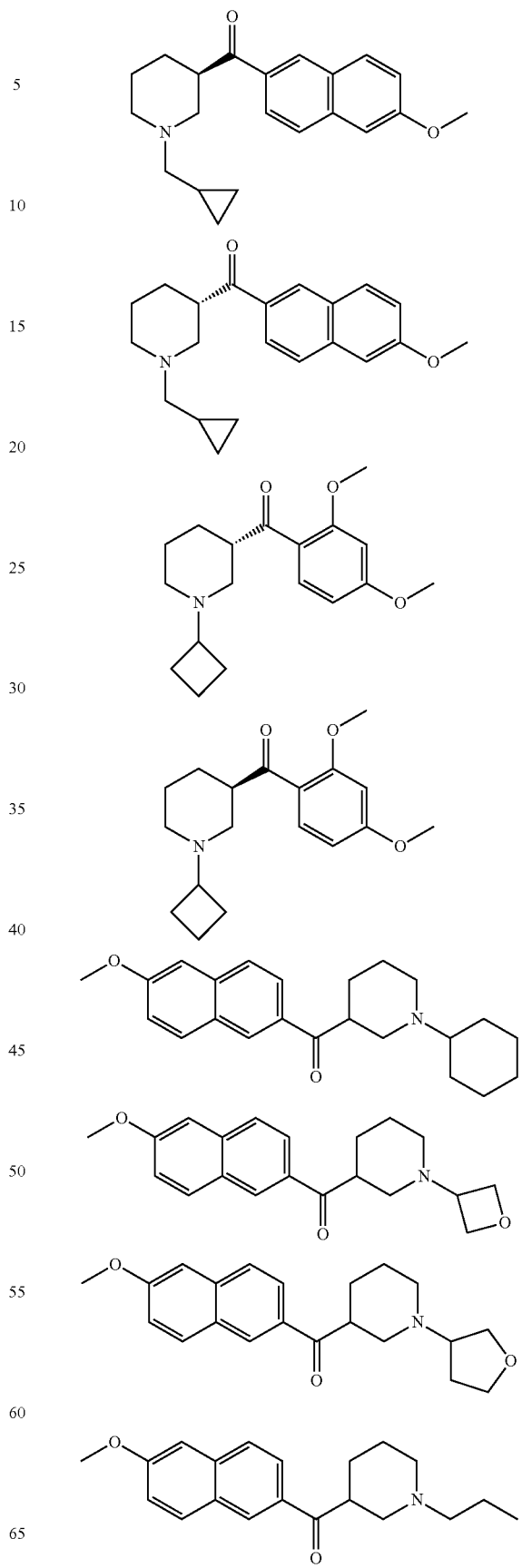

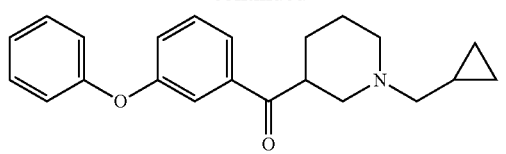
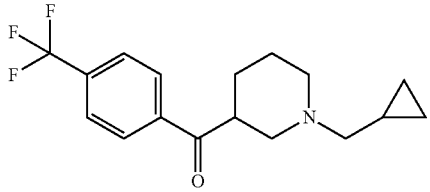
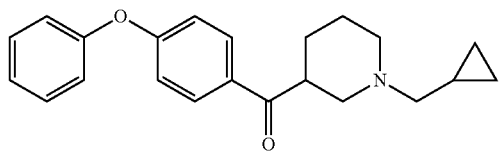
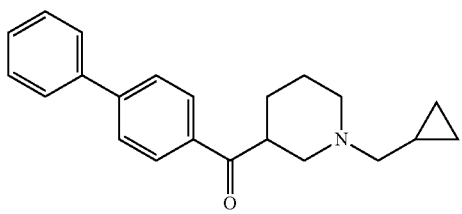
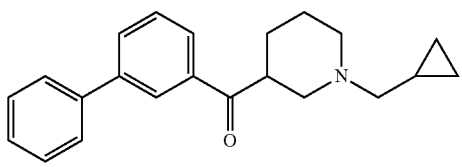
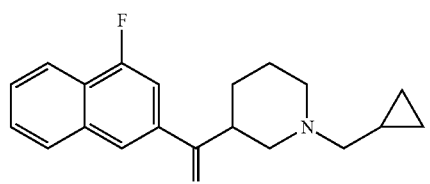
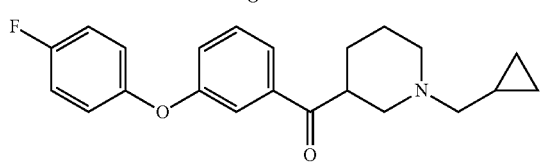
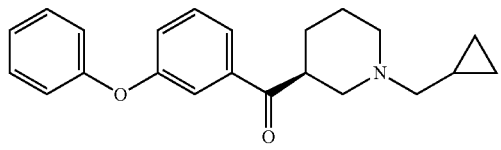
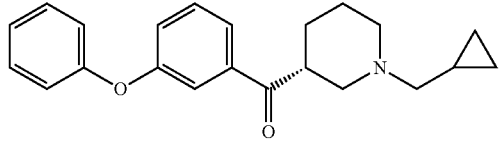
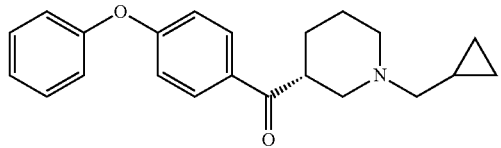
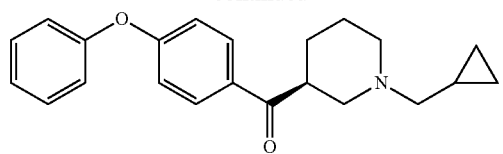
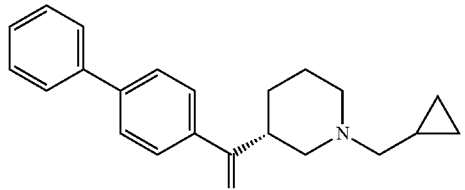
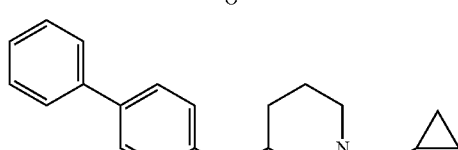
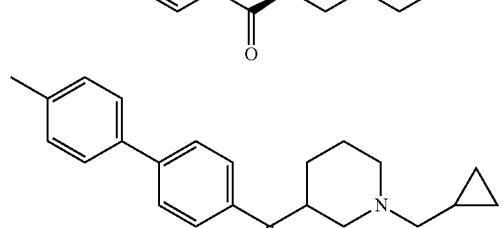
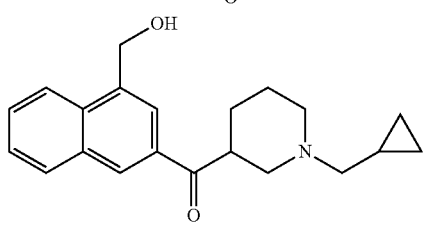
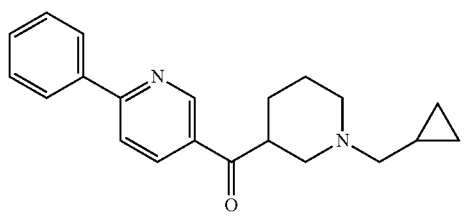
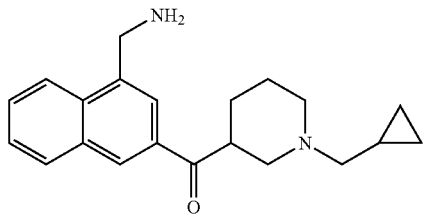
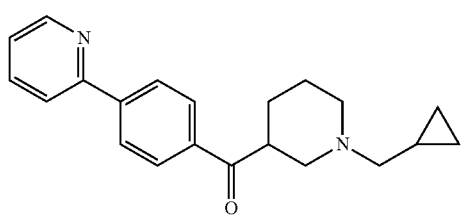

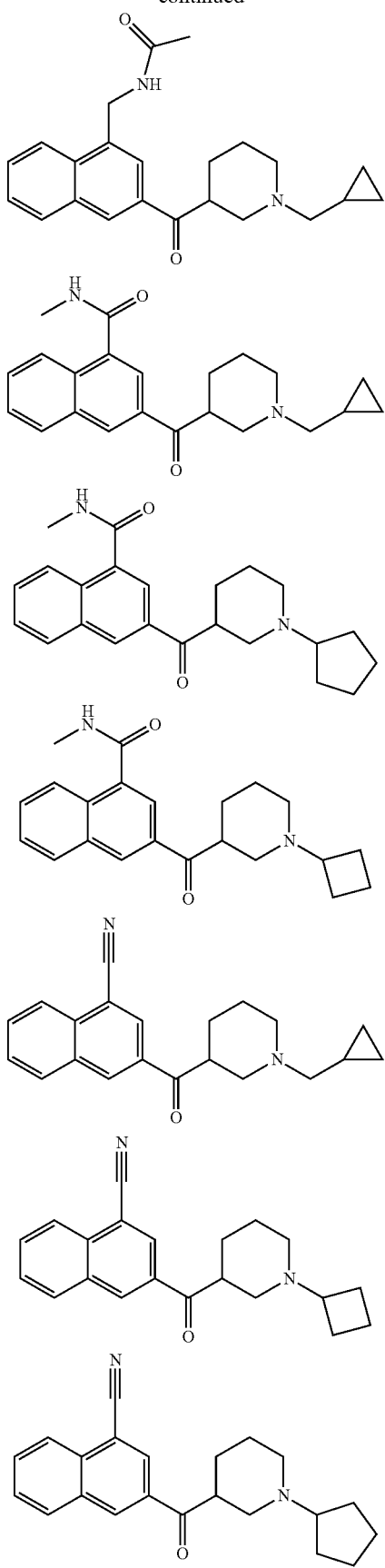
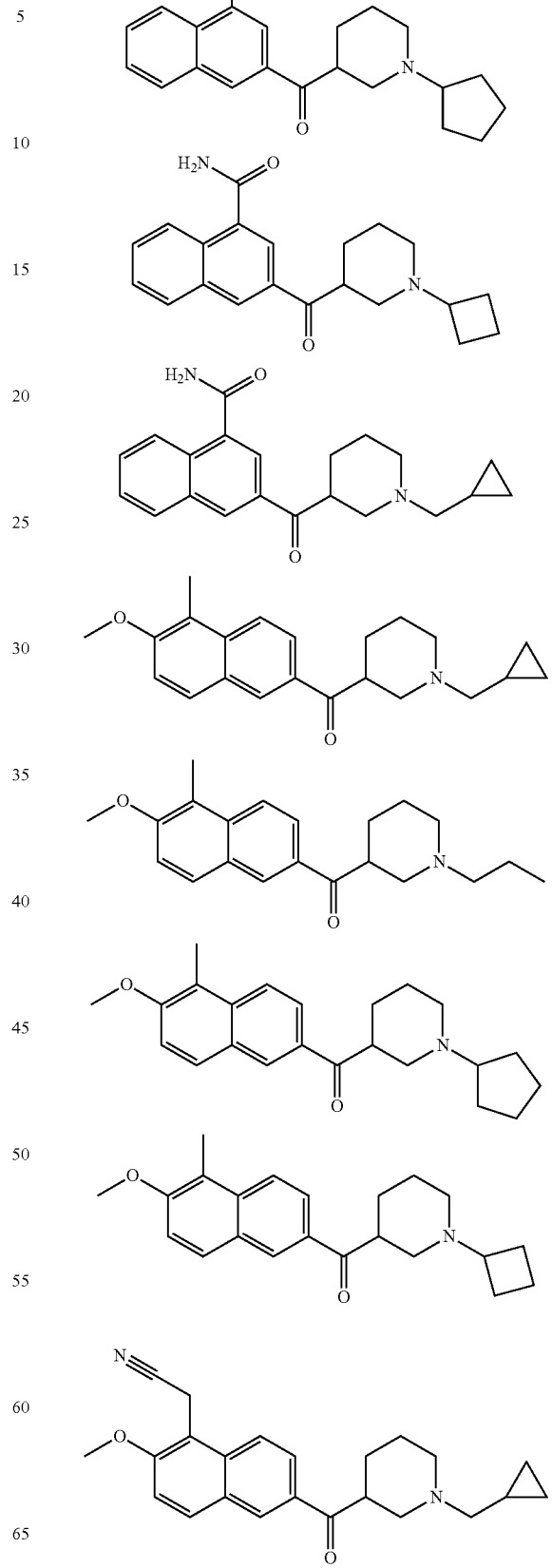

79
-continued
80
-continued
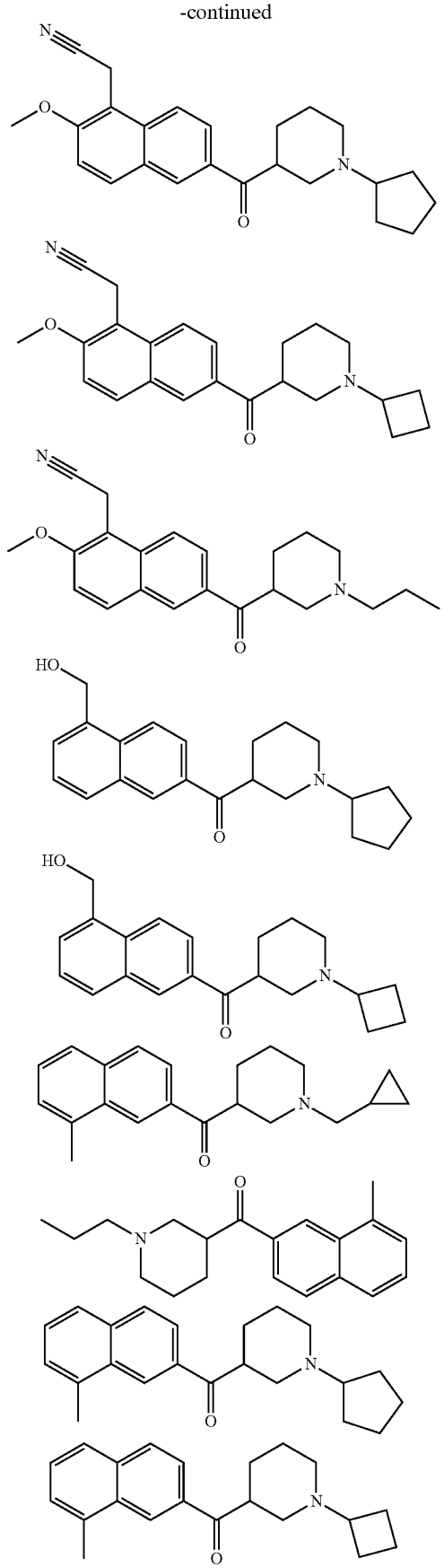
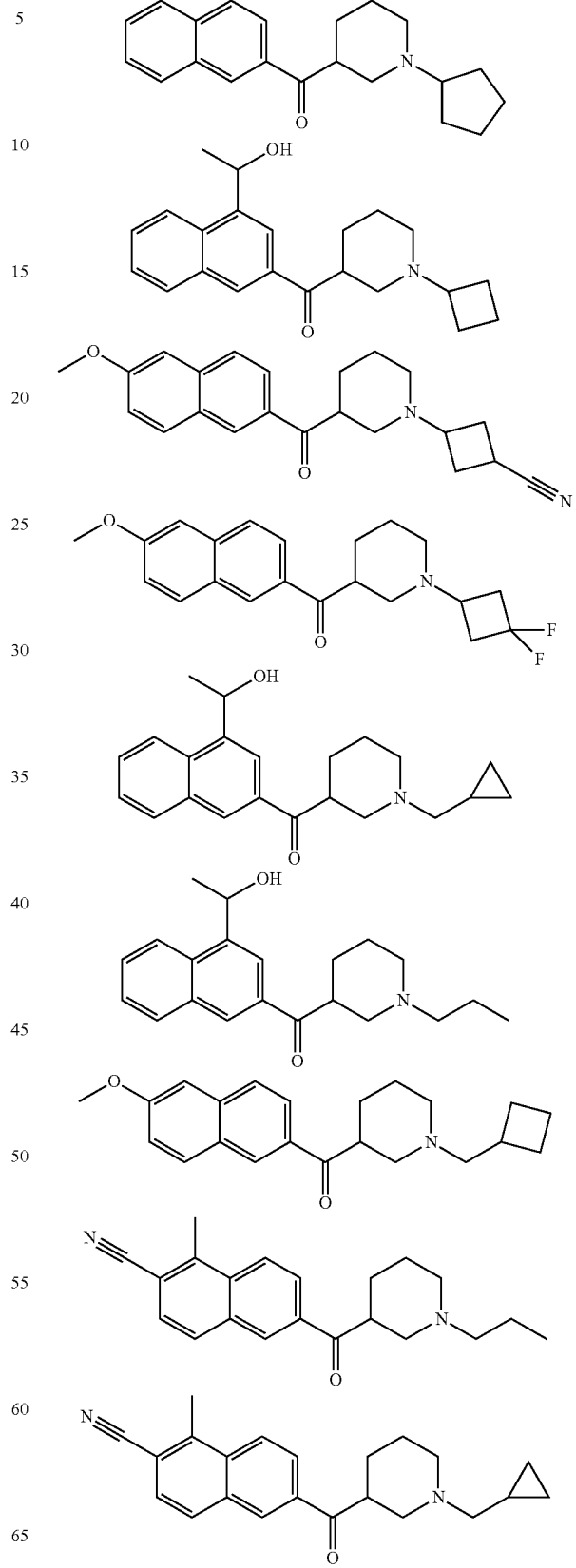

81
-continued
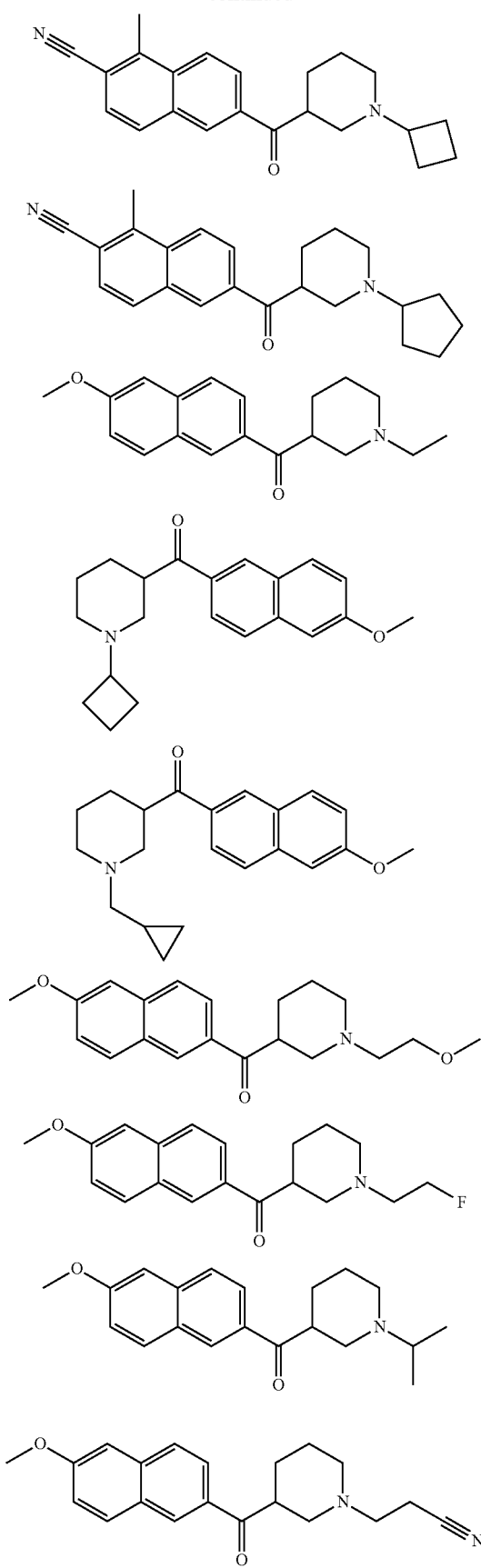
82
-continued
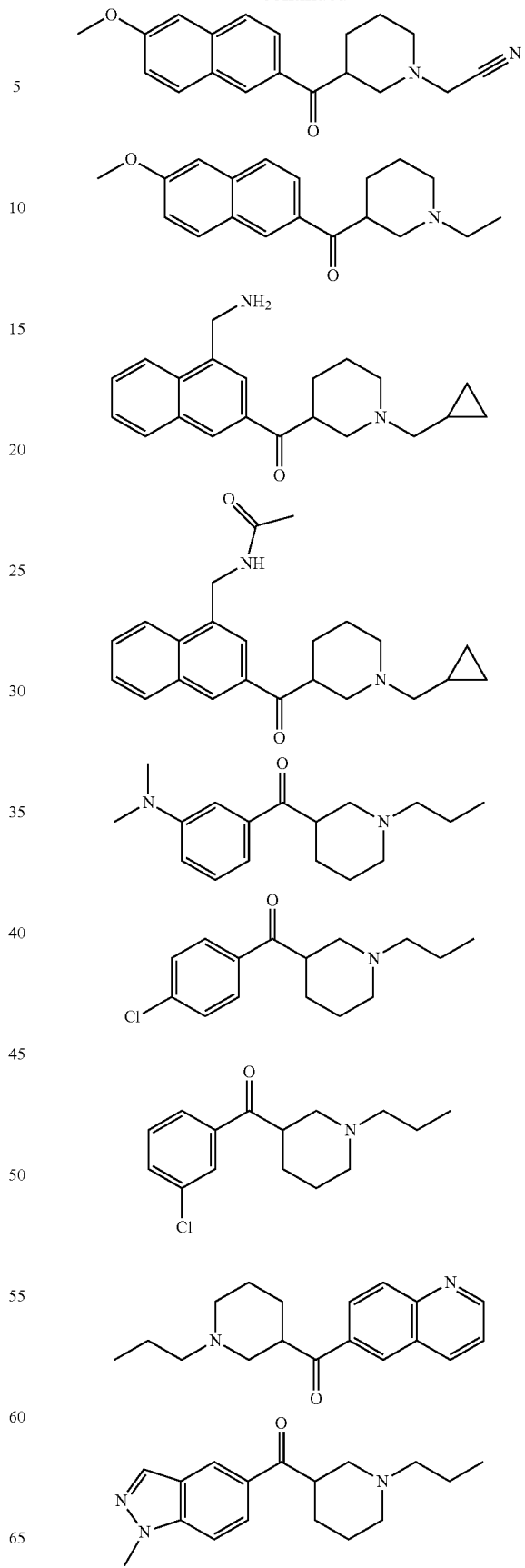

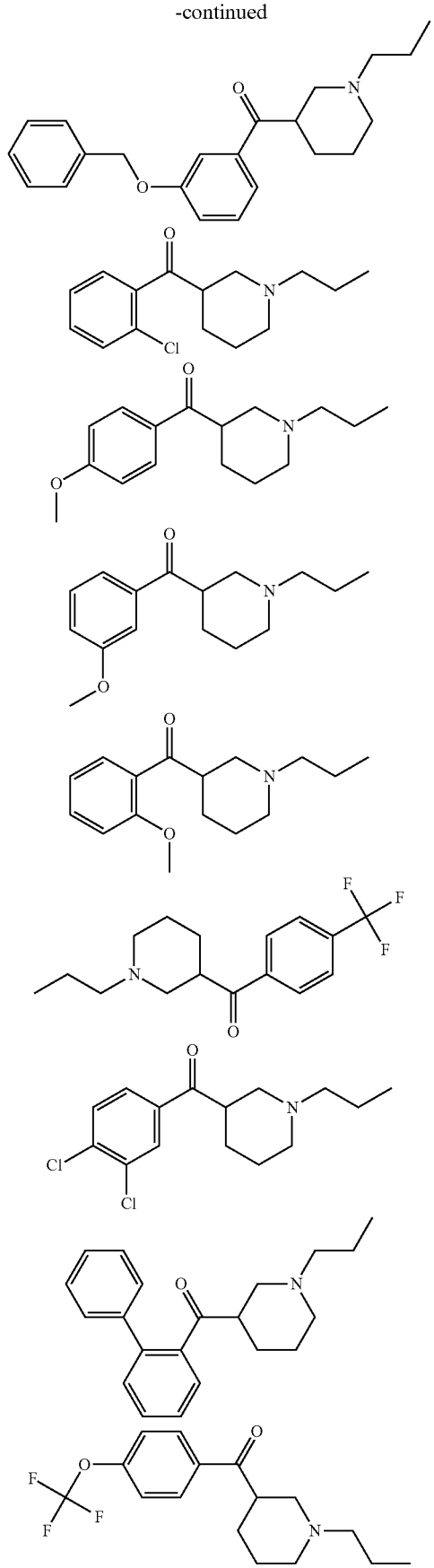
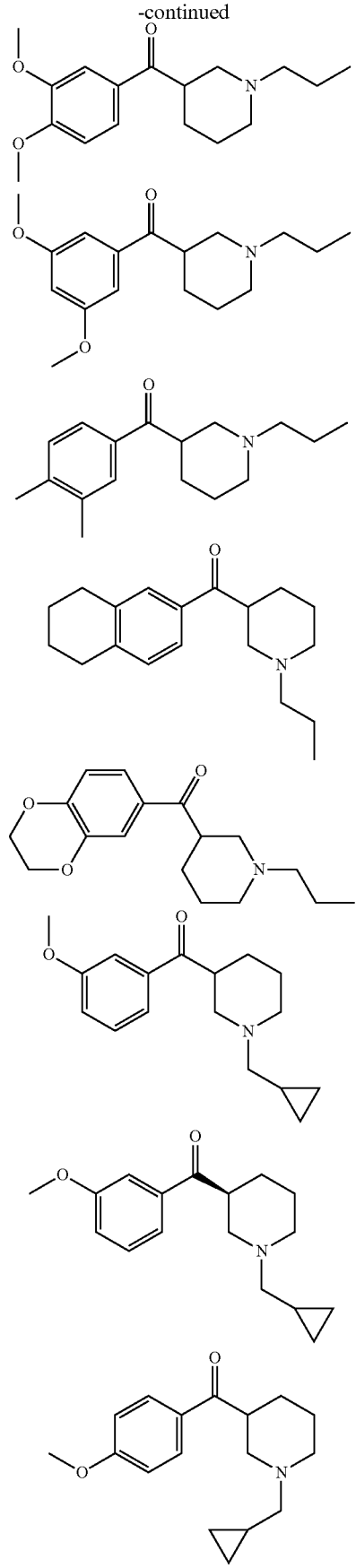

-continued
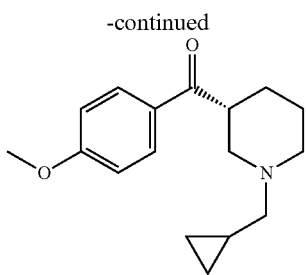
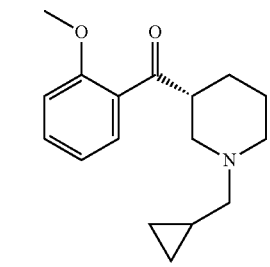
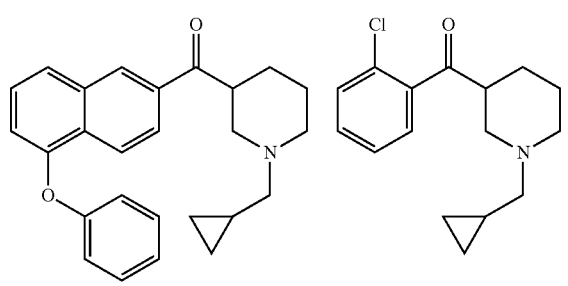
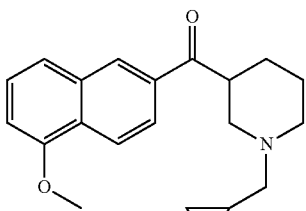
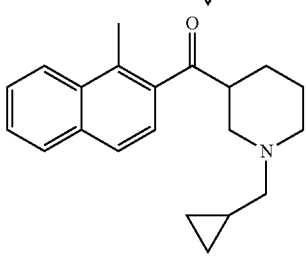
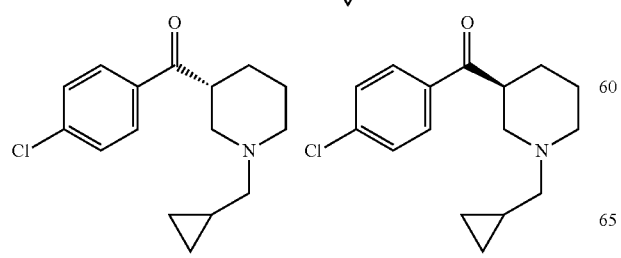
-continued
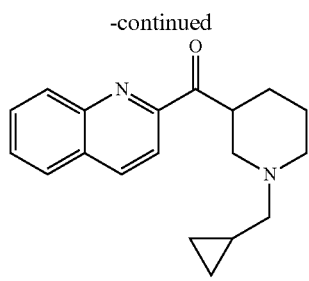
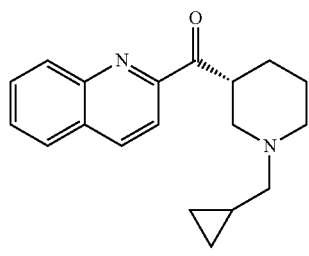
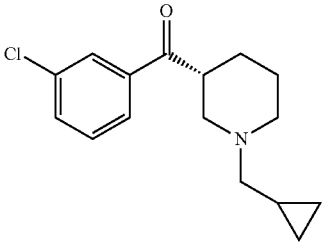
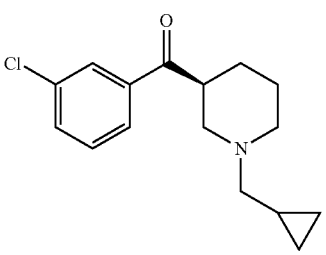
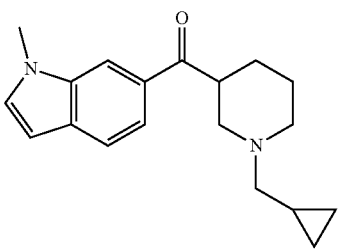
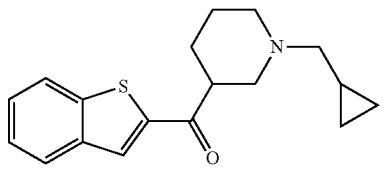
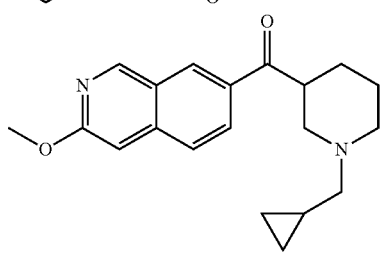

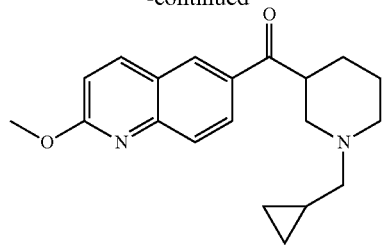
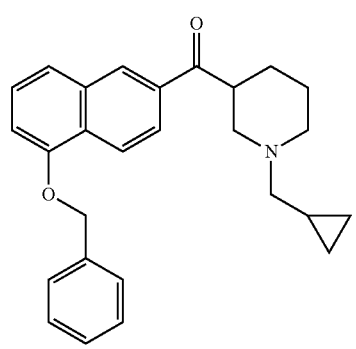
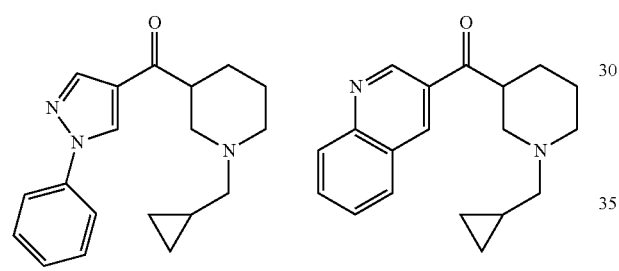
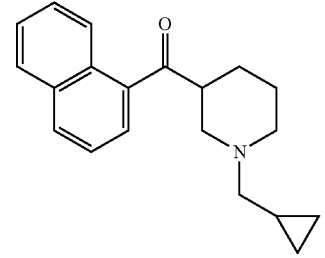
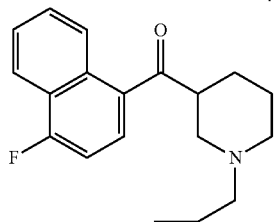
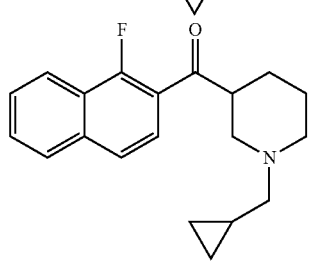
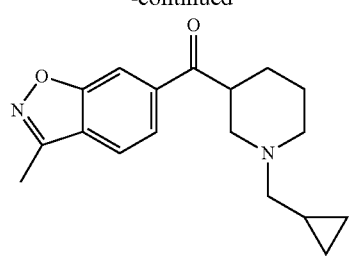
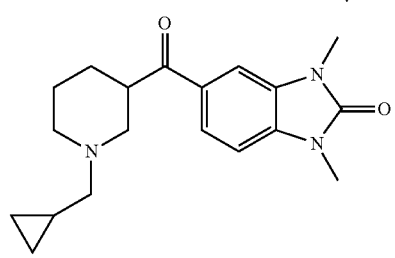
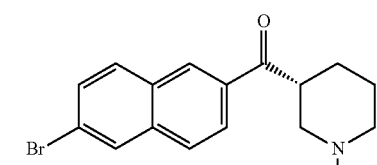
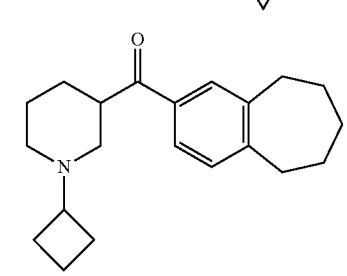
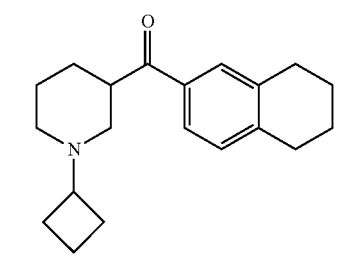
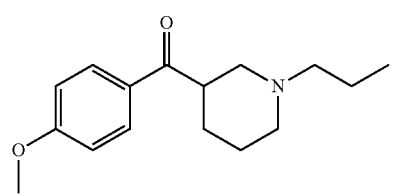

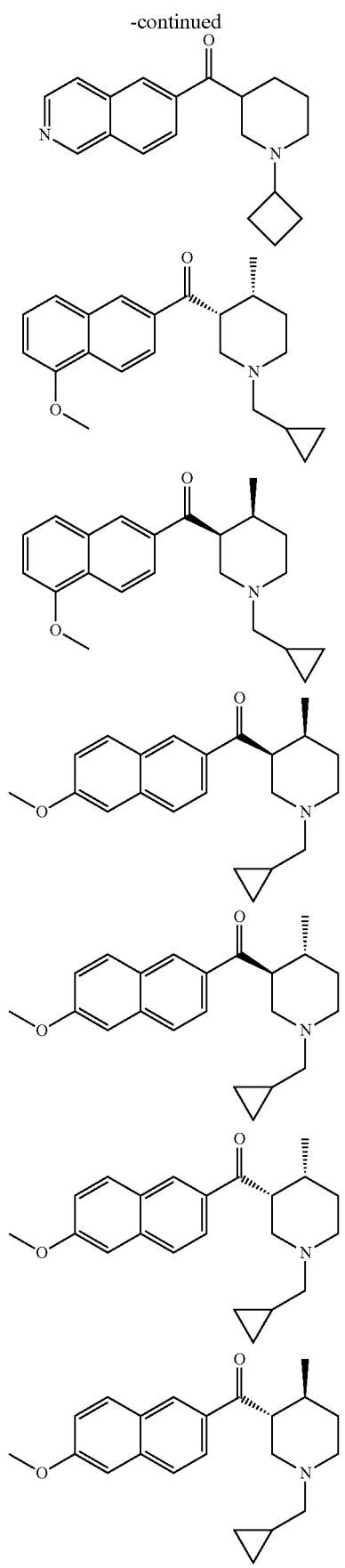
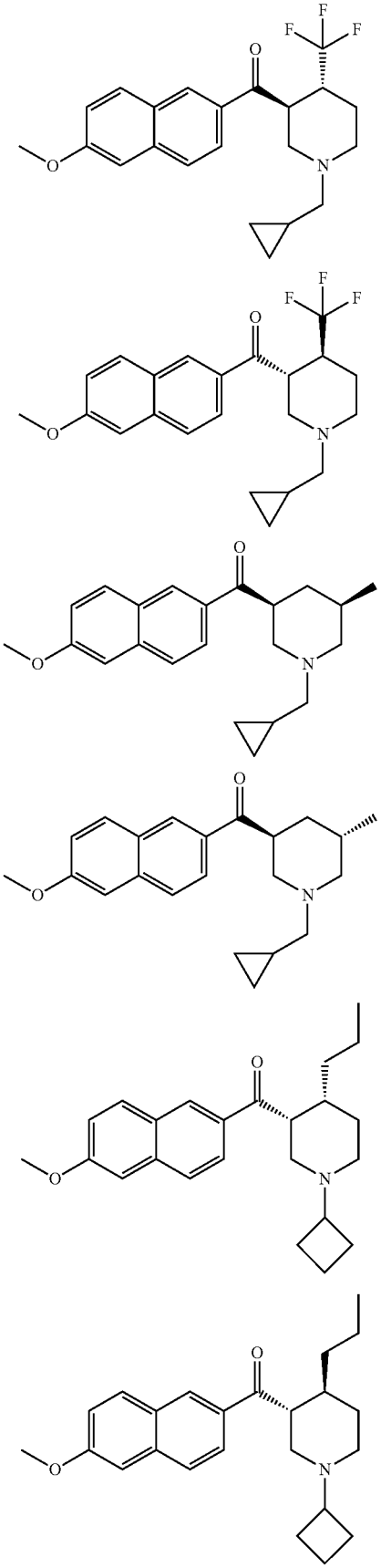

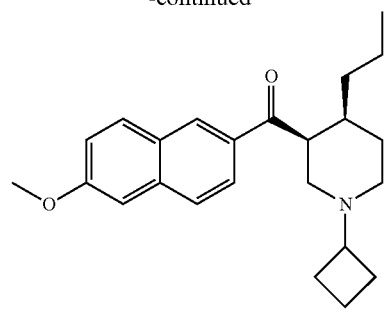
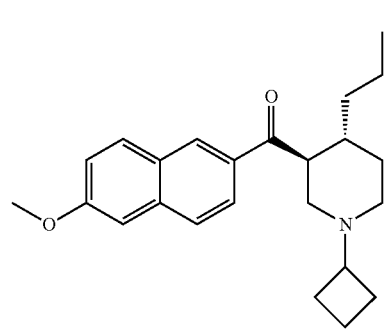
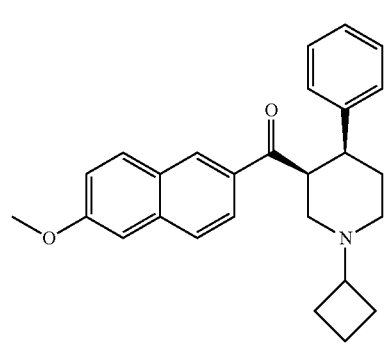
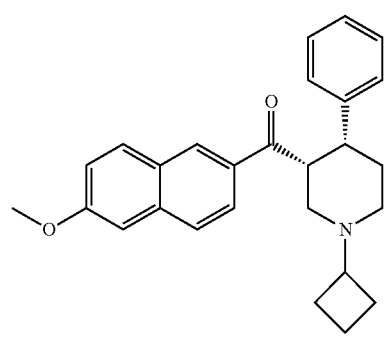
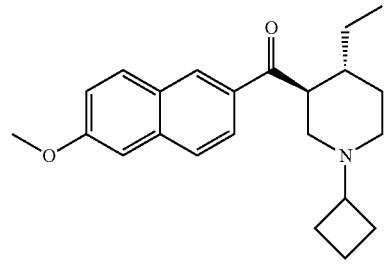
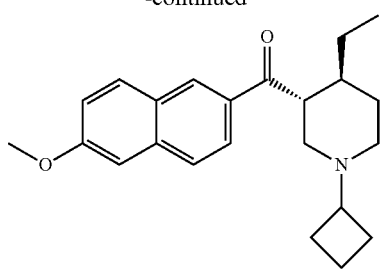
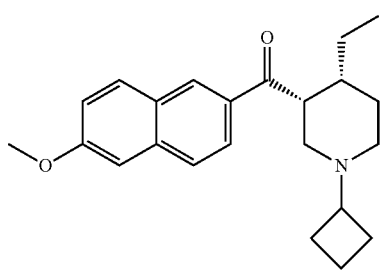
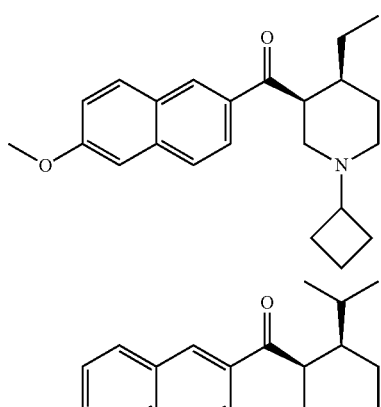
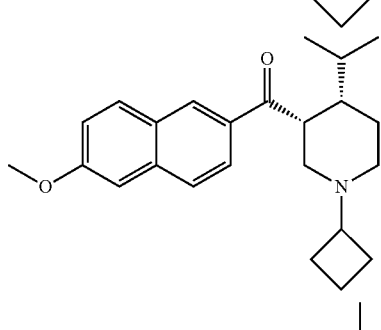
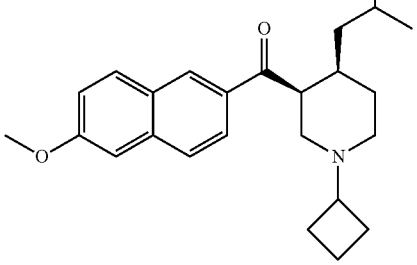

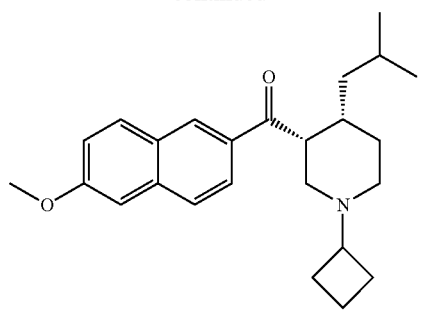
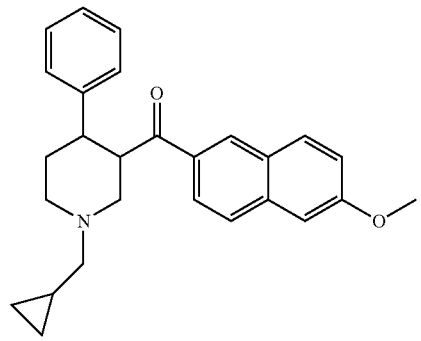
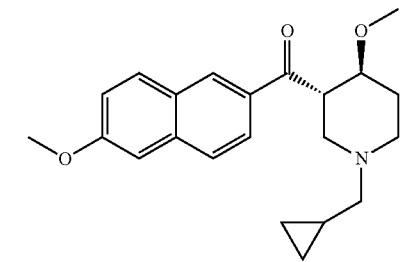
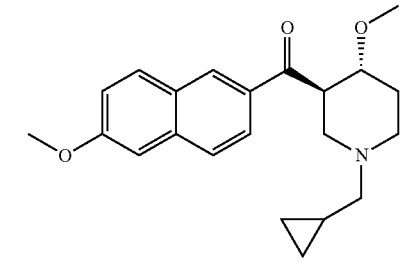
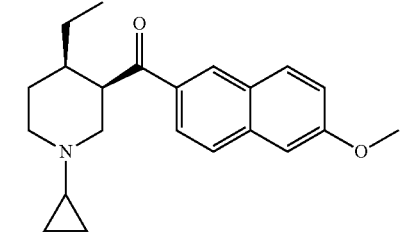
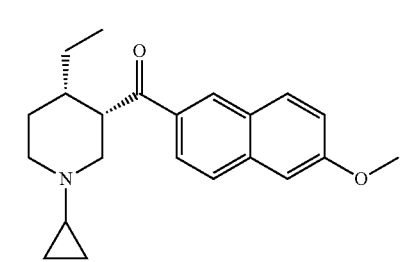
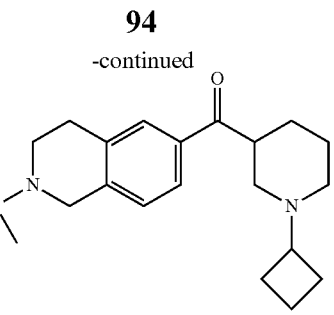
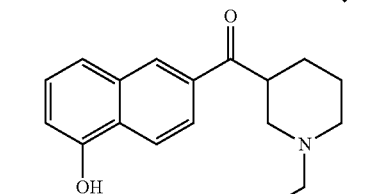
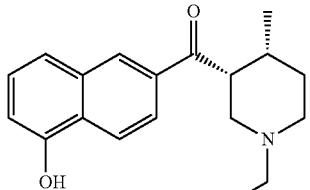
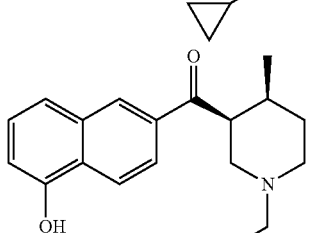
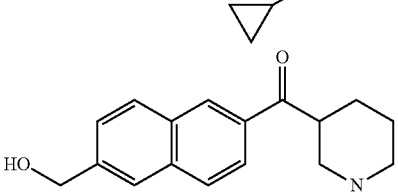
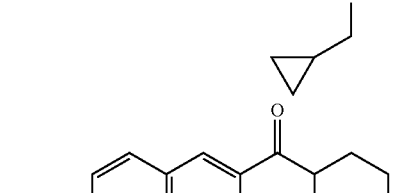
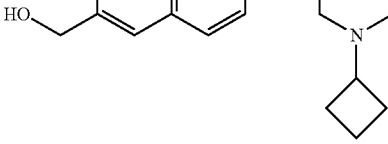
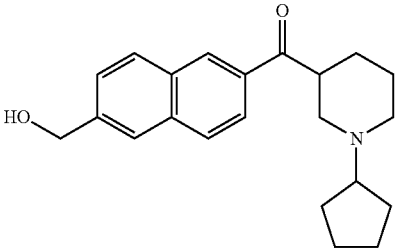

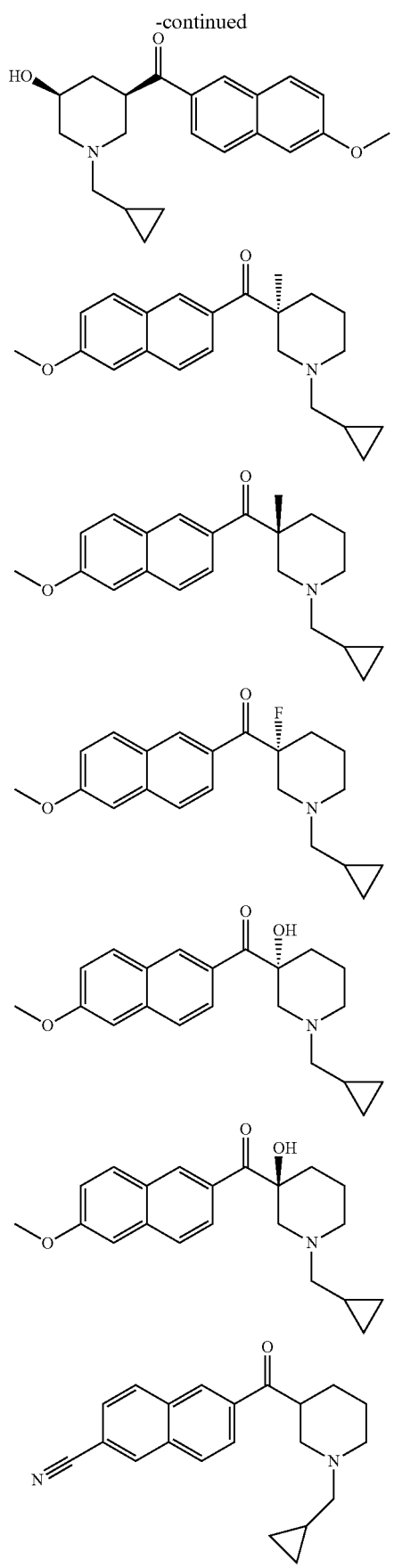
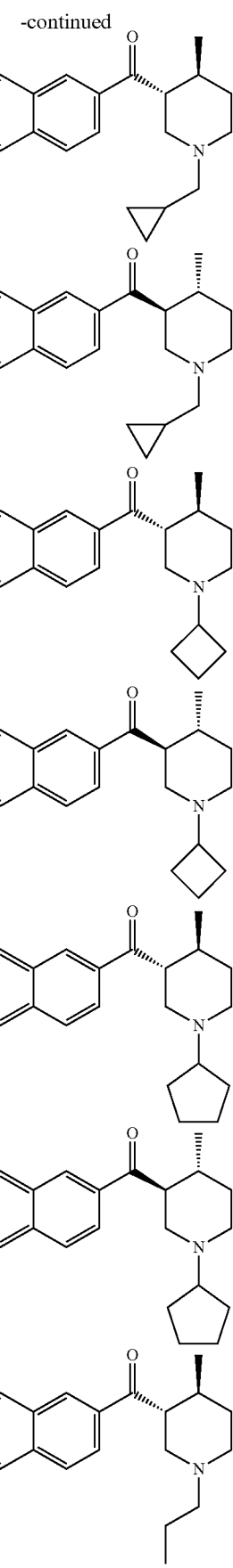

97
-continued
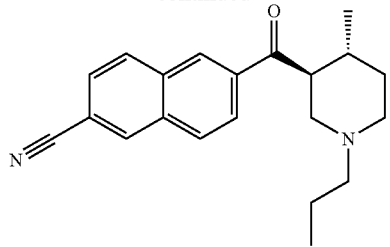
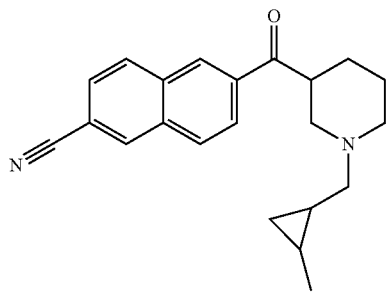
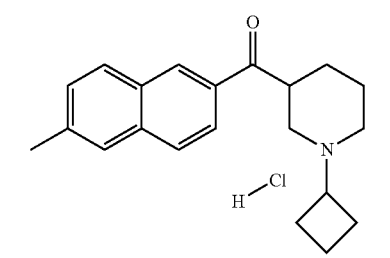
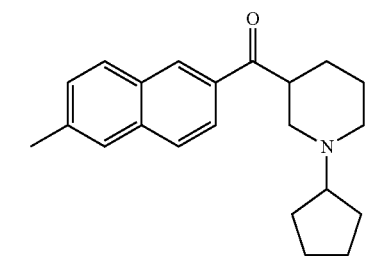
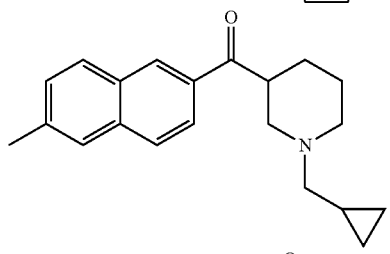
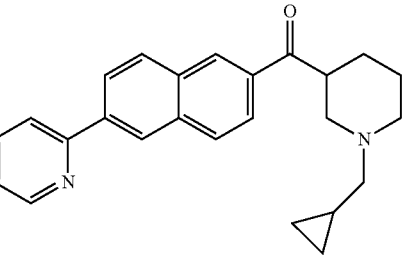
98
-continued
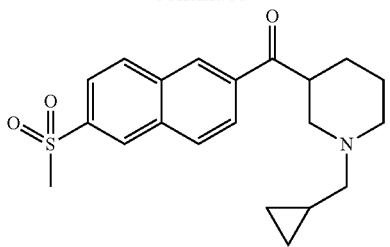
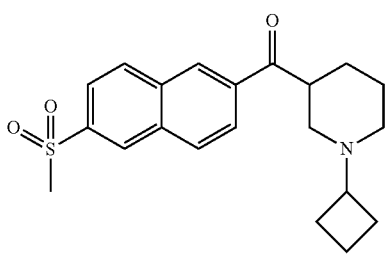
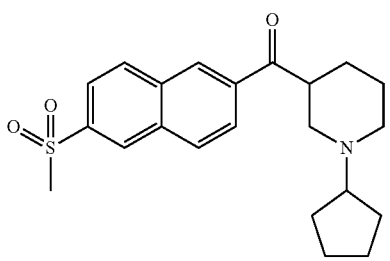
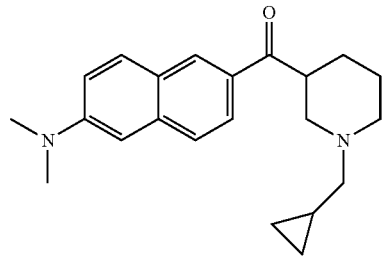
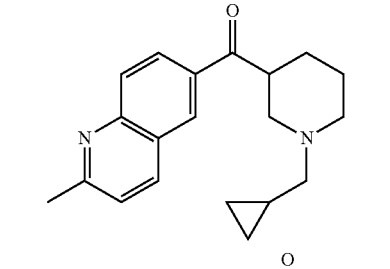
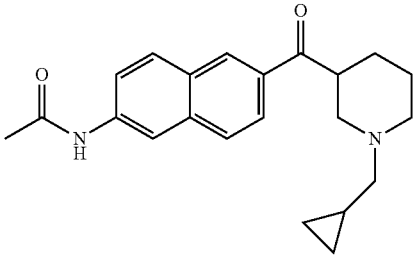

99
-continued
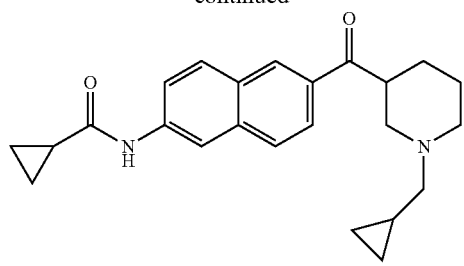
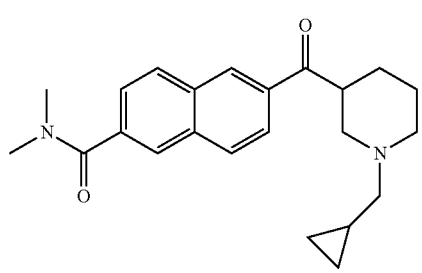
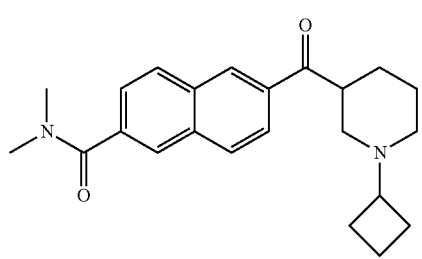
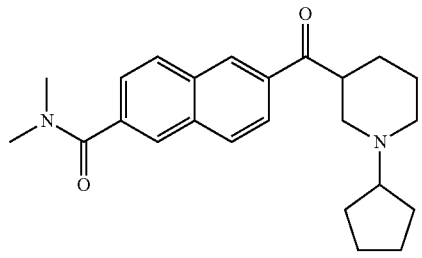
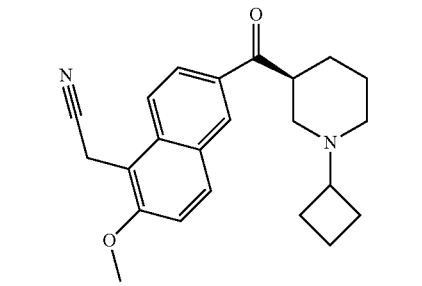
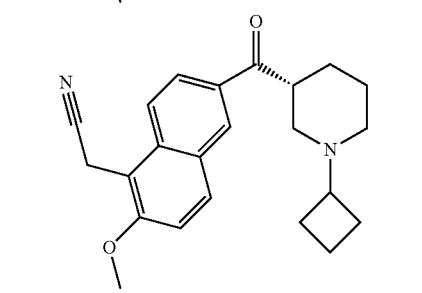
100
-continued
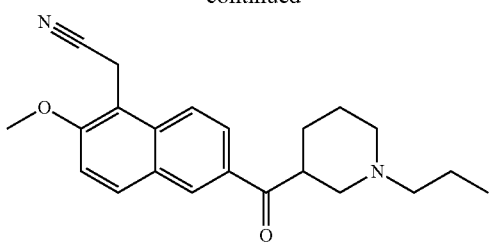
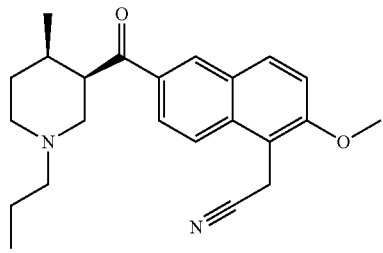
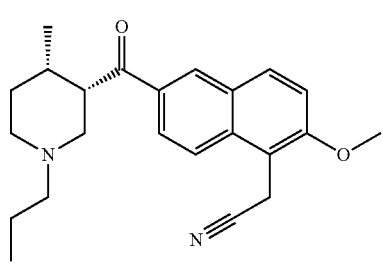
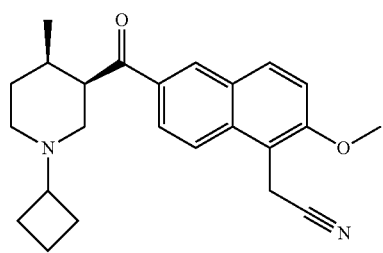
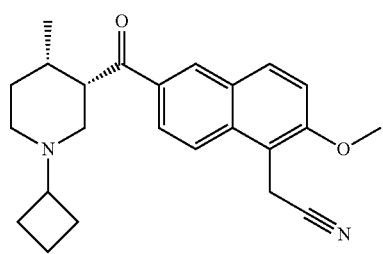
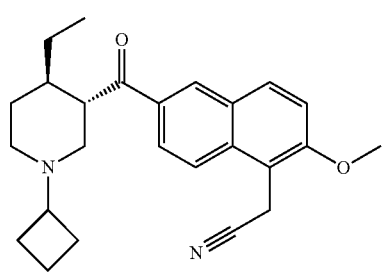

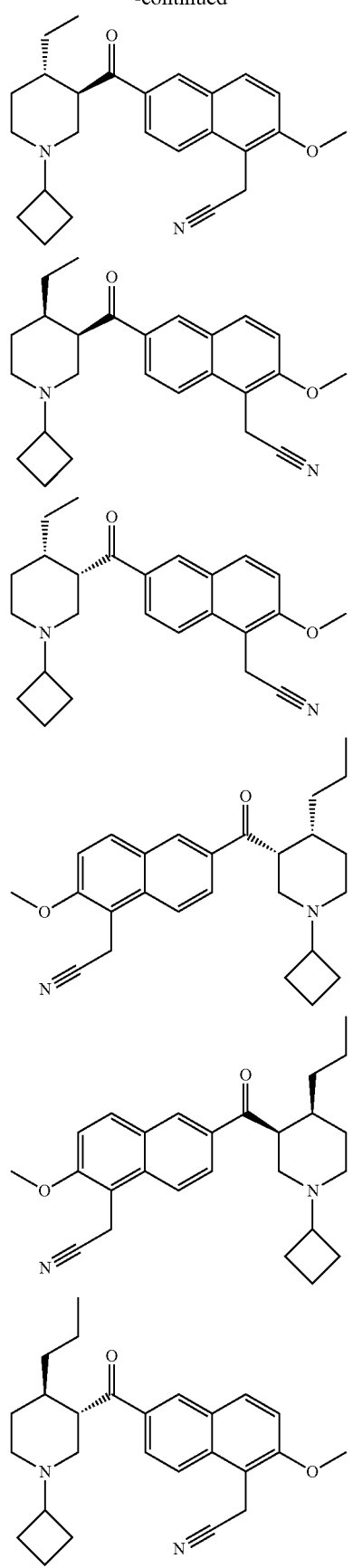
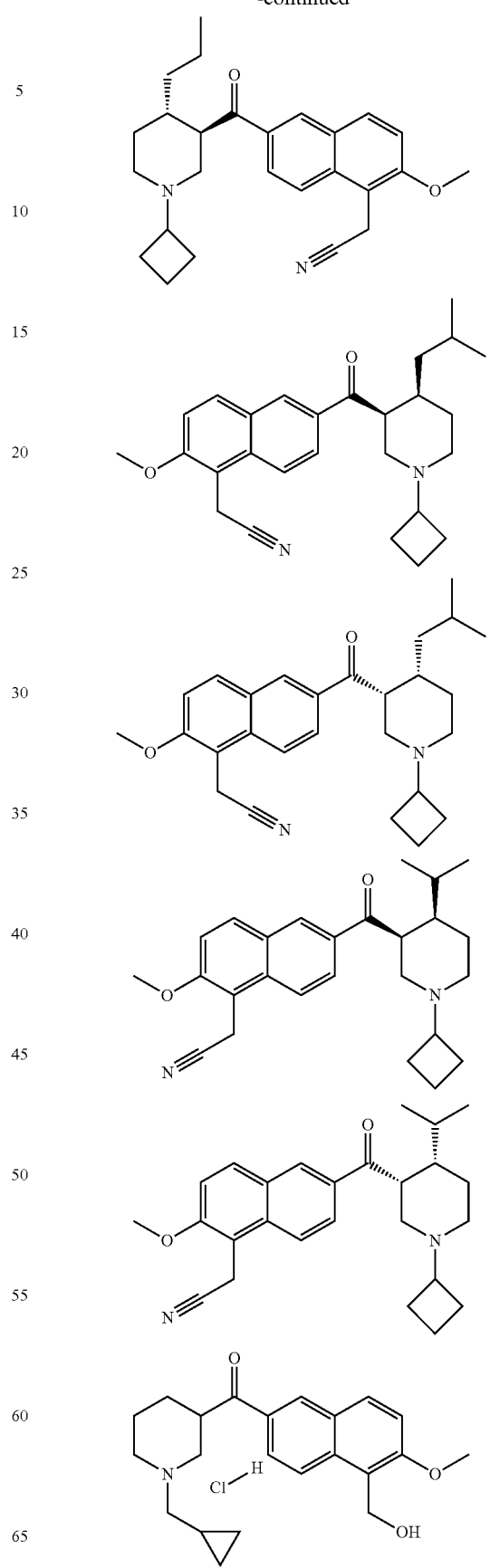

103
-continued
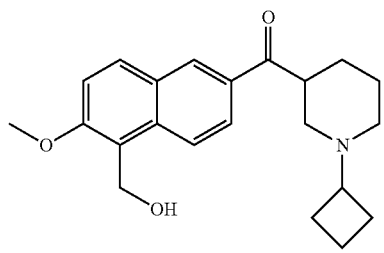
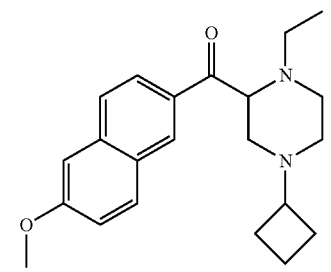
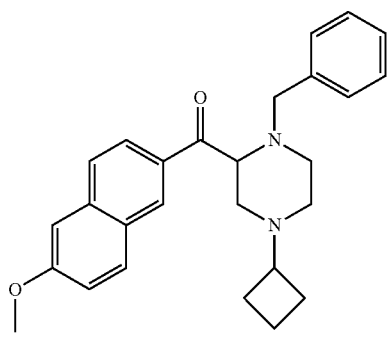
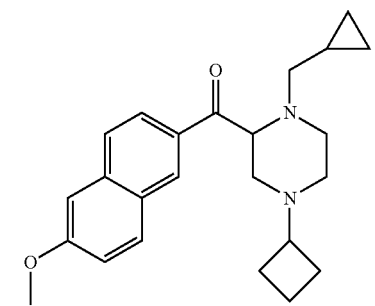
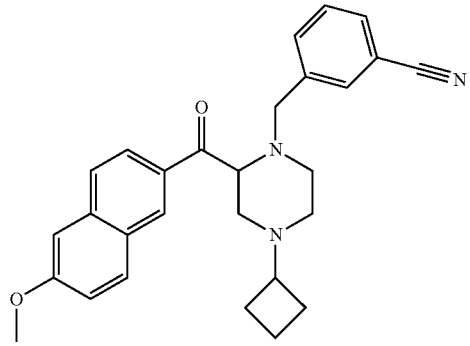
104
-continued
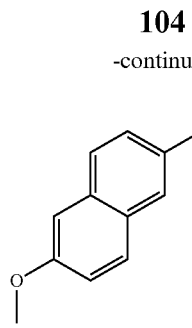
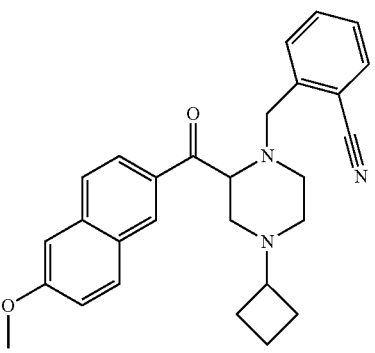
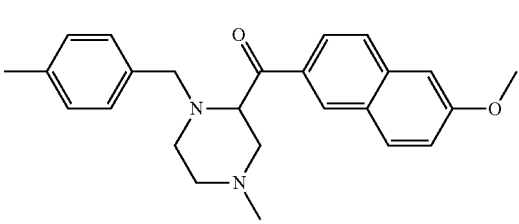
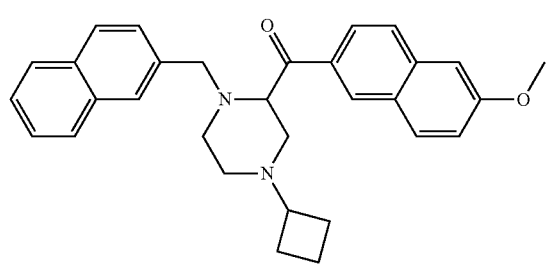
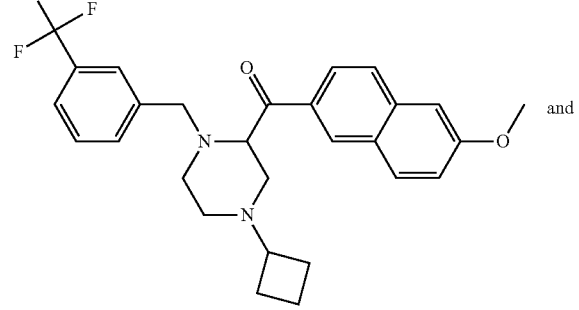 and -continued

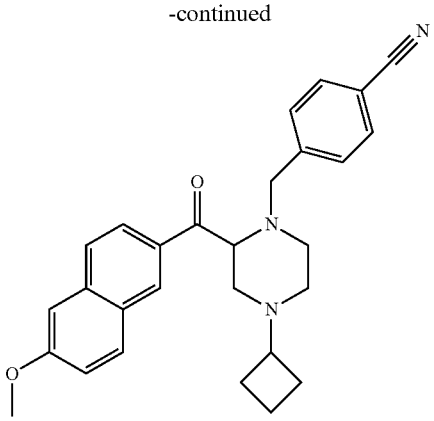

and salts thereof.

Uses, Formulation and Administration

Pharmaceutically Acceptable Compositions

Another aspect includes a pharmaceutical composition comprising a compound as described herein or a pharmaceutically acceptable salt thereof. In one embodiment, the composition further comprises a pharmaceutically acceptable carrier, adjuvant, or vehicle. In another embodiment, the composition further comprises an amount of the compound effective to measurably inhibit KDM2b. In certain embodiments, the composition is formulated for administration to a patient in need thereof certain embodiments.

The term "patient" or "individual" as used herein, refers to an animal, such as a mammal, such as a human. In one embodiment, patient or individual refers to a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions comprising a compound as described herein may be administered orally, parenterally, by inhalation spray, topically, transdermally, rectally, nasally, buccally, sublingually, vaginally, intraperitoneal, intrapulmonary, intradermal, epidural or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

In one embodiment, the composition comprising a compound as described herein is formulated as a solid dosage form for oral administration. Solid dosage forms for oral administration include capsules, tablets, pills, powders, and granules. In certain embodiments, the solid oral dosage form comprising a compound as described herein further comprises one or more of (i) an inert, pharmaceutically acceptable excipient or carrier, such as sodium citrate or dicalcium phosphate, and (ii) filler or extender such as starches, lactose, sucrose, glucose, mannitol, or silicic acid, (iii) binders such as carboxymethylcellulose, alginates, gelatin, polyvinylpyrrolidinone, sucrose or acacia, (iv) humectants such as glycerol, (v) disintegrating agent such as agar, calcium carbonate, potato or tapioca starch, alginic acid, certain silicates or sodium carbonate, (vi) solution retarding agents such as paraffin, (vii) absorption accelerators such as quaternary ammonium salts, (viii) a wetting agent such as cetyl alcohol or glycerol monostearate, (ix) absorbent such as kaolin or bentonite clay, and (x) lubricant such as talc, calcium stearate, magnesium stearate, polyethylene glycols or sodium lauryl sulfate. In certain embodiments, the solid oral dosage form is formulated as capsules, tablets or pills. In certain embodiments, the solid oral dosage form further comprises buffering agents. In certain embodiments, such compositions for solid oral dosage forms may be formulated as fillers in soft and hard-filled gelatin capsules comprising one or more excipients such as lactose or milk sugar, polyethylene glycols and the like.

In certain embodiments, tablets, dragees, capsules, pills and granules of the compositions comprising a compound as described herein optionally comprise coatings or shells such as enteric coatings. They may optionally comprise opacifying agents and can also be of a composition that they release the active ingredient(s) only, or preferentially, in a certain part of the intestinal tract, optionally, in a delayed manner. Examples of embedding compositions include polymeric substances and waxes, which may also be employed as fillers in soft and hard-filled gelatin capsules using such excipients as lactose or milk sugar as well as high molecular weight polethylene glycols and the like.

In another embodiment, a composition comprises microencapsulated compound as described herein, and optionally, further comprises one or more excipients.

In another embodiment, compositions comprise liquid dosage formulations comprising a compound as described herein for oral administration, and optionally further comprise one or more of pharmaceutically acceptable emulsions, microemulsions, solutions, suspensions, syrups and elixirs. In certain embodiments, the liquid dosage form optionally, further comprise one or more of an inert diluent such as water or other solvent, a solubilizing agent, and an emulsifier such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols or fatty acid esters of sorbitan, and mixtures thereof. In certain embodiments, liquid oral compositions optionally further comprise one or more adjuvant, such as a wetting agent, a suspending agent, a sweetening agent, a flavoring agent and a perfuming agent.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound as described herein, it may be desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In certain embodiments, the composition for rectal or vaginal administration are formulated as suppositories which can be prepared by mixing a compound as described herein with suitable non-irritating excipients or carriers such as cocoa butter, polyethylene glycol or a suppository wax, for example those which are solid at ambient temperature but liquid at body temperature and therefore melt in the rectum or vaginal cavity and release the compound.

Example dosage forms for topical or transdermal administration of a compound as described herein include ointments, pastes, creams, lotions, gels, powders, solutions, sprays, inhalants or patches. The compound as described herein is admixed under sterile conditions with a pharmaceutically acceptable carrier, and optionally preservatives or buffers. Additional formulation examples include an ophthalmic formulation, ear drops, eye drops, transdermal patches. Transdermal dosage forms can be made by dissolving or dispensing the compound as described herein in medium, for example ethanol or dimethylsulfoxide. Absorption enhancers can also be used to increase the flux of the compound across the skin. The rate can be controlled by either providing a rate controlling membrane or by dispersing the compound in a polymer matrix or gel.

Nasal aerosol or inhalation formulations of a compound as described herein may be prepared as solutions in saline, employing benzyl alcohol or other suitable preservatives, absorption promotors to enhance bioavailability, fluorocarbons, and/or other conventional solubilizing or dispersing agents.

In certain embodiments, pharmaceutical compositions may be administered with or without food. In certain embodiments, pharmaceutically acceptable compositions are administered without food. In certain embodiments, pharmaceutically acceptable compositions of this invention are administered with food.

Specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a compound as described herein in the composition will also depend upon the particular compound in the composition.

In one embodiment, the therapeutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 5 to about 100 mg of the compound of the invention.

An example tablet oral dosage form comprises about 2 mg, 5 mg, 25 mg, 50 mg, 100 mg, 250 mg or 500 mg of a compound as described herein, and further comprises about 95-30 mg anhydrous lactose, about 5-40 mg sodium croscarmellose, about 5-30 mg polyvinylpyrrolidone (PVP) K30 and about 1-10 mg magnesium stearate. The process of formulating the tablet comprises mixing the powdered ingredients together and further mixing with a solution of the PVP. The resulting composition can be dried, granulated, mixed with the magnesium stearate and compressed to tablet form using conventional equipment. An example of an aerosol formulation can be prepared by dissolving about 2-500 mg of a compound as described herein, in a suitable buffer solution, e.g. a phosphate buffer, and adding a tonicifier, e.g. a salt such sodium chloride, if desired. The solution may be filtered, e.g. using a 0.2 micron filter, to remove impurities and contaminants.

Uses of Compounds and Pharmaceutically Acceptable Compositions

Another aspect includes the use of a compound as described herein for the inhibition of KDM2b. Compounds as described herein may also be used to inhibit the removal of methyl marks on histone lysine residues, including inhibiting the removal of methyl marks from mono-, di- or tri-methylation of histones H1, H2A, H2B, H3 and H4, such as H3K36 (including for example the KDM2b substrate H3K36me2), thereby altering interactions of these histone proteins with DNA and/or other proteins, and altering certain subsequent genetic or protein expression. Compounds as described herein may also be used to inhibit KDM2b and reduce the activity of a cancer stein/progenitor cell population and/or deplete a cancer stem/progenitor cell population.

In certain embodiments, the binding or inhibition activity of a compound as described herein may be determined by running a competition experiment where the compound is incubated with the KDM2b enzyme bound to known radioligands. Detailed conditions for assaying a compound as an inhibitor of KDM2b or a mutant thereof are set forth in the Examples below.

In certain embodiments, detection of KDM2b activity is achieved with in vitro assays, which can be either direct binding (non-catalytic) or enzymatic (catalytic) assays. Types of substrates that are used in such assays may include: short synthetic peptides corresponding to a number of residues from the N-terminus of histone sequences comprising the target lysine residue, single recombinant histone polypeptides, histone octamers reconstituted with recombinant histone proteins, and reconstituted nucleosomes (using reconstituted octamers and specific recombinant DNA fragments). The reconstituted nucleosomes may be mononucleosomes or oligonucleosomes.

Another aspect includes a method of treating or preventing a disease responsive to the inhibition of KDM2b activity in a patient. The method includes administering a therapeutically effective amount of a compound as described herein to a patient in need thereof.

Another aspect includes the use of a compound as described herein, in therapy. Another aspect includes the use of a pharmaceutical composition comprising a compound as described herein, in therapy.

Another aspect includes the use of a compound as described herein, in treating a disease associated with KDM2b activity. Another aspect includes the use of a pharmaceutical composition comprising a compound as described herein, in treating a disease associated with KDM2b activity.

Another aspect includes the use of a compound as described herein, in the manufacture of a medicament for the treatment of a disease associated with KDM2b activity. Another aspect includes the use of a pharmaceutical composition comprising a compound as described herein, in the manufacture of a medicament for the treatment of a disease associated with KDM2b activity.

In certain embodiments, the disease or condition is a hyperproliferative disease, cancer, stroke, diabetes, hepatomegaly, cardiovascular disease, multiple sclerosis, Alzheimer's disease, cystic fibrosis, viral disease, autoimmune diseases, atherosclerosis, restenosis, psoriasis, rheumatoid arthritis, inflammatory bowel disease, asthma, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, liver disease, pathologic immune conditions involving T cell activation, CNS disorders or a myeloproliferative disorder.

In certain embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Another aspect includes a method for treating, ameliorating or preventing cancer, drug-resistant cancer or another proliferative disorder by administration of an effective amount of a compound as described herein to a mammal, for example a human, in need of such treatment. In certain embodiments, the disease to be treated is cancer.

Examples of cancers that may be treated using the compounds and methods described herein include, but are not limited to, adrenal cancer, acinic cell carcinoma, acoustic neuroma, acral lentigious melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, androgen dependent cancer, angioimmunoblastic T-cell lymphoma, angiomyolipoma, angiosarcoma, astrocytoma, atypical teratoid rhabdoid tumor, B-cell chronic lymphocytic leukemia, B-cell lymphoma, basal cell carcinoma, biliary tract cancer, bladder cancer, blastoma, bone cancer, Brenner tumor, Brown tumor, Burkitt's lymphoma, breast cancer (e.g., triple negative-breast cancer), brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, leukemia, leydig cell tumor, liposarcoma, lung cancer, lymphangioma, lymphangiosarcoma, lymphoepithelioma, lymphoma, acute lymphocytic leukemia (e.g., T-cell or B-cell), acute myelogeous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, acute myeloid leukemia, chronic myeloid leukemia, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor and Wilms' tumor.

Another embodiment includes a method for the treatment of benign proliferative disorders. Examples of benign proliferative disorders include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma and juvenile polyposis syndrome.

Another embodiment includes a therapeutic method useful for modulating protein methylation, gene expression, cell proliferation, cell differentiation and/or apoptosis in vivo in diseases mentioned above, in particular cancer, comprising administering to a patient in need of such therapy a pharmacologically active and therapeutically effective amount of one or more of the compounds as described herein.

Another embodiment includes a method for regulating endogenous or heterologous promotor activity by contacting a cell with a compound as described herein.

Another embodiment includes the use of a compound as described herein for the production of pharmaceutical compositions which are employed for the treatment and/or prophylaxis and/or amelioration of the diseases, disorders, illnesses and/or conditions as mentioned herein.

Another embodiment includes the use of a compound as described herein for the production of pharmaceutical compositions which are employed for the treatment and/or prophylaxis of diseases and/or disorders responsive or sensitive to the inhibition of histone demethylases, particularly those diseases mentioned above, such as e.g. cancer.

Compounds as described herein may be administered using any amount and any route of administration effective for treating or lessening the severity of the disorder. The exact amount required will vary from patient to patient, depending on the species, age, and general condition of the patient, for example the severity of the disorder, the particular compound, its mode of administration, and the like. The total daily usage of a compound as described herein by a given patient will be decided by the attending physician within the scope of sound medical judgment. The specific effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Another embodiment includes a method of inhibiting KDM2b activity in a biological sample comprising contacting said biological sample with a compound as described herein.

The term "biological sample", as used herein, includes, without limitation, a cell, cell cultures or extracts thereof; biopsied material obtained from a mammal or extracts thereof; and blood, saliva, urine, feces, semen, tears, or other body fluids or extracts thereof.

Co-Administration of Compounds and Other Agents

The compound as described herein may be employed alone or in combination with other agents for treatment. For example, the second agent of the pharmaceutical combination formulation or dosing regimen may have complementary activities to the compound as described herein such that they do not adversely affect each other. The compounds may be administered together in a unitary pharmaceutical composition or separately. In one embodiment a compound or a pharmaceutically acceptable salt can be co-administered with a cytotoxic agent to treat proliferative diseases and cancer.

The term "co-administering" refers to either simultaneous administration, or any manner of separate sequential administration, of a compound as described herein, and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Typically, any agent that has activity against a disease or condition being treated may be co-administered. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound as described herein and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG(geldanamyein), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranrnbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) antiandrogens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the antiinterleukin-12 (ABT-874/J695, Wyeth Research and Abbott Laboratories) which is a recombinant exclusively human-sequence, full-length IgG$_1$ λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., J. Biol. Chem. 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenylamino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quirtolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyOmethoxy]phenyl]-6[5[[[2methylsulfonypethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-Smith-Kline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOSC or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicarn, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

Chemotherapeutic agents also include treatments for Alzheimer's Disease such as donepezil hydrochloride and rivastigmine; treatments for Parkinson's Disease such as L-DOPA/carbidopa, entacapone, ropinrole, pramipexole, bromocriptine, pergolide, trihexephendyl, and amantadine; agents for treating multiple sclerosis (MS) such as beta interferon (e.g., Avonex® and Rebif®), glatiramer acetate, and mitoxantrone; treatments for asthma such as albuterol and montelukast sodium; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Additionally, chemotherapeutic agents include pharmaceutically acceptable salts, acids or derivatives of any of chemotherapeutic agents, described herein, as well as combinations of two or more of them.

The amount of both the compound as described herein and additional agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

The additional therapeutic agent and the compound as described herein may act synergistically. Therefore, the amount of additional therapeutic agent in such compositions may be less than that required in a monotherapy utilizing only that therapeutic agent, or there may be fewer side effects for the patient given that a lower dose is used. In certain embodiments, in such compositions a dosage of between 0.01-1,000 µg/kg body weight/day of the additional therapeutic agent can be administered.

In particular, provided herein are methods of treating cancer in an individual comprising administering to the individual (a) a compound as described herein and (b) a cytotoxic agent (e.g., targeted therapy, chemotherapy, and/or radiotherapy).

In certain embodiments of any of the methods, the cytotoxic agent is a targeted therapy. In certain embodiments, the targeted therapy is one or more of an EGFR antagonist, RAF inhibitor, and/or PI3K inhibitor.

In certain embodiments of any of the methods, the targeted therapy is an EGFR antagonist. In certain embodiments of any of the methods, the EGFR antagonist is N-(3-ethynylphenyl)-6,7-bis(2-methoxyethoxy)-4-quinazolinamine and/or a pharmaceutical acceptable salt thereof. In certain embodiments, the EGFR antagonist is N-(3-ethynylphenyl)-6,7-bis(2-methoxyethoxy)-4-quinazolinamine. In certain embodiments, the EGFR antagonist is N-(4-(3-fluorobenzyloxy)-3-chlorophenyl)-6-(5-((2-(methylsulfonyl)ethylamino)methyl)furan-2-yl)quinazolin-4-amine,di4-methylbenzenesulfonate or a pharmaceutically acceptable salt thereof (e.g., lapatinib).

In certain embodiments of any of the methods, targeted therapy is a RAF inhibitor. In certain embodiments, the RAF inhibitor is a BRAF inhibitor. In certain embodiments, the RAF inhibitor is a CRAF inhibitor. In certain embodiments, the BRAF inhibitor is vemurafenib. In certain embodiments, the RAF inhibitor is 3-(2-cyanopropan-2-yl)-N-(4-methyl-3-(3-methyl-4-oxo-3,4-dihydroquinazolin-6-ylamino)phenyl)benzamide or a pharmaceutically acceptable salt thereof (e.g, AZ628 (CAS#878739-06-1)).

In certain embodiments of any of the methods, the targeted therapy is a PI3K inhibitor.

In certain embodiments of any of the methods, the cytotoxic agent is chemotherapy. In certain embodiments of any of the methods, the chemotherapy is a taxane. In certain embodiments, the taxane is paclitaxel. In certain embodiments, the taxane is docetaxel.

In certain embodiments of any of the methods, the cytotoxic agent is a platinum agent. In certain embodiments, the platinum agent is carboplatin. In certain embodiments, the platinum agent is cisplatin. In certain embodiments of any of the methods, the cytotoxic agent is a taxane and a platinum agent. In certain embodiments, the taxane is paclitaxel. In certain embodiments, the taxane is docetaxel. In certain embodiments, the platinum agent is carboplatin. In certain embodiments, the platinum agent is cisplatin.

In certain embodiments of any of the methods, the cytotoxic agent is a vinea alkyloid. In certain embodiments, the vinca alkyloid is vinorelbine. In certain embodiments of any of the methods, the chemotherapy is a nucleoside analog. In certain embodiments, the nucleoside analog is gemcitabine.

In certain embodiments of any of the methods, the cytotoxic agent is radiotherapy.

In certain embodiments of any of the methods, the compound as described herein is concomitantly administered with the cytotoxic agent (e.g., targeted therapy, chemotherapy, and/or radiotherapy). In certain embodiments, the compound as described herein is administered prior to and/or concurrently with the cytotoxic agent (e.g., targeted therapy, chemotherapy, and/or radiotherapy).

In certain embodiments of any of the methods, the cancer is lung cancer (e.g., non-small cell lung cancer), breast cancer (e.g., triple-negative breast cancer), pancreatic cancer, leukemia (e.g., AML, CML, ALL (e.g., T-cell or B-cell), MLL), lymphoma, bladder cancer, prostate cancer and/or seminoma. In certain embodiments, the cancer is lung. In certain embodiments, the lung cancer is NSCLC. In certain embodiments, the cancer is leukemia. In certain embodiments, the cancer is lymphoma.

EXEMPLIFICATION

As depicted in the Examples below, in certain exemplary embodiments, compounds are prepared according to the following general procedures. It will be appreciated that, although the general methods depict the synthesis of certain compounds, the following general methods, and other methods known to one of ordinary skill in the art, can typically be applied to all compounds and subclasses and species of each of these compounds, as described herein.

The general synthetic methods illustrated in Schemes 1-2 were used to prepare the compounds of the Examples as detailed below.

Generic Scheme:

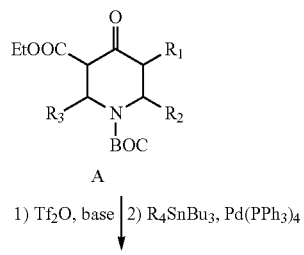

A

1) Tf$_2$O, base  2) R$_4$SnBu$_3$, Pd(PPh$_3$)$_4$

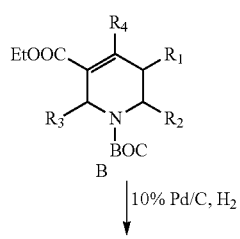

B

10% Pd/C, H$_2$

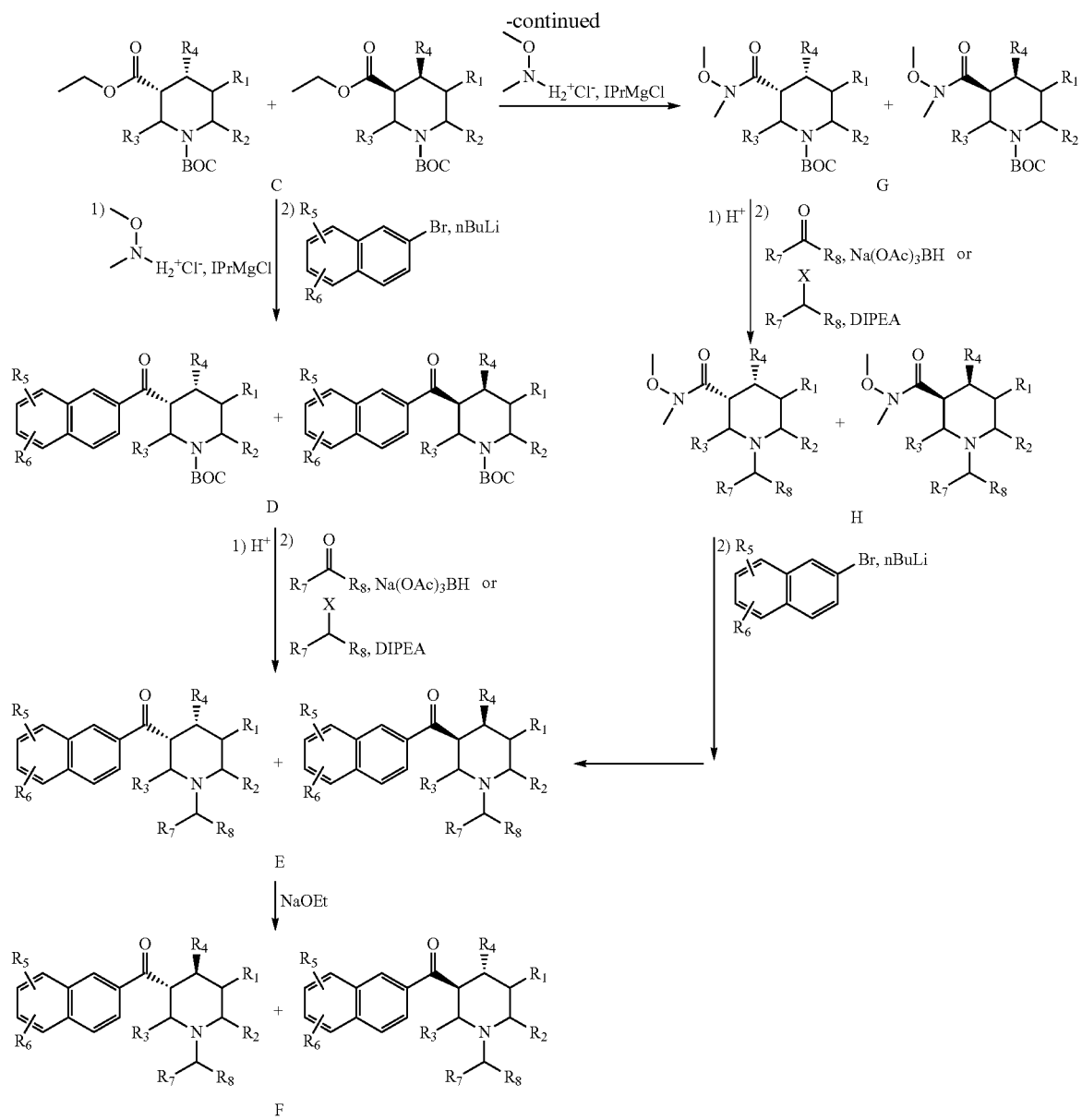

Treatment of β-ketoesters as exemplified by formula A in an organic solvent such as, but not limited to, DCM with triflouromethanesulfonic anhydride in the presence of an organic base such as, but not limited to, diisopropylethyl amine at a temperature of −78° C. can provide the corresponding vinyl-triflate. Treatment of the vinyl-triflate with a nucleophile such as, but not limited to, an alkyl stannane in the presence of a catalyst such as, but not limited to, palladium triphenylphosphine tetrakis can then provide □□□□unsaturated esters as exemplified by formula B. These entities can then be reduced using conditions such as, but not limited to, hydrogenation in the presence of palladium to predominantly afford the cis-diasteroemers of the corresponding BOC-protected piperidine esters as exemplified by formula C. Both cis diastereomers can then be transformed into the weinreb amide by treating with N,O-dimethylhydroxylamine hydrochloride in the presence of isopropylmagnesium chloride in an organic solvent such as, but not limited to, THF at a temperature between −78° C. and 0° C. The weinreb amides can then be converted to the corresponding ketones as exemplified by formula D under conditions such as, but not limited to, lithium halogen exchange conditions with both commercially available and custom synthesized arylbromides. The BOC group can then be cleaved to reveal the free amine of the piperidine sub-unit by exposure to strong acid such as, but not limited to, triflouroacetic acid in an organic solvent such as, but not limited to, DCM. Next, the free amine can be treated with ketones and aldehydes in the presence of a reducing agent such as, but not limited to, sodium triacetoxyborohydride or treated with alkylhalides in the presence of an organic base such as, but not limited to, diisopropylethylamine to produce N-alkylated piperidine ketones as exemplified by formula E. In addition, the cis-enantiomers can be transformed into the corresponding trans-enantiomers exemplified by formula F by exposure to a strong base such as, but not limited to, sodium ethoxide in an organic solvent such as, but not limited to ethanol.

Alternatively, the unsaturated esters exemplified by formula C can be converted to the corresponding weinreb amides as exemplified by formula G through previously described conditions. These intermediates can then be BOC deprotected and N-alkylated using previously described conditions to afford the N-alkylated weinreb amides as exemplified H. These entities can then be converted into the corresponding aryl ketones as exemplified by formula E using previously described conditions.

Synthesis of Intermediates

Intermediate 1 tert-butyl 3-(6-methoxy-2-naphthoyl)piperidine-1-carboxylate

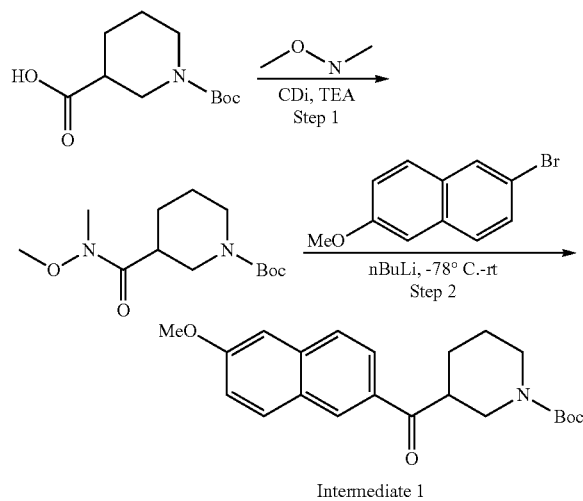

Intermediate 1

Step 1:

Benzyl 3-[methoxy(methyl)carbamoyl]piperidine-1-carboxylate

To a solution of 1-benzyloxycarbonylpiperidine-3-carboxylic acid (10 g, 43.6 mmol) in THF (100 mL) at 0° C. was added 1,1'-carbonyldiimidazole (38.57 g, 52.3 mmol). The mixture was stirred at 0° C. for 1 h. Triethylamine (7.13 g, 69.8 mmol) was added followed by N-methoxymethanamine hydrochloride (6.38 g, 65.4 mmol). The mixture was allowed to warm to room temperature and stirred for 16 h. The mixture was diluted with EtOAc, washed with 0.5 N HCl, sat. NaHCO₃, and brine. The organic layer was dried (Na₂SO₄), filtered and concentrated. The crude product was purified by silica flash chromatography (0-30% EtOAc/heptane) to give the title compound (11.03 g, 93% yield) as a colorless oil. $^1$H NMR (400 MHz, Chloroform-d) δ 7.40-7.28 (m, 5H), 5.20-5.07 (m, 2H), 4.15 (d, J=34.48 Hz, 2H), 3.66 (d, J=38.49 Hz, 3H), 3.16 (s, 3H), 2.94 (d, J=12.21 Hz, 1H), 1.99-1.88 (m, 1H), 1.79-1.62 (m, 2H), 1.57 (s, 2H). LCMS (ESI) m/z 307.2 [M+H⁺].

Step 2:

tert-butyl 3-(6-methoxy-2-naphthoyl)piperidine-1-carboxylate

A solution of 2-bromo-6-methoxy-naphthalene (3.56 g, 15 mmol) in THF (60 mL) was cooled to −78° C. A solution of nBuLi (2.5 M in hexane, 6.0 mL, 15 mmol) was added dropwise. After stirring for 1 h at −78° C., a solution of tert-butyl 3-[methoxy(methyl)carbamoyl]piperidine-1-carboxylate (2.723 g, 10 mmol) in THF (5 mL) was added dropwise. The mixture was allowed to warm to room temperature and stirred for 2 h. The reaction was quenched with sat. NH₄Cl, extracted with DCM (3×). The combined organic layers were dried (Na₂SO₄), filtered and concentrated. The crude product was purified by silica flash chromatography (0-5% EtOAc/DCM) to give the title compound (3.36 g, 91% yield) as a pale yellow foam. $^1$H NMR (400 MHz, Chloroform-d) δ 8.42 (d, J=1.71 Hz, 1H), 8.00 (dd, J=1.82, 8.65 Hz, 1H), 7.87 (d, J=8.94 Hz, 1H), 7.78 (d, J=8.62 Hz, 1H), 7.21 (dd, J=2.52, 8.97 Hz, 1H), 7.17 (s, 1H), 4.5-4.303 (m, 1H), 4.16-4.12 (m, 1H), 3.95 (s, 3H), 3.60-3.49 (m, 1H), 3.03-2.97 (m, 1H), 2.81-2.75 (m, 1H), 2.11-2.07 (m, 1H), 1.85-1.59 (m, 3H), 1.48 (s, 9H). LCMS (ESI) m/z 370.2 [M+H⁺].

Intermediate 2 tert-butyl 3-[4-[[tert-butyl(dimethyl)silyl]oxymethyl]naphthalene-2-carbonyl]piperidine-1-carboxylate

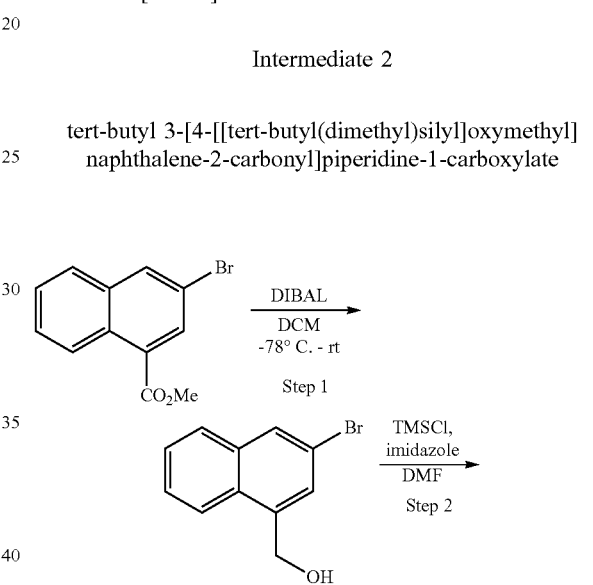

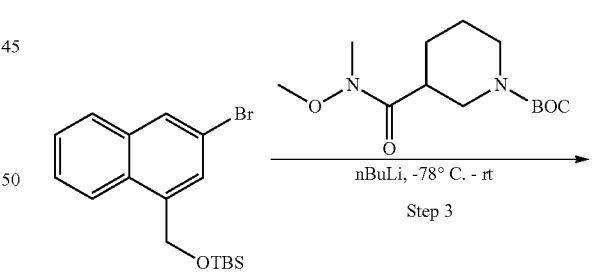

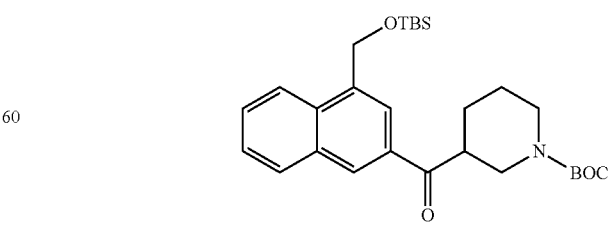

Intermediate 2

Step 1:

(3-bromo-1-naphthyl)methanol

To a solution of methyl 3-bromonaphthalene-1-carboxylate (800 mg, 3.02 mmol) in DCM (12 mL) at −78° C. was added DIBAL-H (1 M in THF, 9 mL, 9 mmol) dropwise. The mixture was warmed to room temperature and stirred for 2 h. The reaction was cooled to −78° C., charged with 2 mL of methanol, warmed to room temperature, and poured into 40 mL of a 25% Rochelle's salt aqueous solution. The resulting mixture was vigorously stirred. Once the organic layer became clear, it was separated and extracted with EtOAc (3×). The combined organics were dried (Na$_2$SO$_4$), filtered and concentrated to give the title compound (715 mg, 99.9% yield) as a light yellow solid which was used directly without purification. $^1$H NMR (400 MHz, Chloroform-d) δ 8.05-8.01 (m, 1H), 7.96 (d, J=2.08 Hz, 1H), 7.79-7.77 (m, 1H), 7.67-7.64 (m, 1H), 7.58-7.49 (m, 2H), 5.14 (d, J=5.82 Hz, 2H), 1.78 (td, J=1.28, 5.98 Hz, 1H).

Step 2:

(3-bromo-1-naphthyl)methoxy-tert-butyl-dimethyl-silane

The mixture of (3-bromo-1-naphthyl)methanol (715 mg, 3.02 mmol), imidazole (514 mg, 7.545 mmol), and TMSCl (586 mg, 3.77 mmol) in DMF (15 mL) was stirred at room temperature for 16 h. The mixture was diluted with EtOAc and washed with sat. aqueous NaCl twice. The aqueous phase was back-extracted with EtOAc (2×). The combined organic layers were dried (Na$_2$SO$_4$), filtered and concentrated. The crude product was purified by silica flash chromatography (0-10% EtOAc/heptane) to give the title compound (971 mg, 91.6% yield) as a colorless oil. $^1$H NMR (400 MHz, Chloroform-d) δ 7.96-7.85 (m, 2H), 7.79-7.72 (m, 1H), 7.69-7.68 (m, 1H), 7.53-7.44 (m, 2H), 5.16 (t, J=0.88 Hz, 2H), 0.97 (s, 9H), 0.15 (s, 6H).

Step 3:

tert-butyl 3-[4-[[tert-butyl(dimethyl)silyl]oxymethyl]naphthalene-2-carbonyl]piperidine-1-carboxylate A solution of (3-bromo-1-naphthyl)methoxy-tert-butyl-dimethyl-silane (719 mg, 2.0 mmol) in THF (6 mL) was cooled to −78° C. before a solution of nBuLi (2.5 M in hexane, 0.8 mL, 2.0 mml) was added dropwise. After stirring for 1 h at −78° C., a solution of tert-butyl 3-[methoxy(methyl)carbamoyl]piperidine-1-carboxylate (364 mg, 1.34 mmol) in THF (2 mL) was added dropwise. The mixture was allowed to warm to room temperature and stirred for 2 h. The reaction was quenched with sat. NH$_4$Cl and extracted with DCM (3×). The combined organic layers were dried (Na$_2$SO$_4$), filtered and concentrated. The crude product was purified by silica flash chromatography (0-25% EtOAc/heptane) to give the title compound (451 mg, 69.8% yield) as a colorless oil. $^1$H NMR (400 MHz, Chloroform-d) δ 8.42 (s, 1H), 8.13 (d, J=1.63 Hz, 1H), 8.02 (t, J=7.59 Hz, 2H), 7.63 (ddd, J=1.41, 6.73, 8.28 Hz, 1H), 7.57 (t, J=7.72 Hz, 1H), 5.21 (s, 2H), 4.31 (brs, 1H), 4.20-4.08 (m, 1H), 3.61-3.55 (m, 1H), 3.06 (brs, 1H), 2.79 (t, J=12.67 Hz, 1H), 2.18-2.06 (m, 1H), 1.85-1.59 (m, 3H), 1.47 (s, 9H), 0.97 (s, 9H), 0.15 (s, 6H). LCMS (ESI) m/z 484.2 [M+H$^+$].

Intermediate 3 tert-butyl 3-(4-carbamoylnaphthalene-2-carbonyl)piperidine-1-carboxylate

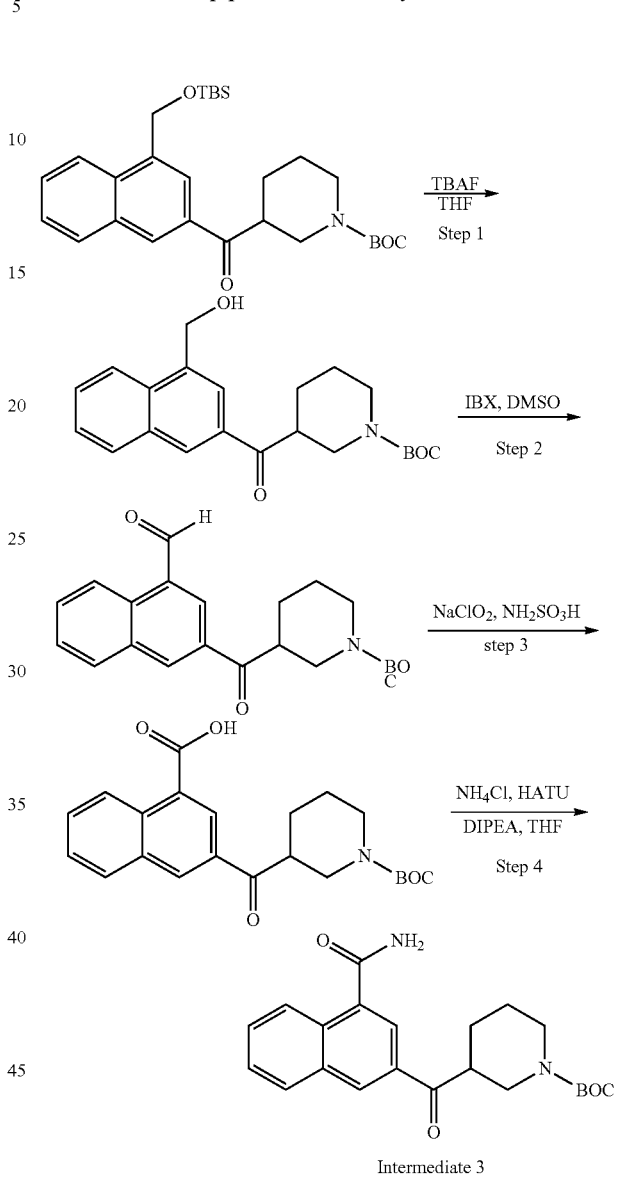

Intermediate 3

Step 1:

tert-butyl 3-[4-(hydroxymethyl)naphthalene-2-carbonyl]piperidine-1-carboxylate

To a solution of tert-butyl 3-[4-[[tert-butyl(dimethyl)silyl]oxymethyl]naphthalene-2-carbonyl]piperidine-1-carboxylate (1.46 g, 3.02 mmol) in THF (15 mL) was added TBAF (1.0 M in THF, 4.5 mL). The mixture was stirred at room temperature for 1.5 h. The mixture was quenched with sat. aqueous NH$_4$Cl and extracted with DCM (3×). The combined organic layers were dried (Na$_2$SO$_4$), filtered and concentrated. The crude product was purified by silica-gel flash chromatography (0-60% EtOAc/heptane) to give the title compound (930 mg, 83.4% yield) as a yellow oil. LCMS (ESI) m/z 370.2 [M+H$^+$].

Step 2:

tert-butyl 3-(4-formylnaphthalene-2-carbonyl)piperidine-1-carboxylate

To a solution of tert-butyl 3-[4-(hydroxymethyl)naphthalene-2-carbonyl]piperidine-1-carboxylate (680 mg, 1.84 mmol) in DMSO (12 mL) was added 2-iodobenzoic acid (1.718 g, 2.761 mmol). The mixture was stirred at room temperature for 3 h. The mixture was diluted with EtOAc and washed with sat. NaHCO₃ (1×), water (3×). The organic phase was dried (Na₂SO₄), filtered and concentrated. The crude product was purified by silica flash chromatography (0-25% EtOAc/heptane) to give the title compound (488 mg, 72.2% yield) as a white solid. LCMS (ESI) m/z 368.2 [M+H⁺].

Step 3:

3-(1-(tert-butoxycarbonyl)piperidine-3-carbonyl)-1-naphthoic acid tert-butyl-3-(4-formylnaphthalene-2-carbonyl)piperidine-1-carboxylate (606 mg, 1.65 mmol) was dissolved in DCM (12 mL) and water (12 mL). Sulfamic acid (192 mg, 1.98 mmol) was added and the mixture was stirred vigorously at 0° C. for 5 min. A solution of sodium chlorite (179 mg, 1.98 mmol) in water (1 mL) was then added and the mixture was stirred at room temperature for 2 h. The mix was diluted with water and the layers were separated. The aqueous layer was extracted with DCM (2×). The combined organics were dried (Na₂SO₄), filtered and concentrated to give the title compound (679 mg, quantitative yield) as a light yellow foam. ¹H NMR (400 MHz, DMSO-d6) δ 13.38 (s, 1H), 8.94 (s, 1H), 8.89 (d, J=8.66 Hz, 1H), 8.55 (d, J=1.77 Hz, 1H), 8.24 (d, J=8.15 Hz, 1H), 7.84-7.76 (m, 1H), 7.71 (t, J=7.47 Hz, 1H), 4.05-4.02 (m, 1H), 3.76-3.72 (m, 2H), 2.93 (t, J=11.66 Hz, 1H), 2.08-1.90 (m, 1H), 1.84-1.71 (m, 1H), 1.61-1.56 (m, 2H), 1.34 (s, 9H). LCMS (ESI) m/z 384.2 [M+H⁺].

Step 4:

tert-butyl 3-(4-carbamoylnaphthalene-2-carbonyl)piperidine-1-carboxylate

A mixture of 3-(1-tert-butoxycarbonylpiperidine-3-carbonyl)naphthalene-1-carboxylic acid (1.252 mmol, 480 mg), NH₄Cl (335 mg, 6.26 mmol), HATU (589 mg, 1.502 mmol) and DIPEA (404 mg, 3.13 mmol) in THF (5 mL) was stirred at room temperature for 16 h. The reaction was quenched with sat. NH₄Cl and extracted with EtOAc (3×). The combined organic layers were dried (Na₂SO₄), filtered and concentrated. The crude product was purified by silica flash chromatography (0-80% EtOAc/heptane) to give the title compound (491 mg, 99% yield) as a white solid. ¹H NMR (400 MHz, DMSO-d6) δ 8.79 (s, 1H), 8.34 (d, J=8.25 Hz, 1H), 8.24-8.15 (m, 1H), 8.09 (s, 1H), 8.06 (d, J=1.66 Hz, 1H), 7.73 (ddd, J=1.48, 6.85, 8.52 Hz, 1H), 7.67 (ddd, J=1.44, 6.94, 8.24 Hz, 2H), 4.06-4.00 (m, 1H), 3.90-3087 (m, 1H), 3.74-3.70 (m, 1H), 2.86 (t, J=11.42 Hz, 1H), 2.04-2.01 (m, 1H), 1.75-1.73 (m, 1H), 1.61-1.57 (m, 1H), 0.86 (t, J=6.74 Hz, 2H). LCMS (ESI) m/z 383.2 [M+H⁺].

Intermediate 4 tert-butyl 3-(4-cyanonaphthalene-2-carbonyl)piperidine-1-carboxylate

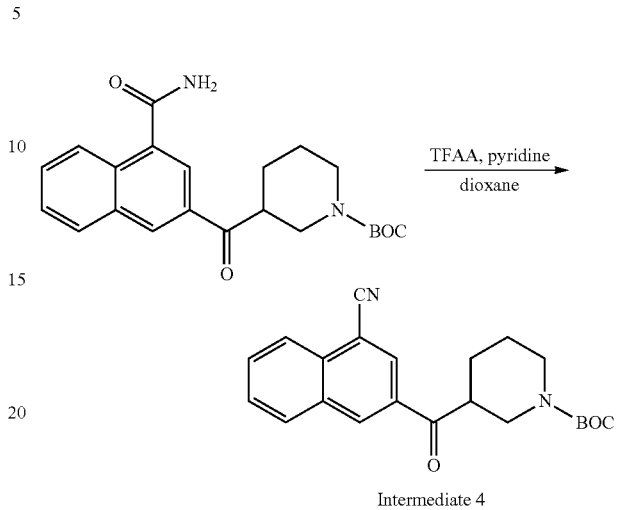

Intermediate 4

To a cloudy solution of tert-butyl 3-(4-carbamoylnaphthalene-2-carbonyl)piperidine-1-carboxylate (292 mg, 0.764 mmol) in 1,4-dioxane (2 mL) at room temperature was added pyridine (211 mg, 2.673 mmol) followed by trifluoroacetic anhydride (353 mg, 1.68 mmol). The mixture was stirred at room temperature for 2 h. The reaction was quenched with water and extracted with EtOAc (3×). The combined organic layers were washed with 10% citric acid, brine, dried (Na₂SO₄), filtered and concentrated. The crude product was purified by silica flash chromatography (0-25% EtOAc/heptane) to give the title compound (228 mg, 81.9% yield) as a white solid. ¹H NMR (400 MHz, Chloroform-d) δ 8.75-8.67 (m, 1H), 8.46 (d, J=1.68 Hz, 1H), 8.32-8.27 (m, 1H), 8.09 (d, 0.1=7.96 Hz, 1H), 7.88-7.80 (m, 1H), 7.73 (t, J==7.57 Hz, 1H), 4.32 br (s, 1H), 4.13-4.11 (m, 1H), 3.55-3.51 (m, 1H), 3.04 (brs, 1H), 2.83 (t, J=12.25 Hz, 1H), 2.10-2.07 (m, 1H), 1.84-1.72 (m, 2H), 1.68-1.64 (m, 1H), 1.48 (s, 9H). LCMS (ESI) m/z 365.2 [M+H⁺].

Intermediate 5 tert-butyl 3-[5-(cyanomethyl)-6-methoxy-naphthalene-2-carbonyl]piperidine-1-carboxylate

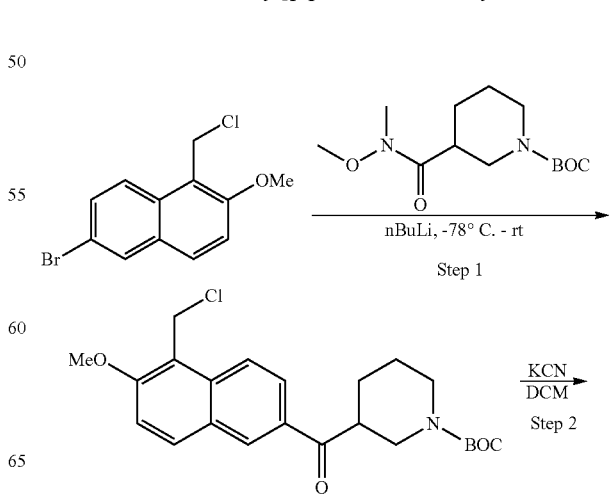

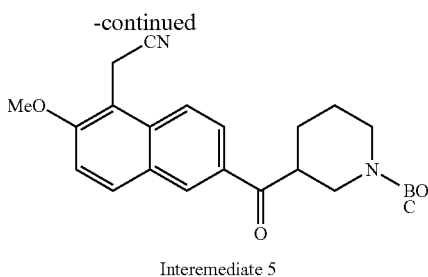

Interemediate 5

Step 1:

tert-butyl 3-[5-(chloromethyl)-6-methoxy-naphthalene-2-carbonyl]piperidine-1-carboxylate A solution of 6-bromo-(chloromethyl)-2-methoxynaphthalene (530 mg, 1.8 mmol) in THF (8 mL) was cooled to −78° C. before a solutions of nBuLi (2.5 M in hexane, 0.86 mL, 2.16 mmol) was added dropwise. After stirring for 1 h at −78° C., a solution of tert-butyl-3-[methoxy(methyl) carbamoyl]piperidine-1-carboxylate (327 mg, 1.2 mmol) in THF (2 mL) was added dropwise. The mixture was allowed to warm to room temperature and stirred for 2 h. The reaction was quenched with sat. NH$_4$Cl and extracted with DCM (3×). The combined organic layers were dried (Na$_2$SO$_4$), filtered and concentrated. The crude product was purified by silica flash chromatography (0-25% EtOAc/heptane) to give the title compound (380 mg, 75.8% yield) as a colorless oil. $^1$H NMR (400 MHz, Chloroform-d) δ 8.46 (s, 1H), 8.12-8.09 (m, 2H), 8.01 (d, J=9.20 Hz, 1H), 7.35 (d, J=9.17 Hz, 1H), 5.16 (s, 2H), 4.33 (brs, 1H), 4.16-4.13 (m, 1H), 4.05 (s, 3H), 3.60-3.48 (m, 1H), 3.00 (brs, 1H), 2.82-2.76 (m, 1H), 2.11-2.07 (m, 1H), 1.85-1.69 (m, 2H), 1.74-1.61 (m, 1H), 1.48 (s, 9H).

Step 2:

tert-butyl 3-[5-(cyanomethyl)-6-methoxy-naphthalene-2-carbonyl]piperidine-1-carboxylate To a solution of tert-butyl 3-[5-(chloromethyl)-6-methoxy-naphthalene-2-carbonyl]piperidine-1-carboxylate (340 mg, 0.814 mmol) and benzyltriethylammonium chloride (37 mg, 0.1623 mmol) in DCM (4 mL) was added a solution of KCN (270 mg, 4.1 mmol) in water (500 uL). The mixture was heated at 35° C. for 6 h, The mixture was diluted with water and extracted with DCM (3×). The combined organics were dried (Na$_2$SO$_4$), filtered and concentrated. The crude product was purified by silica flash chromatography (0-50% EtOAc/heptane) to give the title compound (265 mg, 79.6% yield) as a white solid. $^1$H NMR (400 MHz, Chloroform-d) δ 8.48 (d, J=1.77 Hz, 1H), 8.13 (dd, J=1.86, 8.95 Hz, 1H), 8.03 (d, J=9.07 Hz, 1H), 7.95 (d, J=8.96 Hz, 1H), 7.37 (d, J=9.07 Hz, 1H), 4.34 (brs, 1H), 4.16-4.14 (, 1H), 4.12 (s, 2H), 4.06 (s, 3H), 3.56-3.52 ms, 1H), 3.01 (brs, 1H), 2.86-2.73 (m, 1H), 2.11-2.07 (m, 1H), 1.85-1.69 (m, 2H), 1.68-1.62 (m, 1H), 1.48 (s, 9H). LCMS (ESI) m/z 409.2 [M+H$^+$].

Intermediate 6 tert-butyl 3-(8-methylnaphthalene-2-carbonyl)piperidine-1-carboxylate

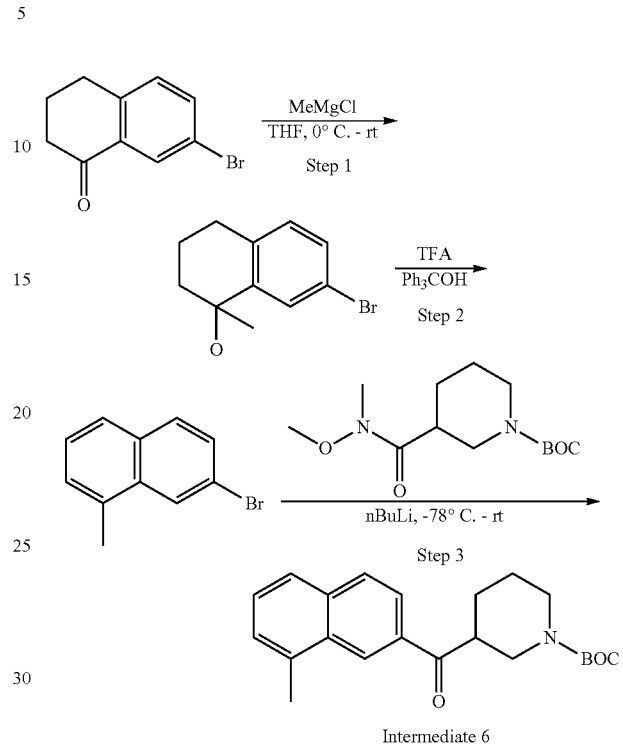

Intermediate 6

Step 1:

7-bromo-1-methyl-1,2,3,4-tetrahydronaphthalen-1-ol

To a solution of 7-bromotetralin-1-one (1.0 g, 4.44 mmol) in THF (20 mL) at 0° C. was added MeMgCl (3 M in THF, 5.92 mL, 17.8 mmol) dropwise. The mixture was stirred at room temperature for 2 h. The reaction was quenched with Sat. NH$_4$Cl and extracted with DCM (3×). The combined organic layers were dried (Na$_2$SO$_4$), filtered and concentrated to a yellow oil to afford the title compound (715 mg, 99.9% yield) that was used without purification. $^1$H NMR (400 MHz, Chloroform-d) δ 7.71 (d, J=2.10 Hz, 1H), 7.29-7.23 (m, 1H), 6.94 (dt, J=1.00, 8.28 Hz, 1H), 3.77-3.69 (m, 1H), 2.72 (q, J=6.25, 7.13 Hz, 2H), 1.95-1.79 (m, 4H).

Step 2:

7-bromo-1-methylnaphthalene

The crude product from Step 1 was combined with triphenylmethanol (1.55 g, 5.77 mmol) and TFA (2.53 g, 22.2 mmol). The resulting dark brown mixture was stirred at room temperature for 18 h. The mixture was diluted with water and extracted with DCM (3×). The combine organic layers were washed with sat. NaHCO$_3$, dried (Na$_2$SO$_4$), filtered and concentrated. The oily residue was treated with heptane. The precipitate was filtered off and washed with heptane. The filtrate was concentrated, and purified by silica flash chromatography (100% heptane) to give the title compound (736 mg, 75% yield) as a colorless oil. $^1$H NMR (400 MHz, Chloroform-d) δ 8.13 (d, J=1.77 Hz, 1H), 7.68 (d, J=8.71 Hz, 1H), 7.64 (d, J=8.04 Hz, 1H), 7.53 (dd, J=1.92, 8.68 Hz, 1H), 7.36 (t, J=7.53 Hz, 1H), 7.33 (s, 1H), 2.63 (s, 3H).

Step 3:

tert-butyl 3-(8-methylnaphthalene-2-carbonyl)piperidine-1-carboxylate

A solution of 7-bromo-1-methylnaphthalene (338 mg, 1.5 mmol) in THF (5 mL) was cooled to −78° C. before a solution of nBuLi (2.5 M in hexane, 0.8 mL, 2.00 mmol) was added dropwise. After stirring for 1 h at −78° C., a solution of tert-butyl 3-[methoxy(methyl)carbamoyl]piperidine-1-carboxylate (272 mg, 1.0 mmol) in THF (2 mL) was added dropwise. The mixture was allowed to warm to room temperature and stirred for 2 h. The reaction was quenched with sat. NH$_4$Cl and extracted with DCM (3×). The combined organic layers were dried (Na$_2$SO$_4$), filtered and concentrated. The crude product was purified by silica flash chromatography (0-20% EtOAc/heptane) to give the title compound (0.7414 mmol, 74.1% yield, 262 mg) as a colorless oil. $^1$H NMR (400 MHz, Chloroform-d) δ 8.70 (s, 1H), 8.02 (dd, J=1.73, 8.56 Hz, 1H), 7.91 (d, J=8.60 Hz, 1H), 7.74 (d, J=8.18 Hz, 1H), 7.50 (dd, J=6.99, 8.23 Hz, 1H), 7.43-7.37 (m, 1H), 4.15-4.10 (m, 2H), 3.96 (brs, 1H), 3.61-3.57 (m, 1H), 2.79 (s, 3H), 2.83-2.79 (m, 2H), 2.15-2.07 (m, 1H), 1.86-1.69 (m, 3H), 1.48 (s, 9H). LCMS (ESI) m/z 354.2 [M+H$^+$].

Intermediate 7 tert-butyl 3-[4-(1-hydroxyethyl)naphthalene-2-carbonyl]piperidine-1-carboxylate

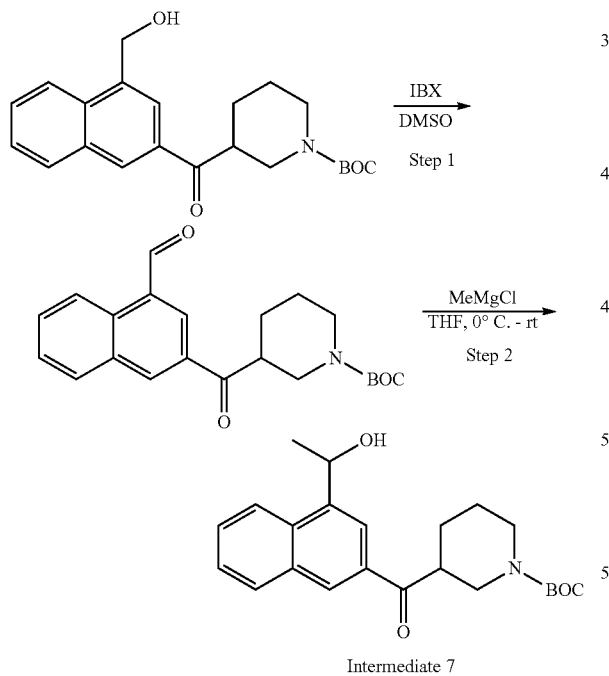

Intermediate 7

Step 1:

tert-butyl 3-(4-formylnaphthalene-2-carbonyl)piperidine-1-carboxylate

To a solution of tert-butyl 3-[4-(hydroxymethyl)naphthalene-2-carbonyl]piperidine-1-carboxylate (1.900 mmol, 702 mg) in DMSO (12 mL) was added 2-iodoxybenzoic acid (1.77 g, 2.851 mmol). The mixture was stirred at room temperature for 2 h. The mixture was diluted with EtOAc and washed with sat. NaHCO$_3$ (1×) and water (3×). The organic phase was dried (Na$_2$SO$_4$), filtered and concentrated. The crude product was purified by silica flash chromatography (0-25% EtOAc/heptane) to give the title compound (708 mg, 99% yield) as a white solid. $^1$H NMR (300 MHz, Chloroform-d) δ 10.45 (s, 1H), 9.30 (d, J=8.57 Hz, 1H), 8.72 (s, 1H), 8.56 (d, J=1.82 Hz, 1H), 8.09 (dd, J=1.16, 8.22 Hz, 1H), 7.83 (ddd, J=1.38, 6.85, 8.49 Hz, 1H), 7.69 (t, J=7.68 Hz, 1H), 4.36 (brs, 1H), 4.21-4.07 (m, 1H), 3.63-3.59 (m, 1H), 3.06 (brs, 1H), 2.83 (t, J=12.31 Hz, 1H), 2.14-2.10 (m, 1H), 1.91-1.59 (m, 3H), 1.48 (s, 9H). LCMS (ESI) m/z 368.2 [M+H$^+$].

Step 2:

tert-butyl 3-[4-(1-hydroxyethyl)naphthalene-2-carbonyl]piperidine-1-carboxylate

To a solution of tert-butyl 3-(4-formylnaphthalene-2-carbonyl)piperidine-1-carboxylate (350 mg, 0.95 mmol) in THF (12 mL) in a salt-ice bath was added MeMgCl (3 M in THF, 0.36 mL, 1.08 mmol) dropwise. The mixture was stirred in a salt-ice bath for 5 min. The reaction was then quenched with sat. NH$_4$Cl at 0° C. and extracted with DCM (2×). The combined organic layers were dried (Na$_2$SO$_4$), filtered, and concentrated to give the title compound (369 mg, 101% yield) as a white solid, which was used without purification. $^1$H NMR (400 MHz, Chloroform-d) δ 8.41 (t, J=2.17 Hz, 1H), 8.24 (s, 1H), 8.15 (td, J=2.84, 6.66, 7.63 Hz, 1H), 8.02 (dd, J=1.35, 8.26 Hz, 1H), 7.65 (ddd, J=1.46, 6.85, 8.42 Hz, 1H), 7.57 (t, J=7.55 Hz, 1H), 5.75-5.60 (m, 1H), 4.34 br (s, 1H), 4.15-4.11 (m, 1H), 3.62-3.58 (m, 1H), 3.00 (brs, 1H), 2.87-2.72 (m, 1H), 2.13-2.08 (m, 1H), 1.83-1.78 (m, 1H), 1.70 (dd, J=2.24, 6.50 Hz, 3H), 1.67-1.60 (m, 3H), 1.48 (s, 9H). LCMS (ESI) m/z 400.2 [M+H$^+$].

Intermediate 8 tert-butyl 3-(6-cyano-5-methyl-naphthalene-2-carbonyl)piperidine-1-carboxylate

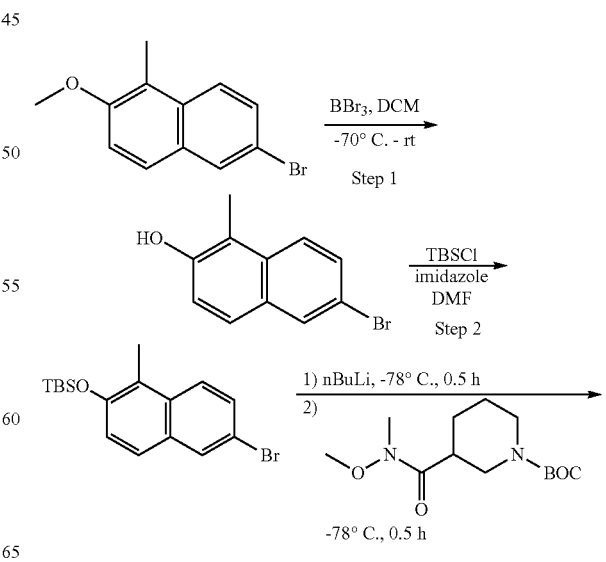

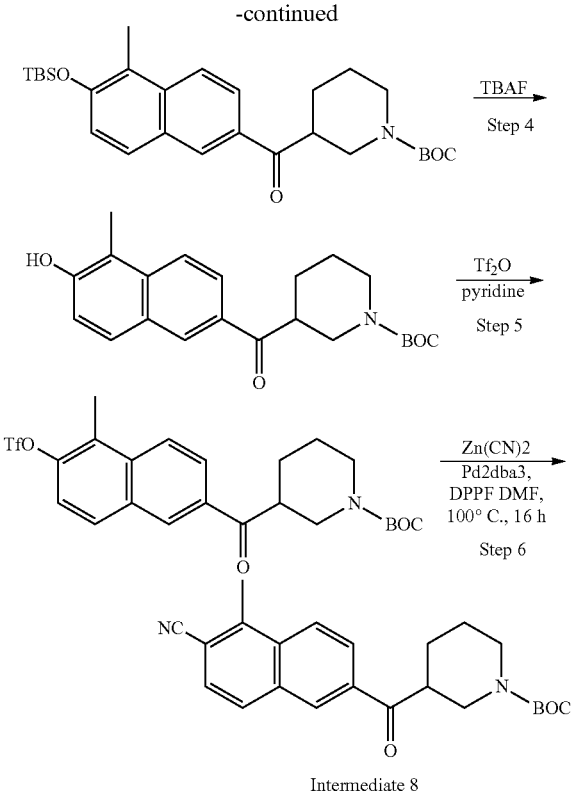

Intermediate 8

Step 1:

6-bromo-1-methyl-naphthalen-2-ol

To a solution of 6-bromo-2-methoxy-1-methyl-naphthalene (576 mg, 2.29 mmol) in DCM (5 mL) at −78° C. was added BBr$_3$ (1 M in DCM, 2.75 mL, 2.75 mml) dropwise. The mixture was slowly warmed to room temperature. After stirring for 1.5 h at room temperature, the reaction was quenched with ice-water and extracted with DCM (2×). The combined organics were dried (Na$_2$SO$_4$), filtered and concentrated. The crude product was purified by silica flash chromatography (0-25% EtOAc/heptane) to give the title compound (524 mg, 96% yield) as a white solid. $^1$H NMR (400 MHz, Chloroform-d) δ 7.91 (d, J=2.11 Hz, 1H), 7.78 (d, J=9.02 Hz, 1H), 7.57-7.49 (m, 2H), 7.07 (d, J=8.79 Hz, 1H), 4.92 (s, 1H), 2.51 (s, 3H). LCMS (ESI) m/z 237.0 [M+H$^+$].

Step 2:

(6-bromo-1-methyl-2-naphthyl)oxy-tert-butyl-dimethyl-silane

The mixture of 6-bromo-1-methyl-naphthalen-2-ol (613 mg, 2.58 mmol), imidazole (264 mg, 3.88 mmol), and TBSCl (482 mg, 3.1 mmol) in DMF (5 mL) was stirred at room temperature for 16 h. The mixture was diluted with EtOAc and washed with sat. NaCl twice. The aqueous phase was back-extracted with EtOAc once. The combined organic layers were dried (Na$_2$SO$_4$), filtered and concentrated. The crude product was purified by silica flash chromatography (0-5% EtOAc/heptane) to give the title compound (859 mg, 94.6% yield) as a white solid. $^1$H NMR (400 MHz, Chloroform-d) δ 7.91 (d, J=2.08 Hz, 1H), 7.78 (d, J=9.04 Hz, 1H), 7.55-7.47 (m, 2H), 7.08 (d, J=8.82 Hz, 1H), 2.50 (s, 3H), 1.05 (s, 9H), 0.23 (s, 6H).

Step 3:

tert-butyl 3-[6-[tert-butyl(dimethyl)silyl]oxy-5-methyl-naphthalene-2-carbonyl]piperidine-1-carboxylate A solution of (6-bromo-1-methyl-2-naphthyl)oxy-tert-butyl-dimethyl-silane (1.668 mmol, 598 mg, 1.67 mmol) in THF (8 mL) was cooled to −78° C. before a solution of nBuLi (2.5 M in hexane, 1.0 mL, 2.5 mmol) was added dropwise. After stirring for 30 min at −78° C., a solution of ten-butyl 3-[methoxy(methyl)carbamoyl]piperidine-1-carboxylate (1.751 mmol, 476.8 mg) in THF (2 mL) was added dropwise. The mixture was stirred at −78° C. for 30 min. The reaction was quenched with sat. NH$_4$Cl and extracted with DCM (3×). The combined organic layers were dried (Na$_2$SO$_4$), filtered and concentrated. The crude product was purified by silica flash chromatography (0-15% EtOAc/heptane) to give the title compound (562 mg, 69.7% yield) as a colorless oil. $^1$H NMR (400 MHz, Chloroform-d) δ 8.41 (d, J=1.77 Hz, 1H), 8.02 (dd, J=1.82, 8.94 Hz, 1H), 7.98 (s, 1H), 7.73 (d, J=8.87 Hz, 1H), 7.13 (d, J=8.85 Hz, 1H), 4.33 (s, 1H), 4.20-4.10 (m, 1H), 3.96 (s, 1H), 3.55 (dd, J=8.91, 12.85 Hz, 1H), 2.78 (t, J=12.02 Hz, 1H), 2.53 (s, 3H), 2.09 (d, J=12.55 Hz, 1H), 1.83-1.59 (m, 4H), 1.48 (s, 9H), 1.06 (s, 9H), 0.26 (s, 6H). LCMS (ESI) m/z 484.2 [M+H+].

Step 4:

tert-butyl 3-(6-hydroxy-5-methyl-naphthalene-2-carbonyl)piperidine-1-carboxylate To a solution of tert-butyl-3-[6-[tert-butyl(dimethyl)silyl]oxy-5-methyl-naphthalene-2-carbonyl]piperidine-1-carboxylate (562 mg, 1.16 mmol) in THF (12 mL) was added TBAF (1 M in THF, 2.3 mL, 2.3 mmol) dropwise. The reaction mixture was stirred at room temperature for 30 min. The mixture was quenched with sat. NH$_4$Cl and extracted with DCM (3×). The combined organic layers were dried (Na$_2$SO$_4$), filtered and concentrated. The crude product was purified by silica flash chromatography (0-100% EtOAc/heptane) to give the title compound (354 mg, 82.5% yield) as a white solid. $^1$H NMR (400 MHz, Chloroform-d) δ 8.38 (d, J=1.87 Hz, 1H), 8.05-7.98 (m, 1H), 7.94 (d, J=9.01 Hz, 1H), 7.72 (d, J=8.79 Hz, 1H), 7.12 (d, J=8.79 Hz, 1H), 5.31 (brs, 1H), 4.34 (brs, 1H), 4.15-4.13 (m, 1H), 3.54 (tt, J=3.68, 11.01 Hz, 1H), 3.01-2.99 (m 1H), 2.79 (t, J=12.58 Hz, 1H), 2.53 (s, 3H), 2.08 (d, J=12.84 Hz, 1H), 1.85-1.71 (m, 2H), 1.71-1.59 (m, 1H), 1.49 (s, 9H).

Step 5:

tert-butyl-3-[5-methyl-6-(trifluoromethylsulfonyloxy)naphthalene-2-carbonyl]piperidine-1-carboxylate To a solution of tert-butyl 3-(6-hydroxy-5-methyl-naphthalene-2-carbonyl)piperidine-1-carboxylate (0.9367 mmol, 346 mg) in pyridine (4 mL) at 0° C. was added trifluromethanesulfonic anhydride (317 mg, 1.12 mmol) dropwise. The reaction mixture was stirred at 0° C. for 1 h. The mix was diluted with water and extracted with EtOAc (2×). The combined organic layers were washed with 10% citric acid, brine, dried (Na$_2$SO$_4$), filtered and concentrated. The crude product was purified by silica flash chromatography (0-30% EtOAc/heptane) to give the title compound (460 mg, 97.9% yield) as a colorless oil which solidified when drying in high vacuum. ¹H NMR (400 MHz, Chloroform-d) δ 8.51 (s, 1H), 8.15 (d, J=1.45 Hz, 2H), 7.93 (d, 0.1=9.04 Hz, 1H), 7.45 (d, J=9.02 Hz, 1H), 4.34 (brs, 1H), 4.15-4.11 (m, 1H), 3.58-3.53 (m, 1H), 3.01 (brs, 1H), 2.81 (td, J=2.81, 12.64, 13.25 Hz, 1H), 2.72 (s, 3H), 2.15-2.04 (m, 1H), 1.86-1.70 (m, 2H), 1.68-1.61 (m, 1H). LCMS (ESI) m/z 502 [M+H⁺].

Step 6:

tert-butyl 3-(6-cyano-5-methyl-naphthalene-2-carbonyl)piperidine-1-carboxylate

A mixture of tert-butyl-3-[5-methyl-6-(trifluoromethylsulfonyloxy)naphthalene-2-carbonyl]piperidine-1-carboxylate (417 mg, 0.83 mmol), ZnCN (98 mg, 0.83 mmol), Pd₂dba₃ (16 mg, 0.0166 mmol) and 1,1'-bisIdiphenylphosphino)ferrocene (234 mg, 0.042 mmol) in DMF (8 mL) was heated at 100° C. under N₂ for 16 h. The mixture was filtered through celite and concentrated. The crude product was purified by silica flash chromatography (0-30% EtOAc/heptane) to give the title compound (249 mg, 79% yield) as a colorless oil. ¹H NMR (400 MHz, Chloroform-d) δ 8.49 (s, 1H), 8.15 (d, J=1.54 Hz, 2H), 7.90 (d, J=8.55 Hz, 1H), 7.61 (d, J=8.52 Hz, 1H), 4.46-4.24 (m, 1H), 4.18-4.06 (m, 1H), 3.57 (7t, J=3.44, 10.40 Hz, 1H), 3.11-2.95 (m, 1H), 2.94 (s, 3H), 2.88-2.78 (m, 1H), 2.16-2.05 (m, 1H), 1.85-1.72 (m, 2H), 1.68-1.64 (m, 1H), 1.49 (s, 9H). LCMS (ESI) m/z 379 [M+H⁺].

Synthesis of Final Compounds

Example 1

(1-cyclobutylpiperidin-3-yl)(6-methoxynaphthalen-2-yl)methanone

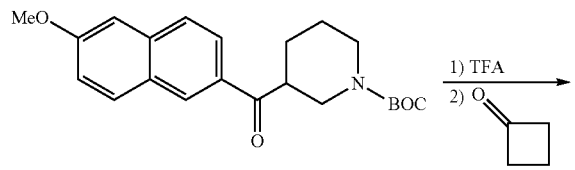

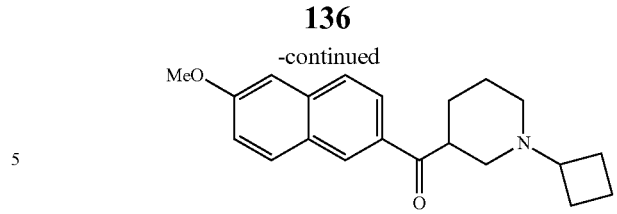

To a solution of tert-butyl 3-(6-methoxynaphthalene-2-carbonyl)piperidine-1-carboxylate (1.666 g, 4.51 mmol) in DCM (5 mL) was added TFA (5.142 g, 45.1 mmol). The mixture was stirred at room temperature for 1 h. The mixture was concentrated to give (6-methoxynaphthalen-2-yl)(piperidin-3-yl)methanone as a colorless oil and used directly without purification. A mixture of (6-methoxy-2-naphthyl)-(3-piperidyl)methanone (80 mg, 0.297 mmol), cyclopentanone (75 mg, 0.891 mmol), AcOH (36 mg, 0.594 mmol) and NaBH(OCH₃)₃ (99.4 mg, 0.446 mmol) in 1,2-dichloroethane (1.5 mL) was stirred at room temperature for 16 h. The reaction was quenched with 1 N NaOH and extracted with EtOAc (3×). The combined organic layers were dried (Na₂SO₄), filtered and concentrated. The crude product was purified by preparative reverse phase HPLC (Phenomenx Gemini NX, 20-60% ACN in 0.1% NH₄OH (aq)) to give the title compound (57.2 mg, 57% yield) as a yellow oil. ¹H NMR (400 MHz, DMSO-d6) δ 8.60 (d, J=1.47 Hz, 1H), 8.06 (d, J=8.99 Hz, 1H), 7.94-7.86 (m, 2H), 7.40 (d, J=2.57 Hz, 1H), 7.26 (dd, J=2.56, 8.96 Hz, 1H), 3.92 (s, 3H), 3.72 (tt, J=3.48, 10.84 Hz, 1H), 3.07-3.00 (m, 1H), 2.93 (m, 1H), 2.51 (m, 3H), 2.13-2.05 (m, 1H), 1.98-1.82 (m, 2H), 1.80-1.64 (m, 3H), 1.60-1.26 (m, 7H). LCMS (ESI) m/z 338 [M+H⁺], The following compounds were prepared in a manner similar to example 1: (1-cyclobutylpiperidin-3-yl)(6-methoxynaphthalen-2-yl)methanone. In some cases, racemic mixtures are exemplified. In those cases where a specific enantiomer is exemplified, purification was conducted using super-fluid chromatography with the following conditions to separate enantiomers. SFC conditions: CHIRALPAK AD (250×30 mm, 5 µm particle size) at 20% MeOH w/0.1% NH₄OH; 60 mL/min, 100 bars, 40° C.

| Example | Compound Name | ¹H NMR | (m/z) M + H |
|---|---|---|---|
| 3 | (3-chlorophenyl)-(1-cyclopentyl-3-piperidyl)methanone | ¹H NMR (400 MHz, DMSO-d6) δ 7.90 (dp, J = 1.60, 4.87 Hz, 2H), 7.70 (ddd, J = 1.09, 2.17, 8.00 Hz, 1H), 7.57 (t, J = 8.05 Hz, 1H), 3.60-3.52 (m, 1H), 2.99-2.92 (m, 1H), 2.84 (m, 1H), 2.08 (dd, J = 9.99, 11.30 Hz, 1H), 1.94 (td, J = 3.40, 11.07 Hz, 1H), 1.84-1.40 (m, 10H), 1.34 (m, 3H) | 292 |
| 5 | (1-cyclobutyl-3-piperidyl)-(2,4-dimethoxyphenyl)methanone | ¹H NMR (400 MHz, DMSO-d6) δ 7.49 (d, J = 8.66 Hz, 1H), 6.64 (d, J = 2.27 Hz, 1H), 6.59 (dd, J = 2.31, 8.65 Hz, 1H), 3.88 (s, 3H), 3.83 (s, 3H), 3.38-3.31 (m, 1H), 2.83-2.75 (m, 1H), 2.68-2.58 (m, 2H), 1.97-1.86 (m, 2H), 1.81-1.54 (m, 8H), 1.54-1.39 (m, 1H), 1.33-1.18 (m, 1H) | 304 |
| 6 | (6-methoxy-2-naphthyl)-(1-tetrahydropyran-4-yl-3-piperidyl)methanone | ¹H NMR (400 MHz, DMSO-d6) δ 8.59 (s, 1H), 8.06 (dd, J = 3.27, 8.92 Hz, 1H), 7.90 (p, J = 2.06 Hz, 2H), 7.40 (q, J = 2.50 Hz, 1H), 7.25 (dq, J = 2.32, 8.83 Hz, 1H), 3.92 (s, 3H), 3.86-3.83 (m, 2H), 3.75-3.63 (m, 1H), 3.29-3.18 (m, 3H), 3.02-2.09 (m, 1H), 2.91-2.88 (m, 1H), 2.36-2.25 (m, 1H), 2.15-2.09 (m, 1H), 1.89-1.86 (m, 1H), 1.72-1.60 (m, 4H), 1.43-1.37 (m, 3H) | 354 |

-continued

| Example | Compound Name | $^1$H NMR | (m/z) M + H |
|---|---|---|---|
| 7 | [(3R)-1-(cyclopropylmethyl)-3-piperidyl]-(6-methoxy-2-naphthyl)methanone | $^1$H NMR (DMSO-d6) δ: 8.69-8.54 (m, 1H), 8.06 (d, J = 9.0 Hz, 1H), 7.98-7.83 (m, 2H), 7.40 (d, J = 2.5 Hz, 1H), 7.26 (dd, J = 9.0, 2.5 Hz, 1H), 3.92 (s, 3H), 3.82-3.67 (m, 1H), 3.13-2.93 (m, 2H), 2.29-2.06 (m, 3H), 2.02-1.83 (m, 2H), 1.78-1.65 (m, 2H), 1.49-1.29 (m, 1H), 0.90-0.74 (m, 1H), 0.49-0.36 (m, 2H), 0.10-0.01 (m, 2H) | 324 |
| 8 | [(3S)-1-(cyclopropylmethyl)-3-piperidyl]-(6-methoxy-2-naphthyl)methanone | $^1$H NMR (DMSO-d6) δ: 8.69-8.57 (m, 1H), 8.06 (d, J = 9.0 Hz, 1H), 7.99-7.85 (m, 2H), 7.40 (d, J = 2.5 Hz, 1H), 7.26 (dd, J = 9.0, 2.5 Hz, 1H), 3.92 (s, 3H), 3.82-3.69 (m, 1H), 3.13-2.93 (m, 2H), 2.31-2.05 (m, 3H), 2.03-1.83 (m, 2H), 1.78-1.64 (m, 2H), 1.46-1.30 (m, 1H), 0.88-0.75 (m, 1H), 0.50-0.35 (m, 2H), 0.12-0.01 (m, 2H) | 324 |
| 9 | [(3R)-1-cyclopentyl-3-piperidyl]-(6-methoxy-2-naphthyl)methanone | $^1$H NMR (400 MHz, DMSO-d6) d 8.60 (d, J = 1.45 Hz, 1H), 8.06 (d, J = 9.00 Hz, 1H), 7.96-7.86 (m, 2H), 7.40 (d, J = 2.55 Hz, 1H), 7.26 (dd, J = 2.55, 8.94 Hz, 1H), 3.91 (s, 3H), 3.72 (tt, J = 3.53, 10.77 Hz, 1H), 3.08-3.00 (m, 1H), 2.93 (d, J = 11.20 Hz, 1H), 2.58-2.52 (m, 1H), 2.13-2.04 (m, 1H), 1.93 (td, J = 3.81, 10.93 Hz, 1H), 1.89-1.82 (m, 1H), 1.82-1.23 (m, 11H) | 338 |
| 10 | [(3S)-1-cyclopentyl-3-piperidyl]-(6-methoxy-2-naphthyl)methanone | $^1$H NMR (400 MHz, DMSO-d6) d 8.60 (d, J = 1.46 Hz, 1H), 8.06 (d, J = 8.93 Hz, 1H), 7.95-7.85 (m, 2H), 7.40 (d, J = 2.55 Hz, 1H), 7.26 (dd, J = 2.56, 8.94 Hz, 1H), 3.72 (tt, J = 3.49, 10.82 Hz, 1H), 3.03 (ddd, J = 1.82, 3.59, 11.30 Hz, 1H), 2.96-2.88 (m, 1H), 2.59-2.51 (m, 1H), 2.14-2.04 (m, 1H), 1.93 (td, J = 3.90, 10.99 Hz, 1H), 1.86 (dd, J = 3.43, 12.73 Hz, 1H), 1.79-1.25 (m, 11H). | 338 |
| 11 | [(3S)-1-cyclobutyl-3-piperidyl]-(2,4-dimethoxyphenyl)methanone | $^1$H NMR (400 MHz, DMSO-d6) d 7.49 (d, J = 8.55 Hz, 1H), 6.64 (d, J = 2.27 Hz, 1H), 6.59 (dd, J = 2.30, 8.64 Hz, 1H), 3.88 (s, 3H), 3.83 (s, 3H), 3.39-3.32 (m, 1H), 2.84-2.75 (m, 1H), 2.69-2.56 (m, 2H), 1.99-1.86 (m, 2H), 1.81-1.38 (m, 9H), 1.33-1.19 (m, 1H) | 304 |
| 12 | [(3R)-1-cyclobutyl-3-piperidyl]-(2,4-dimethoxyphenyl)methanone | $^1$H NMR (400 MHz, DMSO-d6) d 7.49 (d, J = 8.58 Hz, 1H), 6.64 (d, J = 2.26 Hz, 1H), 6.59 (dd, J = 2.30, 8.68 Hz, 1H), 3.88 (s, 3H), 3.83 (s, 3H), 3.38-3.31 (m, 1H), 2.84-2.76 (m, 1H), 2.69-2.58 (m, 2H), 1.97-1.87 (m, 2H), 1.79-1.41 (m, 9H), 1.32-1.20 (m, 1H) | 304 |
| 13 | (1-cyclohexyl-3-piperidyl)-(6-methoxy-2-naphthyl)methanone | $^1$H NMR (400 MHz, DMSO-d6) δ 8.58 (s, 1H), 8.06 (d, J = 9.00 Hz, 1H), 7.95-7.86 (m, 2H), 7.40 (d, J = 2.76 Hz, 1H), 7.26 (dd, J = 2.59, 8.91 Hz, 1H), 3.92 (s, 3H), 3.72-3.61 (m, 1H), 2.95 (d, J = 11.17 Hz, 1H), 2.82 (d, J = 10.83 Hz, 1H), 2.36 (t, J = 10.71 Hz, 1H), 2.31-2.27 (m, 1H), 2.25-2.15 (m, 1H), 1.89-1.85 (m, 1H), 1.72-1.62 (m, 6H), 1.56-1.52 (m, 1H), 1.45-1.31 (m, 1H), 1.21-1.14 (m, 4H), 1.6-1.024 (m, 1H) | 355 |
| 14 | (6-methoxy-2-naphthyl)-[1-(oxetan-3-yl)-3-piperidyl]methanone | $^1$H NMR (400 MHz, DMSO-d6) δ 8.63 (s, 1H), 8.08 (dd, J = 2.52, 8.77 Hz, 1H), 7.97-7.87 (m, 2H), 7.40 (d, J = 2.84 Hz, 1H), 7.26 (dd, J = 2.58, 9.02 Hz, 1H), 4.5-4.492 (m, 2H), 4.45-4.38 (m, 2H), 3.92 (s, 3H), 3.78-3.72 (m, 1H), 3.42 (p, J = 6.31 Hz, 1H), 2.83-2.79 (m, 1H), 2.75-2.65 (m, 1H), 2.04-1.87 (m, 2H), 1.85-1.68 (m, 3H), 1.44.382 (m, 1H) | 326 |
| 15 | (6-methoxy-2-naphthyl)-(1-tetrahydrofuran-3-yl-3-piperidyl)methanone | $^1$H NMR (400 MHz, DMSO-d6) δ 8.61 (d, J = 3.48 Hz, 1H), 8.07 (dd, J = 1.67, 8.97 Hz, 1H), 7.97-7.86 (m, 2H), 7.40 (d, J = 2.52 Hz, 1H), 7.26 (dd, J = 2.60, 8.91 Hz, 1H), 3.92 (s, 3H), 3.80-3.68 (m, 3H), 3.62-3.58 (m, 1H), 3.49-3.44 (m, 1H), 3.06-2.68 (m, 3H), 224-2.128 (m, 1H), 2.07-1.83 (m, 3H), 1.78-1.61 (m, 3H), 1.47-1.32 (m, 1H) | 340 |

-continued

| Example | Compound Name | $^1$H NMR | (m/z) M + H |
|---|---|---|---|
| 18 | (6-methoxy-2-naphthyl)-(1-propyl-3-piperidyl)methanone | $^1$H NMR (400 MHz, DMSO-d6) δ 8.60 (d, J = 1.45 Hz, 1H), 8.06 (d, J = 9.03 Hz, 1H), 7.95-7.86 (m, 2H), 7.40 (d, J = 2.55 Hz, 1H), 7.26 (dd, J = 2.54, 8.95 Hz, 1H), 3.92 (s, 3H), 3.76-3.70 (m, 1H), 3.01-2.94 (m, 1H), 2.89-2.96 (m, 1H), 2.29 (t, J = 7.44 Hz, 2H), 2.12 (t, J = 10.81 Hz, 1H), 1.99-1.83 (m, 2H), 1.74-1.68 (m, 2H), 1.50-1.32 (m, 3H), 0.83 (t, J = 7.39 Hz, 3H) | 312 |
| 21 | [1-(cyclopropylmethyl)-3-piperidyl]-(3-phenoxyphenyl)methanone | $^1$H NMR (400 MHz, DMSO-d6) δ 7.73 (dt, J = 1.20, 7.80 Hz, 1H), 7.55 (t, J = 7.92 Hz, 1H), 7.46-7.38 (m, 3H), 7.29 (ddd, J = 0.97, 2.50, 8.20 Hz, 1H), 7.23-7.16 (m, 1H), 7.09-7.03 (m, 2H), 3.52 (tt, J = 3.50, 10.88 Hz, 1H), 3.03-2.96 (m, 1H), 2.94-2.86 (m, 1H), 2.23-2.11 (m, 2H), 2.07 (t, J = 10.70 Hz, 1H), 1.92 (td, J = 3.28, 11.12 Hz, 1H), 1.85-1.76 (m, 1H), 1.72-1.54 (m, 2H), 1.31 (qd, J = 4.49, 11.72 Hz, 1H), 0.81-0.72 (m, 1H), 0.46-0.35 (m, 2H), 0.05-0.01 (m, 2H) | 336 |
| 22 | [1-(cyclopropylmethyl)-3-piperidyl]-[4-(trifluoromethyl)phenyl]methanone | $^1$H NMR (400 MHz, DMSO-d6) δ 8.13 (d, J = 8.11 Hz, 2H), 7.89 (d, J = 8.26 Hz, 2H), 3.62 (tt, J = 3.55, 10.36 Hz, 1H), 3.03-2.98 (m, 1H), 2.90 (dt, J = 3.94, 11.08 Hz, 1H), 2.26-2.10 (m, 3H), 1.97 (td, J = 3.39, 11.00 Hz, 1H), 1.5-1.802 (m, 1H), 1.75-1.57 (m, 2H), 1.39-1.29 (m, 1H), 0.82-0.737 (m, 1H), 0.45-0.34 (m, 2H), 0.08-0.00 (m, 2H) | 312 |
| 23 | [1-(cyclopropylmethyl)-3-piperidyl]-(4-phenoxyphenyl)methanone | $^1$H NMR (400 MHz, DMSO-d6) δ 8.03-7.94 (m, 2H), 7.50-7.42 (m, 2H), 7.25 (t, J = 7.39 Hz, 1H), 7.16-7.10 (m, 2H), 7.08-7.00 (m, 2H), 3.54 (tt, J = 3.48, 10.90 Hz, 1H), 3.05-2.98 (m, 1H), 2.96-2.93 (m, 1H), 2.19 (qd, J = 6.57, 12.68 Hz, 2H), 2.07 (t, J = 10.81 Hz, 1H), 1.91 (td, J = 3.53, 11.12 Hz, 1H), 1.84-1.80 (m, 1H), 1.73-1.57 (m, 2H), 1.31 (qd, J = 4.75, 11.70 Hz, 1H), 0.83-0.75 (m, 1H), 0.48-0.36 (m, 2H), 0.09-0.01 (m, 2H) | 336 |
| 24 | [1-(cyclopropylmethyl)-3-piperidyl]-(4-phenylphenyl)methanone | $^1$H NMR (400 MHz, DMSO-d6) δ 8.07-8.00 (m, 2H), 7.87-7.80 (m, 2H), 7.77-7.72 (m, 2H), 7.55-7.48 (m, 2H), 7.46-7.40 (m, 1H), 3.62 (ddt, J = 3.50, 6.98, 13.90 Hz, 1H), 3.08-3.03 (m, 1H), 2.98-2.93 (m, 1H), 2.21 (qd, J = 6.56, 12.67 Hz, 2H), 2.11 (dd, J = 10.32, 11.27 Hz, 1H), 1.94 (td, J = 3.86, 10.99 Hz, 1H), 1.90-1.81 (m, 1H), 1.75-1.60 (m, 2H), 1.40-1.28 (m, 1H), 0.87-0.75 (m, 1H), 0.48-0.37 (m, 2H), 0.10-0.01 (m, 2H) | 320 |
| 25 | [1-(cyclopropylmethyl)-3-piperidyl]-(3-phenylphenyl)methanone | $^1$H NMR (400 MHz, DMSO-d6) δ 8.15 (t, J = 1.79 Hz, 1H), 7.97-7.89 (m, 2H), 7.76-7.70 (m, 2H), 7.63 (t, J = 7.73 Hz, 1H), 7.55-7.47 (m, 2H), 7.44-7.38 (m, 1H), 3.70 (tt, J = 3.53, 10.73 Hz, 1H), 3.10-3.02 (m, 1H), 2.95-2.92 (m, 1H), 2.27-2.08 (m, 3H), 1.95 (td, J = 4.24, 10.78 Hz, 1H), 1.87-1.84 (m, 1H), 1.72-1.65 (m, 2H), 1.43-1.29 (m, 1H), 0.86-0.73 (m, 1H), 0.47-0.34 (m, 2H), 0.09-0.01 (m, 2H) | 320 |
| 26 | [1-(cyclopropylmethyl)-3-piperidyl]-(4-fluoro-2-naphthyl)methanone | $^1$H NMR (400 MHz, DMSO-d6) δ 8.62 (t, J = 0.99 Hz, 1H), 8.27 (dt, J = 1.61, 8.12 Hz, 1H), 8.11 (dd, J = 1.22, 8.21 Hz, 1H), 7.77 (dddd, J = 1.34, 6.96, 8.21, 20.50 Hz, 2H), 7.69 (dd, J = 1.47, 11.60 Hz, 1H), 3.84-3.74 (m, 1H), 3.10-3.08 (m, 1H), 3.01-2.93 (m, 1H), 2.29-2.11 (m, 3H), 2.01-1.86 (m, 2H), 1.75-1.69 (m, 2H), 1.45-1.31z (m, 1H), 0.87-0.75 (m, 1H), 0.47-0.36 (m, 2H), 0.10-0.01 (m, 2H) | 312 |
| 27 | [1-(cyclopropylmethyl)-3-piperidyl]-[3-(4-fluorophenoxy)phenyl]methanone | $^1$H NMR (400 MHz, DMSO-d6) δ 7.76-7.69 (m, 1H), 7.54 (t, J = 7.92 Hz, 1H), 7.41 (dd, J = 1.56, 2.55 Hz, 1H), 7.31-7.22 (m, 3H), 7.16-7.08 (m, 2H), 3.52 (tt, J = 3.52, 10.76 Hz, 1H), 3.01-2.98 (m, 1H), | 354 |

| Example | Compound Name | ¹H NMR | (m/z) M + H |
|---|---|---|---|
| | | 2.92-2.89 (m, 1H), 2.23-2.11 (m, 2H), 2.11-2.03 (m, 1H), 1.92 (td, J = 3.40, 11.12 Hz, 1H), 1.82-1.78 (m, 1H), 1.72-1.53 (m, 2H), 1.31 (qd, J = 4.55, 11.72 Hz, 1H), 0.83-0.70 (m, 1H), 0.47-0.35 (m, 2H), 0.08-0.01 (m, 2H) | |
| 28 | [(3S)-1-(cyclopropylmethyl)-3-piperidyl]-(3-phenoxyphenyl)methanone | ¹H NMR (400 MHz, DMSO-d6) d 7.73 (dt, J = 1.23, 7.77 Hz, 1H), 7.55 (t, J = 7.91 Hz, 1H), 7.47-7.38 (m, 3H), 7.28 (ddd, J = 0.98, 2.56, 8.20 Hz, 1H), 7.22-7.16 (m, 1H), 7.10-7.01 (m, 2H), 3.52 (tt, J = 3.45, 10.62 Hz, 1H), 3.03-2.96 (m, 1H), 2.91-2.88 (m, 1H), 2.24-2.11 (m, 2H), 2.07 (t, J = 10.71 Hz, 1H), 1.92 (td, J = 3.34, 11.21 Hz, 1H), 1.82-1.78 (m, 1H), 1.73-1.53 (m, 2H), 1.31 (qd, J = 4.45, 11.60 Hz, 1H), 0.85-0.69 (m, 1H), 0.46-0.33 (m, 2H), 0.08-0.00 (m, 2H) | 336 |
| 29 | [(3R)-1-(cyclopropylmethyl)-3-piperidyl]-(3-phenoxyphenyl)methanone | ¹H NMR (400 MHz, DMSO-d6) d 7.73 (dt, J = 1.21, 7.77 Hz, 1H), 7.58-7.51 (m, 1H), 7.46-7.38 (m, 3H), 7.28 (ddd, J = 0.94, 2.49, 8.19 Hz, 1H), 7.23-7.16 (m, 1H), 7.09-7.03 (m, 2H), 3.52 (tt, J = 3.56, 10.21 Hz, 1H), 3.03-2.95 (m, 1H), 2.91-2.88 (m, 1H), 2.23-2.11 (m, 2H), 2.07 (dd, J = 10.12, 11.29 Hz, 1H), 1.92 (td, J = 3.32, 11.16 Hz, 1H), 1.84-1.76 (m, 1H), 1.72-1.53 (m, 2H), 1.37-1.25 (m, 1H), 0.80-0.73 (m, 1H), 0.46-0.34 (m, 2H), 0.07-0.00 (m, 2H) | 336 |
| 30 | [(3R)-1-(cyclopropylmethyl)-3-piperidyl]-(4-phenoxyphenyl)methanone | ¹H NMR (400 MHz, DMSO-d6) d 8.02-7.94 (m, 2H), 7.50-7.42 (m, 2H), 7.28-7.21 (m, 1H), 7.16-7.09 (m, 2H), 7.07-7.01 (m, 2H), 3.54 (tt, J = 3.43, 11.21 Hz, 1H), 3.05-2.98 (m, 1H), 2.96-2.93 (m, 1H), 2.19 (qd, J = 6.51, 12.62 Hz, 2H), 2.07 (t, J = 10.84 Hz, 1H), 1.91 (td, J = 3.65, 11.19 Hz, 1H), 1.84-1.80 (m, 1H), 1.73-1.57 (m, 2H), 1.31 (qd, J = 4.84, 11.81 Hz, 1H), 0.86-0.74 (m, 1H), 0.48-0.36 (m, 2H), 0.09-0.01 (m, 2H) | 336 |
| 31 | [(3S)-1-(cyclopropylmethyl)-3-piperidyl]-(4-phenoxyphenyl)methanone | ¹H NMR (400 MHz, DMSO-d6) d 8.03-7.92 (m, 2H), 7.51-7.42 (m, 2H), 7.29-7.21 (m, 1H), 7.16-7.10 (m, 2H), 7.07-6.99 (m, 2H), 3.61-3.47 (m, 1H), 3.03-2.99 (m, 1H), 2.97-2.89 (m, 1H), 2.19 (qd, J = 6.54, 12.64 Hz, 2H), 2.07 (t, J = 10.83 Hz, 1H), 1.91 (td, J = 3.57, 11.12 Hz, 1H), 1.86-1.78 (m, 1H), 1.69-1.62 (m, 2H), 1.39-1.24 (m, 1H), 0.82-0.78 (m, 1H), 0.49-0.35 (m, 2H), 0.09-0.01 (m, 2H) | 336 |
| 32 | [(3R)-1-(cyclopropylmethyl)-3-piperidyl]-(4-phenylphenyl)methanone | ¹H NMR (400 MHz, DMSO-d6) d 8.07-8.00 (m, 2H), 7.86-7.80 (m, 2H), 7.77-7.72 (m, 2H), 7.55-7.47 (m, 2H), 7.47-7.40 (m, 1H), 3.62 (tt, J = 3.50, 10.43 Hz, 1H), 3.08-3.03 (m, 1H), 2.97-2.93 (m, 1H), 2.21 (qd, J = 6.51, 12.62 Hz, 2H), 2.11 (t, J = 10.79 Hz, 1H), 1.94 (td, J = 3.89, 10.99 Hz, 1H), 1.88-1.85 (m, 1H), 1.74-1.60 (m, 2H), 1.42-1.28 (m, 1H), 0.86-0.75 (m, 1H), 0.49-0.37 (m, 2H), 0.09-0.01 (m, 2H) | 320 |
| 33 | [(3S)-1-(cyclopropylmethyl)-3-piperidyl]-(4-phenylphenyl)methanone | ¹H NMR (400 MHz, DMSO-d6) d 8.07-8.00 (m, 2H), 7.87-7.80 (m, 2H), 7.78-7.71 (m, 2H), 7.55-7.47 (m, 2H), 7.47-7.39 (m, 1H), 3.67-3.57 (m, 1H), 3.09-3.01 (m, 1H), 3.00-2.91 (m, 1H), 2.21 (qd, J = 6.54, 12.66 Hz, 2H), 2.11 (t, J = 10.79 Hz, 1H), 1.94 (td, J = 3.89, 10.98 Hz, 1H), 1.90-1.82 (m, 1H), 1.75-1.60 (m, 2H), 1.40-1.28 (m, 1H), 0.86-0.76 (m, 1H), 0.48-0.36 (m, 2H), 0.10-0.01 (m, 2H) | 320 |
| 34 | [1-(cyclopropylmethyl)-3-piperidyl]-[4-(p-tolyl)phenyl]methanone | ¹H NMR (400 MHz, DMSO-d6) δ 8.08-7.98 (m, 2H), 7.87-7.77 (m, 2H), 7.69-7.60 (m, 2H), 7.37-7.27 (m, 2H), 3.61 (tt, J = 3.46, 10.95 Hz, 1H), 3.10-3.01 (m, 1H), 2.97-2.94 (m, 1H), 2.36 (s, 3H), 2.20 (qd, J = 6.54, 12.65 Hz, 2H), 2.14-2.05 (m, 1H), 1.94 (td, J = 3.90, 10.99 Hz, 1H), 1.87-1.84 (m, 1H), 1.75-1.59 (m, 2H), 1.34 (qd, J = 5.22, | 334 |

-continued

| Example | Compound Name | ¹H NMR | (m/z) M + H |
|---|---|---|---|
| | | 11.63 Hz, 1H), 0.83-0.79 (m, 1H), 0.50-0.35 (m, 2H), 0.10-0.01 (m, 2H) | |
| 35 | [1-(cyclopropylmethyl)-3-piperidyl]-[4-(hydroxymethyl)-2-naphthyl]methanone | ¹H NMR (400 MHz, DMSO-d6) δ 8.61 (s, 1H), 8.18 (dd, J = 1.38, 8.09 Hz, 1H), 8.11 (d, J = 8.45 Hz, 1H), 8.03 (d, J = 1.72 Hz, 1H), 7.71 (ddd, J = 1.48, 6.82, 8.42 Hz, 1H), 7.65 (ddd, J = 1.27, 6.80, 8.07 Hz, 1H), 5.44 (t, J = 5.44 Hz, 1H), 5.01 (d, J = 5.00 Hz, 2H), 3.9-3.947 (m, 1H), 2.08-1.93 (m, 1H), 1.85-1.81 (m, 2H), 1.50-1.45 (m, 1H), 0.98-0.92 (m, 1H), 0.55-0.51 (m, 2H), 0.21-0.15 (m, 2H) | 324.2 |
| 36 | [1-(cyclopropylmethyl)-3-piperidyl]-(6-phenyl-3-pyridyl)methanone | ¹H NMR (400 MHz, DMSO-d6) δ 9.14 (d, J = 2.29 Hz, 1H), 8.33 (dd, J = 2.29, 8.34 Hz, 1H), 8.14 (dq, J = 2.11, 2.66, 8.35 Hz, 2H), 8.09 (d, J = 8.39 Hz, 1H), 7.55-7.41 (m, 3H), 3.61 (tt, J = 3.47, 10.39 Hz, 1H), 3.01 (dd, J = 2.99, 10.89 Hz, 1H), 2.90-2.86 (m, 1H), 2.25-2.07 (m, 3H), 1.93 (td, J = 4.08, 10.71 Hz, 1H), 1.88-1.78 (m, 1H), 1.72-1.59 (m, 2H), 1.32 (qd, J = 5.24, 11.35 Hz, 1H), 0.84-0.67 (m, 1H), 0.45-0.29 (m, 2H), 0.06--0.03 (m, 2H) | 321 |
| 37 | [4-(aminomethyl)-2-naphthyl]-[1-(cyclopropylmethyl)-3-piperidyl]methanone | ¹H NMR (400 MHz, DMSO-d6) δ 8.57 (d, J = 1.80 Hz, 1H), 8.17-8.14 (m, 1H), 7.97-7.92 (m, 1H), 7.71-7.65 (m, 1H), 7.63-7.56 (m, 2H), 4.86 (s, 2H), 4.22 (d, J = 2.32 Hz, 2H), 3.85-3.71 (m, 1H), 3.09 (d, J = 9.18 Hz, 2H), 2.99 (d, J = 10.88 Hz, 2H), 2.28-2.12 (m, 5H), 1.72 (td, J = 4.94, 8.99, 10.27 Hz, 4H), 0.88-0.72 (m, 2H), 0.45-0.38 (m, 2H), 0.10-0.01 (m, 2H) | 323 |
| 38 | [1-(cyclopropylmethyl)-3-piperidyl]-[4-(2-pyridyl)phenyl]methanone | ¹H NMR (400 MHz, DMSO-d6) δ 8.68 (ddd, J = 0.91, 1.88, 4.78 Hz, 1H), 8.24-8.17 (m, 2H), 8.06-7.99 (m, 3H), 7.90 (td, J = 1.84, 7.73 Hz, 1H), 7.39 (ddd, J = 1.07, 4.79, 7.49 Hz, 1H), 3.60 (tt, J = 3.52, 10.47 Hz, 1H), 3.4-3.002 (m, 1H), 2.91 (dt, J = 3.68, 10.98 Hz, 1H), 2.23-2.10 (m, 2H), 2.07 (t, J = 10.87 Hz, 1H), 1.90 (td, J = 3.85, 11.01 Hz, 1H), 1.85-1.81 (m, 1H), 1.72-1.56 (m, 2H), 1.39-1.23 (m, 1H), 0.79-0.73 (m, 1H), 0.45-0.31 (m, 2H), 0.06--0.04 (m, 2H) | 321 |
| 39 | N-[[3-[1-(cyclopropylmethyl)piperidine-3-carbonyl]-1-naphthyl]methyl]acetamide | ¹H NMR (400 MHz, DMSO-d6) δ 8.67-8.62 (m, 1H), 8.42 (t, J = 5.87 Hz, 1H), 8.20 (dd, J = 1.39, 8.08 Hz, 1H), 8.16-8.09 (m, 1H), 7.88 (d, J = 1.71 Hz, 1H), 7.71 (ddd, J = 1.44, 6.81, 8.39 Hz, 1H), 7.65 (ddd, J = 1.18, 6.88, 8.01 Hz, 1H), 4.75 (d, J = 5.80 Hz, 2H), 3.79 (ddt, J = 3.56, 7.12, 10.86 Hz, 1H), 3.11-3.08 (m, 1H), 3.02-2.99 (m, 2H), 2.30-2.18 (m, 2H), 2.15 (t, J = 9.47 Hz, 1H), 2.02-1.90 (m, 2H), 1.89 (s, 3H), 1.76-1.70 (m, 2H), 1.45-1.31 (m, 1H), 0.89-0.75 (m, 1H), 0.47-0.38 (m, 2H), 0.11-0.01 (m, 2H) | 365 |
| 40 | 3-[1-(cyclopropylmethyl)piperidine-3-carbonyl]-N-methyl-naphthalene-1-carboxamide | ¹H NMR (400 MHz, DMSO-d6) δ 8.83-8.77 (m, 1H), 8.57 (q, J = 4.28 Hz, 1H), 8.28-8.19 (m, 2H), 7.99 (d, J = 1.69 Hz, 1H), 7.74-7.64 (m, 2H), 3.82 (tt, J = 3.45, 10.67 Hz, 1H), 3.11-3.07 (m, 1H), 2.30-2.97 (m, 1H), 2.87 (d, J = 4.57 Hz, 3H), 2.29-2.10 (m, 3H), 2.02-1.84 (m, 2H), 1.5-1.704 (m, 2H), 1.46-1.30 (m, 1H), 0.90-0.74 (m, 1H), 0.49-0.34 (m, 2H), 0.11-0.01 (m, 2H) | 351 |
| 41 | 3-(1-cyclopentylpiperidine-3-carbonyl)-N-methyl-naphthalene-1-carboxamide | ¹H NMR (400 MHz, DMSO-d6) δ 8.80-8.76 (m, 1H), 8.56 (q, J = 4.49 Hz, 1H), 8.23 (ddd, J = 1.32, 8.39, 12.62 Hz, 2H), 7.98 (d, J = 1.72 Hz, 1H), 7.73-7.64 (m, 2H), 3.80 (tt, J = 3.49, 10.64 Hz, 1H), 3.09-3.02 (m, 1H), 2.93 (d, J = 11.17 Hz, 1H), 2.88-2.86 (m, 3H), 2.60-2.52 (m, 1H), 2.12 (t, J = 10.72 Hz, 1H), 2.00-1.85 (m, 2H), 1.82-1.66 (m, 4H), 1.60-1.27 (m, 7H) | 365 |
| 42 | 3-(1-cyclobutylpiperidine-3-carbonyl)-N-methyl-naphthalene-1-carboxamide | ¹H NMR (400 MHz, DMSO-d6) δ 8.78 (t, J = 1.17 Hz, 1H), 8.56 (q, J = 4.63 Hz, 1H), 8.23 (ddd, J = 1.33, 8.44, 10.10 Hz, 2H), 7.98 (d, J = 1.72 Hz, | 351 |

| Example | Compound Name | ¹H NMR | (m/z) M + H |
|---|---|---|---|
| | | 1H), 7.74-7.64 (m, 2H), 3.77 (tt, J = 3.53, 10.90 Hz, 1H), 2.94-2.88 (m, 1H), 2.87 (d, J = 4.58 Hz, 3H), 2.80-2.76 (m, 1H), 2.75-2.69 (m, 1H), 1.98-1.88 (m, 4H), 1.82-1.66 (m, 5H), 1.2-1.581 (m, 2H), 1.44-1.31 (m, 1H) | |
| 43 | 3-[1-(cyclopropylmethyl)piperidine-3-carbonyl]naphthalene-1-carbonitrile | ¹H NMR (400 MHz, DMSO-d6) δ 9.08-9.02 (m, 1H), 8.55 (d, J = 1.69 Hz, 1H), 8.42-8.34 (m, 1H), 8.18 (dd, J = 0.99, 8.30 Hz, 1H), 7.95 (ddd, J = 1.27, 6.93, 8.36 Hz, 1H), 7.83 (ddd, J = 1.15, 6.91, 8.08 Hz, 1H), 3.82 (tt, J = 3.57, 10.14 Hz, 1H), 3.09-3.05 (m, 1H), 3.00-2.90 (m, 1H), 2.29-2.13 (m, 3H), 2.04-1.85 (m, 2H), 1.75-1.69 (m, 1H), 1.43-1.38 (m, 1H), 0.83-0.75 (m, 1H), 0.43-0.37 (m, 2H), 0.10-0.01 (m, 2H) | 319 |
| 44 | 3-(1-cyclobutylpiperidine-3-carbonyl)naphthalene-1-carbonitrile | ¹H NMR (400 MHz, DMSO-d6) δ 9.07-9.01 (m, 1H), 8.54 (d, J = 1.71 Hz, 1H), 8.37 (d, J = 8.02 Hz, 1H), 8.18 (d, J = 8.28 Hz, 1H), 7.95 (ddd, J = 1.23, 6.89, 8.27 Hz, 1H), 7.83 (ddd, J = 1.08, 6.89, 8.08 Hz, 1H), 3.77 (tt, J = 3.57, 10.59 Hz, 1H), 2.94-2.84 (m, 1H), 2.79-2.65 (m, 2H), 2.00-1.86 (m, 4H), 1.82-1.53 (m, 7H), 1.37 (qd, J = 4.64, 11.13 Hz, 1H) | 319 |
| 45 | 3-(1-cyclopentylpiperidine-3-carbonyl)naphthalene-1-carbonitrile | ¹H NMR (400 MHz, DMSO-d6) δ 9.07-8.99 (m, 1H), 8.53 (d, J = 1.70 Hz, 1H), 8.37 (d, J = 7.98 Hz, 1H), 8.17 (d, J = 8.34 Hz, 1H), 7.98-7.91 (m, 1H), 7.87-7.79 (m, 1H), 3.79 (tt, J = 3.48, 10.13 Hz, 1H), 3.05-3.02 (m, 1H), 2.95-2.84 (m, 1H), 2.56-2.51 (m, 1H), 2.15 (t, J = 10.60 Hz, 1H), 1.97 (td, J = 4.31, 10.67 Hz, 1H), 1.91-1.86 (m, 1H), 1.80-1.63 (m, 4H), 1.58-1.54 (m, 2H), 1.51-1.21 (m, 5H) | 333 |
| 46 | 3-(1-cyclopentylpiperidine-3-carbonyl)naphthalene-1-carboxamide | ¹H NMR (400 MHz, DMSO-d6) δ 8.77 (d, J = 1.71 Hz, 1H), 8.33 (d, J = 8.46 Hz, 1H), 8.25-8.19 (m, 1H), 8.11 (s, 1H), 8.03 (d, J = 1.70 Hz, 1H), 7.75-7.61 (m, 3H), 3.79 (ddt, J = 3.44, 7.18, 10.76 Hz, 1H), 3.08-3.05 (m, 1H), 2.95-2.92 (m, 1H), 2.61-2.53 (m, 1H), 2.11 (t, J = 10.82 Hz, 1H), 2.00-1.85 (m, 2H), 1.75-1.68 (m, 4H), 1.62-1.26 (m, 7H) | 351 |
| 47 | 3-(1-cyclobutylpiperidine-3-carbonyl)naphthalene-1-carboxamide | ¹H NMR (400 MHz, DMSO-d6) δ 8.80-8.75 (m, 1H), 8.36-8.29 (m, 1H), 8.25-8.19 (m, 1H), 8.11 (s, 1H), 8.03 (d, J = 1.75 Hz, 1H), 7.76-7.61 (m, 3H), 3.77 (tt, J = 3.47, 10.69 Hz, 1H), 2.93-2.89 (m, 1H), 2.80-2.76 (m, 1H), 2.76-2.69 (m, 1H), 2.02-1.85 (m, 4H), 1.82-1.52 (m, 7H), 1.45-1.31 (m, 1H) | 337 |
| 48 | 3-[1-(cyclopropylmethyl)piperidine-3-carbonyl]naphthalene-1-carboxamide | ¹H NMR (400 MHz, DMSO-d6) δ 8.78 (d, J = 1.68 Hz, 1H), 8.33 (d, J = 8.43 Hz, 1H), 8.21 (dd, J = 1.32, 8.18 Hz, 1H), 8.11 (s, 1H), 8.04 (d, J = 1.70 Hz, 1H), 7.72 (ddd, J = 1.49, 6.87, 8.38 Hz, 1H), 7.69-7.60 (m, 2H), 3.82 (tt, J = 3.53, 10.88 Hz, 1H), 3.14-3.05 (m, 1H), 3.01-2.97 (m, 1H), 2.30-2.10 (m, 3H), 2.02-1.87 (m, 2H), 1.77-1.69 (m, 2H), 1.44-1.34 (m, 1H), 0.86-0.78 (m, 1H), 0.47-0.37 (m, 2H), 0.11-0.01 (m, 2H) | 337 |
| 49 | [1-(cyclopropylmethyl)-3-piperidyl]-(6-methoxy-5-methyl-2-naphthyl)methanone | ¹H NMR (400 MHz, DMSO-d6) δ 8.63 (d, J = 1.81 Hz, 1H), 8.07 (d, J = 9.09 Hz, 1H), 8.02 (d, J = 8.99 Hz, 1H), 7.94 (dd, J = 1.88, 9.01 Hz, 1H), 7.52 (d, J = 9.07 Hz, 1H), 3.96 (s, 3H), 3.81-3.70 (m, 1H), 3.12-3.04 (m, 1H), 3.01-2.97 (m, 1H), 2.48 (s, 3H), 2.21 (qd, J = 6.60, 12.69 Hz, 2H), 2.12 (t, J = 10.85 Hz, 1H), 2.00-1.84 (m, 2H), 1.74-1.68 (m, 2H), 1.43-1.33 (m, 1H), 0.87-0.75 (m, 1H), 0.46-0.37 (m, 2H), 0.10-0.01 (m, 2H) | 338 |
| 50 | (6-methoxy-5-methyl-2-naphthyl)-(1-propyl-3-piperidyl)methanone | ¹H NMR (400 MHz, DMSO-d6) δ 8.61 (d, J = 1.78 Hz, 1H), 8.06 (d, J = 9.05 Hz, 1H), 8.03 (s, 1H), 7.93 (dd, J = 1.82, 9.02 Hz, 1H), 7.52 (d, J = 9.05 Hz, 1H), 3.96 (s, 3H), | 326 |

-continued

| Example | Compound Name | ¹H NMR | (m/z) M + H |
|---|---|---|---|
| 51 | (1-cyclopentyl-3-piperidyl)-(6-methoxy-5-methyl-2-naphthyl)methanone | 3.73 (tt, J = 3.54, 10.60 Hz, 1H), 2.99-2.90 (m, 1H), 2.86-2.83 (m, 1H), 2.48 (s, 3H), 2.25 (t, J = 7.39 Hz, 2H), 2.07 (t, J = 10.77 Hz, 1H), 1.92-1.86 (m, 2H), 1.73-1.64 (m, 2H), 1.48-1.31 (m, 3H), 0.83 (t, J = 7.33 Hz, 3H)<br>¹H NMR (400 MHz, DMSO-d6) δ 8.61 (d, J = 1.78 Hz, 1H), 8.06 (d, J = 9.05 Hz, 1H), 8.03 (s, 1H), 7.93 (dd, J = 1.82, 9.02 Hz, 1H), 7.52 (d, J = 9.05 Hz, 1H), 3.96 (s, 3H), 3.73 (tt, J = 3.54, 10.60 Hz, 1H), 2.99-2.90 (m, 1H), 2.86-2.83 (m, 1H), 2.48 (s, 3H), 2.25 (t, J = 7.39 Hz, 2H), 2.07 (t, J = 10.77 Hz, 1H), 1.92-1.86 (m, 2H), 1.73-1.64 (m, 2H), 1.48-1.31 (m, 3H), 0.83 (t, J = 7.33 Hz, 3H) | 352 |
| 52 | (1-cyclobutyl-3-piperidyl)-(6-methoxy-5-methyl-2-naphthyl)methanone | ¹H NMR (400 MHz, DMSO-d6) δ 8.61 (d, J = 1.78 Hz, 1H), 8.06 (d, J = 9.05 Hz, 1H), 8.03 (s, 1H), 7.93 (dd, J = 1.82, 9.02 Hz, 1H), 7.52 (d, J = 9.05 Hz, 1H), 3.96 (s, 3H), 3.73 (tt, J = 3.54, 10.60 Hz, 1H), 2.99-2.90 (m, 1H), 2.86-2.83 (m, 1H), 2.48 (s, 3H), 2.25 (t, J = 7.39 Hz, 2H), 2.07 (t, J = 10.77 Hz, 1H), 1.92-1.86 (m, 2H), 1.73-1.64 (m, 2H), 1.48-1.31 (m, 3H), 0.83 (t, J = 7.33 Hz, 3H) | 338 |
| 53 | 2-[6-[1-(cyclopropylmethyl)piperidine-3-carbonyl]-2-methoxy-1-naphthyl]acetonitrile | ¹H NMR (400 MHz, DMSO-d6) δ 8.71 (d, J = 1.67 Hz, 1H), 8.27 (d, J = 9.15 Hz, 1H), 8.12 (d, J = 8.97 Hz, 1H), 8.03 (dd, J = 1.78, 8.96 Hz, 1H), 7.63 (d, J = 9.13 Hz, 1H), 4.29 (s, 2H), 4.04 (s, 3H), 3.78 (tt, J = 3.48, 10.84 Hz, 1H), 3.10-3.07 (m, 1H), 3.00-2.97 (m, 1H), 2.29-2.08 (m, 3H), 2.02-1.84 (m, 2H), 1.75-1.69 (m, 2H), 1.43-1.33 (m, 1H), 0.89-0.75 (m, 1H), 0.46-0.37 (m, 2H), 0.11-0.00 (m, 2H) | 363 |
| 54 | 2-[6-(1-cyclopentylpiperidine-3-carbonyl)-2-methoxy-1-naphthyl]acetonitrile | ¹H NMR (400 MHz, DMSO-d6) δ 8.70 (d, J = 1.75 Hz, 1H), 8.26 (d, J = 9.08 Hz, 1H), 8.12 (d, J = 8.99 Hz, 1H), 8.03 (dd, J = 1.79, 8.93 Hz, 1H), 7.63 (d, J = 9.16 Hz, 1H), 4.29 (s, 2H), 4.04 (s, 3H), 3.75 (tt, J = 3.43, 10.57 Hz, 1H), 3.09-3.01 (m, 1H), 2.94-2.91 (m, 1H), 2.58-2.54 (m, 1H), 2.10 (t, J = 10.79 Hz, 1H), 1.99-1.86 (m, 2H), 1.81-1.65 (m, 4H), 1.60-1.27 (m, 7H) | 377 |
| 55 | 2-[6-(1-cyclobutylpiperidine-3-carbonyl)-2-methoxy-1-naphthyl]acetonitrile | ¹H NMR (400 MHz, DMSO-d6) δ 8.70 (d, J = 1.77 Hz, 1H), 8.27 (d, J = 9.10 Hz, 1H), 8.12 (d, J = 8.99 Hz, 1H), 8.03 (dd, J = 1.80, 8.94 Hz, 1H), 7.63 (d, J = 9.13 Hz, 1H), 4.29 (s, 2H), 4.04 (s, 3H), 3.72 (tt, J = 3.57, 10.76 Hz, 1H), 2.91-2.88 (m, 1H), 2.79-2.76 (m, 1H), 2.74-2.65 (m, 1H), 2.02-1.84 (m, 4H), 1.81-1.52 (m, 7H), 1.43-1.34 (m, 1H) | 363 |
| 56 | 2-[2-methoxy-6-(1-propylpiperidine-3-carbonyl)-1-naphthyl]acetonitrile | ¹H NMR (400 MHz, DMSO-d6) δ 8.70 (d, J = 1.78 Hz, 1H), 8.26 (d, J = 9.10 Hz, 1H), 8.12 (d, J = 8.99 Hz, 1H), 8.03 (dd, J = 1.80, 9.01 Hz, 1H), 7.63 (d, J = 9.17 Hz, 1H), 4.29 (s, 2H), 4.04 (s, 3H), 3.75 (tt, J = 3.47, 10.57 Hz, 1H), 2.99-2.91 (m, 1H), 2.86-2.83 (m, 1H), 2.25 (t, J = 7.39 Hz, 2H), 2.09 (t, J = 10.75 Hz, 1H), 1.90 (td, J = 4.26, 10.77 Hz, 2H), 1.74-1.67 (m, 2H), 1.48-1.30 (m, 3H), 0.83 (t, J = 7.37 Hz, 3H) | 351 |
| 57 | (1-cyclopentyl-3-piperidyl)-[4-(hydroxymethyl)-2-naphthyl]methanone | ¹H NMR (400 MHz, DMSO-d6) δ 8.61 (d, J = 1.95 Hz, 1H), 8.21-8.15 (m, 1H), 8.12-8.07 (m, 1H), 8.01 (d, J = 1.74 Hz, 1H), 7.69 (ddd, J = 1.48, 6.86, 8.45 Hz, 1H), 7.63 (ddd, J = 1.27, 6.83, 8.04 Hz, 1H), 5.43 (t, J = 5.19 Hz, 1H), 5.00 (d, J = 4.50 Hz, 2H), 3.77 (tt, J = 3.60, 11.01 Hz, 1H), 3.10-3.02 (m, 1H), 2.96-2.92 (m, 1H), 2.59-2.52 (m, 1H), 2.09 (t, J = 10.77 Hz, 1H), 1.98-1.83 (m, 2H), 1.81-1.64 (m, 4H), 1.61-1.26 (m, 7H) | 338 |
| 58 | (1-cyclobutyl-3-piperidyl)-[4-(hydroxymethyl)-2-naphthyl]methanone | ¹H NMR (400 MHz, DMSO-d6) δ 8.66-8.58 (m, 1H), 8.24-8.14 (m, 1H), 8.10 (d, J = 8.49 Hz, 1H), 8.04-7.97 (m, 1H), 7.69 (ddd, J = 1.66, 6.72, 8.41 Hz, 1H), 7.66-7.58 (m, 1H), 5.43 (s, 1H), 5.00 (d, J = 3.36 Hz, 2H), 3.74 (tt, J = 4.95, 10.40 Hz, 1H), | 324 |

-continued

| Example | Compound Name | ¹H NMR | (m/z) M + H |
|---|---|---|---|
| | | 2.96-2.86 (m, 1H), 2.83-2.75 (m, 1H), 2.70 (p, J = 7.77 Hz, 1H), 2.03-1.83 (m, 4H), 1.81-1.54 (m, 7H), 1.45-1.30 (m, 1H) | |
| 59 | [1-(cyclopropylmethyl)-3-piperidyl]-(8-methyl-2-naphthyl)methanone | ¹H NMR (400 MHz, DMSO-d6) δ 8.65-8.60 (m, 1H), 8.06-7.96 (m, 2H), 7.85 (d, J = 8.06 Hz, 1H), 7.55 (dd, J = 6.98, 8.15 Hz, 1H), 7.47 (dt, J = 1.15, 6.96 Hz, 1H), 3.81 (tt, J = 3.50, 10.33 Hz, 1H), 3.17-3.08 (m, 1H), 2.99-2.94 (m, 1H), 2.75 (s, 3H), 2.27-2.16 (m, 2H), 2.16-2.09 (m, 1H), 1.97-1.89 (m, 2H), 1.75-1.69 (m, 2H), 1.46-1.32 (m, 1H), 0.86-0.76 (m, 1H), 0.48-0.34 (m, 2H), 0.10-0.00 (m, 2H) | 308 |
| 60 | (8-methyl-2-naphthyl)-(1-propyl-3-piperidyl)methanone | ¹H NMR (400 MHz, DMSO-d6) δ 8.64-8.59 (m, 1H), 8.03 (d, J = 8.50 Hz, 1H), 7.98 (dd, J = 1.63, 8.57 Hz, 1H), 7.85 (d, J = 8.22 Hz, 1H), 7.55 (dd, J = 6.98, 8.15 Hz, 1H), 7.49-7.43 (m, 1H), 3.78 (tt, J = 3.48, 10.64 Hz, 1H), 3.01-2.98 (m, 1H), 2.87-2.80 (m, 1H), 2.75 (s, 3H), 2.28-2.22 (m, 2H), 2.07 (t, J = 10.75 Hz, 1H), 1.95-1.88 (m, 2H), 1.77-1.64 (m, 2H), 1.48-1.32 (m, 3H), 0.83 (t, J = 7.35 Hz, 3H) | 296 |
| 61 | (1-cyclopentyl-3-piperidyl)-(8-methyl-2-naphthyl)methanone | ¹H NMR (400 MHz, DMSO-d6) δ 8.65-8.59 (m, 1H), 8.03 (d, J = 8.50 Hz, 1H), 8.00 (s, 1H), 7.85 (d, J = 8.10 Hz, 1H), 7.56 (dd, J = 6.98, 8.15 Hz, 1H), 7.47 (dt, J = 1.19, 7.03 Hz, 1H), 3.78 (tt, J = 3.49, 10.54 Hz, 1H), 3.14-3.05 (m, 1H), 2.94-2.91 (m, 1H), 2.75 (s, 3H), 2.57-2.51 (m, 1H), 2.09 (t, J = 10.77 Hz, 1H), 1.99-1.84 (m, 2H), 1.82-1.64 (m, 4H), 1.62-1.23 (m, 7H) | 322 |
| 62 | (1-cyclobutyl-3-piperidyl)-(8-methyl-2-naphthyl)methanone | ¹H NMR (400 MHz, DMSO-d6) δ 8.63-8.59 (m, 1H), 8.03 (d, J = 8.56 Hz, 1H), 7.98 (dd, J = 1.63, 8.58 Hz, 1H), 7.85 (d, J = 8.13 Hz, 1H), 7.56 (dd, J = 6.99, 8.17 Hz, 1H), 7.47 (dt, J = 1.16, 6.91 Hz, 1H), 3.76 (tt, J = 3.47, 10.59 Hz, 1H), 2.97-2.89 (m, 1H), 2.79-2.77 (m, 1H), 2.76 (s, 3H), 2.72-2.65 (m, 1H), 2.01-1.83 (m, 4H), 1.80-1.53 (m, 7H), 1.46-1.33 (m, 1H) | 308 |
| 63 | (1-cyclopentyl-3-piperidyl)-[4-(1-hydroxyethyl)-2-naphthyl]methanone | ¹H NMR (400 MHz, DMSO-d6) δ 8.59 (t, J = 2.24 Hz, 1H), 8.21-8.15 (m, 2H), 8.12 (d, J = 1.68 Hz, 1H), 7.68 (ddd, J = 1.42, 6.83, 8.38 Hz, 1H), 7.61 (ddd, J = 1.10, 6.80, 8.08 Hz, 1H), 5.54-5.46 (m, 1H), 5.44 (d, J = 3.94 Hz, 1H), 3.76 (tt, J = 3.08, 9.98 Hz, 1H), 3.08-3.05 (m, 1H), 2.95-2.92 (m, 1H), 2.55-2.52 (m, 1H), 2.12-2.04 (m, 1H), 1.99-1.82 (m, 2H), 1.82-1.49 (m, 7H), 1.47 (d, J = 6.33 Hz, 2H), 1.45-1.26 (m, 4H) | 352 |
| 64 | (1-cyclobutyl-3-piperidyl)-[4-(1-hydroxyethyl)-2-naphthyl]methanone | ¹H NMR (400 MHz, DMSO-d6) δ 8.61-8.56 (m, 1H), 8.22-8.16 (m, 2H), 8.12 (d, J = 1.73 Hz, 1H), 7.68 (ddd, J = 1.43, 6.87, 8.42 Hz, 1H), 7.61 (ddd, J = 1.11, 6.84, 8.12 Hz, 1H), 5.50 (t, J = 5.42 Hz, 1H), 5.44 (d, J = 4.10 Hz, 1H), 3.74 (tt, J = 3.41, 10.90 Hz, 1H), 2.92-2.90 (m, 1H), 2.80-2.77 (m, 1H), 2.75-2.65 (m, 1H), 2.01-1.80 (m, 4H), 1.80-1.53 (m, 7H), 1.47 (d, J = 6.36 Hz, 3H), 1.44-1.33 (m, 1H) | 338 |
| 65 | 3-[3-(6-methoxynaphthalene-2-carbonyl)-1-piperidyl]cyclobutanecarbonitrite | ¹H NMR (400 MHz, DMSO-d6) δ 8.63 (d, J = 1.50 Hz, 1H), 8.08 (d, J = 9.03 Hz, 1H), 7.97-7.86 (m, 2H), 7.41 (d, J = 2.56 Hz, 1H), 7.26 (dd, J = 2.55, 8.94 Hz, 1H), 3.92 (s, 3H), 3.71 (tt, J = 3.54, 10.69 Hz, 1H), 3.05-2.97 (m, 1H), 2.92-2.83 (m, 1H), 2.81-2.68 (m, 2H), 2.48-2.41 (m, 2H), 2.12-1.98 (m, 2H), 1.96-1.84 (m, 2H), 1.79-1.60 (m, 3H), 1.35 (qd, J = 4.70, 11.77 Hz, 1H) | 349 |
| 66 | [1-(3,3-difluorocyclobutyl)-3-piperidyl]-(6-methoxy-2-naphthyl)methanone | ¹H NMR (400 MHz, DMSO-d6) δ 8.67-8.61 (m, 1H), 8.08 (d, J = 8.99 Hz, 1H), 7.97-7.87 (m, 2H), 7.41 (d, J = 2.58 Hz, 1H), 7.26 (dd, J = 2.53, 8.99 Hz, 1H), 3.92 (s, 3H), 3.73 (tt, J = 3.49, 10.95 Hz, 1H), 2.4-2.913 (m, 1H), 2.84-2.81 (m, 1H), 2.71-2.64 (m, | 360 |

| Example | Compound Name | ¹H NMR | (m/z) M + H |
|---|---|---|---|
| | | 3H), 2.46-2.27 (m, 2H), 2.00 (t, J = 10.78 Hz, 1H), 1.92-1.89 (m, 1H), 1.82 (td, J = 3.28, 11.01 Hz, 1H), 1.78-1.63 (m, 2H), 1.45-1.29 (m, 1H) | |
| 67 | [1-(cyclopropylmethyl)-3-piperidyl]-[4-(1-hydroxyethyl)-2-naphthyl]methanone | ¹H NMR (400 MHz, DMSO-d6) δ 8.61 (d, J = 1.91 Hz, 1H), 8.22-8.16 (m, 2H), 8.12 (d, J = 1.69 Hz, 1H), 7.68 (ddd, J = 1.45, 6.82, 8.38 Hz, 1H), 7.61 (ddd, J = 1.05, 6.75, 7.90 Hz, 1H), 5.55-5.46 (m, 1H), 5.44 (dd, J = 1.09, 4.33 Hz, 1H), 3.80 (t, J = 11.22 Hz, 1H), 3.11-3.08 (m, 1H), 3.01-2.98 (m, 1H), 2.29-2.08 (m, 3H), 1.98-1.83 (m, 2H), 1.4-1.723 (m, 2H), 1.47 (d, J = 6.30 Hz, 3H), 1.44-1.31 (m, 1H), 0.84-0.80 (m, 1H), 0.48-0.34 (m, 2H), 0.10-0.01 (m, 2H) | 338 |
| 68 | [4-(1-hydroxyethyl)-2-naphthyl]-(1-propyl-3-piperidyl)methanone | ¹H NMR (400 MHz, DMSO-d6) δ 8.59 (d, J = 1.60 Hz, 1H), 8.22-8.14 (m, 2H), 8.12 (d, J = 1.69 Hz, 1H), 7.68 (ddd, J = 1.43, 6.83, 8.35 Hz, 1H), 7.61 (ddd, J = 1.11, 6.88, 8.01 Hz, 1H), 5.55-5.46 (m, 1H), 5.44 (d, J = 4.26 Hz, 1H), 3.77 (td, J = 2.70, 10.80 Hz, 1H), 3.02-2.91 (m, 1H), 2.89-2.84 (m, 1H), 2.25 (t, J = 7.45 Hz, 2H), 2.13-2.01 (m, 1H), 1.91-1.87 (m, 2H), 1.74-1.70 (m, 2H), 1.47 (dd, J = 1.21, 6.33 Hz, 3H), 1.46-1.40 (m, 3H), 0.83 (td, J = 2.36, 7.36 Hz, 3H) | 326 |
| 69 | [1-(cyclobutylmethyl)-3-piperidyl]-(6-methoxy-2-naphthyl)methanone | ¹H NMR (400 MHz, DMSO-d6) δ 8.61 (d, J = 1.43 Hz, 1H), 8.06 (d, J = 8.99 Hz, 1H), 7.95-7.86 (m, 2H), 7.41 (d, J = 2.57 Hz, 1H), 7.26 (dd, J = 2.53, 8.99 Hz, 1H), 3.92 (s, 3H), 3.70 (tt, J = 3.48, 10.90 Hz, 1H), 2.95-2.85 (m, 1H), 2.81-2.77f (m, 1H), 2.48-2.44 (m, 1H), 2.37-2.30 (m, 2H), 2.13-2.03 (m, 1H), 2.02-1.52 (m, 10H), 1.40-1.29 (m, 1H) | 338 |
| 70 | 1-methyl-6-(1-propylpiperidine-3-carbonyl)-2-naphthonitrile | ¹H NMR (DMSO-d6) δ: 8.75 (d, J = 1.8 Hz, 1H), 8.31 (d, J = 8.9 Hz, 1H), 8.18 (d, J = 8.5 Hz, 1H), 8.10 (dd, J = 8.9, 1.8 Hz, 1H), 7.82 (d, J = 8.6 Hz, 1H), 3.77 (tt, J = 10.6, 3.6 Hz, 1H), 3.00-2.92 (m, 1H), 2.91 (s, 3H), 2.87-2.77 (m, 1H), 2.24 (t, J = 7.3 Hz, 2H), 2.11 (t, J = 10.7 Hz, 1H), 1.98-1.84 (m, 2H), 1.78-1.61 (m, 2H), 1.47-1.31 (m, 3H), 0.82 (t, J = 7.3 Hz, 3H) | 321 |
| 71 | 6-(1-(cyclopropylmethyl)piperidine-3-carbonyl)-1-methyl-2-naphthonitrile | ¹H NMR (DMSO-d6) δ: 8.77 (d, J = 1.8 Hz, 1H), 8.31 (d, J = 8.9 Hz, 1H), 8.18 (d, J = 8.6 Hz, 1H), 8.11 (dd, J = 8.9, 1.8 Hz, 1H), 7.82 (d, J = 8.5 Hz, 1H), 3.80 (tt, J = 10.7, 3.6 Hz, 1H), 3.12-3.03 (m, 1H), 2.99-2.92 (m, 1H), 2.91 (s, 3H), 2.29-2.11 (m, 3H), 2.03-1.84 (m, 2H), 1.72 (td, J = 10.7, 10.0, 5.4 Hz, 2H), 1.46-1.31 (m, 1H), 0.86-0.72 (m, 1H), 0.47-0.33 (m, 2H), 0.10-0.01 (m, 2H) | 333 |
| 72 | 6-(1-cyclobutylpiperidine-3-carbonyl)-1-methyl-2-naphthonitrile | ¹H NMR (DMSO-d6) δ: 8.76 (d, J = 1.8 Hz, 1H), 8.31 (d, J = 8.9 Hz, 1H), 8.19 (d, J = 8.6 Hz, 1H), 8.10 (dd, J = 9.0, 1.8 Hz, 1H), 7.82 (d, J = 8.6 Hz, 1H), 3.75 (tt, J = 10.5, 3.5 Hz, 1H), 2.91 (s, 3H), 2.90-2.83 (m, 1H), 2.79-2.66 (m, 2H), 2.00-1.84 (m, 4H), 1.82-1.52 (m, 7H), 1.38 (qd, J = 11.5, 4.4 Hz, 1H) | 333 |
| 73 | 6-(1-cyclopentylpiperidine-3-carbonyl)-1-methyl-2-naphthonitrile | ¹H NMR (DMSO-d6) δ: 8.76 (d, J = 1.7 Hz, 1H), 8.31 (d, J = 8.9 Hz, 1H), 8.18 (d, J = 8.6 Hz, 1H), 8.10 (dd, J = 8.9, 1.8 Hz, 1H), 7.82 (d, J = 8.5 Hz, 1H), 3.77 (tt, J = 10.7, 3.6 Hz, 1H), 3.08-2.99 (m, 1H), 2.94-2.85 (m, 4H), 2.59-2.51 (m, 1H), 2.13 (t, J = 10.7 Hz, 1H), 2.02-1.82 (m, 2H), 1.79-1.21 (m, 12H) | 347 |

Example 74

(1-ethyl-3-piperidyl)-(6-methoxy-2-naphthyl)methanone

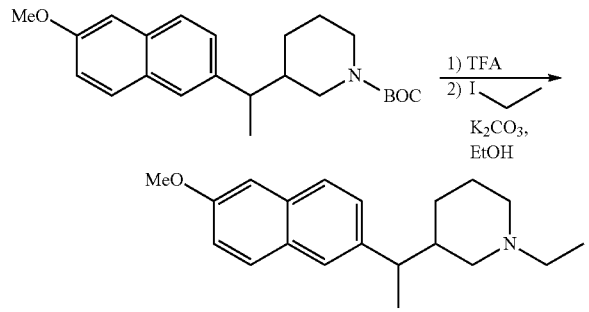

To a solution of tert-butyl 3-(6-methoxynaphthalene-2-carbonyl)piperidine-1-carboxylate (1.666 g, 4.51 mmol) in DCM (5 mL) was added TFA (5.142 g, 45.1 mmol). The mixture was stirred at room temperature for 1 h. The mixture was concentrated to give (6-methoxynaphthalen-2-yl)(piperidin-3-yl)methanone as a colorless oil and used directly without purification. A mixture of (6-methoxy-2-naphthyl)-(3-piperidyl)methanone (67.3 mg, 0.25 mmol), iodoethane (46.8 mg, 0.300 mmol) and $K_2CO_3$ (41.5 mg, 0.3 mmol) in EtOH (1 mL) was heated at 85° C. for 1 h. The mixture was cooled to room temperature. filtered, washed with EtOAc, and concentrated. The crude product was purified by preparative reverse phase HPLC to give the title compound. (52.4 mg, 70.5% yield) as a light yellow oil. $^1$H NMR (400 MHz, DMSO-d6) δ 8.60 (d, J=1.58 Hz, 1H), 8.06 (d, J=9.02 Hz, 1H), 7.96-7.86 (m, 2H), 7.40 (d, J=2.62 Hz, 1H), 7.26 (dd, J=2.56, 8.99 Hz, 1H), 3.92 (s, 3H), 3.72 (tt, J=3.53, 10.88 Hz, 1H), 3.02-2.92 (m, 1H), 2.87 (d, J=11.01 Hz, 1H), 2.35 (qd, J=2.99, 7.15 Hz, 2H), 2.05 (t, J=10.76 Hz, 1H), 1.87 (td, J=3.87, 10.67 Hz, 2H), 1.76-1.63 (m, 2H), 1.45-1.30 (m, 1H), 0.98 (t, J=7.14 Hz, 3H). LCMS (ESI) m/z 298 [M+H$^+$].

The following compounds were prepared in a manner similar to example 74.

| Example | Compound Name | $^1$NMR | m/z (M + H) |
|---|---|---|---|
| 76 | (1-cyclobutyl-3-piperidyl)-(6-methoxy-2-naphthyl)methanone | $^1$H NMR (400 MHz, DMSO-d6) δ 8.65-8.59 (m, 1H), 8.06 (d, J = 9.03 Hz, 1H), 7.96-7.86 (m, 2H), 7.40 (d, J = 2.55 Hz, 1H), 7.26 (dd, J = 2.55, 8.97 Hz, 1H), 3.92 (s, 3H), 3.75 (m, 1H), 3.11-3.04 (m, 1H), 3.03-2.94 (m, 1H), 2.29-2.06 (m, 3H), 2.00-1.84 (m, 2H), 1.71 (m, 2H), 1.44-1.31 (m, 1H), 0.81 (m,, 1H), 0.41 (m, 2H), 0.10-0.01 (m, 2H) | 324 |
| 77 | [1-(cyclopropylmethyl)-3-piperidyl]-(6-methoxy-2-naphthyl)methanone | $^1$H NMR (400 MHz, DMSO-d6) δ 8.64-8.59 (m, 1H), 8.06 (d, J = 8.99 Hz, 1H), 7.96-7.87 (m, 2H), 7.40 (d, J = 2.52 Hz, 1H), 7.26 (dd, J = 2.55, 8.98 Hz, 1H), 3.92 (s, 3H), 3.74 (ddt, J = 3.50, 7.01, 11.34 Hz, 1H), 3.12-3.04 (m, 1H), 2.98 (d, J = 11.13 Hz, 1H), 2.28-2.08 (m, 3H), 1.99-1.84 (m, 2H), 1.71 (ddt, J = 3.67, 7.64, 10.80 Hz, 2H), 1.44-1.31 (m, 1H), 0.86-0.77 (m, 1H), 0.41 (dtd, J = 3.38, 5.13, 8.19 Hz, 2H), 0.08-0.02 (m, 2H) | 324 |
| 78 | [1-(2-methoxyethyl)-3-piperidyl]-(6-methoxy-2-naphthyl)methanone | $^1$H NMR (400 MHz, DMSO-d6) δ 8.60 (d, J = 1.51 Hz, 1H), 8.06 (d, J = 8.97 Hz, 1H), 7.95-7.86 (m, 2H), 7.40 (d, J = 2.53 Hz, 1H), 7.26 (dd, J = 2.55, 8.97 Hz, 1H), 3.92 (s, 3H), 3.72 (tt, J = 3.49, 10.89 Hz, 1H), 3.41 (t, J = 5.80 Hz, 2H), 3.19 (s, 3H), 3.04-2.96 (m, 1H), 2.89-2.86 (m, 1H), 2.16 (t, J = 10.84 Hz, 1H), 2.05-1.95 (m, 1H), 1.88-1.85 (m, 1H), 1.67-1.67 (m, 2H), 1.43-1.29 (m, 1H) | 328 |
| 79 | [1-(2-fluoroethyl)-3-piperidyl]-(6-methoxy-2-naphthyl)methanone | $^1$H NMR (400 MHz, DMSO-d6) δ 8.64-8.58 (m, 1H), 8.06 (d, J = 8.99 Hz, 1H), 7.95-7.86 (m, 2H), 7.40 (d, J = 2.64 Hz, 1H), 7.26 (dd, J = 2.55, 8.95 Hz, 1H), 4.58 (t, J = 4.97 Hz, 1H), 4.46 (t, J = 4.94 Hz, 1H), 3.92 (s, 3H), 3.79-3.68 (m, 1H), 3.06-2.98 (m, 1H), 2.91 (d, J = 11.19 Hz, 1H), 2.69 (td, J = 1.12, 4.70 Hz, 1H), 2.62 (td, J = 1.14, 4.71 Hz, 1H), 2.21 (t, J = 10.87 Hz, 1H), 2.09-1.98 (m, 1H), 1.89 (dd, J = 3.73, 12.68 Hz, 1H), 1.73-1.69 (m, 2H), 1.42-1.31 (m, 1H) | 316 |

-continued

| Example | Compound Name | ¹NMR | m/z (M + H) |
|---|---|---|---|
| 81 | (1-isopropyl-3-piperidyl)-(6-methoxy-2-naphthyl)methanone | ¹H NMR (400 MHz, DMSO-d6) δ 8.62-8.56 (m, 1H), 8.06 (d, J = 8.95 Hz, 1H), 7.96-7.86 (m, 2H), 7.40 (d, J = 2.52 Hz, 1H), 7.26 (dd, J = 2.57, 8.94 Hz, 1H), 3.92 (s, 3H), 3.68 (tt, J = 3.48, 10.72 Hz, 1H), 2.94-2.86 (m, 1H), 2.82-2.64 (m, 2H), 2.29 (t, J = 10.65 Hz, 1H), 2.12 (td, J = 3.07, 11.19 Hz, 1H), 1.88-1.85 (m, 1H), 1.77-1.57 (m, 2H), 1.38 (qd, J = 4.34, 12.11 Hz, 1H), 0.94 (dd, J = 0.67, 6.58 Hz, 6H) | 312 |
| 84 | 3-[3-(6-methoxynaphthalene-2-carbonyl)-1-piperidyl]propanenitrile | ¹H NMR (400 MHz, DMSO-d6) δ 8.66-8.59 (m, 1H), 8.07 (d, J = 9.03 Hz, 1H), 7.97-7.85 (m, 2H), 7.41 (d, J = 2.55 Hz, 1H), 7.26 (dd, J = 2.55, 8.98 Hz, 1H), 3.92 (s, 3H), 3.75-3.69 (m, 1H), 3.07-2.98 (m, 1H), 2.91 (d, J = 11.20 Hz, 1H), 2.70-2.57 (m, 4H), 2.19 (t, J = 10.87 Hz, 1H), 2.05-1.96 (m, 1H), 1.91 (d, J = 12.64 Hz, 1H), 1.75-1.71 (m, 2H), 1.42-1.28 (m, 1H) | 323 |
| 85 | 2-[3-(6-methoxynaphthalene-2-carbonyl)-1-piperidyl]acetonitrile | ¹H NMR (400 MHz, DMSO-d6) δ 8.70-8.57 (m, 1H), 8.06 (d, J = 8.98 Hz, 1H), 7.96-7.82 (m, 2H), 7.41 (d, J = 2.54 Hz, 1H), 7.26 (dd, J = 2.53, 8.99 Hz, 1H), 3.92 (s, 3H), 3.81-3.75 (m, 1H), 3.75 (s, 2H), 3.00-2.92 (m, 1H), 2.86-2.78 (m, 1H), 2.35 (t, J = 10.74 Hz, 1H), 2.17 (td, J = 3.99, 10.87 Hz, 1H), 1.96-1.86 (m, 1H), 1.80-1.71 (m, 2H), 1.42-1.27 (m, 1H) | 309 |
| 87 | (1-ethyl-3-piperidyl)-(6-methoxy-2-naphthyl)methanone | ¹H NMR (400 MHz, DMSO-d6) δ 8.60 (d, J = 1.58 Hz, 1H), 8.06 (d, J = 9.02 Hz, 1H), 7.96-7.86 (m, 2H), 7.40 (d, J = 2.62 Hz, 1H), 7.26 (dd, J = 2.56, 8.99 Hz, 1H), 3.92 (s, 3H), 3.72 (tt, J = 3.53, 10.88 Hz, 1H), 3.02-2.92 (m, 1H), 2.87 (d, J = 11.01 Hz, 1H), 2.35 (qd, J = 2.99, 7.15 Hz, 2H), 2.05 (t, J = 10.76 Hz, 1H), 1.87 (td, J = 3.87, 10.67 Hz, 2H), 1.76-1.63 (m, 2H), 1.45-1.30 (m, 1H), 0.98 (t, J = 7.14 Hz, 3H) | 298 |

Example 88

[4-(aminomethyl)-2-naphthyl]-[1-(cyclopropylmethyl)-3-piperidyl]methanone

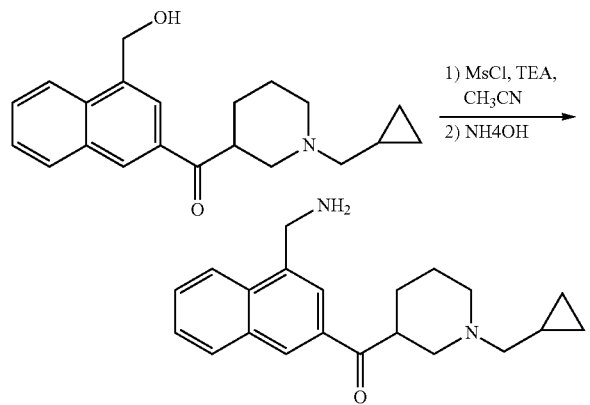

To a solution of [1-(cyclopropylmethyl)-3-piperidyl]-[4-(hydroxymethyl)-2-naphthyl]methanone (263 mg, 0.813 mmol) and TEA (123 mg, 1.22 mmol) in acetonitrile (10 mL) at 0° C. was added methanesulfonyl chloride (1.057 mmol, 121 mg, 1.06 mmol) dropwise. The mixture was then stirred at room temperature for 2 h. This mixture was added to a solution of NH₄OH (28 mass % in water, 20 mL) and acetonitrile (40 mL) at 0° C. The mixture was then warmed to room temperature and stirred for 18 h. The mixture was concentrated and purified by preparative reverse phase HPLC (Phenotrienex Gemini-NX, 5-85% ACN in 0.1% Formic Acid (aq)) to give the title compound as a yellow solid. ¹H NMR (400 MHz, DMSO-d6) δ 8.57 (d, J=1.80 Hz, 1H), 8.17-8.14 (m, 1H), 7.97-7.92 (m, 1H), 7.71-7.65 (m, 1H), 7.63-7.56 (m, 2H), 4.86 (s, 2H), 4.22 (d, J=2.32 Hz, 2H), 3.85-3.71 (m, 1H), 3.09 (d, J=9.18 Hz, 2H), 2.99 (d, J=10.88 Hz, 2H), 2.28-2.12 (m, 5H), 1.72 (td, J=4.94, 8.99, 10.27 Hz, 4H), 0.88-0.72 (m, 2H), 0.45-0.38 (m, 2H), 0.10-0.01 (m, 2H). LCMS (ESI) m/z 323 [M+H⁺].

Example 89

N-[[3-[1-(cyclopropylmethyl)piperidine-3-carbonyl]-1-naphthyl]methyl]acetamide

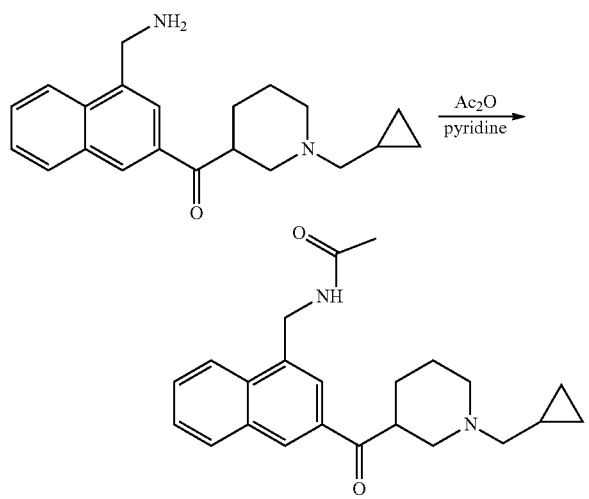

To a solution of [4-(aminomethyl)-2-naphthyl]-[1-(cyclopropylmethyl)-3-piperidyl]methanone (32 mg, 0.1 mmol) in pyridine (0.5 mL) was added acetic anhydride (100 mg, 1.0 mmol). The mixture was stirred at room temperature for 4 h. The mixture was concentrated and purified by preparative reverse phase HPLC (Phenomenex Gemini-NX, 5-85% ACN in 0.1% Formic Acid (aq)) to give the title compound (14.7 mg, 39.7% yield) as a yellow solid. $^1$H NMR (400 MHz, DMSO-d6) δ 8.67-8.62 (m, 1H), 8.42 (t, J=5.87 Hz, 1H), 8.20 (dd, J=1.39, 8.08 Hz, 1H), 8.16-8.09 (m, 1H), 7.88 (d, J=1.71 Hz, 1H), 7.71 (ddd, J=1.44, 6.81, 8.39 Hz, 1H), 7.65 (ddd, J=1.18, 6.88, 8.01 Hz, 1H), 4.75 (d, J=5.80 Hz, 2H), 3.79 (ddt, J=3.56, 7.12, 10.86 Hz, 1H), 3.11-3.08 (m, 1H), 3.02-2.99 (m, 2H), 2.30-2.18 (m, 2H), 2.15 (t, J=9.47 Hz, 1H), 2.02-1.90 (m, 2H), 1.89 (s, 3H), 1.76-1.70 (m, 2H), 1.45-1.31 (m, 1H), 0.89-0.75 (m, 1H), 0.47-0.38 (m, 2H), 0.11-0.01 (m, 2H). LCMS (ESI) m/z 365 [M+H$^4$].

Synthesis of Intermediates

Intermediate 9

N-methoxy-N-methyl-1-propylpiperidine-3-carboxamide

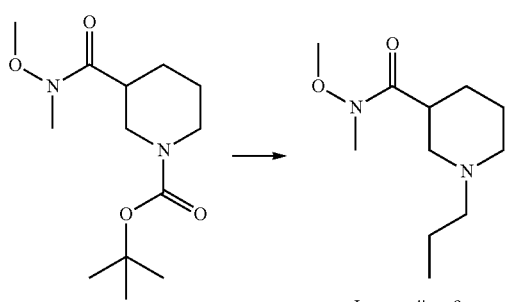

Intermediate 9

A solution of tert-butyl 3-(methoxy(methyl)carbamoyl)piperidine-1-carboxylate (1.0 g, 3.7 mmol) in 5 ml of DCM was charged with 5 ml of TFA and stirred at room temperature for one hour. The mixture was then concentrated in vacuo and azeotroped twice with toluene. The residue was then diluted with 5 ml of THF and 5 ml of methanol and charged with propionaldehyde (450 mg, 7.7 mmol) and Sodium Triacetoxyborohydride (1.6 g, 7.7 mmol). The mixture was then stirred at room temperature for one hour and concentrated in vacuo. The mixture was then diluted with ethyl acetate and water. The aqueous was discarded and the organic layer was washed once with water, dried over Na2SO4, filtered, and concentrated in vacuo. The residue was then purified by silica-gel chromatography (1-10% MeOH in DCM) to afford the title compound (600 mg, 73% yield).

Synthesis of Final Compounds

Example 90

[3-(dimethylamino)phenyl]-(1-propyl-3-piperidyl)methanone

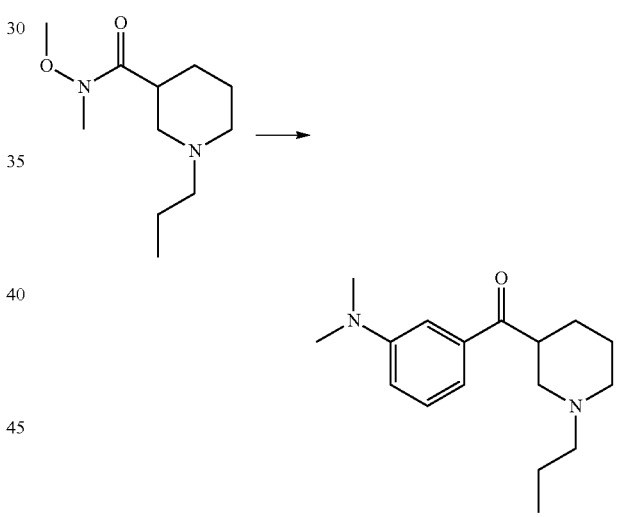

90

A solution of 3-bromo-N,N-dimethylaniline (140 mg, 0.7 mmol) in 1.2 ml of THF was cooled to −78° C. and charged with 2.5 M n-butyl lithium (0.28 ml, 0.7 mmol). After stirring at −78° C. for 5 minutes, N-methoxy-N-methyl-1-propylpiperidine-3-carboxamide (75 mg, 0.35 mmol) dissolved in 250 ul of THF was added dropwise. The mixture was then allowed to warm to room temperature and stirred at room temperature for 30 minutes. The mixture was diluted with ethyl acetate and saturated NaHCO3. The aqueous was discarded and the organic layer was dried over magnesium sulfate and concentrated in vacuo. The residue was then purified by preparatory HPLC (Phenomenex Gemini-NX, 20-60% ACN in NH$_4$OH (aq)) to afford the title compound (31 mg, 31% yield). $^1$H NMR (400 MHz, DMSO-d6) δ 7.32 (t, J=7.9 Hz, 1H), 7.26-7.19 (m, 1H), 7.14 (t, J=2.2 Hz, 1H), 6.98 (dd, J=8.3, 2.7 Hz, 1H), 3.51 (tt, J=10.6, 3.6 Hz, 1H), 3.29 (s, 4H), 2.94 (s, 5H), 2.94-2.85 (m, 1H), 2.80 (dt, J=11.4, 3.7 Hz, 1H), 2.23 (t, J=7.4 Hz, 2H), 1.99 (t, J=10.7 Hz, 1H), 1.92-1.76 (m, 2H), 1.72-1.57 (m, 2H), 1.47-1.36 (m, 2H), 1.39-1.24 (m, 2H), 0.83 (t, J=7.3 Hz, 3H). LCMS m/z: 275 (M+H).

The following compounds were prepared in a manner similar to example 90.

| Example | Compound Name | ¹H NMR | m/z (M + H) |
|---|---|---|---|
| 91 | (4-chlorophenyl)-(1-propyl-3-piperidyl)methanone | ¹H NMR (400 MHz, DMSO-d6) δ 7.99-7.91 (m, 2H), 7.63-7.55 (m, 2H), 3.54 (tt, J = 10.4, 3.7 Hz, 1H), 2.91-2.83 (m, 1H), 2.78 (d, J = 11.1 Hz, 1H), 2.22 (t, J = 7.4 Hz, 2H), 2.03 (t, J = 10.7 Hz, 1H), 1.94-1.76 (m, 2H), 1.74-1.57 (m, 2H), 1.46-1.24 (m, 3H), 0.82 (t, J = 7.4 Hz, 3H). | 261 |
| 92 | (3-chlorophenyl)-(1-propyl-3-piperidyl)methanone | ¹H NMR (400 MHz, DMSO-d6) δ 7.90 (dp, J = 3.2, 1.5 Hz, 2H), 7.70 (ddd, J = 8.0, 2.2, 1.1 Hz, 1H), 7.56 (t, J = 8.1 Hz, 1H), 3.56 (tt, J = 10.2, 3.6 Hz, 1H), 2.91-2.82 (m, 1H), 2.82-2.73 (m, 1H), 2.28-2.17 (m, 2H), 2.05 (dd, J = 11.4, 9.8 Hz, 1H), 1.90 (td, J = 11.0, 3.4 Hz, 1H), 1.80 (dd, J = 12.8, 3.9 Hz, 1H), 1.74-1.54 (m, 2H), 1.39 (dtd, J = 14.8, 7.4, 1.7 Hz, 2H), 1.37-1.25 (m, 1H), 0.82 (t, J = 7.4 Hz, 3H). | 261 |
| 93 | (1-propyl-3-piperidyl)-(6-quinolyl)methanone | | 266 |
| 94 | (1-methylindazol-5-yl)-(1-propyl-3-piperidyl)methanone | ¹H NMR (400 MHz, DMSO-d6) δ 8.52 (d, J = 1.3 Hz, 1H), 8.24 (s, 1H), 7.94 (dd, J = 8.9, 1.5 Hz, 1H), 7.80-7.68 (m, 1H), 4.08 (s, 2H), 3.66 (tt, J = 10.8, 3.6 Hz, 1H), 2.97-2.88 (m, 1H), 2.84 (d, J = 11.0 Hz, 1H), 2.24 (t, J = 7.4 Hz, 2H), 2.05 (t, J = 10.8 Hz, 1H), 1.88 (td, J = 11.1, 4.1 Hz, 2H), 1.75-1.59 (m, 2H), 1.39 (tq, J = 11.4, 6.2, 5.0 Hz, 3H), 0.83 (t, J = 7.3 Hz, 3H). | 266 |
| 95 | (3-benzyloxyphenyl)-(1-propyl-3-piperidyl)methanone | ¹H NMR (400 MHz, DMSO-d6) δ 7.56-7.24 (m, 10H), 5.19 (s, 2H), 3.53 (tt, J = 10.5, 3.5 Hz, 1H), 2.91-2.74 (m, 2H), 2.22 (t, J = 7.4 Hz, 2H), 1.92-1.73 (m, 2H), 1.72-1.57 (m, 2H), 1.46-1.22 (m, 3H), 0.82 (t, J = 7.3 Hz, 3H). | 282 |
| 96 | (2-chlorophenyl)-(1-propyl-3-piperidyl)methanone | | 285 |
| 97 | (4-methoxyphenyl)-(1-propyl-3-piperidyl)methanone | ¹H NMR (400 MHz, DMSO-d6) δ 7.93 (d, J = 8.8 Hz, 2H), 7.04 (d, J = 8.9 Hz, 2H), 3.84 (s, 3H), 3.50 (tt, J = 10.7, 3.5 Hz, 1H), 2.92-2.78 (m, 2H), 2.23 (t, J = 7.4 Hz, 2H), 1.99 (t, J = 10.8 Hz, 1H), 1.91-1.76 (m, 2H), 1.72-1.58 (m, 2H), 1.48-1.23 (m, 3H), 0.83 (t, J = 7.4 Hz, 3H). | 337 |
| 98 | (3-methoxyphenyl)-(1-propyl-3-piperidyl)methanone | ¹H NMR (400 MHz, DMSO-d6) δ 7.53 (d, J = 7.6 Hz, 1H), 7.49-7.35 (m, 2H), 7.20 (dd, J = 8.1, 2.6 Hz, 1H), 3.81 (s, 3H), 3.54 (tt, J = 10.5, 3.6 Hz, 1H), 3.29 (s, 9H), 2.89 (dd, J = 11.6, 3.1 Hz, 1H), 2.79 (d, J = 11.3 Hz, 1H), 2.23 (t, J = 7.4 Hz, 2H), 2.02 (t, J = 10.7 Hz, 1H), 1.93-1.77 (m, 2H), 1.67 (s, 1H), 1.73-1.58 (m, 1H), 1.46-1.24 (m, 3H), 0.82 (t, J = 7.4 Hz, 3H). | 266 |
| 99 | (2-methoxyphenyl)-(1-propyl-3-piperidyl)methanone | ¹H NMR (400 MHz, DMSO-d6) δ 7.50 (td, J = 8.0, 7.5, 1.8 Hz, 1H), 7.37 (dd, J = 7.7, 1.8 Hz, 1H), 7.14 (d, J = 8.3 Hz, 1H), 7.01 (t, J = 7.4 Hz, 1H), 3.86 (s, 2H), 3.29 (s, 10H), 2.86-2.78 (m, 1H), 2.69-2.61 (m, 1H), 2.18 (t, J = 7.3 Hz, 2H), 1.97 (dt, J = 29.3, 10.4 Hz, 2H), 1.78-1.69 (m, 1H), 1.64 (dq, J = 12.6, 4.0 Hz, 1H), 1.55-1.40 (m, 1H), 1.41-1.27 (m, 3H), 0.79 (t, J = 7.4 Hz, 3H). | 261 |
| 100 | (1-propyl-3-piperidyl)-[4-(trifluoromethyl)phenyl]methanone | ¹H NMR (400 MHz, DMSO-d6) δ 8.12 (d, J = 8.2 Hz, 2H), 7.89 (d, J = 8.2 Hz, 2H), 3.60 (tt, J = 10.5, 3.6 Hz, 1H), 2.93-2.85 (m, 1H), 2.77 (d, J = 11.0 Hz, 1H), | 261 |

| Example | Compound Name | ¹H NMR | m/z (M + H) |
|---|---|---|---|
| | | 2.23 (s, 1H), 2.23 (dd, J = 14.7, 1.8 Hz, 1H), 2.07 (dd, J = 11.3, 10.0 Hz, 1H), 1.91 (td, J = 11.0, 3.2 Hz, 1H), 1.87-1.78 (m, 1H), 1.75-1.54 (m, 2H), 1.45-1.27 (m, 3H), 0.81 (t, J = 7.4 Hz, 3H). | |
| 101 | (3,4-dichlorophenyl)-(1-propyl-3-piperidyl)methanone | ¹H NMR (400 MHz, DMSO-d6) δ 8.10 (d, J = 2.0 Hz, 1H), 7.90 (dd, J = 8.4, 2.0 Hz, 1H), 7.80 (d, J = 8.4 Hz, 1H), 3.63-3.51 (m, 1H), 2.91-2.82 (m, 1H), 2.77 (d, J = 11.3 Hz, 1H), 2.28-2.17 (m, 2H), 2.05 (dd, J = 11.3, 10.0 Hz, 1H), 1.90 (td, J = 10.9, 3.4 Hz, 1H), 1.85-1.76 (m, 1H), 1.73-1.54 (m, 1H), 1.46-1.24 (m, 3H), 0.82 (t, J = 7.4 Hz, 3H). | 261 |
| 102 | (2-phenylphenyl)-(1-propyl-3-piperidyl)methanone | ¹H NMR (400 MHz, DMSO-d6) δ 7.58 (td, J = 7.4, 1.7 Hz, 1H), 7.52-7.35 (m, 6H), 7.35-7.28 (m, 2H), 2.50-2.35 (m, 2H), 2.10-2.01 (m, 2H), 1.94-1.78 (m, 2H), 1.54-1.37 (m, 2H), 1.22 (h, J = 7.3 Hz, 3H), 1.18-1.09 (m, 1H), 0.72 (t, J = 7.4 Hz, 3H). | 299 |
| 103 | (1-propyl-3-piperidyl)-[4-(trifluoromethoxy)phenyl]methanone | ¹H NMR (400 MHz, DMSO-d6) δ 8.11-8.03 (m, 2H), 7.53-7.37 (m, 2H), 3.56 (tt, J = 10.5, 3.6 Hz, 1H), 2.93-2.84 (m, 1H), 2.78 (dd, J = 11.0, 4.1 Hz, 1H), 2.29-2.15 (m, 2H), 2.05 (t, J = 10.7 Hz, 1H), 1.86 (dtd, J = 24.2, 13.0, 12.0, 3.6 Hz, 2H), 1.65 (dddd, J = 24.4, 13.1, 9.7, 6.1 Hz, 2H), 1.46-1.17 (m, 3H), 0.82 (t, J = 7.4 Hz, 3H). | 300 |
| 104 | (3,4-dimethoxyphenyl)-(1-propyl-3-piperidyl)methanone | ¹H NMR (400 MHz, DMSO-d6) δ 7.64 (dd, J = 8.4, 2.0 Hz, 1H), 7.41 (d, J = 1.9 Hz, 1H), 7.03 (dd, J = 27.5, 8.3 Hz, 1H), 3.87-3.74 (m, 7H), 3.54 (tt, J = 10.7, 3.5 Hz, 1H), 3.29 (s, 5H), 2.93-2.78 (m, 2H), 2.23 (t, J = 7.4 Hz, 2H), 1.99 (t, J = 10.8 Hz, 1H), 1.91-1.75 (m, 2H), 1.72-1.59 (m, 2H), 1.37 (ddt, J = 33.1, 11.9, 6.2 Hz, 3H), 0.83 (t, J = 7.3 Hz, 3H). | 307 |
| 105 | (3,5-dimethoxyphenyl)-(1-propyl-3-piperidyl)methanone | ¹H NMR (400 MHz, DMSO-d6) δ 7.02 (d, J = 2.2 Hz, 2H), 3.80 (s, 5H), 3.52 (tt, J = 10.7, 3.6 Hz, 1H), 3.29 (s, 3H), 2.92-2.84 (m, 1H), 2.78 (dt, J = 11.7, 3.7 Hz, 1H), 2.23 (t, J = 7.4 Hz, 2H), 2.01 (t, J = 10.7 Hz, 1H), 1.84 (ddt, J = 25.3, 12.9, 6.0 Hz, 2H), 1.65 (dddd, J = 13.1, 9.3, 6.9, 3.1 Hz, 2H), 1.46-1.23 (m, 3H), 0.82 (t, J = 7.3 Hz, 3H). | 315 |
| 106 | (3,4-dimethylphenyl)-(1-propyl-3-piperidyl)methanone | ¹H NMR (400 MHz, DMSO-d6) δ 7.73-7.63 (m, 2H), 7.28 (d, J = 7.8 Hz, 1H), 3.52 (tt, J = 10.8, 3.6 Hz, 1H), 2.92-2.81 (m, 1H), 2.81 (d, J = 11.0 Hz, 1H), 2.29 (s, 5H), 2.23 (t, J = 7.4 Hz, 2H), 1.99 (t, J = 10.8 Hz, 1H), 1.91-1.75 (m, 2H), 1.65 (dtd, J = 15.7, 11.7, 10.2, 4.2 Hz, 2H), 1.47-1.21 (m, 3H), 0.83 (t, J = 7.4 Hz, 3H). | 291 |
| 107 | (1-propyl-3-piperidyl)-tetralin-6-yl-methanone | ¹H NMR (400 MHz, DMSO-d6) δ 7.63 (s, 1H), 7.19 (d, J = 8.1 Hz, 1H), 3.51 (tt, J = 10.7, 3.5 Hz, 1H), 2.92-2.78 (m, 1H), 2.78 (t, J = 5.5 Hz, 5H), 2.27-2.18 (m, 2H), 1.97 (t, J = 10.8 Hz, 1H), 1.90-1.65 (m, 6H), 1.69-1.57 (m, 2H), 1.47-1.37 (m, 2H), 1.40-1.21 (m, 2H), 0.83 (t, J = 7.4 Hz, 3H). | 291 |
| 108 | 2,3-dihydro-1,4-benzodioxin-6-yl-(1-propyl-3-piperidyl)methanone | ¹H NMR (400 MHz, DMSO-d6) δ 7.47 (dd, J = 8.5, 2.2 Hz, 1H), 7.40 (d, J = 2.2 Hz, 1H), 6.97 (d, J = 8.5 Hz, 1H), 4.36-4.24 (m, 4H), 3.52-3.32 (m, 1H), 2.91-2.76 (m, 2H), 2.23 (t, J = 7.4 Hz, 2H), 1.98 (t, J = 10.8 Hz, 1H), 1.90-1.74 (m, 2H), 1.64 (pt, J = 12.8, 6.4 Hz, 2H), 1.40 (q, J = 7.4 Hz, 2H), 1.38-1.19 (m, 2H), 0.83 (t, J = 7.4 Hz, 3H). | 259 |

Synthesis of Intermediates

Intermediate 10 tert-butyl 3-(methoxy(methyl)carbamoyl)-4-methyl-piperidine-1-carboxylate

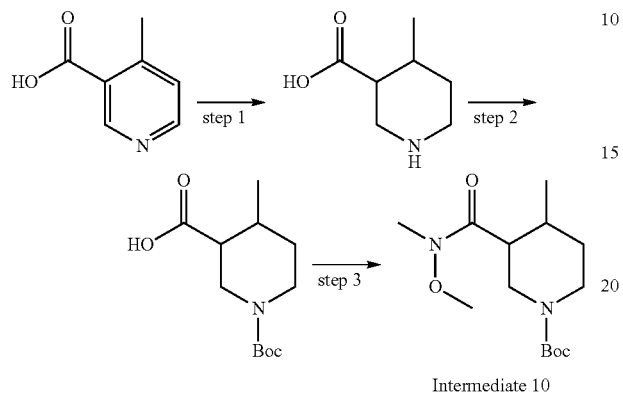

Intermediate 10

Step 1:

4-methylpiperidine-3-carboxylic acid

To a solution of 4-methylnicotinic acid (10.0 g, 73.0 mmol) in AcOH (200 mL) was added PtO₂ (1.0 g). The mixture was stirred at 25° C. under H₂ atmosphere (50 psi) for 72 h and filtered through a short pad of Celite. The filtrate was concentrated to give the crude 4-methylpiperidine-3-carboxylic acid (10.0 g, 96% yield) as a colorless oil. This crude was used directly without further purification.

Step 2:

1-(tert-butoxycarbonyl)-4-methylpiperidine-3-carboxylic acid

To a stirred and cooled (0° C.) solution of 4-methylpiperidine-3-carboxylic acid (10.0 g, 70 mmol) in THF (200 mL) and water (200 mL) was added Na₂CO₃ (22.2 g, 210 mmol) and (Boc)₂O (15.1 g, 70 mmol). After addition, the mixture was allowed to warm to 25° C., and stirred for 2 h. The solvent was removed under reduced pressure, and the residue was purified by column chromatography (petroleum ether:ethyl acetate=2:1) to afford the title compound (10.0 g, 58.8% yield) as a colorless oil.

Step 3:

tert-butyl 3-(methoxy(methyl)carbamoyl)-4-methyl-piperidine-1-carboxylate

To a stirred and cooled (0° C.) solution of 1-(tert-butoxycarbonyl)-4-methylpiperidine-3-carboxylic acid (10.0 g, 41.3 mmol) in THF (300 mL) was added CDI (8.0 g, 49.6 mmol). After addition, stirring was continued for 1 h, then N,O-dimethylhydroxylamine hydrochloride (4.8 g, 49.6 mmol) and Et₃N (7.7 g, 49.6 mmol) was added. The resulting mixture was stirred at 25° C. for 17 h, at which time TLC showed the completion of the reaction. The solvent was removed under reduced pressure. The residue was dissolved in ethyl acetate (200 mL) and washed successively with 0.5 N aq. HCl (50 mL), sat aq. Na₂CO₃ (50 mL) and brine (50 mL). The organic layer was dried over Na₂SO₄ and evaporated under reduced pressure. The residue was purified by silica-gel chromatography (petroleum ether:ethyl acetate=5:1) to give tert-butyl 3-(methoxy(methyl)carbamoyl)-4-methylpiperidine-1-carboxylate (8.5 g, 72.0% yield) as a pale yellow solid.

Intermediate 11 tert-butyl 3-(methoxy(methyl)carbamoyl)-5-methyl-piperidine-1-carboxylate

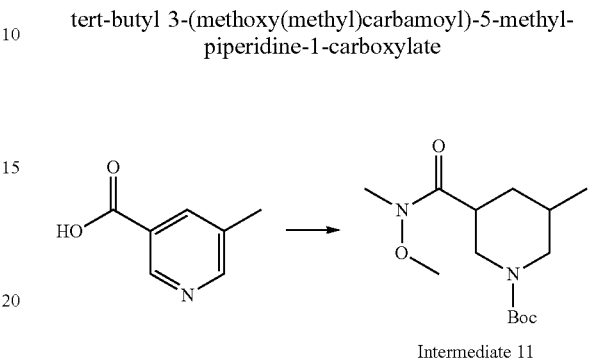

Intermediate 11

Prepared in an analogous manner to tert-butyl 3-(methoxy(methyl)carbamoyl)-4-methylpiperidine-1-carboxylate (Intermediate 10), replacing 4-methylnicotinic acid with 5-methylnicotinic acid.

Intermediate 12 tert-butyl 3-(methoxy(methyl)carbamoyl)-5-(trifluoromethyl) piperidine-1-carboxylate

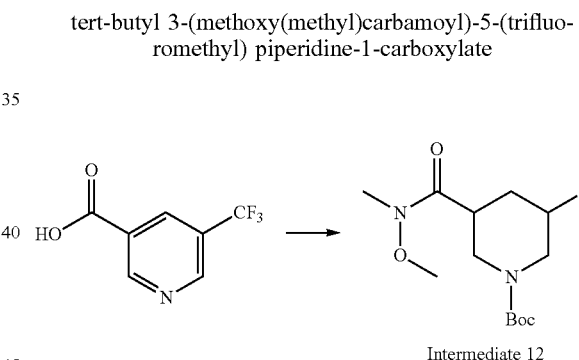

Intermediate 12

Prepared in an analogous manner to tert-butyl 3-(methoxy(methyl)carbamoyl)-4-methylpiperidine-1-carboxylate (Intermediate 10), replacing 4-methylnicotinic acid with 5-(trifluoromethyl)nicotinic acid

Intermediate 13 tert-butyl 3-(methoxy(methyl)carbamoyl)-4-propylpiperidine-1-carboxylate

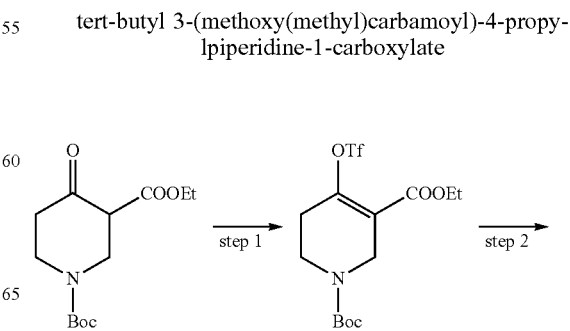

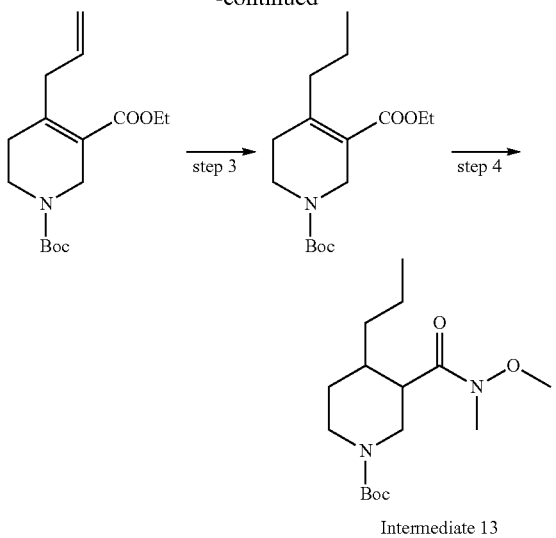

Intermediate 13

Step 1:

1-tert-butyl 3-ethyl 4-(((trifluoromethyl)sulfonyl)oxy)-5,6-dihydropyridine-1,3(2H)-dicarboxylate To a stirred and cooled solution (−78° C.) of 1-tert-butyl 3-ethyl-4-oxopiperidine-1,3-dicarboxylate (11.7 g, 43.2 mmol) in dichloromethane (300 mL) was added diisopropyl ethyl amine (16.7 g, 129.6 mmol), followed by trifluoromethanesulfonic anhydride (14.6 g, 51.8 mmol). After addition, the resulting mixture was stirred at −78° C. for 2 h and then concentrated under reduced pressure. The crude material was purified by silica-gel chromatography (petroleum ether:ethyl acetate=20:1) to give the title compound (8.5 g, 49% yield).

Step 2:

1-tert-butyl 3-ethyl 4-allyl-5,6-dihydropyridine-1,3-dicarboxylate

To a solution of 1-lent-butyl 3-ethyl 4-(((trifluoromethyl)sulfonyl)oxy)-5,6-dihydropyridine-1,3-dicarboxylate (8.0 g, 19.8 mmol) in THF (300 mL) was added LiCl (2.5 g, 59.6 mmol), allyltributylstannane (7.2 g, 21.8 mmol) and Pd(PPh$_3$)$_4$ (1.15 g, 1.0 mmol). The resulting mixture was flushed with nitrogen and heated at 55° C. for 4 h. The solvent was removed under reduced pressure and the residue was extracted with ethyl acetate (3×100 mL). The combined organic layers were washed with brine (50 mL), dried (Na$_2$SO$_4$) and evaporated. The residue was purified by silica-gel chromatography (petroleum ether:ethyl acetate=10:1) to give the title compound (5.0 g, 85.6% yield) as an oil.

Step 3

1-tert-butyl 3-ethyl 4-propylpiperidine-1,3-dicarboxylate

To a solution of 1-tert-butyl 3-ethyl 4-allyl-5,6-dihydropyridine-1,3-dicarboxylate (5.0 g, 17.0 mmol) in AcOH (100 mL) was added PtO$_2$ (0.5 g).). The mixture was stirred at 50° C. under H$_2$ atmosphere (50 psi) for 24 h and then filtered through a short pad of Celite. The filtrate was concentrated under reduced pressure to give the title compound (3.5 g, 69.1% yield) as a yellow oil.

Step 4:

tert-butyl 3-(methoxy(methyl)carbamoyl)-4-propylpiperidine-1-carboxylate

To a stirred and cooled (−20° C.) solution of 1-tert-butyl 3-ethyl 4-propylpiperidine-1,3-dicarboxylate (3.5 g, 11.7 mmol) and N,O-dimethylhydroxylamine hydrochloride (1.7 g, 17.5 mmol) in THF (50 mL) was added isopropylmagnesium chloride (2 N, 17.5 mL, 35.0 mmol) dropwise. After addition, the reaction mixture was warmed to room temperature and stirred at 25° C. for 0.5 h. The mixture was quenched by addition of saturated aqueous NH$_4$Cl (20 mL), and extracted with ethyl acetate (3×100 mL). The combined organic layers were dried (Na$_2$SO$_4$) and concentrated under reduced pressure. The residue and purified by silica gel silica-gel chromatography (petroleum ether:ethyl acetate=5:1) to give the title compound (2.2 g, 61.0% yield) as a yellow oil.

Intermediate 14 tert-butyl 4-isobutyl-3-(methoxy(methyl)carbamoyl)piperidine-1-carboxylate

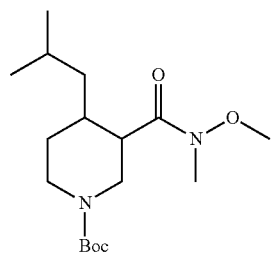

Intermediate 14

Prepared in an analogous manner to text-butyl 3-(methoxy(methyl)carbamoyl)-4-propylpiperidine-1-carboxylate (Intermediate 13), replacing allyltributylstannane with tributyl(2-methylallyl)stannane.

Intermediate 15 tert-butyl 4-ethyl-3-(methoxy(methyl)carbamoyl)piperidine-1-carboxylate

Intermediate 15

Prepared in an analogous manner to tert-butyl 3-(methoxy(methyl)carbamoyl)-4-propylpiperidine-1-carboxylate (Intermediate 13), replacing allyltributylstannane with potassium trifluoro(vinyl)borate.

Intermediate 16 tert-butyl 3-(methoxy(methyl)carbamoyl)-4-phenylpiperidine-1-carboxylate

Intermediate 16

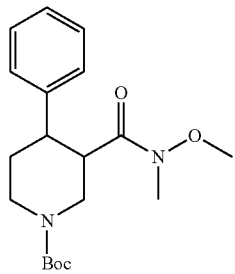

Prepared in an analogous manner to tert-butyl 3-(methoxy(methyl)carbamoyl)-4-propylpiperidine-1-carboxylate (Intermediate 13), replacing allyltributylstannane with phenylboronic acid.

Intermediate 17 tert-butyl 4-isopropyl-3-(methoxy(methyl)carbamoyl)piperidine-1-carboxylate

Intermediate 17

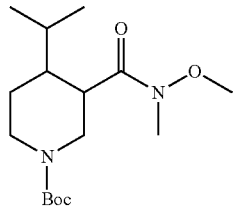

Prepared in an analogous manner to tert-butyl-3-(methoxy(methyl)carbamoyl)-4-propylpiperidine-1-carboxylate (Intermediate 13), replacing allyltributylstannane with potassium isopropenyltrifluoroborate.

Intermediate 18 tert-butyl 4-methoxy-3-(methoxy(methyl)carbamoyl)piperidine-1-carboxylate

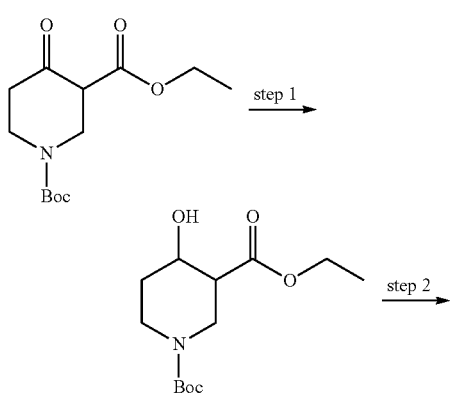

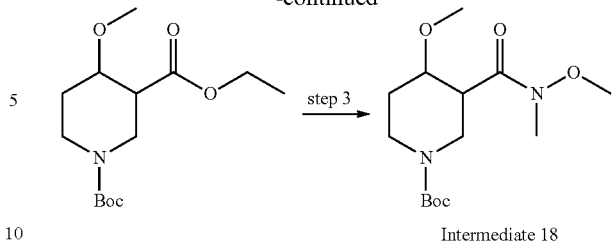

Intermediate 18

Step 1:

1-tert-butyl 3-ethyl 4-hydroxypiperidine-1,3-dicarboxylate

To a stirred and cooled (0° C.) solution of 1-tert-butyl 3-ethyl-4-oxopiperidine-1,3-dicarboxylate (3.0 g, 11.1 mmol) in EtOH (60 mL) was added $NaBH_4$ (253 mg, 6.66 mmol). After addition, the reaction mixture was stirred at room temperature for 2 h. The solvent was evaporated. The crude was diluted with ethyl acetate (100 mL), washed with NaOH (aq. 1 N, 30 mL), dried ($Na_2SO_4$) and concentrated. The residue was purified by silica-gel chromatography (petroleum ether:ethyl acetate=10:1) to give the title compound (2.8 g, 92.7% yield) as a colorless oil.

Step 2:

1-tert-butyl 3-ethyl 4-methoxypiperidine-1,3-dicarboxylate

To a solution of 1-tert-butyl 3-ethyl 4-hydroxypiperidine-1,3-dicarboxylate (1.0 g, 3.66 mmol) in iodomethane (20 mL) was added $CaSO_4$ (7.2 g, 53.0 mmol) and silver oxide (8.5 g, 36.6 mmol) at room temperature. The reaction mixture was stirred at room temperature for 24 h. Iodomethane was removed under reduced pressure. The residue was diluted with ethyl acetate (100 mL) and filtered. The filtrate was dried ($Na_2SO_4$) and concentrated. The crude was purified by silica-gel chromatography (petroleum ether:ethyl acetate=10:1) to give the title compound (500 mg, 47.6% yield) as a yellow oil.

Step 3:

tert-butyl 4-methoxy-3-(methoxy(methyl)carbamoyl)piperidine-1-carboxylate

To a stirred and cooled (−20° C.) solution of 1-tert-butyl 3-ethyl 4-methoxypiperidine-1,3-dicarboxylate (400 mg, 1.39 mmol) and N,O-dimethylhydroxylamine hydrochloride (204 mg, 2.09 mmol) in THF (10 mL) was added isopropylmagnesium chloride (2 N, 2.1 mL, 4.20 mmol) dropwise. After addition, the reaction mixture was warmed to room temperature and stirred at 25° C. for 0.5 h. The mixture was quenched by addition of saturated aqueous $NH_4Cl$ (15 mL), and extracted with ethyl acetate (3×30 mL). The combined organic layers were dried ($Na_2SO_4$) and concentrated under reduced pressure. The residue was purified by silica-gel chromatography (petroleum ether:ethyl acetate=5:1) to give the title compound (250 mg, 59.2% yield) as a yellow oil.

Intermediate 19 tert-butyl 3-(methoxy(methyl)carbamoyl)piperidine-1-carboxylate

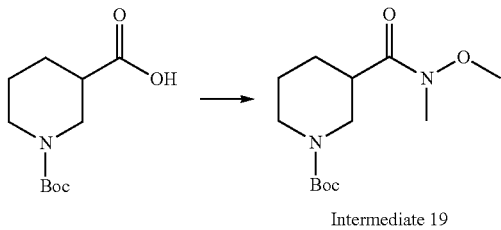 [SMILES: CC(C)(C)OC(=O)N1CCCC(C(=O)O)C1 ; CON(C)C(=O)C1CCCN(C(=O)OC(C)(C)C)C1]

Intermediate 19

To a stirred and cooled (0° C.) solution of 1-(tert-butoxycarbonyl)piperidine-3-carboxylic acid (5.4 g, 23 mmol) in THF (120 mL) was added CDI (4.5 g, 28 mmol). After addition, stirring was continued for 1 h, then N,O-dimethylhydroxylamine hydrochloride (2.7 g, 28 mmol) and Et$_3$N (2.8 g, 28 mmol) were added. The resulting mixture was stirred at 25° C. for 12 h, at which time TLC showed the completion of the reaction. The solvent was removed under reduced pressure. The residue was dissolved in dichloromethane (200 mL) and washed successively with 0.5 N aq. HCl (30 mL), sat aq. Na$_2$CO$_3$ (30 mL) and brine (30 mL). The organic layer was dried over Na$_2$SO$_4$ and evaporated under reduced pressure. The crude product was purified by silica-gel chromatography (petroleum ether:ethyl acetate=2:1) to give the title compound (4.0 g, 58% yield).

Intermediate 20 tert-butyl 3-((tert-butyldimethylsilyl)oxy)-5-(methoxy(methyl) carbamoyl)piperidine-1-dicarboxylate

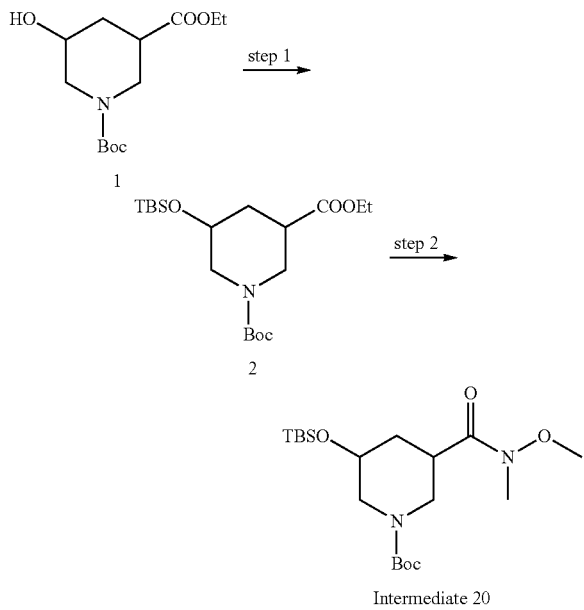

Intermediate 20

Step 1:

1-tert-butyl 3-ethyl 5-((tert-butyldimethylsilyl)oxy) piperidine-1,3-dicarboxylate To a stirred and cooled (0° C.) solution of 1-tert-butyl 3-ethyl 5-hydroxypiperidine-(1,3)-dicarboxylate (1.0 g, 3.7 mmol) in DMF (10 mL) was added TBSCl (0.67 g, 4.4 mmol) and imidazole (0.3 g, 4.4 mmol). After addition, the mixture was stirred at room temperature for 12 h and then diluted with ethyl acetate (50 mL). The resulting solution was washed with brine (3×30 mL), dried (Na$_2$SO$_4$) and concentrated under reduced pressure. The crude product was purified by silica-gel chromatography (petroleum ether:ethyl acetate=10:1) to give the title compound (888 mg, 52% yield) as a colorless oil.

Step 2:

tert-butyl 3-((tert-butyldimethylsilyl)oxy)-5-(methoxy(methyl)carbamoyl) piperidine-1-carboxylate To a stirred and cooled (−20° C.) solution of 1-tert-butyl 3-ethyl 5-((tert-butyldimethyl silyl)oxy)piperidine-1,3-dicarboxylate (800 mg, 2.1 mmol) and N,O-dimethylhydroxylamine hydrochloride (312 mg, 3.2 mmol) in THF (15 mL) was added isopropylmagnesium chloride (2 N, 3.2 mL, 6.4 mmol) dropwise. After addition, the reaction mixture was warmed to room temperature and stirred at 25° C. for 0.5 h. The mixture was quenched by addition of saturated aqueous NH$_4$Cl (15 mL), and extracted with ethyl acetate (3×50 mL). The combined organic layers were dried (Na$_2$SO$_4$) and concentrated under reduced pressure. The crude product was purified by silica-gel chromatography (petroleum ether:ethyl acetate=5:1) to give the title compound (620 mg, 75% yield) as a white solid.

Intermediate 21

2-benzyl-6-bromo-1,2,3,4-tetrahydroisoquinoline

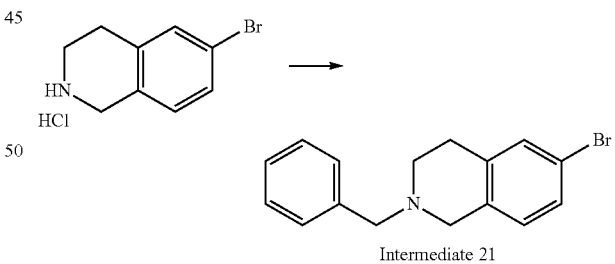

Intermediate 21

To a solution of 6-bromo-1,2,3,4-tetrahydroisoquinoline hydrochloride (2.8 g, 11.3 mmol) in MeCN (50 mL) was added benzyl bromide (2.1 g, 12.4 mmol) and Cs$_2$CO$_3$ (11.1 g, 33.9 mmol). After addition, the resulting mixture was heated at reflux for 1 h. The solvent was evaporated under reduced pressure and the residue was dissolved in ethyl acetate (100 mL). The solution was then washed with brine (100 mL), dried (Na$_2$SO$_4$) and concentrated under reduced pressure. The crude product was purified by silica-gel chromatography (petroleum ether:ethyl acetate=10:1) to give the title compound (2.7 g, 79% yield) as a colourless oil.

Intermediate 22

2-bromo-6,7,8,9-tetrahydro-5-benzo[7]annulene

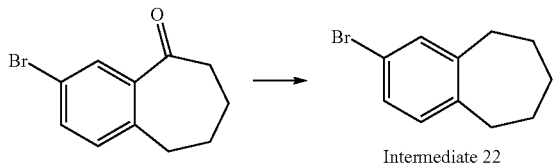 [SMILES: O=C1CCCCc2ccc(Br)cc21 ; Brc1ccc2c(c1)CCCCC2]

Intermediate 22

To a solution of 3-bromo-6,7,8,9-tetrahydro-5-benzo[7]annulen-5-one (0.30 g, 1.2 mmol) in trifluoroacetic acid (4 mL) was added Et₃SiH (2 mL). The resulting mixture was stirred at 25° C. for 12 h. The solvent was evaporated under reduced pressure, and the residue was purified by silica-gel chromatography (petroleum ether:ethyl acetate 20:1) to give the title compound (0.15 g, 53.3% yield).

Intermediate 23

6-bromo-1-phenoxynaphthalene

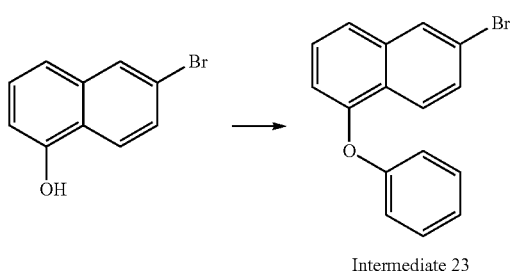 [SMILES: Oc1cccc2cc(Br)ccc12 ; Brc1ccc2c(Oc3ccccc3)cccc2c1]

Intermediate 23

To a solution of 6-bromonaphthalen-1-ol (2.0 g, 9.0 mmol) in DCM (60 mL) was added phenylboronic acid (2.2 g, 18.0 mmol), Cu(OAc)₂ (3.3 g, 18.0 mmol), molecular sieves (1.5 g) and pyridine (5 mL). The resulting mixture was stirred at 25° C. for 18 h. The mixture was filtered through a short pad of Celite. The filtrate was washed successively with HCl (aq., 0.5 N, 20 mL), saturated aqueous Na₂CO₃ (20 mL), brine (20 mL), dried (Na₂SO₄), and evaporated under reduced pressure. The residue was purified by silica-gel chromatography (petroleum ether:ethyl acetate=10:1) to give the title compound (0.4 g, 15% yield).

Intermediate 24

((6-bromonaphthalen-2-yl)methoxy)(tert-butyl)dimethylsilane

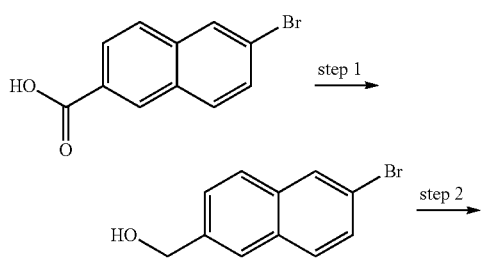

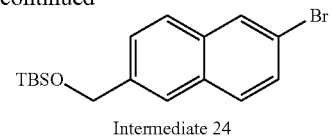

Intermediate 24

Step 1:

(6-bromonaphthalen-2-yl)methanol

To a solution of 6-bromo-2-naphthoic acid (1.0 g, 4.0 mmol) in THF (20 mL) at 0° C. was added DIBAL-H (8.0 mL, 8.0 mmol). After addition, the reaction mixture was stirred at 25° C. for 16 h. The reaction was quenched by the addition of saturated aqueous NH₄Cl (20 mL) and then extracted with ethyl acetate (3×30 mL). The combined organic layers were dried over Na₂SO₄ and concentrated under reduced pressure. The residue was purified by chromatography (petroleum ether:ethyl acetate=2:1) to give the title compound (0.7 g, 74% yield) as a white solid.

Step 2:

((6-bromonaphthalen-2-yl)methoxy)(tert-butyl)dimethylsilane

To a solution of (6-bromonaphthalen-2-yl)methanol (0.7 g, 2.97 mmol) in dichloromethane (20 mL) was added TBSCl (667 mg, 4.45 mmol) and imidazole (302 mg, 4.45 mmol). After the addition, the reaction mixture was stirred at 25° C. for 1 h. The reaction was then quenched by addition of saturated aqueous NH₄Cl (20 mL) and extracted with ethyl acetate (3×30 mL). The combined organic layers were dried over Na₂SO₄ and concentrated under reduced pressure. The residue was purified by silica-gel chromatography (petroleum ether:ethyl acetate=30:1) to give the title compound (0.8 g, 77% yield) as a colorless oil.

Intermediate 25

6-bromo-1-(chloromethyl)-2-methoxynaphthalene

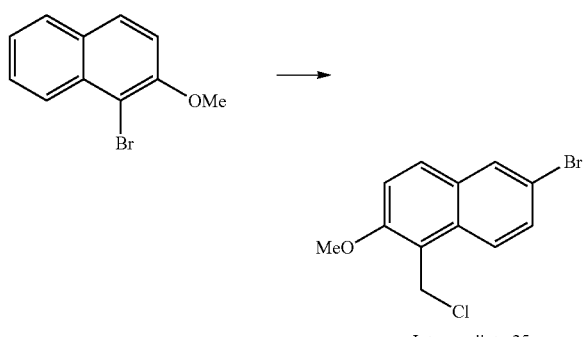

Intermediate 25

HCl (gas) was bubbled into a mixture of 1-bromo-2-methoxynaphthalene (20.0 g, 84 mmol), glacial acetic acid (60 ml), 37% aqueous formaldehyde (11.0 g, 134 mmol) and concentrated hydrochloride acid (42 mL) while at 60° C. for 2 hours. After cooling to room temperature, the crude product was collected by filtration and then recrystallized in acetone to give the title compound (13.0 g, 54% yield) as a purple solid.

Intermediate 26

2-(benzyloxy)-6-bromonaphthalene

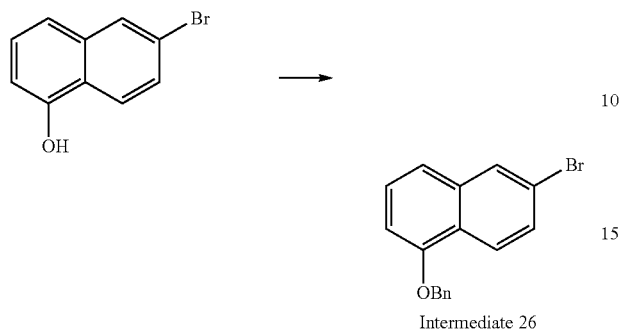

Intermediate 26

To a stirred and cooled (0° C.) solution of 6-bromo-2-naphthol (5.00 g, 22.4 mmol) in DMF (50 mL) was added sodium dydride (60%, 1.16 g, 29.1 mmol) in portions. After addition, stirring was continued for 15 min, and then benzyl bromide (3.5 g, 20.2 mmol) was added. The reaction mixture was stirred at room temperature for 18 h. The mixture was quenched by addition of saturated aqueous $NH_4Cl$ (100 mL) and then extracted with ethyl acetate (3×150 mL). The combined organic layers were washed with water (3×100 mL), brine (100 mL), dried ($Na_2SO_4$) and concentrated under reduced pressure. The residue was purified by silica-gel chromatography (petroleum ether:ethyl acetate=10:1) to give the title compound (5.0 g, 71% yield) as a white solid.

Synthesis of Final Compounds

In many of the Examples below, enantiomers and diastereomers are exemplified by alphabetical designations following the numerical designation. For example, 1a and 1b designations would refer to the two enantiomers of example 1. In addition, 2a, 2b, 2c, and 2d designations would refer to the four diastereomers of example 2. Moreover, when enantiomers or diastereomers are designated, super-fluid chromatography (SFC) using the conditions described per example were used for purification. When racemic mixtures are exemplified, purification by methods other than SFC were used and enantiomers or diastereomers were not separated.

Examples 109a and 109b (1-(cyclopropylmethyl)piperidin-3-yl)(3-methoxyphenyl)methanone

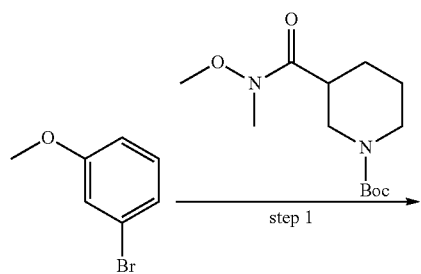

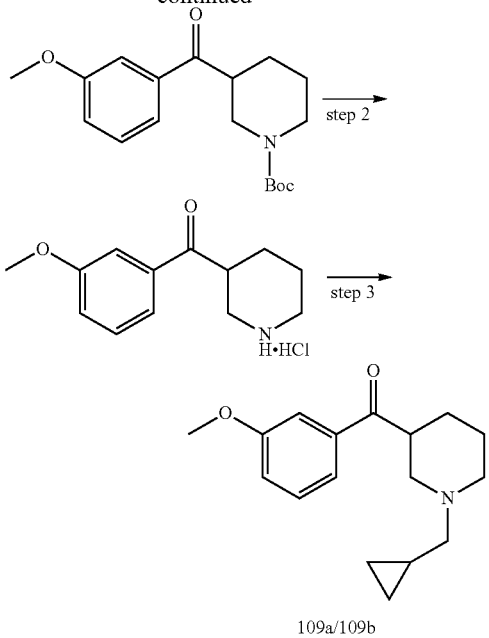

109a/109b

Step 1:

tert-butyl 3-(3-methoxybenzoyl)piperidine-1-carboxylate

To a stirred and cooled (−78° C.) solution of 1-bromo-3-methoxybenzene (187 mg, 1.0 mmol) in THF (10 mL) was added n-BuLi (2.5 M in hexane, 0.4 mL, 1.0 mmol). After addition, stirring at −78° C. was continued for 1 h, and then a solution of tert-butyl 3-(methoxy(methyl)carbamoyl)piperidine-1-carboxylate (Intermediate 10) (272 mg, 1.0 mmol) in THF (5 mL) was added dropwise. The resulting mixture was warmed up to room temperature and stirred for additional 2 h, at which time TLC indicated the reaction was completed. The mixture was quenched by addition of saturated aqueous $NH_4Cl$ (10 mL) and extracted with ethyl acetate (3×30 mL). The combined organic layers were washed with brine, dried over $Na_2SO_4$ and concentrated under reduced pressure, to give crude tert-butyl 3-(3-methoxybenzoyl)piperidine-1-carboxylate (160 mg, 50% yield). This crude was used directly without further purification.

Step 2:

(3-methoxyphenyl)(piperidin-3-yl)methanone hydrochloride

To a solution of tert-butyl 3-(3-methoxybenzoyl)piperidine-1-carboxylate (160 mg, 0.5 mmol) in ethyl acetate (5 mL) was added HCl/ethyl acetate (2 M, 5 mL, 10 mmol). The mixture was stirred for 1 h at room temperature. The solvent was removed under reduced pressure to give the crude (3-methoxyphenyl)(piperidin-3-yl) methanone hydrochloride (128 mg, 99% yield). This crude was used directly in next step without further purification.

Step 3:

(1-(cyclopropylmethyl)piperidin-3-yl)(3-methoxyphenyl)methanone

A solution of (3-methoxyphenyl)(piperidin-3-yl)methanone hydrochloride (128 mg, 0.5 mmol), cyclopropanecarbaldehyde (70 mg, 1.0 mmol) and triethyl amine (2 mL) in dichloromethane (10 mL) was stirred at room temperature for 1 h before NaBH(OAc)$_3$ (212 mg, 1.0 mmol) was added to the mixture. The mixture was stirred for another 1 h and then quenched by addition of saturated aqueous NH$_4$Cl (5 mL). The solution was extracted with dichloromethane (2×20 mL). The combined organic layers were dried (Na$_2$SO$_4$) and concentrated under reduced pressure. The crude was first purified by reverse phase HPLC, then the enantiomers were separated by supercritical fluid chromatography (SFC) to provide 26.7 mg of 109a and 46.3 mg of 109b.

SFC conditions: CHIRALPAK AD (250×30 mm, 5 μm particle size) at 50% MeOH w/0.1% NH$_4$OH; 80 mL/min, 100 bars, 40° C.

109a: $^1$H NMR (400 MHz, CD$_3$OD) δ 7.57 (d, J=7.6 Hz, 1 H), 7.47-7.41 (m, 2 H), 7.17 (dd, J=8.4 Hz, 2.4 Hz, 1 H), 3.85 (s, 3 H), 3.65-3.62 (m, 1 H), 3.21-3.12 (m, 2 H), 2.32-2.31 (m, 2 H), 2.18-2.13 (m, 1 H), 2.04-1.90 (m, 2 H), 1.82-1.78 (m, 2 H), 1.45-1.42 (m, 1 H), 0.90-0.88 (m, 1 H), 0.56-0.52 (m, 2 H), 0.16-0.14 (m, 2 H); LCMS m/z 273.9 (M+H); SFC retention time: 4.15 mm.

109b: $^1$H NMR (400 MHz, CD$_3$OD) δ 7.57 (d, J=7.6 Hz, 1 H), 7.48-7.41 (m, 2 H), 7.17 (dd, J=8.4 Hz, 2.4 Hz, 1 H), 3.85 (s, 3 H), 3.65-3.62 (m, 1 H), 3.21-3.18 (m, 2 H), 2.32-2.31 (m, 2 H), 2.18-2.13 (m, 1 H), 2.03-1.90 (m, 2 H), 1.82-1.78 (m, 2 H), 1.45-1.42 (m, 1 H), 0.90-0.88 (m, 1 H), 0.56-0.52 (m, 2 H), 0.15-0.12 (m, 2 H); LCMS m/z 273.9 (M+H); SFC retention time: 4.75 min.

Examples 110a and 110b (1-(cyclopropylmethyl)piperidin-3-yl)(4-methoxyphenyl)methanone

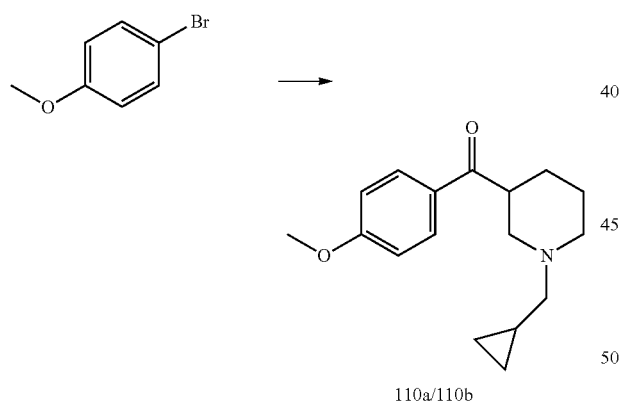

110a/110b

Prepared in an analogous manner to (1-(cyclopropylmethyl)piperidin-3-yl) (3-methoxyphenyl) methanone (Examples 109a and 109b), replacing 1-bromo-3-methoxybenzene with 1-bromo-4-methoxybenzene.

SFC conditions: CHIRALPAK AD (250×30 mm, 5 μm particle size) at 20% MeOH w/0.1% NH$_4$OH; 60 mL/min, 100 bars, 40° C.

110a: $^1$H NMR (400 MHz, CD$_3$OD) δ 7.98 (d, J=8.8 Hz, 2 H), 7.03 (d, J=9.2 Hz, 2 H), 3.88 (s, 3 H), 3.66-3.62 (m, 1 H), 3.20-3.12 (m, 2 H), 2.34-2.32 (m, 2 H), 2.17-2.16 (m, 1 H), 2.05-2.04 (m, 1 H), 1.96-1.92 (m, 1 H), 1.82-1.79 (m, 2 H), 1.46-1.45 (m, 1 H), 0.91-0.90 (m, 1 H), 0.57-0.52 (m, 2 H), 0.17-0.14 (m, 2 H); LCMS m/z 274.2 (M+H); SFC retention time: 6.87 min.

110b: $^1$H NMR (400 MHz, CD$_3$OD) δ 7.99 (d, J=8.8 Hz, 2 H), 7.04 (d, J=8.8 Hz, 2 H), 3.89 (s, 3 H), 3.68-3.66 (m, 1 H), 3.25-3.10 (m, 2 H), 2.44-2.42 (m, 2 H), 2.30-2.29 (m, 1 H), 2.29-2.09 (m, 1 H), 1.94-1.92 (m, 1 H), 1.85-1.82 (m, 2 H), 1.56-1.47 (m, 1 H), 0.95-0.93 (m, 1 H), 0.60-0.56 (m, 2 H), 0.21-0.19 (m, 2 H); LCMS m/z 274.2 (M+H); SFC retention time: 6.19 min.

Example 111

(1-(cyclopropylmethyl)piperidin-3-yl)(2-methoxyphenyl)methanone

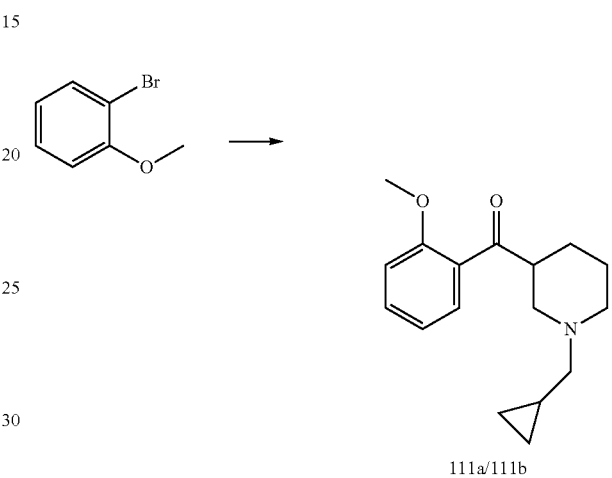

111a/111b

Prepared in an analogous manner to (1-(cyclopropylmethyl)piperidin-3-yl) (3-methoxyphenyl) methanone (Examples 109a and 109b), replacing 1-bromo-3-methoxybenzene with 1-bromo-2-methoxybenzene.

SFC conditions: CHIRALPAK AD (250×30 mm, 5 μm particle size) at 25% MeOH w/0.1% NH$_4$OH; 60 mL/min, 100 bars, 40° C.

111: $^1$H NMR (400 MHz, CD$_3$OD) δ 7.54-7.50 (m, 2 H), 7.13 (d, J=8.8 Hz, 1 H), 7.02 (t, J=7.4 Hz, 1 H), 3.94 (s, 3 H), 3.73-3.68 (m, 1 H), 3.15-3.11 (m, 1 H), 2.49-2.47 (m, 3 H), 2.35-2.33 (m, 1 H), 1.95-1.92 (m, 2 H), 1.80-1.74 (m, 2 H), 1.44-1.40 (m, 1 H), 0.97-0.93 (m, 1 H), 0.59-0.57 (m, 2 H), 0.22-0.20 (m, 2 H); LCMS m/z 273.9 (M+H); SFC retention time: 5.18 min.

Example 112

(1-(cyclopropylmethyl)piperidin-3-yl)(5-phenoxynaphthalen-2-yl)methanone

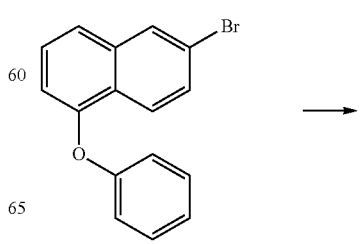

-continued

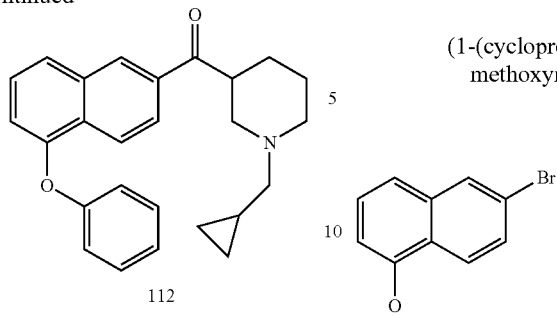

112

Prepared in an analogous manner to (1-(cyclopropylmethyl)piperidin-3-yl) (3-methoxyphenyl) methanone (Examples 109a and 109b), replacing 1-bromo-3-methoxybenzene with 6-bromo-1-phenoxynaphthalene (Intermediate 23).

$^1$H NMR (400 MHz, CD$_3$OD) δ 8.56 (s, 1 H), 8.05 (d, J=8.8 Hz, 1 H), 7.95 (d, J=8.8 Hz, 1 H), 7.75 (d, J=8.8 Hz, 1 H), 7.41 (d, J=8.8 Hz, 2 H), 7.31-7.25 (m, 1 H), 7.25-7.21 (m, 2 H), 7.11-7.09 (m, 2 H), 3.82-3.77 (m, 1 H), 3.31-3.16 (m, 2 H), 2.35-2.33 (m, 2 H), 2.24-2.23 (m, 1 H), 2.07-1.99 (m, 2 H), 1.85-1.80 (m, 2 H), 1.55-1.45 (m, 1 H), 0.91-0.89 (m, 1 H), 0.56-0.52 (m, 2 H), 0.19-0.14 (m, 2 H); LCMS m/z 386.2 (M+H).

Example 113

(2-chlorophenyl)(1-(cyclopropylmethyl)piperidin-3-yl)methanone

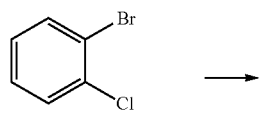

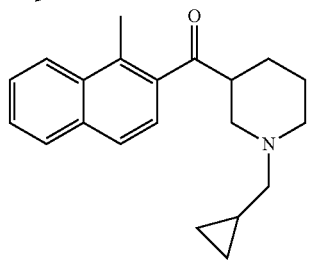

113

Prepared in an analogous manner to (1-(cyclopropylmethyl)piperidin-3-yl) (3-methoxyphenyl) methanone (Examples 109a and 109b), replacing 1-bromo-3-methoxybenzene with 1-bromo-2-chlorobenzene. $^1$H NMR (400 MHz, CD$_3$OD) δ 7.50-7.40 (m, 4 H), 3.39-3.36 (m, 1 H), 3.22-3.19 (m, 1 H), 3.03-3.00 (m, 1 H), 2.30-2.29 (m, 2 H), 2.21-2.19 (m, 1 H), 2.07-2.06 (m, 1 H), 1.91-1.90 (m, 1 H), 1.78-1.77 (m, 1 H), 1.68-1.65 (m, 1 H), 1.47-1.43 (m, 1 H), 0.88-0.84 (m, 1 H), 0.54-0.49 (m, 2 H), 0.13-0.12 (m, 2 H); LCMS m/z 277.8 (M+H).

Example 114

(1-(cyclopropylmethyl)piperidin-3-yl)(5-methoxynaphthalen-2-yl)methanone

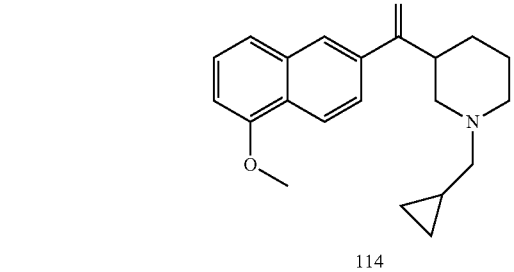

114

Prepared in an analogous manner to (1-(cyclopropylmethyl)piperidin-3-yl) (3-methoxyphenyl) methanone (Examples 109a and 109b), replacing 1-bromo-3-methoxybenzene with 6-bromo-1-methoxynaphthalene. $^1$H NMR (400 MHz, CD$_3$OD) δ 8.44 (s, 1 H), 7.91-7.84 (m, 2 H), 7.75 (d, J=8.8 Hz, 1 H), 7.20 (s, 1 H), 7.15 (dd, J=8.8 Hz, 2.4 Hz, 1 H), 3.88 (s, 3 H), 3.74-3.71 (m, 1 H), 3.20-3.17 (m, 1 H), 3.13-3.10 (m, 1 H), 2.28-2.21 (m, 2 H), 2.18-2.15 (m, 1 H), 1.97-1.95 (m, 2 H), 1.77-1.76 (m, 2 H), 1.45-1.35 (m, 1 H), 0.51-0.48 (m, 2 H), 0.11-0.09 (m, 2 H); LCMS m/z 324.2 (M+H).

Example 115

(1-(cyclopropylmethyl)piperidin-3-yl)(1-methylnaphthalen-2-yl)methanone

115

Prepared in an analogous manner to (1-(cyclopropylmethyl)piperidin-3-yl) (3-methoxyphenyl)methanone (Examples 109a and 109b), replacing 1-bromo-3-methoxybenzene with 2-bromo-1-methylnaphthalene. $^1$H NMR (400 MHz, CD$_3$OD) δ 8.30-8.28 (m, 1 H), 8.03-8.01 (m, 1 H), 7.74 (d, J=8.8 Hz, 1 H), 7.51-7.48 (m, 2 H), 7.33 (d, J=8.8 Hz, 1 H), 3.53-3.52 (m, 1 H), 3.26-3.15 (m, 1 H), 3.01-2.96 (m, 1 H), 2.65 (s, 3 H), 2.20-2.13 (m, 3 H), 1.95-1.94 (m, 1 H), 1.86-1.85 (m, 1 H), 1.70-1.68 (m, 1 H), 1.42-1.41 (m, 1 H), 0.77-0.75 (m, 1 H), 0.43-0.40 (m, 2 H), 0.03-0.02 (m, 2 H); LCMS m/z 308.2 (M+H).

Examples 116a and 116b (4-chlorophenyl)(1-(cyclopropylmethyl)piperidin-3-yl)methanone

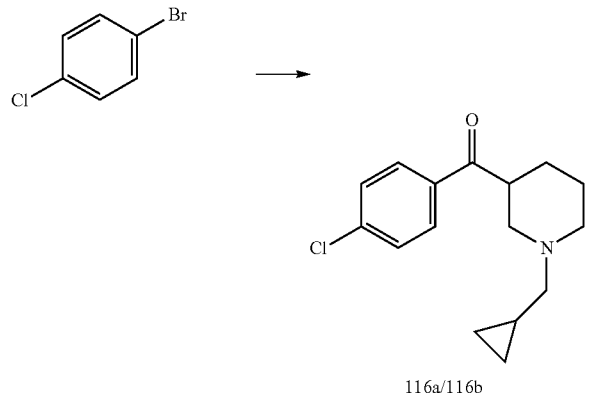

116a/116b

Prepared in an analogous manner to (1-(cyclopropylmethyl)piperidin-3-yl) (3-methoxyphenyl) methanone (Examples 109a and 109b), replacing 1-bromo-3-methoxybenzene with 1-bromo-4-chlorobenzene. SFC conditions: CHIRALPAK AD (250×30 mm, 5 μm particle size) at 25% EtOH w/0.1% NH₄OH; 60 mL/min, 100 bars, 40° C. ¹H NMR (400 MHz, CD₃OD) δ 7.97 (dd, J=6.8 Hz, 1.6 Hz, 2 H), 7.53 (dd, J=6.8 Hz, 1.6 Hz, 2 H), 3.62-3.61 (m, 1 H), 3.20-3.13 (m, 2 H), 2.34-2.32 (m, 2 H), 2.21-2.20 (m, 1 H), 2.06-2.05 (m, 1 H), 1.90-1.83 (m, 1 H), 1.82-1.79 (m, 2 H), 1.45-1.41 (m, 1 H), 0.91-0.90 (m, 1 H), 0.56-0.53 (m, 2 H), 0.17-0.14 (m, 2 H); LCMS m/z 278.1 (M+H); SEC retention time: 5.66 min.

¹H NMR (400 MHz, CD₃OD) δ 7.99 (d, J=8.8 Hz, 2 H), 7.54 (d, J=8.8 Hz, 2 H), 3.69-3.67 (m, 1 H), 3.32-3.19 (m, 2 H), 2.47-2.45 (m, 2 H), 2.23-2.22 (m, 1 H), 2.11-2.10 (m, 1 H), 2.05-1.92 (m, 1 H), 1.86-1.83 (m, 2 H), 1.51-1.49 (m, 1 H), 0.96-0.94 (m, 1 H), 0.61-0.57 (m, 2 H), 0.22-0.20 (m, 2 H); LCMS m/z 278.1 (M+H); SFC retention time: 6.51 min.

Examples 117a and 117b (1-(cyclopropylmethyl)piperidin-3-yl)(quinolin-2-yl)methanone

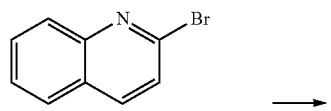

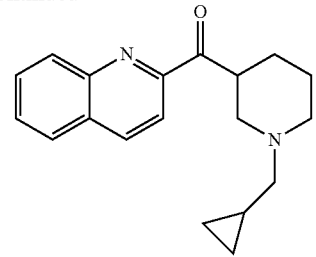

117a/117b

Prepared in an analogous manner to (1-(cyclopropylmethyl)piperidin-3-yl) (3-methoxyphenyl) methanone (Examples 109a and 109b), replacing 1-bromo-3-methoxybenzene with 2-bromoquinoline. SFC conditions: CHIRALPAK AD (250×30 mm, 20 μm particle size) at 30% MeOH w/0.1% NH₄OH; 80 mL/min, 100 bars, 40° C.

117a: ¹H NMR (400 MHz, CD₃OD) δ 8.44 (d, J=8.8 Hz, 1 H), 8.17 (d, J=8.4 Hz, 1 H), 8.08 (d, J=8.8 Hz, 1 H), 7.99 (d, J=8.4 Hz, 1 H), 7.84-7.83 (m, 1 H), 7.73-7.72 (m, 1 H), 4.50-4.45 (m, 1 H), 3.42-3.39 (m, 1 H), 3.18-3.15 (m, 1 H), 2.37-2.35 (m, 2 H), 2.26-2.25 (m, 1 H), 2.10-2.07 (m, 2 H), 1.87-1.84 (m, 2 H), 1.55-1.45 (m, 1 H), 0.93-0.92 (m, 1 H), 0.55-0.51 (m, 2 H), 0.18-0.13 (m, 2 H); LCMS m/z 295.2 (M+H); SFC retention time: 6.81 min.

117b: ¹H NMR (400 MHz, CD₃OD) δ 8.43 (d, J=8.4 Hz, 1 H), 8.17 (d, J=8.8 Hz, 1 H), 8.08 (d, J=8.8 Hz, 1 H), 7.99 (d, J=8.4 Hz, 1 H), 7.84-7.82 (m, 1 H), 7.73-7.71 (m, 1 H), 4.52-4.46 (m, 1 H), 3.45-3.42 (m, 1 H), 3.18-3.17 (m, 1 H), 2.43-2.41 (m, 2 H), 2.41-2.40 (m, 1 H), 2.25-2.23 (m, 1 H), 2.15-2.10 (m, 1 H), 1.89-1.84 (m, 2 H), 1.55-1.45 (m, 1 H), 0.97-0.95 (m, 1 H), 0.58-0.54 (m, 2 H), 0.20-0.17 (m, 2 H); LCMS m/z 295.2 (M+H); SFC retention time: 5.50 min.

Examples 118a and 118b (3-chlorophenyl)(1-(cyclopropylmethyl)piperidin-3-yl)methanone

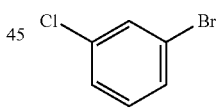

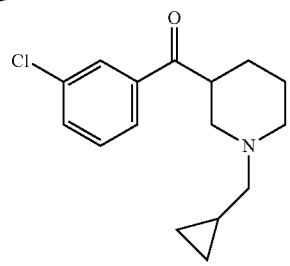

118a/118b

Prepared in an analogous manner to (1-(cyclopropylmethyl)piperidin-3-yl) (3-methoxyphenyl) methanone (Examples 109a and 109b), replacing 1-bromo-3-methoxybenzene with 1-bromo-3-chlorobenzene.

SFC conditions: CHIRALPAK AD (250×30 mm, 20 μm particle size) at 30% MeOH w/0.1% NH₄OH; 80 mL/min, 100 bars, 40° C.

118a: ¹H NMR (400 MHz, CD₃OD) δ 7.95-7.91 (m, 2 H), 7.64-7.62 (m, 1 H), 7.54-7.50 (m, 1 H), 3.62-3.61 (m, 1 H), 3.21-3.13 (m, 2 H), 2.36-2.34 (m, 2 H), 2.18-2.13 (m, 1 H), 2.09-2.08 (m, 1 H), 1.98-1.95 (m, 1 H), 1.83-1.79 (m, 2 H), 1.45-1.44 (m, 1 H), 0.91-0.89 (m, 1 H), 0.57-0.54 (m, 2 H), 0.17-0.16 (m, 2 H); LCMS m/z 277.9 (M+H); SFC retention time: 3.97 min.

118b: ¹H NMR (400 MHz, CD₃OD) δ 7.95-7.91 (m, 2 H), 7.65-7.62 (m, 1 H), 7.55-7.51 (m, 1 H), 3.64-3.61 (m, 1 H), 3.21-3.14 (m, 2 H), 2.36-2.34 (m, 2 H), 2.18-2.13 (m, 1 H), 2.09-2.08 (m, 1 H), 1.98-1.95 (m, 1 H), 1.83-1.79 (m, 2 H), 1.45-1.42 (m, 1 H), 0.91-0.89 (m, 1 H), 0.57-0.53 (m, 2 H), 0.18-0.16 (m, 2 H); LCMS m/z 278.1 (M+H); SFC retention time: 4.26 min.

Example 119

(1-(cyclopropylmethyl)piperidin-3-yl)(1-methyl-1H-indol-6-yl)methanone

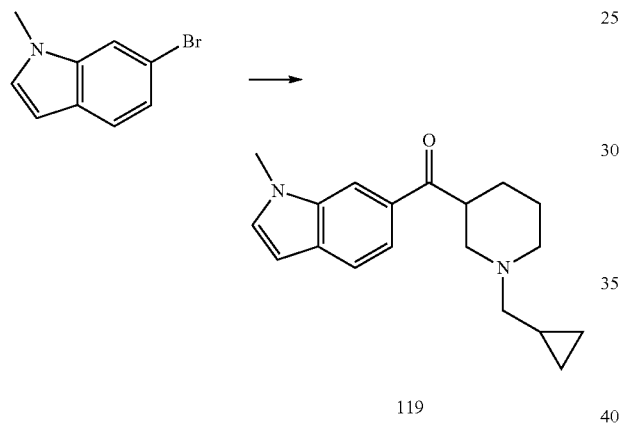

119

Prepared in an analogous manner to (1-(cyclopropylmethyl)piperidin-3-yl) (3-methoxyphenyl)methanone (Examples 109a and 109b), replacing 1-bromo-3-methoxybenzene with 6-bromo-1-methyl-1H-indole.

¹H NMR (400 MHz, CD₃OD) δ 8.09 (s, 1 H), 7.69 (d, J=8.0 Hz, 1 H), 7.61 (d, J=8.0 Hz, 1 H), 7.40 (d, J=4.0 Hz, 1 H), 6.50 (d, J=4.0 Hz, 1 H), 3.89 (s, 3 H), 3.81-3.78 (m, 1H), 3.24-3.15 (m, 2 H), 2.38-2.37 (m, 2 H), 2.01-1.98 (m, 1 H), 1.85-1.79 (m, 2 H), 1.27 (s, 1 H), 0.93-0.88 (m, 1 H), 0.58-0.52 (m, 2 H), 0.16-0.15 (m, 2 H); LCMS m/z 297.2 (M+H).

Example 120

Benzo[b]thiophen-2-yl(1-(cyclopropylmethyl)piperidin-3-yl)methanone

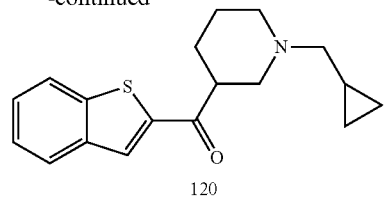

120

Prepared in an analogous manner to (1-(cyclopropylmethyl)piperidin-3-yl) (3-methoxyphenyl) methanone (Examples 109a and 109b), replacing 1-bromo-3-methoxybenzene with 2-bromobenzo[b]thiophene.

¹H NMR (400 MHz, CD₃OD) δ 8.26 (s, 1 H), 8.01-7.99 (m, 1 H), 7.94-7.92 (m, 1 H), 7.52-7.48 (m, 1 H), 7.47-7.43 (m, 1 H), 3.70-3.67 (m, 1 H), 3.32-3.31 (m, 1 H), 3.31-3.25 (m, 1 H), 2.36-2.34 (m, 2 H), 2.25-2.24 (m, 1 H), 2.08-2.04 (m, 2 H), 1.85-1.84 (m, 2 H), 1.56-1.53 (m, 1 H), 0.93-0.92 (m, 1 H), 0.58-0.54 (m, 2 H), 0.17-0.16 (m, 2 H); LCMS m/z 299.8 (M+H).

Example 121

(1-(cyclopropylmethyl)piperidin-3-yl)(3-methoxy-isoquinolin-7-yl)methanone

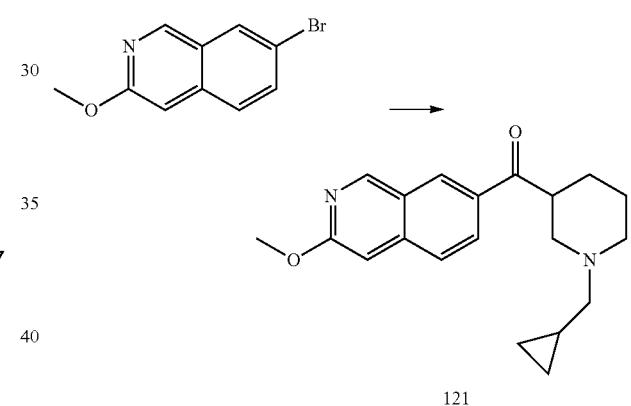

121

Prepared in an analogous manner to (1-(cyclopropylmethyl)piperidin-3-yl) (3-methoxyphenyl) methanone (Examples 109a and 109b), replacing 1-bromo-3-methoxybenzene with 7-bromo-3-methoxyisoquinoline.

¹H NMR (400 MHz, CD₃OD) δ 9.13 (s, 1 H), 8.72 (s, 1 H), 8.11 (d, J=8.8 Hz, 1 H), 7.83 (d, J=8.8 Hz, 1 H), 7.16 (s, 1 H), 4.04 (s, 3 H), 3.82-3.79 (m, 1 H), 3.26-3.17 (m, 2 H), 2.37-2.27 (m, 2 H), 2.26-2.25 (m, 1 H), 2.08-2.01 (m, 2 H), 1.87-1.84 (m, 2 H), 1.55-1.45 (m, 1 H), 0.93-0.91 (m, 1 H), 0.57-0.52 (m, 2 H), 0.17-0.14 (m, 2 H); LCMS m/z 325.2 (M+H).

Example 122

(1-(cyclopropylmethyl)piperidin-3-yl)(2-methoxy-quinolin-6-yl)methanone

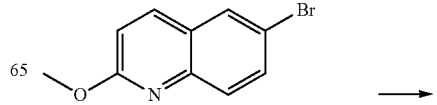

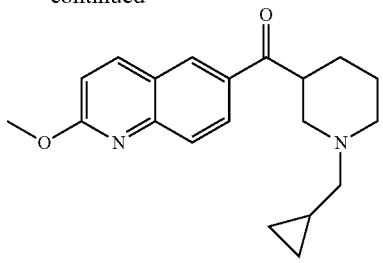

122

Prepared in an analogous manner to (1-(cyclopropylmethyl)piperidin-3-yl) (3-methoxyphenyl) methanone (Examples 109a and 109b), replacing 1-bromo-3-methoxybenzene with 6-bromo-2-methoxyquinoline.

¹H NMR (400 MHz, CD₃OD) δ 8.50 (s, 1 H), 8.25 (d, J=8.8 Hz, 1 H), 8.16 (dd, J=8.8 Hz, 2.0 Hz, 1 H), 7.86 (d, J=8.8 Hz, 1 H), 7.02 (d, J=8.8 Hz, 1 H), 4.07 (s, 3 H), 3.81-3.78 (m, 1 H), 3.32-3.31 (m, 1 H), 3.26-3.17 (m, 1 H), 2.36-2.35 (m, 2 H), 2.29-2.26 (m, 1 H), 2.08-2.05 (m, 2 H), 1.86-1.83 (m, 2 H), 1.51-1.48 (m, 1 H), 0.92-0.90 (m, 1 H), 0.57-0.52 (m, 2 H), 0.18-0.15 (m, 2 H); LCMS m/z 325.2 (M+H).

Example 123

(5-(benzyloxy)naphthalen-2-yl)(1-(cyclopropylmethyl)piperidin-3-yl)methanone

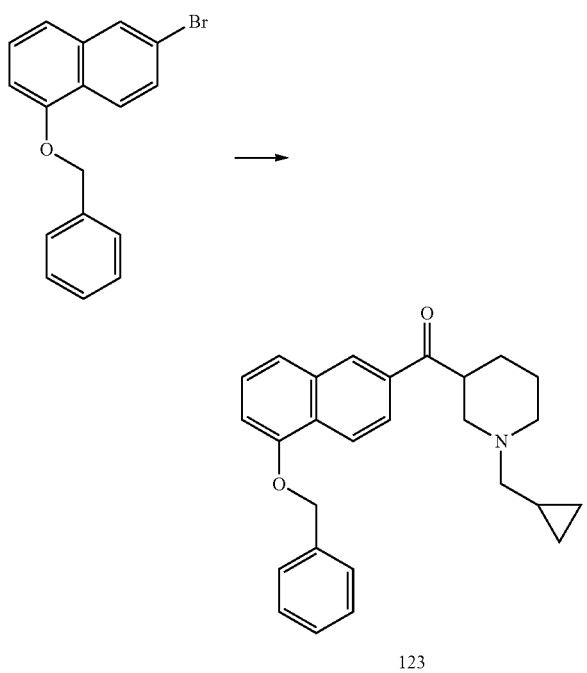

123

Prepared in an analogous manner to (1-(cyclopropylmethyl)piperidin-3-yl) (3-methoxyphenyl) methanone (Examples 109a and 109b), replacing 1-bromo-3-methoxybenzene with 1-(benzyloxy)-6-bromonaphthalene (Intermediate 26)

¹H NMR (400 MHz, CD₃OD) δ 8.53 (s, 1 H), 7.98-7.95 (m, 2 H), 7.85-7.84 (m, 1 H), 7.51-7.49 (m, 2 H), 7.40-7.34 (m, 3 H), 7.32-7.31 (m, 2 H), 5.24 (s, 2 H), 3.85-3.79 (m, 1 H), 3.31-3.28 (m, 1 H), 3.28-3.18 (m, 1 H), 2.39-2.34 (m, 2 H), 2.15-2.10 (m, 1 H), 2.04-2.01 (m, 1 H), 1.87-1.82 (m, 2 H), 1.53-1.48 (m, 2 H), 0.95-0.92 (m, 1 H), 0.57-0.49 (m, 2 H), 0.20-0.17 (m, 2 H); LCMS m/z 400.2 (M+H).

Example 124

(1-(cyclopropylmethyl)piperidin-3-yl)(1-phenyl-1H-pyrazol-4-yl)methanone

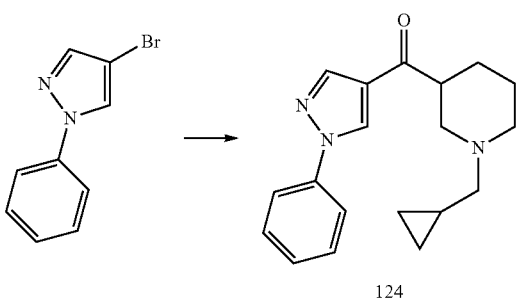 [SMILES: Brc1cnn(-c2ccccc2)c1 ; O=C(c1cnn(-c2ccccc2)c1)C1CCCN(CC2CC2)C1]

124

Prepared in an analogous manner to (1-(cyclopropylmethyl)piperidin-3-yl) (3-methoxyphenyl) methanone (Examples 109a and 109b), replacing 1-bromo-3-methoxybenzene with 4-bromo-1-phenyl-1-pyrazole.

¹H NMR (400 MHz, CD₃OD) δ 8.95 (s, 1 H), 8.19 (s, 1 H), 7.86 (d, J=8.0 Hz, 2 H), 7.55 (t, J=8.0 Hz, 2 H), 7.42 (t, J=7.2 Hz, 1 H), 3.40-3.33 (m, 1 H), 3.24-3.16 (m, 2 H), 2.37-2.35 (m, 2 H), 2.23-2.22 (m, 1 H), 2.07-2.01 (m, 2 H), 1.85-1.82 (m, 2 H), 1.52-1.48 (m, 1 H), 0.96-0.92 (m, 1 H), 0.58-0.56 (m, 2 H), 0.18-0.17 (m, 2 H); LCMS m/z 310.1 (M+H).

Example 125

(1-(cyclopropylmethyl)piperidin-3-yl)(quinolin-3-yl)methanone

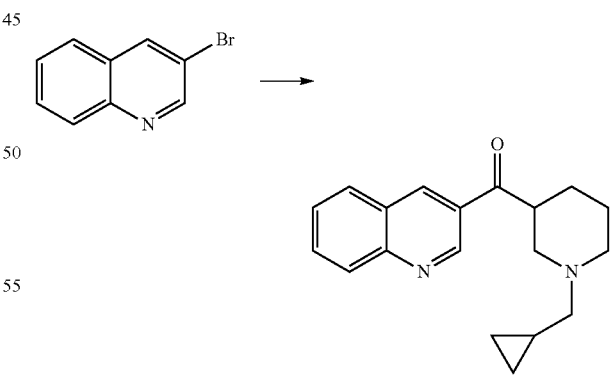

125

Prepared in an analogous manner to (1-(cyclopropylmethyl)piperidin-3-yl) (3-methoxyphenyl) methanone (Examples 109a and 109b), replacing 1-bromo-3-methoxybenzene with 3-bromoquinoline.

¹H NMR (400 MHz, CD₃OD) δ 9.32 (s, 1 H), 9.04 (s, 1 H), 8.16 (d, J=8.4 Hz, 1 H), 8.11 (d, J=8.4 Hz, 1 H), 7.94 (t,

J=7.2 Hz, 1 H), 7.76 (t, J=7.2 Hz, 1 H), 3.84-3.78 (m, 1 H), 3.32-3.30 (m, 1 H), 3.26-3.17 (m, 1 H), 2.39-2.34 (m, 2 H), 2.34-2.33 (m, 2 H), 2.20-2.10 (m, 2 H), 1.90-1.86 (m, 2 H), 1.58-1.45 (m, 1 H), 0.93-0.91 (m, 1 H), 0.57-0.53 (m, 2 H), 0.20-0.17 (m, 2 H); LCMS m/z 295.2 (M+H).

Example 126

(1-(cyclopropylmethyl)piperidin-3-yl)(naphthalen-1-yl)methanone

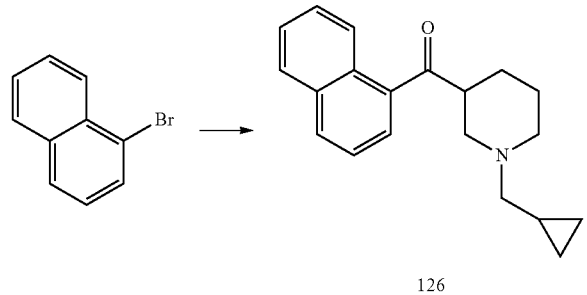 [SMILES: Brc1cccc2ccccc12 ; O=C(c1cccc2ccccc12)C1CCCN(CC2CC2)C1]

126

Prepared in an analogous manner to (1-(cyclopropylmethyl)piperidin-3-yl) (3-methoxyphenyl) methanone (Examples 109a and 109b), replacing 1-bromo-3-methoxybenzene with 1-bromonaphthalene.

$^1$H NMR (400 MHz, CD$_3$OD) δ 8.27-8.25 (m, 1 H), 8.02 (d, J=8.4 Hz, 1H), 7.91-7.87 (m, 2 H), 7.55-7.51 (m, 3 H), 3.65-3.60 (m, 1 H), 3.28-3.23 (m, 1 H), 3.11-3.08 (m, 1 H), 2.41-2.36 (m, 3 H), 2.28-2.27 (m, 1 H), 1.93-1.89 (m, 1 H), 1.78-1.68 (m, 2 H), 1.51-1.48 (m, 1 H), 0.87-0.84 (m, 1 H), 0.51-0.47 (m, 2 H), 0.15-0.11 (m, 2 H); LCMS m/z 294.2 (M+H).

Example 127

(1-(cyclopropylmethyl)piperidin-3-yl)(4-fluoronaphthalen-1-yl)methanone hydrochloride

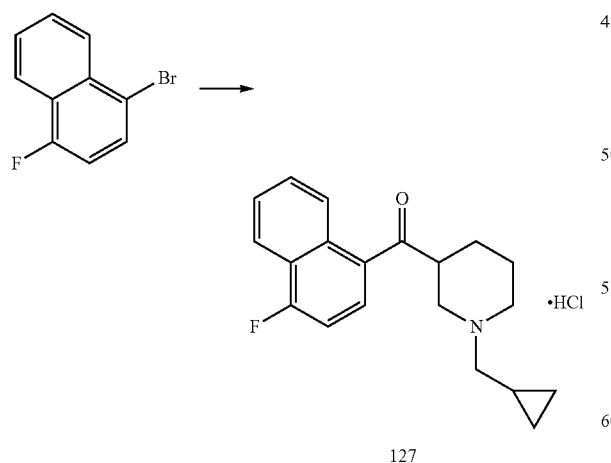

127

Prepared in an analogous manner to (1-(cyclopropylmethyl)piperidin-3-yl) (3-methoxyphenyl) methanone (Examples 109a and 109b), replacing 1-bromo-3-methoxybenzene with 1-bromo-4-fluoronaphthalene.

$^1$H NMR (400 MHz, CD$_3$OD) δ 8.82-8.80 (m, 0.3 H), 8.61-8.59 (m, 0.6 H), 8.22-8.16 (m, 2 H), 7.73-7.69 (m, 2 H), 7.38-7.34 (m, 1 H), 4.30-3.75 (m, 3 H), 3.45-3.00 (m, 4 H), 2.13-1.63 (m, 4 H), 1.23-1.22 (m, 1 H), 0.87-0.80 (m, 2 H), 0.62-0.51 (m, 2 H); LCMS m/z 311.9 (M+H).

Example 128

(1-(cyclopropylmethyl)piperidin-3-yl)(1-fluoronaphthalen-2-yl)methanone

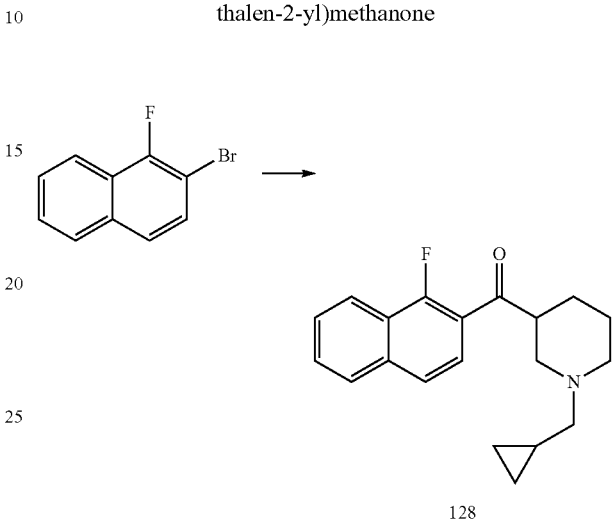

128

Prepared in an analogous manner to (1-(cyclopropylmethyl)piperidin-3-yl) (3-methoxyphenyl) methanone (Examples 109a and 109b), replacing 1-bromo-3-methoxybenzene with 2-bromo-1-fluoronaphthalene.

$^1$H NMR (400 MHz, CD$_3$OD) δ 8.15-8.13 (m, 1 H), 7.88-7.87 (m, 1 H), 7.70-7.61 (m, 4 H), 3.60-3.55 (m, 1 H), 3.31-3.23 (m, 1 H), 3.04-3.01 (m, 1 H), 2.26-2.18 (m, 3 H), 2.02-1.98 (m, 2 H), 1.77-1.75 (m, 2 H), 1.39-1.38 (m, 1 H), 0.84-0.82 (m, 1 H), 0.48-0.46 (m, 2 H), 0.10-0.08 (m, 2 H); LCMS m/z 312.2 (M+H).

Example 129

(1-(cyclopropylmethyl)piperidin-3-yl)(3-methylbenzo[d]isoxazol-6-yl)methanone

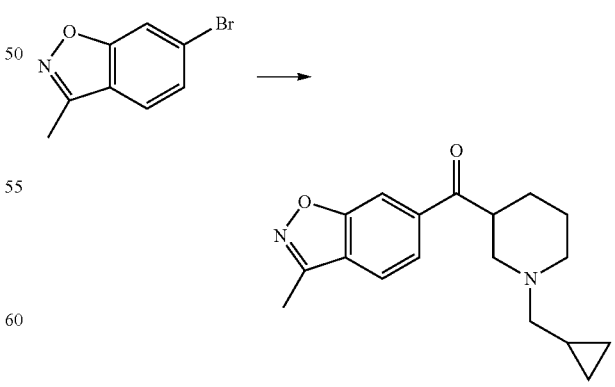

129

Prepared in an analogous manner to (1-(cyclopropylmethyl)piperidin-3-yl) (3-methoxyphenyl) methanone (Examples 109a and 109b), replacing 1-bromo-3-methoxybenzene with 6-bromo-3-methylbenzo[d]isoxazole.

¹H NMR (400 MHz, CD₃OD) δ 8.18 (s, 1 H), 7.93 (d, J=8.4 Hz, 1 H), 7.88 (d, J=8.4 Hz, 1H), 3.75-3.71 (m, 1 H), 3.24-3.22 (m, 1 H), 3.17-3.14 (m, 1 H), 2.59 (s, 3 H), 2.37-2.30 (m, 2 H), 2.28-2.26 (m, 1 H), 2.11-2.10 (m, 1 H), 2.02-2.01 (m, 1 H), 1.84-1.81 (m, 2 H), 1.47-1.44 (m, 1 H), 0.92-0.89 (m, 1 H), 0.56-0.51 (m, 2 H), 0.17-0.15 (m, 2 H); LCMS m/z 298.8 (M+H).

Example 130

5-(1-(cyclopropylmethyl)piperidine-3-carbonyl)-1,3-dimethyl-1H-benzo[d]imidazol-2-one

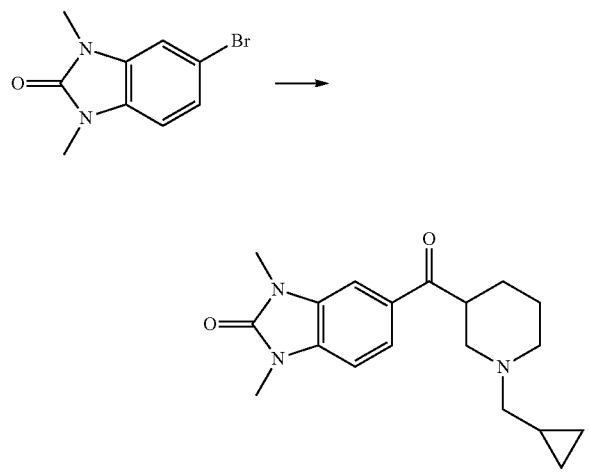

130

Prepared in an analogous manner to (1-(cyclopropylmethyl)piperidin-3-yl) (3-methoxyphenyl) methanone (Examples 109a and 109b), replacing 1-bromo-3-methoxybenzene with 5-bromo-1,3-dimethyl-1H-benzo[d]imidazol-2(3H)-one.

¹H NMR (400 MHz, CD₃OD) δ 7.87 (d, J=8.4 Hz, 1 H), 7.74 (s, 1 H), 7.23 (d, J=8.4 Hz, 1 H), 3.73-3.63 (m, 1 H), 3.46 (s, 3 H), 3.45 (s, 3 H), 3.23-3.16 (m, 2 H), 2.36-2.35 (m, 2 H), 2.23-2.22 (m, 1 H), 2.09-2.07 (m, 1 H), 1.99-1.95 (m, 1 H), 1.83-1.78 (m, 2 H), 1.49-1.45 (m, 1 H), 0.93-0.90 (m, 1 H), 0.56-0.53 (m, 2 H), 0.18-0.15 (m, 2 H); LCMS m/z 328.2 (M+H).

Examples 131a and 131b (6-bromonaphthalen-2-yl)(1-(cyclopropylmethyl)piperidin-3-yl)methanone

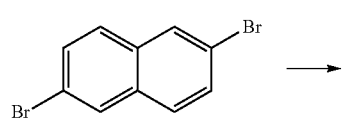

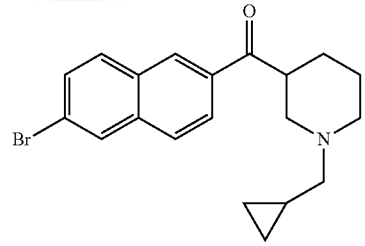

131a/131b

Prepared in an analogous manner to (1-(cyclopropylmethyl)piperidin-3-yl) (3-methoxyphenyl) methanone (Examples 109a and 109b), replacing 1-bromo-3-methoxybenzene with 2,6-dibromonaphthalene.

SFC conditions: CHIRALPAK OJ (250×30 mm, 5 μm particle size) at 20% MeOH w/0.1% NH₄OH; 60 mL/min, 100 bars, 40° C.

131a: ¹H NMR (400 MHz, CD₃OD) δ 8.60 (s, 1 H), 8.16 (s, 1 H), 8.05-7.98 (m, 2 H), 7.93 (d, J=8.4 Hz, 1 H), 7.70 (d, J=8.4 Hz, 1 H), 3.84-3.80 (m, 1 H), 3.26-3.17 (m, 2 H), 2.37-2.35 (m, 3 H), 2.05-2.01 (m, 2 H), 1.87-1.83 (m, 2 H), 1.52-1.48 (m, 1 H), 1.20-1.16 (m, 1 H), 0.94-0.90 (m, 1 H), 0.57-0.52 (m, 2 H), 0.17-0.15 (m, 2 H); LCMS m/z 373.6 (M+H); SFC retention time: 3.38 min.

131b: ¹H NMR (400 MHz, CD₃OD) δ 8.60 (s, 1 H), 8.15 (s, 1 H), 8.05-7.99 (m, 2 H), 7.93 (d, J=8.8 Hz, 1 H), 7.70 (d, J=8.8 Hz, 1 H), 3.84-3.81 (m, 1 H), 3.27-3.17 (m, 2 H), 2.38-2.36 (m, 3 H), 2.05-2.01 (m, 2 H), 1.88-1.84 (m, 2 H), 1.52-1.48 (m, 1 H), 0.94-0.90 (m, 1 H), 0.56-0.53 (m, 2 H), 0.17-0.16 (m, 2 H); LCMS m/z 373.7 (M+H); SFC retention time: 3.99 min.

Example 132

(1-cyclobutylpiperidin-3-yl)(6,7,8,9-tetrahydro-5H-benzo[7]annulen-2-yl)methanoe

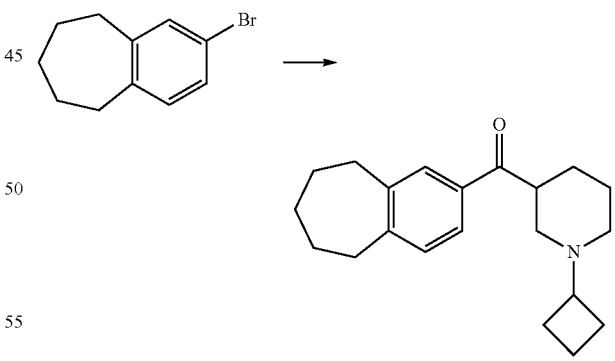

132

Prepared in an analogous manner to (1-(cyclopropylmethyl)piperidin-3-yl) (3-methoxyphenyl) methanone (Examples 109a and 109b), replacing 1-bromo-3-methoxybenzene with 2-bromo-6,7,8,9-tetrahydro-5H-benzo[7]annulene (Intermediate 23), and cyclopropanecarbaldehyde with cyclobutanone.

¹H NMR (400 MHz, CD₃OD) δ 7.69-7.68 (m, 2 H), 7.23-7.21 (m, 1 H), 3.56-3.55 (m, 1 H), 2.95-2.86 (m, 7 H), 2.17-2.03 (m, 2 H), 1.90-1.86 (m, 6 H), 1.78-1.73 (m, 5 H), 1.65-1.55 (m, 4 H), 1.42-1.28 (m, 1 H); LCMS m/z 312.2 (M+H).

Example 133

(1-cyclobutyl-3-piperidyl)-tetralin-6-yl-methanone

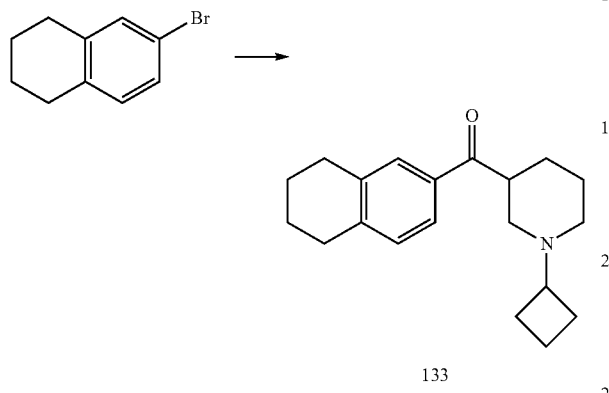

133

Prepared in an analogous manner to (1-(cyclopropylmethyl)piperidin-3-yl) (3-methoxyphenyl) methanone (Examples 109a and 109b), replacing 1-bromo-3-methoxybenzene with 6-bromo-1,2,3,4-tetrahydronaphthalene, and cyclopropanecarbaldehyde with cyclobutanone. It should be noted that the halide-lithium exchange step should be controlled within 15 min.

$^1$H NMR (400 MHz, CD$_3$OD) δ 7.69-7.68 (m, 2 H), 7.20 (d, J=8.8 Hz, 1 H), 3.87-3.82 (m, 1 H), 3.66-3.62 (m, 1 H), 3.40-3.32 (m, 1 H), 3.05-3.01 (m, 1 H), 2.82-2.75 (m, 5 H), 2.33-2.27 (m, 4 H), 2.19-2.14 (m, 1 H), 1.87-1.81 (m, 9 H), 1.62-1.58 (m, 1 H); LCMS m/z 297.9 (M+H).

Example 134

(4-methoxyphenyl)(1-propylpiperidin-3-yl)methanone hydrochloride

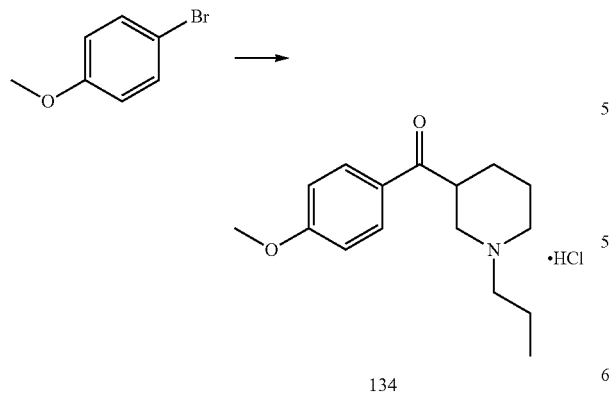

134

Prepared in an analogous manner to (1-(cyclopropylmethyl)piperidin-3-yl) (3-methoxyphenyl) methanone (Examples 109a and 109b), replacing 1-bromo-3-methoxybenzene with 1-bromo-4-methoxybenzene, and cyclopropanecarbaldehyde with propionaldehyde.

$^1$H NMR (400 MHz, CD$_3$OD) δ 8.03-7.98 (m, 2 H), 7.05-7.03 (m, 2 H), 3.92-3.81 (m, 4 H), 3.63-3.60 (m, 1 H), 3.33-3.29 (m, 2 H), 3.17-3.10 (m, 4 H), 2.17-2.06 (m, 2 H), 1.88-1.81 (m, 3 H), 1.09-1.00 (m, 3 H); LCMS m/z 261.9 (M+H).

Example 135

Cyclobutylpiperidin-3-yl)(isoquinolin-6-yl)methanone

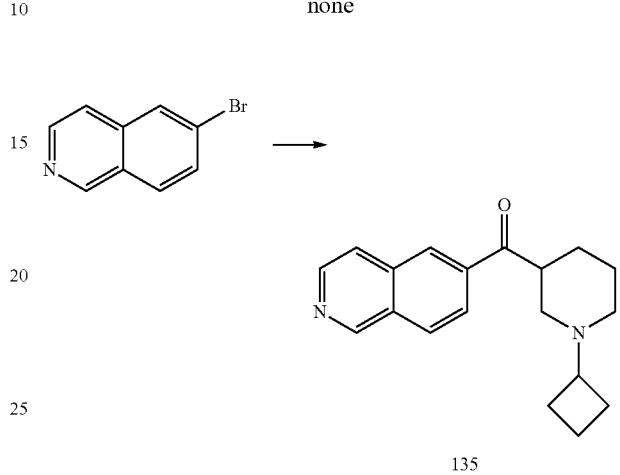

135

Prepared in an analogous manner to (1-(cyclopropylmethyl)piperidin-3-yl) (3-methoxyphenyl) methanone (Examples 109a and 109b), replacing 1-bromo-3-methoxybenzene with 6-bromoisoquinoline, and cyclopropanecarbaldehyde with cyclobutanone.

$^1$H NMR (400 MHz, CD$_3$OD) δ 9.32 (s, 1 H), 8.60 (s, 1 H), 8.55 (d, J=6.0 Hz, 1 H), 8.20-8.19 (m, 1 H), 8.16-8.15 (m, 1 H), 8.01 (d, J=6.0 Hz, 1 H), 3.75-3.74 (m, 1 H), 3.06-3.02 (m, 1 H), 2.95-2.90 (m, 1 H), 2.85-2.83 (m, 1 H), 2.08-2.01 (m, 4 H), 1.91-1.75 (m, 5 H), 1.75-1.72 (m, 2 H), 1.47-1.43 (m, 1 H); LCMS m/z 295.1 (M+H).

Examples 136a and 136b (1-(cyclopropylmethyl)-4-methylpiperidin-3-yl)(5-methoxynaphthalen-2-yl)methanone

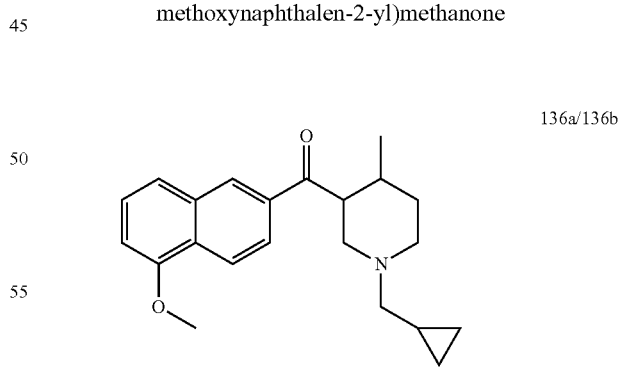

136a/136b

Prepared in an analogous manner to (1-(cyclopropylmethyl)piperidin-3-yl) (3-methoxyphenyl)methanone (Examples 109a and 109b), replacing 1-bromo-3-methoxybenzene with 6-bromo-1-methoxynaphthalene, and tert-butyl 3-(methoxy (methyl)carbamoyl)piperidine-1-carboxylate with tert-butyl 3-(methoxy(methyl) carbamoyl)-4-methylpiperidine-1-carboxylate (Intermediate 10). 129a and 129b correspond to the cis-enantiomers.

SFC conditions: CHIRALPAK AD (250×30 mm, 5 μm particle size) at 50% MeOH w/0.1% NH₄OH; 80 mL/min, 100 bars, 40° C.

129a: ¹H NMR (400 MHz, CD₃OD) δ 8.50 (s, 1 H), 8.00-7.94 (m, 2 H), 7.87 (d, J=8.8 Hz, 1 H), 7.32 (d, J=2.0 Hz, 1 H), 7.24 (d, J=8.8 Hz, 1 H), 4.00-3.94 (m, 4 H), 3.00-2.91 (m, 2 H), 2.75-2.61 (m, 1 H), 2.43-2.34 (m, 4 H), 2.20-2.17 (m, 1 H), 1.70-1.67 (m, 1 H), 0.97-0.92 (m, 1 H), 0.83-0.82 (m, 3 H), 0.60-0.58 (m, 2 H), 0.26-0.22 (m, 2 H); LCMS m/z 337.9 (M+H); SFC retention time: 6.35 min.

129b: ¹H NMR (400 MHz, CD₃OD) δ 8.50 (s, 1 H), 8.00 (d, 8.8 Hz, 2 H), 7.92 (d, J=8.8 Hz, 1 H), 7.36 (d, J=2.0 Hz, 1 H), 7.28 (dd, J=8.8 Hz, 2.4 Hz, 1 H), 4.29-4.28 (m, 1 H), 3.96 (s, 3 H), 3.58-3.50 (m, 2 H), 3.15-3.13 (m, 2 H), 2.63-2.40 (m, 1 H), 1.91-1.81 (m, 1 H), 1.39-1.21 (m, 3 H), 0.92-0.90 (m, 4 H), 0.83-0.80 (m, 2 H), 0.55-0.45 (m, 2 H); LCMS m/z 337.9 (M+H); SFC retention time: 7.46 min.

Examples 137a, 137b, 137c, and 137d (1-(cyclopropylmethyl)-4-methylpiperidin-3-yl)(6-methoxynaphthalen-2-yl)methanone

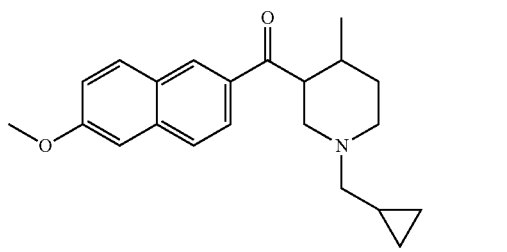

137a/137b/137c/137d

Prepared in an analogous manner to (1-(cyclopropylmethyl)piperidin-3-yl) (3-methoxyphenyl)methanone (Examples 109a and 109b), replacing 1-bromo-3-methoxybenzene with 2-bromo-6-methoxynaphthalene, and tert-butyl 3-(methoxy (methyl)carbamoyl)piperidine-1-carboxylate with tert-butyl 3-(methoxy(methyl) carbamoyl)-4-methylpiperidine-1-carboxylate (Intermediate 10). SFC conditions: CHIRALPAK AD (250×30 mm, 10 μm particle size) at 30% EtOH w/0.1% NH₄OH; 80 mL/min, 100 bars, 40° C.

137a: ¹H NMR (400 MHz, CD₃OD) δ 8.46 (s, 1 H), 7.96-7.91 (m, 2 H), 7.84 (d, J=8.8 Hz, 1 H), 7.29 (s, 1 H), 7.21 (d, J=9.2 Hz, 1 H), 3.96 (s, 3 H), 2.96-2.94 (m, 2 H), 2.86-2.82 (m, 1 H), 2.42-2.37 (m, 4 H), 2.15-2.11 (m, 1 H), 1.68-1.64 (m, 1 H), 0.91-0.78 (m, 4 H), 0.56-0.51 (m, 2 H), 0.22-0.16 (m, 2 H); LCMS m/z 337.9 (M+H); SFC retention time: 3.21 min.

137b: ¹H NMR (400 MHz, CD₃OD) δ 8.53 (s, 1 H), 7.95-7.91 (m, 2 H), 7.82 (d, J=8.8 Hz, 1 H), 7.27 (d, J=2.4 Hz, 1 H), 7.18 (d, J=2.4 Hz, 1 H), 3.91 (s, 3 H), 3.59-3.57 (m, 1 H) 3.19-3.13 (m, 2 H), 2.30-2.28 (m, 2 H), 2.12-2.07 (m, 1 H), 1.97-1.94 (m, 1 H), 1.92-1.88 (m, 1 H), 1.53-1.49 (m, 1 H), 1.26-1.22 (m, 1 H), 0.85 (d, J=6.4 Hz, 4 H), 0.51-0.46 (m, 2 H), 0.10-0.06 (m, 2 H); LCMS m/z 337.9 (M+H); SFC retention time: 2.77 min.

137c: ¹H NMR (400 MHz, CD₃OD) δ 8.44 (s, 1 H), 7.91-7.88 (m, 2 H), 7.81 (d, J=8.8 Hz, 1 H), 7.27 (s, 1 H), 7.19 (d, J=9.2 Hz, 1 H), 3.94-3.91 (m, 4 H), 2.93-2.91 (m, 2 H), 2.86-2.82 (m, 1 H), 2.39-2.34 (m, 4 H), 2.15-2.11 (m, 1 H), 1.66-1.62 (m, 1 H), 0.89-0.76 (m, 4 H), 0.54-0.52 (m, 2 H), 0.19-0.16 (m, 2 H); LCMS m/z 337.9 (M+H); SFC retention time: 3.63 min.

137d: ¹H NMR (400 MHz, CD₃OD) δ 8.53 (s, 1 H), 7.95-7.91 (m, 2 H), 7.82 (d, J=8.8 Hz, 1 H), 7.27 (d, J=2.4 Hz, 1 H), 7.18 (d, J=9.2 Hz, 1 H), 3.91 (s, 3 H), 3.59-3.57 (m, 1 H), 3.19-3.13 (m, 2 H), 2.30-2.28 (m, 2 H), 2.12-2.07 (m, 1 H), 1.97-1.94 (m, 1 H), 1.92-1.88 (m, 1 H), 1.53-1.49 (m, 1 H), 1.26-1.22 (m, 1 H), 0.88-0.82 (m, 4 H), 0.51-0.46 (m, 2 H), 0.11-0.10 (m, 2 H); LCMS m/z 337.9 (M+H); SFC retention time: 3.13 min.

Examples 138a and 138b (1-(cyclopropylmethyl)-4-(trifluoromethyl)piperidin-3-yl)(6-methoxynaphthalen-2-yl)methanone

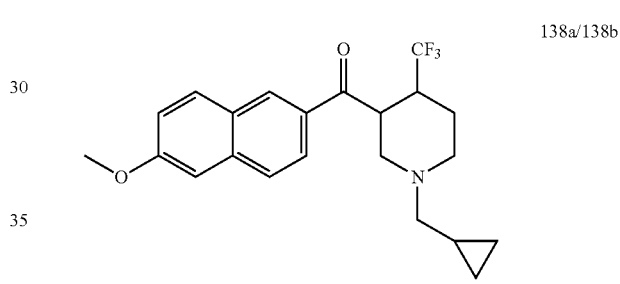

138a/138b

Prepared in an analogous manner to (1-(cyclopropylmethyl)piperidin-3-yl) (3-methoxyphenyl)methanone (Examples 109a and 109b), replacing 1-bromo-3-methoxybenzene with 2-bromo-6-methoxynaphthalene, and tert-butyl 3-(methoxy (methyl)carbamoyl)piperidine-1-carboxylate with tert-butyl 3-(methoxy(methyl) carbamoyl)-5-(trifluoromethyl) piperidine-1-carboxylate (Intermediate 12). 138a and 138b correspond to the cis-enantiomers.

SFC conditions: CHIRALPAK AD (250×30 mm, 20 μm particle size) at 30% MeOH w/0.1% NH₄OH; 80 mL/min, 100 bars, 40° C.

138a: ¹H NMR (400 MHz, CD₃OD) δ 8.56 (s, 1 H), 7.99 (d, J=9.2 Hz, 2 H), 7.90 (d, J=9.2 Hz, 1 H), 7.35 (d, J=2.0 Hz, 1 H), 7.28-7.26 (m, 1 H), 4.14-4.08 (m, 1 H), 3.98 (s, 3 H), 3.30-3.27 (m, 1 H), 2.97-2.93 (m, 1 H), 2.39-2.37 (m, 2 H), 2.24-2.11 (m, 3 H), 1.93-1.89 (m, 1 H), 1.33-1.29 (m, 1 H), 0.94-0.90 (m, 1 H), 0.57-0.53 (m, 2 H), 0.17-0.12 (m, 2 H); LCMS m/z 391.9 (M+H); SFC retention time: 3.74 min.

138b: ¹H NMR (400 MHz, CD₃OD) δ 8.56 (s, 1 H), 7.99 (d, J=9.2 Hz, 2 H), 7.90 (d, J=9.2 Hz, 1 H), 7.35 (d, J=2.0 Hz, 1 H), 7.27 (dd, J=9.2 Hz, 2.4 Hz, 1 H), 4.14-4.08 (m, 1 H), 3.98 (s, 3 H), 3.38-3.30 (m, 2 H), 2.97-2.93 (m, 1 H), 2.39-2.37 (m, 2 H), 2.24-2.11 (m, 3 H), 1.93-1.89 (m, 1 H), 0.93-0.92 (m, 1 H), 0.62-0.51 (m, 2 H), 0.25-0.18 (m, 2 H); LCMS m/z 391.9 (M+H); SFC retention time: 4.27 min.

Example 139a and 139b (1-(cyclopropylmethyl)-5-methylpiperidin-3-yl)(6-methoxynaphthalen-2-yl)methanone

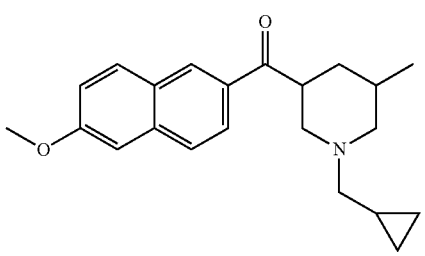

139a/139b

Prepared in an analogous manner to (1-(cyclopropylmethyl)piperidin-3-yl) (3-methoxyphenyl)methanone (Examples 109a and 109b), replacing 1-bromo-3-methoxybenzene with 2-bromo-6-methoxynaphthalene, and tert-butyl 3-(methoxy (methyl)carbamoyl)piperidine-1-carboxylate with 3-(methoxy(methyl)carbamoyl)-5-methylpiperidine-1-carboxylate (Intermediate 11). 139a and 139b correspond to the cis-enantiomers.

139a: $^1$H NMR (400 MHz, CD$_3$OD) δ 8.54 (s, 1 H), 7.99-7.95 (m, 2 H), 7.86 (d, J=8.4 Hz, 1 H), 7.32 (s, 1 H), 7.23 (dd, J=8.4 Hz, 2.0 Hz, 1 H), 3.96 (s, 3 H), 3.86-3.83 (m, 1 H), 3.29-3.27 (m, 1 H), 3.18-3.15 (m, 1 H), 2.42-2.37 (m, 2 H), 2.19-2.14 (m, 1 H), 2.03-2.00 (m, 2 H), 1.73-1.70 (m, 1 H), 1.16-1.13 (m, 1 H), 0.99-0.95 (m, 4 H), 0.59-0.56 (m, 2 H), 0.19-0.17 (m, 2 H); LCMS m/z 337.9 (M+H).

139b: $^1$H NMR (400 MHz, CD$_3$OD) δ 8.46 (s, 1 H), 7.94 (d, J=8.8 Hz, 2 H), 7.87 (d, 9.2 Hz, 1 H), 7.32 (s, 1 H), 7.22 (d, 0.1=2.0 Hz, 1 H), 3.97-3.92 (m, 4 H), 3.03-2.99 (m, 1 H), 2.79-2.77 (m, 1 H), 2.60-2.55 (m, 1 H), 2.36-2.31 (m, 2 H), 2.16-2.12 (m, 2 H), 2.03-2.00 (m, 1 H), 1.56-1.52 (m, 1 H), 1.13-1.10 (d, J=7.2 Hz, 3 H), 0.96-0.94 (m, 1 H), 0.44-0.42 (m, 2 H), 0.12-0.09 (m, 2 H); LCMS m/z 337.9 (M+H).

Examples 140a, 140b, 140c, and 140d (1-cyclobutyl-4-propylpiperidin-3-yl)(6-methoxynaphthalen-2-yl)methanone

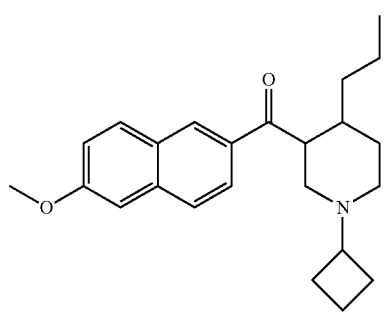

140a/140b/140c/140d

Prepared in an analogous manner to (1-(cyclopropylmethyl)piperidin-3-yl) (3-methoxyphenyl)methanone (Examples 109a and 109b), replacing 1-bromo-3-methoxybenzene with 2-bromo-6-methoxynaphthalene, tert-butyl 3-(methoxy (methyl)carbamoyl)piperidine-1-carboxylate with 3-(methoxy(methyl)carbamoyl)-4-propylpiperidine-1-carboxylate (Intermediate 13), and cyclopropanecarbaldehyde with cyclobutanone.

SFC conditions: CHIRALPAK AD (250×30 mm, 5 μm particle size) at 15% MeOH w/0.1% NH$_4$OH; 50 mL/min, 100 bars, 40° C.

140a: $^1$H NMR (400 MHz, CD$_3$OD) δ 8.44 (s, 1 H), 7.91 (dd, J=8.8 Hz, 2.4 Hz, 2 H), 7.82 (d, J=8.8 Hz, 1 H), 7.27 (d, J=2.4 Hz, 1 H), 7.21-7.19 (m, 1 H), 3.93 (s, 3 H), 3.87-3.84 (m, 1 H), 2.84-2.83 (m, 1 H), 2.74-2.73 (m, 1 H), 2.65-2.55 (m, 1 H), 2.45-2.35 (m, 1 H), 2.20-2.06 (m, 4 H), 1.91-1.84 (m, 4 H), 1.73-1.71 (m, 2 H), 1.39-1.31 (m, 1 H), 1.25-1.15 (m, 1 H), 0.96-0.94 (m, 2 H), 0.65 (t, J=7.6 Hz, 3 H); LCMS m/z 366.1 (M+H); SFC retention time: 5.08 min.

140b: $^1$H NMR (400 MHz, CD$_3$OD) δ 8.56 (s, 1 H), 8.01-7.95 (m, 2 H), 7.87 (d, J=8.8 Hz, 1 H), 7.33 (s, 1 H), 7.27-7.24 (m, 1 H), 3.97 (s, 3 H), 3.70-3.64 (m, 1 H), 3.05-2.96 (m, 2 H), 2.84-2.80 (m, 1 H), 2.13-2.09 (m, 1 H), 1.99-1.88 (m, 7 H), 1.74-1.72 (m, 2 H), 1.40-1.39 (m, 2 H), 1.30-1.20 (m, 4 H), 0.80 (t, J=7.2 Hz, 3 H); LCMS m/z 366.1 (M+H); SFC retention time: 4.39 min.

140c: $^1$H NMR (400 MHz, CD$_3$OD) δ 8.50 (s, 1 H), 7.97-7.93 (m, 2 H), 7.87 (d, J=8.8 Hz, 1 H), 7.32 (d, J=2.4 Hz, 1 H), 7.24 (dd, J=8.8 Hz, 2.4 Hz, 1 H), 4.03-4.01 (m, 1 H), 3.96 (s, 3 H), 3.29-3.20 (m, 1 H), 2.97-2.91 (m, 1 H), 2.89-2.83 (m, 1 H), 2.60-2.50 (m, 1 H), 2.22-2.19 (m, 3 H), 2.19-2.02 (m, 3 H), 1.95-1.85 (m, 1 H), 1.82-1.80 (m, 2 H), 1.48-1.29 (m, 3 H), 1.01-0.98 (m, 2 H), 0.67 (t, J=6.8 Hz, 3 H); LCMS m/z 366.1 (M+H); SFC retention time: 5.84 min.

140d: $^1$H NMR (400 MHz, CD$_3$OD) δ 8.56 (s, 1 H), 8.01-7.95 (m, 2 H), 7.87 (d, J=8.8 Hz, 1 H), 7.33 (s, 1 H), 7.24 (dd, J=9.2 Hz, 2.4 Hz, 1 H), 3.97 (s, 3 H), 3.70-3.64 (m, 1 H), 3.05-2.96 (m, 2 H), 2.84-2.80 (m, 1 H), 2.13-2.09 (m, 1 H), 1.99-1.88 (m, 7 H), 1.74-1.72 (m, 2 H), 1.40-1.39 (m, 2 H), 1.30-1.20 (m, 4 H), 0.80 (t, J=7.2 Hz, 3 H); LCMS m/z 366.0 (M+H); SFC retention time: 4.97 min.

Examples 141a and 141b (1-cyclobutyl-4-phenylpiperidin-3-yl)(6-methoxynaphthalen-2-yl)methanone

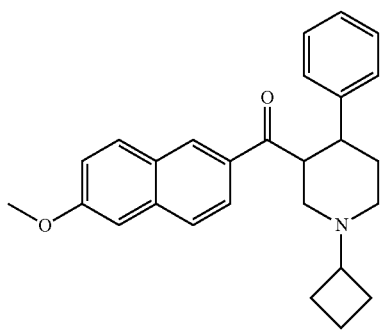

141a/141b

Prepared in an analogous manner to (1-(cyclopropylmethyl)piperidin-3-yl) (3-methoxyphenyl)methanone (Examples 109a and 109b), replacing 1-bromo-3-methoxybenzene with 2-bromo-6-methoxynaphthalene, tert-butyl 3-(methoxy (methyl)carbamoyl)piperidine-1-carboxylate with 3-(methoxy(methyl)carbamoyl)-4-phenylpiperidine-1- carboxylate (Intermediate 16), and cyclopropanecarbaldehyde with cyclobutanone. 141a and 141b correspond to the cis-enantiomers.

SFC conditions: CHIRALPAK AD (250×30 mm, 5 μm particle size) at 40% IPA w/0.1% NH$_4$OH; 80 mL/min, 100 bars, 40° C.

141a: $^1$H NMR (400 MHz, CD$_3$OD) δ 8.29 (s, 1 H), 7.85 (d, J=8.8 Hz, 1 H), 7.74 (s, 2 H), 7.29-7.23 (m, 3 H), 7.16-7.12 (m, 3 H), 7.02-6.95 (m, 1 H), 4.30 (t, J=4.4 Hz, 1 H), 3.91 (s, 3 H), 3.20-3.17 (m, 1 H), 3.10-3.06 (m, 1 H), 2.91-2.82 (m, 1 H), 2.80-2.48 (m, 3 H), 2.19-2.09 (m, 1 H), 2.02-1.90 (m, 4 H), 1.64-1.60 (m, 3 H); LCMS m/z 400.0 (M+H); SFC retention time: 7.39 min.

141b: $^1$H NMR (400 MHz, CD$_3$OD) δ 8.29 (s, 1 H), 7.85 (d, J=9.2 Hz, 1 H), 7.74 (s, 2 H), 7.28-7.23 (m, 3 H), 7.17-7.12 (m, 3 H), 7.02-6.95 (m, 1 H), 4.29-4.28 (m, 1 H), 3.90 (s, 3 H), 3.19-3.12 (m, 1 H), 3.10-3.07 (m, 1H), 2.86-2.80 (m, 1 H), 2.76-2.51 (m, 3 H), 2.17-2.14 (m, 1 H), 2.00-1.90 (m, 4 H), 1.65-1.49 (m, 3 H); LCMS m/z 399.9 (M+H); SFC retention time: 9.22 min.

Examples 142a, 142b, 142c, and 142d (1-cyclobutyl-4-ethylpiperidin-3-yl)(6-methoxynaphthalen-2-yl)methanone

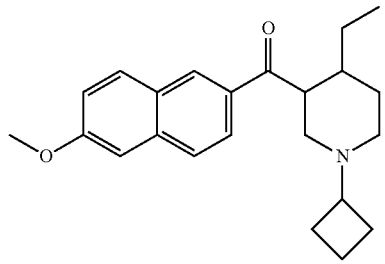

Prepared in an analogous manner to (1-(cyclopropylmethyl)piperidin-3-yl) (3-methoxyphenyl)methanone (Examples 109a and 109b), replacing 1-bromo-3-methoxybenzene with 2-bromo-6-methoxynaphthalene, tert-butyl 3-(methoxy (methyl)carbamoyl)piperidine-1-carboxylate with 3-(methoxy(methyl)carbamoyl)-4-ethylpiperidine-1-carboxylate (Intermediate 15), and cyclopropanecarbaldehyde with cyclobutanone.

SFC conditions: CHIRALPAK OJ (250×30 mm, 5 μm particle size) at 20% IPA w/0.1% NH$_4$OH; 60 mL/min, 100 bars, 40° C.

142a: $^1$H NMR (400 MHz, CD$_3$OD) δ 8.54 (s, 1 H), 7.99-7.95 (m, 2 H), 7.86 (d, J=8.8 Hz, 1 H), 7.31 (d, J=2.8 Hz, 1 H), 7.24 (dd, J=8.8 Hz, 2.4 Hz, 1 H), 3.96 (s, 3 H), 3.65-3.62 (m, 1 H), 3.01-2.95 (m, 2 H), 2.81-2.79 (m, 1 H), 2.12-2.08 (m, 1 H), 1.98-1.70 (m, 9 H), 1.40-1.38 (m, 2 H), 1.17-1.13 (m, 1 H), 0.84 (t, J=7.6 Hz, 3 H); LCMS m/z 351.9 (M+H); SFC retention time: 5.28 min.

142b: $^1$H NMR (400 MHz, CD$_3$OD) δ 8.54 (s, 1 H), 7.99-7.95 (m, 2 H), 7.86 (d, J=8.8 Hz, 1 H), 7.31 (d, J=2.8 Hz, 1 H), 7.23 (dd, J=8.8 Hz, 2.4 Hz, 1 H), 3.96 (s, 3 H), 3.65-3.62 (m, 1 H), 3.01-2.95 (m, 2 H), 2.81-2.79 (m, 1 H), 2.12-2.08 (m, 1 H), 1.98-1.70 (m, 9 H), 1.40-1.38 (m, 2 H), 1.17-1.13 (m, 1 H), 0.84 (t, J=7.6 Hz, 3 H); LCMS m/z 351.9 (M+H); SFC retention time: 5.93 min.

142c: $^1$H NMR (400 MHz, CD$_3$OD) δ 8.50 (s, 1 H), 7.98-7.94 (m, 2 H), 7.87 (d, J=8.8 Hz, 1 H), 7.33 (d, J=2.0 Hz, 1 H), 7.26-7.23 (m, 1 H), 4.00-3.97 (m, 4 H), 3.08-3.01 (m, 1 H), 2.92-2.88 (m, 1 H), 2.75-2.65 (m, 2 H), 2.17-2.13 (m, 3 H), 2.03-1.96 (m, 4 H), 1.80-1.77 (m, 2 H), 1.42-1.38 (m, 1 H), 1.22-1.18 (m, 2 H), 0.73 (t, J=7.6 Hz, 3 H); LCMS m/z 352.2 (M+H); SFC retention time: 7.65 min.

142d: $^1$H NMR (400 MHz, CD$_3$OD) δ 8.51 (s, 1 H), 7.98-7.95 (m, 2 H), 7.87 (d, J=9.2 Hz, 1 H), 7.33 (d, J=2.8 Hz, 1 H), 7.24 (dd, J=7.6 Hz, 2.4 Hz, 1 H), 4.04-3.97 (m, 4 H), 3.14-3.12 (m, 1 H), 2.92-2.88 (m, 1 H), 2.75-2.65 (m, 2 H), 2.17-2.12 (m, 3 H), 2.02-1.96 (m, 4 H), 1.82-1.79 (m, 2 H), 1.42-1.38 (m, 1 H), 1.20-1.17 (m, 2 H), 0.73 (t, J=7.6 Hz, 3 H); LCMS m/z 352.2 (M+H); SFC retention time: 8.25 min.

Examples 143a and 143 b (1-cyclobutyl-4-isopropylpiperidin-3-yl)(6-methoxynaphthalen-2-yl)methanone

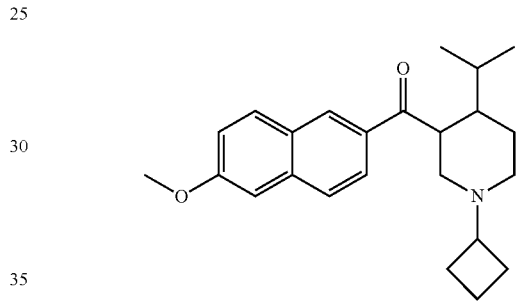

Prepared in an analogous manner to (1-(cyclopropylmethyl)piperidin-3-yl) (3-methoxyphenyl)methanone (Examples 109a and 109b), replacing 1-bromo-3-methoxybenzene with 2-bromo-6-methoxynaphthalene, tert-butyl 3-(methoxy (methyl)carbamoyl)piperidine-1-carboxylate with 3-(methoxy(methyl)carbamoyl)-4-isopropylpiperidine-1-carboxylate (Intermediate 17), and cyclopropanecarbaldehyde with cyclobutanone. 143a and 143b correspond to the cis-enantiomers.

SFC conditions: CHIRALPAK AD (250×30 mm, 10 μm particle size) at 45% IPA w/0.1% NH$_4$OH; 80 mL/min, 100 bars, 40° C.

143a: $^1$H NMR (400 MHz, CD$_3$OD) δ 8.41 (s, 1 H), 7.93-7.89 (m, 2 H), 7.82 (d, J=8.8 Hz, 1 H), 7.28 (d, J=2.4 Hz, 1 H), 7.19 (dd, J=8.8 Hz, 2.4 Hz, 1 H), 3.97-3.96 (m, 1 H), 3.92 (s, 3 H), 3.08-3.05 (m, 1 H), 2.85-2.82 (m, 1 H), 2.60-2.50 (m, 1 H), 2.19-2.16 (m, 2 H), 1.90-1.75 (m, 6 H), 1.59-1.45 (m, 2 H), 1.41-1.31 (m, 1 H), 1.29-1.19 (m, 1 H), 0.94 (d, J=6.8 Hz, 3 H), 0.79 (d, J=6.8 Hz, 3 H); LCMS m/z 366.2 (M+H); SFC retention time: 2.63 min.

143b: $^1$H NMR (400 MHz, CD$_3$OD) δ 8.63 (s, 1 H), 8.02-7.96 (m, 2 H), 7.90 (d, J=8.4 Hz, 1 H), 7.33 (d, J=5.6 Hz, 1 H), 7.43 (dd, J=8.8 Hz, 2.4 Hz, 1 H), 4.48-4.45 (m, 1 H), 3.95 (s, 3 H), 3.70-3.60 (m, 2 H), 3.19-3.16 (m, 1 H), 2.90-2.81 (m, 1 H), 2.50-2.27 (m, 4 H), 2.15-1.98 (m, 3 H), 1.89-1.79 (m, 3 H), 1.52-1.41 (m, 1 H), 1.29-1.19 (m, 1 H), 0.89 (d, J=6.4 Hz, 3 H), 0.77 (d, J=6.4 Hz, 3 H); LCMS m/z 365.9 (M+H); SFC retention time: 6.34 min.

Examples 144a and 144b (1-cyclobutyl-4-isobutylpiperidin-3-yl)(6-methoxynaphthalen-2-yl)methanone

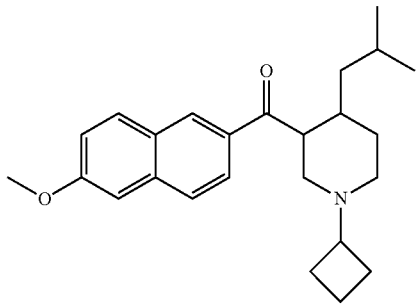

144a/144b

Prepared in an analogous manner to (1-(cyclopropylmethyl)piperidin-3-yl) (3-methoxyphenyl)methanone (Examples 109a and 109b), replacing 1-bromo-3-methoxybenzene with 2-bromo-6-methoxynaphthalene, tert-butyl 3-(methoxy (methyl)carbamoyl)piperidine-1-carboxylate with 3-(methoxy(methyl)carbamoyl)-4-isobutylpiperidine-1-carboxylate (Intermediate 14), and cyclopropanecarbaldehyde with cyclobutanone.

SFC conditions: CHIRALPAK AD (250×30 mm, 10 μm particle size) at 30% EtOH w/0.1% NH₄OH; 80 mL/min, 100 bars, 40° C.

144a: ¹H NMR (400 MHz, CD₃OD) δ 8.36 (s, 1 H), 7.86-7.74 (m, 3 H), 7.21 (d, J=2.4 Hz, 1 H), 7.14-7.11 (m, 1 H), 3.85 (s, 3 H), 3.78-3.75 (m, 1 H), 2.81-2.72 (m, 1 H), 2.70-2.62 (m, 1 H), 2.59-2.50 (m, 1 H), 2.35-2.22 (m, 1 H), 2.19-2.11 (m, 1 H), 2.05-1.92 (m, 3 H), 1.85-1.75 (m, 3 H), 1.68-1.64 (m, 3 H), 1.27-1.18 (m, 3 H), 0.64 (d, J=6.4 Hz, 3 H), 0.32 (d, J=6.4 Hz, 3 H); LCMS m/z 380.0 (M+H); SFC retention time: 6.87 min.

144b: ¹H NMR (400 MHz, DMSO-d6) δ 8.50 (s, 1 H), 8.08 (d, J=9.2 Hz, 1 H), 7.93-7.85 (m, 2 H), 7.42 (d, J=1.6 Hz, 1 H), 7.29 (dd, J=8.4 Hz, 2.0 Hz, 1 H), 4.40-4.38 (m, 1 H), 3.95 (s, 3 H), 3.26-3.21 (m, 2 H), 2.82-2.79 (m, 1 H), 2.42-2.32 (m, 5 H), 2.22-2.18 (m, 2 H), 1.83-1.71 (m, 3 H), 1.45-1.27 (m, 2 H), 0.78-0.72 (m, 4 H), 0.42 (d, J=5.2 Hz, 3 H); LCMS m/z 380.0 (M+H); SFC retention time: 5.88 min.

Example 145

(1-(cyclopropylmethyl)-4-phenylpiperidin-3-yl)(6-methoxynaphthalen-2-yl)methanone

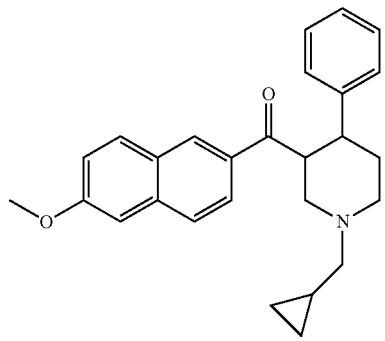

145

Prepared in an analogous manner to (1-(cyclopropylmethyl)piperidin-3-yl) (3-methoxyphenyl)methanone (Examples 109a and 109b), replacing 1-bromo-3-methoxybenzene with 2-bromo-6-methoxynaphthalene, and tert-butyl 3-(methoxy (methyl)carbamoyl)piperidine-1-carboxylate with 3-(methoxy(methyl)carbamoyl)-4-phenylpiperidine-1-carboxylate (Intermediate 16).

¹H NMR (400 MHz, CD₃OD) δ 7.81 (s, 1 H), 7.64-7.60 (m, 1 H), 7.59-7.56 (m, 2 H), 7.13-7.08 (m, 4 H), 6.96-6.94 (m, 2 H), 6.79-6.71 (m, 1 H), 4.57-4.51 (m, 1 H), 4.09-4.05 (m, 1 H), 3.88 (s, 3 H), 3.75-3.72 (m, 1 H), 3.59-3.55 (m, 1 H), 3.46-3.42 (m, 1 H), 3.13 (d, J=7.6 Hz, 2 H), 2.68-2.61 (m, 1 H), 2.04-1.95 (m, 1 H), 1.27-1.10 (m, 2 H), 0.85-0.76 (m, 2 H), 0.56-0.50 (m, 2H); LCMS m/z 399.9 (M+H).

Examples 146a and 146b (1-(cyclopropylmethyl)-4-methoxypiperidin-3-yl)(6-methoxynaphthalen-2-yl)methanone

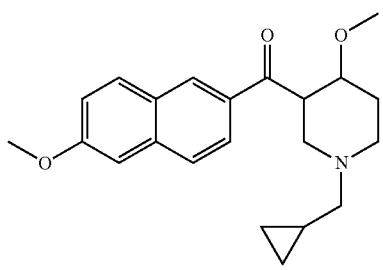

146a/146b

Prepared in an analogous manner to (1-(cyclopropylmethyl)piperidin-3-yl) (3-methoxyphenyl)methanone (Examples 109a and 109b), replacing 1-bromo-3-methoxybenzene with 2-bromo-6-methoxynaphthalene, and tert-butyl 3-(methoxy (methyl)carbamoyl)piperidine-1-carboxylate with 3-(methoxy(methyl)carbamoyl)-4-methoxypiperidine-1-carboxylate (Intermediate 18). 146a and 146b correspond to the cis-enantiomers.

SFC conditions: CHIRALPAK AD (250×30 mm, 5 μm particle size) at 25% MeOH w/0.1% NH₄OH; 55 mL/min, 100 bars, 40° C.

146a: ¹H NMR (400 MHz, CD₃OD) δ 8.42 (s, 1 H), 7.87-7.80 (m, 2 H), 7.71 (d, J8.8 Hz, 1 H), 7.17 (s, 1 H), 7.10-7.08 (m, 1 H), 3.82-3.79 (m, 4 H), 3.57-3.54 (m, 1 H), 3.18 (s, 3 H), 3.06-3.02 (m, 1 H), 2.21-2.07 (m, 5 H), 1.53-1.52 (m, 1 H), 1.15 (s, 1 H), 0.77-0.74 (m, 1 H), 0.42-0.37 (m, 2 H), 0.02-0.00 (m, 2 H); LCMS m/z 353.9 (M+H); SFC retention time: 3.60 min.

146b: ¹H NMR (400 MHz, CD₃OD) δ 8.42 (s, 1 H), 7.87-7.81 (m, 2 H), 7.72 (d, J=8.8 Hz, 1 H), 7.18 (d, J=2.4 Hz, 1 H), 7.09 (dd, J=9.2 Hz, 2.0 Hz, 1 H), 3.82-3.80 (m, 4 H), 3.55-3.54 (m, 1 H), 3.18 (s, 3 H), 3.05-3.02 (m, 1 H), 2.21-2.07 (m, 5 H), 1.53-1.52 (m, 1 H), 1.15 (s, 1 H), 0.77-0.74 (m, 1 H), 0.41-0.37 (m, 2 H), 0.02-0.00 (m, 2 H); LCMS m/z 353.9 (M+H); SFC retention time: 4.18 min.

Examples 147a and 147b (1-cyclopropyl-4-ethylpiperidin-3-yl)(6-methoxynaphthalen-2-yl)methanone

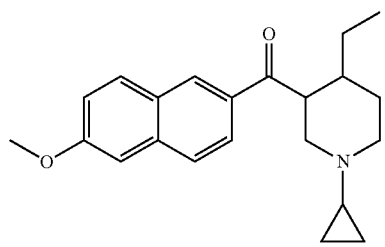

147a/147b

Prepared in an analogous manner to (1-(cyclopropylmethyl)piperidin-3-yl) (3-methoxyphenyl)methanone (Examples 109a and 109b), replacing 1-bromo-3-methoxybenzene with 2-bromo-6-methoxynaphthalene, tert-butyl 3-(methoxy (methyl)carbamoyl)piperidine-1-carboxylate with 3-(methoxy(methyl)carbamoyl)-4-ethylpiperidine-1-carboxylate (Intermediate 15), and cyclopropanecarbaldehyde with (1-ethoxycyclopropoxy)trimethylsilane. 147a and 147b correspond to the cis-enantiomers.

SFC conditions: CHIRALPAK AD (250×50 mm, 10 μm particle size) at 25% IPA w/0.1% NH$_4$OH; 80 mL/min, 100 bars, 40° C.

147a: $^1$H NMR (400 MHz, CD$_3$OD) δ 8.42 (s, 1 H), 7.92-7.88 (m, 2 H), 7.82 (d, J=8.8 Hz, 1 H), 7.28 (d, J=2.4 Hz, 1 H), 7.20 (dd, J=9.2 Hz, 2.8 Hz, 1 H), 3.93 (s, 3 H), 3.88-3.82 (m, 1 H), 2.87-2.85 (m, 2 H), 2.74-2.71 (m, 1 H), 2.53-2.48 (m, 1 H), 2.01-1.98 (m, 1 H), 1.88-1.84 (m, 2 H), 1.73-1.72 (m, 1 H), 1.52-1.43 (m, 1 H), 1.15-1.10 (m, 1 H), 0.70 (t, J=7.6 Hz, 3 H), 0.49-0.40 (m, 3 H), 0.29-0.23 (m, 1 H); LCMS m/z 337.9 (M+H); SFC retention time: 6.75 min.

147b: $^1$H NMR (400 MHz, CD$_3$OD) δ 8.42 (s, 1 H), 7.93-7.88 (m, 2 H), 7.83 (d, J=8.4 Hz, 1 H), 7.28 (d, J=2.4 Hz, 1 H), 7.20 (dd, J=9.2 Hz, 2.8 Hz, 1 H), 3.93 (s, 3 H), 3.88-3.83 (m, 1 H), 2.89-2.88 (m, 2 H), 2.76-2.73 (m, 1 H), 2.53-2.48 (m, 1 H), 2.03-2.00 (m, 1 H), 1.90-1.85 (m, 2 H), 1.78-1.75 (m, 1 H), 1.49-1.43 (m, 1 H), 1.18-1.14 (m, 1 H), 0.71 (t, J=7.6 Hz, 3 H), 0.49-0.43 (m, 3 H), 0.31-0.28 (m, 1 H); LCMS m/z 337.9 (M+H); SFC retention time: 7.26 min.

Example 149

(1-cyclobutylpiperidin-3-yl)(2-(methylsulfonyl)-1,2,3,4-tetrahydroisoquinolin-6-yl)methanone

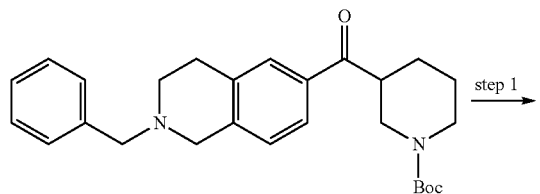

step 1

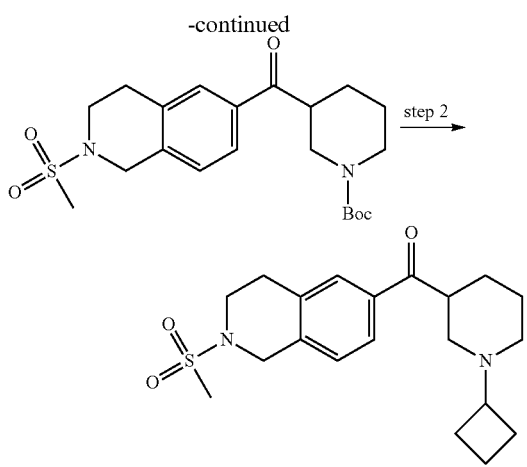

149

Step 1:

tert-butyl 3-(2-(methylsulfonyl)-1,2,3,4-tetrahydroisoquinoline-6-carbonyl) piperidine-1-carboxylate To a stirred and cooled (0° C.) solution of tert-butyl 3-(2-benzyl-1,2,3,4-tetrahydro isoquinoline-6-carbonyl)piperidine-1-carboxylate (430 mg, 1.0 mmol) and Et$_3$N (1.5 mL) in dichloromethane (30 mL) was added 1-chloroethyl carbonochloridate (0.5 mL). The mixture was stirred at room temperature for 3 h and the solvent was evaporated. The residue was dissolved in MeOH (30 mL), stirred for another 16 h and then evaporated under reduced pressure to give crude tert-butyl 3-(2-(methyl sulfonyl)-1,2,3,4-tetrahydroisoquinoline-6-carbonyl)piperidine-1-carboxylate (200 mg, 58% yield).

To a solution of the above crude and Et$_3$N (1.5 mL) in dichloromethane (10 mL) was added MsCl (0.5 mL). The mixture was stirred for 12 h and then evaporated under reduced pressure to give crude tert-butyl 3-(2-(methylsulfonyl)-1,2,3,4-tetrahydro isoquinoline-6-carbonyl)piperidine-1-carboxylate (240 mg, 99% yield).

Step 2:

(2-(methylsulfonyl)-1,2,3,4-tetrahydroisoquinolin-6-yl)(piperidin-3-yl)methanone hydrochloride To a solution of tert-butyl 3-(2-(methylsulfonyl)-1,2,3,4-tetrahydroisoquinoline-6-carbonyl) piperidine-1-carboxylate (211 mg, 0.5 mmol) in ethyl acetate (5 mL) was added HCl (2 N in ethyl acetate, 5 mL). The mixture was stirred at room temperature for 1 h and then evaporated under reduced pressure to give the title compound (177 mg, 99% yield).

Step 3:

(1-cyclobutylpiperidin-3-yl)(2-(methylsulfonyl)-1,2,3,4-tetrahydroisoquinolin-6-yl)methanone A solution of (2-(methylsulfonyl)-1,2,3,4-tetrahydroisoquinolin-6-yl)(piperidin-3-yl) methanone hydrochloride (177 mg, 0.5 mmol), cyclobutanone (70 mg, 1.0 mmol) and Et$_3$N (2 mL) in dichloromethane (10 mL) was stirred at room temperature for 1 h. Then NaBH(OAc)$_3$ (212 mg, 1.0 mmol) was added and stirring was continued for another 1 h. The reaction was quenched by addition of saturated aqueous NH$_4$Cl (10 mL) and extracted with dichloromethane (3×20 mL). The combined organic layers were dried (Na₂SO₄) and concentrated under reduced pressure. The residue was purified by reverse phase HPLC (Phenomenx Gemini NX, 20-60% ACN in 0.1% NH₄OH (aq)) to provide 7.3 mg (11% yield) of the title compound as a white solid.

¹H NMR (400 MHz, CD₃OD) δ 7.88-7.83 (m, 2 H), 7.36-7.34 (m, 1 H), 4.93-4.91 (m, 1 H), 4.52 (s, 2 H), 3.90-3.59 (m, 2 H), 3.57-3.56 (m, 3 H), 3.31-3.29 (m, 1 H), 3.08-3.04 (m, 3 H), 2.94 (s, 3 H), 2.80-2.75 (m, 1 H), 2.38-1.89 (m, 9 H); LCMS m/z 377.1 (M+H).

Example 150

(1-(cyclopropylmethyl)piperidin-3-yl)(5-hydroxynaphthalen-2-yl)methanone

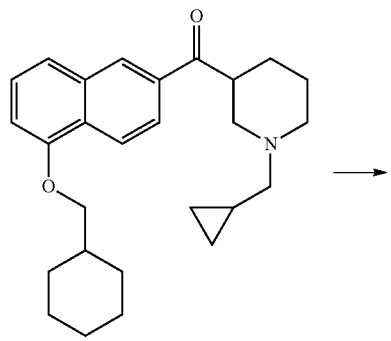

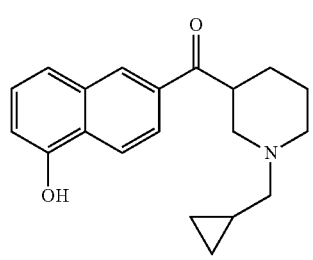

150

A mixture of (5-(benzyloxy)naphthalen-2-yl)(1-cyclopropylmethyl)piperidin-3-yl) methanone (Example 15) (39 mg, 0.1 mmol) and Pd/C (50 mg) in methanol (20 mL) was stirred for 12 h under H₂ atmosphere (15 psi). The reaction mixture was filtered and concentrated under reduced pressure. The residue was purified by preparative HPLC (Phenomenx Gemini NX, 20-60% ACN in 0.1% NH₄OH (aq)) to afford the title compound (22.2 mg, 71%) as a white solid.

¹H NMR (400 MHz, CD₃OD) δ 8.50 (s, 1 H), 7.91 (d, J=8.8 Hz, 2 H), 7.72 (d, J=8.8 Hz, 1 H), 7.16 (d, J=8.0 Hz, 2 H), 3.84-3.81 (m, 1 H), 3.31-3.19 (m, 2 H), 2.39-2.38 (m, 2 H), 2.32-2.29 (m, 1 H), 2.12-2.11 (m, 1 H), 2.04-2.01 (m, 1 H), 1.87-1.85 (m, 2 H), 1.53-1.50 (m, 1 H), 0.96-0.92 (m, 1 H), 0.57-0.55 (m, 2 H), 0.18-0.17 (m, 2 H); LCMS m/z 309.9 (M+H).

Examples 151a and 151b (1-(cyclopropylmethyl)-4-methylpiperidin-3-yl)(5-hydroxynaphthalen-2-yl)methanone

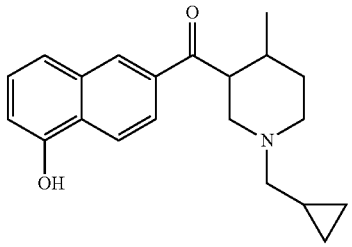

151a/151b

Prepared in an analogous manner to (1-(cyclopropylmethyl)piperidin-3-yl) (5-hydroxynaphthalen-2-yl)methanone (Example 150), replacing tert-butyl 3-(methoxy (methyl) carbamoyl)piperidine-1-carboxylate with 3-(methoxy (methyl)carbamoyl)-4-methylpiperidine-1-carboxylate (Intermediate 10). 151a and 151b correspond to the cis-enantiomers.

SFC conditions: CHIRALPAK AD (250×30 mm, 20 μm particle size) at 50% MeOH w/0.1% NH₄OH; 80 mL/min, 100 bars, 40° C.

151a: ¹H NMR (400 MHz, CD₃OD) δ 8.30 (s, 1 H), 7.70 (t, J=8.0 Hz, 2 H), 7.51 (d, J=8.4 Hz, H), 6.96 (d, J=8.0 Hz, 2 H), 4.00-3.94 (m, 1 H), 3.11-3.01 (m, 2 H), 2.85-2.80 (m, 1 H), 2.69-2.67 (m, 2 H), 2.27-2.23 (m, 1 H), 1.95-1.90 (m, 1 H), 1.60-1.57 (m, 1 H), 1.05-0.90 (m, 2 H), 0.65-0.63 (m, 3 H), 0.51-0.49 (m, 2 H), 0.20-0.19 (m, 2 H); LCMS m/z 323.9 (M+H); SFC retention time: 1.93 min.

151b: ¹H NMR (400 MHz, CD₃OD) δ 8.44 (s, 1 H), 7.84 (t, J=8.0 Hz, 2 H), 7.64 (d, J=8.8 Hz, 1 H), 7.08 (d, J=8.0 Hz, 2 H), 4.15-4.11 (m, 1 H), 3.54-3.11 (m, 3 H), 2.94-2.92 (m, 2 H), 2.42-2.38 (m, 1 H), 2.05-2.02 (m, 1 H), 1.76-1.71 (m, 1 H), 1.19-1.15 (m, 1 H), 1.06-0.97 (m, 1 H), 0.78-0.73 (m, 3 H), 0.67-0.65 (m, 2 H), 0.38-0.35 (m, 2 H); LCMS m/z 323.9 (M+H); SFC retention time: 4.74 min Example 152

(1-(cyclopropylmethyl)piperidin-3-yl)(6-(hydroxymethyl)naphthalen-2-yl)methanone

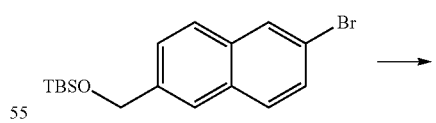

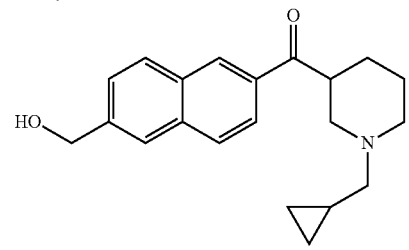

152

Prepared in an analogous manner to (1-(cyclopropylmethyl)piperidin-3-yl) (3-methoxyphenyl)methanone (Examples 109a and 109b), replacing 1-bromo-3-methoxybenzene with ((6-bromonaphthalen-2-yl)methoxy)(tert-butyl)dimethyl silane (Intermediate 24).

¹H NMR (400 MHz, CD₃OD) δ 8.68 (d, J=7.6 Hz, 1 H), 8.12-7.94 (m, 4 H), 7.64 (d, J=8.0 Hz, 1 H), 4.84 (s, 2 H), 4.19-4.13 (m, 1 H), 3.86-3.82 (m, 1 H), 3.31-3.28 (m, 1 H), 3.17-3.04 (m, 3 H), 2.33-2.20 (m, 3 H), 1.90-1.62 (m, 2 H), 1.26-1.22 (m, 1 H), 0.86-0.80 (m, 2 H), 0.53-0.51 (m, 2 H); LCMS m/z 324 (M+H).

Example 153

(1-cyclobutylpiperidin-3-yl)(6-(hydroxymethyl)naphthalen-2-yl)methanone

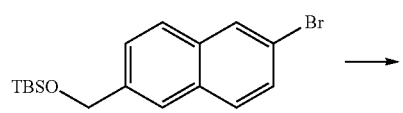

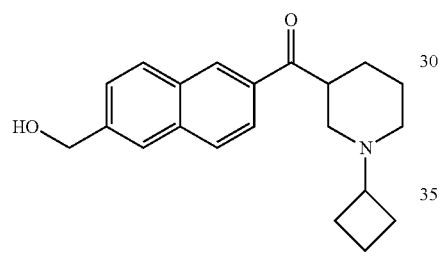

153

Prepared in an analogous manner to (1-(cyclopropylmethyl)piperidin-3-yl) (3-methoxyphenyl)methanone (Examples 109a and 109b), replacing 1-bromo-3-methoxybenzene with ((6-bromonaphthalen-2-yl)methoxy)(tert-butyl)dimethyl silane (Intermediate 24), and cyclopropanecarbaldehyde with cyclobutanone.

¹H NMR (400 MHz, CD₃OD) δ 8.66 (d, J=5.6 Hz, 1 H), 8.13-7.94 (m, 4 H), 7.64 (d, J=8.4 Hz, 1 H), 4.84 (s, 2 H), 4.12-4.09 (m, 1 H), 3.80-3.78 (m, 1.5 H), 3.66-3.63 (m, 1.5 H), 3.12-3.10 (m, 1 H), 2.83-2.79 (m, 1 H), 2.42-2.34 (m, 5 H), 2.13-2.12 (m, 2 H), 1.93-1.91 (m, 2 H), 1.63-1.60 (m, 1 H); LCMS m/z 324 (M+H).

Example 154

(1-cyclopentylpiperidin-3-yl)(6-(hydroxymethyl)naphthalen-2-yl)methanone

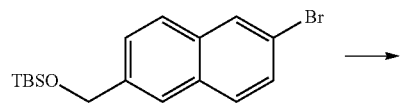

-continued

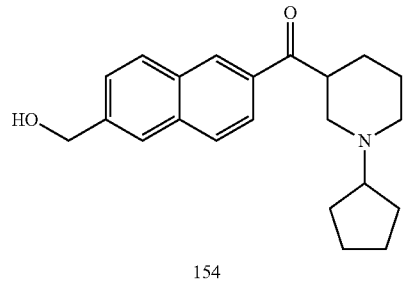

154

Prepared in an analogous manner to (1-(cyclopropylmethyl)piperidin-3-yl) (3-methoxyphenyl)methanone (Examples 109a and 109b), replacing 1-bromo-3-methoxybenzene with ((6-bromonaphthalen-2-yl)methoxy)(tert-butyl)dimethyl silane (Intermediate 24), and cyclopropanecarbaldehyde with cyclopentanone.

¹H NMR (400 MHz, CD₃OD) δ 8.64 (d, J=4.0 Hz, 1 H), 8.07 (d, J=8.4 Hz, 1 H), 8.04-7.96 (m, 2 H), 7.91 (s, 1 H), 7.61 (d, J=8.8 Hz, 1 H), 4.81 (s, 2 H), 4.11-4.10 (m, 1 H), 3.78-3.62 (m, 3 H), 3.27-3.24 (m, 0.5 H), 3.03-2.97 (m, 1.5 H), 2.25-2.12 (m, 5 H), 1.88-1.61 (m, 7 H); LCMS m/z 338 (M+H).

Example 155

(1-(cyclopropylmethyl)-5-hydroxypiperidin-3-yl)(6-methoxynaphthalen-2-yl)methanone

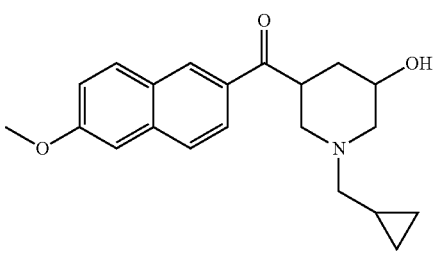

155

Prepared in an analogous manner to (1-(cyclopropylmethyl)piperidin-3-yl) (3-methoxyphenyl)methanone (Examples 109a and 109b), replacing tert-butyl 3-(methoxy(methyl)carbamoyl)piperidine-1-carboxylate with tert-butyl 3-((tert-butyldimethyl silyl)oxy)-5-(methoxy(methyl)carbamoyl)piperidine-1-carboxylate (Intermediate 20).

¹H NMR (400 MHz, CD₃OD) δ 8.50 (s, 1 H), 7.95-7.91 (m, 2 H), 7.83 (d, J=8.8 Hz, 1 H), 7.29 (d, J=2.4 Hz, 1 H), 7.19 (dd, J=8.8 Hz, 2.4 Hz, 1 H), 3.92 (s, 3 H), 3.90-3.80 (m, 2 H), 3.19-3.16 (m, 1 H), 2.38-2.33 (m, 2 H), 2.21-2.12 (m, 2 H), 1.86 (t, J=10.4 Hz, 1 H), 1.44-1.26 (m, 2 H), 0.90-0.87 (m, 1 H), 0.54-0.50 (m, 2 H), 0.14-0.07 (m, 2 H); LCMS m/z 340.2 (M+H).

Examples 156a and 156b (1-(cyclopropylmethyl)-3-methylpiperidin-3-yl)(6-methoxynaphthalen-2-yl)methanone

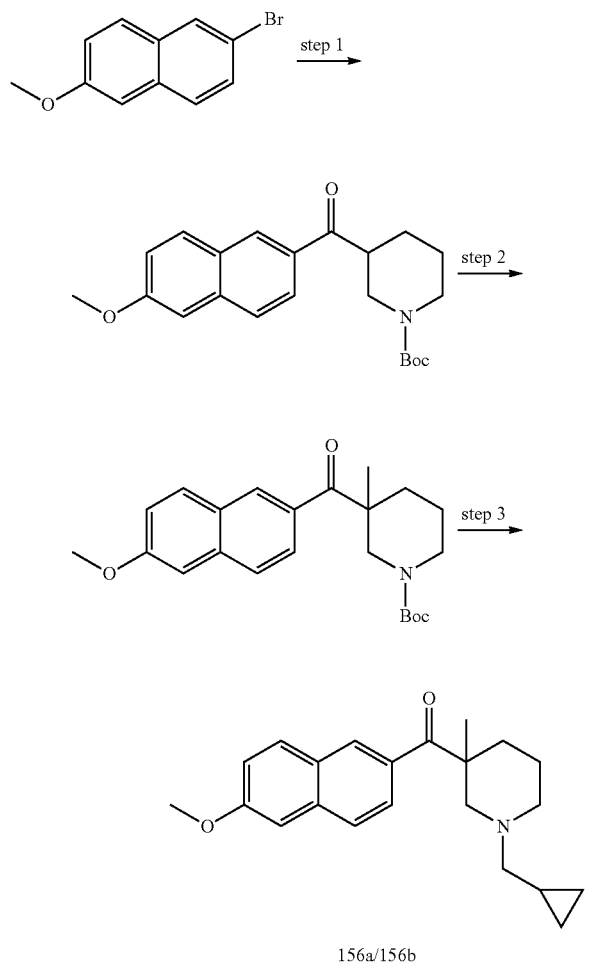 [SMILES: COc1ccc2cc(Br)ccc2c1 ; COc1ccc2cc(C(=O)C3CCCN(C(=O)OC(C)(C)C)C3)ccc2c1 ; COc1ccc2cc(C(=O)C3(C)CCCN(C(=O)OC(C)(C)C)C3)ccc2c1 ; COc1ccc2cc(C(=O)C3(C)CCCN(CC4CC4)C3)ccc2c1]

156a/156b

Step 1:

tert-butyl 3-(6-methoxy-2-naphthoyl)piperidine-1-carboxylate

To a stirred and cooled (−78° C.) solution of 2-bromo-6-methoxynaphthalene (2.36 g, 10.0 mmol) in THF (30 mL) was added n-BuLi (2.5 M in hexane, 4.0 mL, 10.0 mmol). After addition, stirring at −78° C. was continued for 1 h, and then a solution of tert-butyl 3-(methoxy(methyl)carbamoyl) piperidine-1-carboxylate (Intermediate 10) (2.72 g, 10.0 mmol) in THF (10 mL) was added dropwise. The resulting mixture was warmed to room temperature and stirred for an additional 2 h. The mixture was quenched by addition of saturated aqueous NH$_4$Cl (20 mL) and extracted with ethyl acetate (3×100 mL). The combined organic layers were washed with brine, dried (Na$_2$SO$_4$) and concentrated under reduced pressure to give crude tert-butyl 3-(6-methoxy-2-naphthoyl)piperidine-1-carboxylate (1.9 g, 51% yield). This crude was used directly without further purification.

Step 2:

tert-butyl 3-(6-methoxy-2-naphthoyl)-3-methylpiperidine-1-carboxylate

To a stirred and cooled (−78° C.) solution of tert-butyl 3-(6-methoxy-2-naphthoyl) piperidine-1-carboxylate (369 mg, 1.0 mmol) in THF (10 mL) was added LiHMDS (1 N, 1.1 mL, 1.1 mmol). After addition, stirring was continued for 30 min and then MeI (282 mg, 2.0 mmol) was added. The mixture was warmed up to room temperature and stirred for another 2 h. The reaction was quenched by the addition of saturated aqueous NH$_4$Cl (10 mL) and then extracted with ethyl acetate (3×20 mL). The combined organic layers were washed with water (10 mL), brine (10 mL), dried (Na$_2$SO$_4$), and concentrated under reduced pressure. The residue was purified by silica-gel chromatography (petroleum ether:ethyl acetate=5:1) to give tert-butyl 3-(6-methoxy-2-naphthoyl)-3-methyl piperidine-1-carboxylate (200 mg, 52.2% yield) as an oil.

Step 3:

(6-methoxynaphthalen-2-yl)(3-methylpiperidin-3-yl) methanone hydrochloride

To a solution of tert-butyl 3-(6-methoxy-2-naphthoyl)-3-methylpiperidine-1-carboxylate (200 mg, 0.52 mmol) in ethyl aceate (10 mL) was added HCl (2 N in ethyl aceate, 10 mL, 20 mmol). The reaction mixture was stirred at ambient temperature for 2 h and then concentrated under reduced pressure to give crude (6-methoxynaphthalen-2-yl)(3-methylpiperidin-3-yl) methanone hydrochloride (165 mg, 99.6% yield) as an oil.

A solution of (6-methoxynaphthalen-2-yl)(3-methylpiperidin-3-yl)methanone hydrochloride (160 mg, 0.50 mmol), cyclopropanecarbaldehyde (42 mg, 0.60 mmol) and Et$_3$N (2 mL) in dichloroethane (10 mL) was stirred at room temperature for 1 h. Then NaBH(OAc)$_3$ (127 mg, 0.60 mmol) was added to the mixture. The mixture was stirred for another 1 h and then quenched by addition of saturated aqueous NH$_4$Cl (5 mL). The solution was extracted with dichloromethane (2×20 mL). The combined organic layers were dried (Na$_2$SO$_4$) and concentrated under reduced pressure. The residue was purified by reverse phase HPLC (base) then the enantiomers were separated by supercritical fluid chromatography (SFC) to provide 11.1 mg (7% yield) of 155a and 9.4 mg (6% yield) of 155b.

SFC conditions: CHIRALPAK IC (250×50 mm, 5 μm particle size) at 40% EtOH w/0.1% NH$_4$OH; 80 mL/min, 100 bars, 40° C.

156a: $^1$H NMR (400 MHz, CD$_3$OD) δ 8.27 (s, 1 H), 7.87 (d, J=9.2 Hz, 1 H), 7.82-7.77 (m, 2 H), 7.28 (d, J=2.4 Hz, 1 H), 7.20 (dd, J=8.8 Hz, 2.4 Hz, 1 H), 3.94 (s, 3 H), 3.64-3.60 (m, 1 H), 2.81-2.76 (m, 1 H), 2.42-2.04 (m, 4 H), 1.63-1.59 (m, 2 H), 1.47 (s, 3 H), 1.38-1.27 (m, 2 H), 0.59-0.55 (m, 1 H), 0.37-0.30 (m, 2 H), 0.10-0.03 (m, 2 H); LCMS m/z 338.2 (M+H); SFC retention time: 8.58 min.

156b: $^1$H NMR (400 MHz, CD$_3$OD) δ 8.23 (s, 1 H), 7.87 (d, J=9.2 Hz, 1 H), 7.82-7.77 (m, 2 H), 7.26 (d, J=2.4 Hz, 1 H), 7.18 (dd, J=8.8 Hz, 2.4 Hz, 1 H), 3.94 (s, 3 H), 3.64-3.60 (m, 1 H), 2.81-2.76 (m, 1 H), 2.42-2.04 (m, 4 H), 1.63-1.59 (m, 2 H), 1.44 (s, 3 H), 1.38-1.27 (m, 2 H), 0.59-0.55 (m, 1 H), 0.37-0.30 (m, 2 H), 0.10-0.03 (m, 2 H); LCMS m/z 338.2 (M+H); SFC retention time: 6.93 min.

Example 157

(1-(cyclopropylmethyl)-4-methoxypiperidin-3-yl)(6-methoxynaphthalen-2-yl)methanone

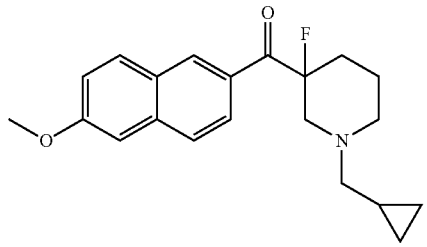

157

Prepared in an analogous manner to (1-(cyclopropylmethyl)-3-methylpiperidin-3-yl) (6-methoxynaphthalen-2-yl)methanone (Examples 156a and 156b), replacing iodomethane with N-Fluorodibenzenesulfonimide. Only one enantiomer was obtained due to stability issue.

SFC conditions: CHIRALPAK OJ (250×30 mm, 5 μm particle size) at 25% IPAw/0.1% NH$_4$OH; 60 mL/min, 100 bars, 40° C.

$^1$H NMR (400 MHz, CDCl$_3$) δ 8.71 (s, 1 H), 8.08-8.05 (m, 1 H), 7.86 (d, J=8.8 Hz, 1 H), 7.76 (d, J=8.8 Hz, 1 H), 7.22-7.19 (m, 1 H), 7.19-7.15 (m, 1 H), 3.96 (s, 3 H), 3.44-3.41 (m, 1 H), 3.13-3.10 (m, 1 H), 2.73-2.65 (m, 1 H), 2.41-2.38 (m, 2 H), 2.22-2.10 (m, 2 H), 2.09-1.97 (m, 2 H), 1.79-1.78 (m, 1 H), 0.93-0.90 (m, 1 H), 0.52-0.50 (m, 2 H), 0.12-0.09 (m, 2 H); LCMS m/z 341.9 (M+H); SFC retention time: 6.20 min.

Examples 158a and 158b (1-(cyclopropylmethyl)-3-hydroxypiperidin-3-yl)(6-methoxynaphthalen-2-yl)methanone

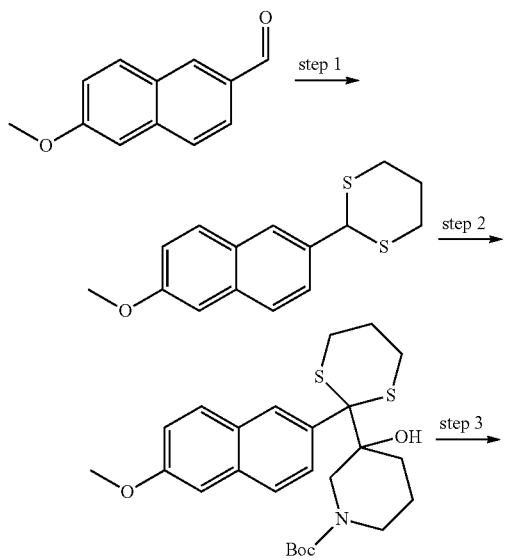

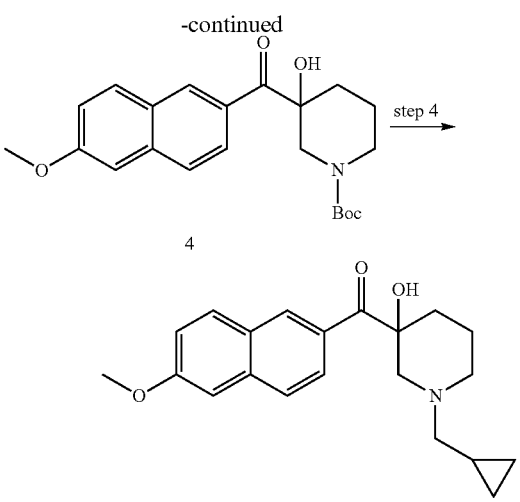

158a/158b

Step 1:

2-(6-methoxynaphthalen-2-yl)-1,3-dithiane

A solution of 6-methoxy-2-naphthaldehyde (1.0 g, 5.4 mmol), propane-1,3-dithiol (618 mg, 6 mmol) and 4-methylbenzenesulfonic acid (172 mg, 1 mmol) in toluene (50 mL) was heated at 120° C. for 16 h. The solvent was removed under reduced pressure, and the residue was purified by silica-gel chromatography (petroleum ether:ethyl acetate=5:1) to give 2-(6-methoxynaphthalen-2-yl)-1,3-dithiane (400 mg, 26.8% yield) as an oil.

Step 2:

tert-butyl 3-hydroxy-3-(2-(6-methoxynaphthalen-2-yl)-1,3-dithian-2-yl)piperidine-1-carboxylate To a stirred and cooled (0° C.) solution of 2-(6-methoxynaphthalen-2-yl)-1,3-dithiane (400 mg, 1.45 mmol) in THF (10 mL) was added LDA (2N, 0.8 mL, 1.6 mmol). After being stirred at −20° C. for 30 min, the mixture was cooled to −78° C. and a solution of tert-butyl 3-oxopiperidine-1-carboxylate (289 mg, 1.45 mmol) in THF (5 mL) was added. The resulting mixture was stirred for another 2 h, and then quenched by the addition of saturated aqueous NH$_4$Cl (10 mL). The mixture was extracted with ethyl acetate (3×20 mL). The combined organic layers were washed with water (15 mL), brine (15 mL), dried (Na$_2$SO$_4$), and concentrated under reduced pressure. The residue was purified by silica-gel chromatography (petroleum ether:ethyl acetate=3:1) to give tert-butyl 3-hydroxy-3-(2-(6-methoxynaphthalen-2-yl)-1,3-dithian-2-yl) piperidine-1-carboxylate (200 mg, 29.0% yield) as an oil.

Step 3:

tert-butyl 3-hydroxy-3-(6-methoxy-2-naphthoyl)piperidine-1-carboxylate

A mixture of tert-butyl 3-hydroxy-3-(2-(6-methoxynaphthalen-2-yl)-1,3-dithian-2-yl)piperidine-1-carboxylate (180 mg, 0.38 mmol), pyridinium bromide perbromide (242 mg, 0.76 mmol) and Tetrabutylammonium bromide (15 mg) in dichloromethane (10 mL) and H$_2$O (3 mL) was stirred at room temperature for 8 h. The reaction mixture was extracted with dichloromethane (3×10 mL). The combined organic layers were dried (Na$_2$SO$_4$) and concentrated under reduced pressure. The residue was purified by chromatography (petroleum ether:ethyl acetate=3:1) to give tert-butyl 3-hydroxy-3-(6-methoxy-2-naphthoyl) piperidine-1-carboxylate (120 mg, 82.1% yield) as a yellow oil.
Step 4:

(3-hydroxypiperidin-3-yl)(6-methoxynaphthalen-2-yl)methanone hydrochloride

To a solution of tert-butyl 3-hydroxy-3-(6-methoxy-2-naphthoyl)piperidine-1-carboxylate (100 mg, 0.26 mmol) in ethyl aceate (10 mL) was added HCl (2 N in ethyl aceate, 10 mL, 20 mmol). The reaction mixture was stirred at ambient temperature for 2 h and then concentrated under reduced pressure to give crude (3-hydroxypiperidin-3-yl)(6-methoxynaphthalen-2-yl) methanone hydrochloride (83 mg, 99.6% yield) as a yellow oil.

A solution of (3-hydroxypiperidin-3-yl)(6-methoxynaphthalen-2-yl)methanone hydrochloride (83 mg, 0.26 mmol), cyclopropanecarbaldehyde (28 mg, 0.40 mmol) and Et$_3$N (1 mL) in dichloroethane (10 mL) was stirred at room temperature for 1 h before NaBH(OAc)$_3$ (84 mg, 0.40 mmol) was added to the mixture. The mixture was stirred for another 1 h and then quenched by addition of saturated aqueous NH$_4$Cl (5 mL). The solution was extracted with dichloromethane (2×20 mL). The combined organic layers were dried (Na$_2$SO$_4$) and concentrated under reduced pressure. The residue was purified by reverse phase HPLC then the enantiomers were separated by supercritical fluid chromatography (SFC) to provide 7.5 mg (11% yield) of 158a and 5.0 mg (9% yield) of 158b.

SFC conditions: CHIRALPAK AS (250×30 mm, 5 μm particle size) at 30% MeOH w/0.1% NH$_4$OH; 60 mL/min, 100 bars, 40° C.

158a: $^1$H NMR (400 MHz, CD$_3$OD) δ 8.86 (s, 1 H), 8.13-8.10 (m, 1 H), 7.87 (d, J=9.2 Hz, 1 H), 7.79 (d, J=9.2 Hz, 1 H), 7.27 (d, J=2.4 Hz, 1 H), 7.18 (dd, J=9.2 Hz, 2.8 Hz, 1 H), 3.94 (s, 3 H), 3.00-2.98 (m, 1 H), 2.82-2.78 (m, 2 H), 2.37-2.27 (m, 3 H), 2.00-1.92 (m, 3 H), 1.76-1.71 (m, 1 H), 0.81-0.78 (m, 1 H), 0.46-0.42 (m, 2 H), 0.09-0.06 (m, 2 H); LCMS m/z 339.8 (M+H); SFC retention time: 7.10 min.

158b: $^1$H NMR (400 MHz, CD$_3$OD) δ 8.70 (s, 1 H), 8.14-8.11 (m, 1 H), 7.88 (d, J=9.2 Hz, 1 H), 7.80 (d, J=9.2 Hz, 1 H), 7.28 (d, J=2.4 Hz, 1 H), 7.19 (dd, J=9.2 Hz, 2.8 Hz, 1 H), 3.94 (s, 3 H), 3.00-2.98 (m, 1 H), 2.82-2.78 (m, 2 H), 2.37-2.27 (m, 3 H), 2.00-1.92 (m, 3 H), 1.76-1.71 (m, 1 H), 0.81-0.78 (m, 1 H), 0.46-0.42 (m, 2 H), 0.09-0.06 (m, 2 H); LCMS m/z 340.2 (M+H); SFC retention time: 6.24 min.

Example 159

6-(1-(cyclopropylmethyl)piperidine-3-carbonyl)-2-naphthonitrile

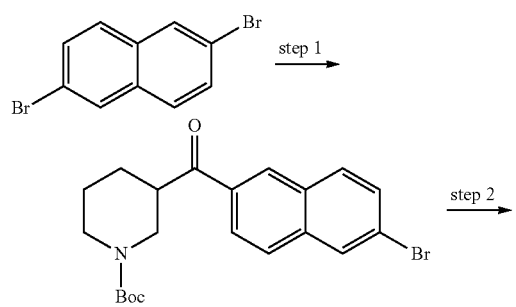

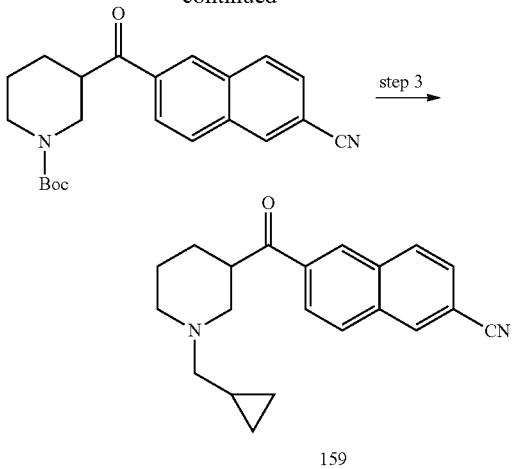

159

Step 1:

tert-butyl 3-(6-bromo-2-naphthoyl)piperidine-1-carboxylate

To a stirred and cooled (−78° C.) solution of 2,6-dibromonaphthalene (2.84 g, 10 mmol) in THF (30 mL) was added n-BuLi (2.5 M in hexane, 4.0 mL, 10.0 mmol). After the addition, stirring at −78° C. was continued for 1 h, and then a solution of tert-butyl 3-(methoxy(methyl)carbamoyl)piperidine-1-carboxylate (Intermediate 10) (3.264 g, 12 mmol) in THF (20 mL) was added dropwise. The resulting mixture was warmed up to room temperature and stirred for additional 2 h. The mixture was quenched by addition of saturated aqueous NH$_4$Cl (50 mL) and extracted with ethyl acetate (3×50 mL). The combined organic layers were washed with brine, dried over Na$_2$SO$_4$ and concentrated under reduced pressure. The residue was purified by silica-gel chromatography (petroleum ether:ethyl acetate=5:1) to give tert-butyl 3-(6-bromo-2-naphthoyl)piperidine-1-carboxylate (3.0 g, 71.9% yield) as a yellow oil.
Step 2:

tert-butyl 3-(6-cyano-2-naphthoyl)piperidine-1-carboxylate

A mixture of tert-butyl 3-(6-bromo-2-naphthoyl)piperidine-1-carboxylate (209 mg, 0.5 mmol), Zn(CN)$_2$ (116 mg, 1.0 mmol), Xant-phos (58 mg, 0.1 mmol), Pd$_2$(dba)$_3$ (46 mg, 0.05 mmol) and Cs$_2$CO$_3$ (650 mg, 2.0 mmol) in dioxane (15.0 mL) was heated at 120° C. for 30 min under microwave conditions. The solvent was evaporated under reduced pressure, and the residue was purified by silica-gel chromatography (petroleum ether:ethyl acetate=5:1) to give tert-butyl 3-(6-cyano-2-naphthoyl) piperidine-1-carboxylate (0.15 g, 82.4% yield).
Step 3:

6-(1-(cyclopropylmethyl)piperidine-3-carbonyl)-2-naphthonitrile

To a solution of tert-butyl 3-(6-cyano-2-naphthoyl)piperidine-1-carboxylate (0.15 g, 0.41 mmol) in ethyl aceate (5.0 mL) was added HCl (2 N in ethyl aceate, 5.0 mL, 10 mmol). The reaction mixture was stirred at 25° C. for 2 h and then concentrated under reduced pressure to give crude 6-(piperidine-3-carbonyl)-2-naphthonitrile hydrochloride (0.12 g, 97.1% yield).

A solution of 6-(piperidine-3-carbonyl)-2-naphthonitrile hydrochloride (0.12 g, 0.4 mmol), cyclopropanecarbaldehyde (56 mg, 0.8 mmol) and Et₃N (1 mL) in dichloroethane (10 mL) was stirred at room temperature for 1 h before NaBH(OAc)₃ (254 mg, 1.2 mmol) was added to the mixture. The mixture was stirred for another 1 h and then quenched by the addition of saturated aqueous NH₄Cl (5 mL). The solution was extracted with dichloromethane (2×20 mL). The combined organic layers were dried (Na₂SO₄) and concentrated under reduced pressure. The residue was purified by preparative HPLC HPLC (Phenomenx Gemini NX, 20-60% ACN in 0.1% NH₄OH (aq)) to give 20.6 mg (15% yield) of the title compound as a white solid.

¹H NMR (400 MHz, CD₃OD) δ 8.76 (s, 1 H), 8.42 (d, J=9.6 Hz, 1 H), 8.26-8.08 (m, 3 H), 7.75 (d, J=7.2 Hz, 1 H), 4.26-4.23 (m, 1 H), 3.85-3.76 (m, 1 H), 3.24-3.20 (m, 2 H), 3.16-3.01 (m, 3 H), 2.28-2.11 (m, 3 H), 1.65-1.59 (m, 1 H), 1.24-1.22 (m, 1 H), 0.81-0.77 (m, 2 H), 0.52-0.46 (m, 2 H); LCMS: m/z 318.9 (M+H).

Examples 160a and 160b 6-(1-(cyclopropylmethyl)-4-methylpiperidine-3-carbonyl)-2-naphthonitrile

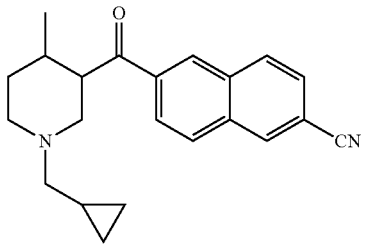

160a/160b

Prepared in an analogous manner to 6-(1-(cyclopropylmethyl)piperidine-3-carbonyl)-2-naphthonitrile (Example 158), replacing tert-butyl 3-(methoxy (methyl)carbamoyl) piperidine-1-carboxylate with tert-butyl 3-(methoxy (methyl) carbamoyl)-4-methylpiperidine-1-carboxylate (Intermediate 10). 160a and 160b correspond to the cis-enantiomers.

SFC conditions: CHIRALPAK AD (250×30 mm, 5 μm particle size) at 25% EtOH w/0.1% NH₄OH; 60 mL/min, 100 bars, 40° C.

160a: ¹H NMR (400 MHz, CD₃OD) δ 8.74 (s, 1 H), 8.47 (s, 1 H), 8.27 (d, 0.1=8.4 Hz, 1 H), 8.18-8.12 (m, 2 H), 7.80 (d, J=8.8 Hz, 1 H), 3.63-3.60 (m, 1 H), 3.31-3.21 (m, 2 H), 2.36 (d, J=6.4 Hz, 1.5 H), 2.20-2.15 (m, 1.5 H), 1.96-1.92 (m, 1 H), 1.87-1.83 (m, 1 H), 1.57-1.54 (m, 1 H), 1.18 (t, J=7.2 Hz, 2 H), 0.91 (d, J=6.4 Hz, 4 H), 0.55-0.51 (m, 2 H), 0.16-0.12 (m, 2 H); LCMS m/z 333.0 (M+H); SFC retention time: 5.84 min.

160b: ¹H NMR (400 MHz, CD₃OD) δ 8.74 (s, 1 H), 8.47 (s, 1 H), 8.27 (d, J=8.8 Hz, 1 H), 8.18-8.12 (m, 2 H), 7.80 (d, J=8.8 Hz, 1 H), 3.63-3.60 (m, 1 H), 3.31-3.21 (m, 2 H), 2.36 (d, J=6.4 Hz, 1.5 H), 2.20-2.15 (m, 1.5 H), 1.96-1.92 (m, 1 H), 1.87-1.83 (m, 1 H), 1.57-1.54 (m, 1 H), 1.17 (t, J=7.2 Hz, 2 H), 0.91 (d, J=6.8 Hz, 4 H), 0.55-0.51 (m, 2 H), 0.16-0.12 (m, 2 H); LCMS m/z 333.2 (M+H); SFC retention time: 6.33 min.

Examples 161a and 161b 6-(1-cyclobutyl-4-methylpiperidine-3-carbonyl)-2-naphthonitrile

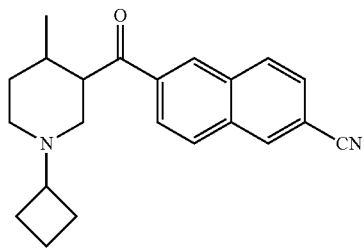

161a/161b

Prepared in an analogous manner to 6-(1-(cyclopropylmethyl)piperidine-3-carbonyl)-2-naphthonitrile (Example 158), replacing tert-butyl 3-(methoxy (methyl)carbamoyl) piperidine-1-carboxylate with tert-butyl 3-(methoxy (methyl) carbamoyl)-4-methylpiperidine-1-carboxylate (Intermediate 10), and cyclopropanecarbaldehyde with cyclobutanone. 161a and 161b correspond to the cis-enantiomers.

SFC conditions: CHIRALPAK OJ (200×30 mm, 5 μm particle size) at 15% EtOH w/0.1% NH₄OH; 50 mL/min, 100 bars, 40° C.

161a: ¹H NMR (400 MHz, CD₃OD) δ 8.74 (s, 1 H), 8.48 (s, 1 FI), 8.28 (d, J=8.4 Hz, 1 H), 8.19-8.13 (m, 2 H), 7.81 (d, J=8.4 Hz, 1 H), 3.62-3.58 (m, 1 H), 3.03-3.00 (m, 2 H), 2.85-2.80 (m, 1 H), 2.12-2.10 (m, 1 H), 1.97-1.91 (m, 7 H), 1.76-1.73 (m, 2 H), 1.54-1.50 (m, 1 H), 0.92 (d, J=6.4 Hz, 3 H); LCMS m/z 332.9 (M+H); SFC retention time: 3.59 min.

161b: ¹H NMR (400 MHz, CD₃OD) δ 8.73 (s, 1 H), 8.48 (s, 1 H), 8.29 (d, J=8.4 Hz, 1 H), 8.18-8.13 (m, 2 H), 7.81 (d, J=8.4 Hz, 1 H), 3.62-3.58 (m, 1 H), 3.03-3.00 (m, 2 H), 2.85-2.80 (m, 1 H), 2.12-2.10 (m, 1 H), 1.97-1.91 (m, 7 H), 1.76-1.73 (m, 2 H), 1.54-1.50 (m, 1 H), 0.92 (d, J=6.4 Hz, 3H); LCMS m/z 332.9 (M+H); SFC retention time: 3.81 min.

Examples 162a and 162b 6-(1-cyclopentyl-4-methylpiperidine-3-carbonyl)-2-naphthonitrile

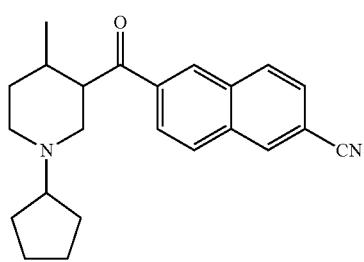

162a/162b

Prepared in an analogous manner to 6-(1-(cyclopropylmethyl)piperidine-3-carbonyl)-2-naphthonitrile (Example 158), replacing tert-butyl 3-(methoxy (methyl)carbamoyl) piperidine-1-carboxylate with tert-butyl 3-(methoxy (methyl) carbamoyl)-4-methylpiperidine-1-carboxylate (Intermediate 10), and cyclopropanecarbaldehyde with cyclopentanone. 162a and 162b correspond to the cis-enantiomers.

SFC conditions: CHIRALPAK AD (250×30 mm, 5 μm particle size) at 30% MeOH w/0.1% NH₄OH; 60 mL/min, 100 bars, 40° C.

162a: ¹H NMR (400 MHz, CD₃OD) δ 8.71 (s, 1 H), 8.45 (s, 1 H), 8.25 (d, J=8.4 Hz, 1 H), 8.14-8.10 (m, 2 H), 7.78 (dd, J=1.6 Hz, 8.4 Hz, 1 H), 3.60-3.58 (m, 1 H), 3.16-3.13 (m, 2 H), 2.64-2.60 (m, 1 H), 2.13-2.07 (m, 2 H), 1.94-1.92 (m, 2 H), 1.84-1.83 (m, 2 H), 1.76-1.74 (m, 2 H), 1.60-1.56 (m, 2 H), 1.50-1.40 (m, 2 H), 1.18-1.14 (m, 1 H), 0.87 (d, J=6.4 Hz, 3 H); LCMS m/z 347.0 (M+H); SFC retention time: 6.15 min.

162b: ¹H NMR (400 MHz, CD₃OD) δ 8.71 (s, 1 H), 8.45 (s, 1 H), 8.25 (d, J=8.4 Hz, 1 H), 8.14-8.10 (m, 2 H), 7.78 (dd, J=1.6 Hz, 8.4 Hz, 1 H), 3.60-3.58 (m, 1 H), 3.16-3.13 (m, 2 H), 2.64-2.60 (m, 1 H), 2.13-2.07 (m, 2 H), 1.94-1.92 (m, 2 H), 1.84-1.83 (m, 2 H), 1.76-1.74v (m, 2 H), 1.60-1.56 (m, 2 H), 1.50-1.40 (m, 2 H), 1.18-1.14 (m, 1 H), 0.87 (d, J=6.4 Hz, 3 H); LCMS m/z 347.0 (M+H); SFC retention time: 6.53 min.

Examples 163a and 163b 6-(4-methyl-1-propylpiperidine-3-carbonyl)-2-naphthonitrile

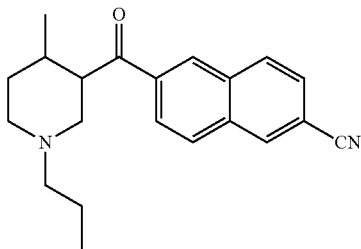

163a/163b

Prepared in an analogous manner to 6-(1-(cyclopropylmethyl)piperidine-3-carbonyl)-2-naphthonitrile (Example 158), replacing tert-butyl 3-(methoxy (methyl)carbamoyl) piperidine-1-carboxylate with tert-butyl 3-(methoxy (methyl) carbamoyl)-4-methylpiperidine-1-carboxylate (Intermediate 10), and cyclopropanecarbaldehyde with propionaldehyde. 163a and 163b correspond to the cis-enantiomers.

SFC conditions: CHIRALPAK AD (250×30 mm, 5 μm particle size) at 20% IPA w/0.1% NH₄OH; 60 mL/min, 100 bars, 40° C.

163a: ¹H NMR (400 MHz, CD₃OD) δ 8.77 (s, 1 H), 8.48 (s, 1 H), 8.29 (d, J=8.4 Hz, 1 H), 8.17-8.13 (m, 2 H), 7.81 (dd, J=1.2 Hz, 8.8 Hz, 1 H), 3.72-3.68 (m, 1 H), 3.16-3.13 (m, 2 H), 2.49-2.45 (m, 2 H), 2.21-2.17 (m, 2 H), 1.98-1.96 (m, 1 H), 1.88-1.85 (m, 1 H), 1.62-1.56 (m, 3 H), 0.96-0.91 (m, 6 H); LCMS m/z 320.9 (M+H); SFC retention time: 5.05 min.

163b: ¹H NMR (400 MHz, CD₃OD) δ 8.76 (s, 1 H), 8.49 (s, 1 H), 8.28 (d, J=8.4 Hz, 1 H), 8.19-8.13 (m, 2 H), 7.81 (dd, J=1.6 Hz, 8.4 Hz, 1 H), 3.69-3.66 (m, 1 H), 3.14-3.11 (m, 2 H), 2.49-2.45 (m, 2 H), 2.21-2.17 (m, 2 H), 1.98-1.96 (m, 1 H), 1.88-1.84 (m, 1 H), 1.60-1.54 (m, 3 H), 0.96-0.91 (m, 6 H); LCMS m/z 320.9 (M+H); SFC retention time: 5.63 min.

Example 164

6-(1-((2-m ethylcyclopropyl)methyl)piperidine-3-carbonyl)-2-naphtho nitrile

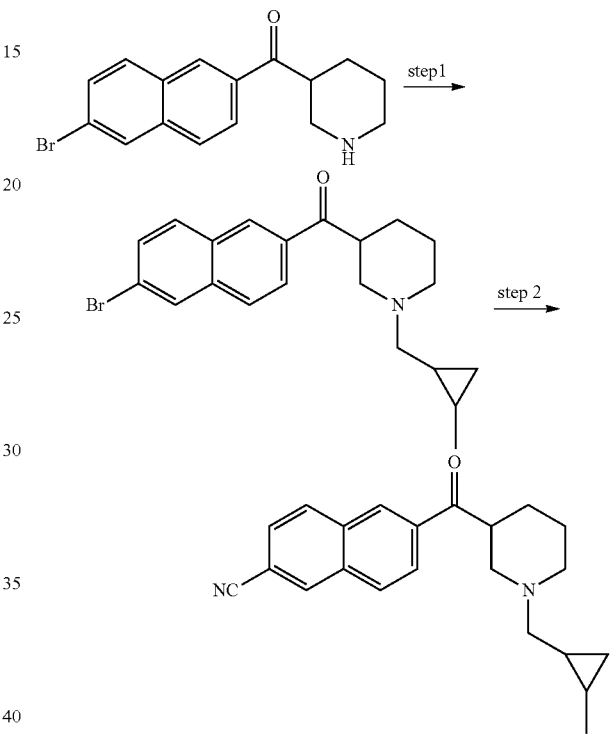

164

Step 1:

(6-bromonaphthalen-2-yl)(1-((2-methylcyclopropyl) methyl)piperidin-3-yl) methanone A solution of (6-bromonaphthalen-2-yl)(piperidin-3-yl) methanone hydrochloride (Examples 23a and 23b) (129 mg, 0.43 mmol), 1-(bromomethyl)-2-methyl cyclopropane (126 mg, 0.85 mmol) and DIPEA (110 mg, 0.85 mmol) in dichloromethane (10 mL) was stirred at room temperature for 3 h. The solvent was evaporated under reduced pressure to give crude (6-bromonaphthalen-2-yl)(1-((2-methylcyclopropyl) methyl)piperidin-3-yl)methanone (100 mg, 61% yield).

Step 2:

6-(1-((2-methylcyclopropyl)methyl)piperidine-3-carbonyl)-2-naphthonitrile

A mixture of (6-bromonaphthalen-2-yl)(1-((2-methylcyclopropyl)methyl)piperidin-3-yl)methanone (100 mg, 0.26 mmol), Zn(CN)₂ (45 mg, 0.388 mmol), Xant-phos (30 mg, 0.052 mmol), Pd₂(dba)₃ (24 mg, 0.026 mmol) and Cs₂CO₃ (169 mg, 0.52 mmol) in dioxane (5.0 mL) was heated at 120° C. for 30 min under microwave conditions. After cooling to room temperature, the mixture was filtered and the filtrate was concentrated under reduced pressure. The residue was purified by reverse phase HPLC (Phenomenx Gemini NX, 20-60% ACN in 0.1% Formic Aid (aq)) to give 20.2 mg (21.2% yield) of example 164.

$^1$H NMR (400 MHz, CD$_3$OD) δ 8.77 (s, 1 H), 8.45 (d, J=7.2 Hz, 1 H), 8.26 (t, J=8.8 Hz, 1 H), 8.18-8.13 (m, 2 H), 7.78 (d, J=7.6 Hz, 1 H), 4.39-4.37 (m, 0.5 H), 4.21-4.17 (m, 0.5 H), 4.09-4.05 (m, 0.5 H), 3.83-3.76 (m, 1.5 H), 3.30-2.98 (m, 3 H), 2.29-2.12 (m, 3 H), 1.82-1.78 (m, 0.5 H), 1.65-1.59 (m, 1.5 H), 1.17-1.09 (m, 3 H), 0.90-0.88 (m, 2 H), 0.65-0.55 (m, 2 H); LCMS: m/z 333.0 (M+H).

Example 165

(1-cyclobutylpiperidin-3-yl)(6-methylnaphthalen-2-yl)methanone hydrochloride

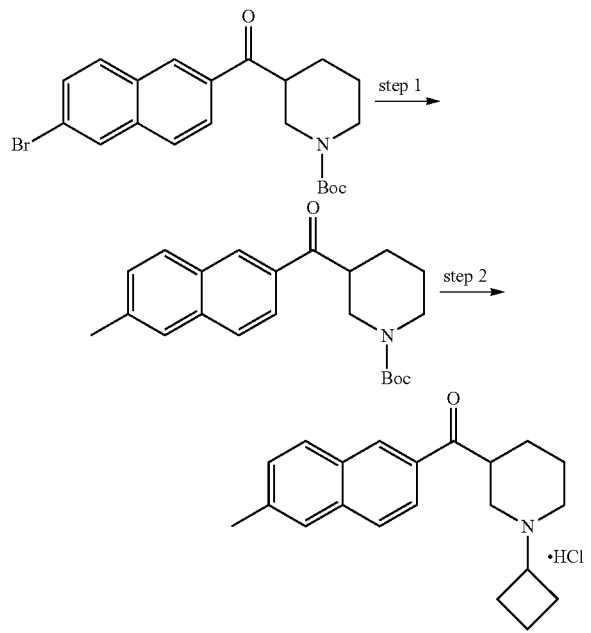

165

Step 1:

tert-butyl 3-(6-methyl-2-naphthoyl)piperidine-1-carboxylate

A mixture of tert-butyl 3-(6-bromo-2-naphthoyl)piperidine-1-carboxylate (Example 51) (450 mg, 1.10 mmol), Pd(PPh$_3$)$_4$ (112 mg, 0.11 mmol), 2,4,6-trimethyl-1,3,5,2,4,6-trioxatriborinane (411 mg, 3.24 mmol) and Cs$_2$CO$_3$ (708 mg, 2.20 mmol) in DMF (10 mL) was heated at 100° C. for 16 h, at which time TLC showed the completion of the reaction. After cooled, the reaction mixture was diluted with water (20 mL) and extracted with dichloromethane (3×30 ml). The combined organic layers were dried (Na$_2$SO$_4$) and concentrated under reduced pressure. The residue was purified by silica-gel chromatography (petroleum ether:ethyl acetate=10:1) to give tert-butyl 3-(6-methyl-2-naphthoyl)piperidine-1-carboxylate (300 mg, 77% yield).

Step 2:

(1-cyclobutylpiperidin-3-yl)(6-methylnaphthalen-2-yl)methanone hydrochloride

To the solution of tert-butyl 3-(6-methyl-2-naphthoyl)piperidine-1-carboxylate (300 mg, 0.85 mmol) in ethyl acetate (20 mL) was added HCl (2 N in ethyl acetate, 15 mL, 30 mmol). The resulting mixture was stirred at ambient temperature for 1 h and then concentrated under reduced pressure to give crude (6-methylnaphthalen-2-yl) (piperidin-3-yl)methanone hydrochloride (244 mg, 99% yield).

A mixture of (6-methylnaphthalen-2-yl)(piperidin-3-yl)methanone hydrochloride (100 mg, 0.35 mmol), cyclobutanone (50 mg, 0.70 mmol) and Et$_3$N (0.5 ml) in dichloromethane (10 mL) was stirred at room temperature for 1 h, then NaBH(OAc)$_3$ (171 mg, 1.04 mmol) was added. The mixture was stirred for another 1 h and then quenched by addition of saturated aqueous NH$_4$Cl (5 mL). The solution was extracted with dichloromethane (3×20 mL). The combined organic layers were dried (Na$_2$SO$_4$) and concentrated under reduced pressure. The residue was purified by preparative HPLC (Phenomenx Gemini NX, 20-60% ACN in 0.1% Formic Acid (aq)) to give 28.0 mg (26.4% yield) of the title compound as a white solid.

$^1$H NMR (400 MHz, CDCl$_3$) δ 12.54 (br. s, 1 H), 8.56 (s, 1 H), 7.97-7.94 (m, 2 H), 7.79 (d, J=8.4 Hz, 1 H), 7.63 (s, 1 H), 7.40 (d, J=7.6 Hz, 1 H), 4.66-4.64 (m, 1 H), 3.60-3.57 (m, 2 H), 3.41-3.25 (m, 1 H), 2.84-2.79 (m, 3 H), 2.63-2.58 (m, 1 H), 2.53 (s, 3 H), 2.43-2.41 (m, 1 H), 2.29-2.26 (m, 3 H), 1.99-1.96 (m, 3 H), 1.79-1.77 (m, 1 H); LCMS m/z 307.8 (M+H).

Example 166

(1-cyclopentylpiperidin-3-yl)(6-methylnaphthalen-2-yl)methanone

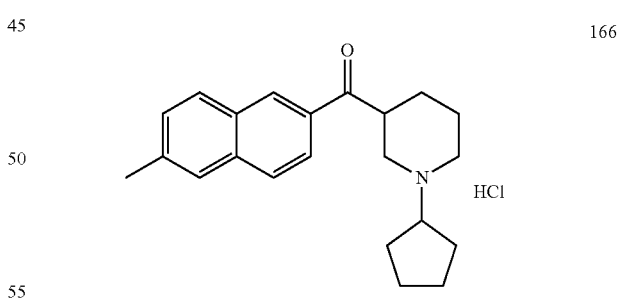

166

Prepared in an analogous manner to (1-cyclobutylpiperidin-3-yl)(6-methyl naphthalen-2-yl)methanone hydrochloride (example 164), replacing cyclobutanone with cyclopentanone.

$^1$H NMR (400 MHz, CDCl$_3$) δ 12.28 (br. s, 1 H), 8.59 (s, 1 H), 7.98-7.96 (m, 2 H), 7.80 (d, J=8.4 Hz, 1 H), 7.63 (s, 1 H), 7.40 (d, J=6.8 Hz, 1 H), 4.79-4.61 (m, 1 H), 3.81-3.65 (m, 2 H), 3.42-3.20 (m, 1 H), 3.05-2.91 (m, 1 H), 2.72-2.58 (m, 2 H), 2.53 (s, 3 H), 2.28-2.14 (m, 5 H), 2.03-1.87 (m, 5 H), 1.63-1.64 (m, 1 H); LCMS m/z 321.8 (M+H).

Example 167

(1-(cyclopropylmethyl)piperidin-3-yl)(6-methyl-naphthalen-2-yl)methanone

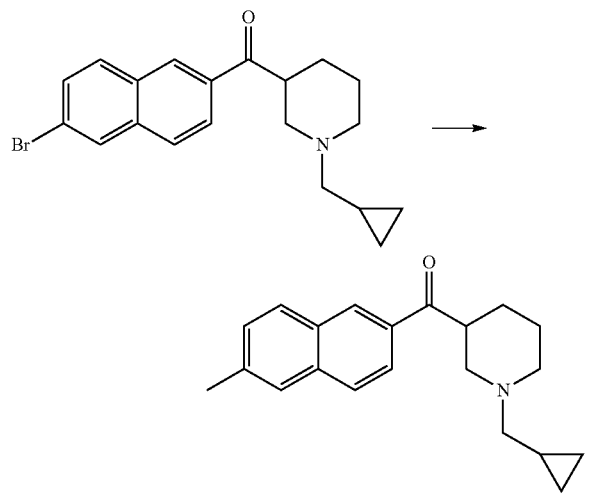

167

A mixture of (6-bromonaphthalen-2-yl)(1-(cyclopropylmethyl)piperidin-3-yl) methanone (100 mg, 0.27 mmol), Pd(PPh$_3$)$_4$ (28 mg, 0.03 mmol), 2,4,6-trimethyl-1,3,5,2,4,6-trioxatriborinane (108 mg, 0.81 mmol) and Cs$_2$CO$_3$ (176 mg, 0.54 mmol) in DMF (10 mL) was heated at 100° C. for 16 h, at which time TLC showed the completion of the reaction. After cooling to room temperature, the reaction mixture was diluted with water (20 mL) and extracted with dichloromethane (3×30 ml). The combined organic layers were dried (Na$_2$SO$_4$) and concentrated under reduced pressure. The residue was purified by preparative HPLC HPLC (Phenomenx Gemini NX, 20-60% ACN in 0.1% NH$_4$OH (aq)) to afford the title compound (19.0 mg, 22.9% yield) as a white solid.

$^1$H NMR (400 MHz, CDCl$_3$) δ 8.47 (s, 1 H), 7.99 (dd, J=8.4 Hz, 1.6 Hz, 1 H), 7.85 (d, J=8.4 Hz, 1 H), 7.80 (d, 8.4 Hz, 1 H), 7.64 (s, 1 H), 7.39 (d, J=8.4 Hz, 1 H), 3.81-3.79 (m, 1 H), 3.28-3.25 (m, 1 H), 3.16-3.13 (m, 1 H), 2.54 (s, 3 H), 2.36-2.22 (m, 3 H), 2.02-1.95 (m, 2 H), 1.85-1.82 (m, 2 H), 1.56-1.45 (m, 1 H), 0.89-0.87 (m, 1 H), 0.52-0.48 (m, 2 H), 0.11-0.98 (m, 2 H); LCMS m/z 308 (M+H).

Example 168

(1-(cyclopropylmethyl)piperidin-3-yl)(6-(pyridin-2-yl)naphthalen-2-yl)methanone

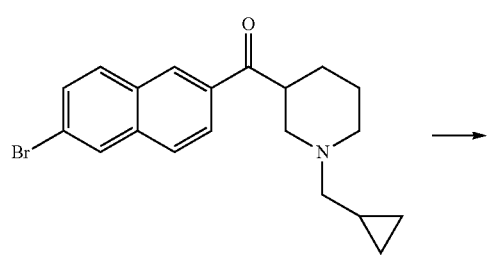

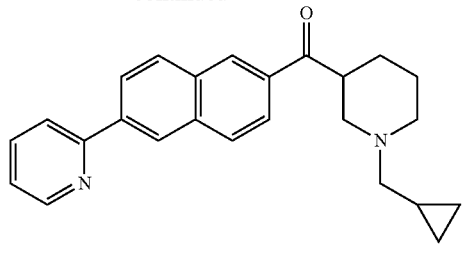

168

Prepared in an analogous manner to (1-(cyclopropylmethyl)piperidin-3-yl)(6-methyl naphthalen-2-yl)methanone (Example 167), replacing 2,4,6-trimethyl-1,3,5,2,4,6-trioxatriborinane with 2-pyridyl boronic acid.

$^1$H NMR (400 MHz, CD$_3$OD) δ 8.96 (d, J=6.0 Hz, 1 H), 8.90-8.88 (m, 1 H), 8.79-8.77 (m, 1 H), 8.67-8.65 (m, 1 H), 8.62-8.60 (m, 1 H), 8.46-8.42 (m, 1 H), 8.24-8.13 (m, 4 H), 4.44-4.32 (m, 1 H), 3.88-3.79 (m, 2 H), 3.17-3.15 (m, 2 H), 3.04-3.00 (m, 1 H) 2.31-2.14 (m, 3 H), 1.80-1.60 (m, 2 H), 1.27-1.23 (m, 1 H), 0.82-0.78 (m, 2 H), 0.54-0.51 (m, 2 H); LCMS m/z 370.9 (M+H).

Example 169

(1-(cyclopropylmethyl)piperidin-3-yl)(6-(methylsulfonyl)naphthalen-2-yl)methanone

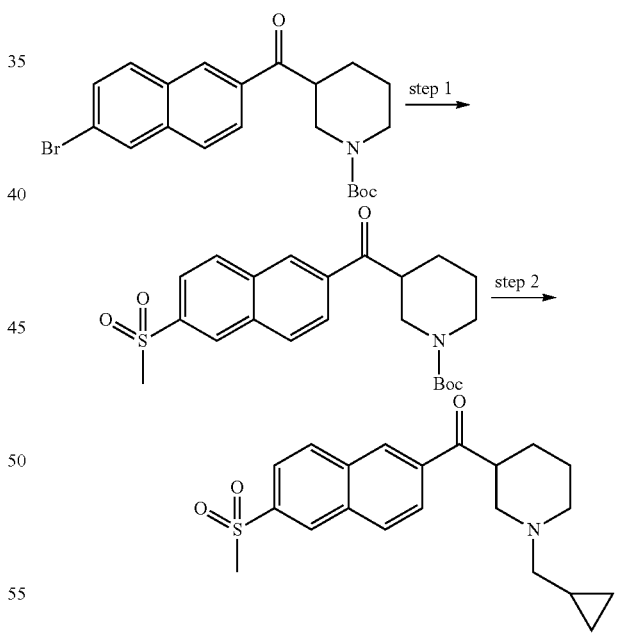

169

Step 1:

tert-butyl 3-(6-(methylsulfonyl)-2-naphthoyl)piperidine-1-carboxylate

A mixture of tert-butyl 3-(6-bromo-2-naphthoyl)piperidine-1-carboxylate (Example 51) (800 mg, 1.92 mmol), NaSO$_2$Me (391 mg, 3.84 mmol), S-proline (350 mg, 1.92 mmol) and CuI (733 mg, 3.84 mmol) in DMSO (30 ml) was heated at 110° C. for 8 h. After cooling to room temperature, the reaction mixture was diluted with water (30 mL) and extracted with dichloromethane (3×50 ml). The combined organic layers were dried (Na₂SO₄) and concentrated under reduced pressure. The residue was purified by silica-gel chromatography (petroleum ether:ethyl acetate=10:1) to give tert-butyl 3-(6-(methylsulfonyl)-2-naphthoyl) piperidine-1-carboxylate (700 mg, 87.5% yield).

Step 2:

(1-(cyclopropylmethyl)piperidin-3-yl)(6-(methylsulfonyl)naphthalen-2-yl)methanone To a solution of tert-butyl 3-(6-(methylsulfonyl)-2-naphthoyl)piperidine-1-carboxylate (209 mg, 0.5 mmol) in ethyl acetate (5 mL) was added HCl (2 N in ethyl acetate, 5 mL, 10 mmol). The mixture was stirred at ambient temperature for 1 h and then evaporated under reduced pressure to give crude (6-(methylsulfonyl) naphthalene-2-yl)(piperidin-3-yl)methanone hydrochloride (177 mg, 99% yield).

A solution of (6-(methylsulfonyl)naphthalen-2-yl)(piperidin-3-yl)methanone hydrochloride (177 mg, 0.5 mmol), cyclopropanecarbaldehyde (70 mg, 1.0 mmol) and Et₃N (2 mL) in dichloromethane (10 mL) was stirred at room temperature for 1 h before NaBH(OAc)₃ (212 mg, 1.0 mmol) was added. The mixture was stirred for another 1 h and then quenched by the addition of saturated aqueous NH₄Cl (5 mL). The solution was extracted with dichloromethane (3×20 mL). The combined organic layers were dried (Na₂SO₄) and concentrated under reduced pressure. The residue was purified by reverse phase HPLC (Phenomenx Gemini NX, 20-60% AGN in 0.1% NH₄OH (aq)) to provide 39.8 mg (41% yield) of the title compound.

¹H NMR (400 MHz, CD₃OD) δ 8.79 (s, 1 H), 8.60 (d, J=4.8 Hz, 1 H), 8.32 (t, J=9.2 Hz, 1 H), 8.22-8.16 (m, 2 H), 8.05-8.03 (m, 1 H), 4.38-4.32 (m, 0.5 H), 4.21-4.10 (m, 1 H), 3.86-3.75 (m, 1.5 H), 3.49-3.43 (m, 0.5 H), 3.25 (s, 3 H), 3.15-3.12 (m, 2 H), 3.01-2.96 (m, 1 H), 2.26-2.12 (m, 3 H), 1.86-1.81 (m, 0.5 H), 1.71-1.50 (m, 1 H), 1.23-1.21 (m, 1 H), 0.81-0.77 (m, 2 H), 0.51-0.48 (m, 2 H); LCMS m/z 371.8 (M+H).

Example 170

(1-cyclobutylpiperidin-3-yl)(6-(methylsulfonyl)naphthalen-2-yl)methanone

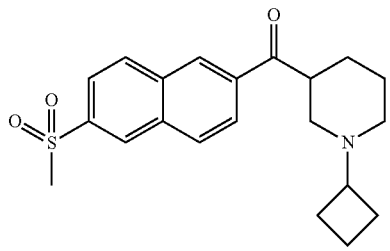

170

Prepared in an analogous manner to (1-(cyclopropylmethyl)piperidin-3-yl) (6-(methylsulfonyl)naphthalen-2-yl) methanone (Example 169), replacing cyclopropanecarbaldehyde with cyclobutanone.

¹H NMR (400 MHz, CD₃OD) δ 8.77 (s, 1 H), 8.62 (d, J=4.4 Hz, 1 H), 8.34 (d, J=8.8 Hz, 1H), 8.22-8.15 (m, 2 H), 8.06-8.05 (m, 1 H), 4.38-4.35 (m, 0.5 H), 4.14-4.08 (m, 1 H), 3.82-3.51 (m, 3 H), 3.38-3.35 (m, 0.5 H), 3.22 (s, 3 H), 3.14-3.06 (m, 1 H), 2.89-2.72 (m, 1H), 2.37-2.25 (m, 5 H), 2.12-2.08 (m, 2 H), 1.94-1.87 (m, 2 H), 1.59-1.55 (m, 1 H); LCMS m/z 371.9 (M+H).

Example 171

(1-cyclopentylpiperidin-3-yl)(6-(methylsulfonyl)naphthalen-2-yl)methanone

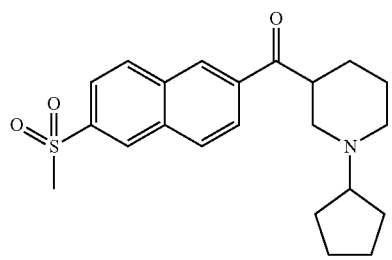

171

Prepared in an analogous manner to (1-(cyclopropylmethyl)piperidin-3-yl) (6-(methylsulfonyl)naphthalen-2-yl) methanone (Example 169), replacing cyclopropanecarbaldehyde with cyclopentanone.

¹H NMR (400 MHz, CD₃OD) δ 8.78 (s, 1 H), 8.61 (s, 1 H), 8.35-8.33 (m, 1 H), 8.23-8.17 (m, 2 H), 8.05 (d, J=8.4 Hz, 1 H), 4.33-4.30 (m, 0.5 H), 4.17-4.11 (m, 1 H), 3.80-3.68 (m, 3 H), 3.64-3.62 (m, 0.5 H), 3.22 (s, 3 H), 2.99-2.95 (m, 1 H), 2.25-2.11 (m, 5 H), 1.85-1.79 (m, 4 H), 1.70-1.53 (m, 3 H); LCMS m/z 385.9 (M+H).

Example 172

(1-(cyclopropylmethyl)piperidin-3-yl)(6-(dimethylamino)naphthalen-2-yl)methanone hydrochloride

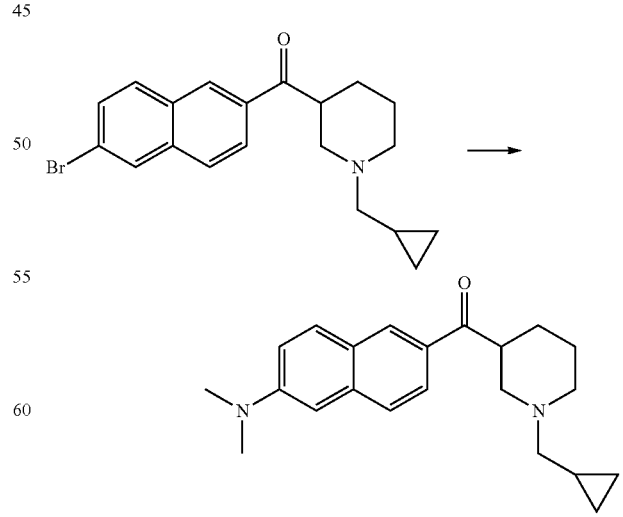

A mixture of (6-bromonaphthalen-2-yl)(1-(cyclopropylmethyl)piperidin-3-yl) methasone (50 mg, 0.13 mmol), dimethylamine hydrochloride (32 mg, 0.39 mmol), Xant-phos (6 mg, 0.01 mmol), Pd₂(dba)₃ (18 mg, 0.02 mmol) and Cs₂CO₃ (127 mg, 0.39 mmol) in dioxane (5.0 mL) was heated at 120° C. for 30 min under microwave conditions. The solvent was evaporated under reduced pressure, and the residue was purified by preparative HPLC (Phenomenx Gemini NX, 20-60% ACN in 0.1% Formic Acid (aq)) to give 2.4 mg (4.8% yield) of the title compound as a white solid.

¹H NMR (400 MHz, CD₃OD) δ 8.65 (d, J=9.2 Hz, 1 H), 8.20-7.96 (m, 3 H), 7.64-7.57 (m, 2 H), 4.34-4.32 (m, 1 H), 4.13-4.09 (m, 1 H), 3.79-3.76 (m, 1 H), 3.31 (s, 6 H), 3.30-3.28 (m, 1 H), 3.14-3.01 (m, 3 H), 2.26-2.14 (m, 2 H), 1.97-1.95 (m, 1 H), 1.75-1.65 (m, 1 H), 1.29-1.21 (m, 1 H), 0.81-0.79 (m, 2 H), 0.60-0.49 (m, 2 H); LCMS m/z 336.9 (M+H).

Example 173

(1-(cyclopropylmethyl)piperidin-3-yl)(3-methyl-benzo[d]isoxazol-6-yl)methanone

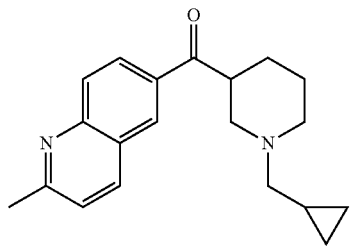

173

Prepared in an analogous manner to (1-(cyclopropylmethyl)piperidin-3-yl) (3-methoxyphenyl)methanone (Examples 109a and 109b), replacing 1-bromo-3-methoxybenzene with 6-bromo-2-methylquinoline.

¹H NMR (400 MHz, CD₃OD) δ 8.63 (s, 1 H), 8.43 (d, J=8.8 Hz, 1 H), 8.25 (dd, J=8.8 Hz, 1.6 Hz, 1 H), 8.03 (d, J=8.8 Hz, 1 H), 7.54 (d, J=8.8 Hz, 1 H), 3.85-3.82 (m, 1 H), 3.35-3.24 (m, 1 H), 3.20-3.17 (m, 1 H), 2.76 (s, 3 H), 2.37-2.36 (m, 2 H), 2.29-2.27 (m, 1 H), 2.06-2.03 (m, 2 H), 1.88-1.85 (m, 2 H), 1.50-1.49 (m, 1 H), 0.94-0.91 (m, 1 H), 0.56-0.53 (m, 2 H), 0.17-0.16 (m, 2 H); LCMS m/z 309.2 (M+H).

Example 174

(1-(cyclopropylmethyl)piperidin-3-yl)(6-(pyridin-2-yl)naphthalen-2-yl)methanone

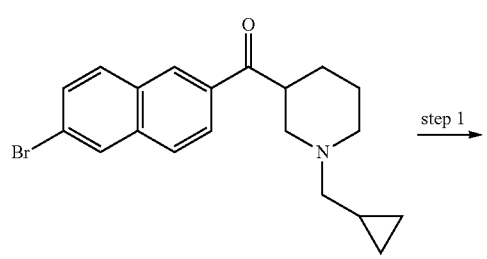

step 1 →

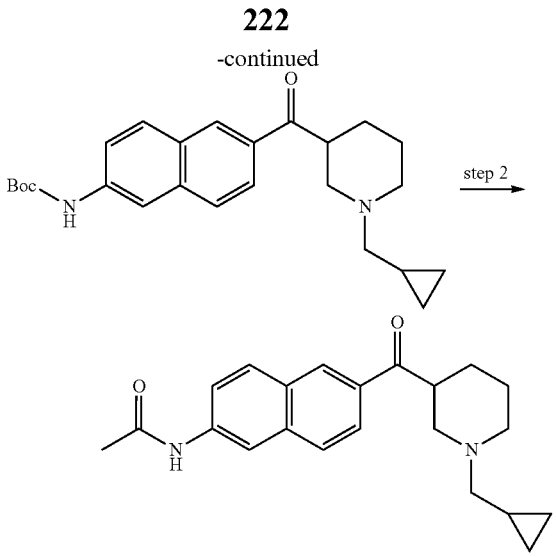

174

Step 1:

tert-butyl (6-(1-(cyclopropylmethyl)piperidine-3-carbonyl)naphthalen-2-yl) carbamate A mixture of (6-bromonaphthalen-2-yl)(1-(cyclopropylmethyl)piperidin-3-yl) methanone (200 mg, 0.54 mmol), tert-butyl carbamate (126 mg, 1.08 mmol), Xant-phos (69.5 mg, 0.12 mmol), Pd₂(dba)₃ (55 mg, 0.06 mmol) and Cs₂CO₃ (352 mg, 1.08 mmol) in dioxane (5.0 mL) was heated at 120° C. for 30 min under microwave conditions. The solvent was evaporated under reduced pressure, and the residue was purified by silica-gel chromatography (petroleum ether: ethyl acetate=2:1) to give tert-butyl (6-(1-(cyclopropylmethyl) piperidine-3-carbonyl)naphthalene-2-yl) carbamate (150 mg, 68.2% yield).

Step 2:

(6-aminonaphthalen-2-yl)(1-(cyclopropylmethyl) piperidin-3-yl)methanone hydrochloride To a solution of tert-butyl (6-(1-(cyclopropylmethyl)piperidine-3-carbonyl) naphthalen-2-yl)carbamate (150 mg, 0.37 mmol) in ethyl acetate (5 mL) was added HCl (2 N in ethyl acetate, 5.0 mL, 10.0 mmol). The resulting mixture was stirred at ambient temperature for 2 h. The solvent was evaporated under reduced pressure to give the crude (6-aminonaphthalen-2-yl)(1-(cyclopropylmethyl)piperidin-3-yl) methanone hydrochloride (126 mg, 100% yield) as a white solid.

To a solution of (6-aminonaphthalen-2-yl)(1-(cyclopropylmethyl)piperidin-3-yl) methanone hydrochloride (60 mg, 0.17 mmol) and Et₃N (52 mg, 0.51 mmol) in THF (5 mL) was added acetic anhydride (35 mg, 0.34 mmol). After the addition, the reaction mixture was stirred at ambient temperature for 3 h and then evaporated under reduced pressure. The residue was purified by preparative HPLC (Phenomenx Gemini NX, 20-60% ACN in 0.1% Formic Acid (aq)) to give 4.9 mg (7.3% yield) of the title compound as a white solid.

¹H NMR (400 MHz, CD₃OD) δ 8.60 (d, J=11.6 Hz, 1 H), 8.35 (d, J=11.2 Hz, 1 H), 8.05-8.02 (m, 2 H), 7.98-7.90 (m, 1 H), 7.68 (d, J=8.8 Hz, 1 H), 4.13-4.10 (m, 1 H), 3.82-3.79 (m, 1 H), 3.14-3.06 (m, 3 H), 2.30-2.13 (m, 6 H), 1.90-1.60

(m, 2 H), 1.30-1.20 (m, 2 H), 0.82-0.78 (m, 2 H), 0.50-0.48 (m, 2 H); LCMS m/z 350.9 (M+H).

Example 175

(1-(cyclopropylmethyl)piperidin-3-yl)(6-(pyridin-2-yl)naphthalen-2-yl)methanone

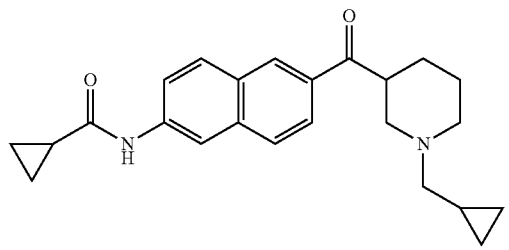

175

Prepared in an analogous manner to N-(6-(1-(cyclopropylmethyl)piperidine-3-carbonyl)naphthalen-2-yl)acetamide (Example 174), replacing acetic anhydride with cyclopropanecarbonyl chloride.

$^1$H NMR (400 MHz, CD$_3$OD) δ 8.57 (d, J=15.6 Hz, 1 H), 8.31 (d, 7.6 Hz, 1 H), 8.03-7.96 (m, 2 H), 7.88 (d, J=5.2 Hz, 1 H), 7.69 (d, 8.8 Hz, 1 H), 4.11-4.08 (m, 1 H), 3.77-3.74 (m, 1 H), 3.13-2.99 (m, 3 H), 2.17-2.10 (m, 3 H), 1.84-1.55 (m, 3 H), 1.28-1.16 (m, 2 H), 1.00-0.99 (m, 2 H), 0.92-0.90 (m, 2 H), 0.80-0.79 (m, 2 H), 0.47-0.46 (m, 2 H); LCMS m/z 377.0 (M+H).

Example 176

6-(1-(cyclopropylmethyl)piperidine-3-carbonyl)-NA-dimethyl-2-naphthamide

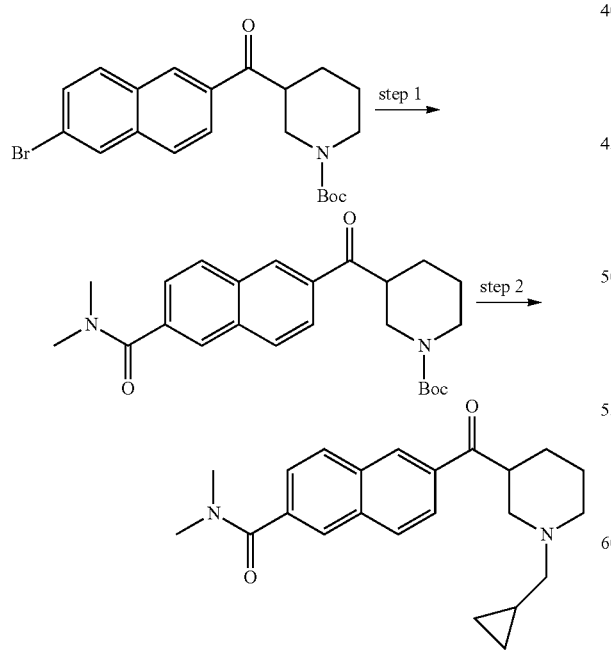

176

Step 1:

tert-butyl 3-(6-(dimethylcarbamoyl)-2-naphthoyl)piperidine-1-carboxylate

A mixture of tert-butyl 3-(6-bromo-2-naphthoyl)piperidine-1-carboxylate (300 mg, 0.72 mmol), Pd(OAc)$_2$ (73 mg, 0.07 mmol), dimethylamine hydrochloride (116.6 mg, 1.44 mmol), Na$_2$CO$_3$ (153 mg, 1.44 mmol) and Xantphos (70 mg, 0.14 mmol) in toluene (30 mL) was heated at 80° C. for 16 h under a CO atmosphere. After cooling to room temperature, the reaction mixture was diluted with water (30 mL) and extracted with dichloromethane (3×30 mL). The combined organic layers were dried (Na$_2$SO$_4$) and concentrated under reduced pressure. The residue was purified by silicagel chromatography (petroleum ether:ethyl acetate=10:1) to give tert-butyl 3-(6-(dimethylcarbamoyl)-2-naphthoyl)piperidine-1-carboxylate (260 mg, 87.7% yield).

Step 2:

6-(1-(cyclopropylmethyl)piperidine-3-carbonyl)-N,N-dimethyl-2-naphthamide

To a solution of tert-butyl 3-(6-(dimethylcarbamoyl)-2-naphthoyl)piperidine-1-carboxylate (205 mg, 0.5 mmol) in ethyl acetate (5 mL) was added HCl (2 N in ethyl acetate, 5 mL, 10 mmol).

The resulting mixture was stirred at ambient temperature for 1 h and then concentrated under reduced pressure to give crude N,N-dimethyl-6-(piperidine-3-carbonyl)-2-naphthamide hydrochloride (173 mg, 99% yield).

A solution of N,N-dimethyl-6-(piperidine-3-carbonyl)-2-naphthamide hydrochloride (173 mg, 0.5 mmol), cyclopropanecarbaldehyde (70 mg, 1.0 mmol) and Et$_3$N (2 mL) in dichloromethane (10 mL) was stirred at room temperature for 1 h before NaBH(OAc)$_3$ (212 mg, 1.0 mmol) was added. The mixture was stirred for another 1 h and then quenched by the addition of saturated aqueous NH$_4$Cl (5 mL). The solution was extracted with dichloromethane (3×20 mL). The combined organic layers were dried (Na$_2$SO$_4$) and concentrated under reduced pressure. The residue was purified by reverse phase HPLC (Phenomenx Gemini NX, 20-60% ACN in 0.1% NH$_4$OH (aq)) to give 9.8 mg (12% yield) of the title compound.

$^1$H NMR (400 MHz, CD$_3$OD) δ 8.72 (s, 1 H), 8.20 (d, J=8.4 Hz, 1 H), 8.17-8.10 (m, 2 H), 8.03 (s, 1 H), 7.63 (d, J=8.4 Hz, 1 H), 4.37-4.31 (m, 0.5 H), 4.17-4.09 (m, 1 H), 3.83-3.75 (m, 1 H), 3.48-3.39 (m, 0.5 H), 3.16 (s, 3 H), 3.13-3.07 (m, 2 H), 3.04 (s, 3 H), 2.26-2.12 (m, 3 H), 1.82-1.51 (m, 2 H), 1.23-1.18 (m, 1 H), 0.82-0.77 (m, 2 H), 0.51-0.47 (m, 2 H); LCMS m/z 364.9 (M+H).

Example 177

6-(1-cyclobutylpiperidine-3-carbonyl)-N,N-dimethyl-2-naphthamide

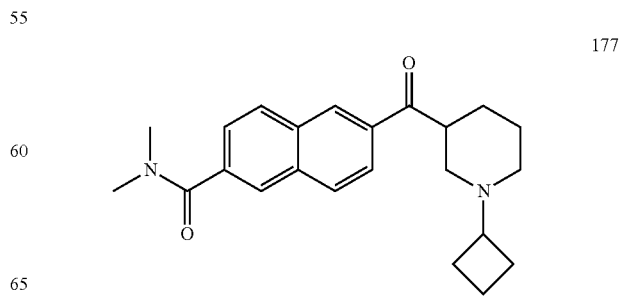

177

225

Prepared in an analogous manner to 6-(1-(cyclopropylmethyl)piperidine-3-carbonyl)-N,N-dimethyl-2-naphthamide (Example 176), replacing cyclopropanecarbaldehyde with cyclobutanone.

¹H NMR (400 MHz, CD₃OD) δ 8.70 (s, 1 H), 8.19 (d, J=8.4 Hz, 1 H), 8.07-8.02 (m, 3 H), 7.62 (d, J=8.4 Hz, 1 H), 4.12-4.06 (m, 1 H), 3.81-3.49 (m, 3 H), 3.40-3.37 (m, 1 H), 3.16 (s, 3 H), 3.04 (s, 3 H), 2.84-2.77 (m, 1 H), 2.37-2.27 (m, 5 H), 2.23-2.05 (m, 2 H), 1.92-1.87 (m, 2 H), 1.59-1.55 (m, 1 H); LCMS m/z 364.9 (M+H).

Example 178

6-(1-cyclobutylpiperidine-3-carbonyl)-N,N-dimethyl-2-naphthamide

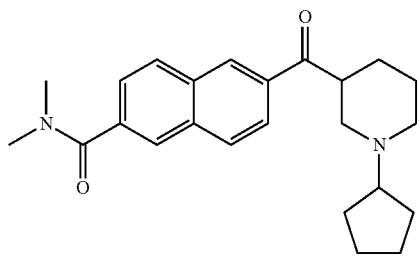

Prepared in an analogous manner to 6-(1-(cyclopropylmethyl)piperidine-3-carbonyl)-N,N-dimethyl-2-naphthamide (Example 176), replacing cyclopropanecarbaldehyde with cyclopentanone.

¹H NMR (400 MHz, CD₃OD) δ 8.71 (s, 1 H), 8.18 (t, J=8.8 Hz, 1 H), 8.10-8.02 (m, 3 H), 7.62 (d, J=8.4 Hz, 1 H), 4.32-4.16 (m, 1 H), 3.88-3.68 (m, 3 H), 3.63-3.60 (m, 0.5 H), 3.26 (s, 3 H), 3.04 (s, 3 H), 3.01-2.93 (m, 0.5 H), 2.28-2.15 (m, 5 H), 1.98-1.75 (m, 5 H), 1.69-1.50 (m, 3 H); LCMS m/z 378.9 (M+H).

Examples 179a and 179b 2-(6-(1-cyclobutylpiperidine-3-carbonyl)-2-methoxynaphthalen-1-yl)acetonitrile

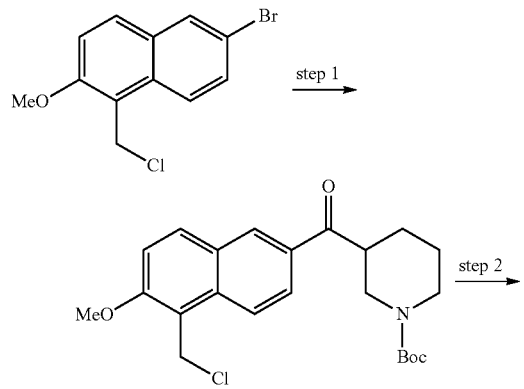

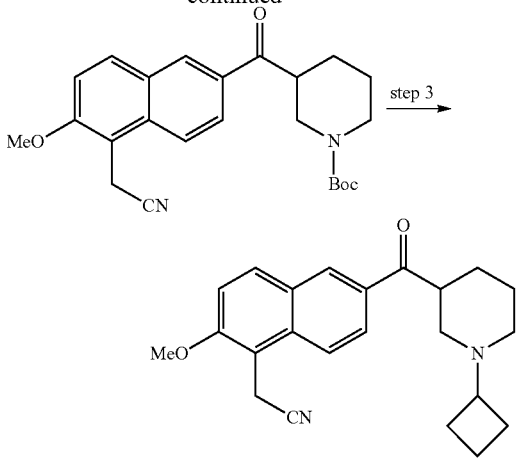

Step 1:

tert-butyl 3-(5-(chloromethyl)-6-methoxy-2-naphthoyl) piperidine-1-carboxylate

To a stirred and cooled (−78° C.) solution of 6-bromo-1-(chloromethyl)-2-methoxy naphthalene (1.5 g, 5.3 mmol) in tetrahydrofuran (50 mL) was added n-BuLi (2.5 M in hexane, 2.6 mL, 6.4 mmol). After the addition, stirring at −78° C. was continued for 1 h, and then a solution of tert-butyl 3-(methoxy(methyl)carbamoyl)piperidine-1-carboxylate (Intermediate 19) (1.4 g, 5.3 mmol) in THF (5 mL) was added dropwise. The resulting mixture was warmed to room temperature and stirred for additional 2 h. The mixture was quenched by the addition of saturated aqueous NH₄Cl (30 mL) and extracted with ethyl acetate (3×50 mL). The combined organic layers were washed with brine, dried over Na₂SO₄ and concentrated under reduced pressure. The residue was purified by silica-gel chromatography (petroleum ether:ethyl acetate=5:1) to give tert-butyl 3-(5-(chloromethyl)-6-methoxy-2-naphthoyl)piperidine-1-carboxylate (1.0 g, 45%) as a yellow solid.

Step 2:

tert-butyl 3-(5-(cyanomethyl)-6-methoxy-2-naphthoyl)piperidine-1-carboxylate

To a solution of tert-butyl 3-(5-(chloromethyl)-6-methoxy-2-naphthoyl)piperidine-1-carboxylate (1.0 g, 2.4 mmol) in acetonitrile (20 mL) was added TMSCN (0.29 g, 2.9 mmol) and Me₄NF (0.27 g, 2.9 mmol). The reaction mixture was stirred at room temperature for 18 h. The reaction was diluted with water (50 mL) and extracted with dichloromethane (3×50 mL). The combined organic layers were washed with brine (50 mL), dried (Na₂SO₄) and concentrated under reduced pressure. The crude was purified by silica-gel chromatography (petroleum ether:ethyl acetate=2:1) to give tert-butyl 3-(5-(cyanomethyl)-6-methoxy-2-naphthoyl)piperidine-1-carboxylate (0.5 g, 51%) as a yellow solid.

Step 3:

2-(2-methoxy-6-(piperidine-3-carbonyl)naphthalen-1-yl)acetonitrile 2,2,2-trifluoroacetate To a stirred and cooled (0° C.) solution of tert-butyl 3-(5-(cyanomethyl)-6-methoxy-2-naphthoyl)piperidine-1- carboxylate (500 mg, 1.2 mmol) in dichloromethane (10 mL) was added trifluoroacetic acid (2 mL). The resulting mixture was stirred at ambient temperature for 2 h and then evaporated under reduced pressure to give crude 2-(2-methoxy-6-(piperidine-3-carbonyl)naphthalen-1-yl)acetonitrile 2,2,2-trifluoroacetate (496 mg, 100%).

A solution of 2-(2-methoxy-6-(piperidine-3-carbonyl)naphthalen-1-yl)acetonitrile 2,2,2-trifluoroacetate (496 mg, 1.2 mmol), cyclobutanone (85 mg, 1.2 mmol) and Et$_3$N (2 mL) in dichloromethane (10 mL) was stirred at room temperature for 1 h before NaBH(OAc)$_3$ (254 mg, 1.2 mmol) was added. The mixture was stirred for another 1 h and then quenched by the addition of saturated aqueous NH$_4$Cl (10 mL). The solution was extracted with dichloromethane (3×20 mL). The combined organic layers were dried (Na$_2$SO$_4$) and concentrated under reduced pressure. The residue was purified by reverse phase HPLC (Phenomenx Gemini NX, 20-60% ACN in 0.1% NH$_4$OH (aq)) to afford a racemic mixture of 179a and 179b. The enantiomers were separated by supercritical fluid chromatography (SFC) to provide 88.3 mg of 179a (41% yield) and 64.6 mg (38% yield) of 179b.

SFC conditions: CHIRALPAK AD (250×30 mm, 10 μm particle size) at 35% MeOH w/0.1% NH$_4$OH; 80 mL/min, 100 bars, 40° C.

179a: $^1$H NMR (400 MHz, CDCl$_3$) δ 8.43 (s, 1 H), 8.05 (d, J=8.8 Hz, 1 H), 7.93 (d, J=9.2 Hz, 1 H), 7.86 (d, J=9.2 Hz, 1 H), 7.30 (d, J=8.8 Hz, 1 H), 4.05 (s, 2 H), 3.98 (s, 3 H), 3.04-2.73 (m, 2 H), 1.99-1.36 (m, 14 H); LCMS m/z 363.1 (M+H); SFC retention time: 7.72 min.

179b: $^1$H NMR (400 MHz, CDCl$_3$) δ 8.47 (s, 1 H), 8.09 (d, J=8.4 Hz, 1 H), 7.98 (d, J=9.2 Hz, 1 H), 7.91 (d, J=9.2 Hz, 1 H), 7.35 (d, J=9.2 Hz, 1 H), 4.10 (s, 2 H), 4.03 (s, 3H), 3.71-3.68 (m, 1 H), 3.08-3.05 (m, 1 H), 2.96-2.94 (m, 1 H), 2.79-2.75 (m, 1 H), 2.01-1.49 (m, 12 H); LCMS m/z 363.1 (M+H); SFC retention time: 9.46 min.

Example 180

2-(2-methoxy-6-(1-propylpiperidine-3-carbonyl)naphthalen-1-yl)acetonitrile

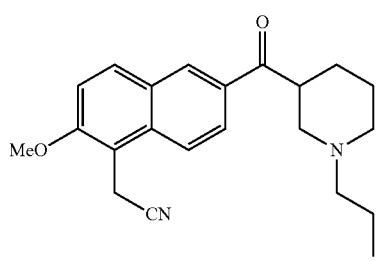

180

Prepared in an analogous manner to 2-(6-(1-cyclobutylpiperidine-3-carbonyl)-2-methoxynaphthalen-1-yl)acetonitrile (Examples 179a and 179b), replacing cyclobutanone with propionaldehyde.

$^1$H NMR (400 MHz, CDCl$_3$) δ 8.48 (s, 1 H), 8.11 (d, J=8.8 Hz, 1 H), 8.03-7.88 (m, 2 H), 7.35 (d, J=8.4 Hz, 1 H), 4.11 (s, 2 H), 4.04 (s, 3 H), 3.73-3.71 (m, 1 H), 3.17-2.93 (m, 2 H), 2.36-2.34 (m, 2 H), 2.20-2.14 (m, 1 H), 2.02-2.98 (m, 2 H), 1.85-1.70 (m, 2 H), 1.65-1.45 (m, 3 H), 0.89 (s, 3 H); LCMS m/z 350.9 (M+H).

Examples 181a and 181b 2-(2-methoxy-6-(4-methyl-1-propylpiperidine-3-carbonyl)naphthalen-1-yl)acetonitrile

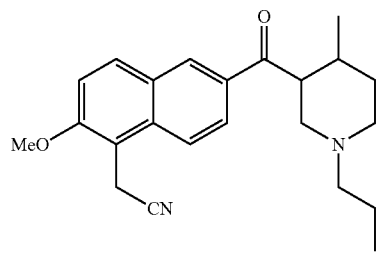

181a/181b

Prepared in an analogous manner to 2-(6-(1-cyclobutylpiperidine-3-carbonyl)-2-methoxynaphthalen-1-yl)acetonitrile (Examples 180a and 180b), replacing tert-butyl 3-(methoxy(methyl)carbamoyl)piperidine-1-carboxylate (Intermediate 19) with tert-butyl 3-(methoxy(methyl)carbamoyl)-4-methylpiperidine-1-carboxylate (Intermediate 10), and cyclobutanone with propionaldehyde. 181a and 181b correspond to the cis-enantiomers.

SFC conditions: CHIRALPAK AD (250×30 mm, 20 μm particle size) at 40% MeOH w/0.1% NH$_4$OH; 80 mL/min, 100 bars, 40° C.

181a: $^1$H NMR (400 MHz, CD$_3$OD) δ 8.71 (s, 1 H), 8.22 (d, J=9.2 Hz, 1 H), 8.13-8.10 (m, 2 H), 7.62 (d, J=9.2 Hz, 1 H), 4.61 (s, 1 H), 4.39-4.37 (m, 1 H), 4.28 (s, 2 H), 4.12 (s, 3 H), 3.51-3.35 (m, 2 H), 3.22-3.16 (m, 2 H), 2.61-2.48 (m, 1 H), 1.88-1.86 (m, 3 H), 1.55-1.31 (m, 2 H), 1.07 (t, J=7.6 Hz, 3 H), 0.90 (d, J=6.8 Hz, 3 H); LCMS m/z 365.2 (M+H); SFC retention time: 8.76 min.

181b: $^1$H NMR (400 MHz, CD$_3$OD) δ 8.70 (s, 1 H), 8.22 (d, J=9.2 Hz, 1 H), 8.13-8.11 (m, 2 H), 7.62 (d, J=9.2 Hz, 1 H), 4.61 (s, 1 H), 4.28 (s, 2 H), 4.12 (s, 3 H), 4.08 (s, 1 H), 3.50-3.32 (m, 2 H), 3.24-3.15 (m, 2 H), 2.22-2.18 (m, 1 H), 1.88-1.86 (m, 3 H), 1.48-1.31 (m, 2 H), 1.05 (t, J=7.2 Hz, 3 H), 0.90 (d, J=7.2 Hz, 3 H); LCMS m/z 365.2 (M+H); SFC retention time: 7.29 min.

Examples 182a and 182b 2-(6-(1-cyclobutyl-4-methylpiperidine-3-carbonyl)-2-methoxynaphthalen-1-yl)acetonitrile

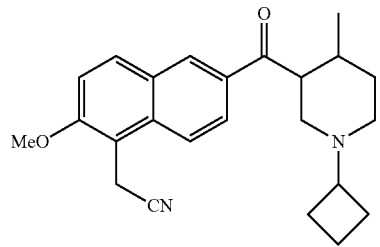

182a/182b

Prepared in an analogous manner to 2-(6-(1-cyclobutylpiperidine-3-carbonyl)-2-methoxynaphthalen-1-yl)acetonitrile (Examples 179a and 179b), replacing tert-butyl 3-(methoxy(methyl)carbamoyl)piperidine-1-carboxylate (Intermediate 19) with tert-butyl 3-(methoxy(methyl)carbamoyl)-4-methylpiperidine-1-carboxylate (Intermediate 10). 182a and 182b correspond to the cis-enantiomers.

SFC conditions: CHIRALPAK AD (250×30 mm, 5 μm particle size) at 50% MeOH w/0.1% NH$_4$OH; 80 mL/min, 100 bars, 40° C.

182a: $^1$H NMR (400 MHz, CDCl$_3$) δ 8.41 (s, 1 H), 8.07 (d, J=8.8 Hz, 1 H), 7.99 (d, J=8.8 Hz, 1 H), 7.93 (d, J=8.8 Hz, 1 H), 7.36 (d, J=9.2 Hz, 1 H), 4.12 (s, 2 H), 4.05 (s, 3 H), 3.88-3.85 (m, 1 H), 2.87-2.83 (m, 2 H), 2.78-2.75 (m, 1 H), 2.41-2.38 (m, 2 H), 2.12-2.08 (m, 4 H), 1.92-1.89 (m, 2 H), 1.73-1.70 (m, 3 H), 0.80 (d, J=3.2 Hz, 3 H); LCMS m/z 376.9 (M+H); SFC retention time: 5.07 min.

182b: $^1$H NMR (400 MHz, CDCl$_3$) δ 8.41 (s, 1 H), 8.07 (d, J=8.8 Hz, 1 H), 7.99 (d, J=8.8 Hz, 1 H), 7.93 (d, J=8.8 Hz, 1 H), 7.36 (d, J=9.6 Hz, 1 H), 4.12 (s, 2 H), 4.05 (s, 3 H), 3.88-3.85 (m, 1 H), 2.87-2.83 (m, 2 H), 2.78-2.75 (m, 1 H), 2.41-2.38 (m, 2 H), 2.12-2.08 (m, 4 H), 1.92-1.89 (m, 2 H), 1.73-1.70 (m, 3 H), 0.80 (d, J=2.8 Hz, 3 H); LCMS m/z 376.9 (M+H); SFC retention time: 5.70 min.

Examples 183a, 183b, 183c, and 183d 2-(6-(1-cyclobutyl-4-ethylpiperidine-3-carbonyl)-2-methoxynaphthalen-1-yl)acetonitrile

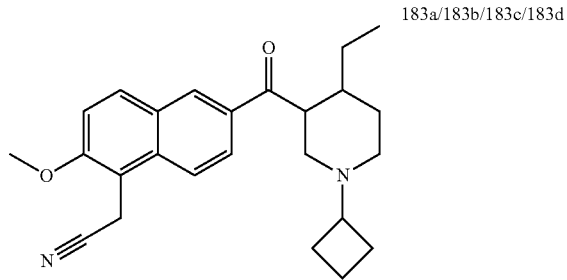 [SMILES: CCC1CCN(C2CCC2)CC1C(=O)c1ccc2c(CC#N)c(OC)ccc2c1]

183a/183b/183c/183d

Prepared in an analogous manner to 2-(6-(1-cyclobutylpiperidine-3-carbonyl)-2-methoxynaphthalen-1-yl)acetonitrile (Examples 179a and 179b), replacing tert-butyl 3-(methoxy(methyl)carbamoyl)piperidine-1-carboxylate (Intermediate 19) with tert-butyl 3-(methoxy(methyl)carbamoyl)-4-ethylpiperidine-1-carboxylate (Intermediate 15).

SFC conditions: CHIRALPAK AD (250×30 mm, 5 μm particle size) at 20% MeOH 183a: $^1$H NMR (400 MHz, CD$_3$OD) δ 8.63 (s, 1 H), 8.18 (d, J=9.2 Hz, 1 H), 8.13-8.06 (m, 2 H), 7.58 (d, J=9.2 Hz, 1 H), 4.25 (s, 2 H), 4.09 (s, 3 H), 3.69-3.65 (m, 1 H), 3.06-2.97 (m, 2 H), 2.84-2.80 (m, 1 H), 2.13-2.10 (m, 1 H), 2.00-1.89 (m, 6 H), 1.73-1.71 (m, 3 H), 1.41-1.36 (m, 2 H), 1.38-1.35 (m, 1 H), 0.84 (t, J=7.2 Hz, 3 H); LCMS m/z 391.0 (M+H); SFC retention time: 4.75 min.

183b: $^1$H NMR (400 MHz, CD$_3$OD) δ 8.66 (s, 1 H), 8.20 (d, J=9.6 Hz, 1 H), 8.15-8.08 (m, 2 H), 7.60 (d, J=9.2 Hz, 1 H), 4.27 (s, 2 H), 4.11 (s, 3 H), 3.72-3.68 (m, 1 H), 3.07-2.98 (m, 2 H), 2.84-2.82 (m, 1 H), 2.15-2.05 (m, 1 H), 2.01-1.87 (m, 6 H), 1.75-1.73 (m, 3 H), 1.40-1.37 (m, 2 H), 1.40-1.37 (m, 1 H), 0.86 (t, J=7.6 Hz, 3 H); LCMS m/z 391.1 (M+H); SFC retention time: 5.10 min.

183c: NMR (400 MHz, CD$_3$OD) 8.56 (s, 1 H), 8.15 (d, J=9.2 Hz, 1 H), 8.06 (s, 2 H), 7.56 (d, J=9.2 Hz, 1 H), 4.24 (s, 2 H), 4.08 (s, 3 H), 3.91-3.89 (m, 1 H), 2.86-2.84 (m, 1 H), 2.80-2.76 (m, 1 H), 2.60-2.56 (m, 1 H), 2.52-2.46 (m, 1 H), 2.15-2.03 (m, 4 H), 1.95-1.86 (m, 4 H), 1.75-1.72 (m, 2 H), 1.47-1.43 (m, 1 H), 1.12-1.10 (m, 1 H), 0.69 (t, J=7.6 Hz, 3 H); LCMS m/z 391.0 (M+H); SFC retention time: 5.68 min.

183d: $^1$H NMR (400 MHz, CD$_3$OD) δ 8.56 (s, 1 H), 8.15 (d, J=9.2 Hz, 1 H), 8.06 (s, 2 H), 7.56 (d, J=9.2 Hz, 1 H), 4.24 (s, 2 H), 4.08 (s, 3 H), 3.92-3.89 (m, 1 H), 2.86-2.84 (m, 1 H), 2.80-2.76 (m, 1 H), 2.60-2.56 (m, 1 H), 2.52-2.46 (m, 1 H), 2.15-2.03 (m, 4 H), 1.95-1.86 (m, 4 H), 1.75-1.72 (m, 2 H), 1.47-1.43 (m, 1 H), 1.12-1.10 (m, 1 H), 0.69 (t, J=7.6 Hz, 3 H); LCMS m/z 391.2 (M+H); SFC retention time: 6.35 min.

Examples 184a, 184b, 184c, and 184d 2-(6-(1-cyclobutyl-4-propylpiperidine-3-carbonyl)-2-methoxynaphthalen-1-yl)acetonitrile

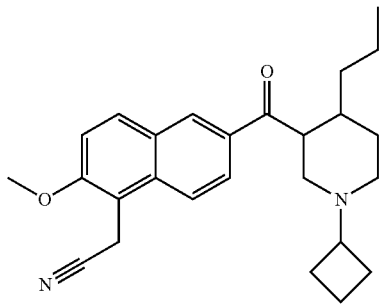

184a/184b/184c/184d

Prepared in an analogous manner to 2-(6-(1-cyclobutylpiperidine-3-carbonyl)-2-methoxynaphthalen-1-yl)acetonitrile (Examples 179a and 179b), replacing tert-butyl 3-(methoxy(methyl)carbamoyl)piperidine-1-carboxylate (Intermediate 19) with tert-butyl 3-(methoxy(methyl)carbamoyl)-4-propylpiperidine-1-carboxylate (Intermediate 13).

SFC conditions: CHIRALPAK AD (250×30 mm, 10 μm particle size) at 35% MeOH w/0.1% NH$_4$OH; 80 mL/min, 100 bars, 40° C.

184a: $^1$H NMR (400 MHz, CDCl$_3$) δ 8.42 (s, 1 H), 8.08 (d, J=8.0 Hz, 1 H), 8.01 (d, J=8.8 Hz, 1 H), 7.94 (d, J=9.2 Hz, 1 H), 7.37 (d, J=8.8 Hz, 1 H), 4.13 (s, 2 H), 4.06 (s, 3 H), 3.93-3.91 (m, 1 H), 2.88-2.81 (m, 2 H), 2.50-2.44 (m, 1 H), 2.18-1.95 (m, 9 H), 1.74-1.70 (m, 2 H), 0.98-0.85 (m, 4 H), 0.70 (t, J=7.6 Hz, 3 H); LCMS m/z 405.0 (M+H); SFC retention time: 8.72 min.

184b: $^1$H NMR (400 MHz, CDCl$_3$) δ 8.41 (s, 1 H), 8.07 (d, J=9.2 Hz, 1 H), 8.00 (d, J=9.2 Hz, 1 H), 7.93 (d, J=8.8 Hz, 1 H), 7.36 (d, J=9.2 Hz, 1 H), 4.12 (s, 2 H), 4.05 (s, 3 H), 3.90-3.88 (m, 1 H), 2.86-2.82 (m, 2 H), 2.50-2.44 (m, 1 H), 2.08-1.69 (m, 11 H), 1.73-1.69 (m, 1 H), 0.97-0.94 (m, 3 H), 0.69 (t, J=7.2 Hz, 3 H); LCMS m/z 405.0 (M+H); SFC retention time: 9.46 min.

184c: $^1$H NMR (400 MHz, CD$_3$OD) δ 8.66 (s, 1 H), 8.20 (d, J=9.2 Hz, 1 H), 8.15-8.08 (m, 2 H), 7.60 (d, J=9.2 Hz, 1 H), 4.27 (s, 2 H), 4.11 (s, 3 H), 3.68-3.66 (m, 1 H), 3.06-2.97 (m, 2 H), 2.82-2.80 (m, 1 H), 2.15-2.10 (m, 1 H), 2.00-1.88 (m, 7 H), 1.73-1.72 (m, 2 H), 1.41-1.25 (m, 5 H), 0.80 (t, J=6.8 Hz, 3 H); LCMS m/z 405.0 (M+H); SFC retention time: 7.26 min.

184d: $^1$H NMR (400 MHz, CD$_3$OD) δ 8.63 (s, 1 H), 8.18 (d, J=9.2 Hz, 1 H), 8.13-8.06 (m, 2 H), 7.57 (d, J=9.2 Hz, 1 H), 4.25 (s, 2 H), 4.09 (s, 3 H), 3.66-3.63 (m, 1 H), 3.04-2.96

(m, 2 H), 2.80-2.78 (m, 1 H), 2.12-2.08 (m, 1 H), 1.98-1.87 (m, 7 H), 1.70-1.70 (m, 2 H), 1.38-1.14 (m, 5 H), 0.78 (t, J=7.2 Hz, 3 H); LCMS m/z 405.0 (M+H); SFC retention time: 8.34 min.

Examples 185a and 185b 2-(6-(1-cyclobutyl-4-isobutylpiperidine-3-carbonyl)-2-methoxynaphthalen-1-yl)acetonitrile 185a/185b

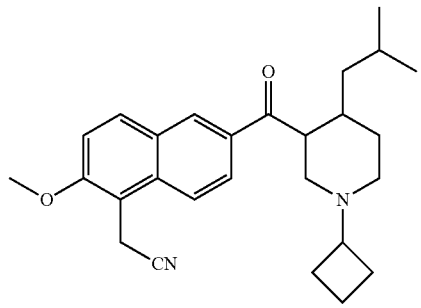

Prepared in an analogous manner to 2-(6-(1-cyclobutylpiperidine-3-carbonyl)-2-methoxynaphthalen-1-yl)acetonitrile (Examples 179a and 179b), replacing tert-butyl 3-(methoxy(methyl)carbamoyl)piperidine-1-carboxylate (Intermediate 19) with tert-butyl 3-(methoxy(methyl)carbamoyl)-4-isobutylpiperidine-1-carboxylate (Intermediate 14).

SFC conditions: CHIRALPAK OD (250×30 mm, 5 μm particle size) at 30% MeOH w/0.1% NH₄OH; 50 mL/min, 100 bars, 40° C. 185a and 185b correspond to the cis-enantiomers.

185a: ¹H NMR (400 MHz, CD₃OD) δ 8.46 (s, 1 H), 8.09-8.05 (m, 1 H), 7.98 (d, J=8.8 Hz, 2 H), 7.46 (d, J=9.2 Hz, 1 H), 4.15 (s, 2 H), 3.98 (s, 3 H), 3.83-3.80 (m, 1 H), 2.86-2.80 (m, 1 H), 2.72-2.69 (m, 1 H), 2.52-2.61 (m, 1 H), 2.41-2.25 (m, 1 H), 2.20-2.11 (m, 1 H), 2.09-1.91 (m, 3 H), 1.89-1.81 (m, 3 H), 1.67-1.65 (m, 3 H), 1.28-1.24 (m, 3 H), 0.82-0.63 (m, 3 H), 0.33 (d, J=6.0 Hz, 3 H); LCMS m/z 419.0 (M+H); SFC retention time: 4.61 min.

185b: ¹H NMR (400 MHz, CD₃OD) δ 8.55 (s, 1 H), 8.15 (d, J=9.2 Hz, 1 H), 8.06 (d, J=8.8 Hz, 2 H), 7.56 (d, J=9.2 Hz, 1 H), 4.24 (s, 2 H), 4.07 (s, 3 H), 3.91-3.87 (m, 1 H), 2.93-2.82 (m, 1 H), 2.80-2.75 (m, 1 H), 2.69-2.61 (m, 1 H), 2.47-2.36 (m, 1 H), 2.31-2.21 (m, 1 H), 2.20-2.05 (m, 3 H), 1.97-1.89 (m, 3 H), 1.76-1.73 (m, 3 H), 1.37-1.33 (m, 3 H), 0.87-0.72 (m, 3 H), 0.41 (d, J=6.4 Hz, 3 H); LCMS m/z 419.1 (M+H); SFC retention time: 5.26 min.

Examples 186a and 186b 2-(6-(1-cyclobutyl-4-isopropylpiperidine-3-carbonyl)-2-methoxynaphthalen-1-yl)acetonitrile 186a/186b

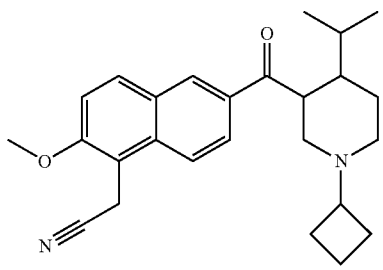

Prepared in an analogous manner to 2-(6-(1-cyclobutylpiperidine-3-carbonyl)-2-methoxynaphthalen-1-yl)acetonitrile (Examples 179a and 179b), replacing tert-butyl 3-(methoxy(methyl)carbamoyl)piperidine-1-carboxylate (Intermediate 19) with tert-butyl 3-(methoxy(methyl)carbamoyl)-4-isopropylpiperidine-1-carboxylate (Intermediate 17). 186a and 186b correspond to the cis-enantiomers.

SFC conditions: CHIRALPAK AD (250×30 mm, 10 μm particle size) at 15% IPA w/0.1% NH₄OH; 80 mL/min, 100 bars, 40° C.

186a: ¹H NMR (400 MHz, CD₃OD) δ 8.52 (s, 1 H), 8.13-8.03 (m, 3 H), 7.58-7.45 (m, 1 H), 4.24 (s, 2 H), 4.07 (s, 3 H), 4.01-3.98 (m, 1 H), 3.11-3.08 (m, 1 H), 2.83-2.78 (m, 1 H), 2.63-2.51 (m, 1 H), 2.21-2.12 (m, 2 H), 1.91-1.76 (m, 6 H), 1.54-1.52 (m, 2 H), 1.45-1.21 (m, 2 H), 0.95 (d, J=6.8 Hz, 3 H), 0.81 (d, J=6.4 Hz, 3 H); LCMS m/z 404.9 (M+H); SFC retention time: 1.84 min.

186b: ¹H NMR (400 MHz, CD₃OD) δ 8.52 (s, 1 H), 8.13-8.03 (m, 3 H), 7.53 (d, J=9.2 Hz, 1 H), 4.23 (s, 2 H), 4.06 (s, 3 H), 4.00-3.99 (m, 1 H), 3.10-3.07 (m, 1 H), 2.89-2.81 (m, 1 H), 2.61-2.56 (m, 1 H), 2.20-2.16 (m, 2 H), 1.90-1.70 (m, 6 H), 1.62-1.45 (m, 2 H), 1.41-1.30 (m, 2 H), 0.95 (d, J=6.8 Hz, 3 H), 0.81 (d, J=6.8 Hz, 3 H); LCMS m/z 405.0 (M+H); SFC retention time: 4.26 min.

Example 188

(1-(cyclopropylmethyl)piperidin-3-yl)(5-(hydroxymethyl)-6-methoxynaphthalen-2-yl)methanone hydrochloride

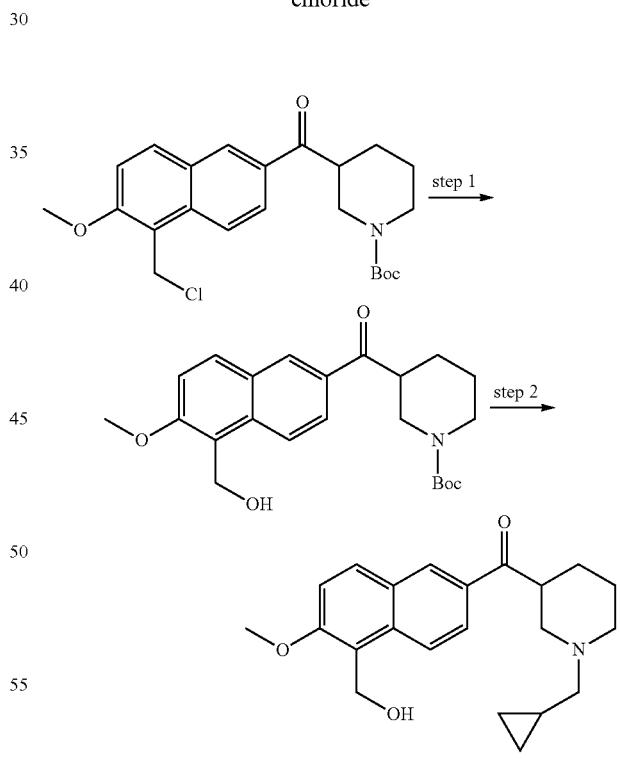

188

Step 1:

tert-butyl 3-(5-(hydroxymethyl)-6-methoxy-2-naphthoyl)piperidine-1-carboxylate

To a solution of tert-butyl 3-(5-(chloromethyl)-6-methoxy-2-naphthoyl)piperidine-1-carboxylate (Examples 71a and 71b) (600 mg, 1.44 mmol) in dioxane (30 mL) and H₂O (30 mL) was added CaCO₃ (720 mg, 7.2 mmol). The reaction mixture was heated at 85° C. for 12 h. The mixture was filtered while hot and the filtrate was concentrated under reduced pressure to give crude tert-butyl 3-(5-(hydroxymethyl)-6-methoxy-2-naphthoyl) piperidine-1-carboxylate (550 mg, 95.6% yield).

Step 2:

(1-(cyclopropylmethyl)piperidin-3-yl)(5-(hydroxymethyl)-6-methoxynaphthalen-2-yl)methanone hydrochloride To a solution of tert-butyl 3-(5-(hydroxymethyl)-6-methoxy-2-naphthoyl)piperidine-1-carboxylate (200 mg, 0.5 mmol) in ethyl acetate (5 mL) was added HCl (2 N in ethyl acetate, 5 mL, 10 mmol). The resulting mixture was stirred at ambient temperature for 1 h and then concentrated under reduced pressure to give crude (5-(hydroxymethyl)-6-methoxynaphthalen-2-yl)(piperidin-3-yl)methanone hydrochloride (168 mg, 99% yield).

A solution of (5-(hydroxymethyl)-6-methoxynaphthalen-2-yl)(piperidin-3-yl) methasone hydrochloride (168 mg, 0.5 mmol), cyclopropanecarbaldehyde (70 mg, 1.0 mmol) and Et₃N (2 mL) in dichloromethane (10 mL) was stirred at room temperature for 1 h before NaBH(OAc)₃ (212 mg, 1.0 mmol) was added. The mixture was stirred for another 1 h and then quenched by the addition of saturated aqueous NH₄Cl (10 mL). The solution was extracted with dichloromethane (3×20 mL). The combined organic layers were dried (Na₂SO₄) and concentrated under reduced pressure. The residue was purified by reverse phase HPLC to provide 3.0 mg (2% yield) of the title compound.

¹H NMR (400 MHz, DMSO-d6) δ 10.3 (br. s, 1 H), 8.38-8.30 (m, 1 H), 7.88-7.77 (m, 2 H), 7.67-7.65 (m, 1 H), 7.25-7.20 (m, 1 H), 4.84 (s, 2 H), 3.89-3.80 (m, 1 H), 3.64-3.57 (m, 3 H), 3.29-3.22 (m, 2 H), 2.75-2.52 (m, 4 H), 1.73-1.55 (m, 3 H), 1.12-1.01 (m, 1 H), 0.80-0.69 (m, 1 H), 0.24-0.23 (m, 2 H), 0.02-0.00 (m, 2 H); LCMS m/z 353.9 (M+H).

Example 189

(1-cyclobutylpiperidin-3-yl)(5-(hydroxymethyl)-6-methoxynaphthalen-2-yl)methanone hydrochloride

189

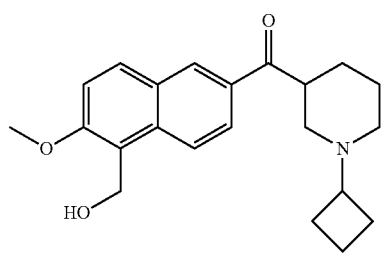

Prepared in an analogous manner to (1-(cyclopropylmethyl)piperidin-3-yl)(5-(hydroxymethyl)-6-methoxynaphthalen-2-yl)methanone hydrochloride (Example 184), replacing cyclopropanecarbaldehyde with cyclobutanone.

¹H NMR (400 MHz, DMSO-d6) δ 11.1 (br. s, 1 H), 8.71 (s, 1 H), 8.26-8.23 (m, 1 H), 8.17-8.15 (m, 1 H), 8.04-8.02 (m, 1 H), 7.63-7.60 (m, 1 H), 5.22 (s, 2 H), 4.23-4.17 (m, 1 H), 4.02 (s, 3 H), 3.65-3.61 (m, 1 H), 2.92-2.89 (m, 2 H), 2.75-2.61 (m, 2 H), 2.44-2.37 (m, 2 H), 2.18-2.09 (m, 4 H), 1.93-1.89 (m, 1 H), 1.75-1.60 (m, 2 H), 1.55-1.45 (m, 1 H); LCMS m/z 353.9 (M+H).

Synthesis of Intermediates

Intermediate 27

(4-cyclobutylpiperazin-2-yl)(6-methoxynaphthalen-2-yl)methanone

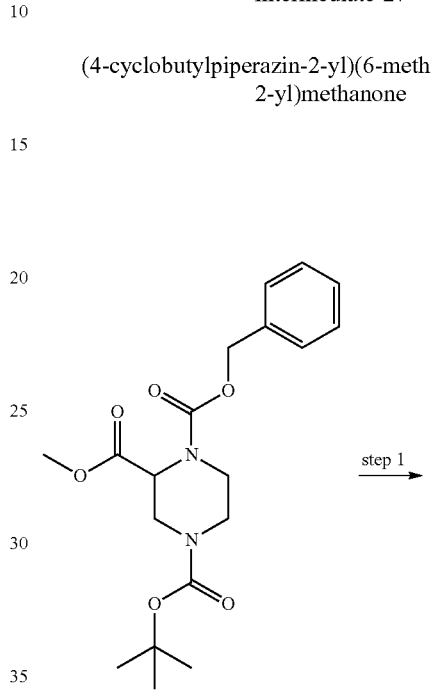

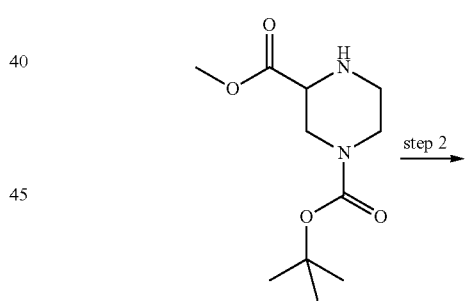

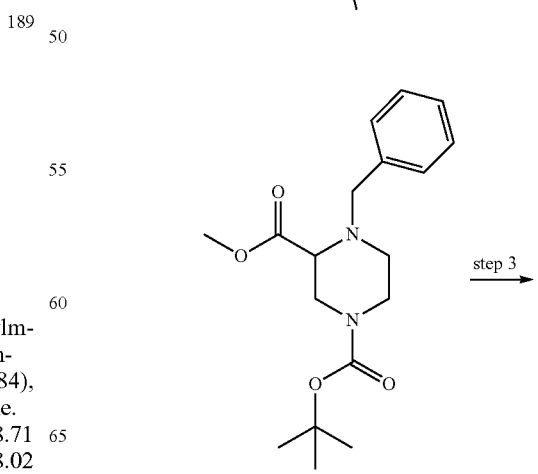

-continued

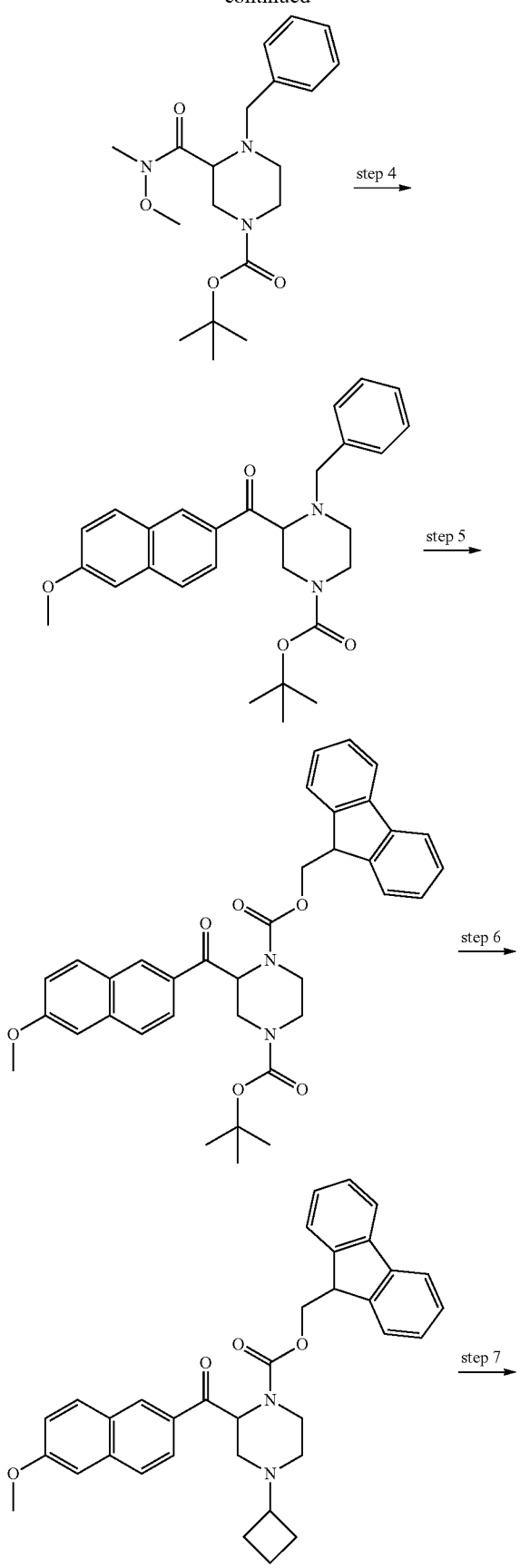

-continued

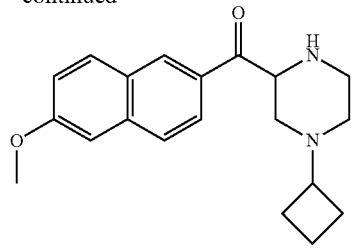

Intermediate 27

Step 1:

1-tert-butyl 3-methyl piperazine-1,3-dicarboxylate 1-benzyl 4-tert-butyl 2-methyl piperazine-1,2,4-tricarboxylate (10.0 g, 73.0 mmol) was dissolved in 150 ml of methanol and eluted over a cartridge of 10% Pd/C charged with H₂ at a pressure of 20 bar. The eluent was then concentrated in vacuo to afford the crude desired product.

Step 2:

1-tert-butyl 3-methyl 4-benzylpiperazine-1,3-dicarboxylate

To a solution of 1-tert-butyl 3-methyl piperazine-1,3-dicarboxylate (10.0 g, 70 mmol) in THF (200 mL) was added triethyl amine and benzyl bromide. The mixture was then stirred at room temperature for 12 hours and concentrated in vacuo. The residue was then diluted with ethyl acetate and water. The aqueous layer was discarded and the organic layer was washed once with water, dried over Na2SO4, filtered, and concentrated in vacuo. The residue was then purified by silica-gel chromatography (0-10% MeOH in DCM) to afford the desired product.

Step 3:

1-tert-butyl 3-methyl 4-benzylpiperazine-1,3-dicarboxylate

To a mixture of N,O-Dimethylamine Hydrochloride (3.5 g, 36 mmol) cooled to −78° C. in THF (100 ml) was added a 2M isopropyl magnesium chloride in THF solution (36 ml, 72 mmol) dropwise. After addition, stirring was continued at −78° C. for 5 minutes. The mixture was then warmed to 0° C. and ☐° C. stirred at for 5 minutes. The mixture was then retooled to −78° C. and charged dropwise with a solution of 1-tert-butyl 3-methyl 4-benzylpiperazine-1,3-dicarboxylate (6.0 g, 18 mmol) in 20 ml of THF. The mixture was then warmed to room temperature and stirred at room temperature for 30 minutes. The mixture was then diluted with ethyl acetate and water. The aqueous layer was discarded and the organic layer was washed once with water, dried over Na2SO4, filtered, and concentrated in vacuo. The residue was then purified by silica-gel chromatography (1-10% MeOH in DCM) to afford the title compound (6.5 g, 100% yield).

Step 4:

1-tert-butyl 4-benzyl-3-(6-methoxy-2-naphthoyl) piperazine-1-carboxylate

A solution of 2-bromo-6-methoxynaphthalene (3.9 g, 17 mmol) in THF was cooled to −78° C. and charged with 2.5 M n-BuLi (7 ml, 17.5 mmol). The mixture was then stirred at −78° C. for 5 minutes and then charged dropwise with a solution of 1-tert-butyl 3-methyl 4-benzylpiperazine-1,3-dicarboxylate (1.5 g, 4.1 mmol) in 5 ml of THF. The mixture was then warmed to room temperature and stirred at room temperature for 30 minutes. The mixture was then diluted with ethyl acetate and 1M NaHCO$_3$. The aqueous layer was discarded and the organic was washed once with water, dried over Na$_2$SO$_4$, filtered, and concentrated in vacuo. The residue was then purified by silica-gel chromatography (1-10% MeOH in DCM) to afford the title compound (1.52 g, 80% yield).

Step 5:

1-(9H-fluoren-9-yl) methyl-4-tert-butyl-2-(6-methoxy-2-naphthoyl) piperazine-1,4-dicarboxylate A solution of 1-tert-butyl-4-benzyl-3-(6-methoxy-2-naphthoyl)piperazine-1-carboxylate (640 mg, 1.4 mmol) in 5 ml of DCM was charged with (9H-fluoren-9-yl)methyl chloroformate (1.4 g, 5.6 mmol) and heated at 120° C. for 3 hours. The mixture was then directly loaded onto silica and purified by silica-gel chromatography (25 to 50% ethyl acetate in heptane) to afford the title compound (500 mg, 60% yield).

Step 6

(9H-fluoren-9-yl)methyl-4-cyclobutyl-2-(6-methoxy-2-naphthoyl)piperazine-1-carboxylate A solution of 1-(9H-fluoren-9-yl) methyl-4-tert-butyl-2-(6-methoxy-2-naphthoyl)piperazine-1,4-dicarboxylate (750 mg, 1.5 mmol) was dissolved in 5 ml of DCM and charged with 5 ml of TFA. The mixture was then stirred at room temperature for 1 hour, concentrated in vacuo, and azeotroped twice with methanol.

The crude residue was then diluted with 5 ml of DCM and charged with cyclobutanone (420 mg, 6.0 mmol) and sodium triacetoxyborohydride (1.3 g, 6.0 mmol). The mixture was then stirred at room temperature for one hour and concentrated in vacuo. The residue was then diluted with ethyl acetate and water. The aqueous was discarded and the organic was washed once with water, dried over Na$_2$SO$_4$, filtered, and concentrated in vacuo. The residue was then purified by silica-gel chromatography (1-10% MeOH in DCM) to afford the title compound.

Step 7:

(4-cyclobutylpiperazin-2-yl)(6-methoxynaphthalen-2-yl)methanone 9H-fluoren-9-ylmethyl To a solution of 4-cyclobutyl-2-(6-methoxynaphthalene-2-carbonyl)piperazine-1-carboxylate (150 mg, 0.27 mmol) in 500 ul of DCM was added 500 ul of Diethylamine. The mixture was stirred at room temperature for one hour and concentrated in vacuo to afford the title compound (100 mg, 100% yield).

Synthesis of Final Compounds

Example 190

4-cyclobutyl-1-ethyl-piperazin-2-yl)-(6-methoxy-2-naphthyl)methanone

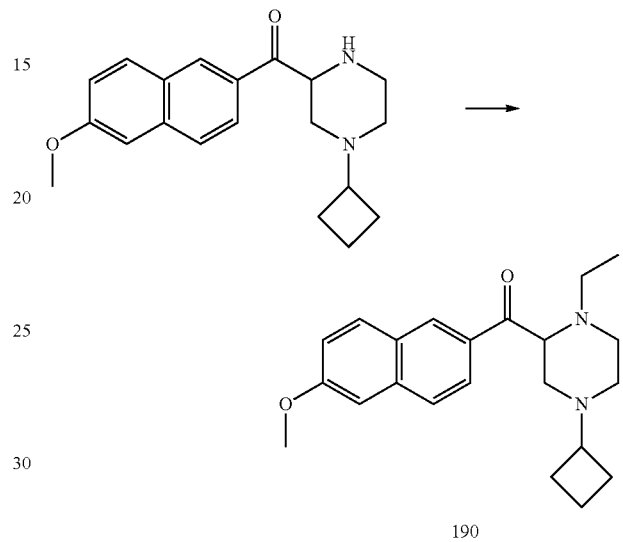

To a solution of (4-cyclobutylpiperazin-2-yl)-(6-methoxy-2-naphthyl)methanone (30 mg, 0.09 mmol) in 200 ul of THF was added triethylamine (47 mg, 0.46 mmol) and iodoethane (72 mg, 0.46 mmol). The mixture was then stirred at room temperature for one hour. It was then diluted with ethyl acetate and saturated NaHCO$_3$. The aqueous layer was discarded and the organic layer was dried over magnesium sulfate and concentrated in vacuo. The residue was then purified by silica-gel chromatography (0-10% MeOH in DCM) to afford the title compound (12 mg, 30% yield). $^1$H NMR (400 MHz, DMSO-d6) δ 8.80 (s, 1H), 8.04 (dd, J=9.0, 2.7 Hz, 2H), 7.94-7.70 (m, 2H), 7.40 (d, J=2.6 Hz, 1H), 7.26 (dd, J=8.9, 2.5 Hz, 1H), 4.09 (s, 1H), 3.92 (s, 3H), 3.28 (s, 1H), 3.12 (d, J=11.0 Hz, 1H), 2.68 (t, J=7.3 Hz, 1H), 2.66-2.51 (m, 3H), 2.37-2.25 (m, 2H), 2.18 (dt, J=19.5, 10.0 Hz, 2H), 2.05-1.94 (m, 1H), 1.79-1.51 (m, 3H), 0.96 (dt, J=21.1, 7.2 Hz, 3H). M+1 (m/z)=353.2.

The following compounds were prepared in a manner similar to Example 190.

| Example | Compound Name | 1H NMR | m/z (M + H) |
|---|---|---|---|
| 191 | (1-benzyl-4-cyclobutyl-piperazin-2-yl)-(6-methoxy-2-naphthyl)methanone | 1H NMR (400 MHz, DMSO-d6) δ 8.79 (s, 1H), 8.10-8.00 (m, 1H), 7.91 (d, J = 8.8 Hz, 1H), 7.41 (d, J = 2.5 Hz, 1H), 7.37-7.17 (m, 1H), 5.75 (s, 1H), 4.24 (s, 1H), 3.92 (s, 3H), 3.78 (d, J = 13.4 Hz, 1H), 3.36 (d, J = 13.4 Hz, 1H), 3.28 (s, 0H), 2.93 (s, 1H), 2.73-2.65 (m, 2H), 2.51 (s, 2H), 2.32 (dt, J = 21.1, 9.6 Hz, 2H), 2.15 (t, J = 9.7 Hz, 1H), 1.76-1.67 (m, 1H), 1.57 (s, 3H). | 415 |

-continued

| Example | Compound Name | 1H NMR | m/z (M + H) |
|---|---|---|---|
| 192 | [4-cyclobutyl-1-(cyclopropylmethyl)piperazin-2-yl]-(6-methoxy-2-naphthyl)methanone | 1H NMR (400 MHz, DMSO-d6) δ 8.78 (s, 1H), 8.08-7.95 (m, 2H), 7.95-7.66 (m, 2H), 7.43-7.15 (m, 1H), 5.75 (s, 1H), 4.17 (s, 1H), 3.90 (d, J = 8.3 Hz, 2H), 3.37 (q, J = 7.2 Hz, 2H), 3.27 (s, 2H), 3.21 (s, 1H), 3.01 (s, 1H), 2.73-2.54 (m, 3H), 2.49-2.39 (m, 2H), 2.14 (dd, J = 12.6, 7.2 Hz, 1H), 2.07-1.94 (m, 1H), 1.79-1.53 (m, 2H), 1.23 (t, J = 7.2 Hz, 3H), 1.04-0.94 (m, 1H), 0.45-0.29 (m, 1H), 0.38 (s, 1H), 0.06 (d, J = 5.4 Hz, 1H), −0.08 (d, J = 4.6 Hz, 2H). | 440 |
| 193 | 3-[[4-cyclobutyl-2-(6-methoxynaphthalene-2-carbonyl)piperazin-1-yl]methyl]benzonitrile | 1H NMR (400 MHz, DMSO-d6) δ 8.74 (s, 1H), 8.07 (d, J = 9.1 Hz, 1H), 8.03-7.95 (m, 1H), 7.90 (d, J = 8.6 Hz, 1H), 7.74-7.61 (m, 4H), 7.51 (q, J = 8.1 Hz, 1H), 7.41 (d, J = 2.6 Hz, 1H), 7.27 (dd, J = 9.0, 2.5 Hz, 1H), 3.92 (s, 3H), 3.81 (d, J = 14.2 Hz, 1H), 3.48 (d, J = 14.1 Hz, 1H), 3.29 (d, J = 18.7 Hz, 4H), 2.69 (d, J = 10.5 Hz, 3H), 2.36 (s, 2H), 2.20 (d, J = 10.7 Hz, 1H), 1.72 (d, J = 10.0 Hz, 1H), 1.56 (s, 4H), 1.24 (s, 1H). | 338 |
| 194 | (4-cyclobutyl-1-methyl-piperazin-2-yl)-(6-methoxy-2-naphthyl)methanone | 1H NMR (400 MHz, DMSO-d6) δ 8.78 (s, 1H), 8.10-7.99 (m, 2H), 7.89 (d, J = 8.6 Hz, 1H), 7.40 (d, J = 2.5 Hz, 1H), 7.26 (dd, J = 8.9, 2.5 Hz, 1H), 3.92 (s, 3H), 2.95 (d, J = 11.2 Hz, 1H), 2.69 (dt, J = 21.4, 8.9 Hz, 3H), 2.32 (t, J = 10.8 Hz, 1H), 2.19-2.02 (m, 5H), 1.88 (s, 2H), 1.71 (td, J = 18.0, 17.2, 8.0 Hz, 2H), 1.62-1.52 (m, 2H), 1.28-1.15 (m, 1H). | 440 |
| 195 | 2-[[4-cyclobutyl-2-(6-methoxynaphthalene-2-carbonyl)piperazin-1-yl]methyl]benzonitrile | 1H NMR (400 MHz, DMSO-d6) δ 8.65 (s, 1H), 8.05 (d, J = 9.0 Hz, 1H), 7.98-7.86 (m, 2H), 7.76 (t, J = 6.5 Hz, 1H), 7.67 (s, 1H), 7.75-7.56 (m, 2H), 1H, 4.66 (d, J = 5.5 Hz, 1H), 4.10-3.95 (m, 2H), 3.92 (s, 3H), 3.27 (s, 2H), 3.17 (d, J = 5.2 Hz, 2H), 2.65 (t, J = 7.5 Hz, 1H), 2.58 (s, 1H), 2.51-2.42 (m, 1H), 2.31 (s, 3H), 1.66 (q, J = 9.2 Hz, 1H), 1.51 (s, 1H), 1.52-1.39 (m, 1H), 1.23 (s, 1H), 0.98 (t, J = 7.1 Hz, 1H). | 429 |
| 196 | [4-cyclobutyl-1-(p-tolylmethyl)piperazin-2-yl]-(6-methoxy-2-naphthyl)methanone | 1H NMR (400 MHz, DMSO-d6) δ 8.79 (s, 1H), 8.10-7.98 (m, 1H), 7.97-7.80 (m, 2H), 7.17-7.01 (m, 6H), 4.18 (d, J = 7.9 Hz, 1H), 3.92 (s, 3H), 3.96-3.82 (m, 1H), 3.17 (s, 2H), 2.96-2.87 (m, 1H), 2.76-2.60 (m, 3H), 2.37-2.24 (m, 1H), 2.25 (s, 1H), 1.88 (d, J = 15.9 Hz, 1H), 1.78-1.66 (m, 1H), 1.60-1.50 (m, 3H), 1.23 (s, 1H), 1.14-0.94 (m, 1H). | 429 |
| 197 | [4-cyclobutyl-1-(2-naphthylmethyl)piperazin-2-yl]-(6-methoxy-2-naphthyl)methanone | 1H NMR (400 MHz, DMSO-d6) δ 8.82 (s, 1H), 8.06 (t, J = 8.8 Hz, 2H), 7.99-7.66 (m, 4H), 7.59-7.34 (m, 5H), 7.27 (dd, J = 9.0, 2.6 Hz, 1H), 4.30 (s, 1H), 3.93 (d, J = 18.7 Hz, 1H), 3.92 (s, 3H), 3.29-3.14 (m, 4H), 2.98 (d, J = 12.2 Hz, 1H), 2.89 (s, 3H), 2.19 (d, J = 10.0 Hz, 1H), 1.86 (s, 3H), 1.57 (s, 4H), 1.24 (s, 2H). | 465 |
| 198 | [4-cyclobutyl-1-[[3-(trifluoromethyl)phenyl]methyl]piperazin-2-yl]-(6-methoxy-2-naphthyl)methanone | 1H NMR (400 MHz, DMSO-d6) δ 8.79 (s, 1H), 8.10-7.98 (m, 2H), 7.97-7.80 (m, 2H), 7.46-7.17 (m, 2H), 7.17-7.01 (m, 6H), 4.18 (d, J = 7.9 Hz, 1H), 3.92 (s, 3H), 3.96-3.82 (m, 1H), 3.78-3.68 (m, 1H), 3.17 (s, 2H), 2.96-2.87 (m, 1H), 2.76-2.60 (m, 3H), 2.37-2.24 (m, 1H), 2.25 (s, 3H), 2.13 (t, J = 10.3 Hz, 1H), 1.88 (d, J = 15.9 Hz, | 483 |

| Example | Compound Name | 1H NMR | m/z (M + H) |
|---|---|---|---|
| | | 3H), 1.78-1.66 (m, 1H), 1.60-1.50 (m, 3H), 1.23 (s, 1H), 1.14-0.94 (m, 1H). | |
| 199 | 4-[[4-cyclobutyl-2-(6-methoxynaphthalene-2-carbonyl)piperazin-1-yl]methyl]benzonitrile | 1H NMR (400 MHz, DMSO-d6) δ 8.72 (s, 1H), 8.06 (d, J = 9.0 Hz, 1H), 8.02-7.95 (m, 1H), 7.90 (d, J = 8.7 Hz, 1H), 7.75 (dd, J = 8.0, 1.6 Hz, 2H), 7.56-7.49 (m, 2H), 7.40 (d, J = 2.5 Hz, 1H), 7.27 (dd, J = 8.9, 2.5 Hz, 1H), 4.05 (q, J = 5.3 Hz, 3H), 3.85 (d, J = 14.4 Hz, 1H), 3.52 (d, J = 14.5 Hz, 1H), 3.17 (dd, J = 5.3, 1.5 Hz, 3H), 2.94 (s, 1H), 2.68 (d, J = 10.3 Hz, 2H), 2.43 (s, 1H), 2.20 (d, J = 9.6 Hz, 1H), 1.84 (s, 2H), 1.71 (d, J = 10.2 Hz, 1H), 1.55 (s, 3H). | 440 |

Example 200

KDM2B TR-FRET Assay for Determining Inhibitor IC$_{50}$

Full length KDM2B was cloned, expressed, and purified to homogeneity. Compound inhibition of KDM2B demethylase activity was assessed by monitoring the methylation status of a biotin-H3K36me2 peptide substrate (H2N-RK-SAPATGGV(KMe2)KPHRYRPGTV-NTPEGBiot; New England Peptide) in the presence of α-keotglutarate (2-OG) and iron (Fe$^{2+}$) using the TR-FRET assay technology (Cisbio). Specifically, in a 384 well ProxiPlate KDM2B (5 mM final), ascorbate (500 μM final) and DTT (2 mM final) were combined with the biotin-H3K36me2 peptide substrate (200 nM final), 2-OG (0.3 μM or 6 μM final; Sigma K2010) and Fe$^{2+}$ (100 μM final; Sigma F1543) in 50 mM HEPES (pH 6.5) and 0.01% Triton-X 100 either in the presence of DMSO (final 0.25% DMSO) or compound dilution series in DMSO and mixed. After a two hour incubation at room temperature, a mixture of EU-anti-H3K36me1 antibody (2 nM final; Cisbio #64CUSKAZ), and Streptavidin-d2 (50 nM final; Cisbio #64CUS000) in 200 mM KF, 200 mM EDTA, 0.1% BSA and 50 mM HEPES (pH 6.5) was added. After 1 hour incubation, the plates were read on an Envision instrument, the readouts were transformed into % inhibition, and IC$_{50}$ values were generated using a four parameter logistic model (XLFIT5). The KDM2B TR-FRET Assay described above represents an additional embodiment of the invention.

Data for representative compounds from the assay described in Example 200 is provided in the following Table.

TABLE

| Example | Structure | KDM2B HTRF IC50 (uM) |
|---|---|---|
| 1 | 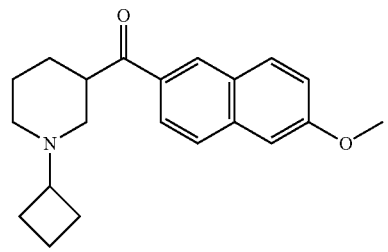 [SMILES: COc1ccc2cc(C(=O)C3CCCN(C4CCC4)C3)ccc2c1] | 0.25 |
| 3 | 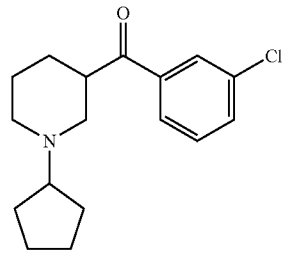 [SMILES: O=C(c1cccc(Cl)c1)C1CCCN(C2CCCC2)C1] | 23 |

TABLE-continued

| Example | Structure | KDM2B HTRF IC50 (uM) |
|---------|-----------|----------------------|
| 5 | 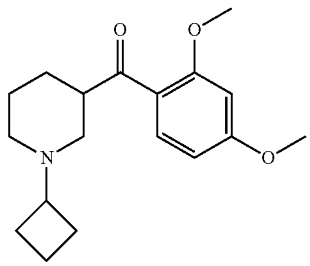 [SMILES: COc1ccc(C(=O)C2CCCN(C3CCC3)C2)c(OC)c1] | 2.5 |
| 6 | 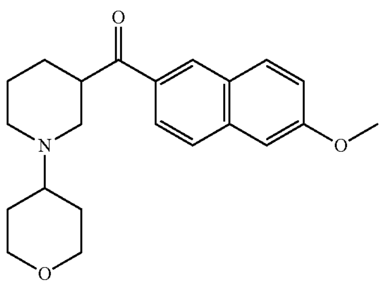 [SMILES: COc1ccc2cc(C(=O)C3CCCN(C4CCOCC4)C3)ccc2c1] | 2.6 |
| 7 | 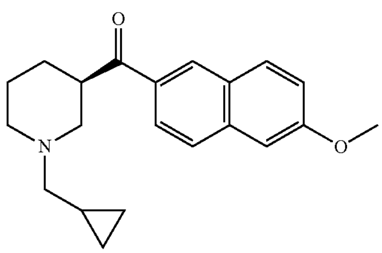 [SMILES: COc1ccc2cc(C(=O)[C@@H]3CCCN(CC4CC4)C3)ccc2c1] | 0.123 |
| 8 | 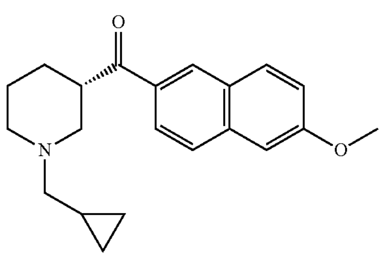 | 2.7 |
| 9 | 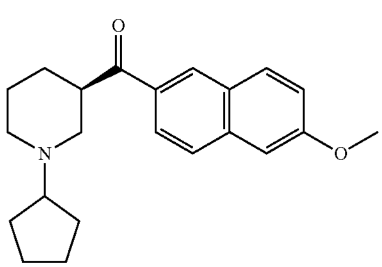 [SMILES: COc1ccc2cc(C(=O)[C@@H]3CCCN(C4CCCC4)C3)ccc2c1] | 3 |

TABLE-continued
| Example | Structure | KDM2B HTRF IC50 (uM) |
|---|---|---|
| 10 | 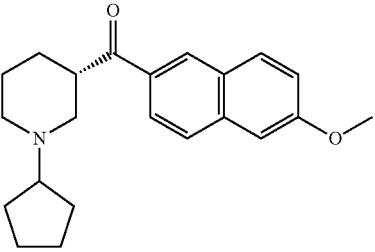 [SMILES: COc1ccc2cc(C(=O)[C@H]3CCCN(C4CCCC4)C3)ccc2c1] | 0.0566 |
| 11 | 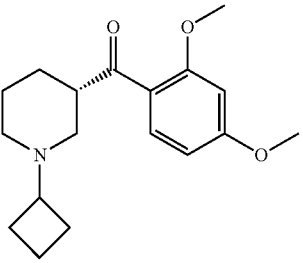 [SMILES: COc1ccc(C(=O)[C@H]2CCCN(C3CCC3)C2)c(OC)c1] | 0.153 |
| 12 | 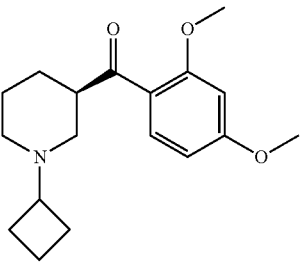 [SMILES: COc1ccc(C(=O)[C@@H]2CCCN(C3CCC3)C2)c(OC)c1] | 9 |
| 13 | 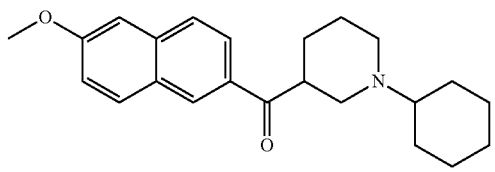 [SMILES: COc1ccc2cc(C(=O)C3CCCN(C4CCCCC4)C3)ccc2c1] | 0.713 |
| 14 | 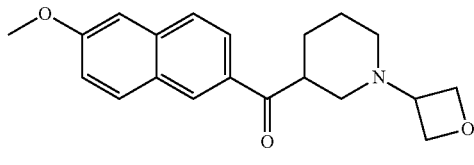 [SMILES: COc1ccc2cc(C(=O)C3CCCN(C4COC4)C3)ccc2c1] | 1.2 |
| 15 | 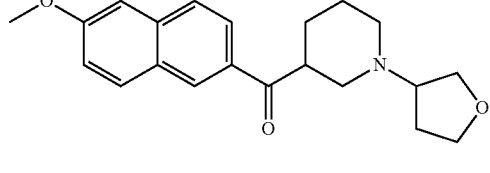 | 0.43 |
| 18 | 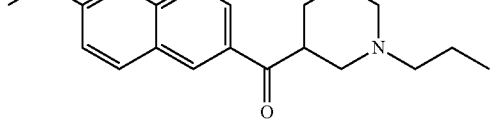 | 0.161 |

TABLE-continued

| Example | Structure | KDM2B HTRF IC50 (uM) |
|---------|-----------|----------------------|
| 21 | 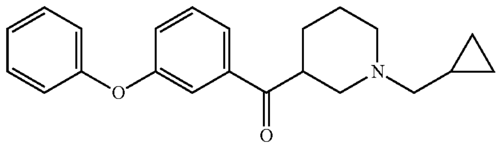 | 0.461 |
| 22 | 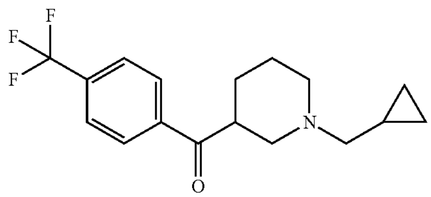 [SMILES: O=C(c1ccc(C(F)(F)F)cc1)C1CCCN(CC2CC2)C1] | 1.4 |
| 23 | 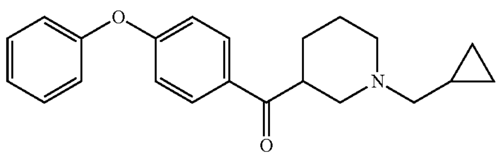 [SMILES: O=C(c1ccc(Oc2ccccc2)cc1)C1CCCN(CC2CC2)C1] | 2.1 |
| 24 | 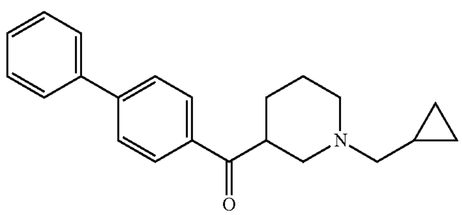 | 25++ |
| 25 | 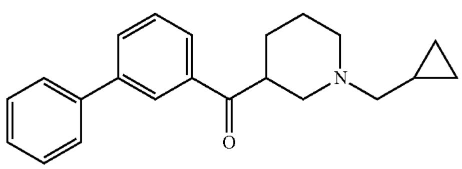 [SMILES: O=C(c1cccc(-c2ccccc2)c1)C1CCCN(CC2CC2)C1] | 1.4 |
| 26 | 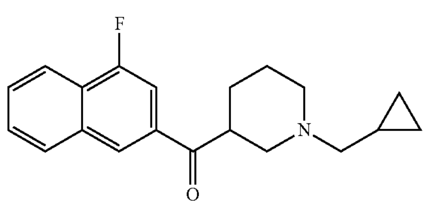 [SMILES: O=C(c1cc(F)c2ccccc2c1)C1CCCN(CC2CC2)C1] | 0.551 |
| 27 | 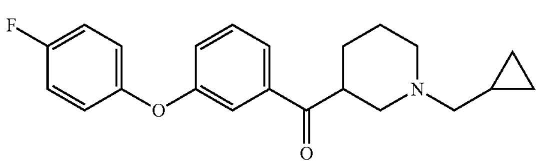 [SMILES: O=C(c1cccc(Oc2ccc(F)cc2)c1)C1CCCN(CC2CC2)C1] | 0.221 |
| 28 | 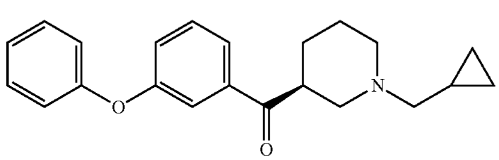 [SMILES: O=C(c1cccc(Oc2ccccc2)c1)[C@H]1CCCN(CC2CC2)C1] | 1.7 |

TABLE-continued

| Example | Structure | KDM2B HTRF IC50 (uM) |
|---|---|---|
| 29 | 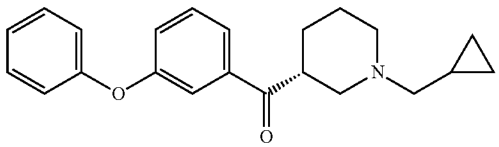 [SMILES: O=C(c1cccc(Oc2ccccc2)c1)[C@@H]1CCCN(CC2CC2)C1] | 0.148 |
| 30 | 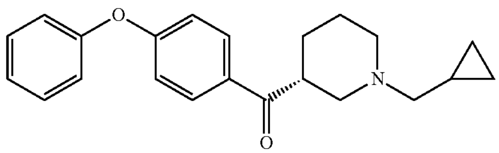 [SMILES: O=C(c1ccc(Oc2ccccc2)cc1)[C@@H]1CCCN(CC2CC2)C1] | 5.9 |
| 31 | 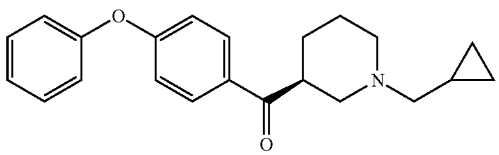 [SMILES: O=C(c1ccc(Oc2ccccc2)cc1)[C@H]1CCCN(CC2CC2)C1] | 0.136 |
| 32 | 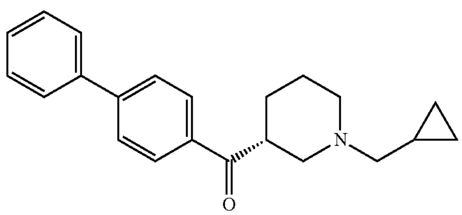 [SMILES: O=C(c1ccc(-c2ccccc2)cc1)[C@@H]1CCCN(CC2CC2)C1] | 4.1 |
| 33 | 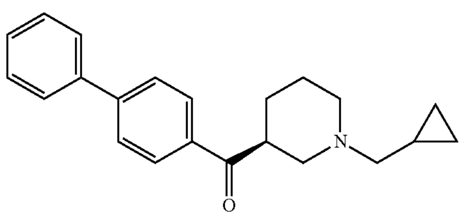 [SMILES: O=C(c1ccc(-c2ccccc2)cc1)[C@H]1CCCN(CC2CC2)C1] | 0.0954 |
| 34 | 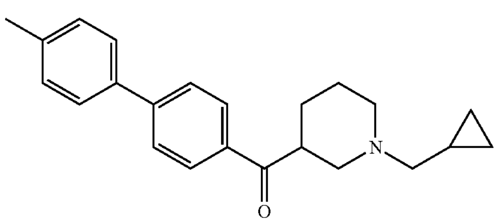 [SMILES: Cc1ccc(-c2ccc(C(=O)C3CCCN(CC4CC4)C3)cc2)cc1] | 0.402 |
| 35 | 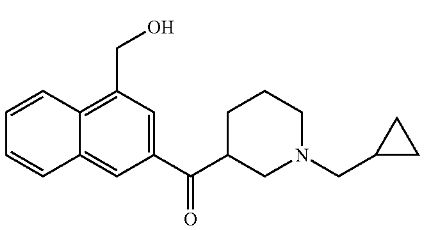 [SMILES: O=C(c1cc(CO)c2ccccc2c1)C1CCCN(CC2CC2)C1] | 0.169 |

TABLE-continued

| Example | Structure | KDM2B HTRF IC50 (uM) |
|---------|-----------|----------------------|
| 36 | 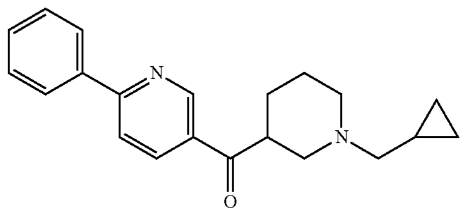 [SMILES: O=C(c1ccc(-c2ccccc2)nc1)C1CCCN(CC2CC2)C1] | 0.533 |
| 37 | 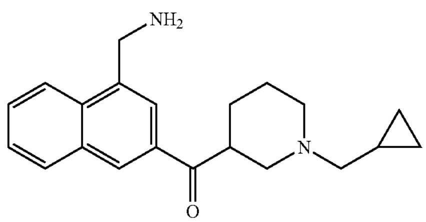 | 0.62 |
| 38 | 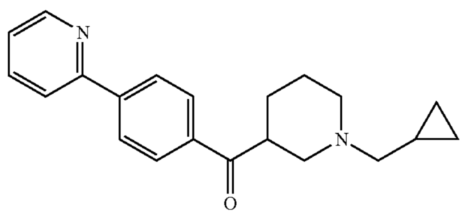 [SMILES: O=C(c1ccc(-c2ccccn2)cc1)C1CCCN(CC2CC2)C1] | 0.596 |
| 39 | 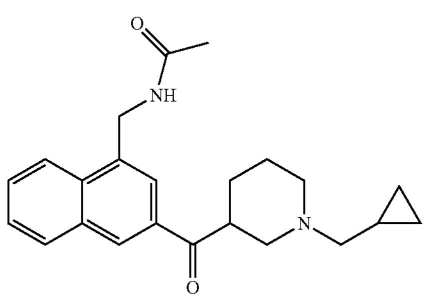 [SMILES: CC(=O)NCc1cc(C(=O)C2CCCN(CC3CC3)C2)cc2ccccc12] | 0.46 |
| 40 | 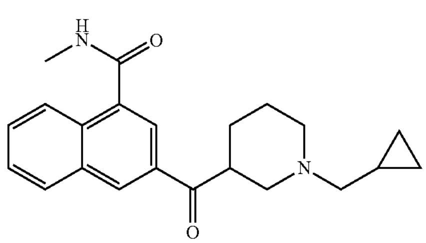 [SMILES: CNC(=O)c1cc(C(=O)C2CCCN(CC3CC3)C2)cc2ccccc12] | 0.626 |
| 41 | 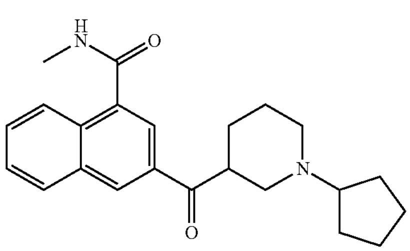 [SMILES: CNC(=O)c1cc(C(=O)C2CCCN(C3CCCC3)C2)cc2ccccc12] | 0.7 |

US 10,280,149 B2
TABLE-continued
| Example | Structure | KDM2B HTRF IC50 (uM) |
|---|---|---|
| 42 | 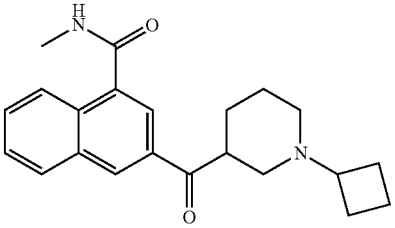 [SMILES: CNC(=O)c1cc(C(=O)C2CCCN(C3CCC3)C2)cc2ccccc12] | 0.243 |
| 43 | 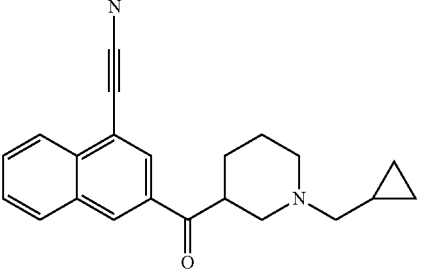 [SMILES: NC#Cc1cc(C(=O)C2CCCN(CC3CC3)C2)cc2ccccc12] | 0.143 |
| 44 | 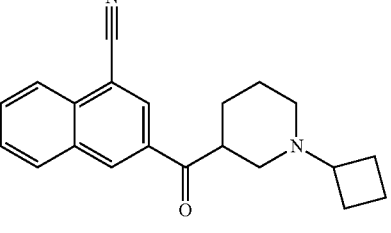 | 0.101 |
| 45 | 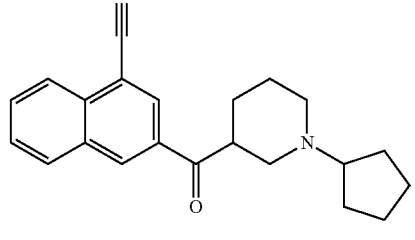 | 0.267 |
| 46 | 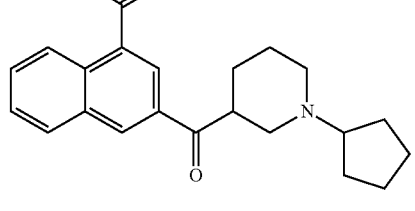 | 0.209 |
| 47 | 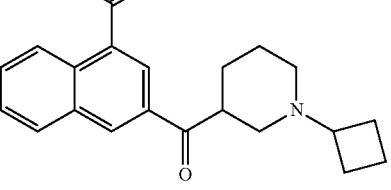 | 0.0997 |

TABLE-continued

| Example | Structure | KDM2B HTRF IC50 (uM) |
|---|---|---|
| 48 | 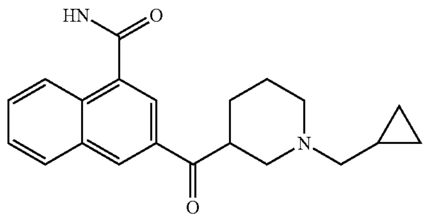 [SMILES: NC(=O)c1cc(C(=O)C2CCCN(CC3CC3)C2)cc2ccccc12] | 0.18 |
| 49 | 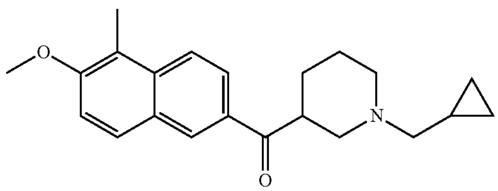 [SMILES: COc1ccc2cc(C(=O)C3CCCN(CC4CC4)C3)ccc2c1C] | 0.163 |
| 50 | 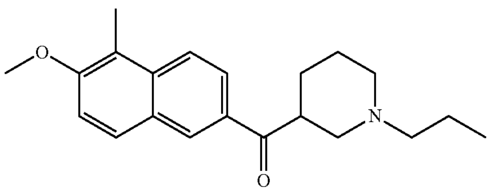 [SMILES: CCCN1CCCC(C(=O)c2ccc3c(C)c(OC)ccc3c2)C1] | 0.026 |
| 51 | 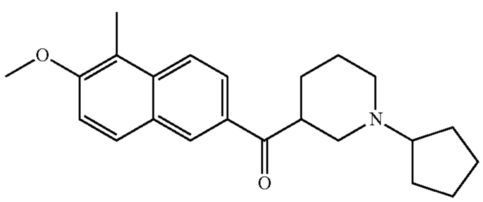 [SMILES: COc1ccc2cc(C(=O)C3CCCN(C4CCCC4)C3)ccc2c1C] | 0.118 |
| 52 | 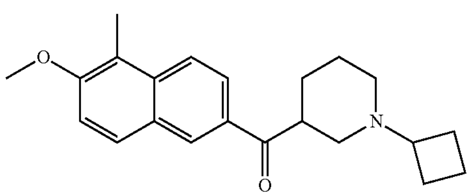 [SMILES: COc1ccc2cc(C(=O)C3CCCN(C4CCC4)C3)ccc2c1C] | 0.0394 |
| 53 | 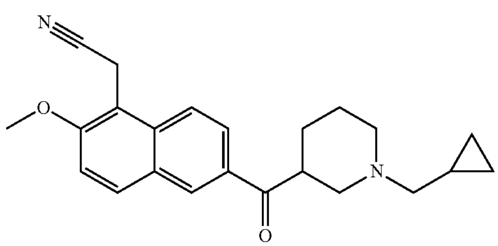 [SMILES: COc1ccc2cc(C(=O)C3CCCN(CC4CC4)C3)ccc2c1CC#N] | 0.0335 |
| 54 | 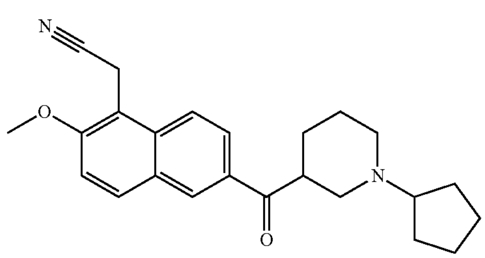 [SMILES: COc1ccc2cc(C(=O)C3CCCN(C4CCCC4)C3)ccc2c1CC#N] | 0.0395 |

TABLE-continued
| Example | Structure | KDM2B HTRF IC50 (uM) |
|---------|-----------|----------------------|
| 55 | 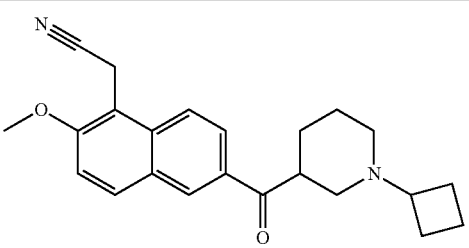 [SMILES: COc1ccc2cc(C(=O)C3CCCN(C4CCC4)C3)ccc2c1CC#N] | 0.0132 |
| 56 | 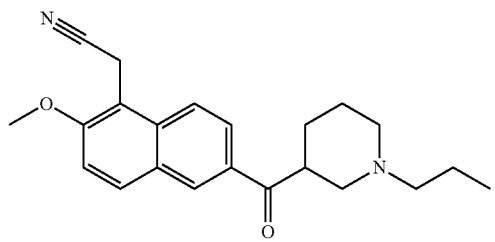 [SMILES: CCCN1CCCC(C(=O)c2ccc3c(CC#N)c(OC)ccc3c2)C1] | 0.27 |
| 57 | 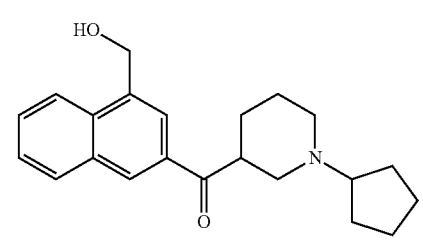 [SMILES: O=C(c1cc(CO)c2ccccc2c1)C1CCCN(C2CCCC2)C1] | 0.125 |
| 58 | 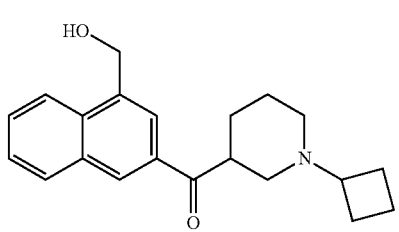 [SMILES: O=C(c1cc(CO)c2ccccc2c1)C1CCCN(C2CCC2)C1] | 0.0476 |
| 59 | 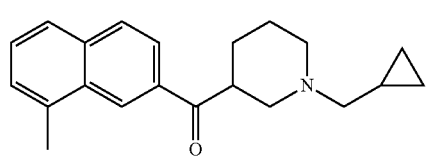 [SMILES: Cc1cccc2ccc(C(=O)C3CCCN(CC4CC4)C3)cc12] | 0.169 |
| 60 | 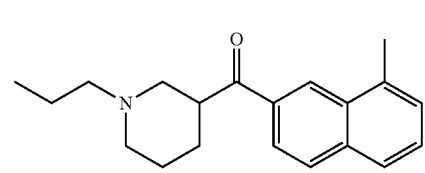 [SMILES: CCCN1CCCC(C(=O)c2ccc3cccc(C)c3c2)C1] | 0.125 |
| 61 | 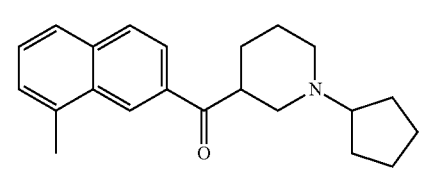 [SMILES: Cc1cccc2ccc(C(=O)C3CCCN(C4CCCC4)C3)cc12] | 0.174 |

TABLE-continued

| Example | Structure | KDM2B HTRF IC50 (uM) |
|---|---|---|
| 62 | 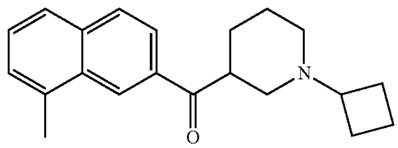 [SMILES: Cc1cccc2ccc(C(=O)C3CCCN(C4CCC4)C3)cc12] | 0.103 |
| 63 | 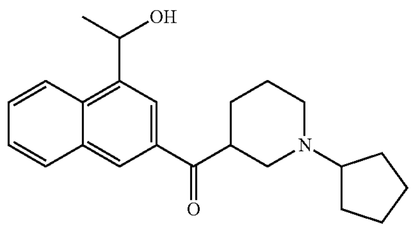 [SMILES: CC(O)c1cc(C(=O)C2CCCN(C3CCCC3)C2)cc2ccccc12] | 0.15 |
| 64 | 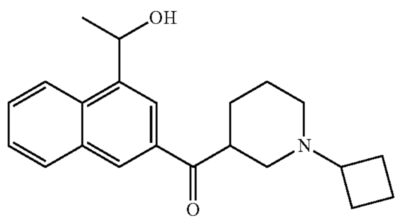 [SMILES: CC(O)c1cc(C(=O)C2CCCN(C3CCC3)C2)cc2ccccc12] | 0.0438 |
| 65 | 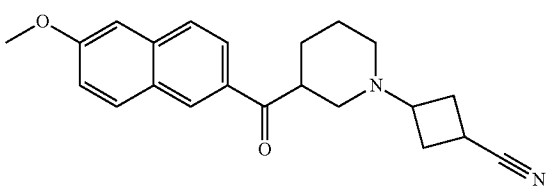 [SMILES: COc1ccc2cc(C(=O)C3CCCN(C4CC(C#N)C4)C3)ccc2c1] | 0.309 |
| 66 | 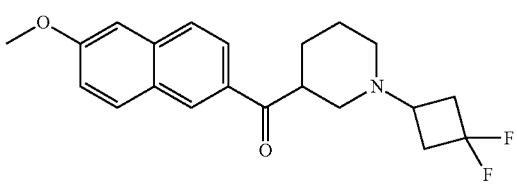 [SMILES: COc1ccc2cc(C(=O)C3CCCN(C4CC(F)(F)C4)C3)ccc2c1] | 0.0675 |
| 67 | 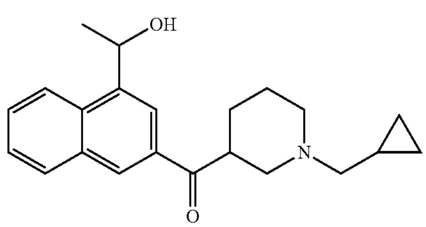 [SMILES: CC(O)c1cc(C(=O)C2CCCN(CC3CC3)C2)cc2ccccc12] | 0.148 |
| 68 | 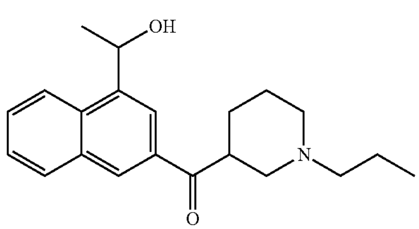 [SMILES: CCCN1CCCC(C(=O)c2cc(C(C)O)c3ccccc3c2)C1] | 0.0762 |

TABLE-continued
| Example | Structure | KDM2B HTRF IC50 (uM) |
|---|---|---|
| 69 | 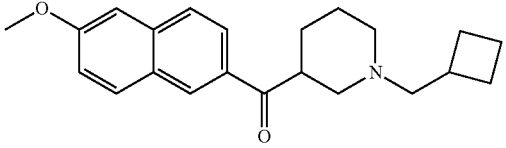 [SMILES: COc1ccc2cc(C(=O)C3CCCN(CC4CCC4)C3)ccc2c1] | 0.15 |
| 70 | 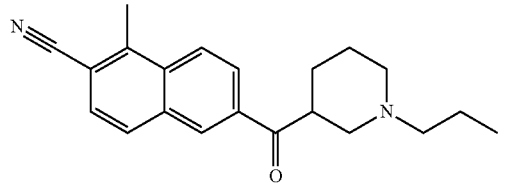 [SMILES: CCCN1CCCC(C(=O)c2ccc3c(C)c(C#N)ccc3c2)C1] | 0.0918 |
| 71 | 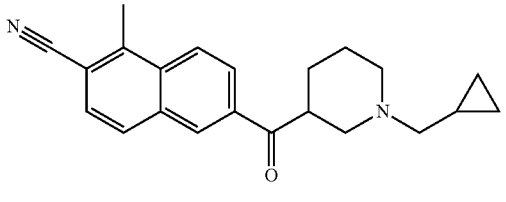 [SMILES: Cc1c(C#N)ccc2cc(C(=O)C3CCCN(CC4CC4)C3)ccc12] | 0.132 |
| 72 | 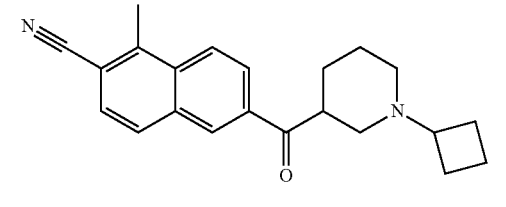 [SMILES: Cc1c(C#N)ccc2cc(C(=O)C3CCCN(C4CCC4)C3)ccc12] | 0.0875 |
| 73 | 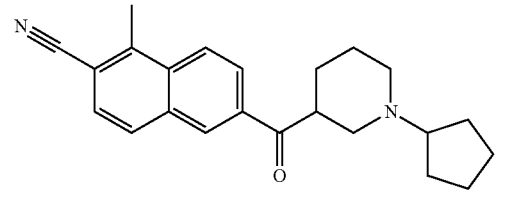 [SMILES: Cc1c(C#N)ccc2cc(C(=O)C3CCCN(C4CCCC4)C3)ccc12] | 0.327 |
| 74 | 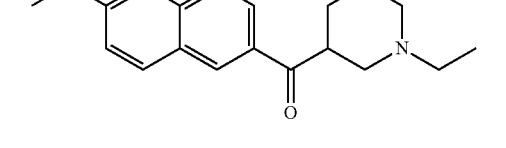 | 1.15 |
| 76 | 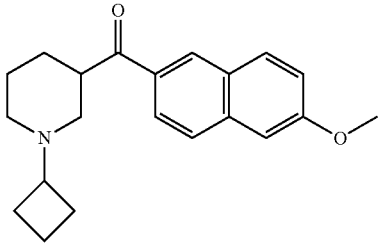 [SMILES: COc1ccc2cc(C(=O)C3CCCN(C4CCC4)C3)ccc2c1] | 0.619 |

TABLE-continued
| Example | Structure | KDM2B HTRF IC50 (uM) |
|---|---|---|
| 77 | 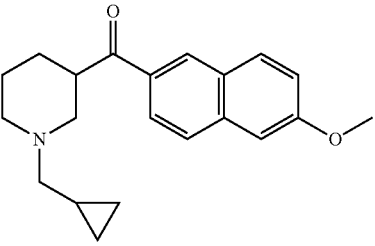 [SMILES: COc1ccc2cc(C(=O)C3CCCN(CC4CC4)C3)ccc2c1] | 0.208 |
| 78 | 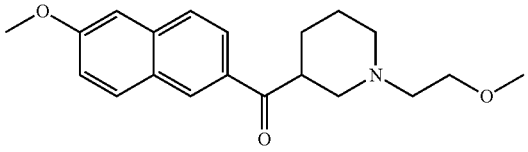 | 2.4 |
| 79 | 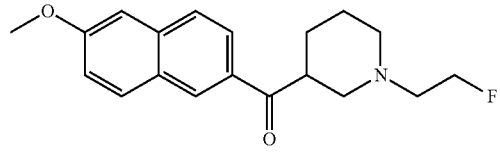 [SMILES: COc1ccc2cc(C(=O)C3CCCN(CCF)C3)ccc2c1] | 1.8 |
| 81 | 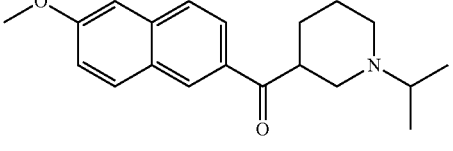 | 6.5 |
| 84 | 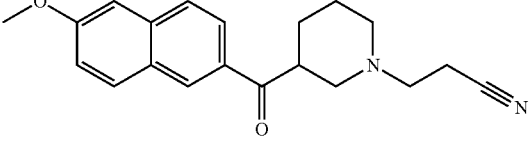 | 0.709 |
| 85 | 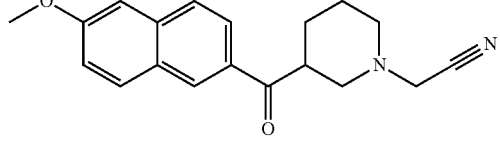 | 25++ |
| 87 | 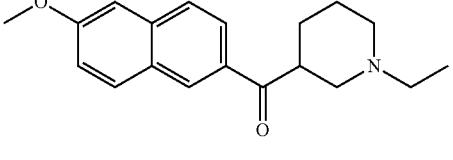 | |
| 88 | 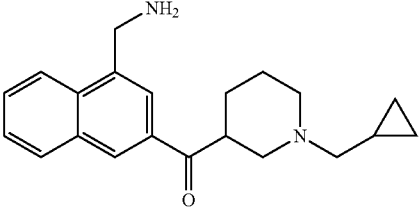 [SMILES: NCc1cc(C(=O)C2CCCN(CC3CC3)C2)cc2ccccc12] | |

TABLE-continued

| Example | Structure | KDM2B HTRF IC50 (uM) |
|---|---|---|
| 89 | 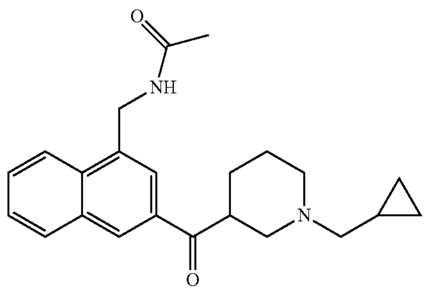 [SMILES: CC(=O)NCc1cc(C(=O)C2CCCN(CC3CC3)C2)cc2ccccc12] | |
| 90 | 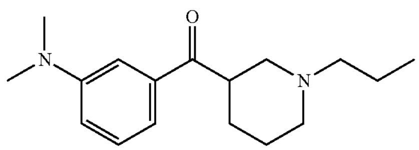 [SMILES: CCCN1CCCC(C(=O)c2cccc(N(C)C)c2)C1] | 1.6 |
| 91 | 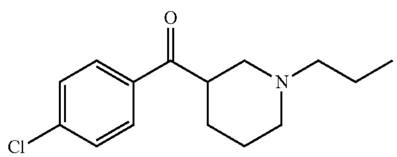 [SMILES: CCCN1CCCC(C(=O)c2ccc(Cl)cc2)C1] | 1.6 |
| 92 | 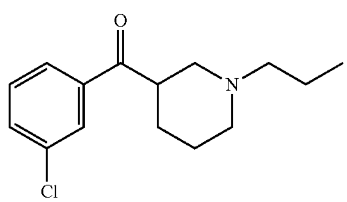 [SMILES: CCCN1CCCC(C(=O)c2cccc(Cl)c2)C1] | 0.723 |
| 93 | 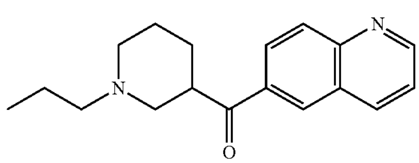 [SMILES: CCCN1CCCC(C(=O)c2ccc3ncccc3c2)C1] | |
| 94 | 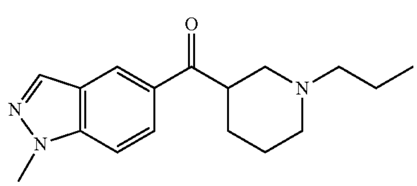 [SMILES: CCCN1CCCC(C(=O)c2ccc3c(cnn3C)c2)C1] | 0.122 |
| 95 | 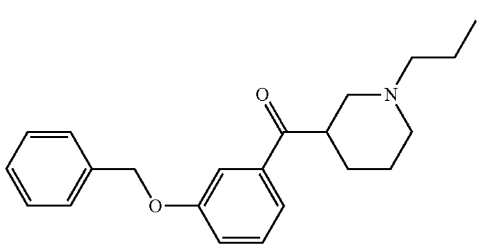 [SMILES: CCCN1CCCC(C(=O)c2cccc(OCc3ccccc3)c2)C1] | 0.823 |
| 96 | 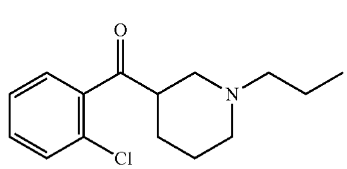 [SMILES: CCCN1CCCC(C(=O)c2ccccc2Cl)C1] | |

TABLE-continued

| Example | Structure | KDM2B HTRF IC50 (uM) |
|---|---|---|
| 97 | (4-methoxyphenyl)(1-propylpiperidin-3-yl)methanone | 0.93 |
| 98 | (3-methoxyphenyl)(1-propylpiperidin-3-yl)methanone | 1.6 |
| 99 | (2-methoxyphenyl)(1-propylpiperidin-3-yl)methanone | 5.5 |
| 100 | (1-propylpiperidin-3-yl)(4-(trifluoromethyl)phenyl)methanone | 1.2 |
| 101 | (3,4-dichlorophenyl)(1-propylpiperidin-3-yl)methanone | 0.279 |
| 102 | ([1,1'-biphenyl]-2-yl)(1-propylpiperidin-3-yl)methanone | 5.8 |
| 103 | (1-propylpiperidin-3-yl)(4-(trifluoromethoxy)phenyl)methanone | 2 |

TABLE-continued
| Example | Structure | KDM2B HTRF IC50 (uM) |
|---|---|---|
| 104 | 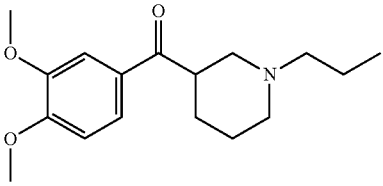 [SMILES: CCCN1CCCC(C(=O)c2ccc(OC)c(OC)c2)C1] | 0.744 |
| 105 | 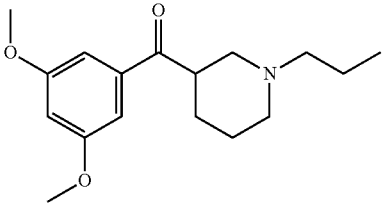 [SMILES: CCCN1CCCC(C(=O)c2cc(OC)cc(OC)c2)C1] | 0.272 |
| 106 | 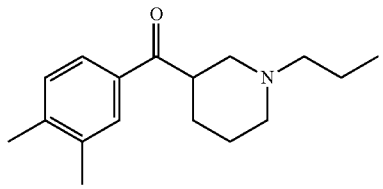 [SMILES: CCCN1CCCC(C(=O)c2ccc(C)c(C)c2)C1] | 0.247 |
| 107 | 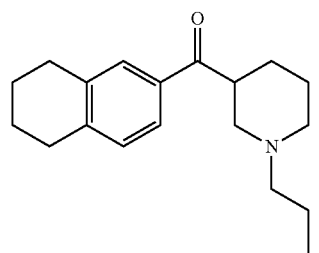 [SMILES: CCCN1CCCC(C(=O)c2ccc3c(c2)CCCC3)C1] | 0.0998 |
| 108 | 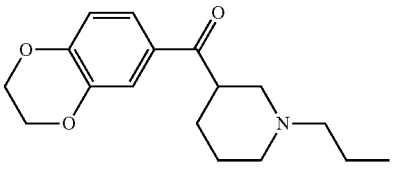 [SMILES: CCCN1CCCC(C(=O)c2ccc3c(c2)OCCO3)C1] | 0.297 |
| 109a | 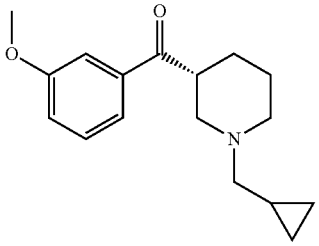 [SMILES: COc1cccc(C(=O)[C@@H]2CCCN(CC3CC3)C2)c1] | 14.1 |
| 109b | 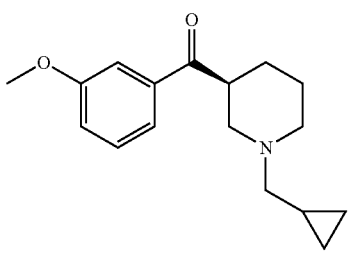 [SMILES: COc1cccc(C(=O)[C@H]2CCCN(CC3CC3)C2)c1] | 1.3 |

TABLE-continued
| Example | Structure | KDM2B HTRF IC50 (uM) |
|---|---|---|
| 110a | 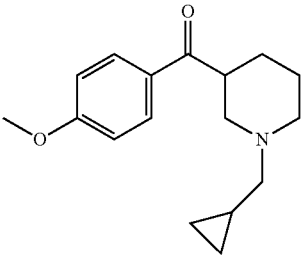 | 2 |
| 110b | 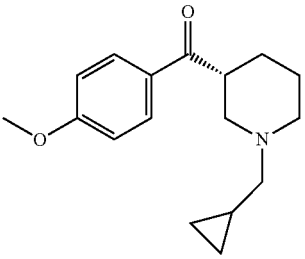 [SMILES: COc1ccc(C(=O)[C@@H]2CCCN(CC3CC3)C2)cc1] | 5.3 |
| 111 | 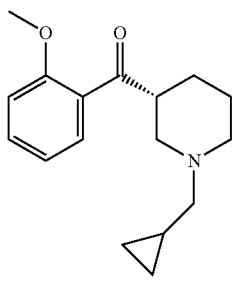 [SMILES: COc1ccccc1C(=O)[C@@H]1CCCN(CC2CC2)C1] | 3.1 |
| 112 | 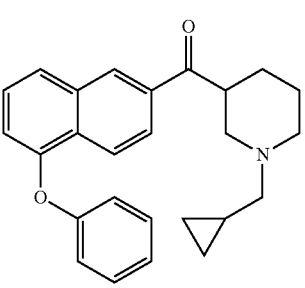 [SMILES: O=C(c1ccc2c(Oc3ccccc3)cccc2c1)C1CCCN(CC2CC2)C1] | 0.175 |
| 113 | 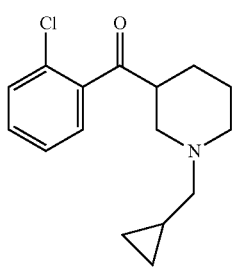 [SMILES: O=C(c1ccccc1Cl)C1CCCN(CC2CC2)C1] | 5.4 |

TABLE-continued
| Example | Structure | KDM2B HTRF IC50 (uM) |
|---|---|---|
| 114 | 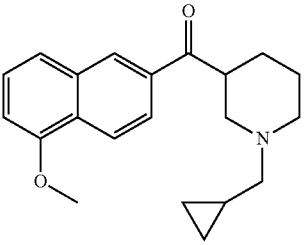 [SMILES: COc1cccc2cc(C(=O)C3CCCN(CC4CC4)C3)ccc12] | 0.22 |
| 115 | 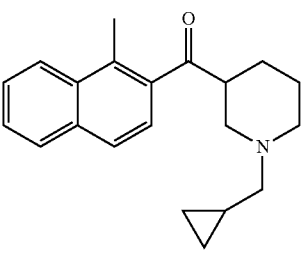 [SMILES: Cc1c(C(=O)C2CCCN(CC3CC3)C2)ccc2ccccc12] | 0.439 |
| 116a | 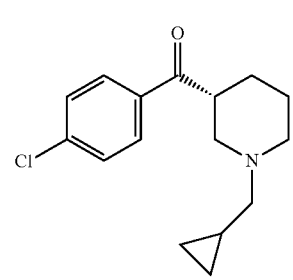 [SMILES: O=C(c1ccc(Cl)cc1)[C@@H]1CCCN(CC2CC2)C1] | 5.8 |
| 116b | 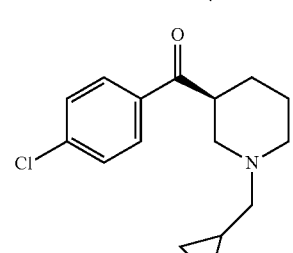 | 1.4 |
| 117a | 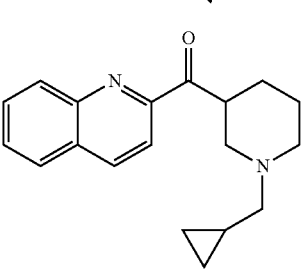 | 0.356 |
| 117b | 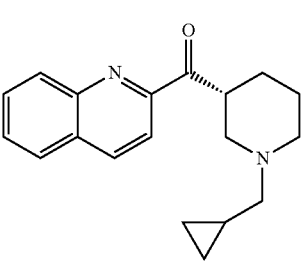 [SMILES: O=C(c1ccc2ccccc2n1)[C@@H]1CCCN(CC2CC2)C1] | 0.75 |

TABLE-continued

| Example | Structure | KDM2B HTRF IC50 (uM) |
|---------|-----------|----------------------|
| 118a | 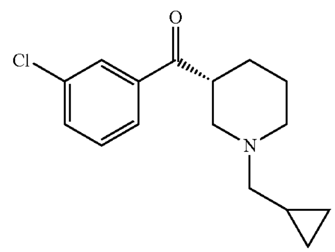 [SMILES: O=C(c1cccc(Cl)c1)[C@@H]1CCCN(CC2CC2)C1] | 6.8 |
| 118b | 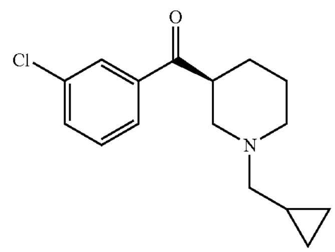 [SMILES: O=C(c1cccc(Cl)c1)[C@H]1CCCN(CC2CC2)C1] | 0.661 |
| 119 | 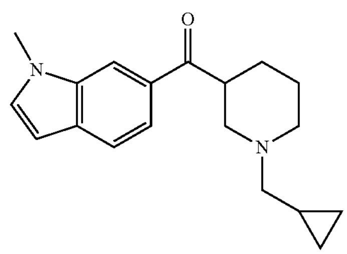 [SMILES: Cn1ccc2ccc(C(=O)C3CCCN(CC4CC4)C3)cc21] | 2.3 |
| 120 | 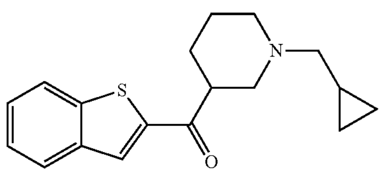 [SMILES: O=C(c1cc2ccccc2s1)C1CCCN(CC2CC2)C1] | 0.389 |
| 121 | 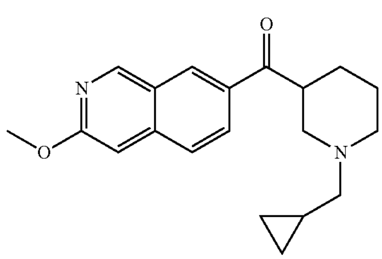 [SMILES: COc1cc2ccc(C(=O)C3CCCN(CC4CC4)C3)cc2cn1] | 0.38 |
| 122 | 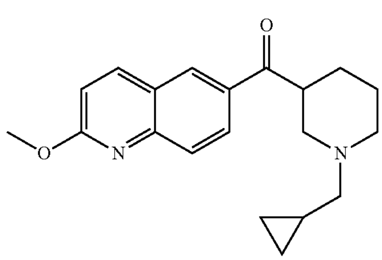 [SMILES: COc1ccc2cc(C(=O)C3CCCN(CC4CC4)C3)ccc2n1] | 0.205 |

TABLE-continued
| Example | Structure | KDM2B HTRF IC50 (uM) |
|---|---|---|
| 123 | 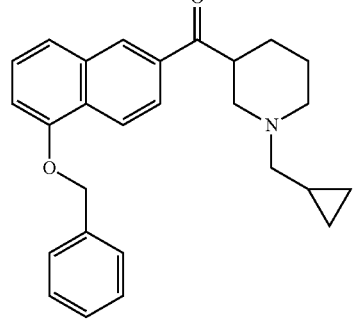 | 0.0909 |
| 124 | 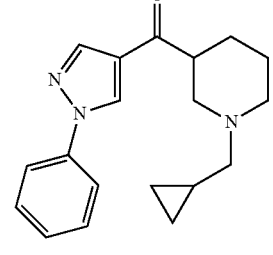 | 0.656 |
| 125 | 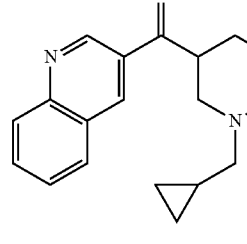 | 0.489 |
| 126 | 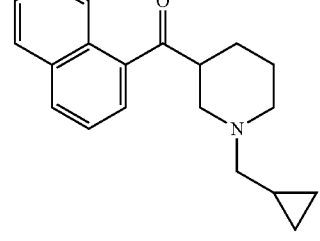 | 3.8 |
| 127 | 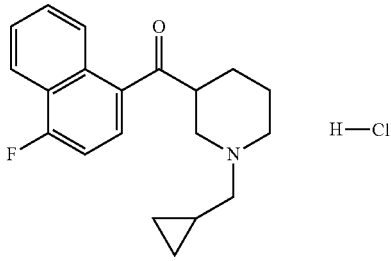 [SMILES: O=C(c1ccc(F)c2ccccc12)C1CCCN(CC2CC2)C1 ; Cl] | 1.9 |

TABLE-continued
| Example | Structure | KDM2B HTRF IC50 (uM) |
|---------|-----------|----------------------|
| 128 | 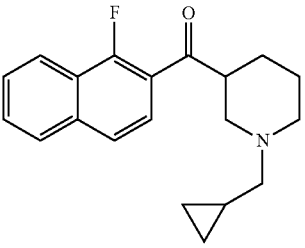 [SMILES: O=C(c1ccc2ccccc2c1F)C1CCCN(CC2CC2)C1] | 0.133 |
| 129 | 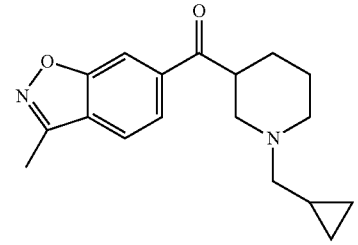 [SMILES: Cc1noc2cc(C(=O)C3CCCN(CC4CC4)C3)ccc12] | 0.492 |
| 130 | 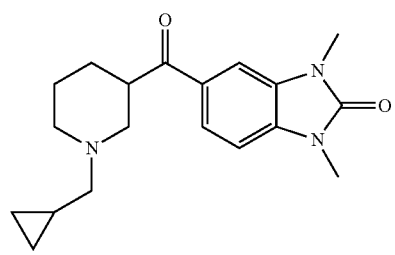 [SMILES: Cn1c(=O)n(C)c2cc(C(=O)C3CCCN(CC4CC4)C3)ccc21] | 0.442 |
| 131a | 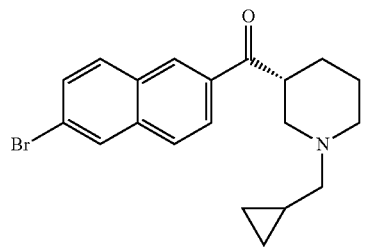 [SMILES: O=C(c1ccc2cc(Br)ccc2c1)[C@@H]1CCCN(CC2CC2)C1] | 0.226 |
| 131b | 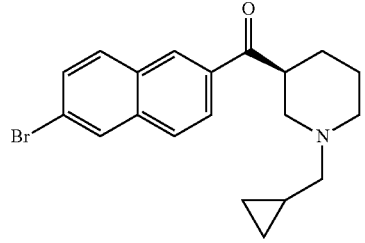 [SMILES: O=C(c1ccc2cc(Br)ccc2c1)[C@H]1CCCN(CC2CC2)C1] | 0.181 |
| 132 | 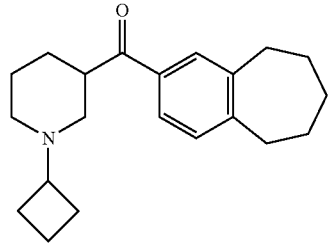 [SMILES: O=C(c1ccc2c(c1)CCCCC2)C1CCCN(C2CCC2)C1] | 0.0553 |

TABLE-continued
| Example | Structure | KDM2B HTRF IC50 (uM) |
|---------|-----------|----------------------|
| 133 | 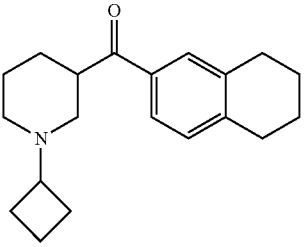 [SMILES: O=C(c1ccc2c(c1)CCCC2)C1CCCN(C2CCC2)C1] | 0.103 |
| 134 | 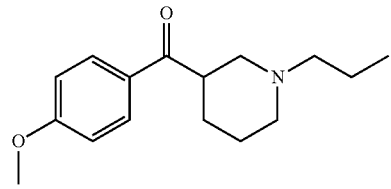 [SMILES: CCCN1CCCC(C(=O)c2ccc(OC)cc2)C1] | |
| 135 | 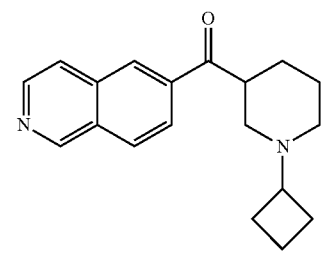 [SMILES: O=C(c1ccc2cnccc2c1)C1CCCN(C2CCC2)C1] | 0.226 |
| 136a | 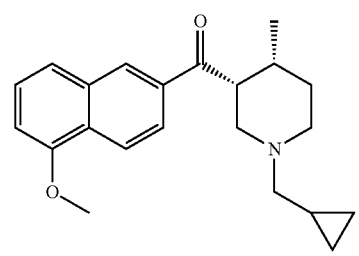 [SMILES: COc1cccc2cc(C(=O)[C@H]3CN(CC4CC4)CC[C@H]3C)ccc12] | 0.0414 |
| 136b | 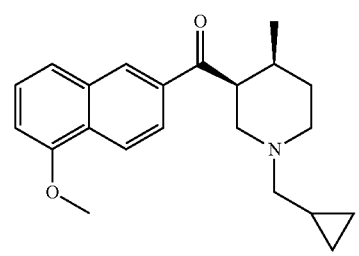 [SMILES: COc1cccc2cc(C(=O)[C@@H]3CN(CC4CC4)CC[C@@H]3C)ccc12] | 1.2 |
| 137a | 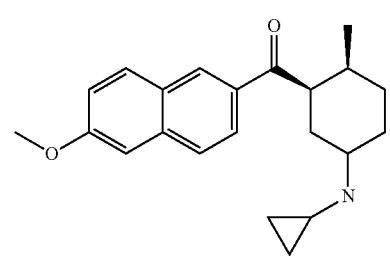 [SMILES: COc1ccc2cc(C(=O)[C@@H]3CC(NC4CC4)CC[C@@H]3C)ccc2c1] | 0.0706 |

TABLE-continued

| Example | Structure | KDM2B HTRF IC50 (uM) |
|---|---|---|
| 137b | 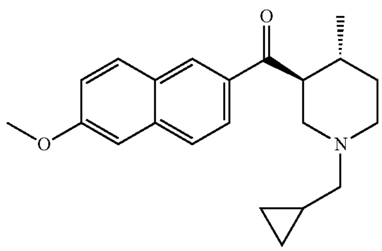 [SMILES: COc1ccc2cc(C(=O)[C@@H]3CN(CC4CC4)CC[C@H]3C)ccc2c1] | 0.0928 |
| 137c | 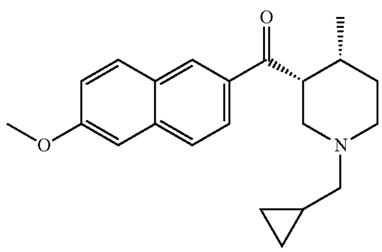 [SMILES: COc1ccc2cc(C(=O)[C@H]3CN(CC4CC4)CC[C@H]3C)ccc2c1] | 1.1 |
| 137d | 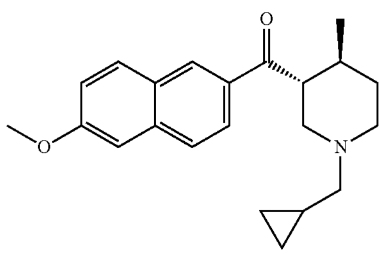 [SMILES: COc1ccc2cc(C(=O)[C@H]3CN(CC4CC4)CC[C@@H]3C)ccc2c1] | 3.3 |
| 138a | 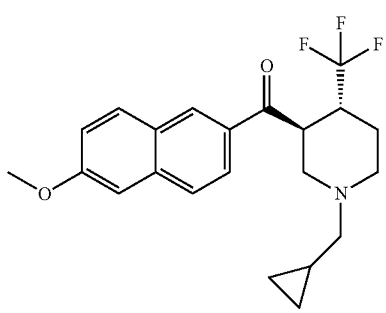 [SMILES: COc1ccc2cc(C(=O)[C@@H]3CN(CC4CC4)CC[C@H]3C(F)(F)F)ccc2c1] | 0.137 |
| 138b | 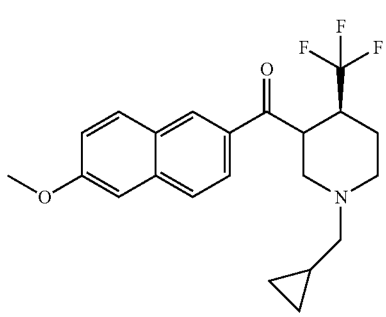 [SMILES: COc1ccc2cc(C(=O)C3CN(CC4CC4)CC[C@@H]3C(F)(F)F)ccc2c1] | 4.8 |

TABLE-continued

| Example | Structure | KDM2B HTRF IC50 (uM) |
|---------|-----------|----------------------|
| 139a | 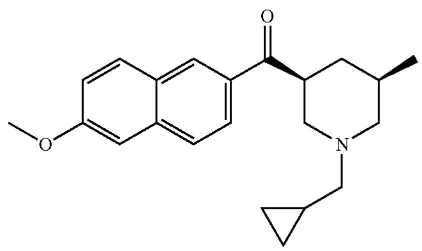 | 0.333 |
| 139b | 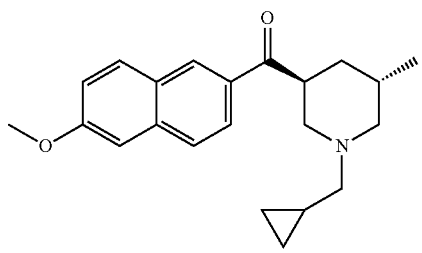 | 9.7+ |
| 140a | 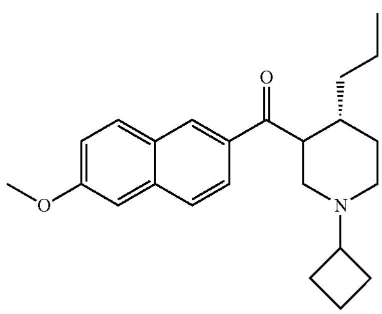 [SMILES: CCC[C@@H]1CCN(C2CCC2)CC1C(=O)c1ccc2cc(OC)ccc2c1] | 0.31 |
| 140b | 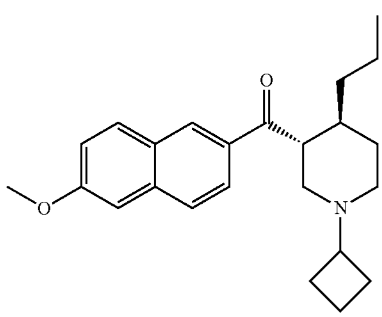 [SMILES: CCC[C@H]1CCN(C2CCC2)C[C@@H]1C(=O)c1ccc2cc(OC)ccc2c1] | 0.328 |
| 140c | 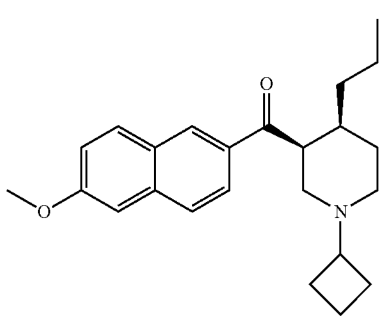 [SMILES: CCC[C@H]1CCN(C2CCC2)C[C@H]1C(=O)c1ccc2cc(OC)ccc2c1] | 0.00548 |

TABLE-continued
| Example | Structure | KDM2B HTRF IC50 (uM) |
|---|---|---|
| 140d | 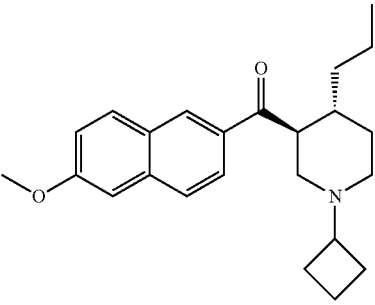 [SMILES: CCC[C@@H]1CCN(C2CCC2)C[C@H]1C(=O)c1ccc2cc(OC)ccc2c1] | 0.00996 |
| 141a | 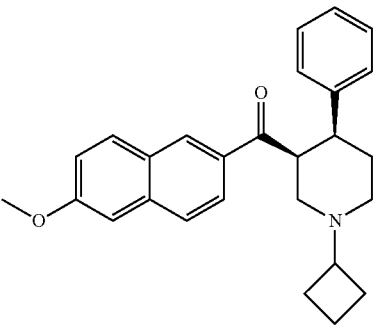 [SMILES: COc1ccc2cc(C(=O)[C@@H]3CN(C4CCC4)CC[C@@H]3c3ccccc3)ccc2c1] | 1 |
| 141b | 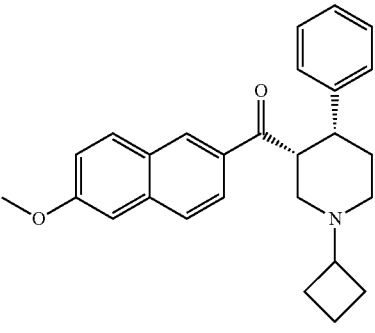 [SMILES: COc1ccc2cc(C(=O)[C@H]3CN(C4CCC4)CC[C@H]3c3ccccc3)ccc2c1] | 0.0987 |
| 142a | 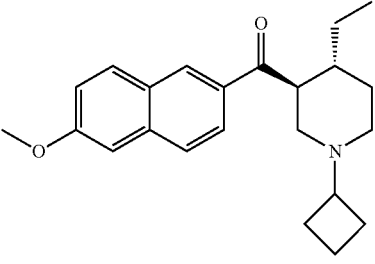 [SMILES: CC[C@@H]1CCN(C2CCC2)C[C@H]1C(=O)c1ccc2cc(OC)ccc2c1] | 0.0114 |
| 142b | 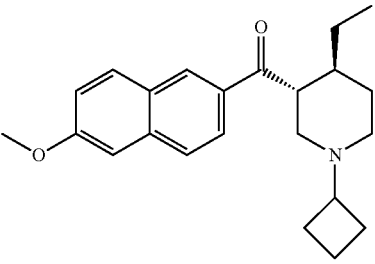 [SMILES: CC[C@H]1CCN(C2CCC2)C[C@@H]1C(=O)c1ccc2cc(OC)ccc2c1] | 0.349 |

TABLE-continued

| Example | Structure | KDM2B HTRF IC50 (uM) |
|---|---|---|
| 142c | 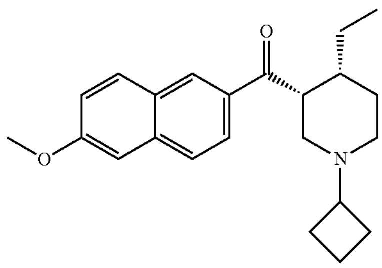 [SMILES: CC[C@@H]1CCN(C2CCC2)C[C@@H]1C(=O)c1ccc2cc(OC)ccc2c1] | 0.207 |
| 142d | 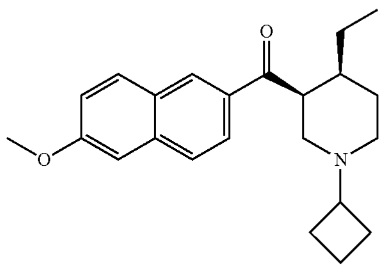 [SMILES: CC[C@H]1CCN(C2CCC2)C[C@H]1C(=O)c1ccc2cc(OC)ccc2c1] | 0.00656 |
| 143a | 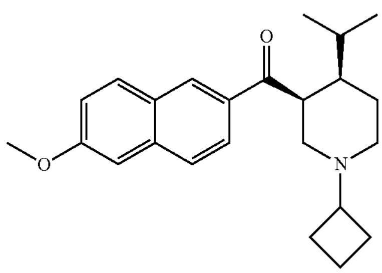 [SMILES: COc1ccc2cc(C(=O)[C@@H]3CN(C4CCC4)CC[C@@H]3C(C)C)ccc2c1] | 0.635 |
| 143b | 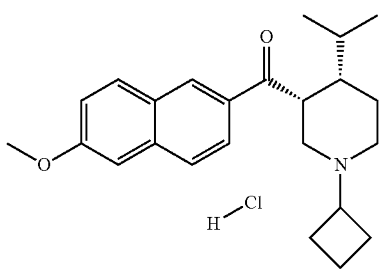 [SMILES: COc1ccc2cc(C(=O)[C@H]3CN(C4CCC4)CC[C@H]3C(C)C)ccc2c1 ; Cl] | 0.0159 |
| 144a | 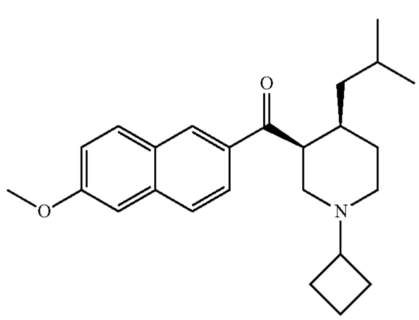 [SMILES: COc1ccc2cc(C(=O)[C@@H]3CN(C4CCC4)CC[C@@H]3CC(C)C)ccc2c1] | 0.0056 |

TABLE-continued
| Example | Structure | KDM2B HTRF IC50 (uM) |
|---|---|---|
| 144b | 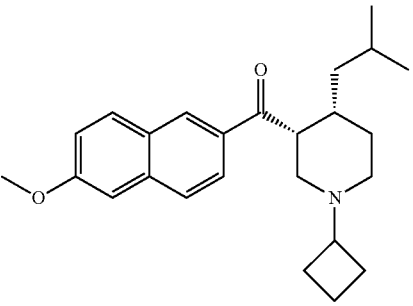 [SMILES: COc1ccc2cc(C(=O)[C@H]3CN(C4CCC4)CC[C@H]3CC(C)C)ccc2c1] | 0.269 |
| 145 | 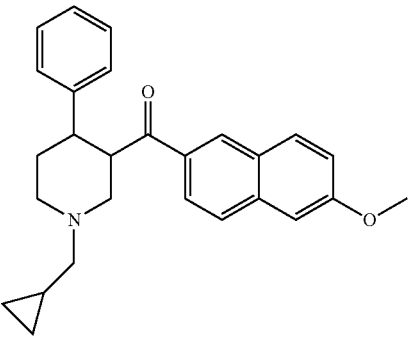 [SMILES: COc1ccc2cc(C(=O)C3CN(CC4CC4)CCC3c3ccccc3)ccc2c1] | 0.312 |
| 146a | 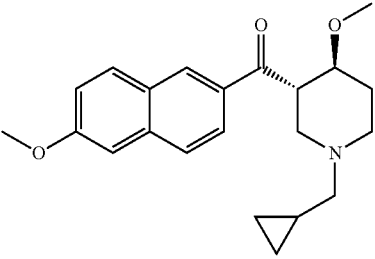 | 0.382 |
| 146b | 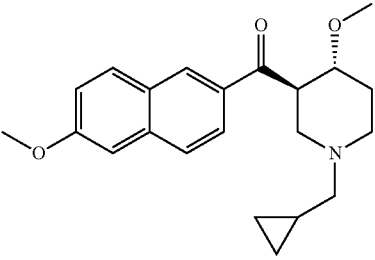 | 0.129 |
| 147a | 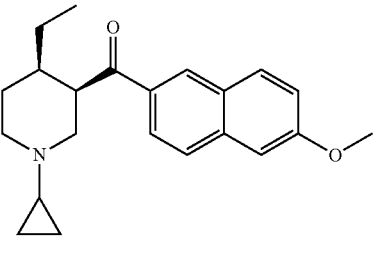 [SMILES: CC[C@@H]1CCN(C2CC2)C[C@@H]1C(=O)c1ccc2cc(OC)ccc2c1] | 2 |

TABLE-continued

| Example | Structure | KDM2B HTRF IC50 (uM) |
|---|---|---|
| 147b | 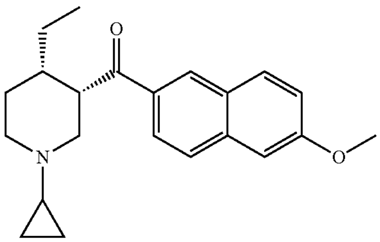 [SMILES: CC[C@H]1CCN(C2CC2)C[C@H]1C(=O)c1ccc2cc(OC)ccc2c1] | 0.0049 |
| 149 | 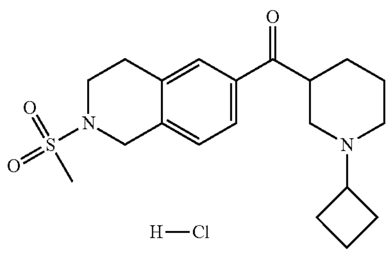 [SMILES: CS(=O)(=O)N1CCc2cc(C(=O)C3CCCN(C4CCC4)C3)ccc2C1 ; Cl] | 0.163 |
| 150 | 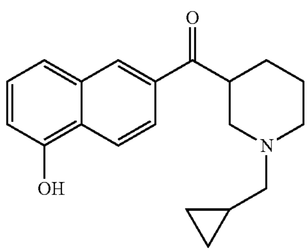 [SMILES: O=C(c1ccc2c(O)cccc2c1)C1CCCN(CC2CC2)C1] | 0.133 |
| 151a | 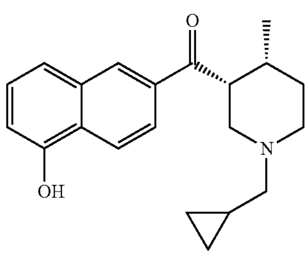 [SMILES: C[C@@H]1CCN(CC2CC2)C[C@@H]1C(=O)c1ccc2c(O)cccc2c1] | 0.315 |
| 151b | 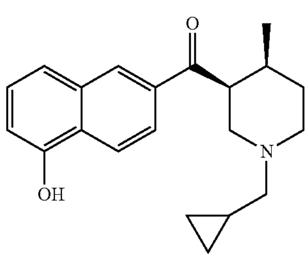 [SMILES: C[C@H]1CCN(CC2CC2)C[C@H]1C(=O)c1ccc2c(O)cccc2c1] | 0.0395 |
| 152 | 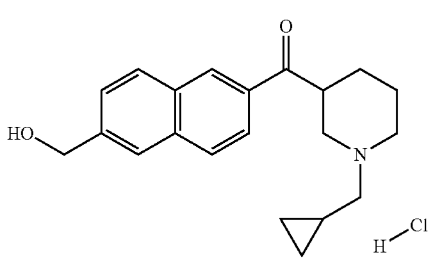 | 0.234 |

TABLE-continued

| Example | Structure | KDM2B HTRF IC50 (uM) |
|---------|-----------|----------------------|
| 153 | 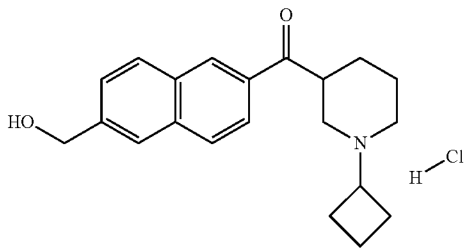 | 0.409 |
| 154 | 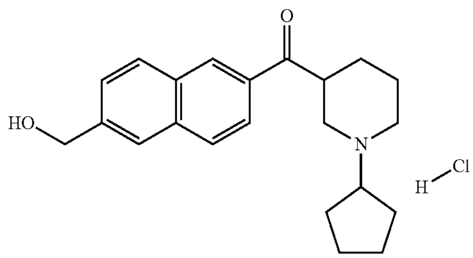 | 0.183 |
| 155 | 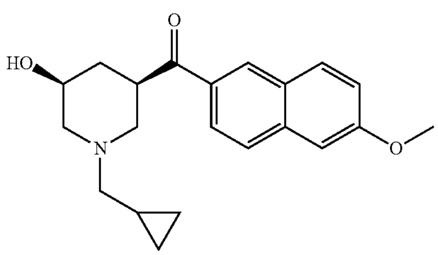 [SMILES: COc1ccc2cc(C(=O)[C@@H]3C[C@H](O)CN(CC4CC4)C3)ccc2c1] | 0.779 |
| 156a | 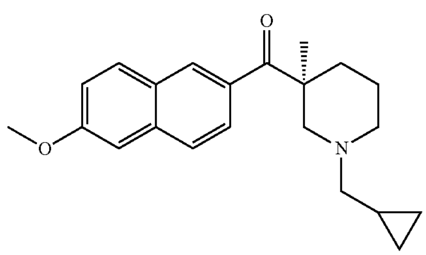 [SMILES: COc1ccc2cc(C(=O)[C@@]3(C)CCCN(CC4CC4)C3)ccc2c1] | 25++ |
| 156b | 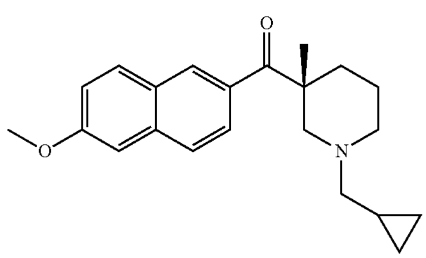 [SMILES: COc1ccc2cc(C(=O)[C@]3(C)CCCN(CC4CC4)C3)ccc2c1] | 25++ |
| 157 | 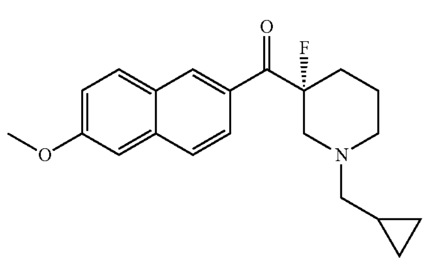 | 6.1 |

| Example | Structure | KDM2B HTRF IC50 (uM) |
|---|---|---|
| 158a | (6-methoxynaphthalen-2-yl)(3-hydroxy-1-(cyclopropylmethyl)piperidin-3-yl)methanone, R-enantiomer | 1.9 |
| 158b | (6-methoxynaphthalen-2-yl)(3-hydroxy-1-(cyclopropylmethyl)piperidin-3-yl)methanone, S-enantiomer | 11.5 |
| 159 | (6-cyanonaphthalen-2-yl)(1-(cyclopropylmethyl)piperidin-3-yl)methanone hydrochloride | 0.0688 |
| 160a | (6-cyanonaphthalen-2-yl)(trans-4-methyl-1-(cyclopropylmethyl)piperidin-3-yl)methanone | 1.7 |
| 160b | (6-cyanonaphthalen-2-yl)(trans-4-methyl-1-(cyclopropylmethyl)piperidin-3-yl)methanone, enantiomer | 0.113 |
| 161a | (6-cyanonaphthalen-2-yl)(trans-4-methyl-1-cyclobutylpiperidin-3-yl)methanone | 3 |

TABLE-continued

| Example | Structure | KDM2B HTRF IC50 (uM) |
|---------|-----------|----------------------|
| 161b | 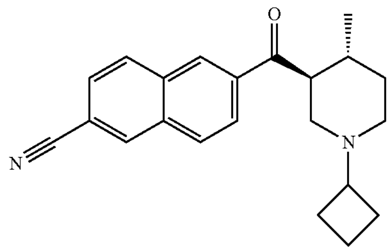 [SMILES: C[C@@H]1CCN(C2CCC2)C[C@H]1C(=O)c1ccc2cc(C#N)ccc2c1] | 0.0123 |
| 162a | 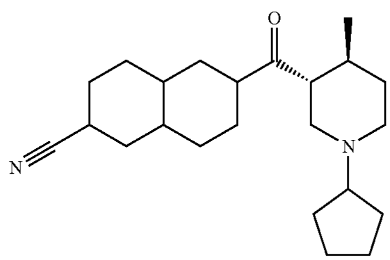 [SMILES: C[C@H]1CCN(C2CCCC2)C[C@@H]1C(=O)C1CCC2CC(C#N)CCC2C1] | 0.814 |
| 162b | 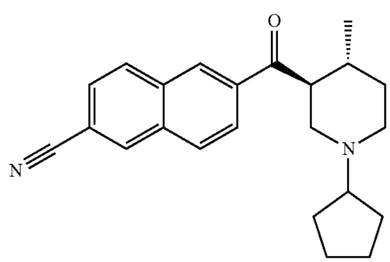 [SMILES: C[C@@H]1CCN(C2CCCC2)C[C@H]1C(=O)c1ccc2cc(C#N)ccc2c1] | 0.0857 |
| 163a | 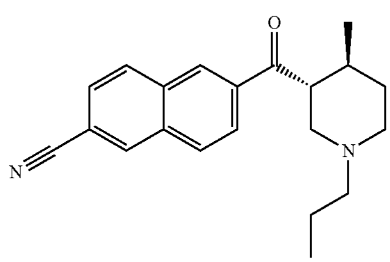 [SMILES: CCCN1CC[C@H](C)[C@@H](C(=O)c2ccc3cc(C#N)ccc3c2)C1] | 0.993 |
| 163b | 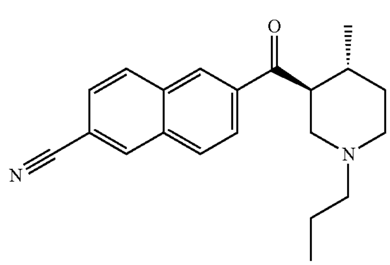 [SMILES: CCCN1CC[C@@H](C)[C@H](C(=O)c2ccc3cc(C#N)ccc3c2)C1] | 0.0454 |

TABLE-continued

| Example | Structure | KDM2B HTRF IC50 (uM) |
|---------|-----------|----------------------|
| 164 | 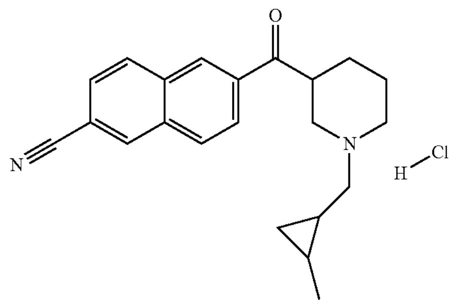 | 0.436 |
| 165 | 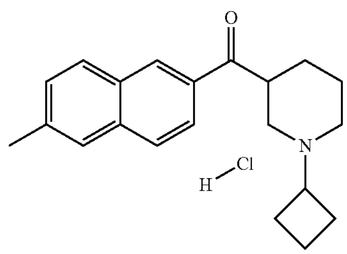 | 0.163 |
| 166 | 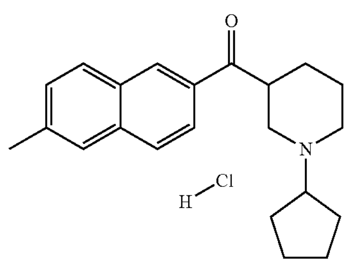 | 0.24 |
| 167 | 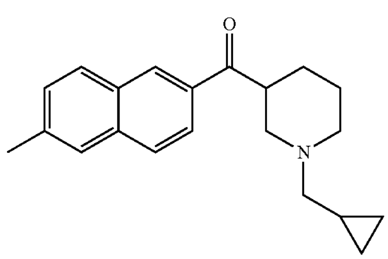 [SMILES: Cc1ccc2cc(C(=O)C3CCCN(CC4CC4)C3)ccc2c1] | 0.171 |
| 168 | 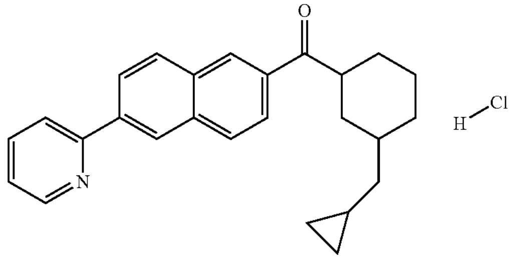 | 0.182 |

TABLE-continued
| Example | Structure | KDM2B HTRF IC50 (uM) |
|---|---|---|
| 169 | 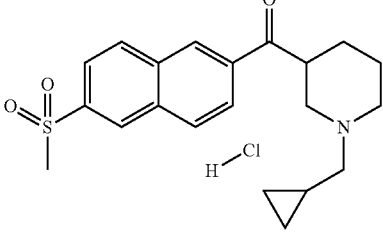 | 0.112 |
| 170 | 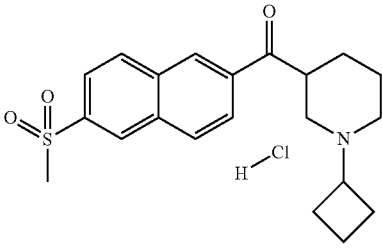 | 0.0426 |
| 171 | 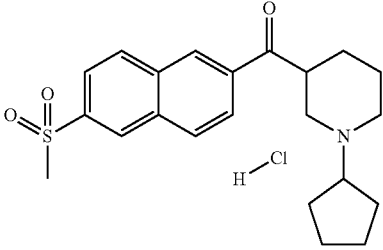 | 0.102 |
| 172 | 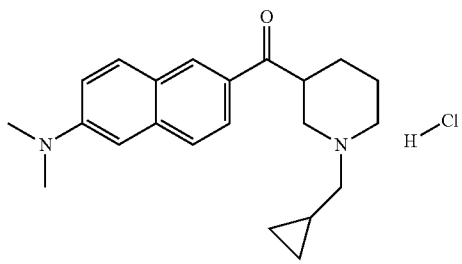 | 0.316 |
| 173 | 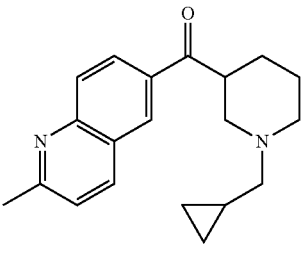 [SMILES: Cc1ccc2cc(C(=O)C3CCCN(CC4CC4)C3)ccc2n1] | 0.255 |
| 174 | 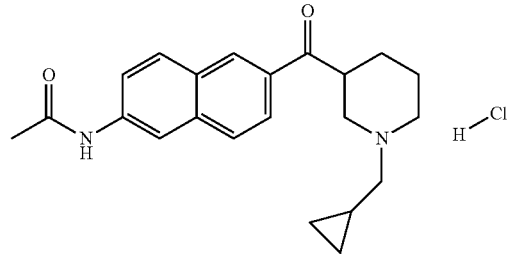 | 1.8 |

TABLE-continued

| Example | Structure | KDM2B HTRF IC50 (uM) |
|---|---|---|
| 175 | 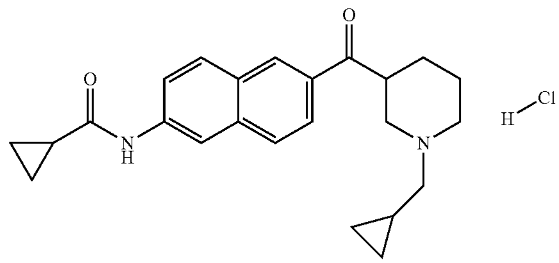 | 0.355 |
| 176 | 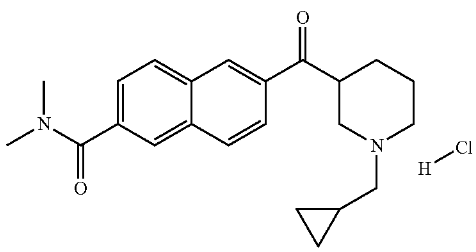 | 0.214 |
| 177 | 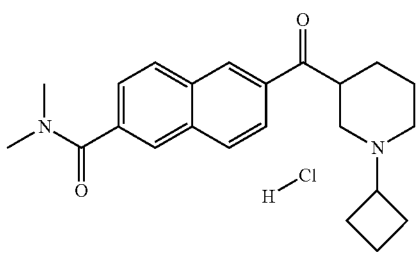 [SMILES: CN(C)C(=O)c1ccc2cc(C(=O)C3CCCN(C4CCC4)C3)ccc2c1 ; Cl] | 0.113 |
| 178 | 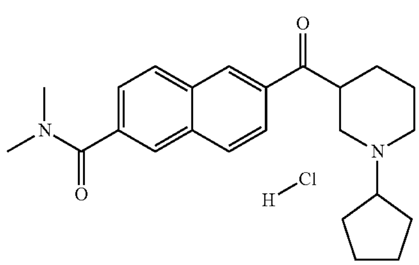 | 0.188 |
| 179a | 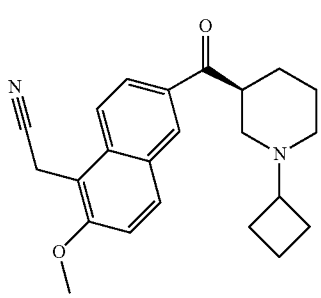 [SMILES: COc1ccc2cc(C(=O)[C@H]3CCCN(C4CCC4)C3)ccc2c1CC#N] | 0.00565 |

TABLE-continued

| Example | Structure | KDM2B HTRF IC50 (uM) |
|---|---|---|
| 179b | 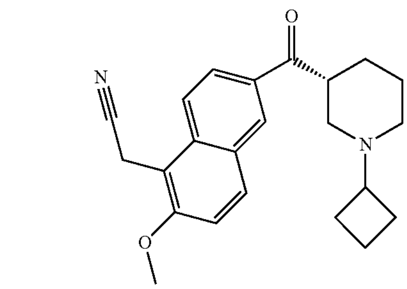 [SMILES: COc1ccc2cc(C(=O)[C@@H]3CCCN(C4CCC4)C3)ccc2c1CC#N] | 0.361 |
| 180 | 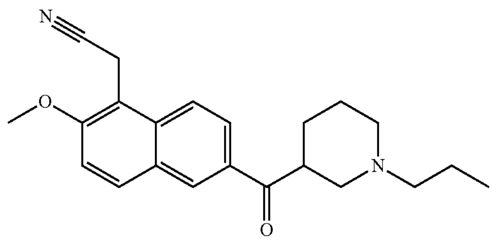 [SMILES: CCCN1CCCC(C(=O)c2ccc3c(CC#N)c(OC)ccc3c2)C1] | |
| 181a | 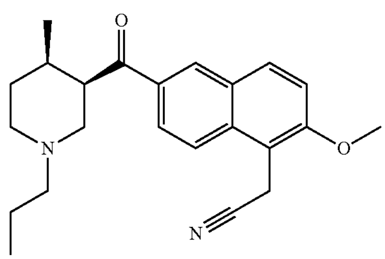 [SMILES: CCCN1CC[C@@H](C)[C@@H](C(=O)c2ccc3c(CC#N)c(OC)ccc3c2)C1] | 1.3 |
| 181b | 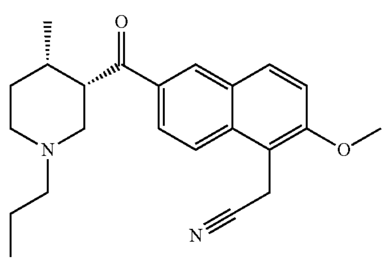 [SMILES: CCCN1CC[C@H](C)[C@H](C(=O)c2ccc3c(CC#N)c(OC)ccc3c2)C1] | 0.0123 |
| 182a | 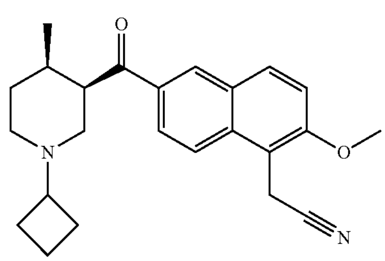 [SMILES: COc1ccc2cc(C(=O)[C@H]3CN(C4CCC4)CC[C@H]3C)ccc2c1CC#N] | 0.29 |
| 182b | 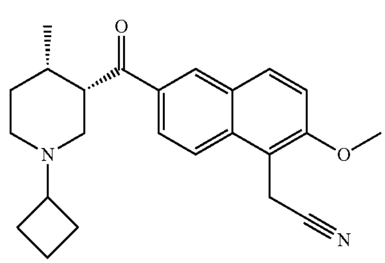 [SMILES: COc1ccc2cc(C(=O)[C@@H]3CN(C4CCC4)CC[C@@H]3C)ccc2c1CC#N] | 0.00112 |

TABLE-continued

| Example | Structure | KDM2B HTRF IC50 (uM) |
|---|---|---|
| 183a | 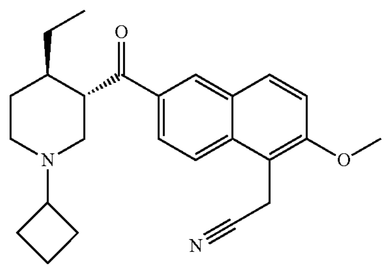 [SMILES: CC[C@@H]1CCN(C2CCC2)C[C@H]1C(=O)c1ccc2c(CC#N)c(OC)ccc2c1] | 0.0552 |
| 183b | 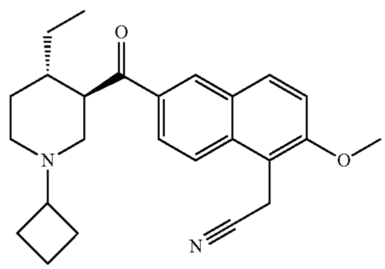 [SMILES: CC[C@H]1CCN(C2CCC2)C[C@@H]1C(=O)c1ccc2c(CC#N)c(OC)ccc2c1] | 0.00206 |
| 183c | 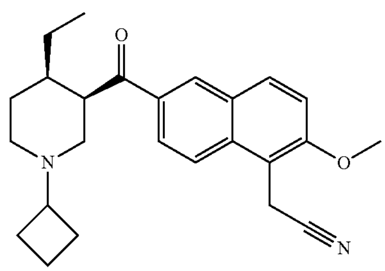 [SMILES: CC[C@@H]1CCN(C2CCC2)C[C@@H]1C(=O)c1ccc2c(CC#N)c(OC)ccc2c1] | 0.078 |
| 183d | 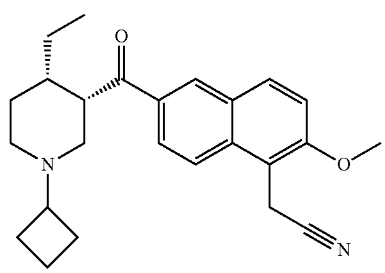 [SMILES: CC[C@H]1CCN(C2CCC2)C[C@H]1C(=O)c1ccc2c(CC#N)c(OC)ccc2c1] | 0.00153 |
| 184a | 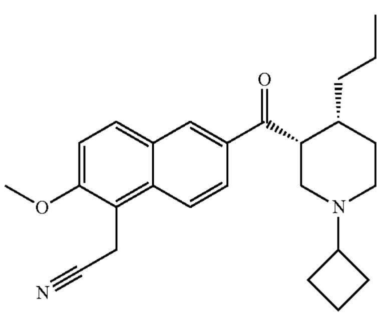 [SMILES: CCC[C@@H]1CCN(C2CCC2)C[C@@H]1C(=O)c1ccc2c(CC#N)c(OC)ccc2c1] | 0.0774 |

TABLE-continued

| Example | Structure | KDM2B HTRF IC50 (uM) |
|---------|-----------|----------------------|
| 184b | 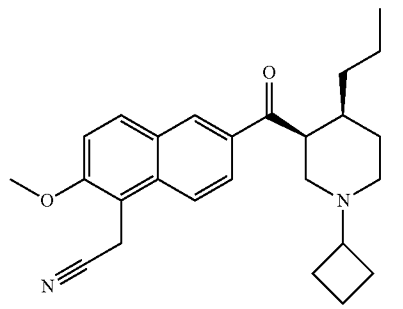 [SMILES: CCC[C@H]1CCN(C2CCC2)C[C@H]1C(=O)c1ccc2c(CC#N)c(OC)ccc2c1] | 0.00141 |
| 184c | 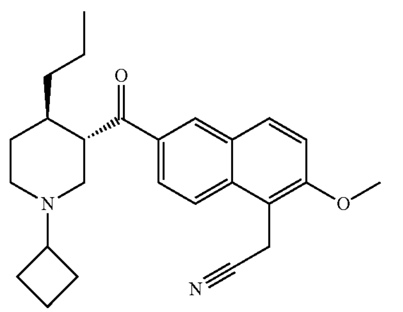 [SMILES: CCC[C@@H]1CCN(C2CCC2)C[C@H]1C(=O)c1ccc2c(CC#N)c(OC)ccc2c1] | 0.00313 |
| 184d | 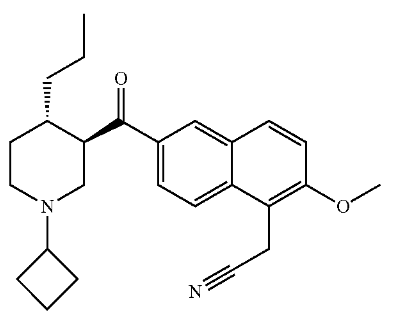 [SMILES: CCC[C@H]1CCN(C2CCC2)C[C@@H]1C(=O)c1ccc2c(CC#N)c(OC)ccc2c1] | 0.263 |
| 185a | 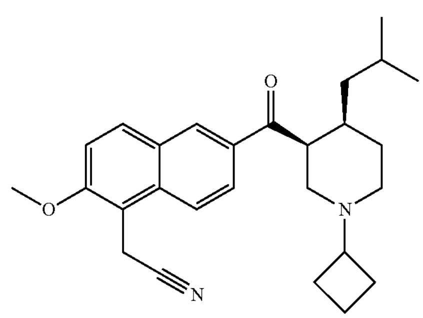 [SMILES: COc1ccc2cc(C(=O)[C@@H]3CN(C4CCC4)CC[C@@H]3CC(C)C)ccc2c1CC#N] | 0.0535 |
| 185b | 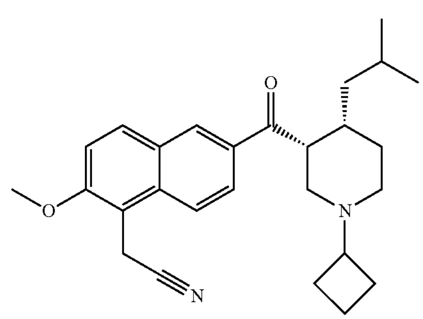 [SMILES: COc1ccc2cc(C(=O)[C@H]3CN(C4CCC4)CC[C@H]3CC(C)C)ccc2c1CC#N] | 0.002 |

TABLE-continued
| Example | Structure | KDM2B HTRF IC50 (uM) |
|---|---|---|
| 186a | 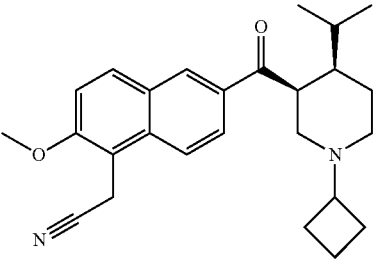 [SMILES: COc1ccc2cc(C(=O)[C@@H]3CN(C4CCC4)CC[C@@H]3C(C)C)ccc2c1CC#N] | 0.0701 |
| 186b | 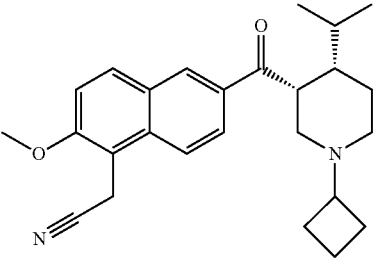 [SMILES: COc1ccc2cc(C(=O)[C@H]3CN(C4CCC4)CC[C@H]3C(C)C)ccc2c1CC#N] | 0.00212 |
| 188 | 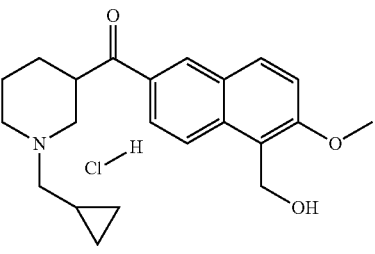 | 0.133 |
| 189 | 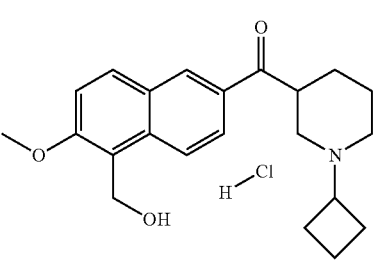 | 0.0553 |
| 190 | 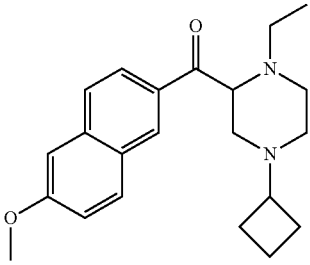 [SMILES: CCN1CCN(C2CCC2)CC1C(=O)c1ccc2cc(OC)ccc2c1] | 0.979 |

TABLE-continued

| Example | Structure | KDM2B HTRF IC50 (uM) |
|---|---|---|
| 191 | 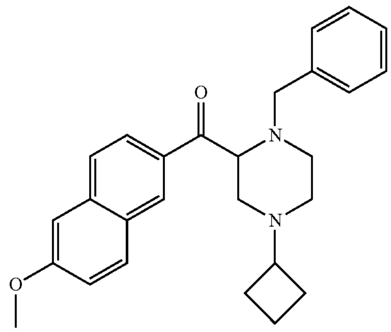 [SMILES: COc1ccc2cc(C(=O)C3CN(C4CCC4)CCN3Cc3ccccc3)ccc2c1] | 0.102 |
| 192 | 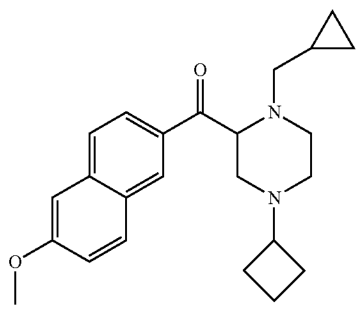 [SMILES: COc1ccc2cc(C(=O)C3CN(C4CCC4)CCN3CC3CC3)ccc2c1] | 0.385 |
| 193 | 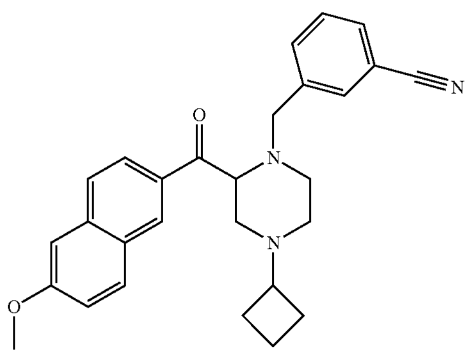 [SMILES: COc1ccc2cc(C(=O)C3CN(C4CCC4)CCN3Cc3cccc(C#N)c3)ccc2c1] | 0.0223 |
| 194 | 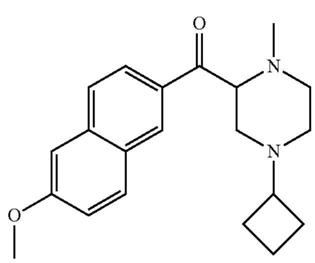 [SMILES: COc1ccc2cc(C(=O)C3CN(C4CCC4)CCN3C)ccc2c1] | 1.7 |

TABLE-continued

| Example | Structure | KDM2B HTRF IC50 (uM) |
|---------|-----------|----------------------|
| 195 | 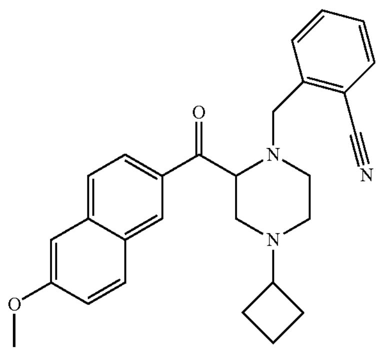 [SMILES: COc1ccc2cc(C(=O)C3CN(C4CCC4)CCN3Cc3ccccc3C#N)ccc2c1] | 0.176 |
| 196 | 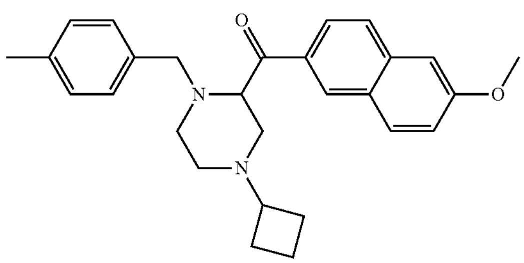 | 0.138 |
| 197 | 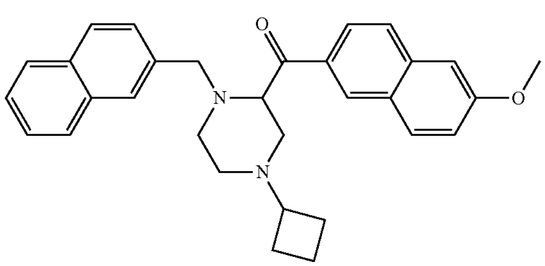 [SMILES: COc1ccc2cc(C(=O)C3CN(C4CCC4)CCN3Cc3ccc4ccccc4c3)ccc2c1] | 0.165 |
| 198 | 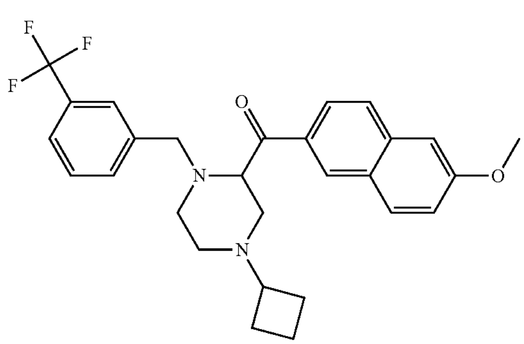 [SMILES: COc1ccc2cc(C(=O)C3CN(C4CCC4)CCN3Cc3cccc(C(F)(F)F)c3)ccc2c1] | 0.302 |

TABLE-continued

| Example | Structure | KDM2B HTRF IC50 (uM) |
|---|---|---|
| 199 | 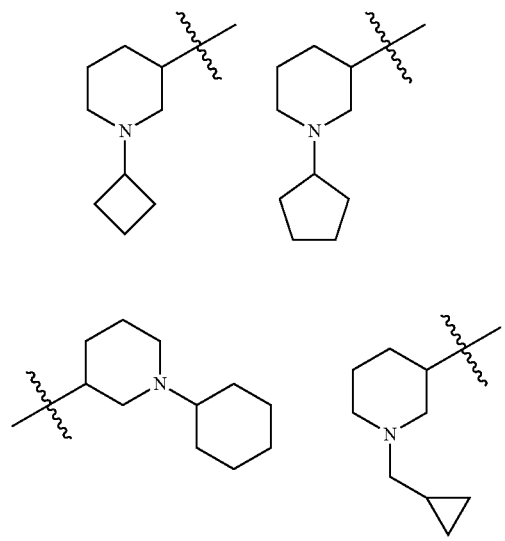 | 0.0309 |

While a number of embodiments have been described, these examples may be altered to provide other embodiments that utilize the compounds and methods described herein. Therefore, the scope of this invention is to be defined by the appended claims rather than by the specific embodiments that have been represented by way of example.

We claim:

1. A compound of formula (I):

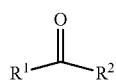

(I)

or a salt thereof, wherein:

$R^1$ is:

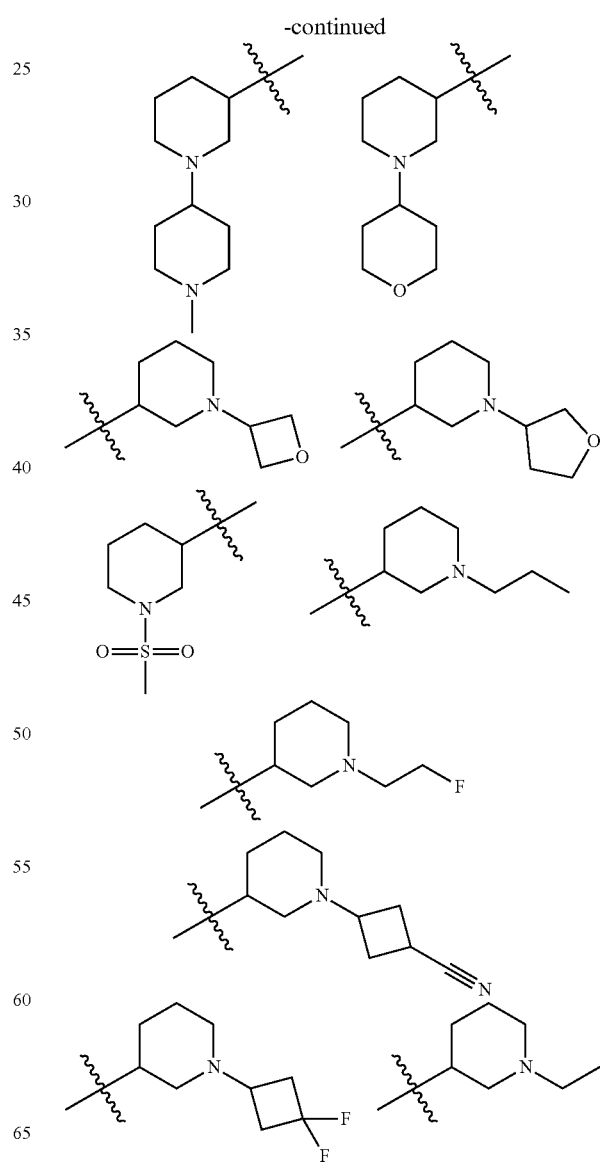

321
-continued
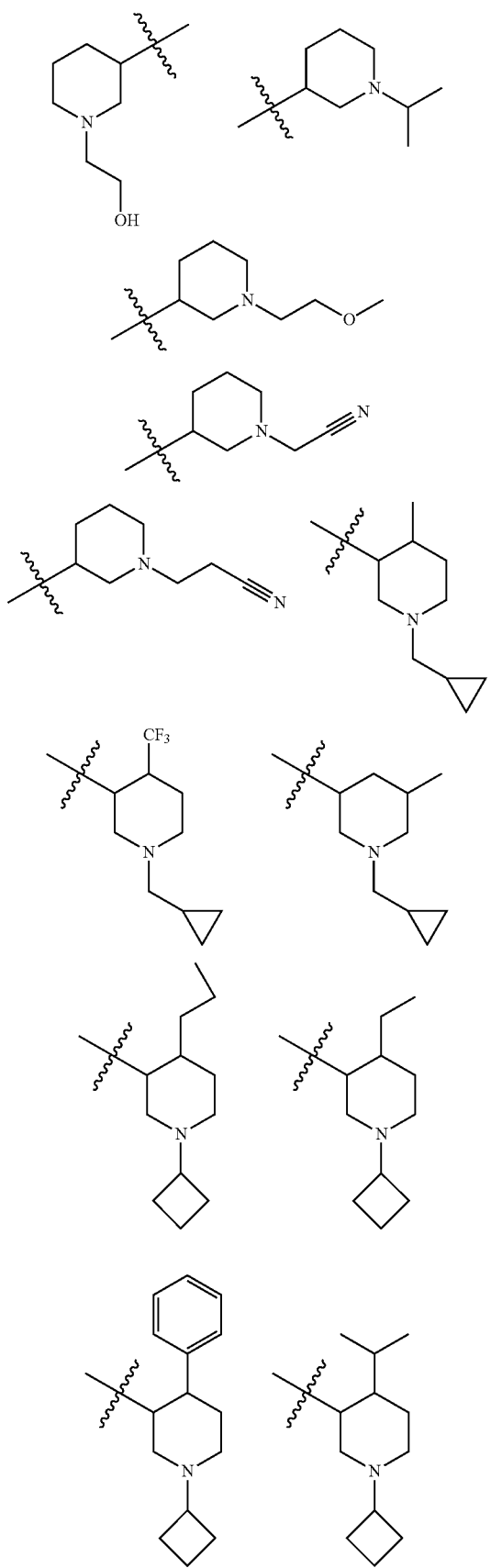
322
-continued
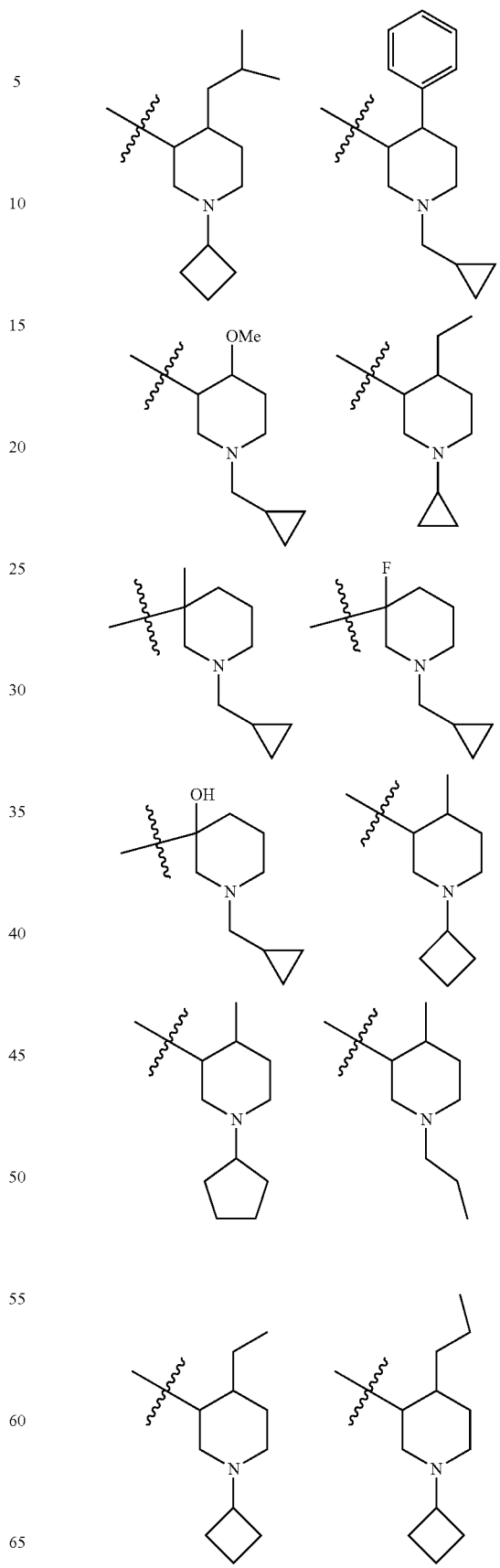

323
-continued
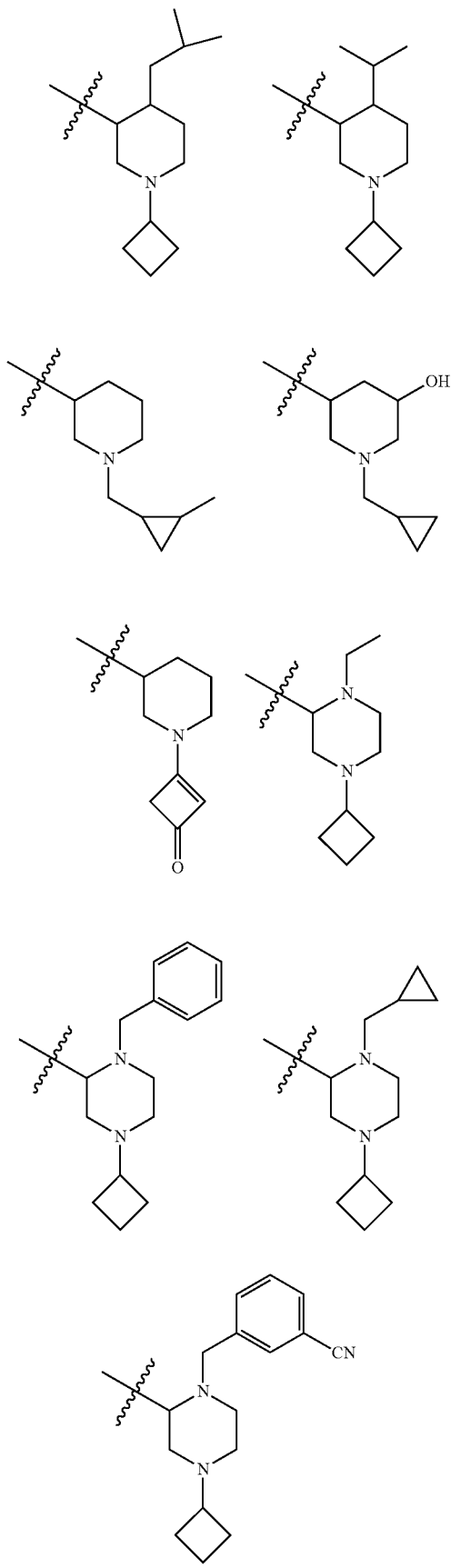
324
-continued
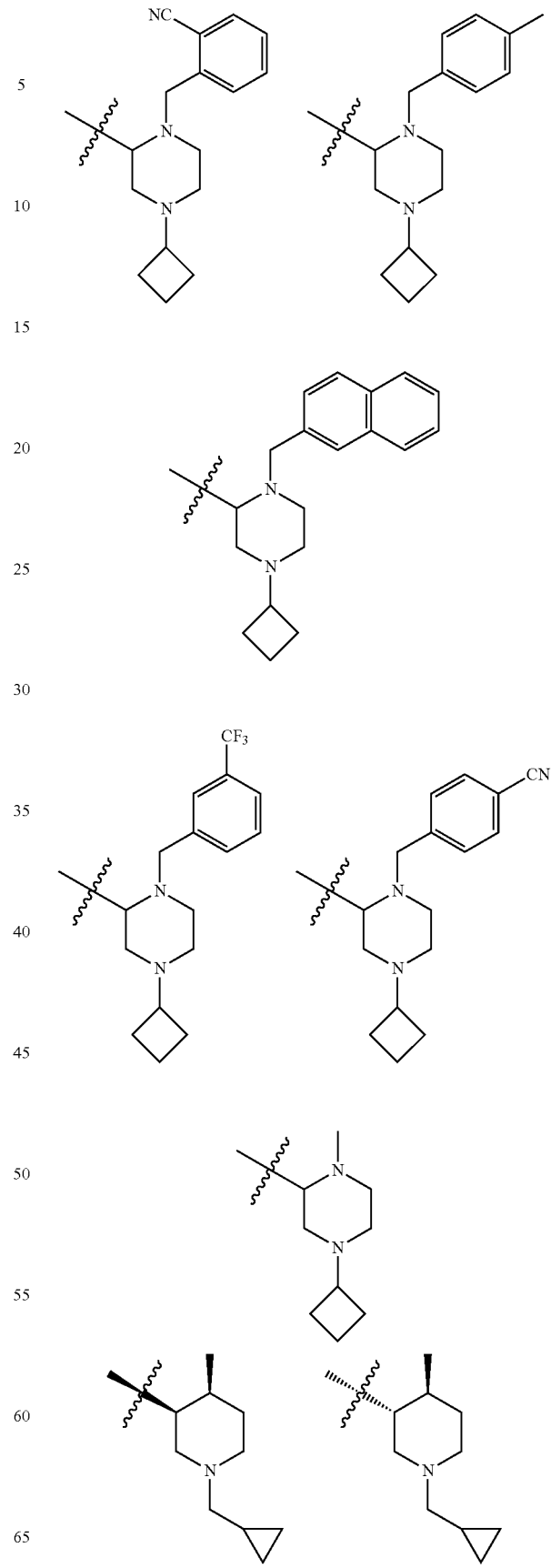

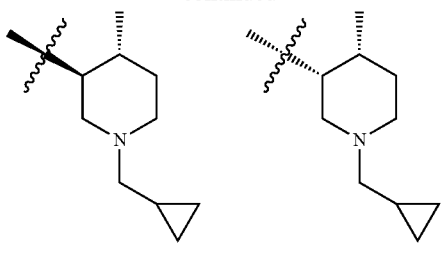
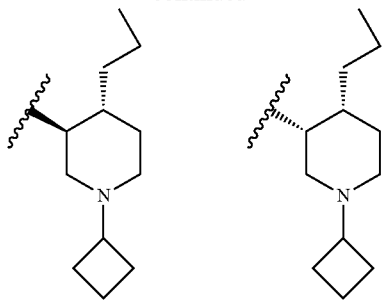

327
-continued
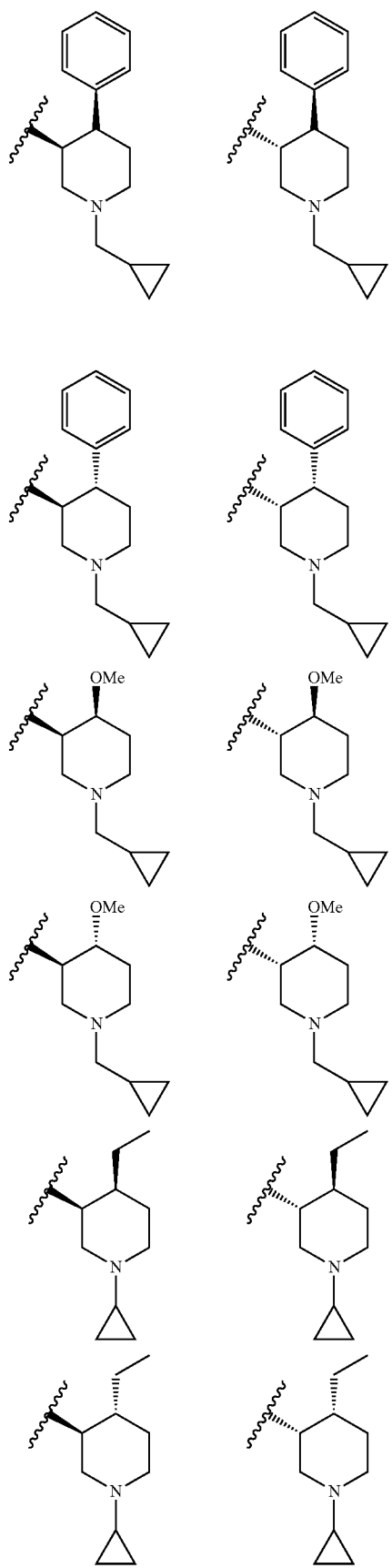
328
-continued
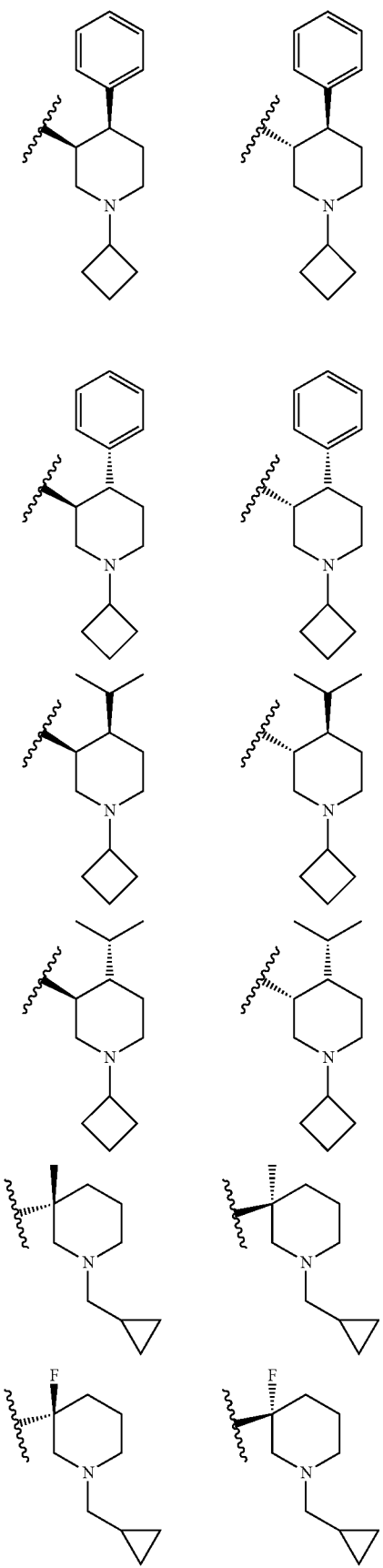

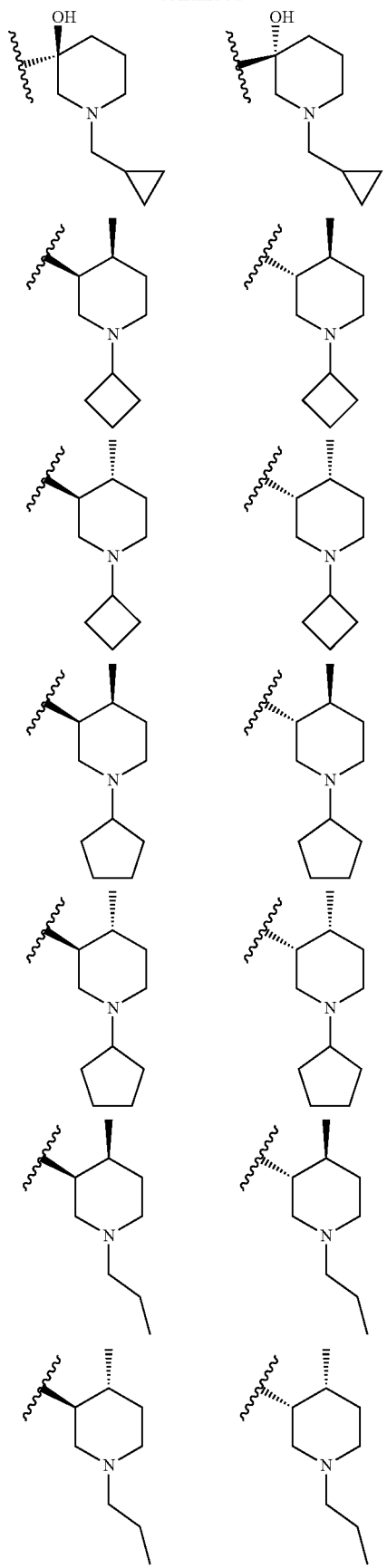
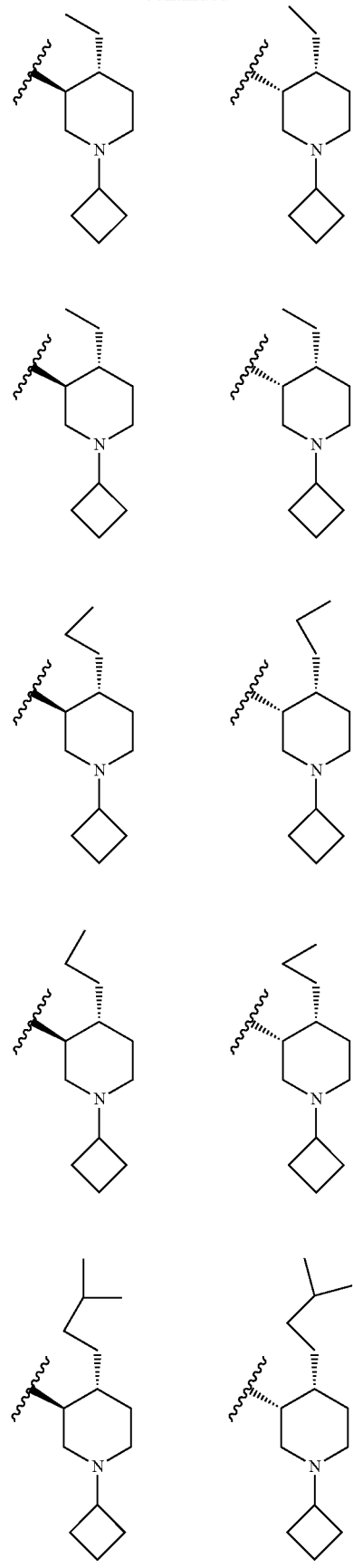

-continued

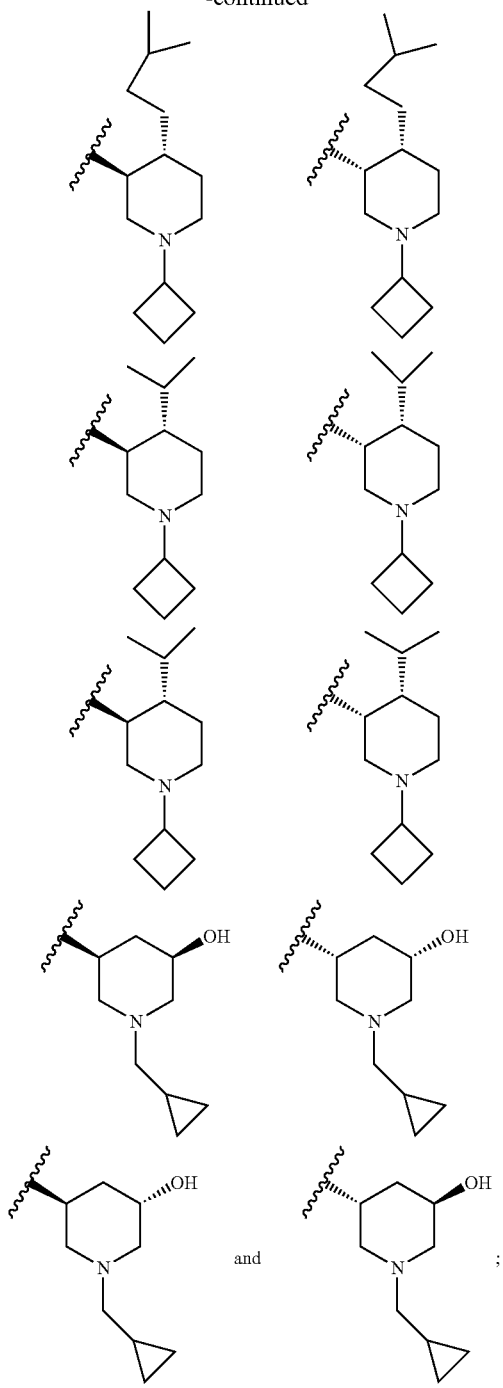

$R^2$ is a 5-10 membered heteroaryl or a 6-12 membered aryl, which 5-10 membered heteroaryl, and 6-12 membered aryl is optionally substituted with one or more groups independently selected from the group consisting of $C_{1-6}$alkyl, $C_{2-6}$alkenyl, $C_{2-6}$alkynyl, carbocycle, heterocycle, aryl, heteroaryl, halo, $-NO_2$, $-N(R^d)_2$, $-CN$, $-C(O)-N(R^d)_2$, $-S(O)-N(R^d)_2$, $-S(O)_2-N(R^d)_2$, $-O-R^d$, $-S-R^d$, $-O-C(O)-R^d$, $-C(O)-R^d$, $-C(O)-OR^d$, $-S(O)-R^d$, $-S(O)_2-R^d$, $-N(R^d)-C(O)-R^d$, $-N(R^d)-S(O)-R^d$, $-N(R^d)-C(O)-N(R^d)_2$, and $-N(R^d)-S(O)_2-R^d$; wherein each $C_{1-6}$alkyl, $C_{2-6}$alkenyl, $C_{2-6}$alkynyl, carbocycle, heterocycle, aryl, and heteroaryl is optionally substituted with one or more groups independently selected from the group consisting of halo, $-NO_2$, $-N(R^d)_2$, $-CN$, $-C(O)-N(R^d)_2$, $-S(O)-N(R^d)_2$, $-S(O)_2-N(R^d)_2$, $-O-R^d$, $-S-R^d$, $-O-C(O)-R^d$, $-C(O)-R^d$, $-C(O)-OR^d$, $-S(O)-R^d$, $-S(O)_2-R^d$, $-N(R^d)-C(O)-R^d$, $-N(R^d)-S(O)-R^d$, $-N(R^d)-C(O)-N(R^d)_2$, $-N(R^d)-S(O)_2-R^d$, and $C_{1-6}$alkyl that is optionally substituted with one or more groups independently selected from halo;

each $R^d$ is independently selected from the group consisting of hydrogen, $C_{1-6}$alkyl, $C_{2-6}$alkenyl, aryl, and $C_{2-6}$alkynyl, wherein each $C_{1-6}$alkyl, $C_{2-6}$alkenyl, aryl, and $C_{2-6}$alkynyl is optionally substituted with one or more groups independently selected from the group consisting of halo, $-N(R^e)_2$, $-CN$, $-C(O)-N(R^e)_2$, $-S(O)-N(R^e)_2$, $-S(O)_2-N(R^e)_2$, $-O-R^e$, $-S-R^e$, $-O-C(O)-R^e$, $-C(O)-R^e$, $-C(O)-OR^e$, $-S(O)-R^e$, $-S(O)_2-R^e$, $-N(R^e)-C(O)-R^e$, $-N(R^c)-S(O)-R^e$, $-N(R^e)-C(O)-N(R^e)_2$, and $-N(R^e)-S(O)_2-R^e$; or two $R^d$ are taken together with the nitrogen to which they are attached to form a pyrrolidino, piperidino, or piperazino ring; and each $R^e$ is independently selected from the group consisting of hydrogen, $C_{1-6}$alkyl, $C_{2-6}$alkenyl, and $C_{2-6}$alkynyl, wherein each $C_{1-6}$alkyl, $C_{2-6}$alkenyl, and $C_{2-6}$alkynyl is optionally substituted with one or more groups independently selected from the group consisting of oxo, halo, amino, hydroxy, and $C_{1-6}$alkoxy; or two $R^e$ are taken together with the nitrogen to which they are attached to form a heterocyclyl that is optionally substituted with one or more groups independently selected from the group consisting of oxo, halo and $C_{1-3}$alkyl that is optionally substituted with one or more groups independently selected from the group consisting of oxo and halo;

provided that when $R^2$ is 6-methoxy-2-naphthyl, then $R^1$ is not 1-(cyclopropylmethyl)piperidin-3-yl, 1-(cyclobutyl)piperidin-3-yl, 1-(cyclopentyl)piperidin-3-yl, or 1-(tetrahydropyranyl)piperidin-3-yl; and provided that when $R^2$ is phenyl, naphthyl, 4-quinolyl, 5-quinolyl, 6-quinolyl, 7-quinolyl, 8-quinolyl, 2-methyl-6-quinolyl, 1,5-benzodioxepin-7-yl, benzo[b]thien-7-yl, 2,3-dihydro-1,4-benzodioxin-6-yl, 1H-1-(tert-butoxycarbonyl)-4-bromo-indol-2-yl, 1H-1-(tert-butoxycarbonyl)-4-cyano-indol-2-yl, 3,4-dihydroxyphenyl, 3-methoxy-4-hydroxyphenyl, 3,4-dimethoxyphenyl, 3-methoxycarbonyl-4-hydroxyphenyl, 4-hydroxyphenyl, or 2-hydroxyphenyl, then $R^1$ is not optionally substituted piperizin-2-yl.

2. The compound of claim 1 wherein $R^1$ is selected from the group consisting of:

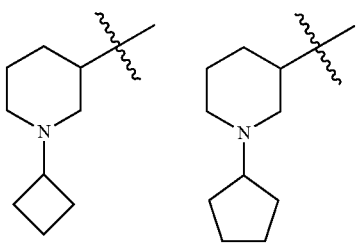

333
-continued
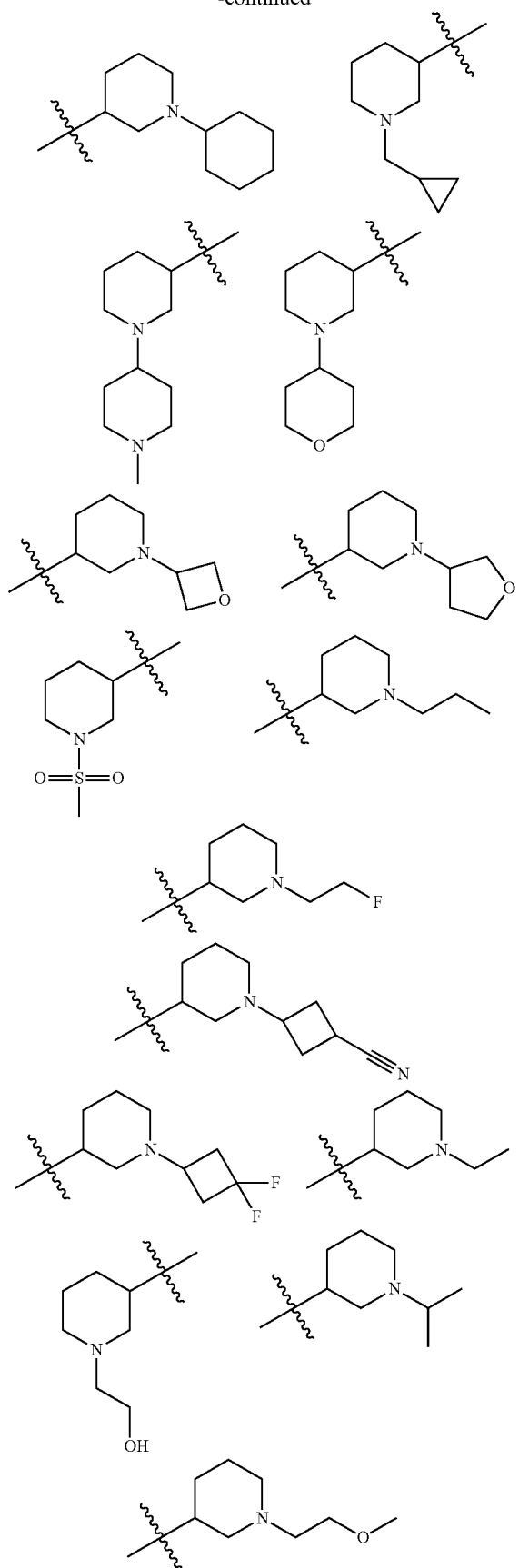
334
-continued
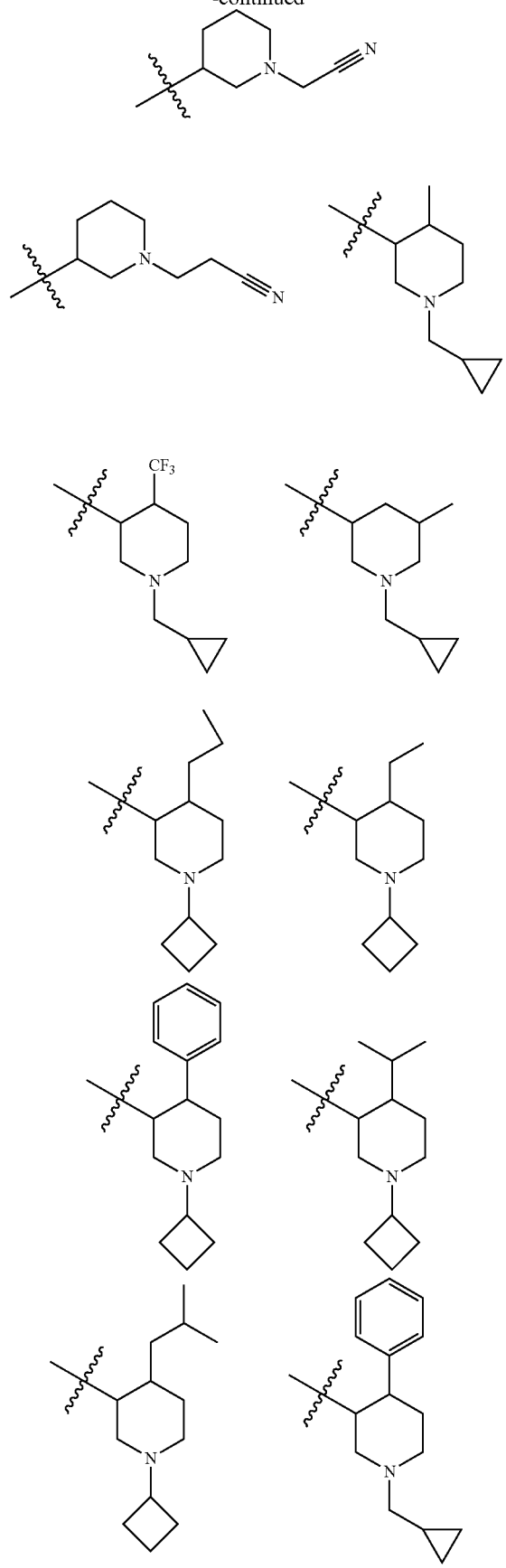

335
-continued
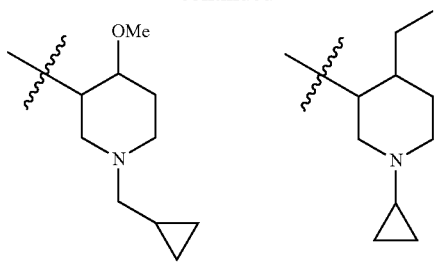
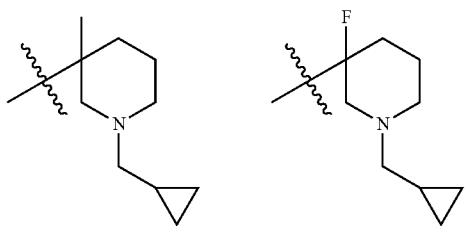
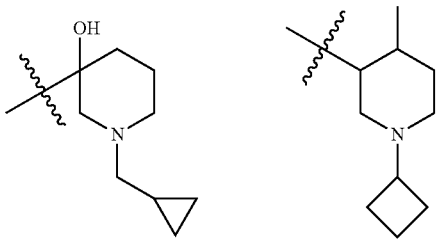
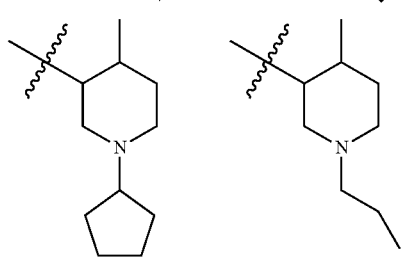
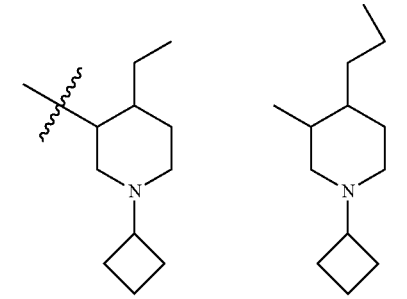
336
-continued
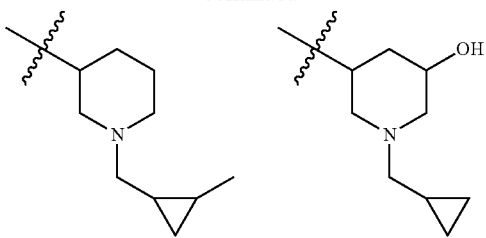
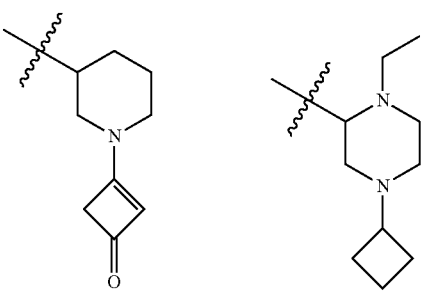
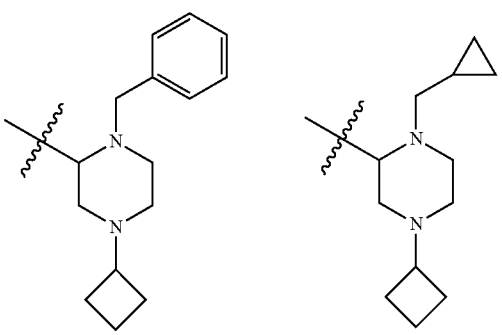
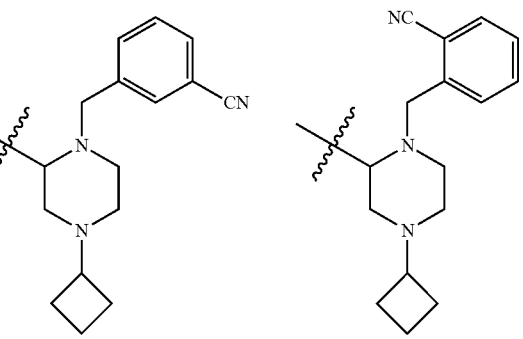
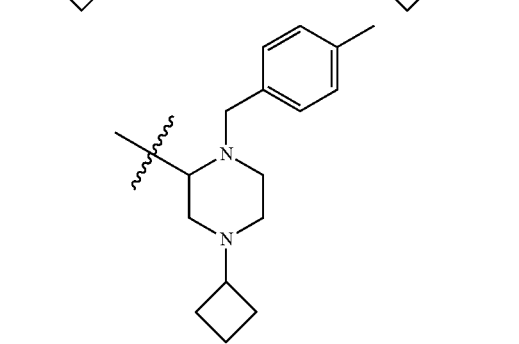

337
-continued
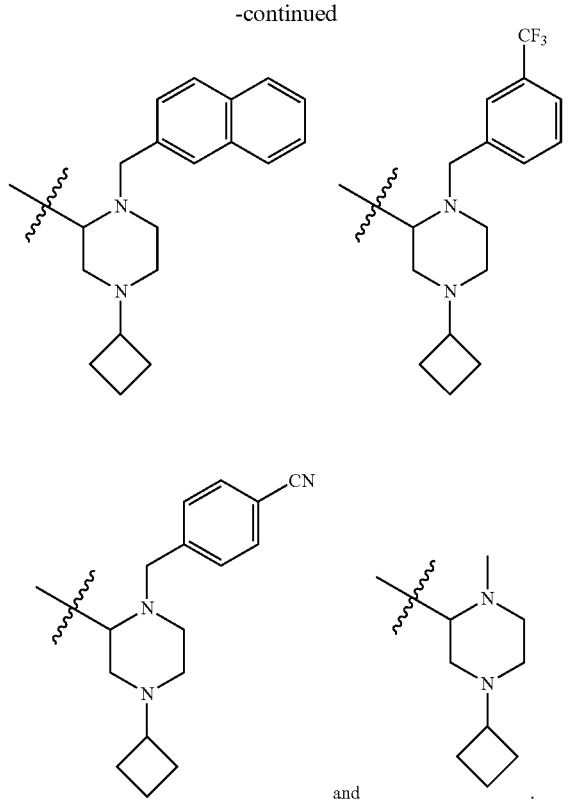
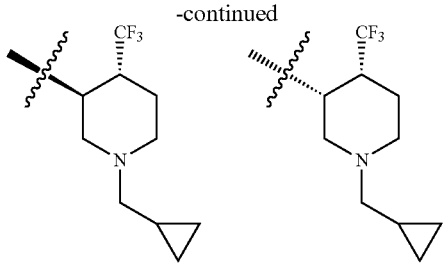
3. The compound of claim 1 wherein $R^1$ is selected from the group consisting of:
338
-continued
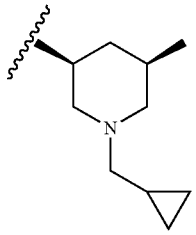
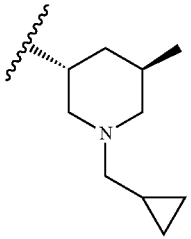
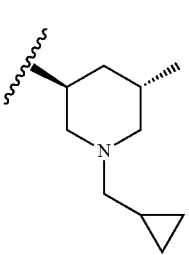
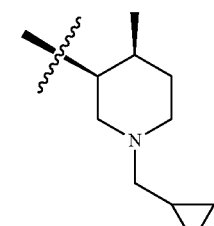
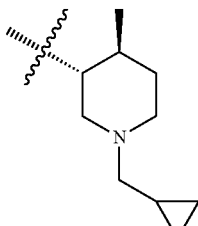
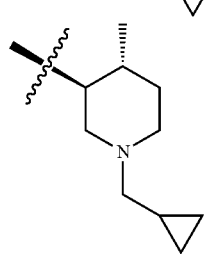
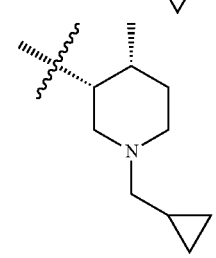
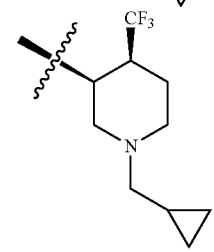
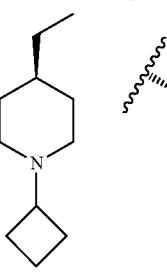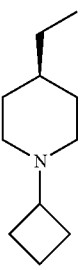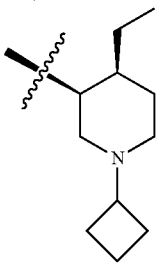

339
-continued
340
-continued
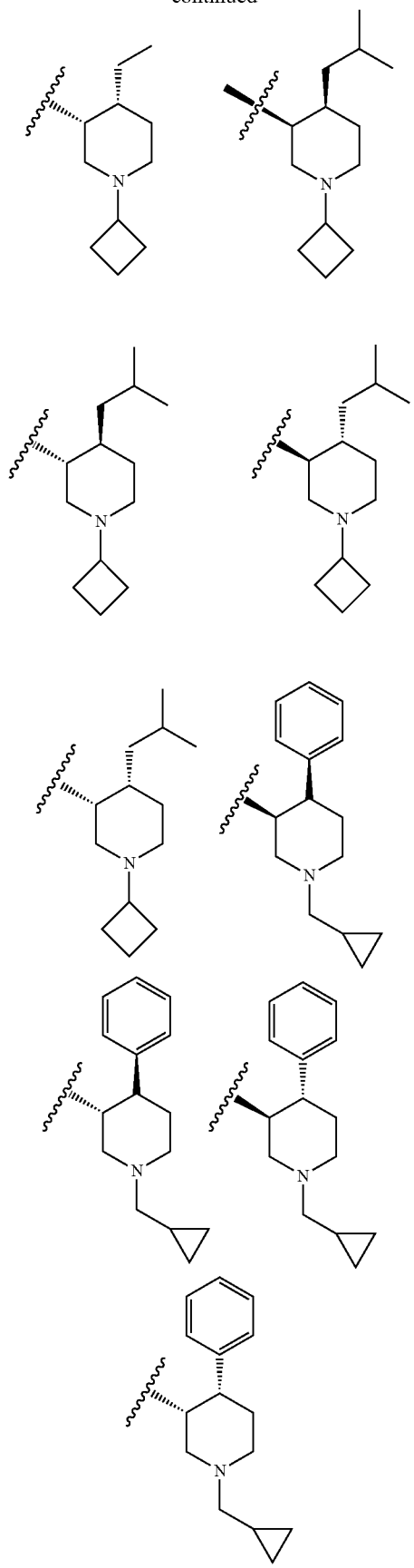
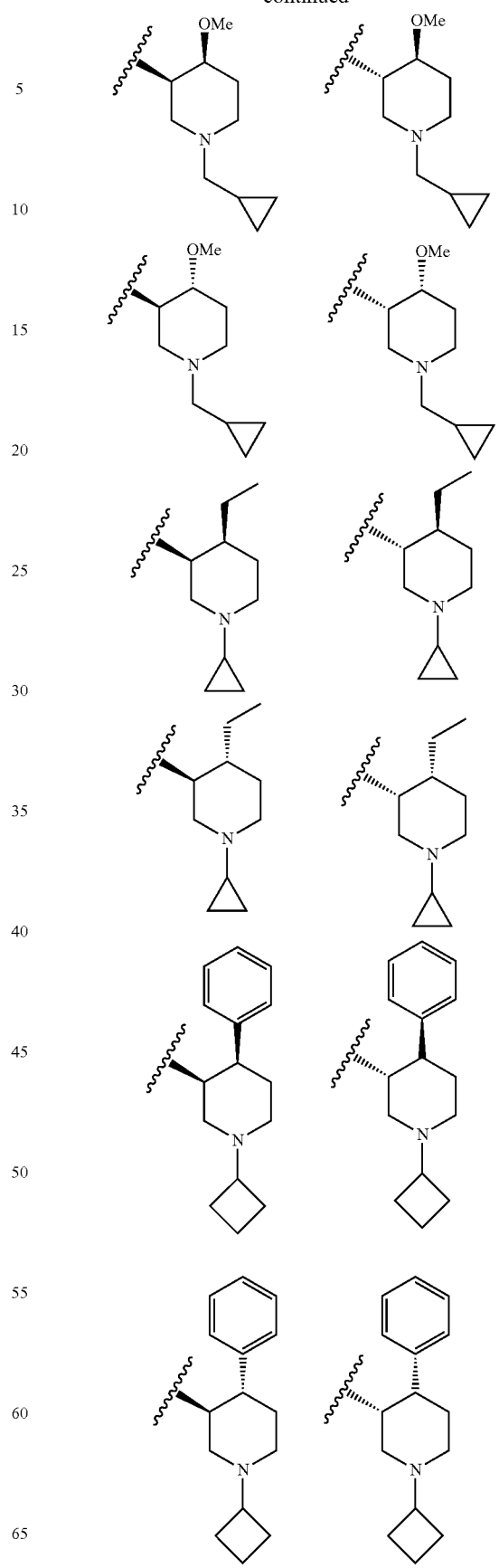

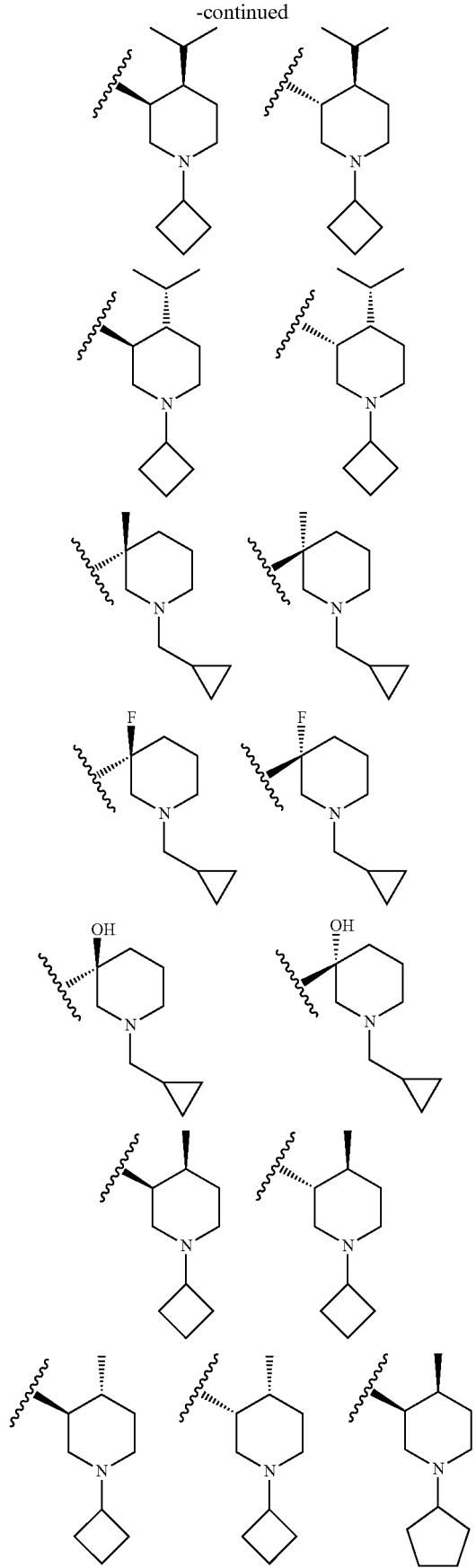
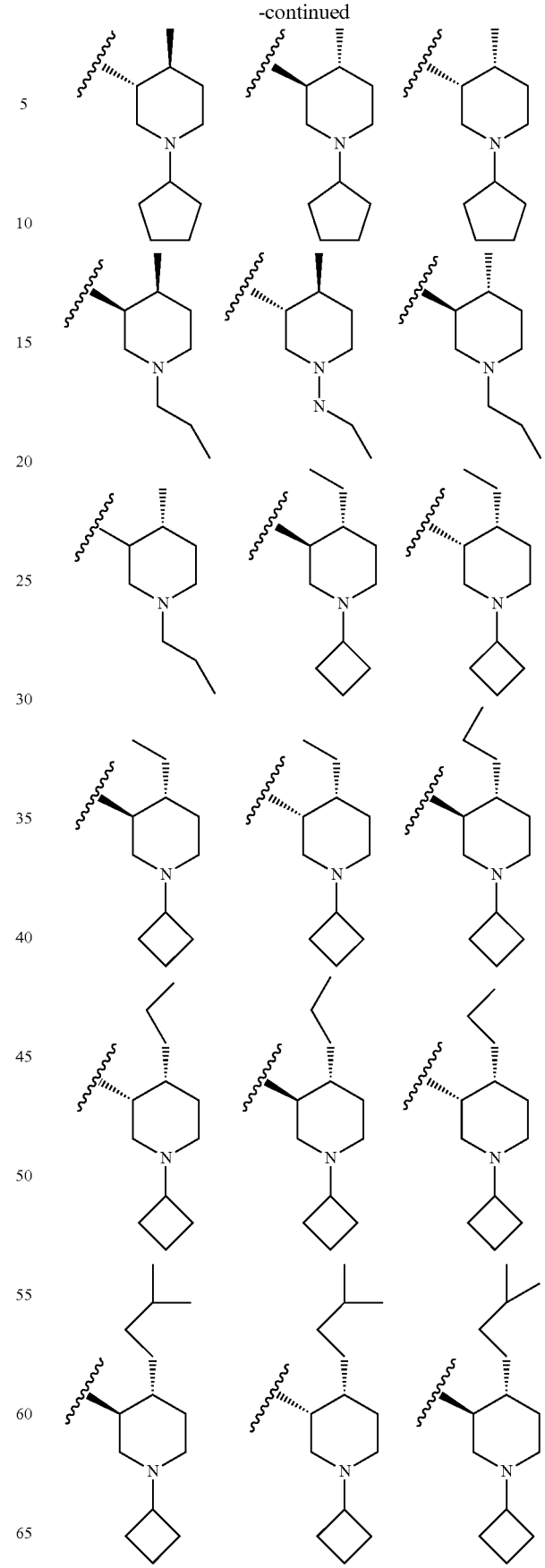

-continued

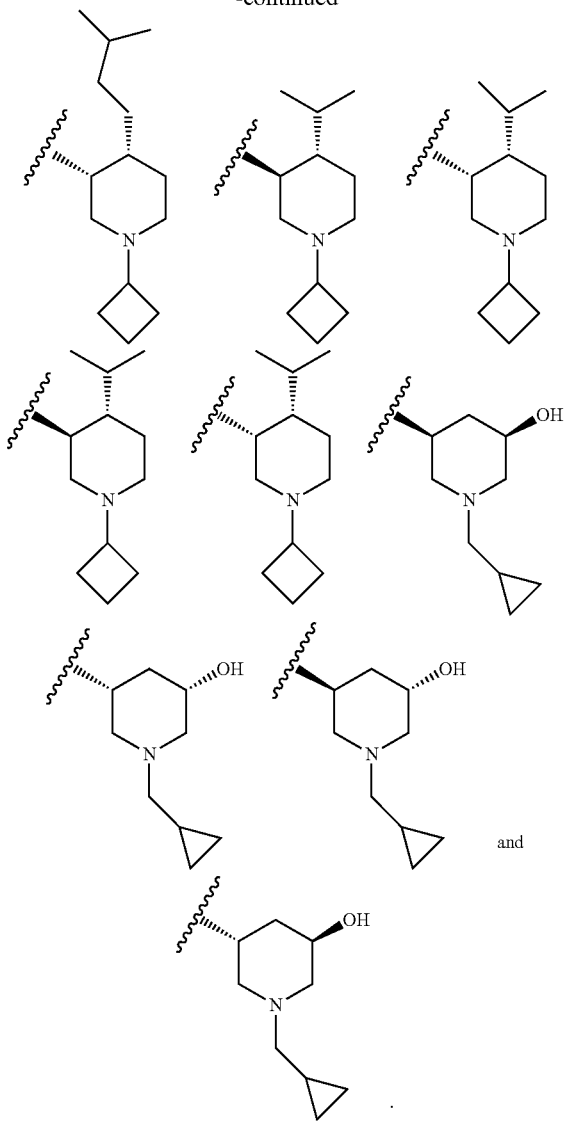

4. The compound of claim 1 wherein $R^2$ is a ring selected from the group consisting of naphthyl, tetralinyl, phenyl, benzisoxazolyl, benzo[7]annulenyl, 1,4-benzodioxinyl, benzimidazolyl-2-one, indolyl, indazolyl, thiophenyl, pyridyl, quinolyl, tetrahydroquinolyl, isoquinolyl, tetrahydroisoquinolyl, and pyrazolyl; which ring is optionally substituted with one or more groups independently selected from the group consisting of $C_{1-6}$alkyl, $C_{2-6}$alkenyl, $C_{2-6}$alkynyl, carbocycle, heterocycle, aryl, heteroaryl, halo, —$NO_2$, —$N(R^d)_2$, —CN, —C(O)—$N(R^d)_2$, —S(O)—$N(R^d)_2$, —S(O)$_2$—$N(R^d)_2$, —O—$R^d$, —S—$R^d$, —O—C(O)—$R^d$, —C(O)—$R^d$, —C(O)—$OR^d$, —S(O)—$R^d$, —S(O)$_2$—$R^d$, —$N(R^d)$—C(O)—$R^d$, —$N(R^d)$—S(O)—$R^d$, —$N(R^d)$—C(O)—$N(R^d)_2$, and —$N(R^d)$—S(O)$_2$—$R^d$; wherein each $C_{1-6}$alkyl, $C_{2-6}$alkenyl, $C_{2-6}$alkynyl, carbocycle, heterocycle, aryl, and heteroaryl is optionally substituted with one or more groups independently selected from the group consisting of halo, —$NO_2$—$N(R^d)_2$, —CN, —C(O)—$N(R^d)_2$, —S(O)—$N(R^d)_2$, —S(O)$_2$—$N(R^d)_2$, —O—$R^d$, —S—$R^d$, —O—C(O)—$R^d$, —C(O)—$R^d$, —C(O)—$OR^d$, —S(O)—$R^d$, —S(O)$_2$—$R^d$, —$N(R^d)$—C(O)—$R^d$, —$N(R^d)$—S(O)—$R^d$, —$N(R^d)$—C(O)—$N(R^d)_2$, —$N(R^d)$—S(O)$_2$—$R^d$, and $C_{1-6}$alkyl that is optionally substituted with one or more groups independently selected from halo.

5. The compound of claim 1 wherein $R^2$ is a naphthyl ring that is optionally substituted with one or more groups independently selected from the group consisting of $C_{1-6}$alkyl, $C_{2-6}$alkenyl, $C_{2-6}$alkynyl, carbocycle, heterocycle, aryl, heteroaryl, halo, —$NO_2$, —$N(R^d)_2$, —CN, —C(O)—$N(R^d)_2$, —S(O)—$N(R^d)_2$, —S(O)$_2$—$N(R^d)_2$, —O—$R^d$, —S—$R^d$, —O—C(O)—$R^d$, —C(O)—$R^d$, —C(O)—$OR^d$, —S(O)—$R^d$, —S(O)$_2$—$R^d$, —$N(R^d)$—C(O)—$R^d$, —$N(R^d)$—S(O)—$R^d$, —$N(R^d)$—C(O)—$N(R^d)_2$, and —$N(R^d)$—S(O)$_2$—$R^d$; wherein each $C_{1-6}$alkyl, $C_{2-6}$alkenyl, $C_{2-6}$alkynyl, carbocycle, heterocycle, aryl, and heteroaryl is optionally substituted with one or more groups independently selected from the group consisting of halo, —$NO_2$—$N(R^d)_2$, —CN, —C(O)—$N(R^d)_2$, —S(O)—$N(R^d)_2$, —S(O)$_2$—$N(R^d)_2$, —O—$R^d$, —S—$R^d$, —O—C(O)—$R^d$, —C(O)—$R^d$, —C(O)—$OR^d$, —S(O)—$R^d$, —S(O)$_2$—$R^d$, —$N(R^d)$—C(O)—$R^d$, —$N(R^d)$—S(O)—$R^d$, —$N(R^d)$—C(O)—$N(R^d)_2$, —$N(R^d)$—S(O)$_2$—$R^d$, and $C_{1-6}$alkyl that is optionally substituted with one or more groups independently selected from halo.

6. The compound of claim 1 wherein $R^2$ is a phenyl ring that is optionally substituted with one or more groups independently selected from the group consisting of $C_{1-6}$alkyl, $C_{2-6}$alkenyl, $C_{2-6}$alkynyl, carbocycle, heterocycle, aryl, heteroaryl, halo, —$NO_2$, —$N(R^d)_2$, —CN, —C(O)—$N(R^d)_2$, —S(O)—$N(R^d)_2$, —S(O)$_2$—$N(R^d)_2$, —O—$R^d$, —S—$R^d$, —O—C(O)—$R^d$, —C(O)—$R^d$, —C(O)—$OR^d$, —S(O)—$R^d$, —S(O)$_2$—$R^d$, —$N(R^d)$—C(O)—$R^d$, —$N(R^d)$—S(O)—$R^d$, —$N(R^d)$—C(O)—$N(R^d)_2$, and —$N(R^d)$—S(O)$_2$—$R^d$; wherein each $C_{1-6}$alkyl, $C_{2-6}$alkenyl, $C_{2-6}$alkynyl, carbocycle, heterocycle, aryl, and heteroaryl is optionally substituted with one or more groups independently selected from the group consisting of halo, —$NO_2$—$N(R^d)_2$, —CN, —C(O)—$N(R^d)_2$, —S(O)—$N(R^d)_2$, —S(O)$_2$—$N(R^d)_2$, —O—$R^d$, —S—$R^d$, —O—C(O)—$R^d$, —C(O)—$R^d$, —C(O)—$OR^d$, —S(O)—$R^d$, —S(O)$_2$—$R^d$, —$N(R^d)$—C(O)—$R^d$, —$N(R^d)$—S(O)—$R^d$, —$N(R^d)$—C(O)—$N(R^d)_2$, —$N(R^d)$—S(O)$_2$—$R^d$, and $C_{1-6}$alkyl that is optionally substituted with one or more groups independently selected from halo.

7. The compound of claim 1 wherein $R^2$ is a quinolyl or isoquinolyl ring, which ring is optionally substituted with one or more groups independently selected from the group consisting of $C_{1-6}$alkyl, $C_{2-6}$alkenyl, $C_{2-6}$alkynyl, carbocycle, heterocycle, aryl, heteroaryl, halo, —$NO_2$, —$N(R^d)_2$, —CN, —C(O)—$N(R^d)_2$, —S(O)—$N(R^d)_2$, —S(O)$_2$—N$(R^d)_2$, —O—$R^d$, —S—$R^d$, —O—C(O)—$R^d$, —C(O)—$R^d$, —C(O)—$OR^d$, —S(O)—$R^d$, —S(O)$_2$—$R^d$, —$N(R^d)$—C(O)—$R^d$, —$N(R^d)$—S(O)—$R^d$, —$N(R^d)$—C(O)—$N(R^d)_2$, and —$N(R^d)$—S(O)$_2$—$R^d$; wherein each $C_{1-6}$alkyl, $C_{2-6}$alkenyl, $C_{2-6}$alkynyl, carbocycle, heterocycle, aryl, and heteroaryl is optionally substituted with one or more groups independently selected from the group consisting of halo, —$NO_2$—$N(R^d)_2$, —CN, —C(O)—$N(R^d)_2$, —S(O)—$N(R^d)_2$, —S(O)$_2$—$N(R^d)_2$, —O—$R^d$, —S—$R^d$, —O—C(O)—$R^d$, —C(O)—$R^d$, —C(O)—$OR^d$, —S(O)—$R^d$, —S(O)$_2$—$R^d$, —$N(R^d)$—C(O)—$R^d$, —$N(R^d)$—S(O)—$R^d$, —$N(R^d)$—C(O)—$N(R^d)_2$, —$N(R^d)$—S(O)$_2$—$R^d$, and $C_{1-6}$alkyl that is optionally substituted with one or more groups independently selected from halo.

8. The compound of claim 1 wherein $R^2$ is selected from the group consisting of:

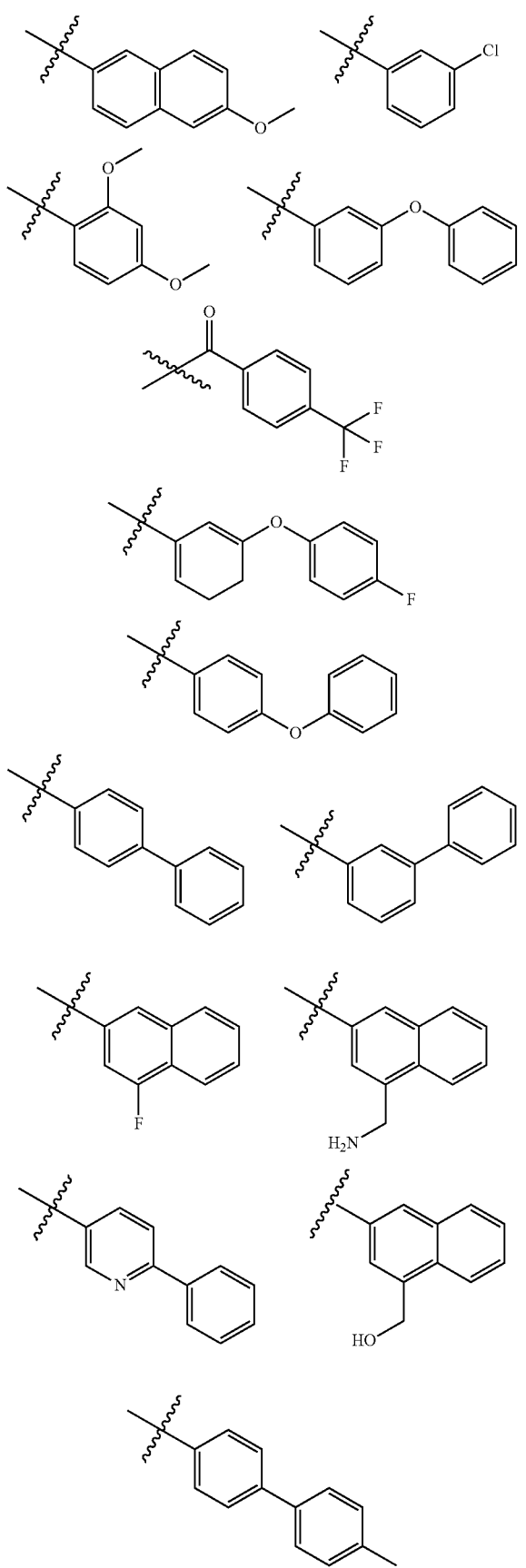
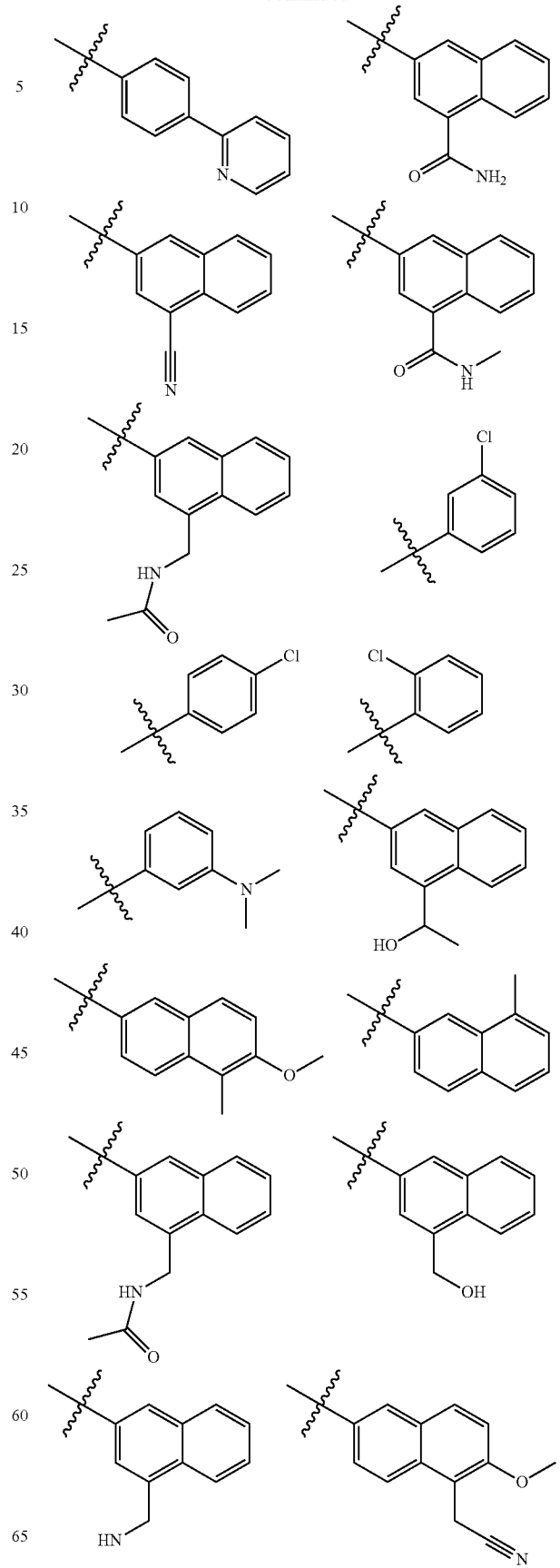

347
-continued
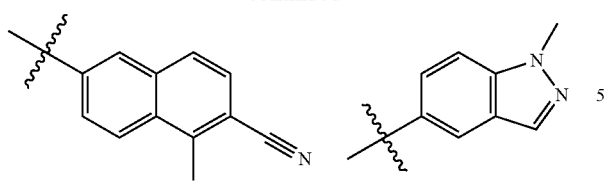
348
-continued
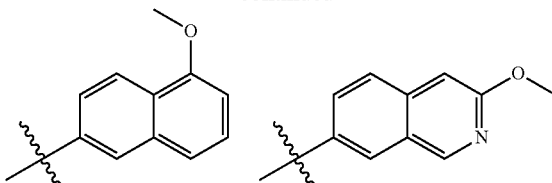
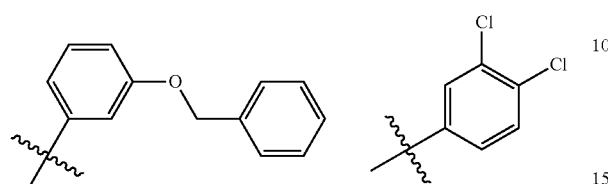
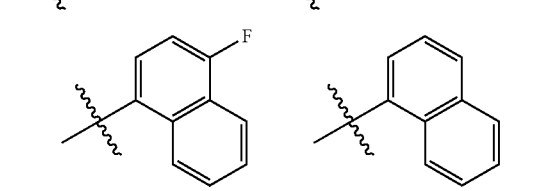
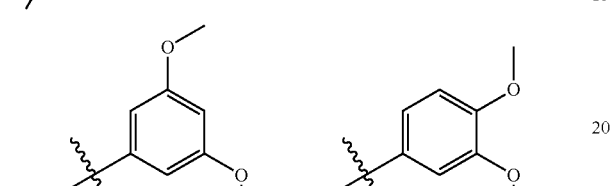
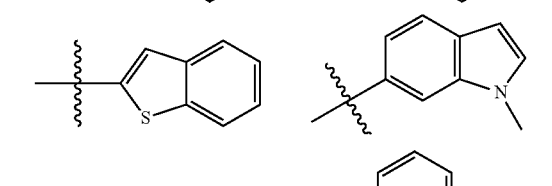
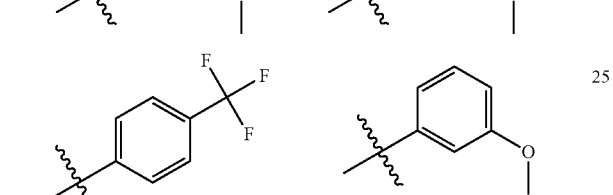
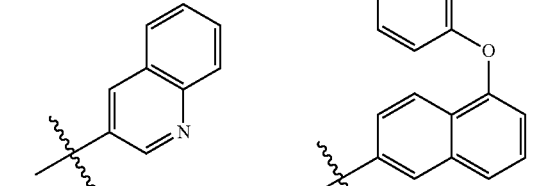
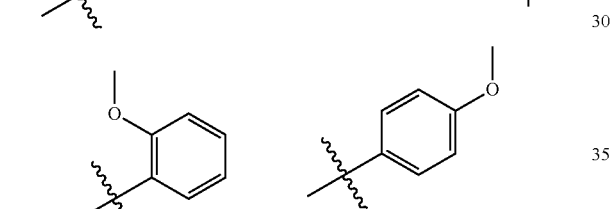
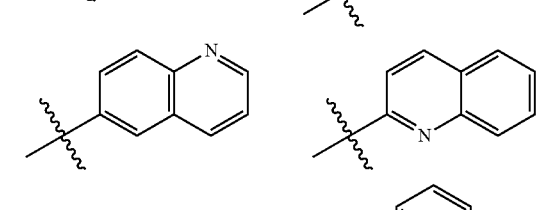
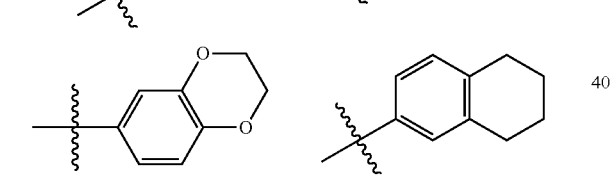
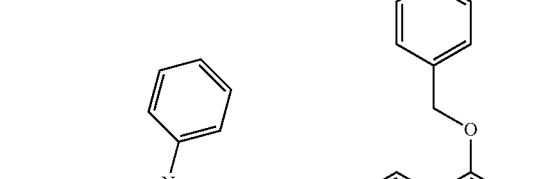
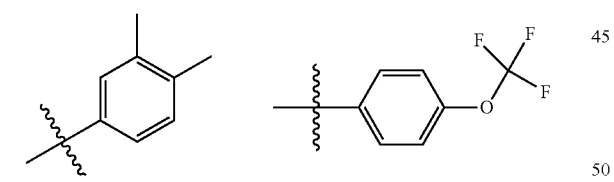
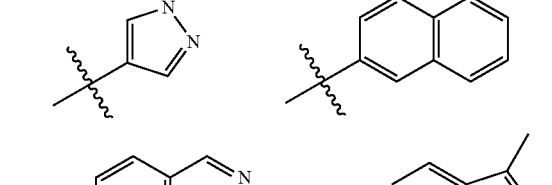
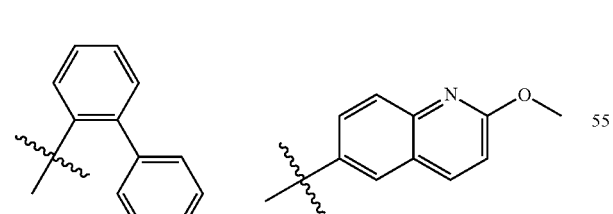
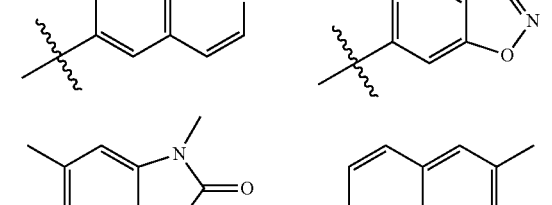
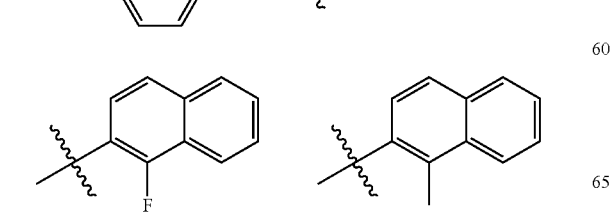
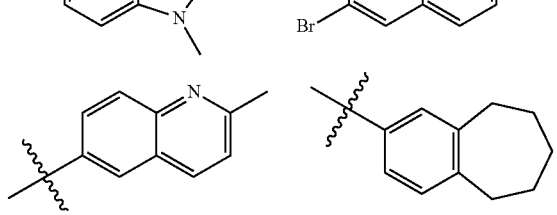

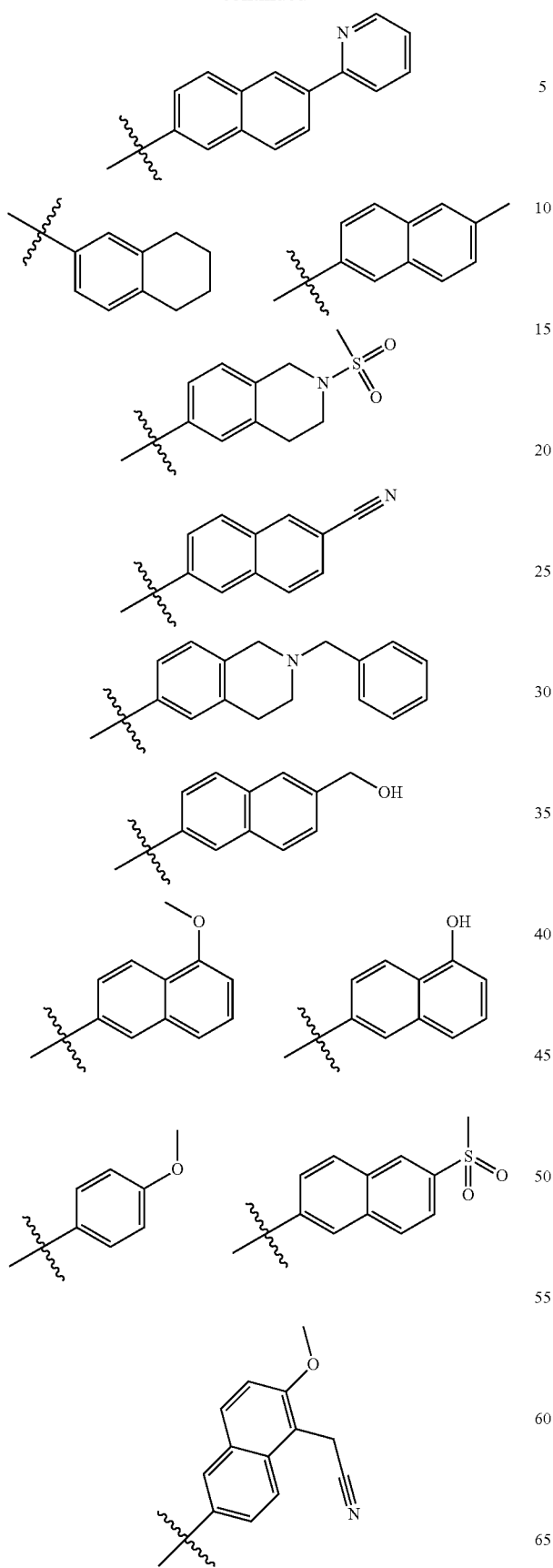
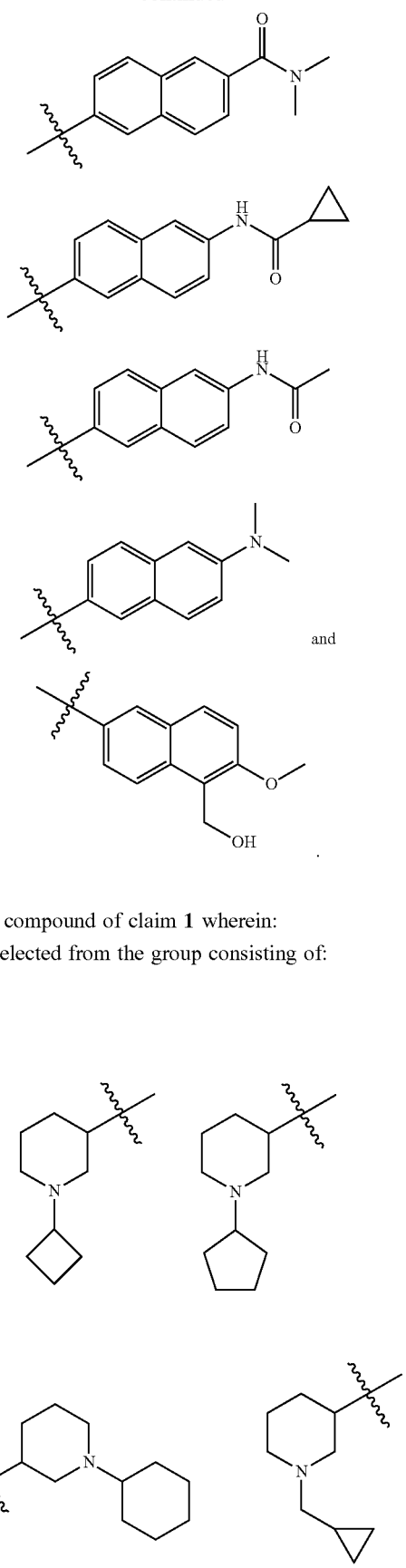
9. The compound of claim 1 wherein:
R[1] is selected from the group consisting of:
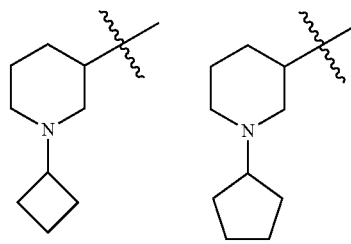
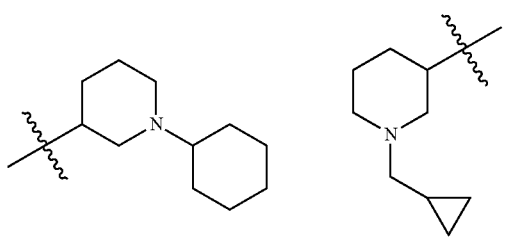

351
-continued
352
-continued
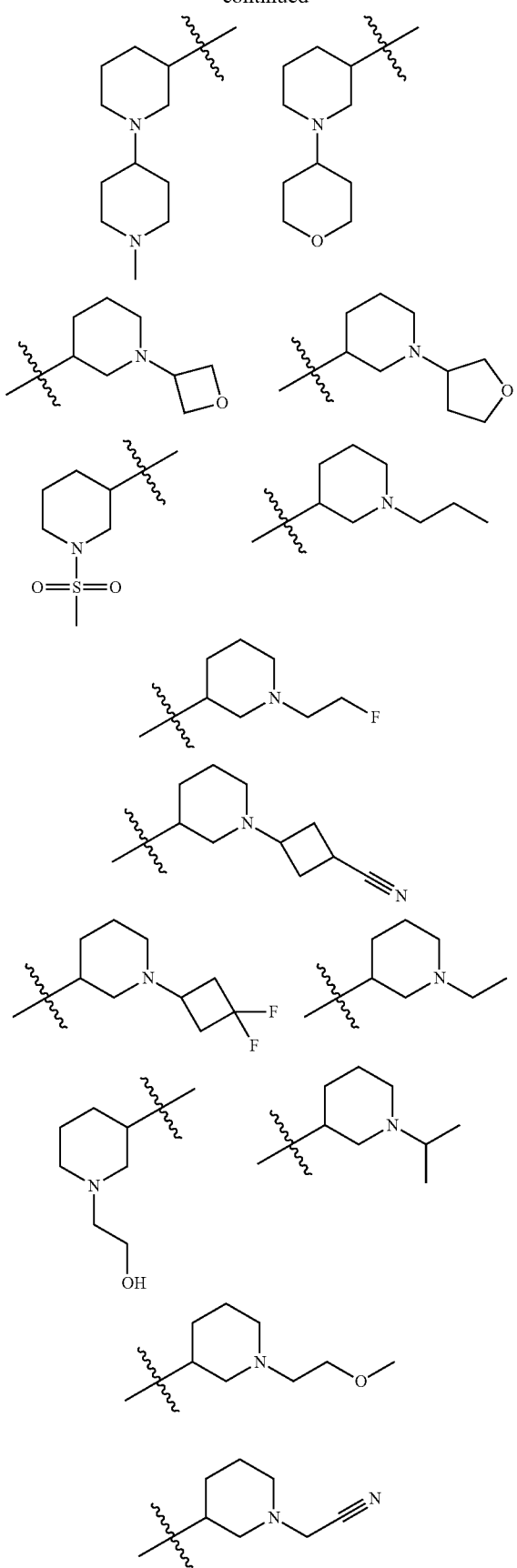
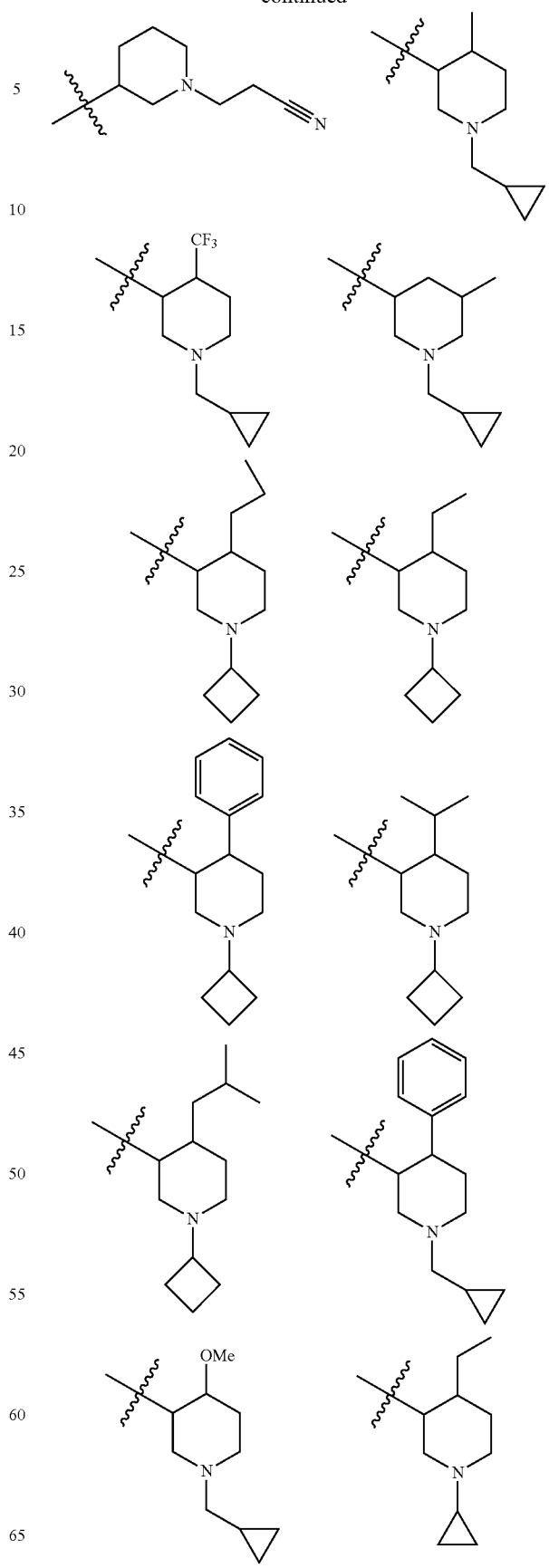

353
-continued
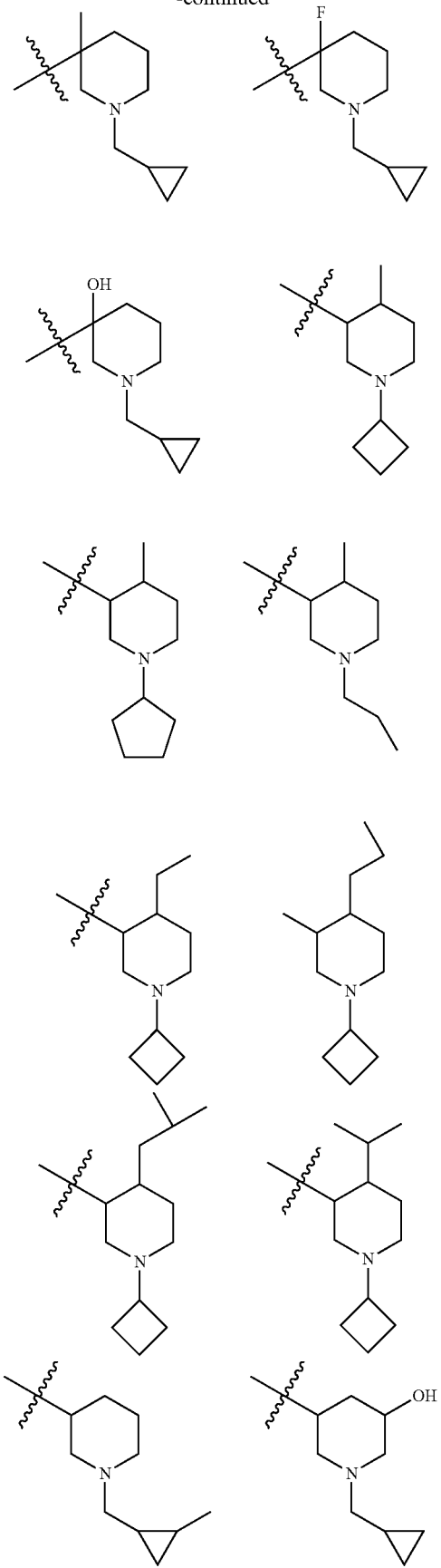
354
-continued
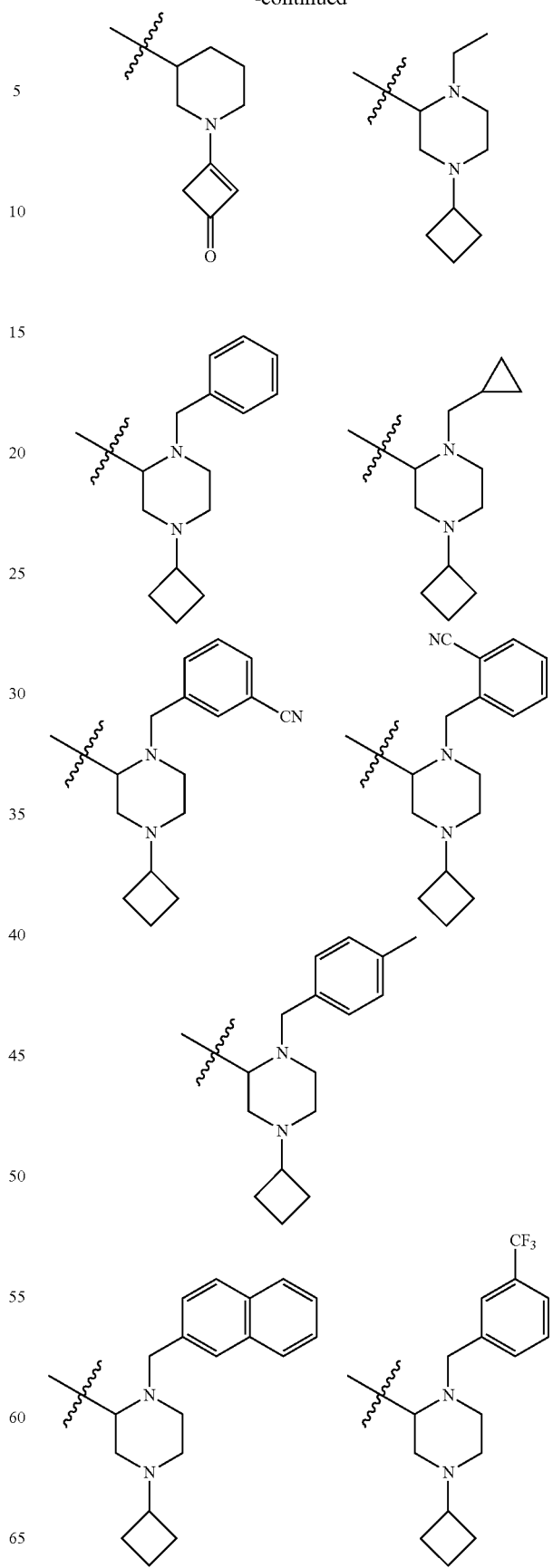

355

-continued

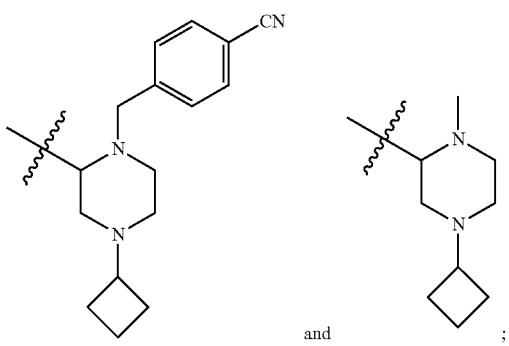 [SMILES: *C1CN(C2CCC2)CCN1Cc1ccc(C#N)cc1 ; *C1CN(C2CCC2)CCN1C]

and and

R² is a ring selected from the group consisting of:

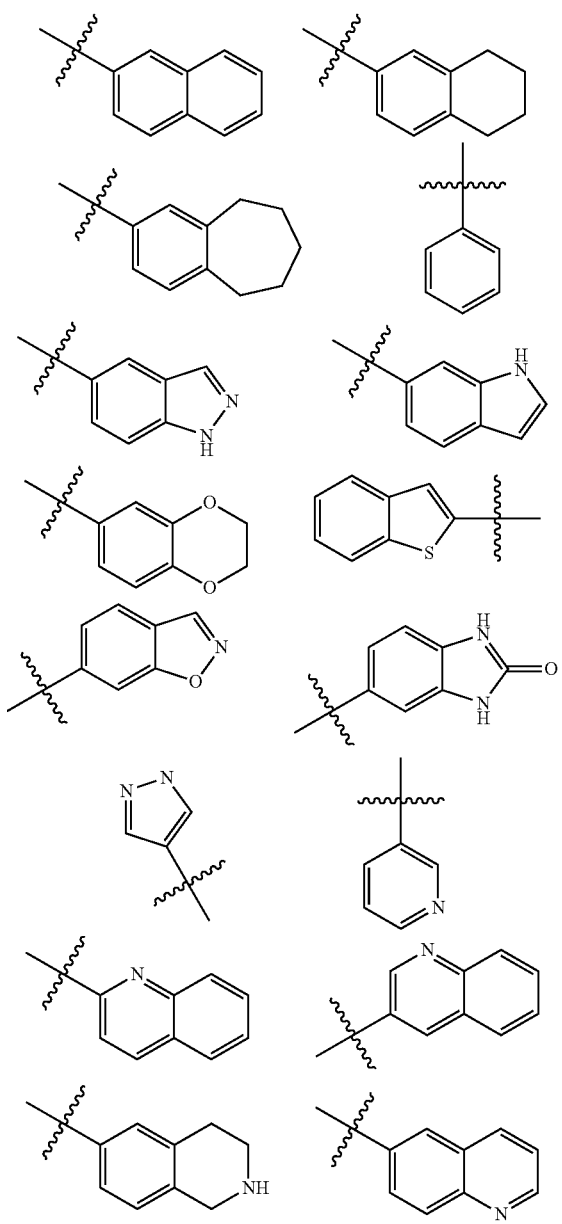

356

-continued

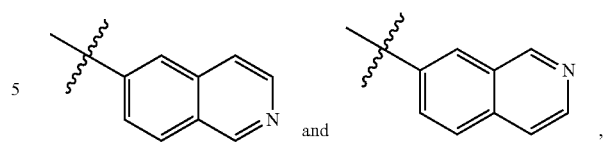

and , which ring is optionally substituted with one or more groups independently selected from the group consisting of $C_{1-6}$alkyl, $C_{2-6}$alkenyl, $C_{2-6}$alkynyl, carbocycle, heterocycle, aryl, heteroaryl, halo, $-NO_2$, $-N(R^d)_2$, $-CN$, $-C(O)-N(R^d)_2$, $-S(O)-N(R^d)_2$, $-S(O)_2-N(R^d)_2$, $-O-R^d$, $-S-R^d$, $-O-C(O)-R^d$, $-C(O)-R^d$, $-C(O)-OR^d$, $-S(O)-R^d$, $-S(O)_2-R^d$, $-N(R^d)-C(O)-R^d$, $-N(R^d)-S(O)-R^d$, $-N(R^d)-C(O)-N(R^d)_2$, and $-N(R^d)-S(O)_2-R^d$; wherein each $C_{1-6}$alkyl, $C_{2-6}$alkenyl, $C_{2-6}$alkynyl, carbocycle, heterocycle, aryl, and heteroaryl is optionally substituted with one or more groups independently selected from the group consisting of halo, $-NO_2$, $-N(R^d)_2$, $-CN$, $-C(O)-N(R^d)_2$, $-S(O)-N(R^d)_2$, $-S(O)_2-N(R^d)_2$, $-O-R^d$, $-S-R^d$, $-O-C(O)-R^d$, $-C(O)-R^d$, $-C(O)-OR^d$, $-S(O)-R^d$, $-S(O)_2-R^d$, $-N(R^d)-C(O)-R^d$, $-N(R^d)-S(O)-R^d$, $-N(R^d)-C(O)-N(R^d)_2$, $-N(R^d)-S(O)_2-R^d$, and $C_{1-6}$alkyl that is optionally substituted with one or more groups independently selected from halo.

10. The compound of claim 1 wherein:

R¹ is selected from the group consisting of:

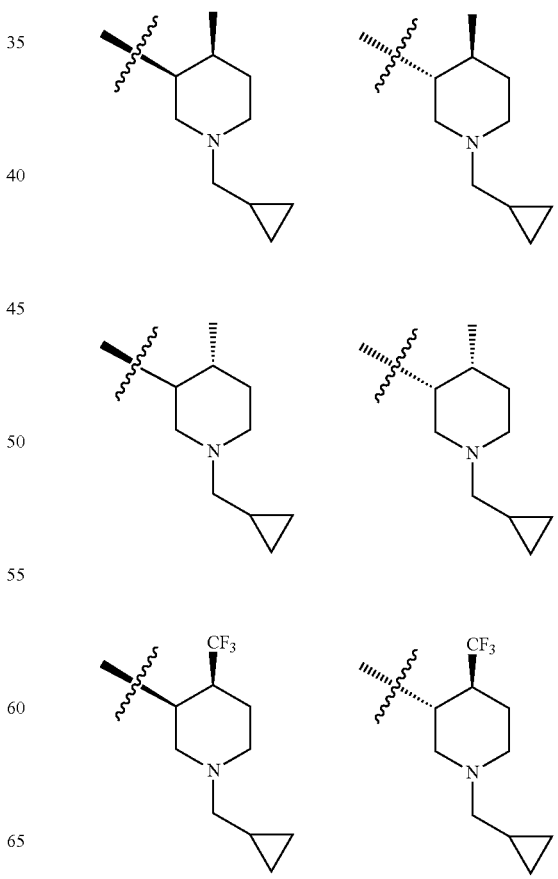

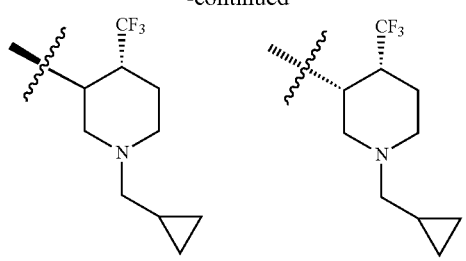
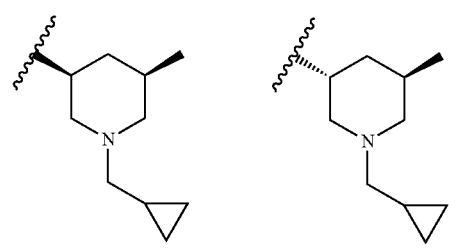
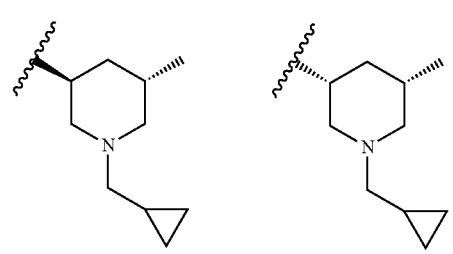
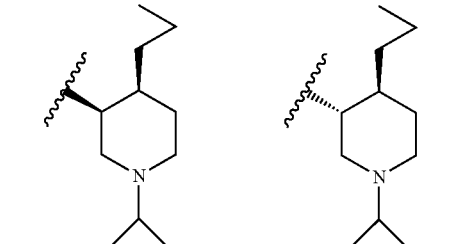
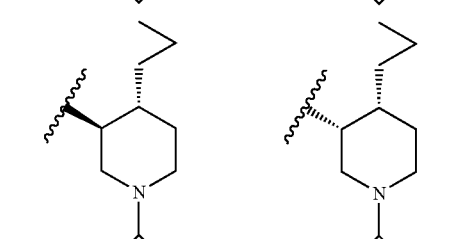
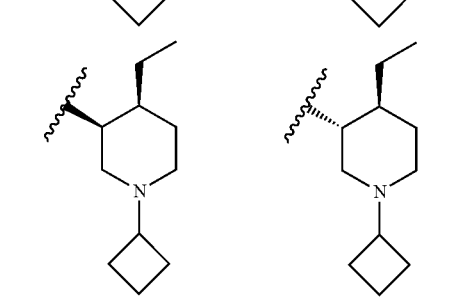
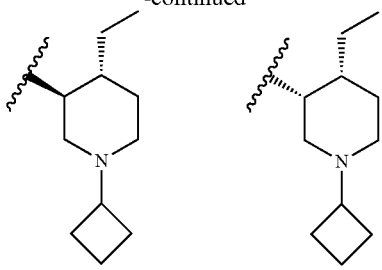
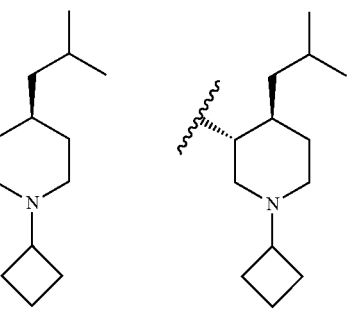
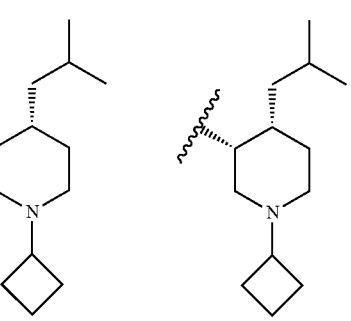
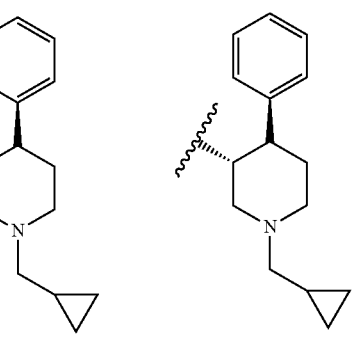
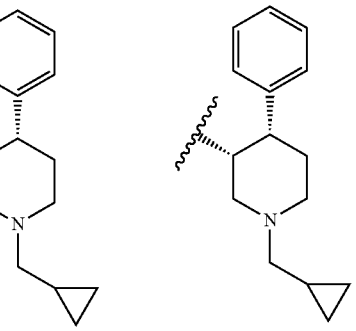

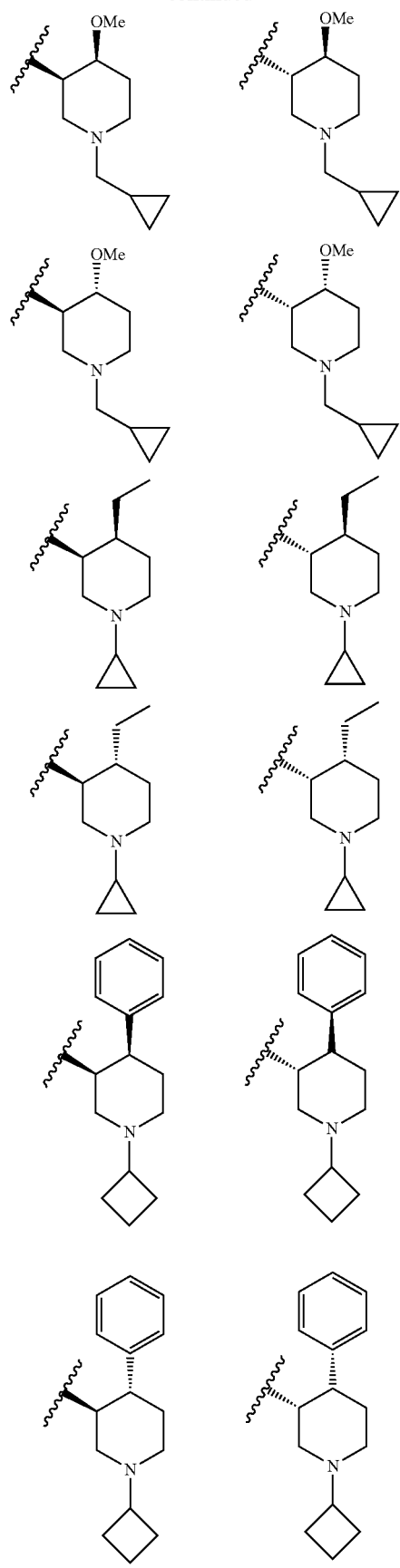
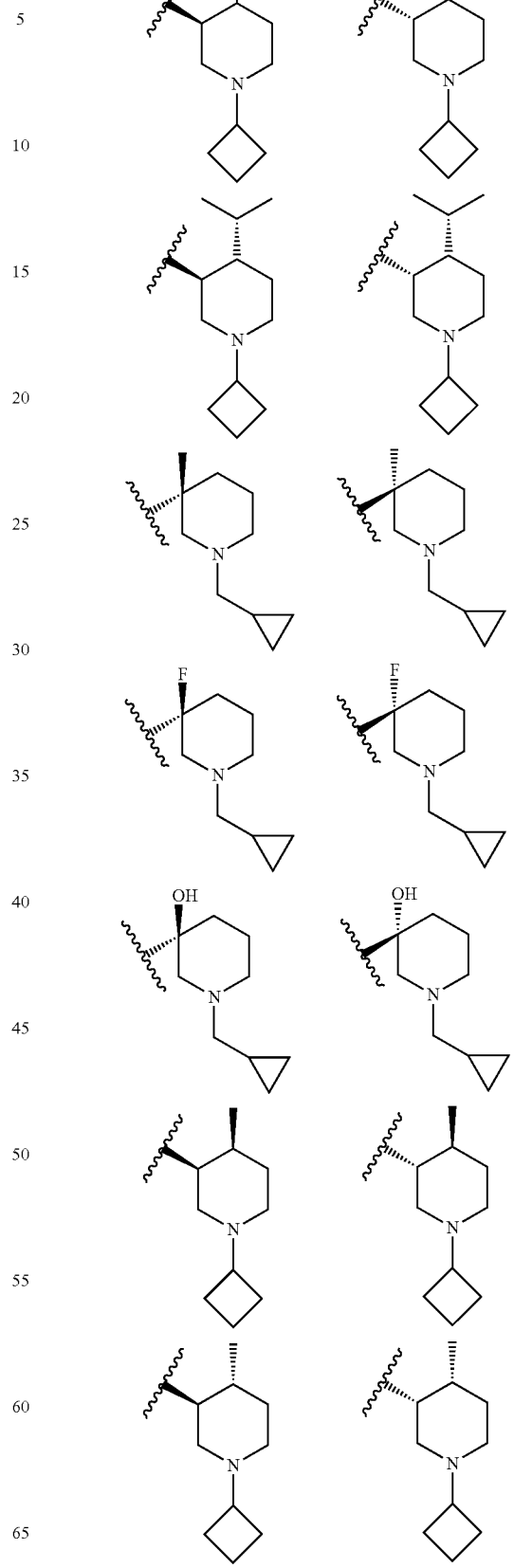

361
-continued
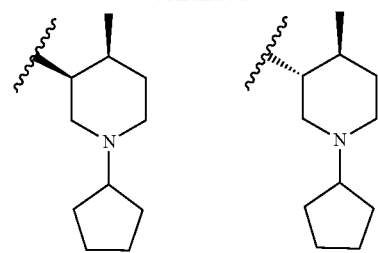
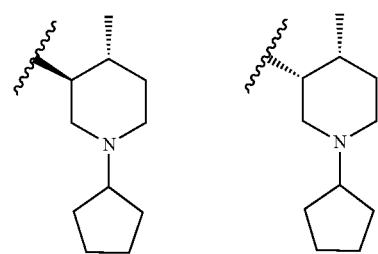
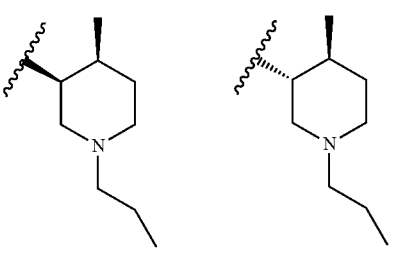
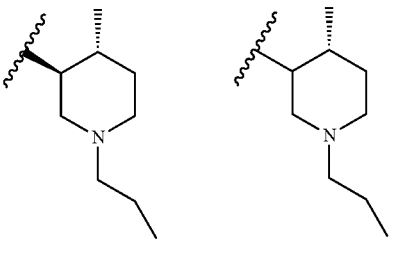
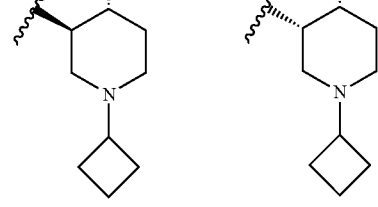
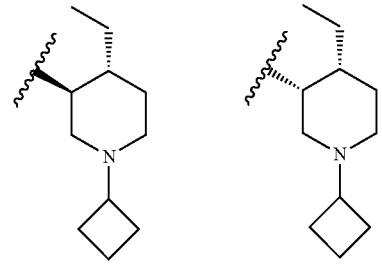
362
-continued
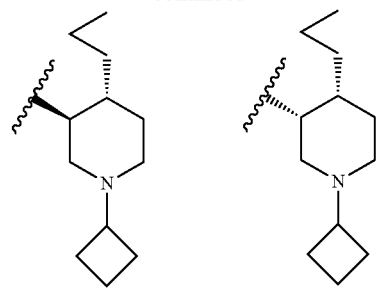
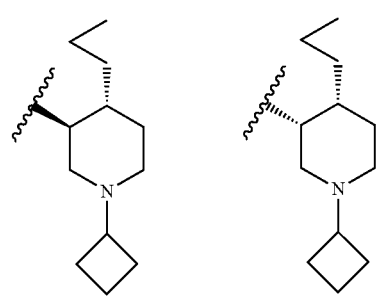
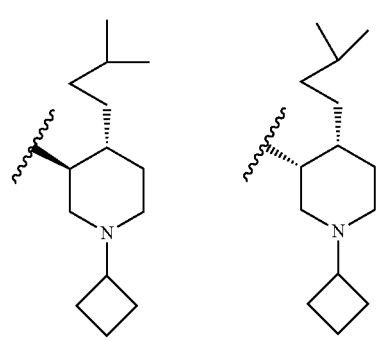
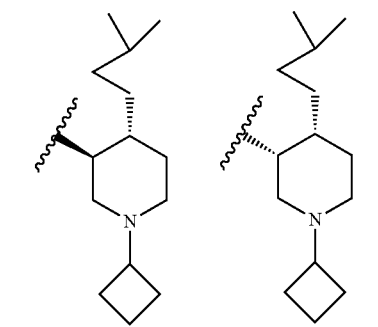
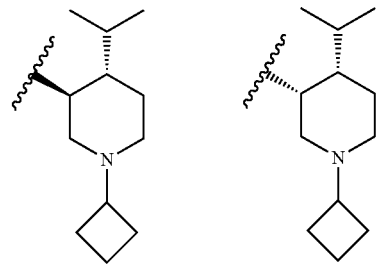

363

-continued

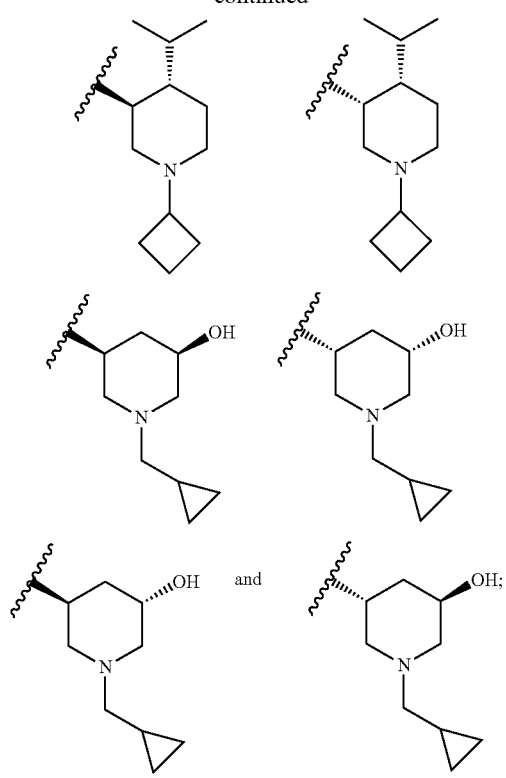

and

R² is a ring selected from the group consisting of:

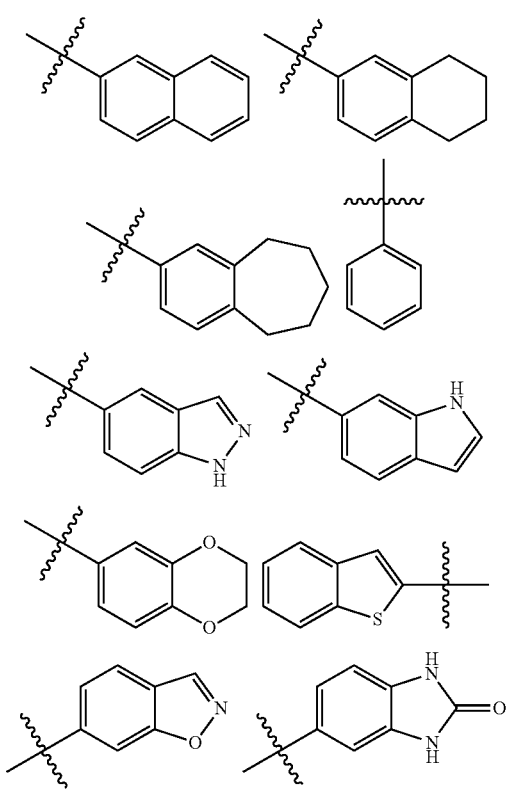

364

-continued

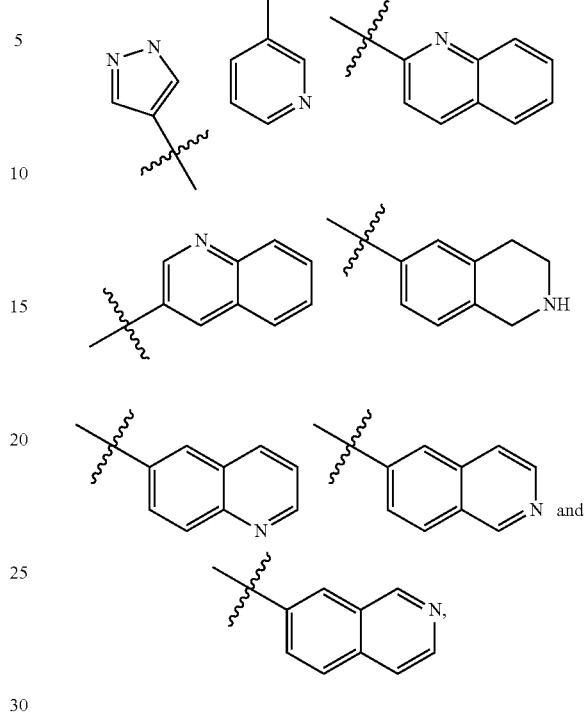

which ring is optionally substituted with one or more groups independently selected from the group consisting of $C_{1-6}$alkyl, $C_{2-6}$alkenyl, $C_{2-6}$alkynyl, carbocycle, heterocycle, aryl, heteroaryl, halo, —$NO_2$, —$N(R^d)_2$, —CN, —C(O)—$N(R^d)_2$, —S(O)—$N(R^d)_2$, —$S(O)_2$—$N(R^d)_2$, —O—$R^d$, —S—$R^d$, —O—C(O)—$R^d$, —C(O)—$R^d$, —C(O)—$OR^d$, —S(O)—$R^d$, —$S(O)_2$—$R^d$, —$N(R^d)$—C(O)—$R^d$, —$N(R^d)$—S(O)—$R^d$, —$N(R^d)$—C(O)—$N(R^d)_2$, and —$N(R^d)$—$S(O)_2$—$R^d$; wherein each $C_{1-6}$alkyl, $C_{2-6}$alkenyl, $C_{2-6}$alkynyl, carbocycle, heterocycle, aryl, and heteroaryl is optionally substituted with one or more groups independently selected from the group consisting of halo, —$NO_2$—$N(R^d)_2$, —CN, —C(O)—$N(R^d)_2$, —S(O)—$N(R^d)_2$, —$S(O)_2$—$N(R^d)_2$, —O—$R^d$, —S—$R^d$, —O—C(O)—$R^d$, —C(O)—$R^d$, —C(O)—$OR^d$, —S(O)—$R^d$, —$S(O)_2$—$R^d$, —$N(R^d)$—C(O)—$R^d$, —$N(R^d)$—S(O)—$R^d$, —$N(R^d)$—C(O)—$N(R^d)_2$, —$N(R^d)$—$S(O)_2$—$R^d$, and $C_{1-6}$alkyl that is optionally substituted with one or more groups independently selected from halo.

11. The compound of claim 1 wherein:

R¹ is selected from the group consisting of:

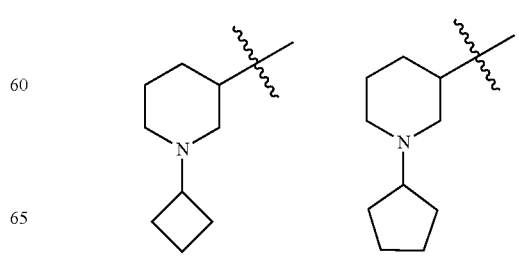

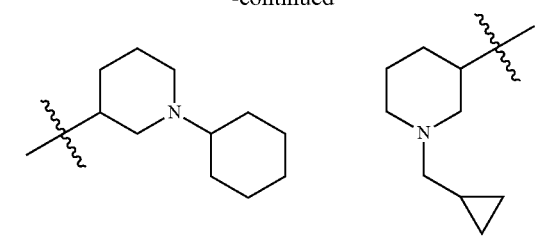
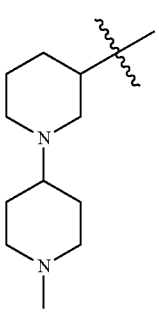
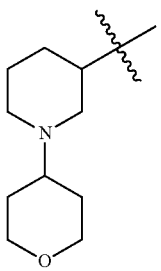
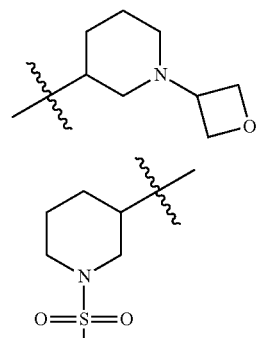
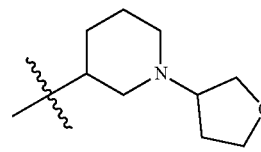
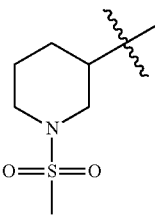
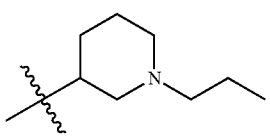
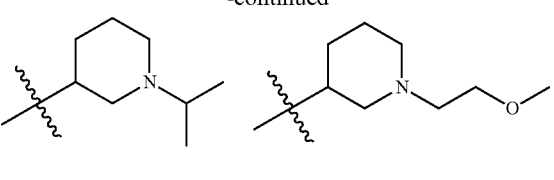
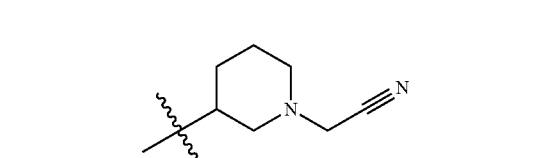
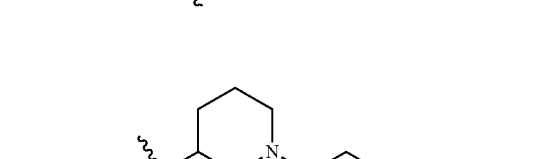
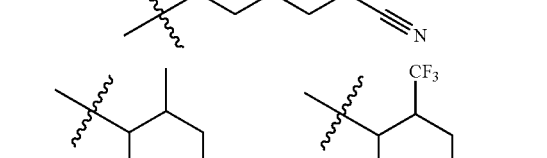
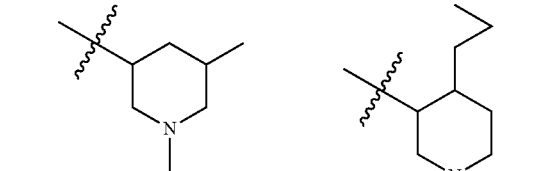
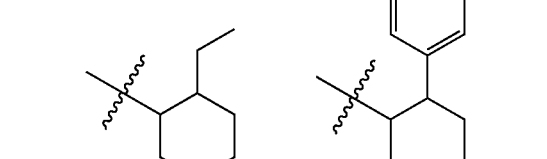
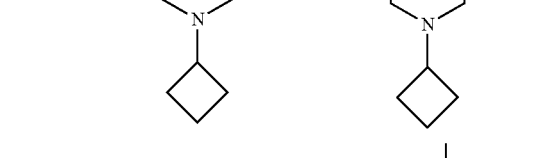
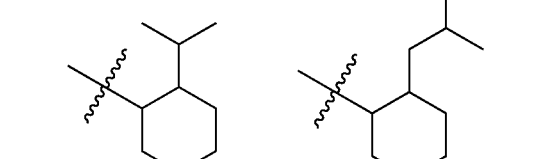

367
-continued
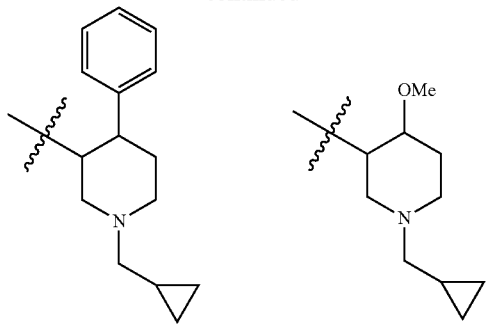
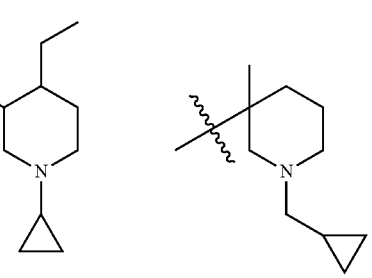
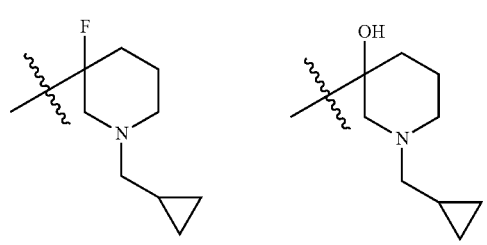
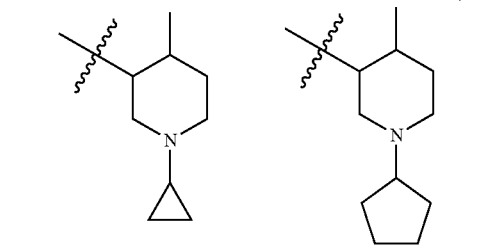
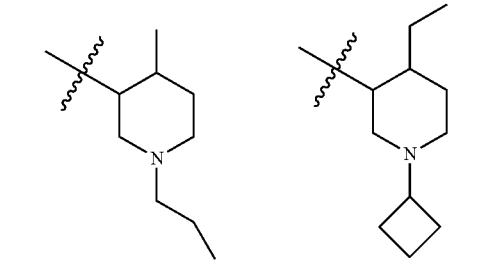
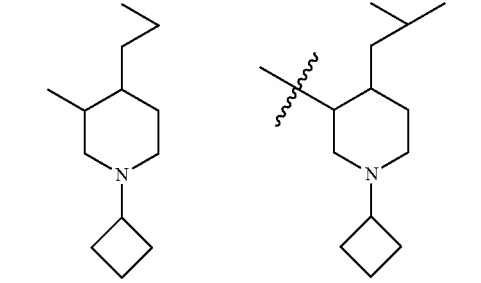
368
-continued
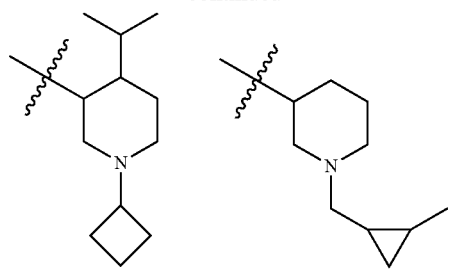
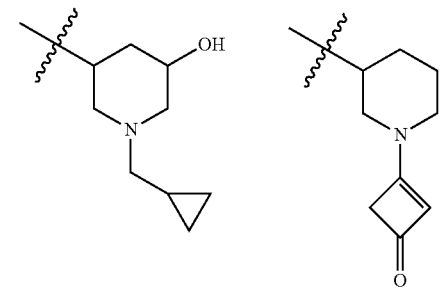
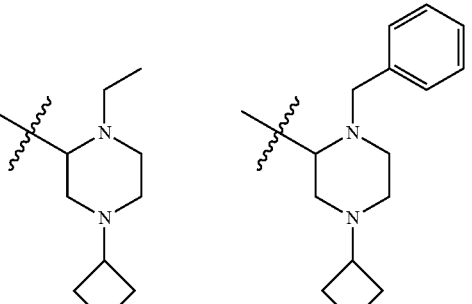
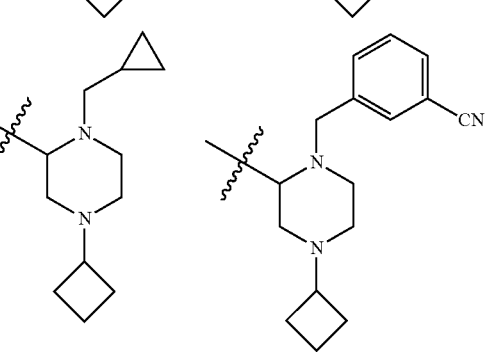
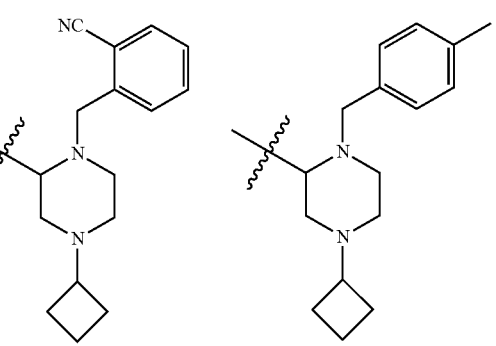

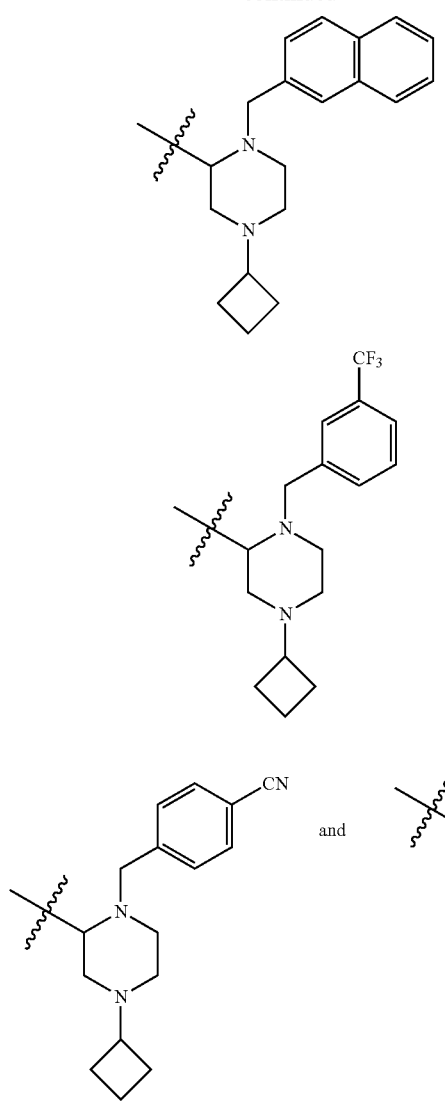
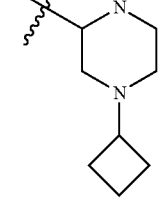
and
R² is selected from the group consisting of:
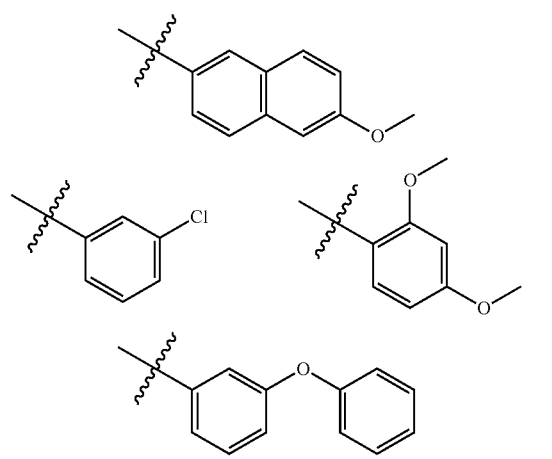
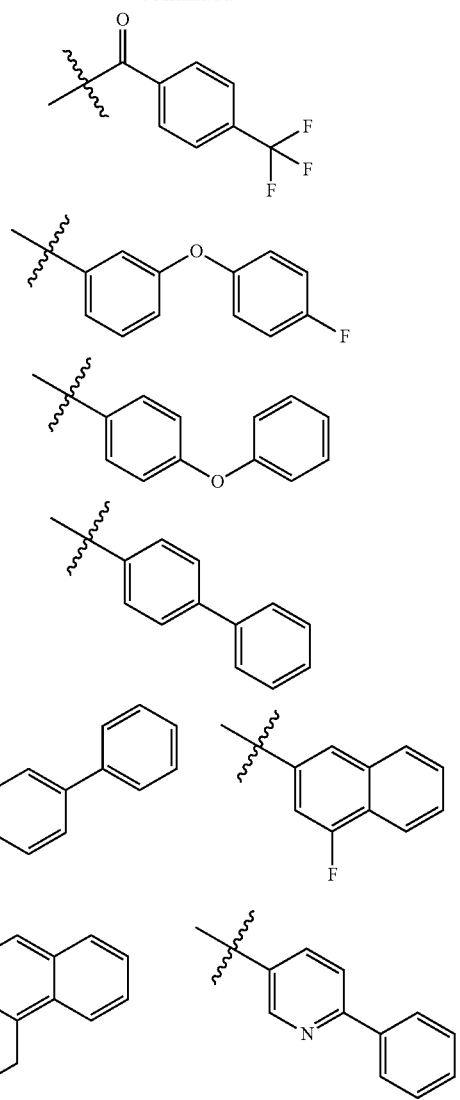
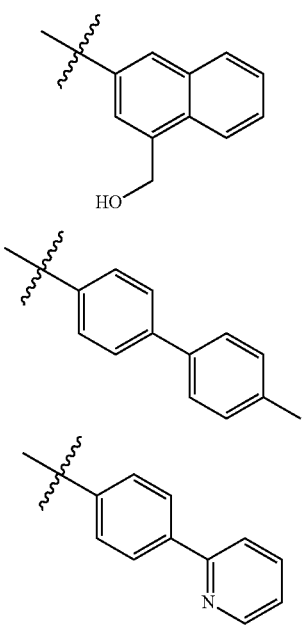

-continued
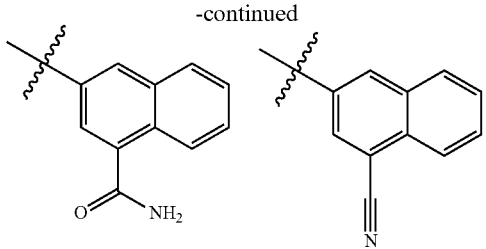
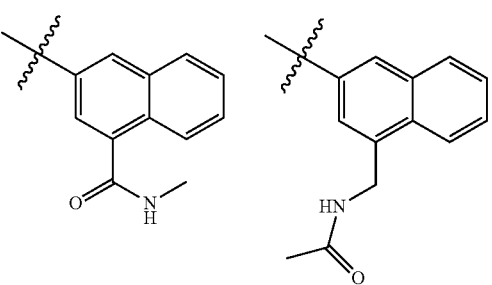
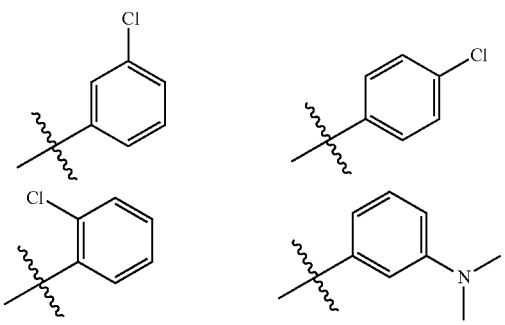
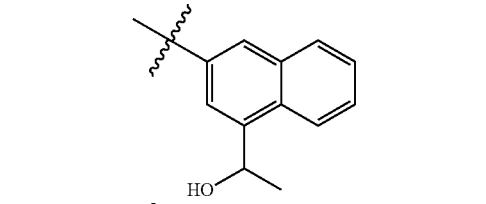
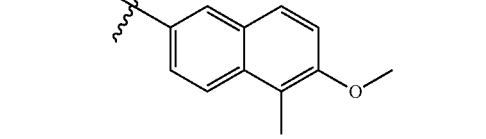
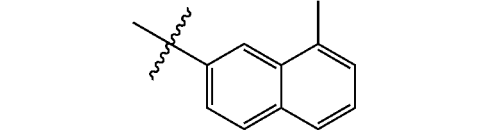
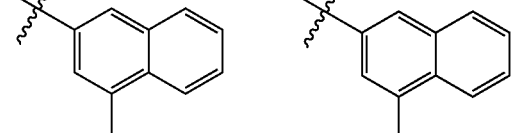
-continued
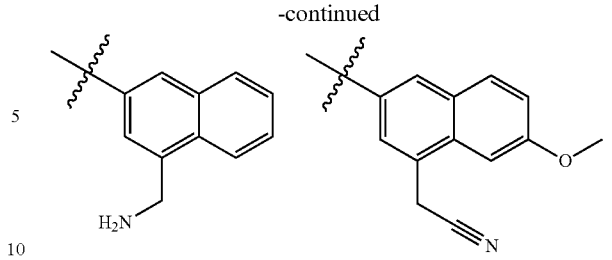
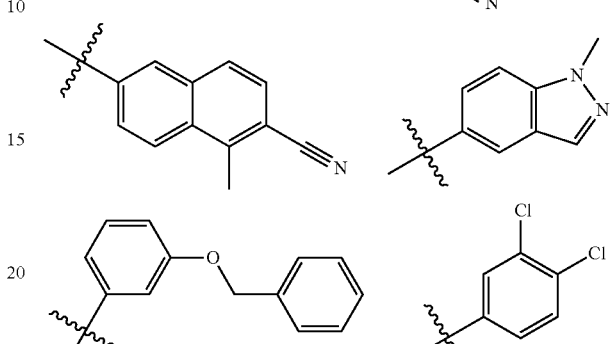
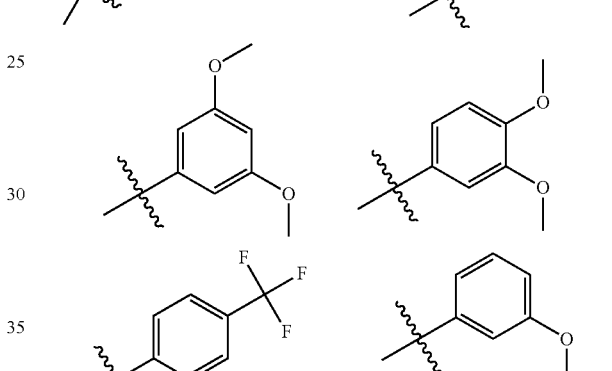
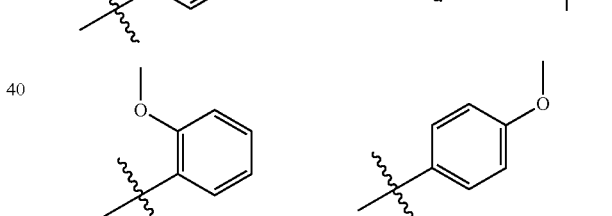
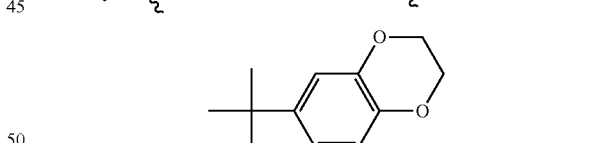
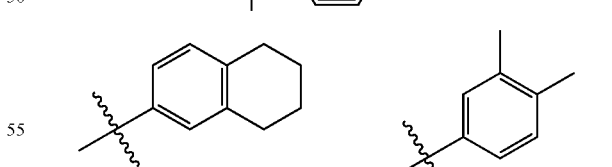
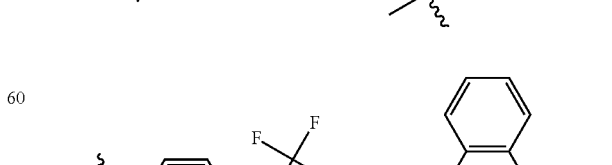
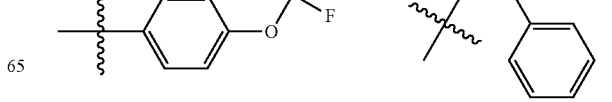

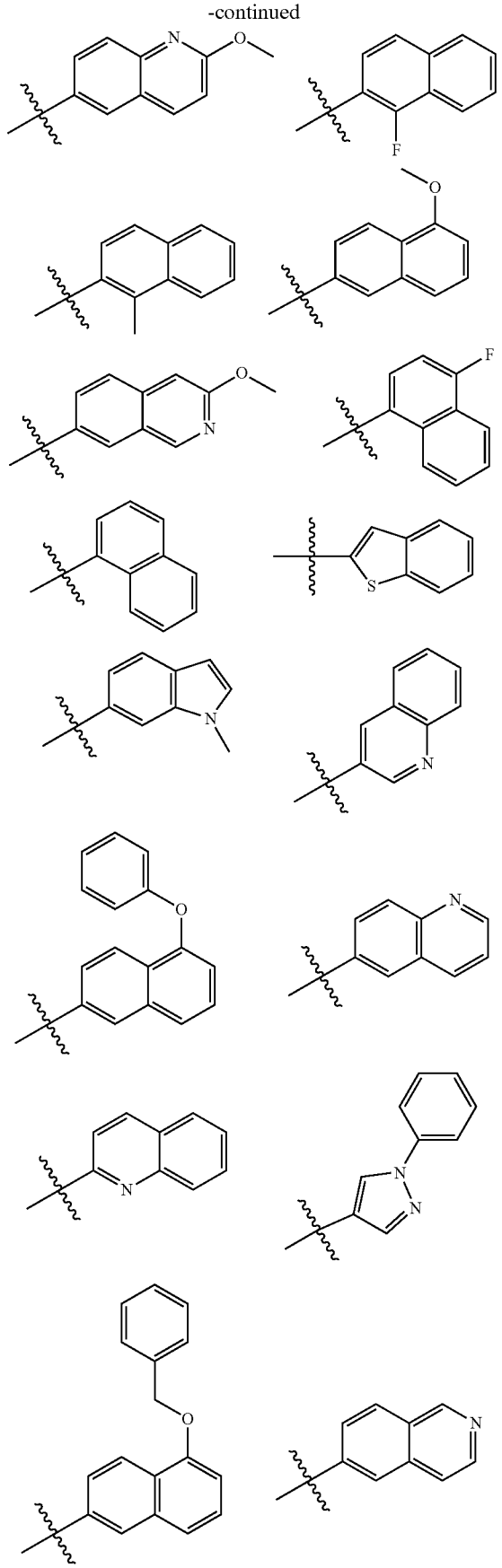
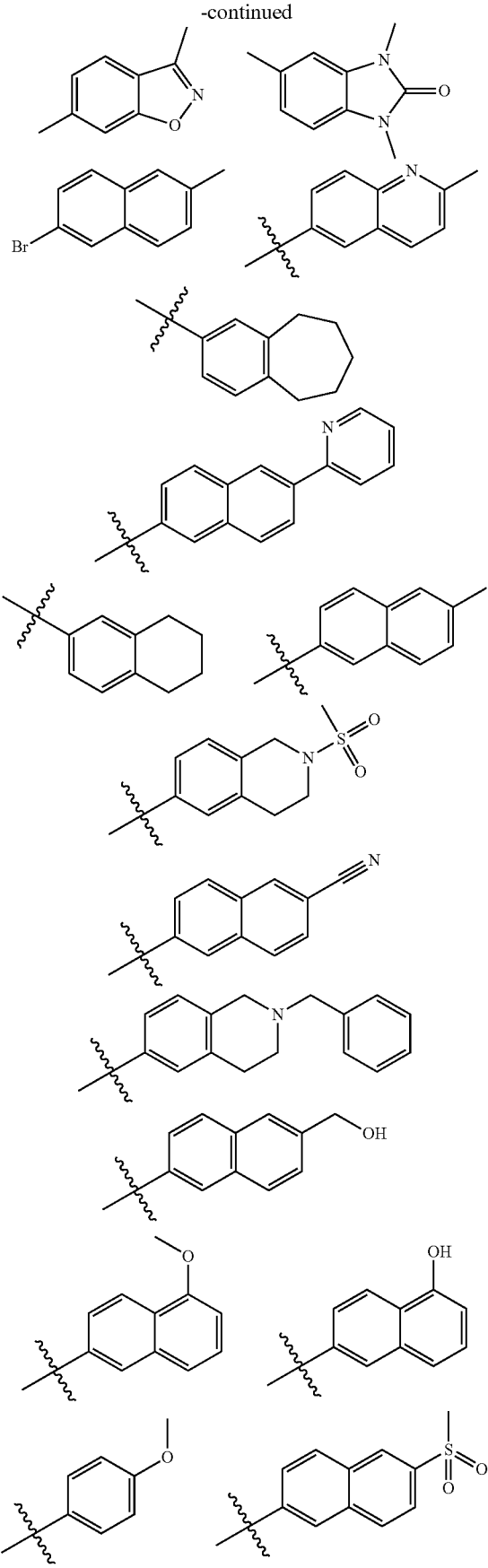

-continued
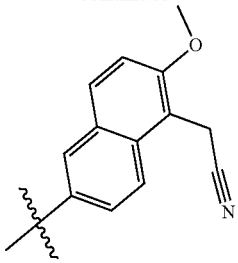
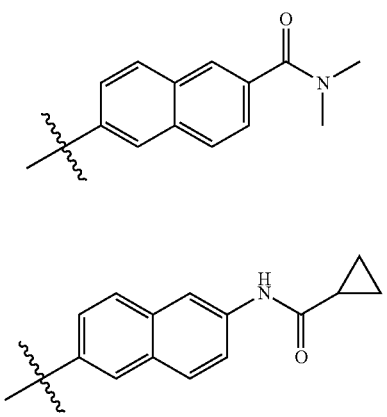
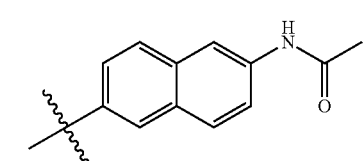
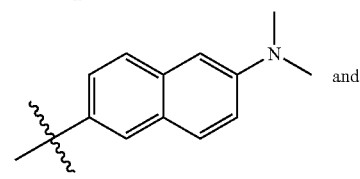
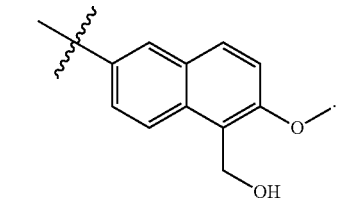 and
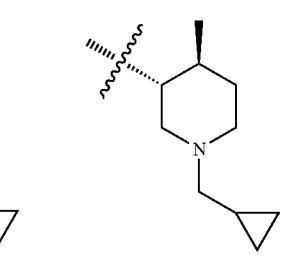
12. The compound of claim 1 wherein:
R¹ is selected from the group consisting of:
-continued
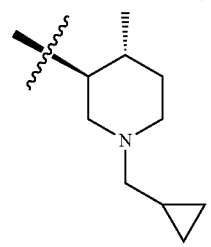
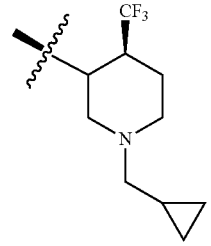
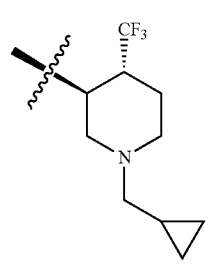
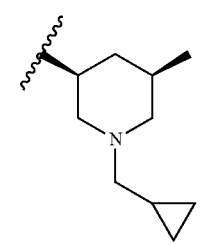
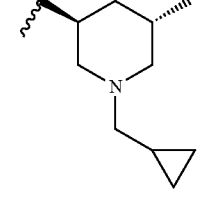
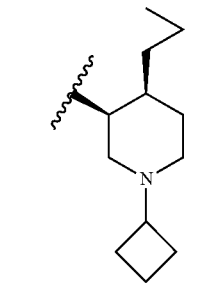 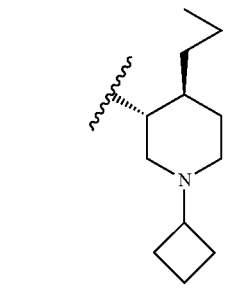

377
-continued
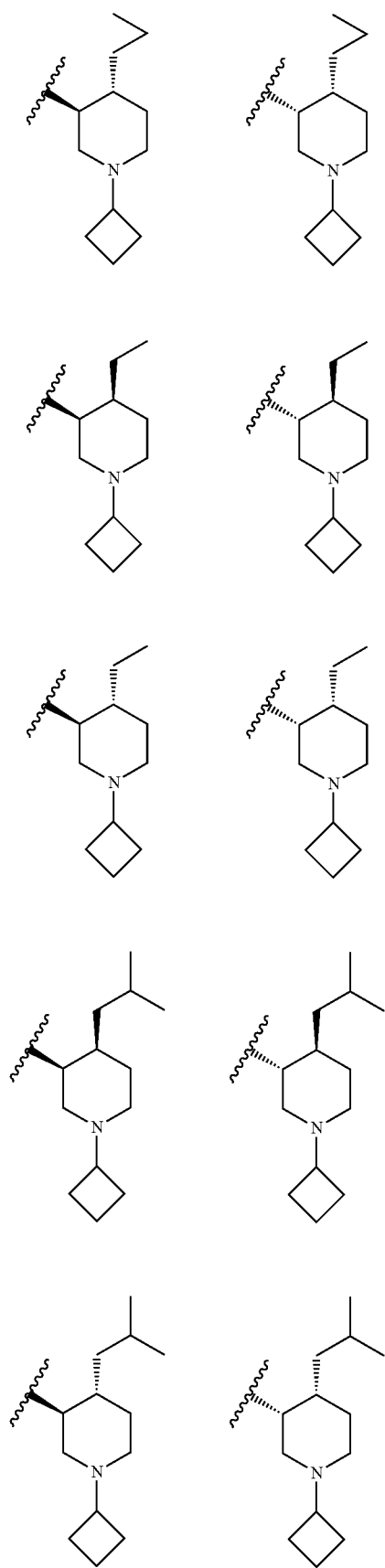
378
-continued
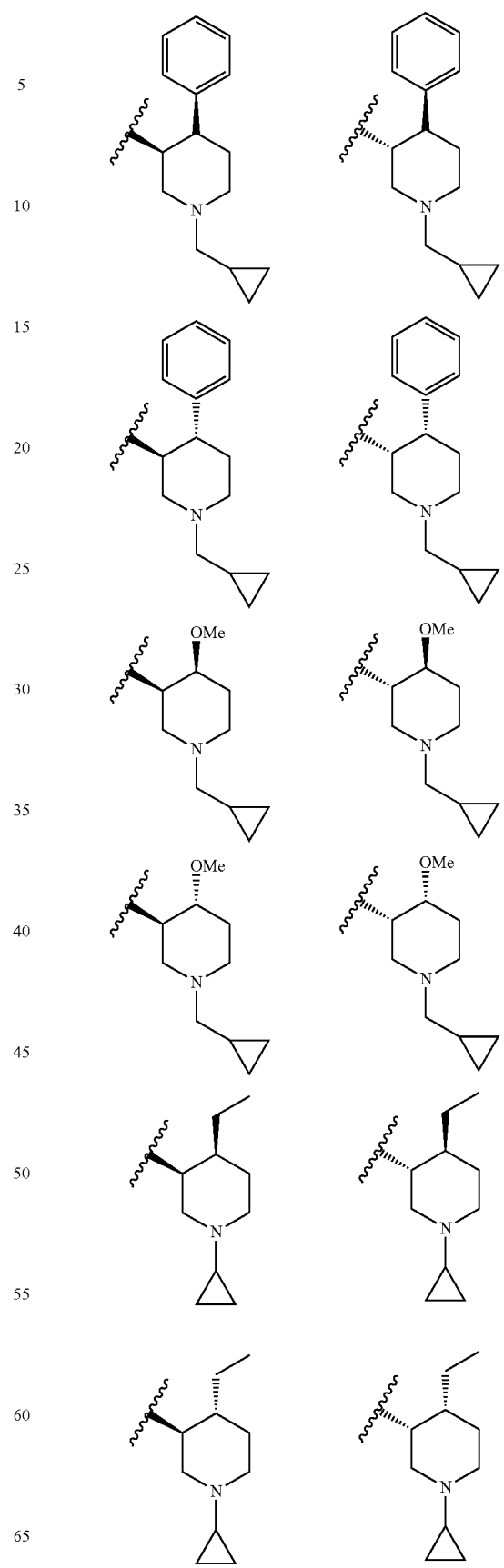

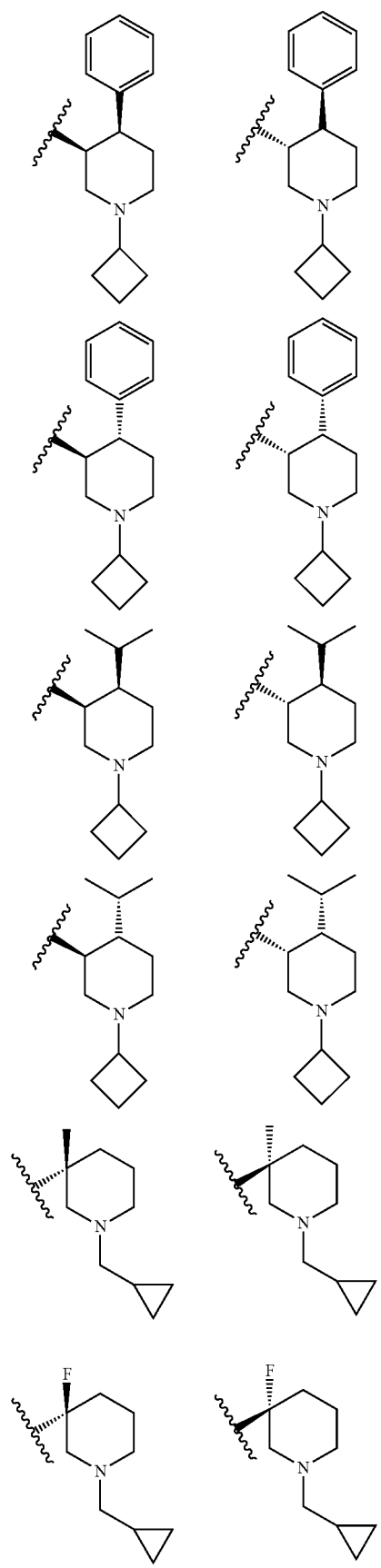
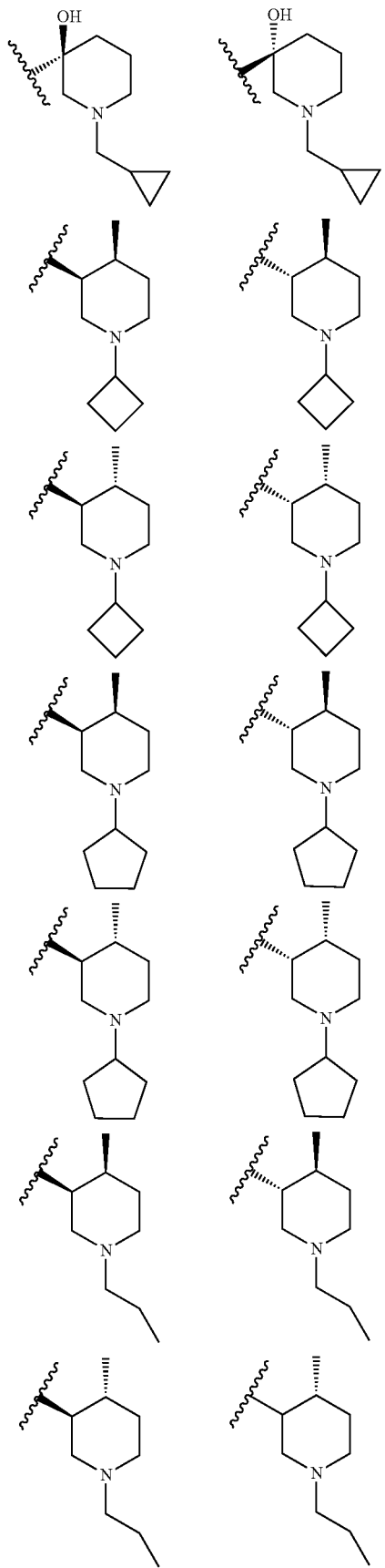

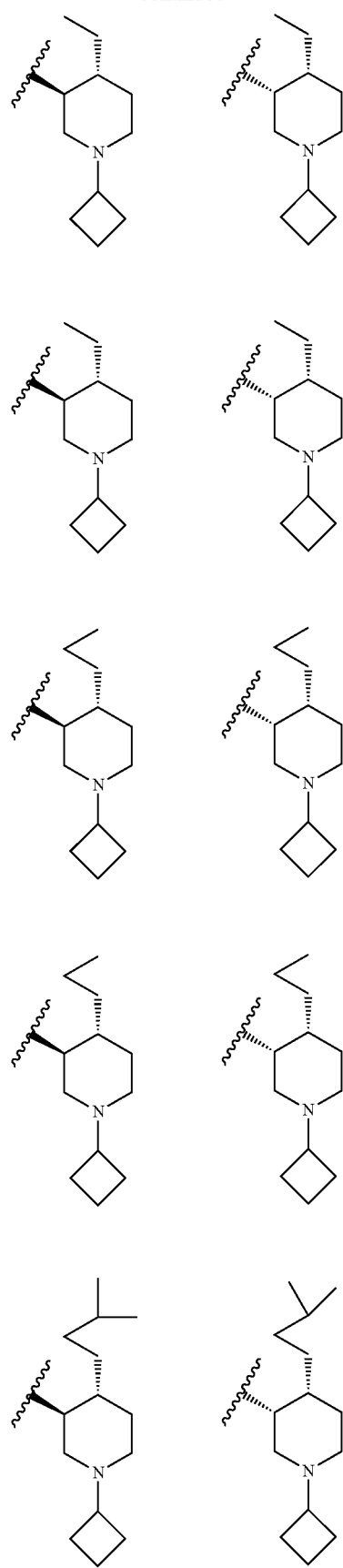
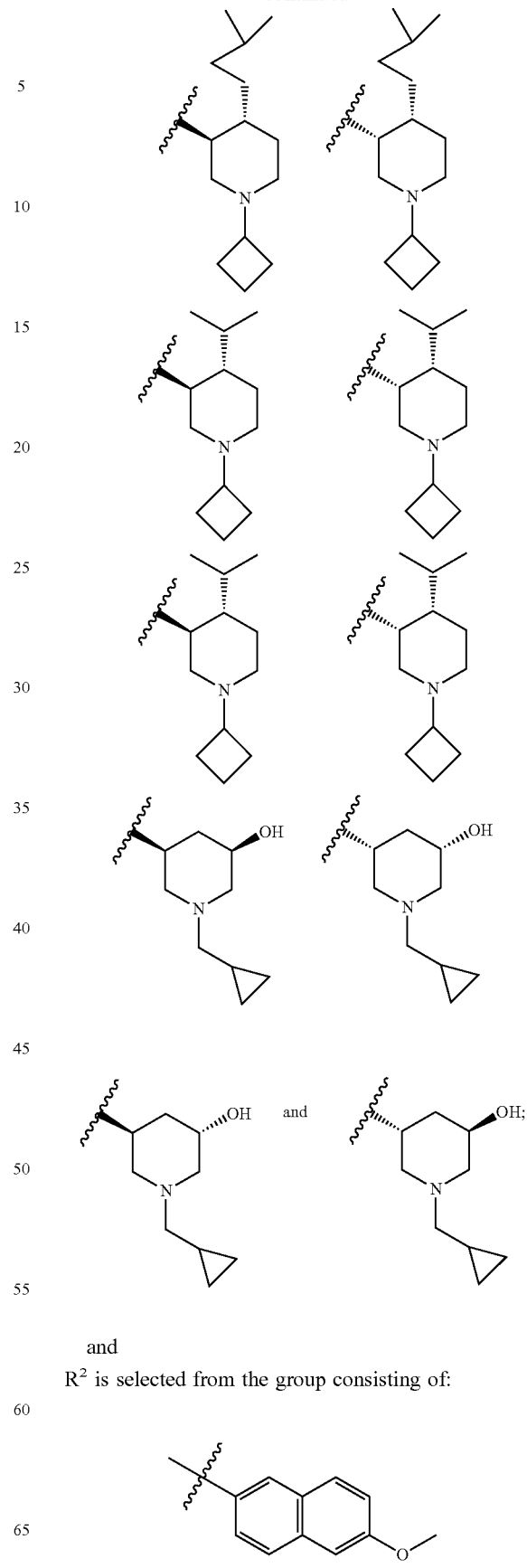
and
R² is selected from the group consisting of:

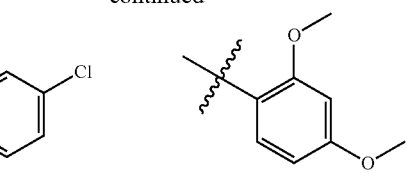
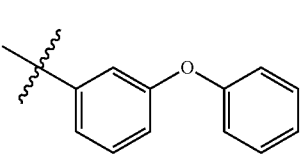
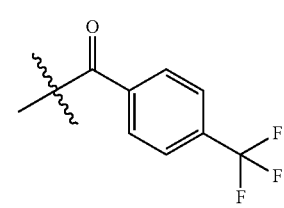
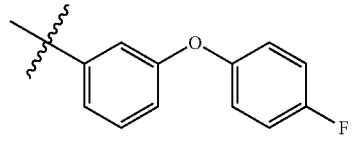
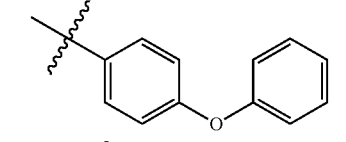
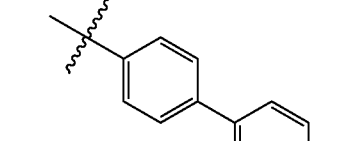
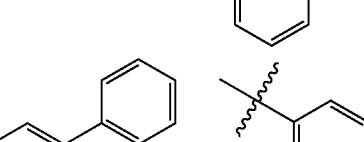
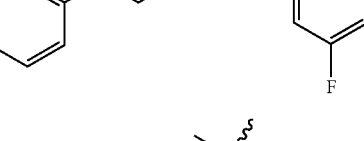
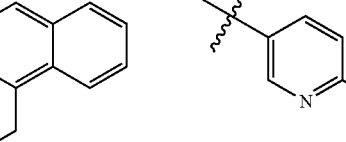
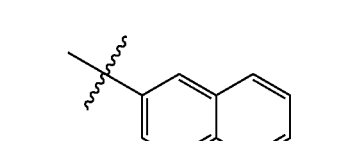
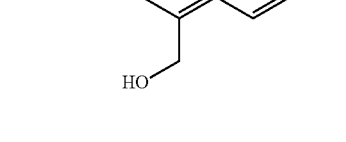
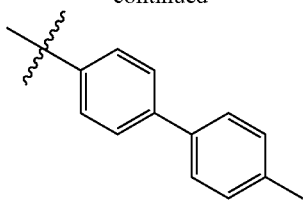
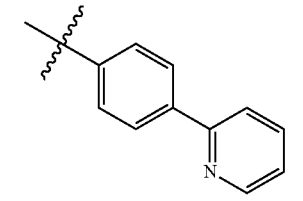
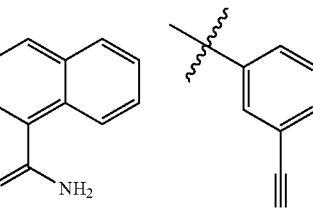
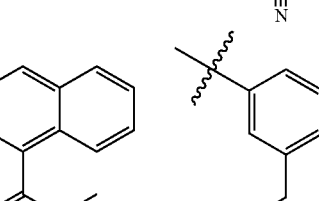
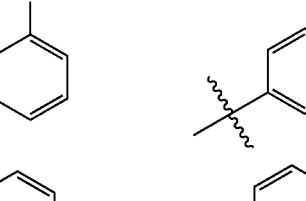
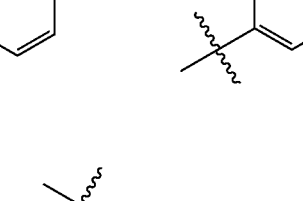
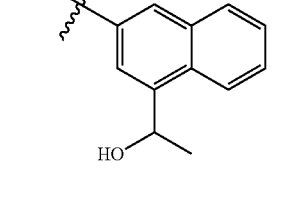
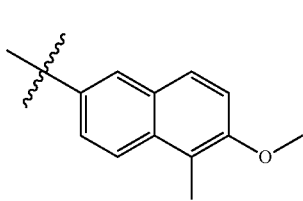

385
-continued
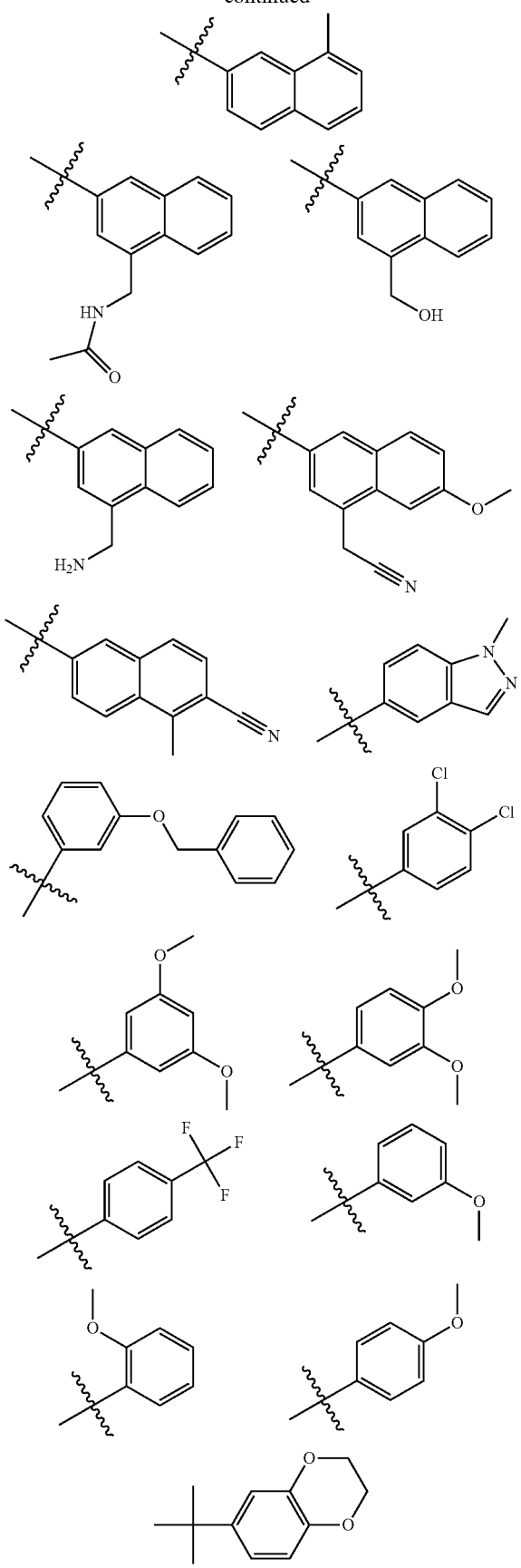
386
-continued
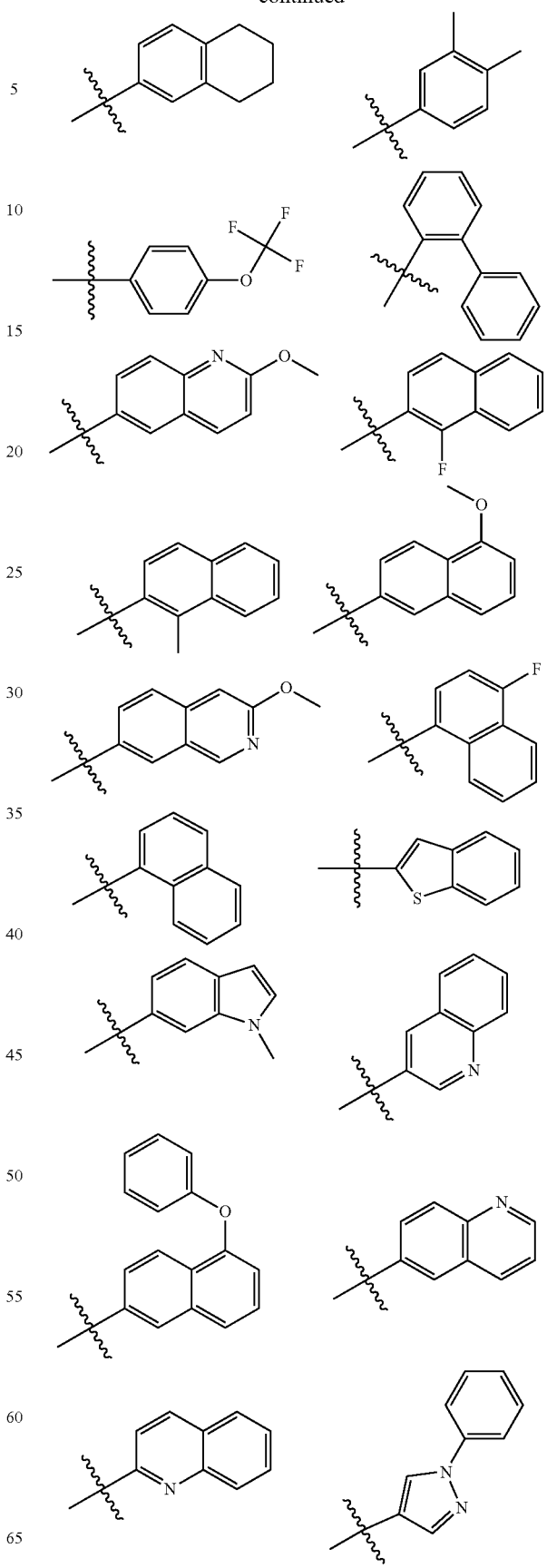

387
-continued
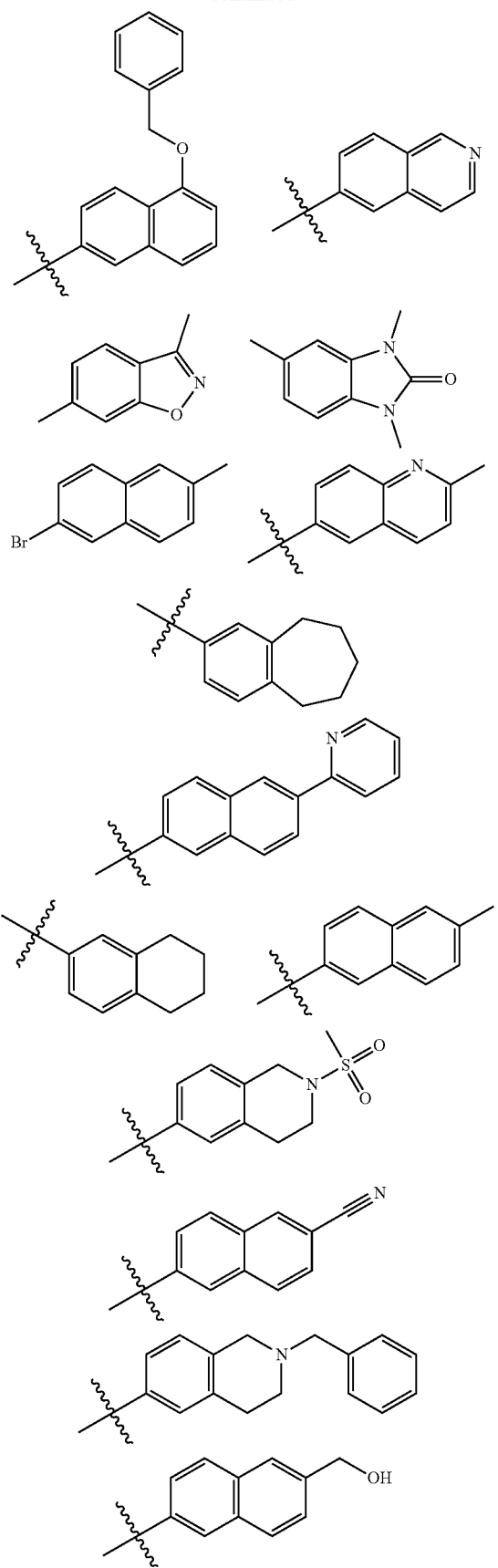
388
-continued
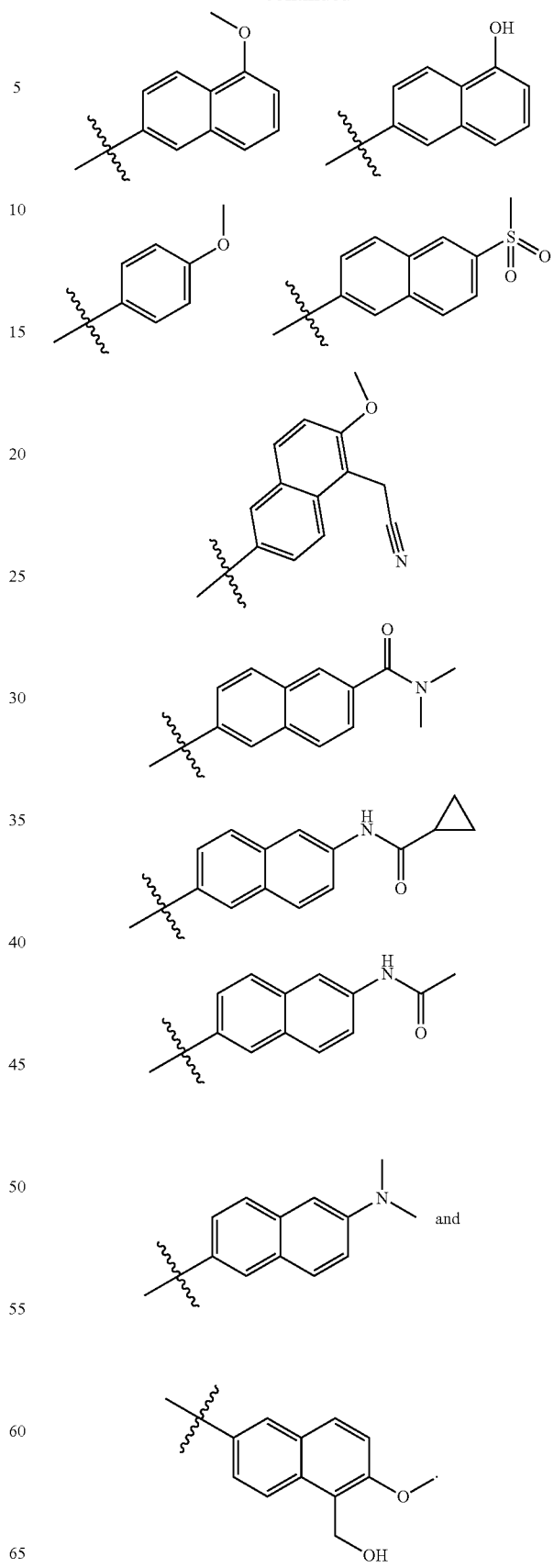
and

13. A compound selected from the group consisting of:
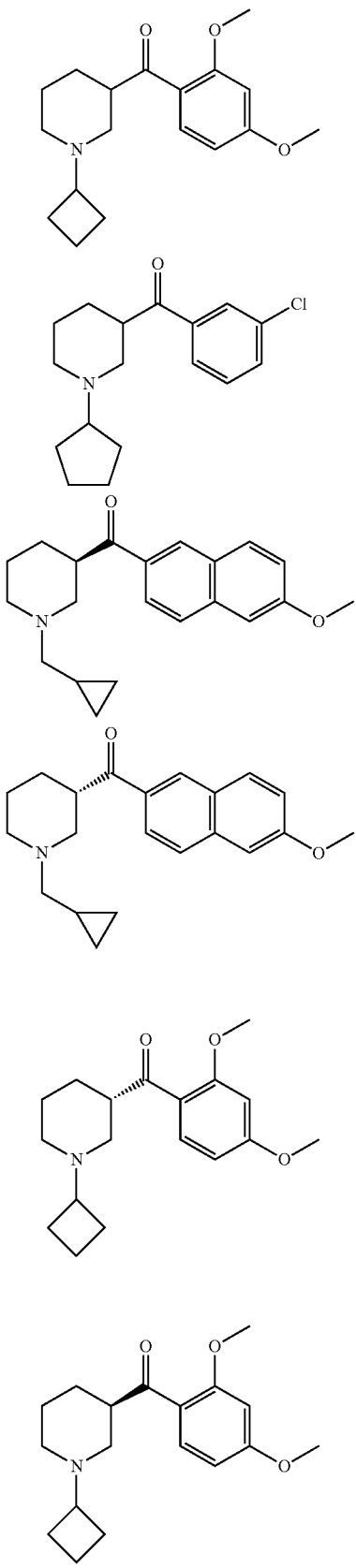
-continued
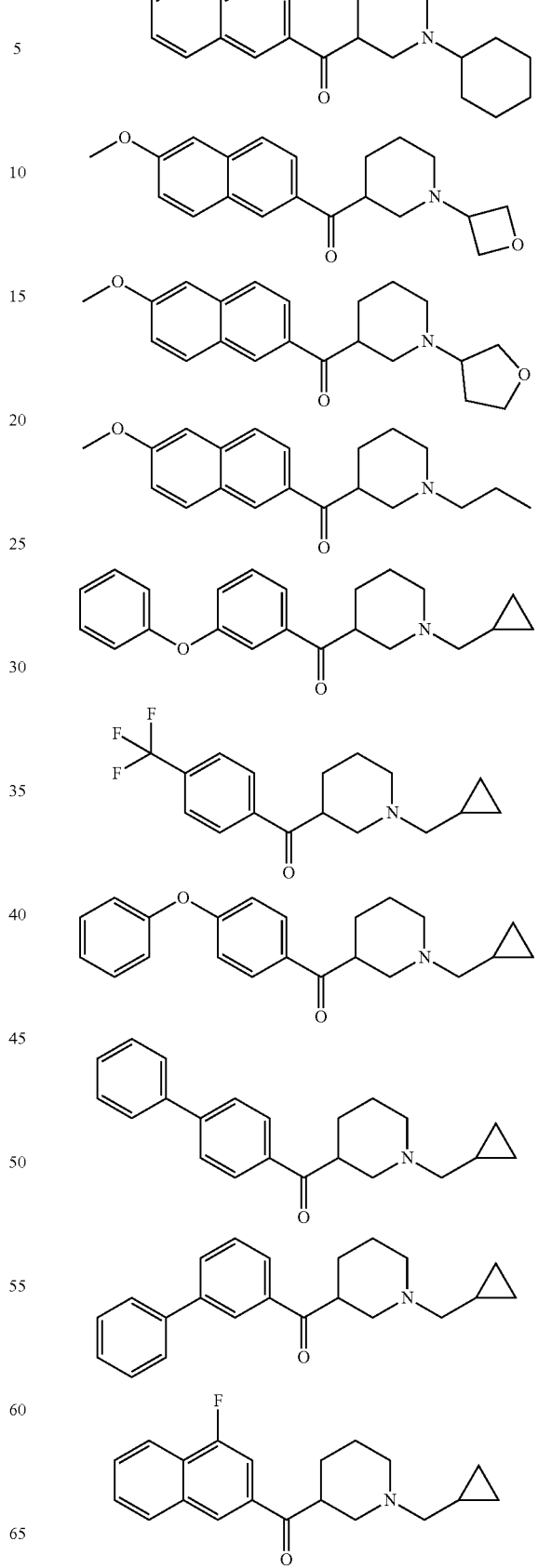

391
-continued
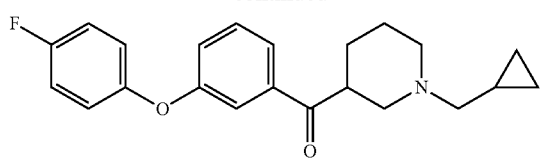
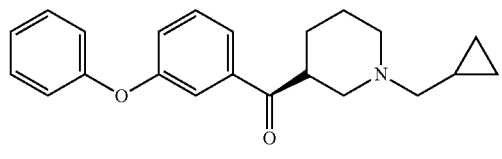
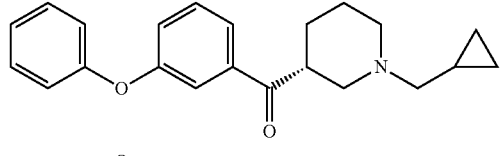
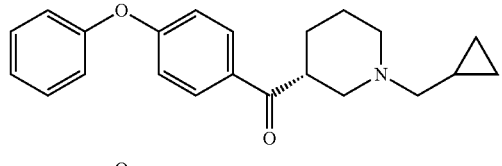
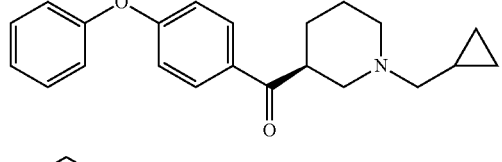
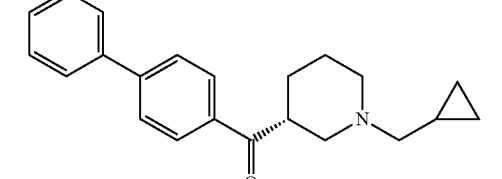
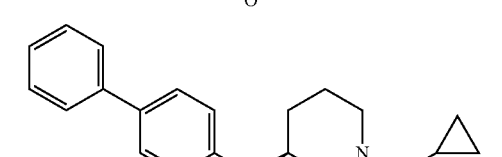
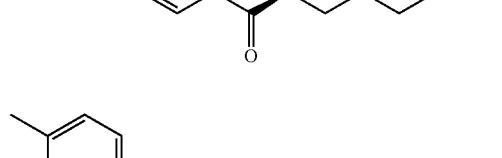
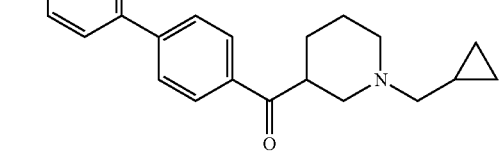
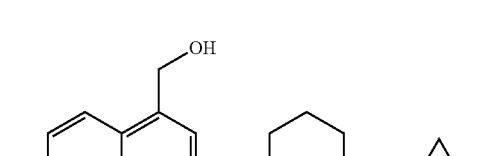
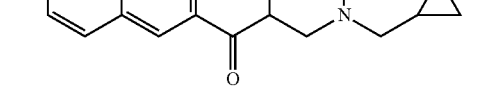
392
-continued
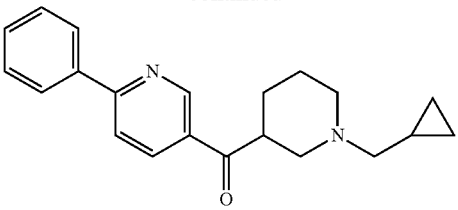
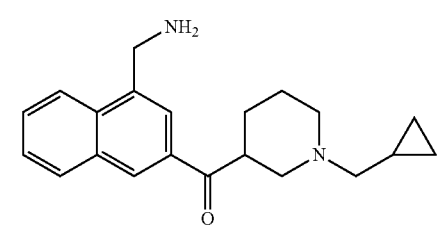
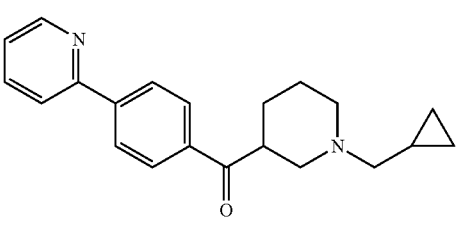
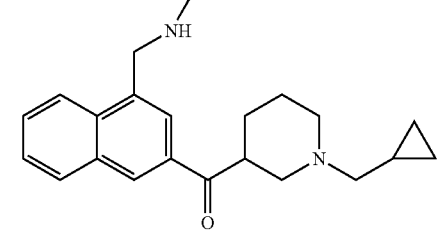
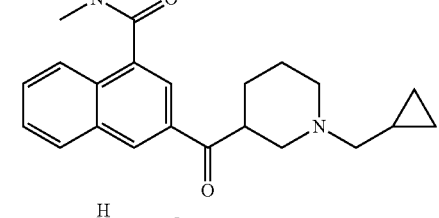
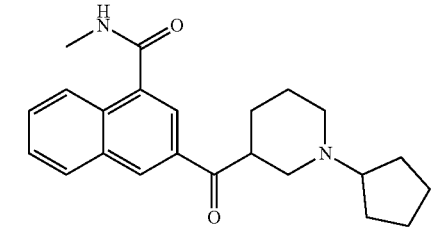
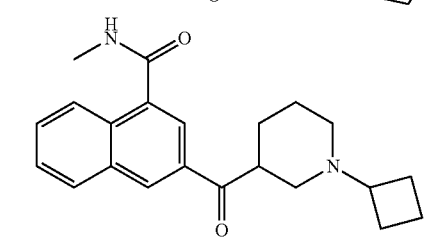

393
-continued
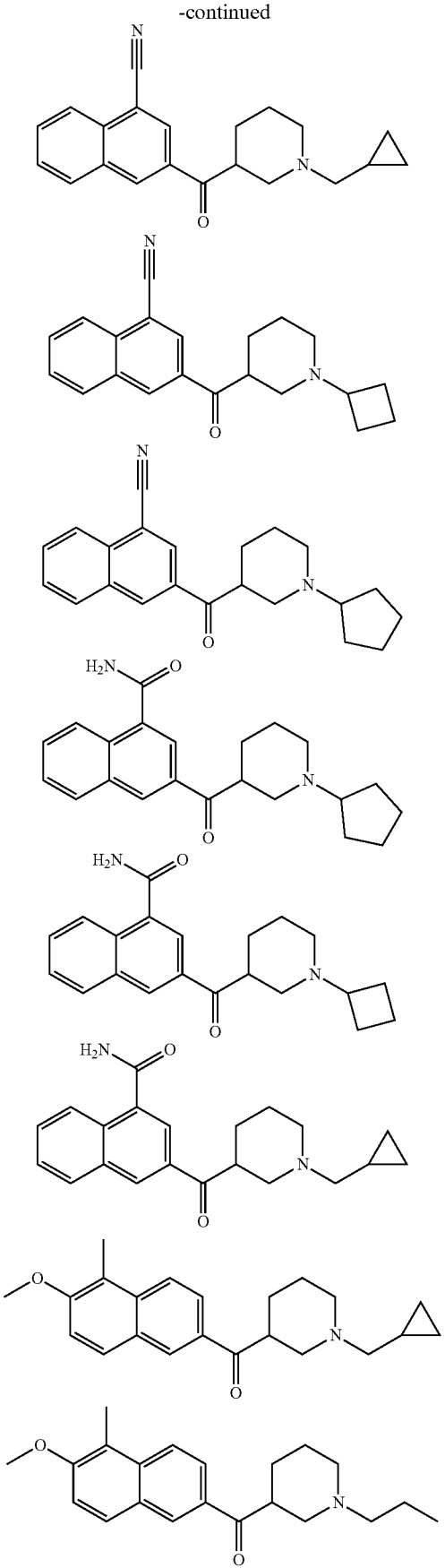
394
-continued
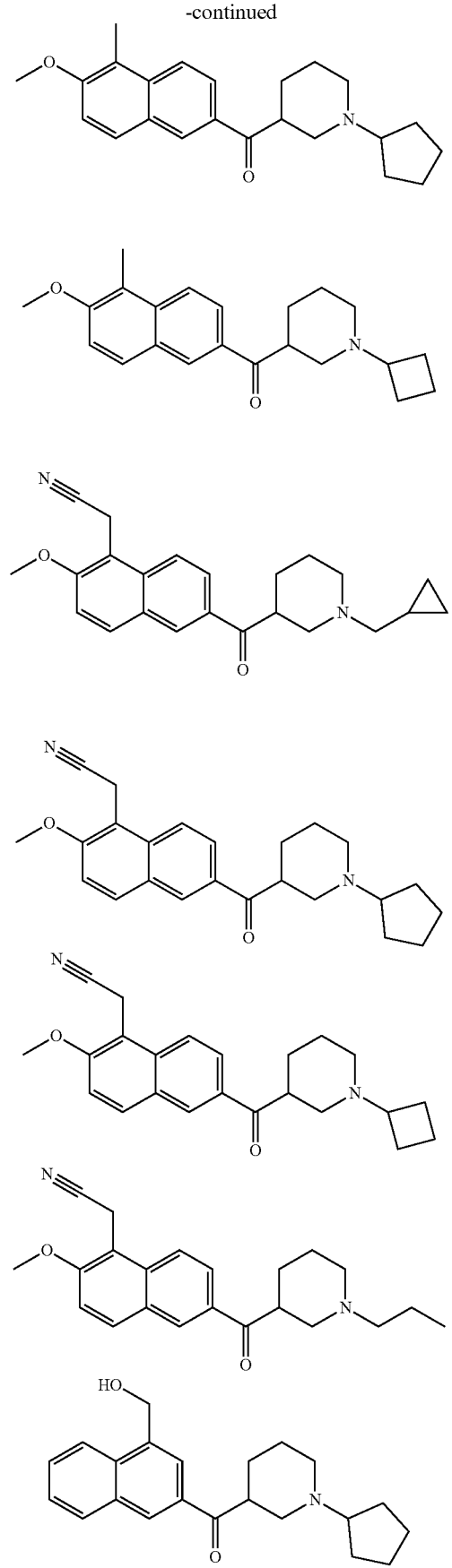

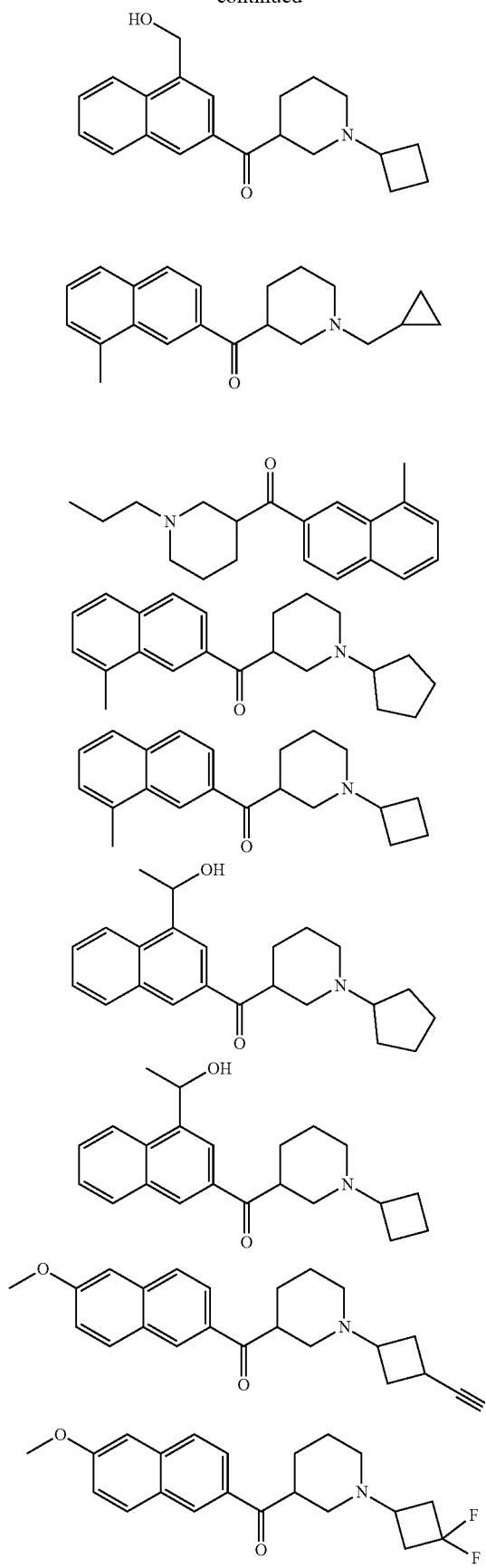
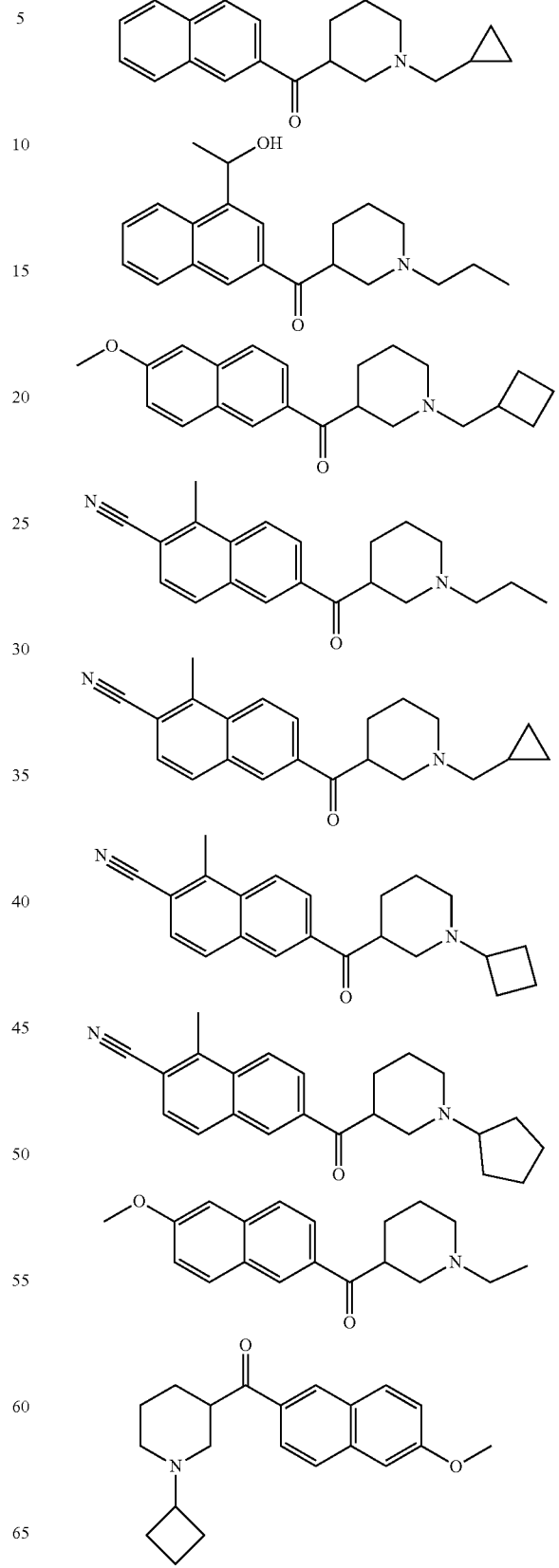

397
-continued
398
-continued
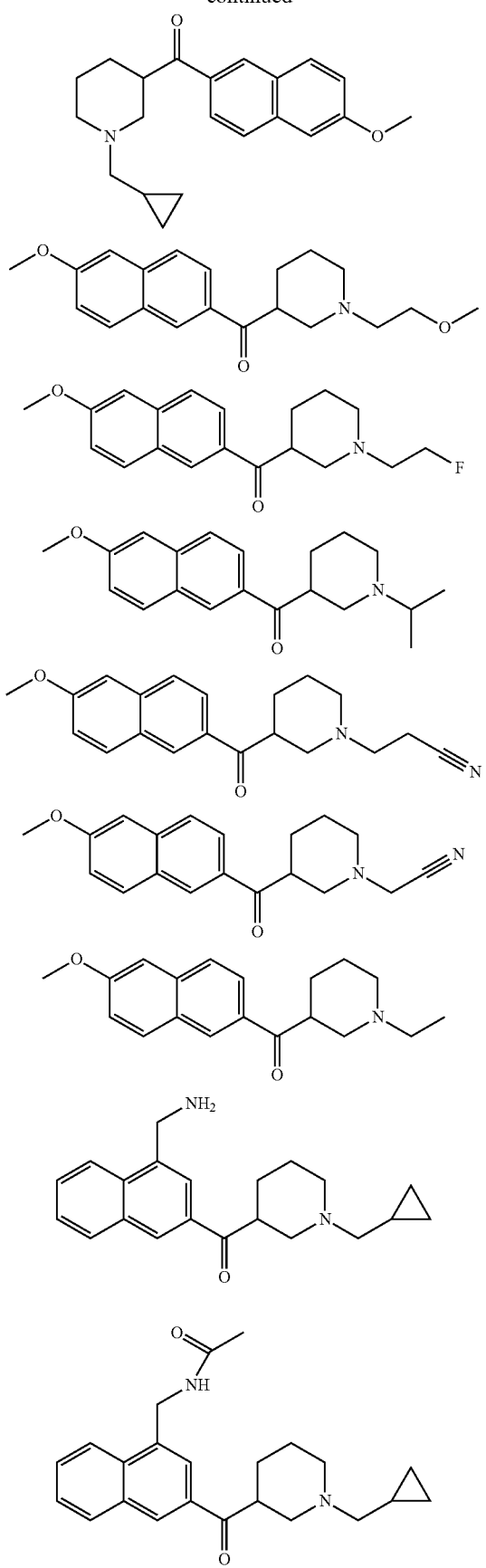
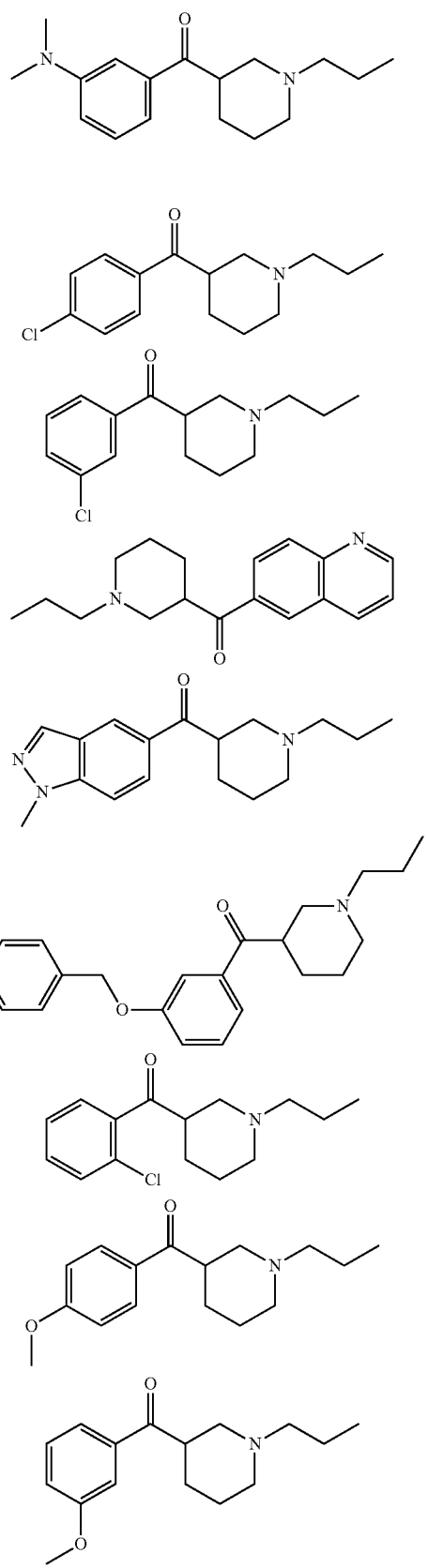

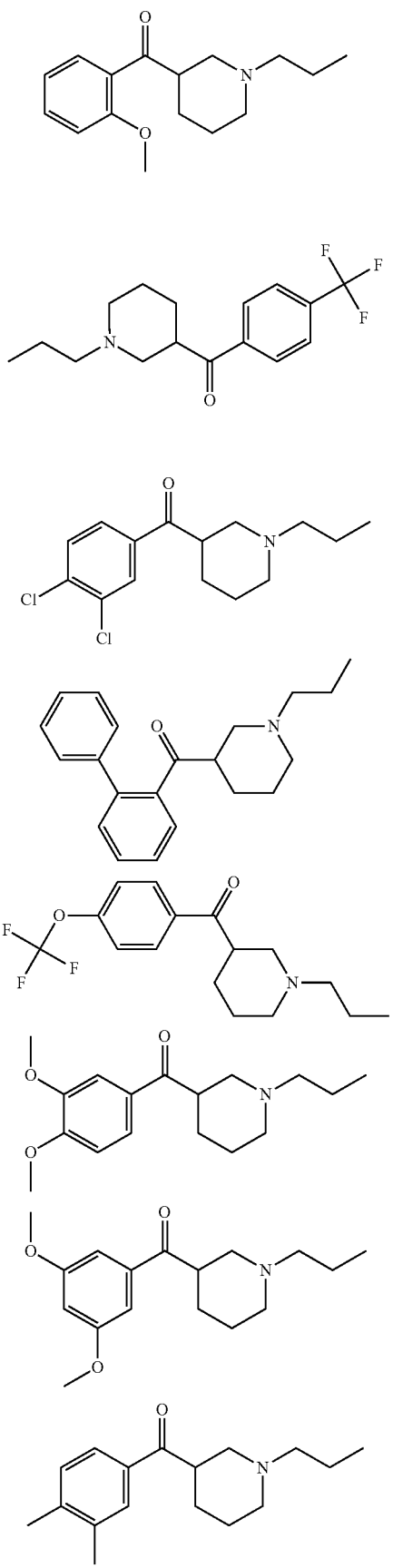
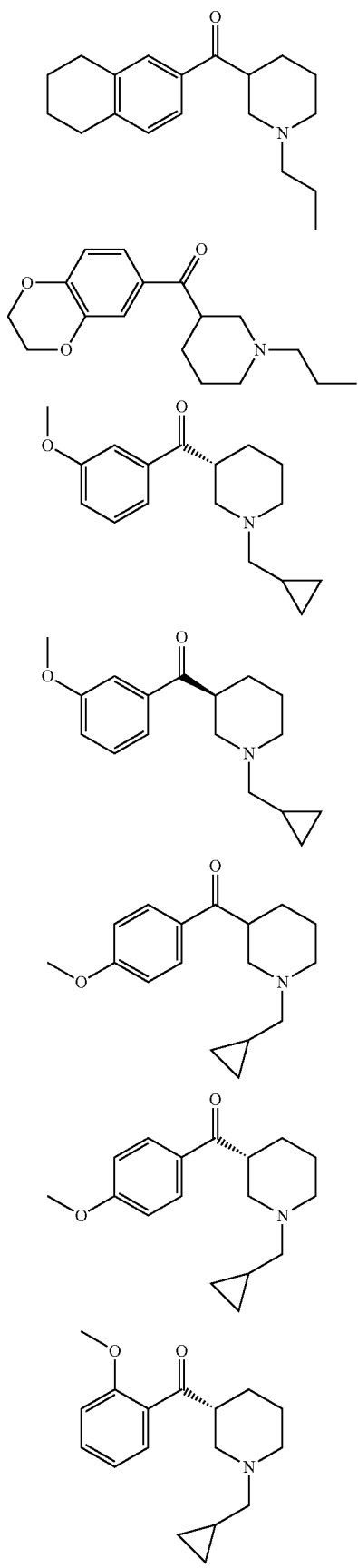

-continued

403
-continued
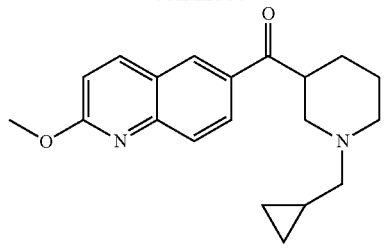
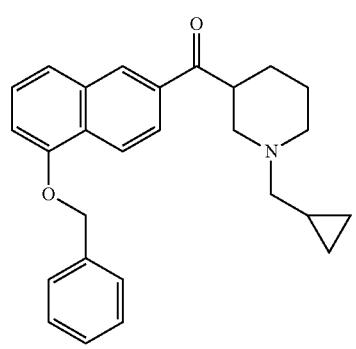
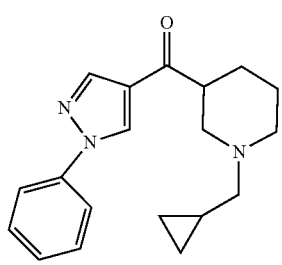
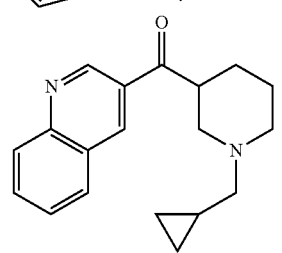
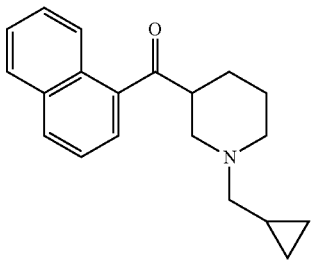
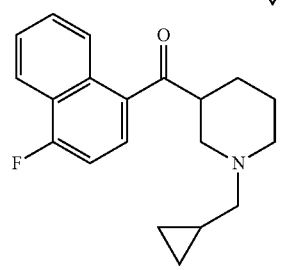
404
-continued
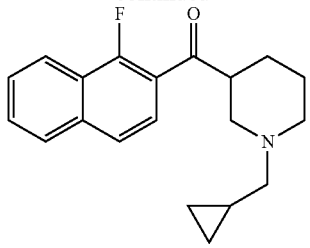
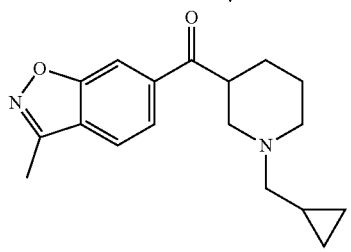
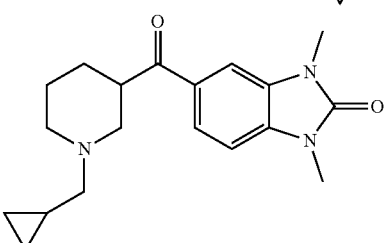
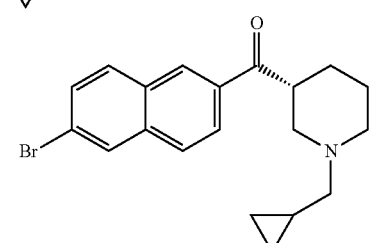
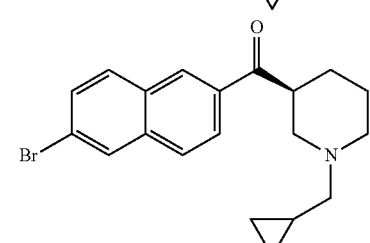
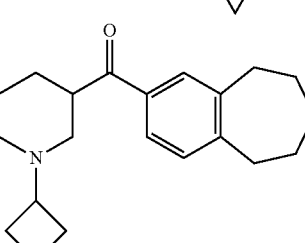
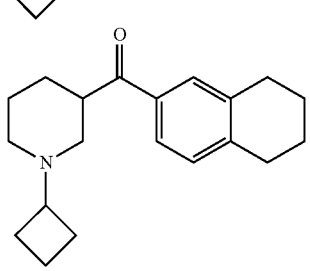

405
-continued
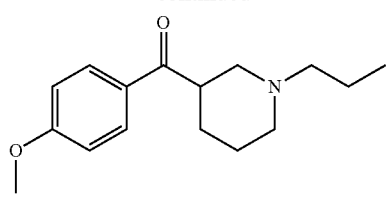
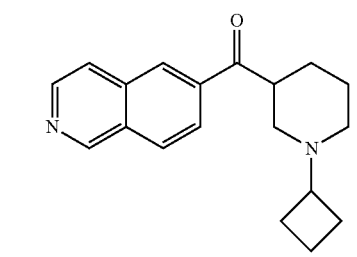
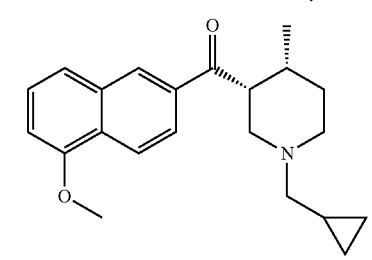
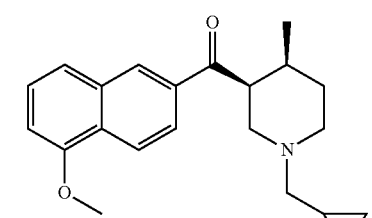
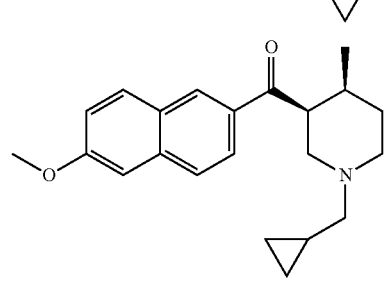
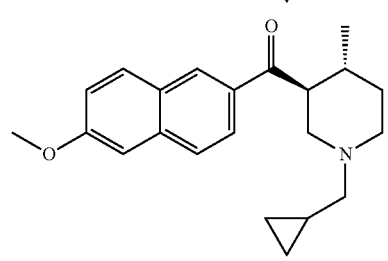
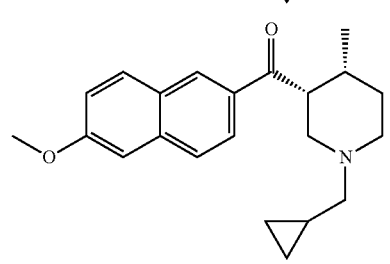
406
-continued
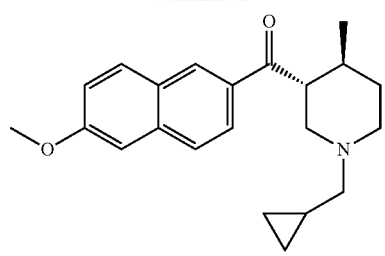
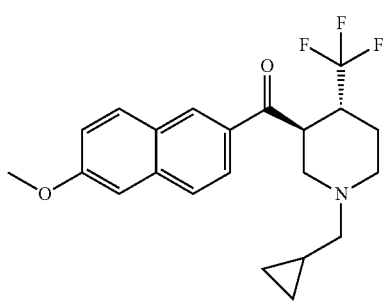
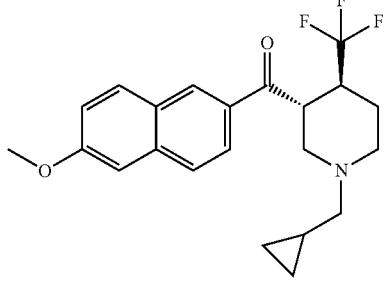
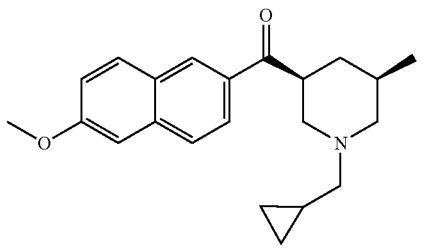
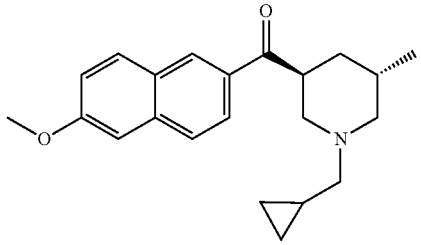
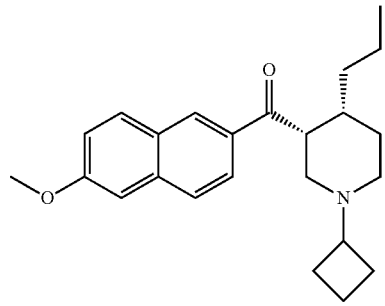

407
-continued
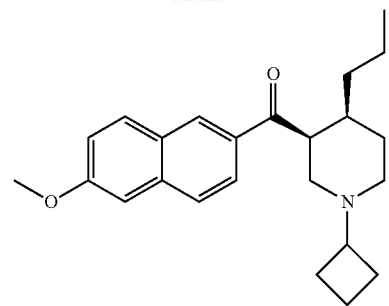
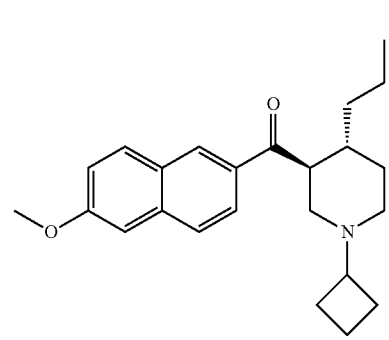
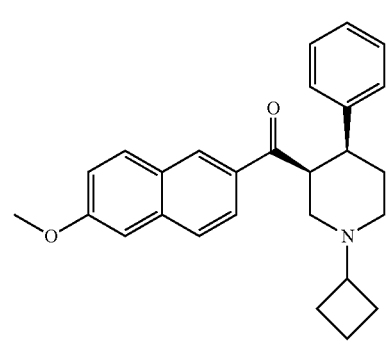
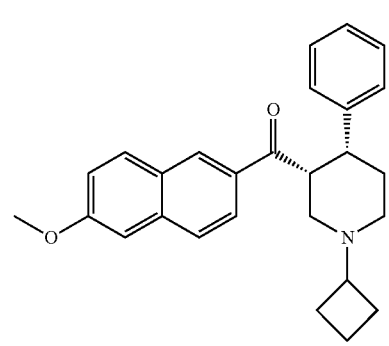
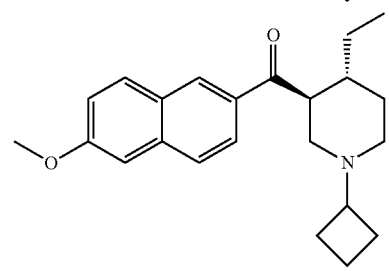
408
-continued
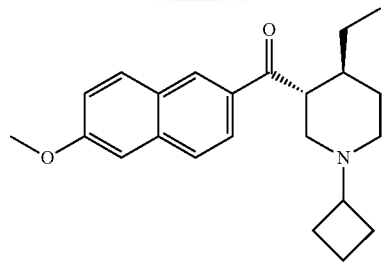
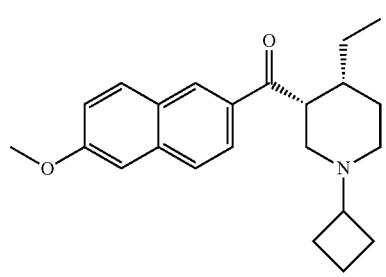
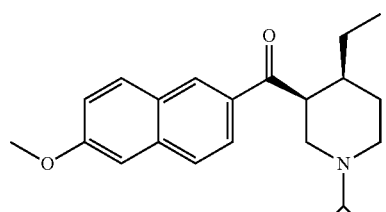
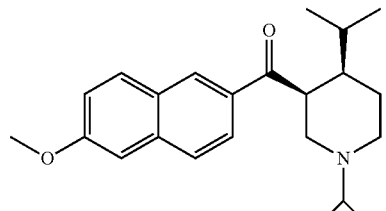
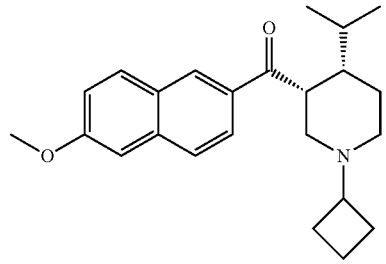
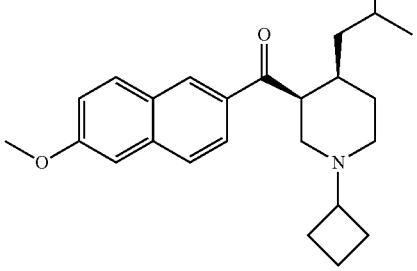

409
-continued
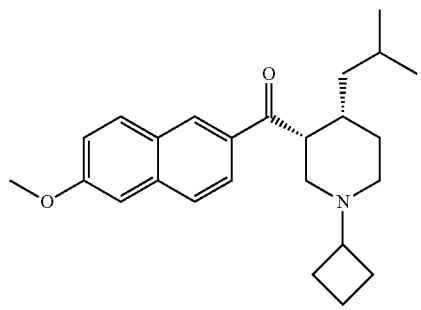
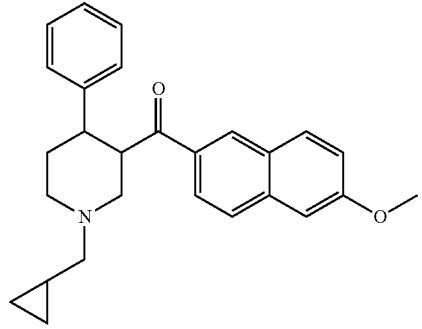
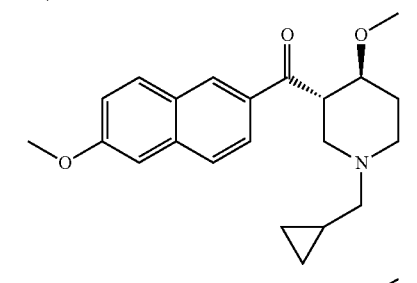
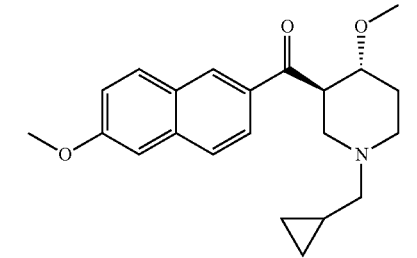
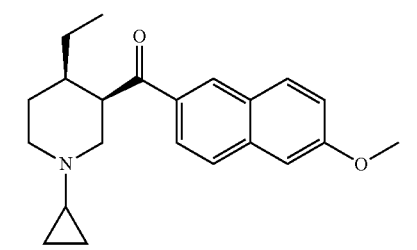
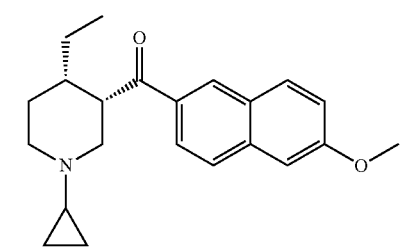
410
-continued
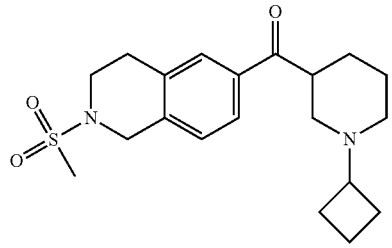
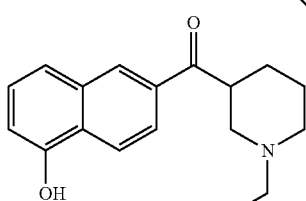
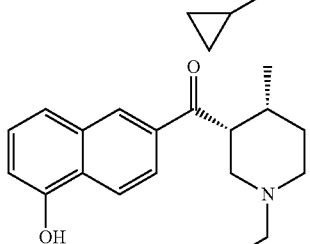
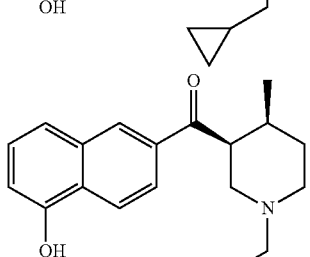
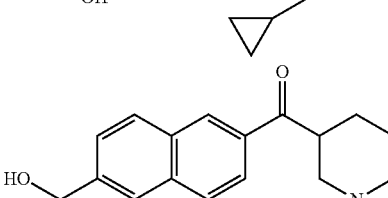
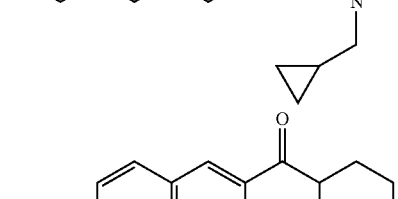
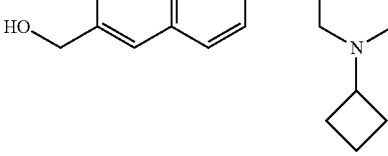
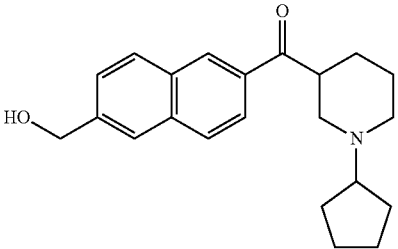

411
-continued
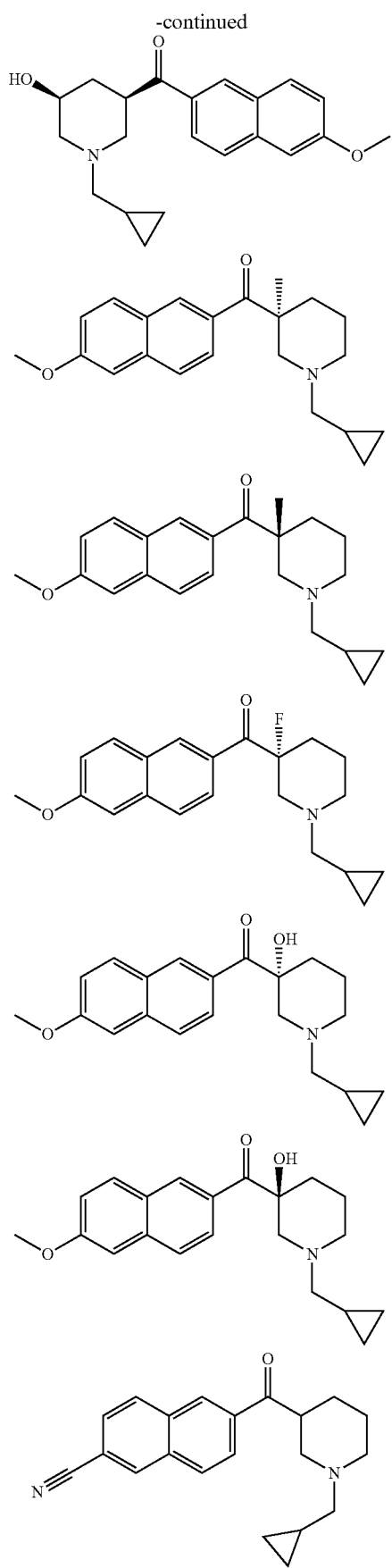
412
-continued
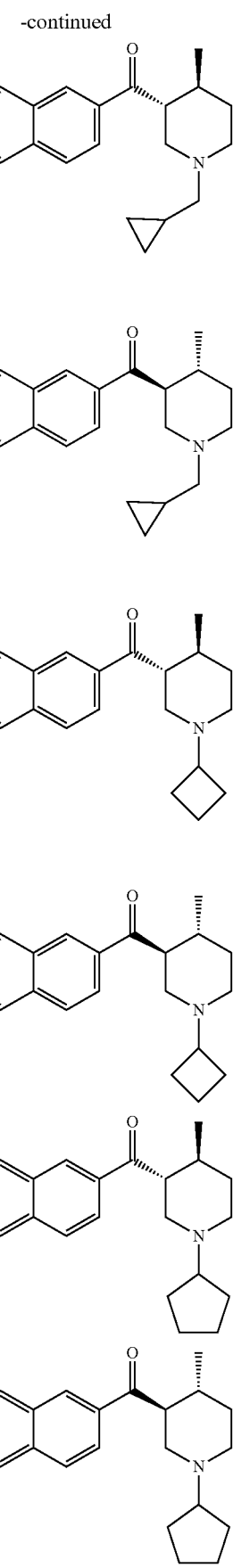

413
-continued
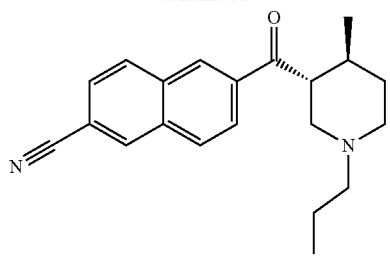
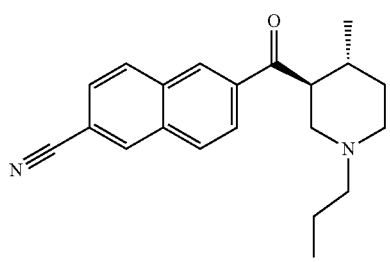
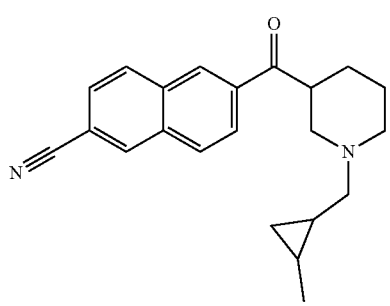
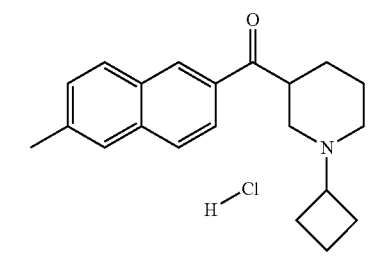
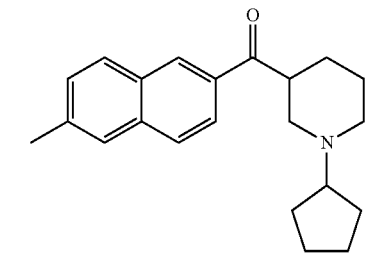
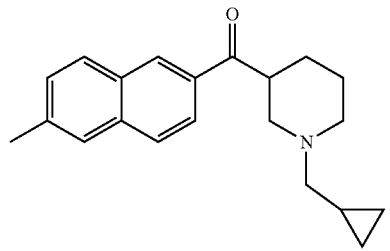
414
-continued
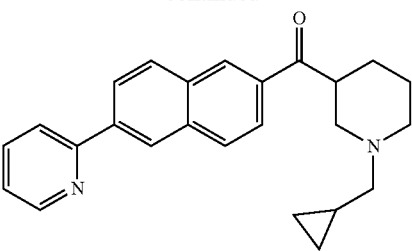
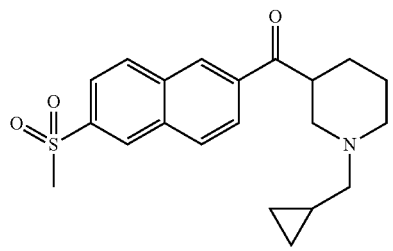
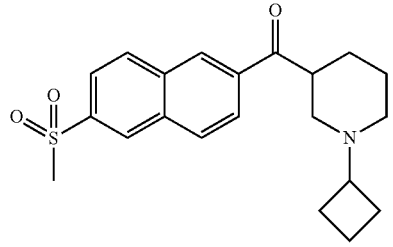
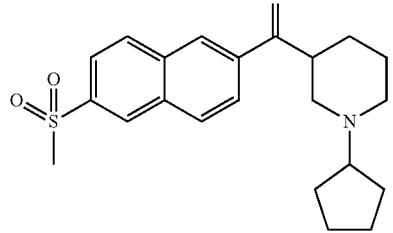
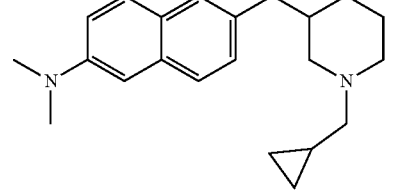
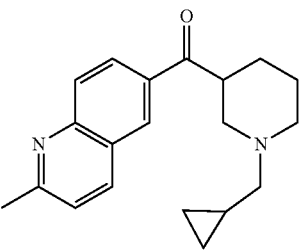

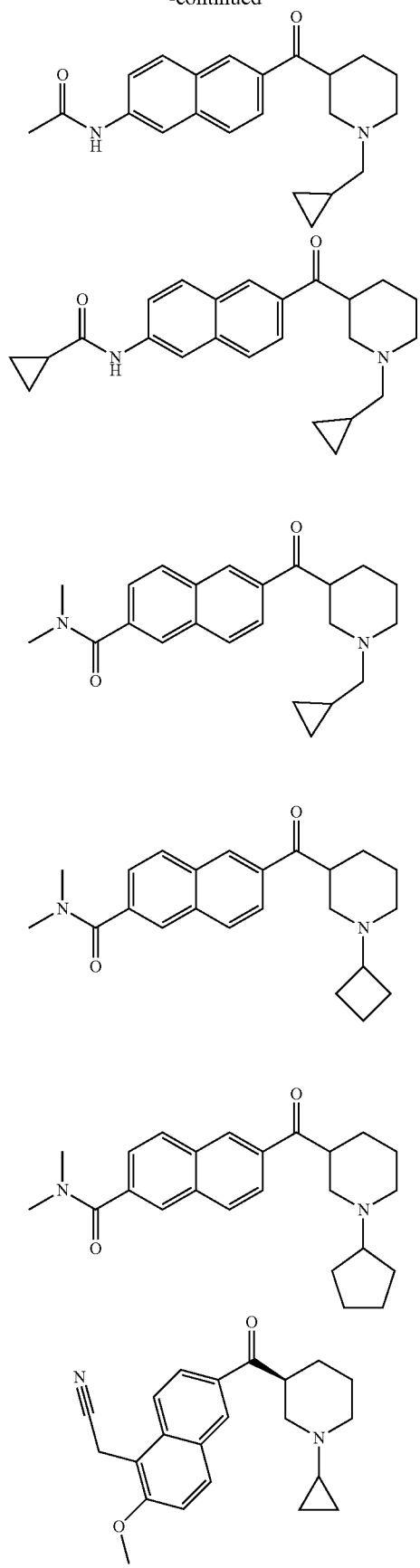
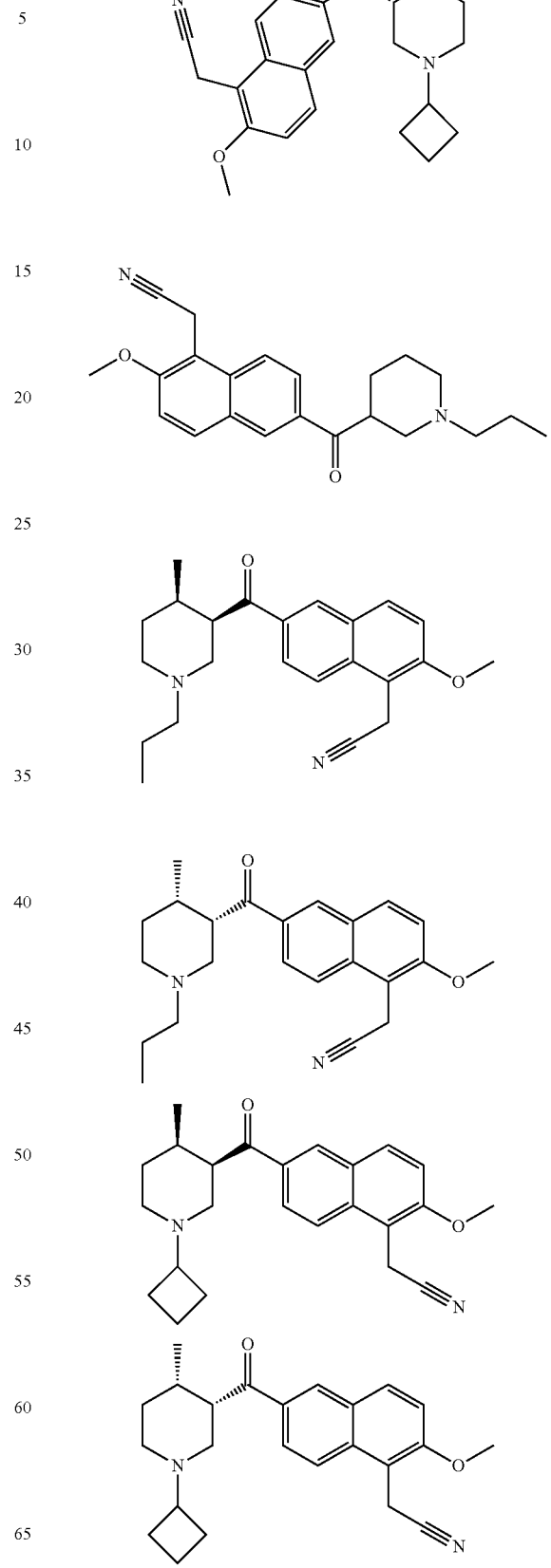

417
-continued
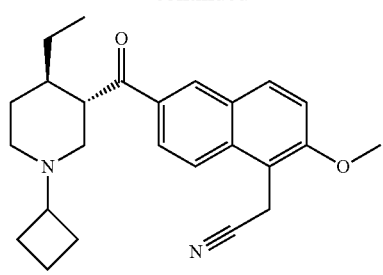
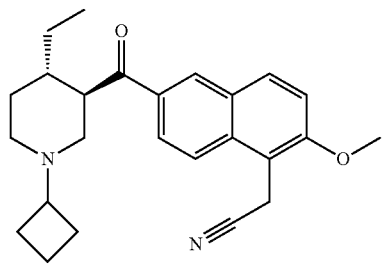
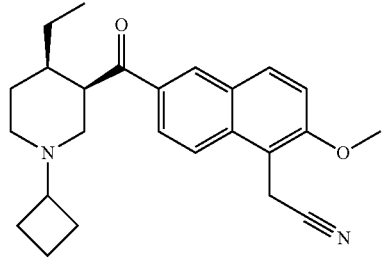
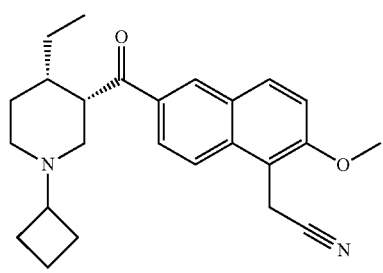
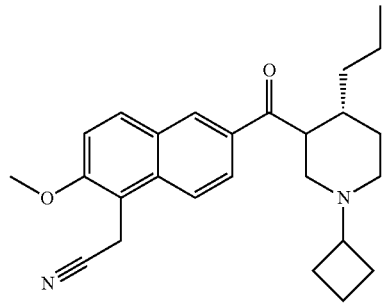
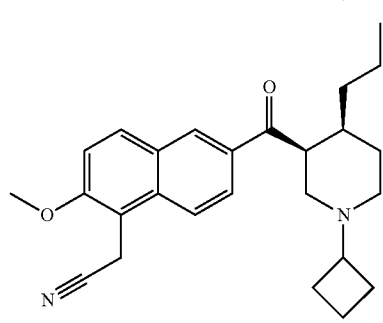
418
-continued
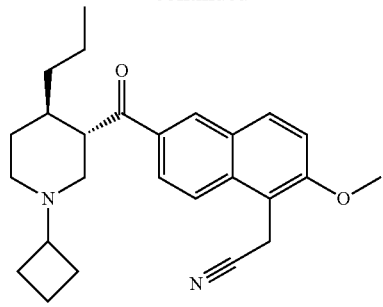
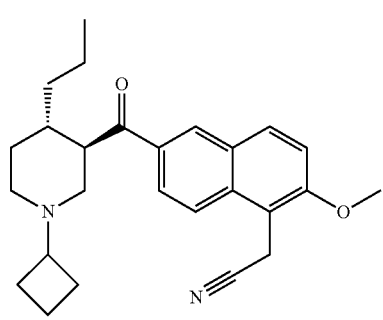
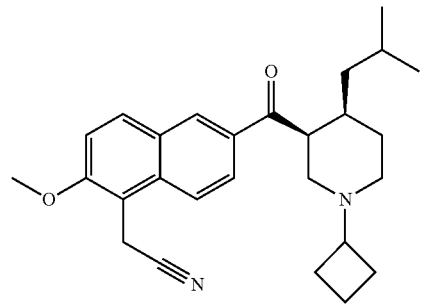
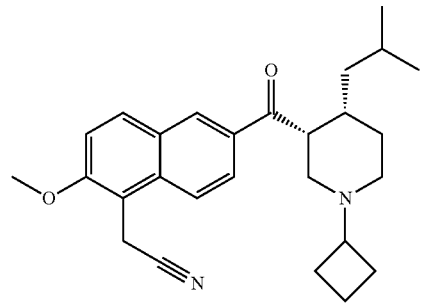
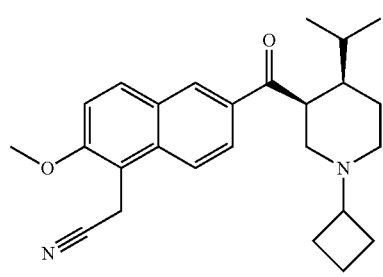

419
-continued
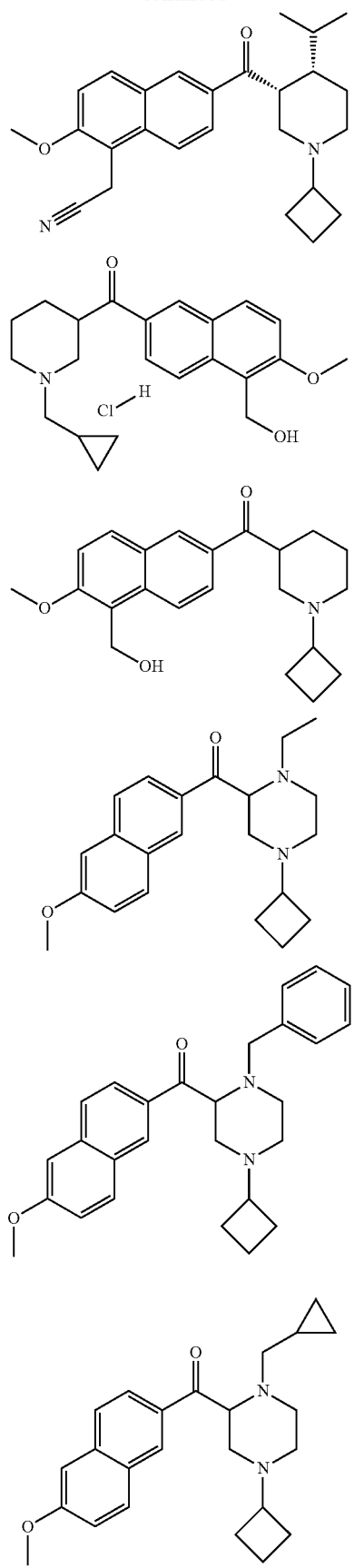
420
-continued
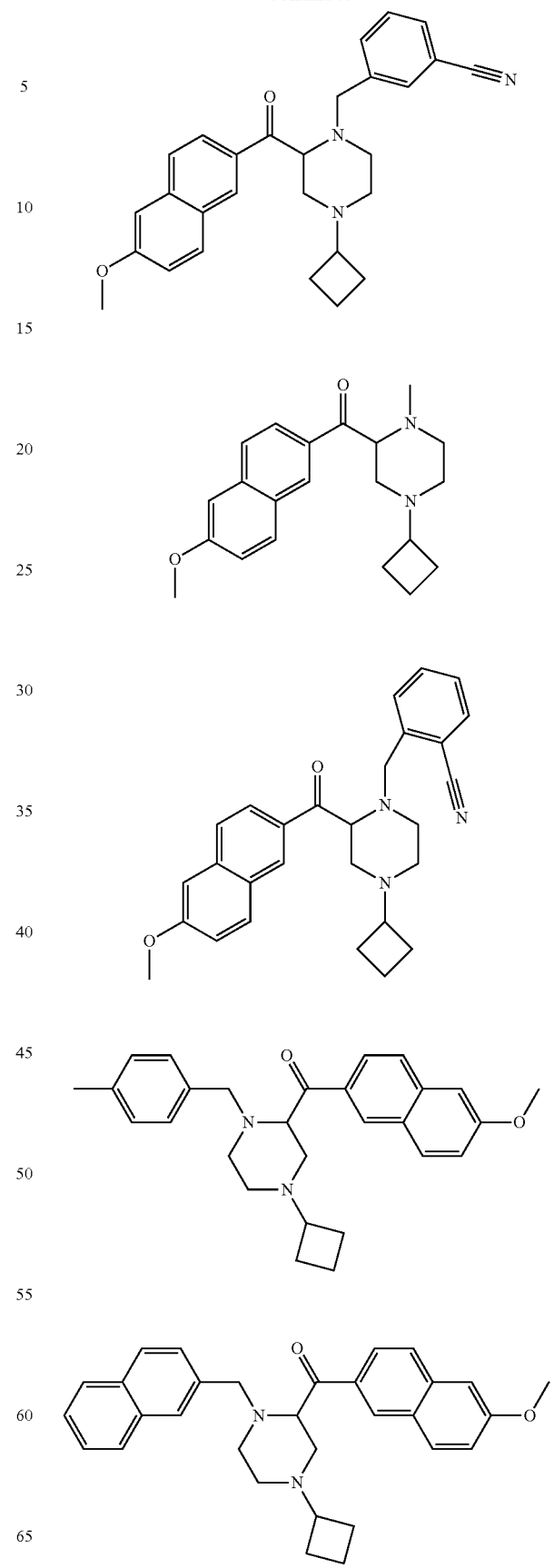

-continued

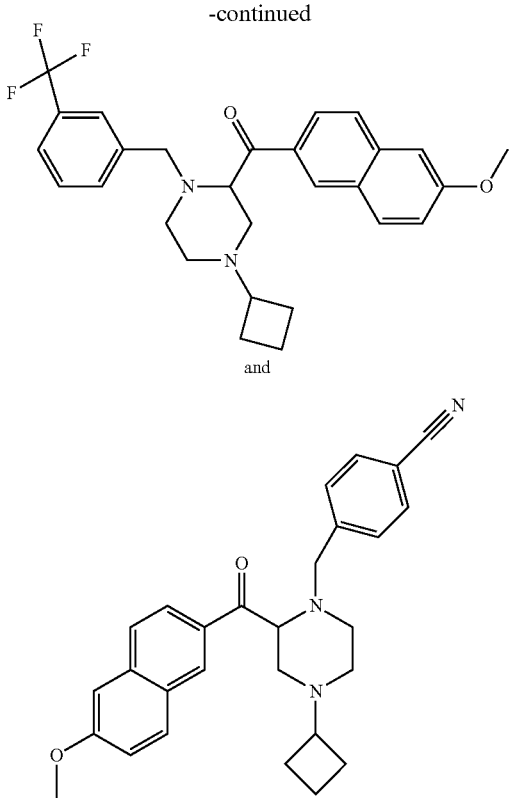

or a salt thereof.

14. A composition comprising a compound as described in claim 1, or a pharmaceutically acceptable salt thereof, and a pharmaceutically acceptable adjuvant, carrier, or vehicle.

15. A method of treating cancer in a mammal in need thereof, comprising administering to the mammal, an effective amount of a compound as described in claim 1, or a pharmaceutically acceptable salt thereof.

16. A method of inducing differentiation of a cancer stem/progenitor cell(s) in a mammal in need thereof, comprising administering to the mammal, an effective amount of a compound as described in claim 1, or a pharmaceutically acceptable salt thereof.

17. A method of reducing activity of a cancer stem/progenitor cell(s) in a mammal in need thereof, comprising administering to the mammal, an effective amount of a compound as described in claim 1, or a pharmaceutically acceptable salt thereof.

18. A method of depleting a cancer stem/progenitor cell in a mammal in need thereof, comprising administering to the mammal, an effective amount of a compound as described in claim 1, or a pharmaceutically acceptable salt thereof.

19. A method of decreasing cancer initiation in a mammal in need thereof, comprising administering to the mammal, an effective amount of a compound as described in claim 1, or a pharmaceutically acceptable salt thereof.

20. A compound of formula (I):

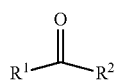

(I)

or a salt thereof, wherein:
$R^1$ is:
  a) a carbon-linked piperidine ring that is substituted on the piperidine ring nitrogen with a group $R^x$ and that is optionally further substituted with one or more groups independently selected from the group consisting of $C_{1-6}$alkyl, $C_{2-6}$alkenyl, $C_{2-6}$alkynyl, $C_{3-8}$carbocycle, 3-8 membered heterocycle, aryl, heteroaryl, halo, —$NO_2$, —$N(R^b)_2$, —CN, —C(O)—N($R^b$)$_2$, —S(O)—N($R^b$)$_2$, —S(O)$_2$—N($R^b$)$_2$, —O—$R^b$, —S—$R^b$, —O—C(O)—$R^b$, —C(O)—$R^b$, —C(O)—O$R^b$, —S(O)—$R^b$, —S(O)$_2$—$R^b$, —N($R^b$)—C(O)—$R^b$, —N($R^b$)—S(O)—$R^b$, —N($R^b$)—C(O)—N($R^b$)$_2$, and —N($R^b$)—S(O)$_2$—$R^b$; wherein each $C_{1-6}$alkyl, $C_{2-6}$alkenyl, $C_2$-6alkynyl, $C_{3-8}$carbocycle, 3-8 membered heterocycle, aryl, and heteroaryl is optionally substituted with one or more groups independently selected from the group consisting of halo, —$NO_2$—N($R^b$)$_2$, —CN, —C(O)—N($R^b$)$_2$, —S(O)—N($R^b$)$_2$, —S(O)$_2$—N($R^b$)$_2$, —O—$R^b$, —S—$R^b$, —O—C(O)—$R^b$, —C(O)—$R^b$, —C(O)—O$R^b$, —S(O)—$R^b$, —S(O)$_2$—$R^b$, —N($R^b$)—C(O)—$R^b$, —N($R^b$)—S(O)—$R^b$, —N($R^b$)—C(O)—N($R^b$)$_2$, —N($R^b$)—S(O)$_2$—$R^b$, and $C_{1-6}$alkyl that is optionally substituted with one or more groups independently selected from halo; or
  b) a carbon-linked piperazine ring that is substituted with one or more groups independently selected from the group consisting of $C_{1-6}$alkyl, $C_{2-6}$alkenyl, $C_{2-6}$alkynyl, $C_{3-8}$carbocycle, 3-8 membered heterocycle, aryl, heteroaryl, halo, —$NO_2$, —$N(R^b)_2$, —CN, —C(O)—N($R^b$)$_2$, —S(O)—N($R^b$)$_2$, —S(O)$_2$—N($R^b$)$_2$, —O—$R^b$, —S—$R^b$, —O—C(O)—$R^b$, —C(O)—$R^b$, —C(O)—O$R^b$, —S(O)—$R^b$, —S(O)$_2$—$R^b$, —N($R^b$)—C(O)—$R^b$, —N($R^b$)—S(O)—$R^b$, —N($R^b$)—C(O)—N($R^b$)$_2$, and —N($R^b$)—S(O)$_2$—$R^b$; wherein each $C_{1-6}$alkyl, $C_{2-6}$alkenyl, $C_{2-6}$alkynyl, $C_{3-8}$carbocycle, 3-8 membered heterocycle, aryl, and heteroaryl is optionally substituted with one or more groups independently selected from the group consisting of halo, —$NO_2$—N($R^b$)$_2$, —CN, —C(O)—N($R^b$)$_2$, —S(O)—N($R^b$)$_2$, —S(O)$_2$—N($R^b$)$_2$, —O—$R^b$, —S—$R^b$, —O—C(O)—$R^b$, —C(O)—$R^b$, —C(O)—O$R^b$, —S(O)—$R^b$, —S(O)$_2$—$R^b$, —N($R^b$)—C(O)—$R^b$, —N($R^b$)—S(O)—$R^b$, —N($R^b$)—C(O)—N($R^b$)$_2$, —N($R^b$)—S(O)$_2$—$R^b$, and $C_{1-6}$alkyl that is optionally substituted with one or more groups independently selected from halo;
each $R^b$ is independently selected from the group consisting of hydrogen, $C_{1-6}$alkyl, $C_{2-6}$alkenyl, aryl, and $C_{2-6}$alkynyl, wherein each $C_{1-6}$alkyl, $C_{2-6}$alkenyl, aryl, and $C_{2-6}$alkynyl is optionally substituted with one or more groups independently selected from the group consisting of halo, —$N(R^c)_2$, —CN, —C(O)—N($R^c$)$_2$, —S(O)—N($R^c$)$_2$, —S(O)$_2$—N($R^c$)$_2$, —O—$R^c$, —S—$R^c$, —O—C(O)—$R^c$, —C(O)—$R^c$, —C(O)—O$R^c$, —S(O)—$R^c$, —S(O)$_2$—$R^c$, —N($R^c$)—C(O)—$R^c$, —N($R^c$)—S(O)—$R^c$, —N($R^c$)—C(O)—N($R^c$)$_2$, and —N($R^c$)—S(O)$_2$—$R^c$; or two $R^b$ are taken together with the nitrogen to which they are attached to form a pyrrolidino, piperidino, or piperazino ring;
each $R^c$ is independently selected from the group consisting of hydrogen, $C_{1-6}$alkyl, $C_{2-6}$alkenyl, and $C_{2-6}$alkynyl, wherein each $C_{1-6}$alkyl, $C_{2-6}$alkenyl, and $C_2$-6alkynyl is optionally substituted with one or more groups independently selected from the group consisting of oxo, halo, amino, hydroxy, and $C_{1-6}$alkoxy; or two $R^c$ are taken together with the nitrogen to which they are attached to form a heterocyclyl that is optionally substituted with one or more groups independently selected from the group consisting of oxo, halo and C$_{1-3}$alkyl that is optionally substituted with one or more groups independently selected from the group consisting of oxo and halo;

R$^x$ is C$_{1-6}$alkyl, C$_{2-6}$alkenyl, C$_{2-6}$alkynyl, C$_{3-8}$carbocycle, oxetanyl, tetrahydrofuranyl, or tetrahydropyranyl, wherein each C$_{1-6}$alkyl, C$_{2-6}$alkenyl, C$_{2-6}$alkynyl, C$_{3-8}$carbocycle is optionally substituted with one or more groups independently selected from the group consisting of halo, —CN, C$_{1-3}$alkoxy, oxetanyl, tetrahydrofuranyl, tetrahydropyranyl, and C$_{3-8}$carbocycle that is optionally substituted with one or more groups independently selected from the group consisting of halo and C$_{1-3}$alkyl;

R$^2$ is

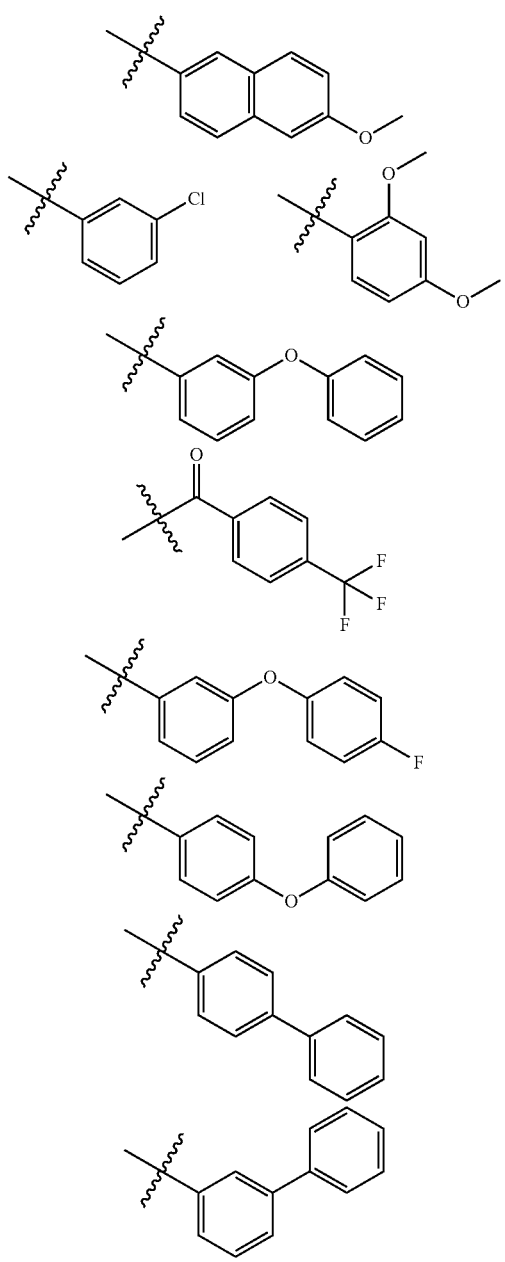
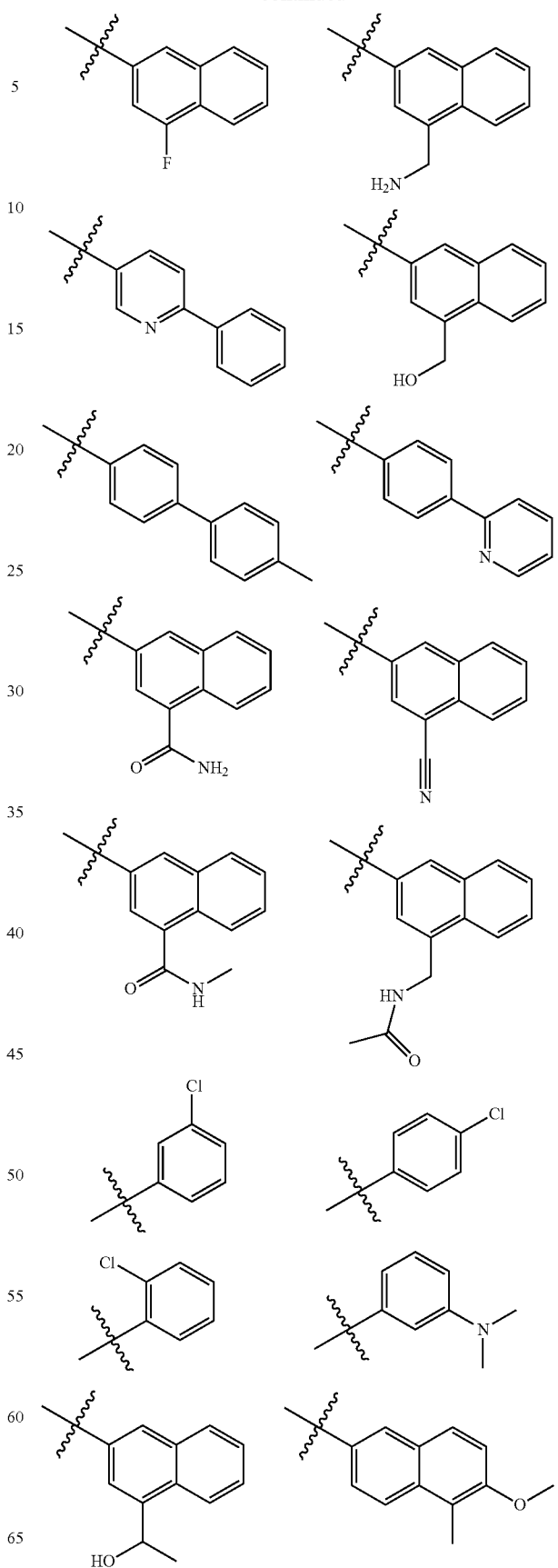

425
-continued
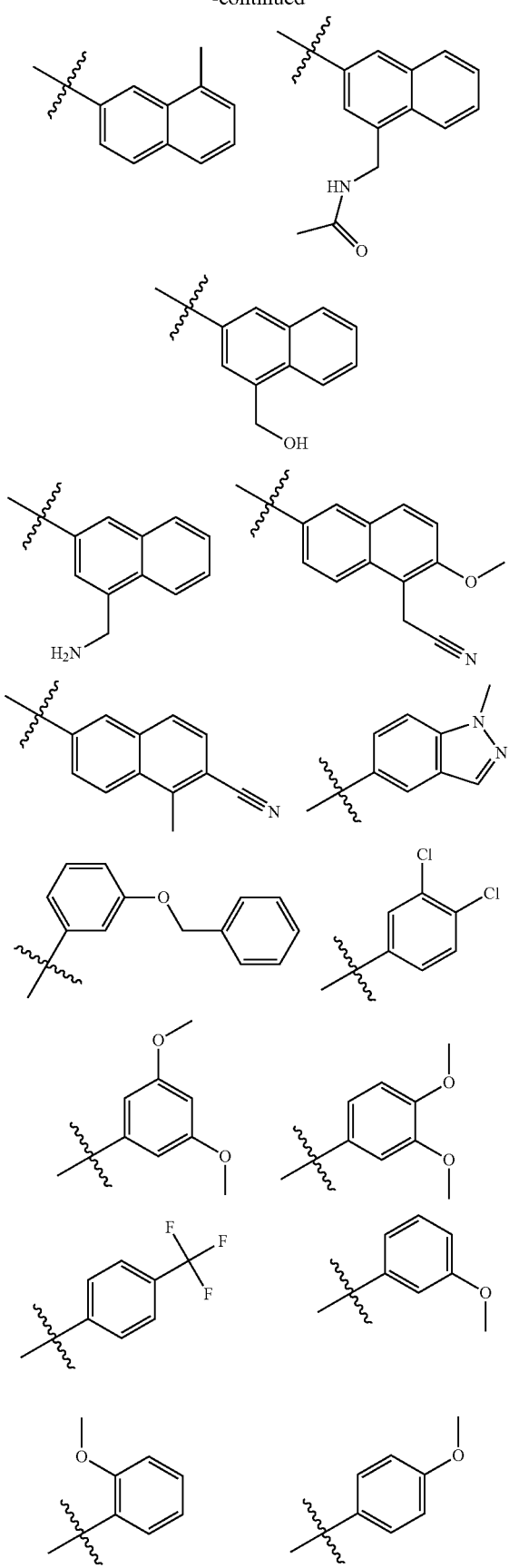
426
-continued
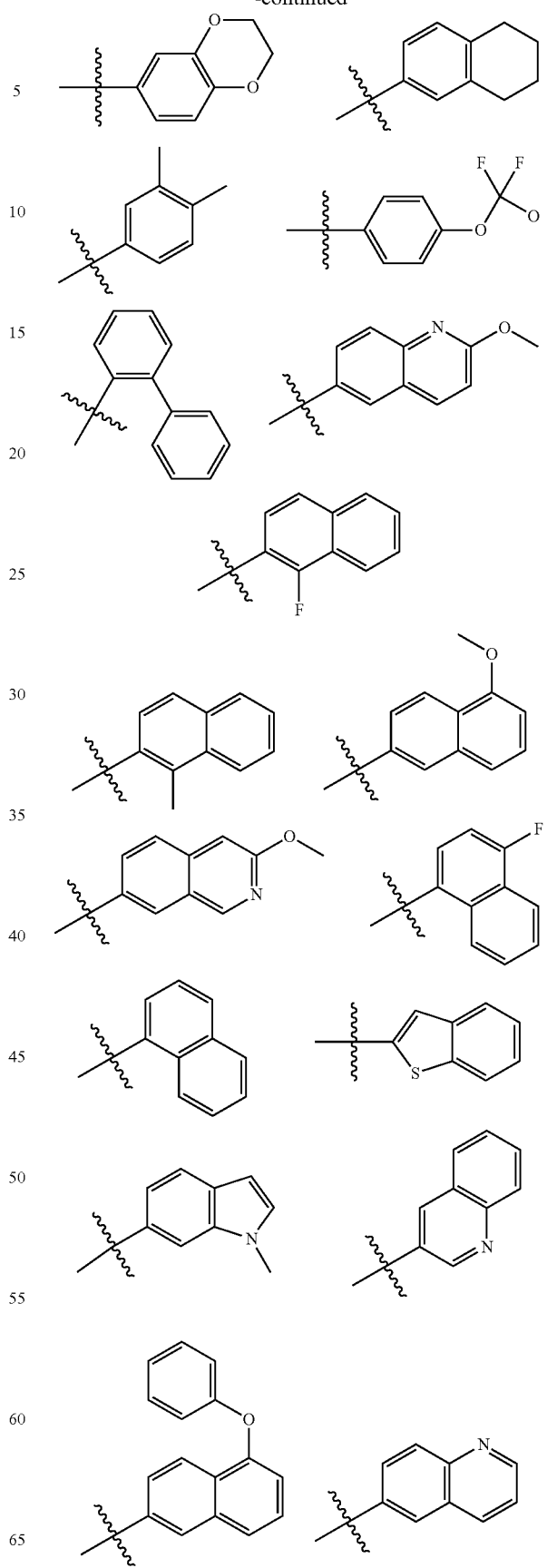

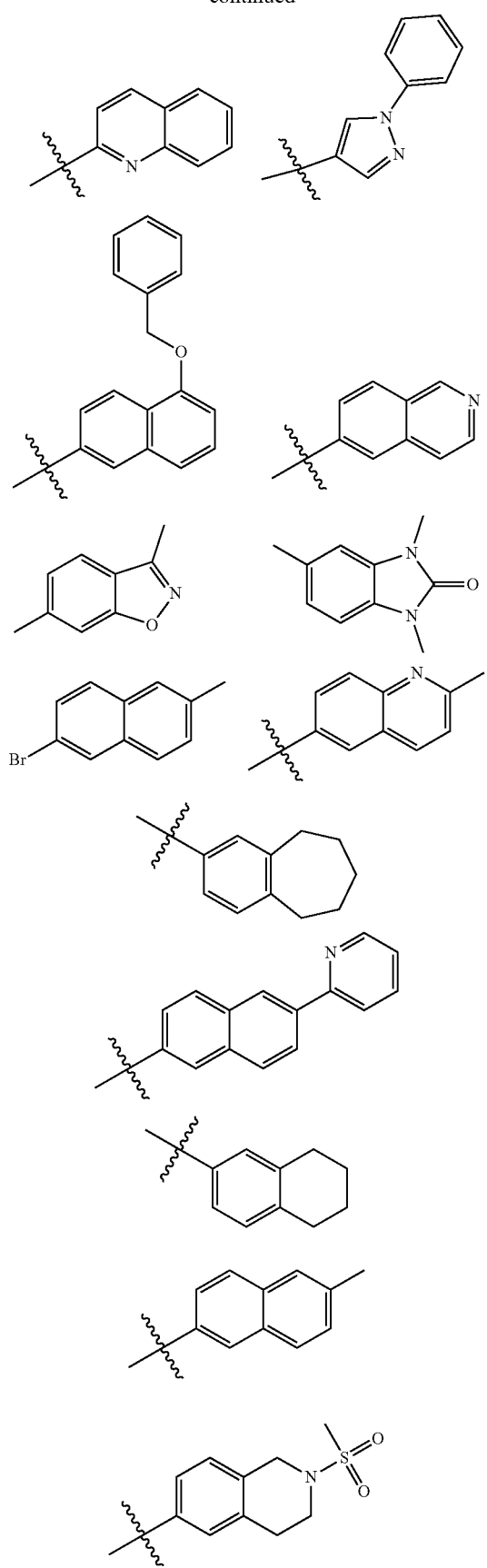
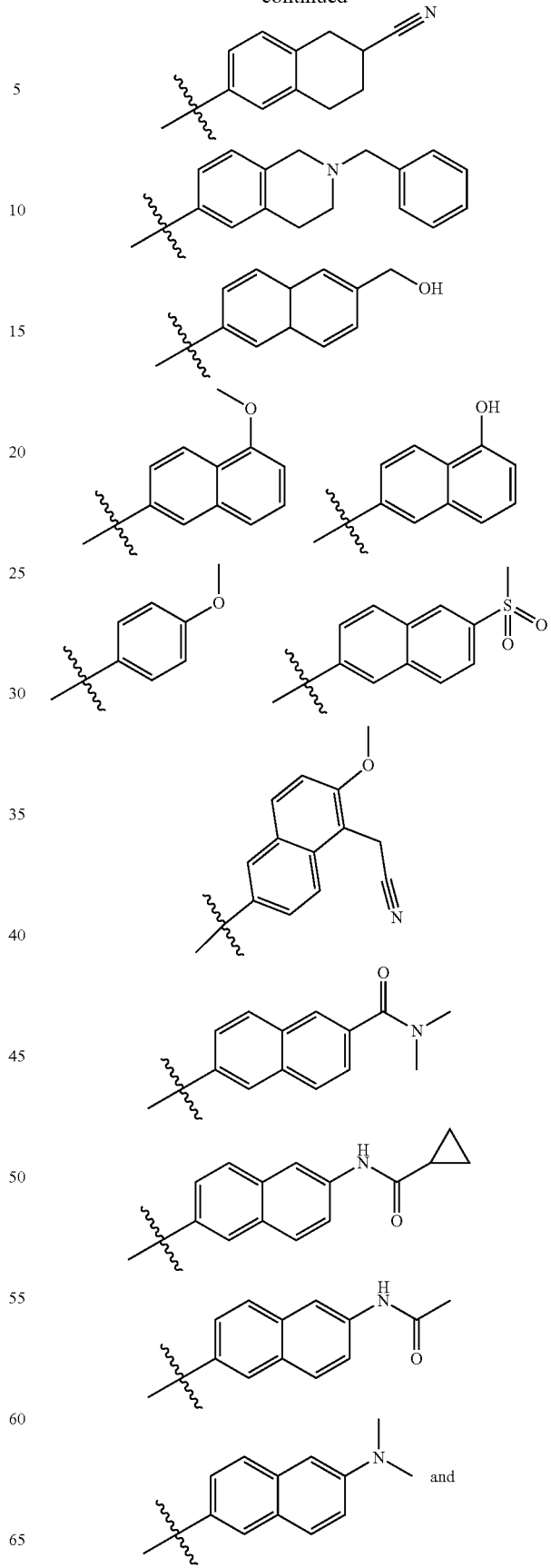

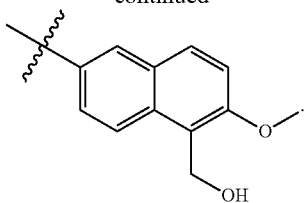

provided that when $R^2$ is 6-methoxy-2-naphthyl, then $R^1$ is not 1-(cyclopropylmethyl)piperidin-3-yl, 1-(cyclobutyl)piperidin-3-yl, 1-(cyclopentyl)piperidin-3-yl, or 1-(tetrahydropyranyl)piperidin-3-yl; and provided that when $R^2$ is naphthyl, 6-quinolyl, 2-methyl-6-quinolyl, 2,3-dihydro- 1,4-benzodioxin-6yl, or 3,4-dimethoxyphenyl, the $R^1$ is not optionally substituted piperizin-2-yl.

21. A composition comprising a compound as described in claim 20, or a pharmaceutically acceptable salt thereof, and a pharmaceutically acceptable adjuvant, carrier, or vehicle.

\* \* \* \* \*